(12) United States Patent
Zhao et al.

(10) Patent No.: US 11,873,281 B2
(45) Date of Patent: *Jan. 16, 2024

(54) CONJUGATES OF CELL BINDING MOLECULES WITH CYTOTOXIC AGENTS

(71) Applicants: HANGZHOU DAC BIOTECH CO., LTD., Hangzhou (CN); R. Yongxin Zhao, Lexington, MA (US); Yue Zhang, Shenzhen (CN); Yourang Ma, Zhengzhou (CN)

(72) Inventors: R. Yongxin Zhao, Lexington, MA (US); Yue Zhang, Shenzhen (CN); Yourang Ma, Zhengzhou (CN)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 795 days.

This patent is subject to a terminal disclaimer.

(21) Appl. No.: 16/782,456

(22) Filed: Feb. 5, 2020

(65) Prior Publication Data

US 2020/0172480 A1 Jun. 4, 2020

Related U.S. Application Data

(63) Continuation-in-part of application No. 16/407,367, filed on May 9, 2019, which is a continuation of application No. 14/253,881, filed on Apr. 16, 2014, now Pat. No. 10,399,941, which is a continuation of application No. PCT/IB2012/053554, filed on Jul. 12, 2012.

(51) Int. Cl.
| | |
|---|---|
| *C07D 207/40* | (2006.01) |
| *A61K 47/68* | (2017.01) |
| *A61K 45/06* | (2006.01) |
| *A61K 47/64* | (2017.01) |

(52) U.S. Cl.
CPC ............ *C07D 207/40* (2013.01); *A61K 45/06* (2013.01); *A61K 47/64* (2017.08); *A61K 47/6803* (2017.08); *A61K 47/6811* (2017.08); *A61K 47/6849* (2017.08); *A61K 47/6851* (2017.08); *A61K 47/6855* (2017.08); *A61K 47/6863* (2017.08); *A61K 47/6867* (2017.08); *Y02A 50/30* (2018.01)

(58) Field of Classification Search
CPC ........ A61K 47/55; A61K 47/56; A61K 47/62; A61K 47/64; A61K 47/65; A61K 47/68; A61K 47/6801; A61K 47/6803; C07D 207/38; C07D 207/40

See application file for complete search history.

(56) References Cited

U.S. PATENT DOCUMENTS

| | | | |
|---|---|---|---|
| 10,399,941 | B2 | 9/2019 | Zhao et al. |
| 10,501,412 | B2 | 12/2019 | Zhao et al. |
| 2005/0238649 | A1* | 10/2005 | Doronina ............... A61P 43/00 514/18.9 |
| 2006/0128754 | A1 | 6/2006 | Hoefle et al. |
| 2010/0048490 | A1 | 2/2010 | Vlahov et al. |
| 2011/0294998 | A1 | 12/2011 | Davis et al. |
| 2015/0250896 | A1 | 9/2015 | Zhao |
| 2015/0284416 | A1 | 10/2015 | Zhao |
| 2015/0314017 | A1 | 11/2015 | Zhao |
| 2017/0173168 | A1 | 6/2017 | Zhao |
| 2018/0021448 | A9 | 1/2018 | Zhao et al. |
| 2019/0127400 | A1 | 5/2019 | Zhao et al. |
| 2019/0330149 | A1 | 10/2019 | Zhao et al. |
| 2019/0367453 | A1 | 12/2019 | Zhao et al. |
| 2020/0069814 | A1 | 3/2020 | Zhao et al. |
| 2020/0276261 | A1 | 9/2020 | Zhao et al. |
| 2021/0308277 | A1 | 10/2021 | Zhao et al. |
| 2021/0369855 | A1 | 12/2021 | Zhao et al. |
| 2022/0249594 | A1 | 8/2022 | Zhao et al. |

FOREIGN PATENT DOCUMENTS

| | | |
|---|---|---|
| CN | 101678124 A | 3/2010 |
| CN | 105641707 A | 6/2016 |
| CN | 109912683 A | 6/2019 |
| EP | 3 411 074 A2 | 12/2018 |

(Continued)

OTHER PUBLICATIONS

Pinton et al (Cancer Chemotherapy and Pharmacology, 2011, vol. 67, pp. 275-284) (Year: 2011).*
Guichard et al, Nature, 2010, vol. 467, pp. 854-858 (Year: 2010).*
Gyles, Canadian Journal of Microbiology, 1992, vol. 38, pp. 734-746 (Year: 1992).*
Musselli et al, International Journal of Cancer, 2002, vol. 97, pp. 660-667 (Year: 2002).*
May et al, Journal of Immunology, 2003, vol. 171, pp. 4905-4912 (Year: 2003).*
Mansur et al, Am J Respir Crit Care Med, 1999, vol. 159, pp. 1796-1802 (Year: 1999).*
Cheever et al, Clinical Cancer Research, 2009, Vo. 15, pp. 5323-5337 (Year: 2009).*
Kelley et al (Biochemistry, 1992, vol. 31, pp. 5434-5441) (Year: 1992).*

(Continued)

*Primary Examiner* — Karen A. Canella
(74) *Attorney, Agent, or Firm* — BUCHANAN, INGERSOLL & ROONEY PC

(57) ABSTRACT

A conjugate of a potent cytotoxic agent with a cell-binding molecule having a structure represented by Formula (I), wherein T, L, m, n, -----, $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined herein, can be used for targeted treatment of cancer, autoimmune disease, and infectious disease.

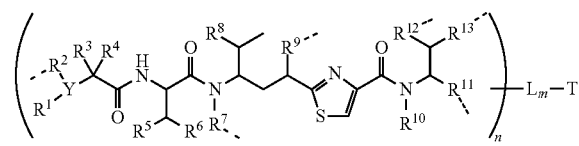

17 Claims, 25 Drawing Sheets

(56) References Cited

FOREIGN PATENT DOCUMENTS

| | | | |
|---|---|---|---|
| JP | 2017-160205 A | 9/2017 | |
| JP | 2020-063254 A | 4/2020 | |
| JP | 2021-006531 A | 1/2021 | |
| TW | 202041237 A | 11/2020 | |
| WO | 2008112873 A2 | 9/2008 | |
| WO | 2009/012958 A1 | 1/2009 | |
| WO | 2009/134279 A1 | 11/2009 | |
| WO | 2011017249 A1 | 2/2011 | |
| WO | 2011069116 A1 | 6/2011 | |
| WO | 2012171020 A1 | 12/2012 | |
| WO | 2013/085925 A1 | 6/2013 | |
| WO | 2015/151078 A2 | 10/2015 | |
| WO | 2015/151081 A2 | 10/2015 | |
| WO | 2016/059622 A2 | 4/2016 | |
| WO | 2018/086139 A1 | 5/2018 | |
| WO | 2018/185526 A1 | 10/2018 | |
| WO | 2019/127607 A1 | 7/2019 | |
| WO | 2020/073345 A1 | 4/2020 | |
| WO | 2020/257998 A1 | 12/2020 | |
| WO | 2020/258893 A1 | 12/2020 | |
| WO | 2021/000067 A1 | 1/2021 | |

OTHER PUBLICATIONS

Mohanty et al, Breast Cancer Research, 2007, vol. 104, pp. 1-11 (Year: 2007).*
Hsu et al, Blood, 1997, vol. 89, pp. 3129-3135 (Year: 1997).*
Macworth-Young et al, Journal of clinical Investiagation, 1987, vol. 79, pp. 572-581 (Year: 1987).*
Swisher et al, Seminars in Oncology, 2002, vol. 29, pp. 95-101 (Year: 2002).*
Decision to grant a European Patent pursuant to Article 97(1) EPC dated Jan. 8, 2020, by the European Patent Office in corresponding European Patent Application No. 12880769.0. (2 pages).
Communication pursuant to Article 94(3) EPC dated Jul. 8, 2020, by the European Patent Office in corresponding European Patent Application No. 17151529.9. (6 pages).
Office Action dated Aug. 31, 2022, by the U.S. Patent and Trademark Office in related U.S. Appl. No. 16/407,367. (18 pages).
Office Action dated Aug. 29, 2022, by the U.S. Patent and Trademark Office in related U.S. Appl. No. 16/539,342. (16 pages).
Liu et al., "On the Dynamics of TCR:CD3 Complex Cell Surface Expression and Downmodulation," Immunity, Nov. 2000, vol. 12, pp. 665-675.
Doronina et al., "Novel Peptide Linkers for Highly Potent Antibody—Auristatin Conjugate," Bioconjugate Chemistry, 2008, vol. 19, No. 10, pp. 1960-1963.
Goldmacher et al., "Antibody-drug conjugates: using monoclonal antibodies for delivery of cytotoxic payloads to cancer cells," Therapeutic Delivery, 2011, vol. 2, No. 3, pp. 397-416.
Leamon et al. "Folate Targeting Enables Durable and Specific Antitumor Responses from a Therapeutically Null Tubulysin B Analogue," Cancer Research, Dec. 1, 2008, vol. 68, No. 23, pp. 9839-9844.
International Preliminary Report on Patentability (Form PCT/IB/373) dated Jan. 13, 2015, by the International Bureau of WIPO in International Application No. PCT/IB2012/053554. (1 page).
International Search Report (Form PCT/ISA/210) dated Apr. 25, 2013, by the State Intellectual Property Office of the People's Republic of China in International Application No. PCT/IB2012/053554. (4 pages).
Written Opinion of the International Searching Authority (Form PCT/ISA/237), dated Apr. 25, 2013 by the State Intellectual Property Office of the People's Republic of China in International Application No. PCT/IB2012/053554. (6 pages).
Patent Examination Report No. 1 dated Sep. 17, 2015, by the Australian Government in Australian Patent Application No. 2012385228 (8 pages).
Notice of Grant for Patent dated Jan. 19, 2017, by the Australian Government in Australian Patent Application No. 2012385228 (1 page).
Notification of Reasons for Refusal dated Feb. 26, 2016, by the Japanese Patent Office in Japanese Patent Application No. 2015-521075 with an English translation of the Notification (8 pages).
Decision to Grant a Patent dated Feb. 10, 2017, by the Japanese Patent Office in Japanese Patent Application No. 2015-521075 with an English translation (5 pages).
Office Action dated Mar. 11, 2016, by the Canadian Patent Office in Canadian Patent Application No. 2,878,733 (7 pages).
Partial Supplementary European Search Report dated Oct. 14, 2015, by the European Patent Office in European Patent Application No. 12880769.0 (8 pages).
Extended European Search Report dated Feb. 9, 2016, by the European Patent Office in European Patent Application No. 12880769.0 (18 pages).
Balasubramanian, R. et al., Total Synthesis and Biological Evaluation of Tubulysin U, Tubulysin V, and Their Analogues, J. Med. Chem., 2009, 52 (2), pp. 238-240.
Office Action dated Apr. 28, 2017, by the Canadian Patent Office in Canadian Patent Application No. 2,878,733 (3 pages).
Extended European Search Report dated Jul. 4, 2017, by the European Patent Office in European Patent Application No. 17151529.9 (10 pages).
Office Action dated Jun. 20, 2018, by the Canadian Patent Office in Canadian Patent Application No. 2,977,032. (5 pages).
Communication pursuant to Article 94(3) EPC dated Jan. 17, 2018, by the European Patent Office in European Patent Application No. 12 880 769.0. (8 pages).
Office Action dated Mar. 1, 2017, by the Australian Patent Office in Australian Patent Application No. 2016228256. (4 pages).
Office Action dated Mar. 17, 2017, by the Australian Patent Office in Australian Patent Application No. 2016228256. (4 pages).
Notice of grant dated Aug. 3, 2017, by the Australian Patent Office in Australian Patent Application No. 2016228256. (1 page).
Office Action dated Feb. 5, 2018, by the Canadian Patent Office in Canadian Patent Application No. 2,878,733. (3 pages).
The extended European search report dated May 24, 2018, by the European Patent Office in European Patent Application No. 17206539.3. (10 pages).
Notification of Reasons for Refusal dated Mar. 1, 2016, by the Japanese Patent Office in Japanese Patent Application No. 2015-521075 and an English translation of the Office Action. (5 pages).
Robin et al., "Dibromomaleimide end functional polymers by RAFT polymerization without the need of protecting groups," (2012). (36 pages).
Ryan et al., "Tunable reagents for multi-functional bioconjugation: reversible or permanent chemical modification of proteins and peptides by control of maleimide hydrolysis," Chemical Communications, (2011), vol. 47, No. 19. (10 pages).
Schumacher et al., "In Situ Maleimide Bridging of Disulfides and a New Approach to Protein PEGylation," Bioconjugate Chemistry, (2011), vol. 22, pp. 132-136.
Office Action dated Feb. 11, 2019, by the U.S. Patent and Trademark Office in related U.S. Appl. No. 14/430,230. (22 pages).
Li et al., "Advances in the discovery of novel antimicrobials targeting the assembly of bacterial cell division protein FtsZ," European Journal of Medicinal Chemistry (2015), vol. 95, pp. 1-15.
Irani et al., "Molecular properties of human IgC subclasses and their implications for designing therapeutic monoclonal antibodies against infectious diseases," Molecular Immunology, (2015), vol. 67, pp. 171-182.
Pelegrin et al., "Antiviral Monoclonal Antibodies: Can They Be More Than Simple Neutralizing Agents?," Trends in Microbiology, (2015), vol. 23, No. 10, pp. 653-665.
Turner et al., "Antigens of selected Acanthamoeba species detected with monoclonal antibodies," Journal for Parasitology, (2005), vol. 35, pp. 981-990.
Douek et al., "HLA-DO is an intracellular class II molecule with distinctive thymic expression," International Immunology, (1997), vol. 9, No. 3, pp. 355-364.

(56) References Cited

OTHER PUBLICATIONS

Baeckstrom et al., "Expression of the Leukocyte-associated Sialoglycoprotein CD43 by a Colon Carcinoma Cell Line," The Journal of Biological Chemistry, (1995), vol. 270, No. 23, pp. 13688-13692.
Grossbard et al., "Serotherapy of B-Cell Neoplasms with Anti-B4-Blocked Ricin: A Phase I Trail of Daily Bolus Infusion," Blood, (1992), vol. 79, No. 3, pp. 576-585.
Pinto et al., "Schedule treatment design and quantitative in vitro evaluation of chemotherapeutic combinations for metastatic prostate cancer therapy," Chemotherapy and Pharmacology, (2011), vol. 67, pp. 275-284.
Office Action dated Aug. 10, 2018, by the U.S. Patent and Trademark Office in related U.S. Appl. No. 14/253,881. (16 pages).
Office Action dated Jan. 7, 2019, by the U.S. Patent and Trademark Office in related U.S. Appl. No. 14/253,881 (14 pages).
Notice of Allowance dated Apr. 3, 2019, by the U.S. Patent and Trademark Office in related U.S. Appl. No. 14/253,881. (8 pages).
Notice of Allowance dated Jul. 25, 2019, by the U.S. Patent and Trademark Office in related U.S. Appl. No. 14/430,230. (23 pages).
Office Action dated Dec. 17, 2018, by the Canadian Patent Office in Canadian Patent Application No. 2,878,733. (3 pages).
Communication under Rule 71(3) EPC dated Aug. 29, 2019, by the European Patent Office in European Patent Application No. 12 880 769.0. (5 pages).
Communication under Rule 94(3) EPC dated Sep. 6, 2019, by the European Patent Office in European Patent Application No. 17 151 529.9. (5 pages).
Office Action dated Nov. 6, 2019, by the Canadian Patent Office in Canadian Patent Application No. 2,977,032. (8 pages).
Extended European Search Report dated Jul. 5, 2021, by the European Patent Office in corresponding European Patent Application No. 21155131.2. (13 pages).
Communication pursuant to Article 94(3) EPC dated Aug. 12, 2021, by the European Patent Office in corresponding European Patent Application No. 17151529.9. (5 pages).
Carter et al., "Antibody-Drug Conjugates for Cancer Therapy," The Cancer Journal, May/Jun. 2008, vol. 14, No. 3, pp. 154-169.
Office Action dated Mar. 3, 2022, by the U.S. Patent and Trademark Office in related U.S. Appl. No. 16/539,342. (19 pages).
Communication pursuant to Article 94(3) EPC dated Mar. 10, 2022, by the European Patent Office in corresponding European Patent Application No. 17206539.3. (7 pages).
Decision to Grant a Patent dated Feb. 22, 2022, by the Japanese Patent Office in corresponding Japanese Patent Application No. 2021-016477 and an English translation of the Decision. (6 pages).
Office Action dated Mar. 3, 2022, by the U.S. Patent and Trademark Office in related U.S. Appl. No. 16/407,367. (14 pages).
Decision to Grant a Patent dated Jan. 5, 2021, by the Japanese Patent Office in corresponding Japanese Patent Application No. 2019-095746, and an English translation of the Decision. (5 pages).
Decision to grant a European patent dated Nov. 24, 2022, by the European Patent Office in corresponding European Application No. 17151529.9. (2 pages).
Communication dated Aug. 17, 2022, by the European Patent Office in corresponding European Application No. 17151529.9. (6 pages).
Office Action issued by the U.S. Patent and Trademark Office in the U.S. Appl. No. 16/539,342, dated Mar. 22, 2023, U.S. Patent and Trademark Office, Alexandria, VA. (14 pages).
Lopez-Bueno, A. et al. "Host-Selected Amino Acid Changes at the Sialic Acid Binding Pocket of the Parvovirus Capsid Modulate Cell Binding Affinity and Determine Virulence", Journal of Virology, vol. 80, No. 3, pp. 1563-1573, Year 2006.
Ramming, A. et. al. "Homotypic T-cell/T-cell interaction induces T-cell activation, proliferation, and differentiation", Human Immunology, vol. 70, pp. 873-881, Year 2009.
Office Action issued by the U.S. Patent and Trademark Office in the U.S. Appl. No. 16/407,367, dated Apr. 6, 2023, U.S. Patent and Trademark Office, Alexandria, VA. (14 pages).

\* cited by examiner

CONJUGATES OF CELL BINDING MOLECULES WITH CYTOTOXIC AGENTS

CROSS REFERENCE OF RELATED APPLICATIONS

This application is a continuation-in-part of U.S. patent application Ser. No. 16/407,367, filed on May 9, 2019, entitled "CONJUGATES OF CELL BINDING MOLECULES WITH CYTOTOXIC AGENTS," which in turn is a continuation of U.S. patent application Ser. No. 14/253,881, filed on Apr. 16, 2014, now U.S. Pat. No. 10,399,941, which in turn is a continuation of PCT/IB2012/053554, filed on Jul. 12, 2012. The entire content of each of the prior applications is hereby incorporated by reference.

FIELD OF THE INVENTION

This invention relates to conjugates of potent antimitotic agents with a cell-surface receptor binding molecules for targeted therapy. The invention also relates to use of the compositions comprising binding molecule-antimitotic agent conjugates for treating cancer, autoimmune disease, and infectious disease.

BACKGROUND OF THE INVENTION

The targeted delivery of highly active cytotoxic drugs by antibodies or other cell-surface receptor binding agents to specific sites of disease in human body, which in turn can dramatically increase therapeutic windows of the cytotoxic drugs, has proven a particularly promising approach for targeted treatment (Van den Mooter, T. et al Expert Opin Biol Ther. 2015, 15, 749-60). In particular, since US FDA approvals of Adcetris (brentuximab vedotin) in 2011 and Kadcyla (ado-trastuzumab emtansine) in 2013, almost every major pharmaceutical and biotech company has adopted the applications of antibody-drug conjugate (ADC) for targeted treatment of cancers (Chari, R. et al, Angew. Chem., Int. Ed. 2014, 53, 3796-3827; Sievers, E. L. et al. Annu Rev Med. 2013, 64, 15-29; Mehrling, T. Future Oncol, 2015, 11, 549). So far, the majority of ADCs in clinical evaluation utilize the highly potent tubulin-interacting agents, maytansinoids or auristatins. A few ADCs in the clinic have incorporated other potent effector molecules, such as the topoisomerase 1 inhibitor SN-38 or the DNA interacting agents calicheamicin and pyrrolobenzodiazepines (Anderl, J. et al, Methods Mol Biol. 2013; 1045:51-70; Thomas, A., et al, Lancet Oncol. 2016 June; 17(6):e254-e262).

Several short peptidic compounds that found to have biological activity have been isolated from natural sources. One of them, Tubulysins (structures shown below), which were the first time isolated by Hofle and Reichenbach et al. (GBF Braunschweig) from a culture growth of the myxobacterial strains of Archangium gephyra (F. Sasse et al. J. Antibiot. 2000, 53, 879-885; WO9813375), are members of group of antimitotic peptides that inhibit tubulin polymerization in dividing cells, and thus inducing apoptosis. With the exceptional potency exceeding that of vinblastine, taxol and epothilones (Wipf, et al, *Org. Lett.* 2004, 6, 4057-60; Peltier, et al, J. Am.

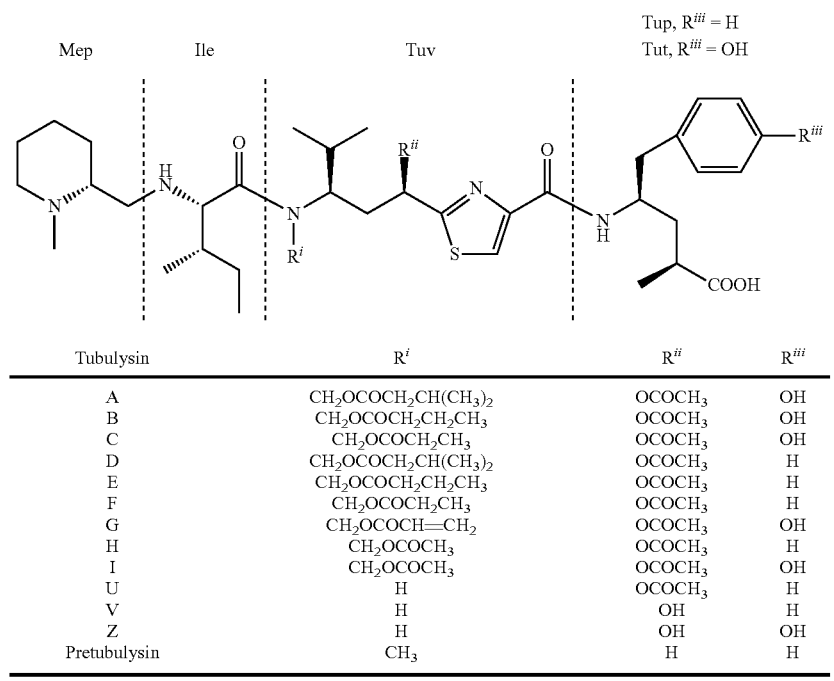

| Tubulysin | $R^i$ | $R^{ii}$ | $R^{iii}$ |
|---|---|---|---|
| A | $CH_2OCOCH_2CH(CH_3)_2$ | $OCOCH_3$ | OH |
| B | $CH_2OCOCH_2CH_2CH_3$ | $OCOCH_3$ | OH |
| C | $CH_2OCOCH_2CH_3$ | $OCOCH_3$ | OH |
| D | $CH_2OCOCH_2CH(CH_3)_2$ | $OCOCH_3$ | H |
| E | $CH_2OCOCH_2CH_2CH_3$ | $OCOCH_3$ | H |
| F | $CH_2OCOCH_2CH_3$ | $OCOCH_3$ | H |
| G | $CH_2OCOCH=CH_2$ | $OCOCH_3$ | OH |
| H | $CH_2OCOCH_3$ | $OCOCH_3$ | H |
| I | $CH_2OCOCH_3$ | $OCOCH_3$ | OH |
| U | H | $OCOCH_3$ | H |
| V | H | OH | H |
| Z | H | OH | OH |
| Pretubulysin | $CH_3$ | H | H |

(The structures of existing tubulysin compounds)

Chem. Soc. 2006, 128, 16018-9; Wipf, et al, *Org. Lett.,* 2007, 9, 1605-1607; Wang, et al, Chem. Biol. Drug Des. 2007, 70, 75-86; Pando, et al, Org. Lett. 2009, 11, 5567-9), these antimitotic peptides are exciting leads for targeted therapies. Structurally, the tetrapeptide tubulysins are comprising of N-methylpipecolinic acid (Mep) at the N-terminus, isoleucine (Ile) as the second residue, the unique thiazole-containing tubuvaline (Tuv) as the third residue, and two possible γ-amino acids at the C-terminus (tubutyrosine (Tut) or tubuphenylalanine (Tup)). Despite several tubulysins have recently been synthesized, significant general toxicities (>20% animal body weight loss) of the existing tubulysins at doses required for achieving a therapeutic effect compromise their efficacy (US Patent appl. 2010/0048490). We have been interested in the art of a conjugate of a cell surface binding ligand, particularly using an antibody to conjugate with tubulysin derivatives for having significantly lower general toxicity, yet useful therapeutic efficiency. Although the natural tubulysins are ideal payloads for ADCs with their extreme potency in tens picomolar ranges of $IC_{50}$ values against many cell lines, we found that the natural tubulysin conjugates were hardly metabolized in animal livers, resulting in severe liver toxicity. A simpler analog, such as using 2-(dimethylamino)-2-methylpropanoic acid to replace 1-methylpiperidine-2-carboxylic acid at the far left side of natural tubulysin structures did not alternate much potency of the compounds conjugated to an antibody, but reduced significant liver toxicity of the conjugates. Here this patent discloses these tubulysin conjugates with a cell surface binding ligand and using these conjugates for treating cancer and immune disorders.

SUMMARY OF THE INVENTION

In one illustrative embodiment of the invention provides a conjugate of formula (I):

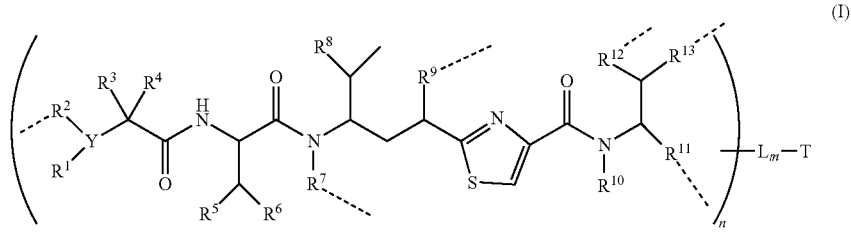

or their pharmaceutically acceptable salts, hydrates, or hydrated salts; or the polymorphic crystalline structures of these compounds; or their optical isomers, racemates, diastereomers or enantiomers thereof;

Wherein T is a targeting or binding ligand; L is a releasable linker; ----- is a linkage bond that L connects to an atom inside the bracket independently; n is 1-20 and m is 1-10;

Inside the bracket is a potent antimitotic agent wherein $R^1$, $R^2$, $R^3$, and $R^4$ are independently linear or branched $C_1$-$C_8$ of alkyl, alkylalcohol; $C_2$-$C_8$ of heteroalkyl, alkylcycloalkyl, heterocycloalkyl, alkyl ether, alkyl carboxylate, alkyl amine, alkyl ester, alkyl amide; $C_3$-$C_8$ of aryl, Ar-alkyl, heterocyclic, carbocyclic, cycloalkyl, heteroalkylcycloalkyl, alkylcarbonyl; or two R's: $R^1R^2$, $R^3R^4$, $R^5R^6$, or $R^{12}R^{13}$ independently together form a 3~7 membered carbocyclic, cycloalkyl, heterocyclic, heterocycloalkyl, aromatic or heteroaromatic ring system; Y is N or C; In addition, $R^1$, $R^2$, $R^3$, and $R^4$ can be independently absent;

Wherein $R^5$, $R^6$, $R^8$ and $R^{10}$ are independently selected from H and linear or branched $C_1$-$C_4$ of alkyl or $C_2$-$C_4$ of heteroalkyl;

Wherein $R^7$ is selected from H, $R^{14}$, or —$R^{14}$C(=O) $X^1R^{15}$; —$R^{14}X^1R^{15}$; $X^1$ is selected from O, S, S—S, NH, or $NR^{14}$;

Wherein $R^9$ is H, —O—, —$OR^{14}$, —OC(=O)$R^{14}$—, —OC(=O)$NHR^{14}$—, —OC(=O)$NR^{14}R^{15}$—, —OC(=O) $R^{14}SSR^{15}$—, OP(=O)($OR^{14}$)—, or $OR^{14}$OP (=O)($OR^{15}$);

Wherein $R^{11}$ is H, $R^{14}$, —$R^{14}$C(=O)$R^{16}$, —$R^{14}$C(=O) $X^2R^{16}$, —$R^{14}X^2R^{16}$, —$R^{14}$C(=O)$X^2$, wherein $X^2$ is —O—, —S—, —NH—, —NHS($O_2$), —N($R^{14}$)—, —O—$R^{14}$—, —S—$R^{14}$—, —S(=O)—$R^{14}$—, or —$NHR^{14}$—;

Wherein $R^{12}$ is H, $R^{14}$, —O—, —S—, —N—, =N—, —OH, —SH, —$NH_2$, =NH, =$NNH_2$, —NH($R^{14}$), —$OR^{14}$, —C(O)O—, —C(O)$OR^{16}$—, —$COR^{16}$, —$COOR^{14}$—, C(O)NH—, C(O)$NH_2$, C(O)$NHR^{14}$, —$SR^{14}$, —S(=O)$R^{14}$, —P(=O)($OR^{16}$)$_2$, —OP(=O) ($OR^{16}$)$_2$, —$CH_2$OP(=O)($OR^{16}$)$_2$, —$SO_2R^{16}$;

Wherein $R^{13}$ is linear or branched $C_1$-$C_{10}$ of alkyl, alkyl acid, alkyl amide, alkyl amine; or $C_2$-$C_{10}$ of heteroalkyl; or $C_3$-$C_{10}$ of Ar; Ar refers to an aromatic or hetero aromatic group, composed of one or several rings, comprising four to ten carbon atoms, preferentially four to six carbon atoms. The term of hetero aromatic group refers to an aromatic group that has one or several carbon atoms replaced by hetero atoms, preferentially one, two or three carbon atoms replaced by O, N, Si, Se, P or S, more preferentially O, S, N. The term aryl or Ar also refers to an aromatic group, wherein one or several H atoms can be replaced independently by $R^{17}$, F, Cl, Br, I, $OR^{16}$, $SR^{16}$, $NR^{16}R^{17}$, N=$NR^{16}$, N=$R^{16}$, $NR^{16}R^{17}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, OP(O) ($OR^{17}$)$_2$, $OCH_2$OP(O)($OR^{17}$)$_2$, OC(O)OP(O)($OR^{17}$)$_2$, PO($OR^{16}$)($OR^{17}$), OP(O)($OR^{17}$)OP(O)($OR^{17}$)$_2$, OC(O)$R^{17}$ or OC(O)$NHR^{17}$;

Wherein $R^{14}$ and $R^{15}$ are independently H; linear or branched $C_1$-$C_8$ of alkyl; $C_2$-$C_8$ of alkenyl, alkynyl, heteroalkyl, heterocyclic, carbocyclic; $C_3$-$C_8$ of aryl, cycloalkyl, alkylcycloalkyl, heterocycloalkyl, heteroaralkyl, heteroalkylcycloalkyl, alkylcarbonyl;

Wherein when $R^{14}$ is bivalent, it is a $R^{14}$ that is further connected to an additional functional group of one to four amino acid units, or ($CH_2CH_2O$)$_r$, r is an integer ranging from 0 to 12, or $C_4$-$C_{12}$ of glycosides, or $C_1$-$C_8$ of carboxylic acid;

Wherein $R^{16}$ is H, OH, $R^{14}$ or one to four amino acid units;

Wherein $R^{17}$ is H, linear or branched $C_1$-$C_8$ of alkyl; $C_2$-$C_8$ of alkenyl, alkynyl, heteroalkyl, heterocyclic; $C_3$-$C_8$ of aryl, carbocyclic, cycloalkyl, alkylcycloalkyl, heterocycloalkyl, heteroalkylcycloalkyl, heteroaralkyl, alkylcarbonyl or $C_4$-$C_{12}$ of glycosides, or pharmaceutical salts.

In another embodiment, the linker L of the potent antimitotic agent-binding molecule conjugates has the formula:

—Ww-(Aa)r-Vv-; wherein: —W— is a Stretcher unit; w is 0 or 1; each -Aa- is independently an Amino Acid unit; r is independently an integer ranging from 0 to 12; —V— is a Spacer unit; and v is 0, 1 or 2. The Stretcher unit W may independently contain a self-immolative spacer, peptidyl units, a hydrazone bond, disulfide or thioether bonds.

In another embodiment, the cell-surface binding molecule T may be of any kind presently known, or which become known cell binding ligands, such as peptides and non-peptides. Generally the binding molecule T is an antibody; a single chain antibody; an antibody fragment that binds to the target cell; a monoclonal antibody; a single chain monoclonal antibody; or a monoclonal antibody fragment that binds the target cell; a chimeric antibody; a chimeric antibody fragment that binds to the target cell; a domain antibody; a domain antibody fragment that binds to the target cell; adnectins that mimic antibodies; DARPins; a lymphokine; a hormone; a vitamin; a growth factor; a colony stimulating factor; or a nutrient-transport molecule (a transferrin); a binding peptide, or protein, or antibody, or small molecule attached on albumin, polymers, dendrimers, liposomes, nanoparticles, vesicles, (viral) capsids. Preferably the binding molecule T is a monoclonal antibody.

In yet another aspect, a compound of formula I~VII or a pharmaceutically acceptable salt or solvate thereof is used for treating cancer, an autoimmune disease or an infectious disease in a human or an animal.

DETAILED DESCRIPTION OF THE INVENTION

Definitions

Figure 1:
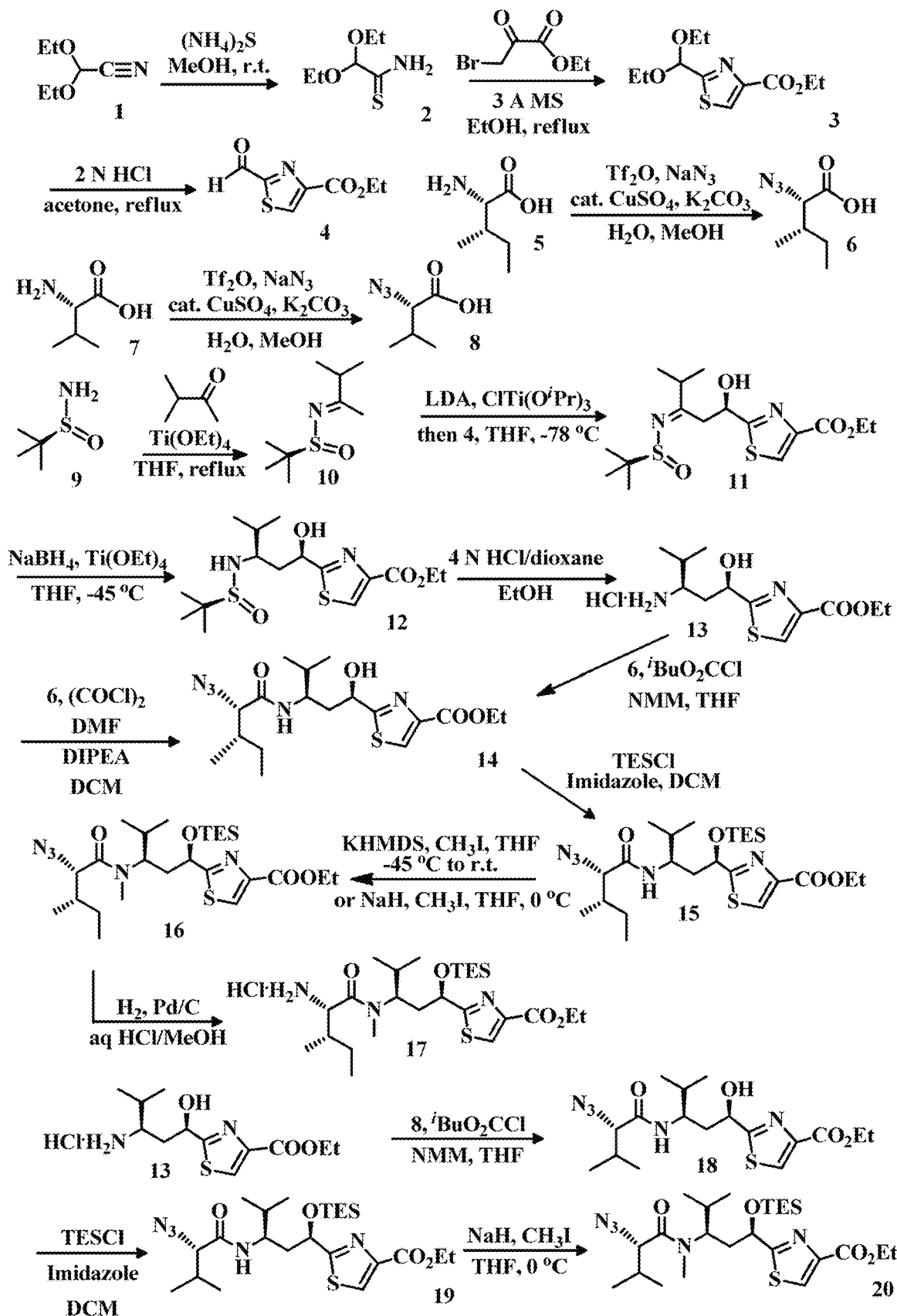
FIG. 1 shows the general synthesis of Tuv component of a Tubulysin analog.
Figure 2:
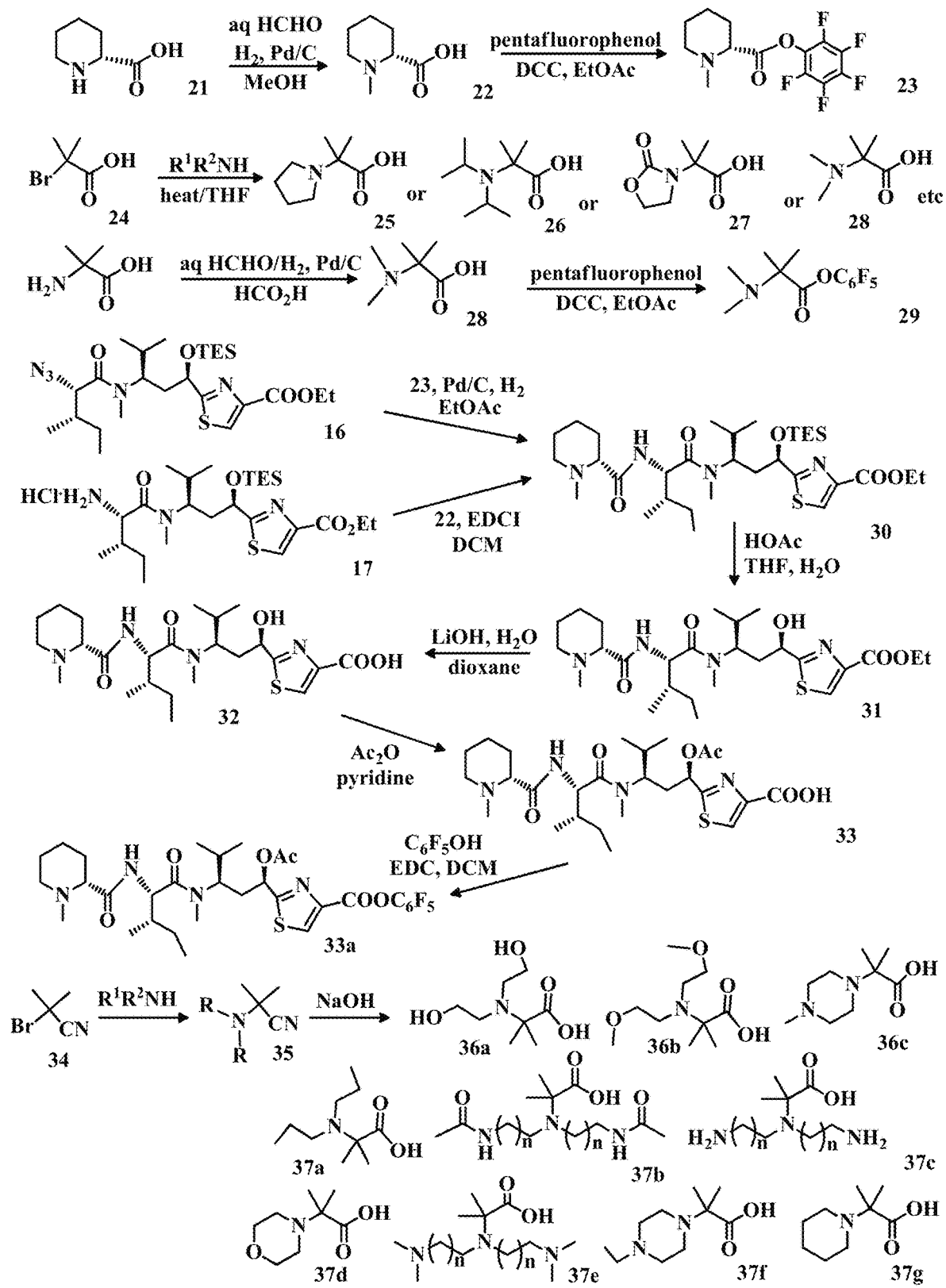
FIG. 2 shows the synthesis of tubulysin components.
Figure 3:
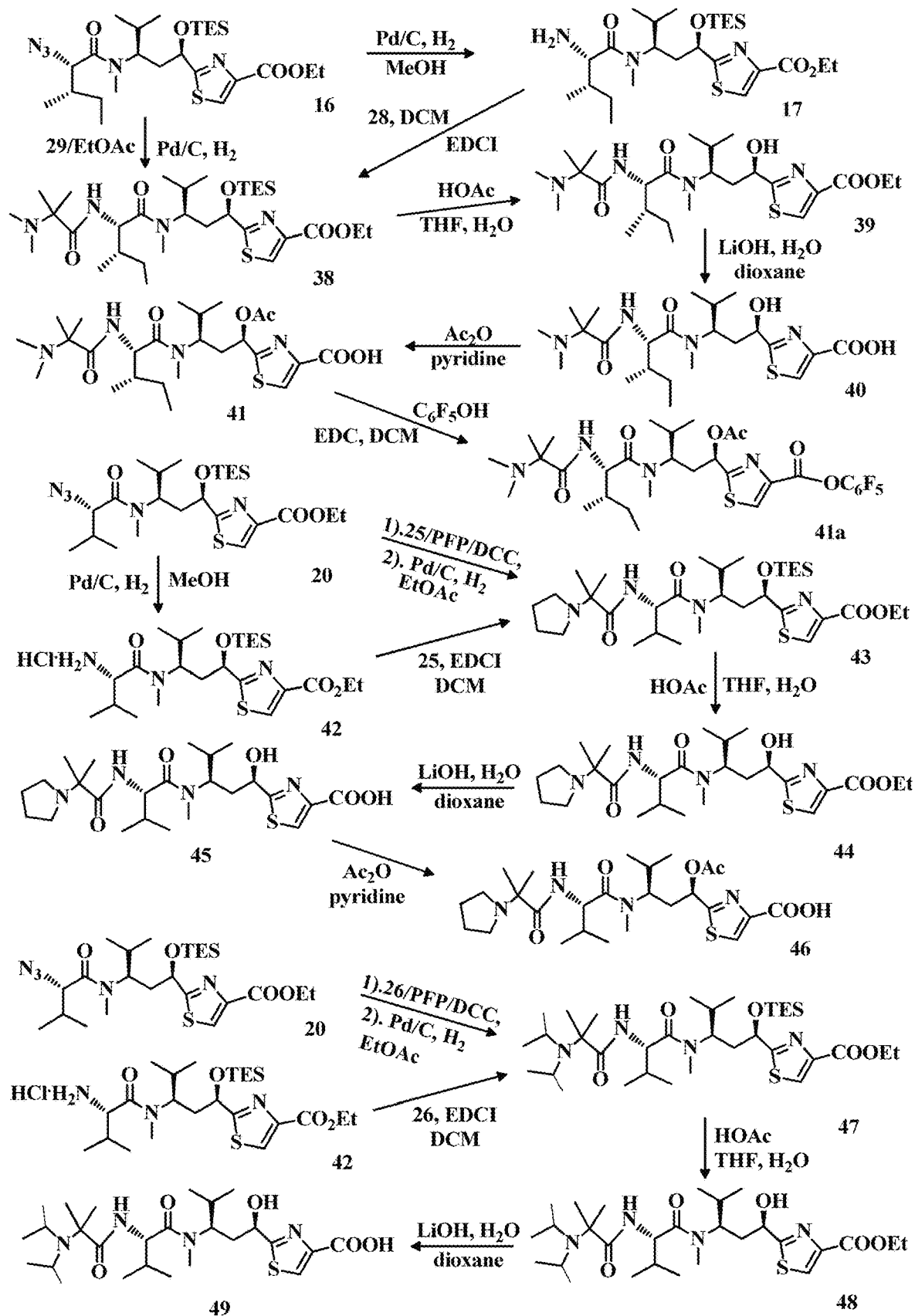
FIG. 3 shows the synthesis of tubulysin components.
Figure 4:
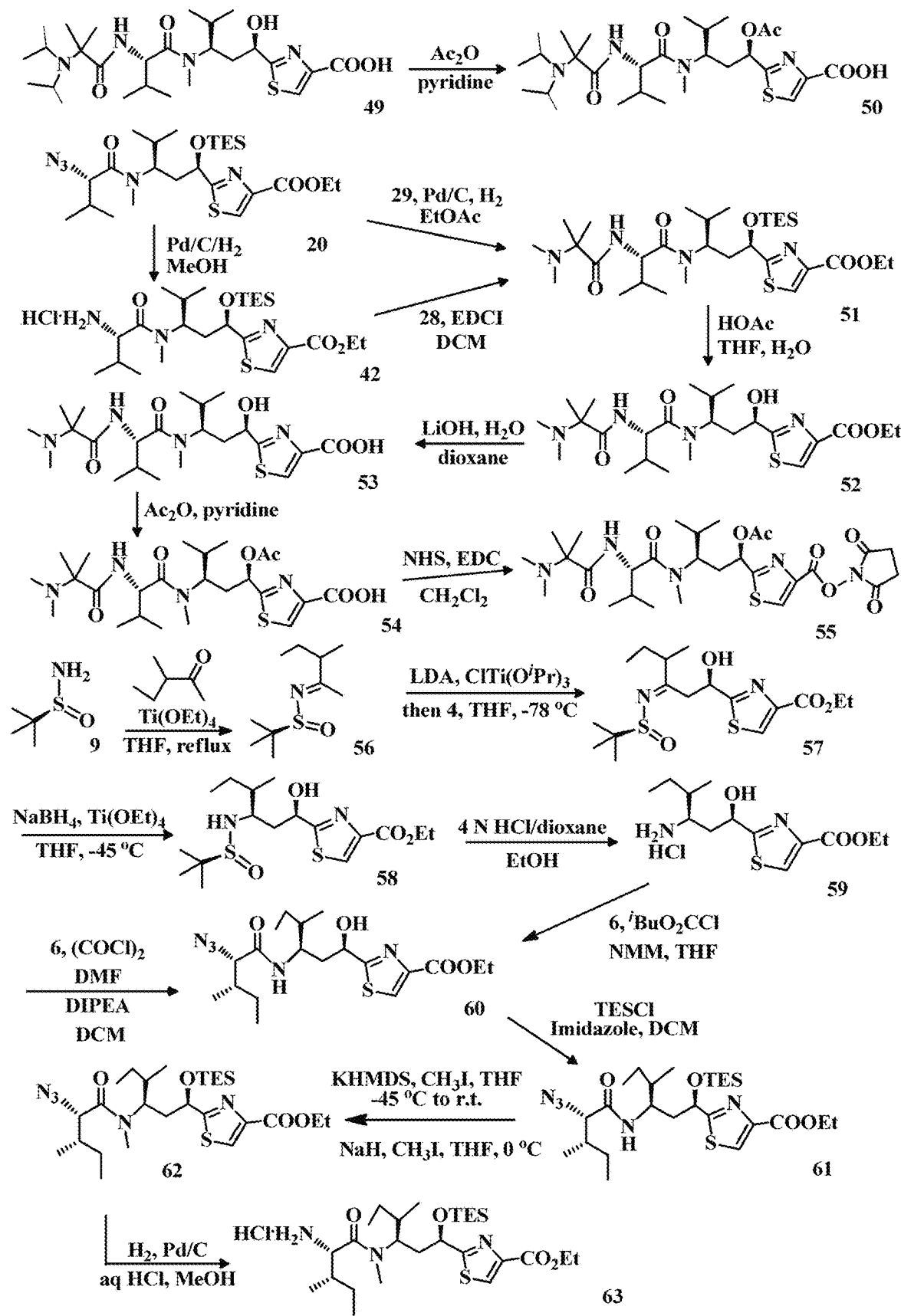
FIG. 4 shows the synthesis of components of tubulysin analogs.
Figure 5:
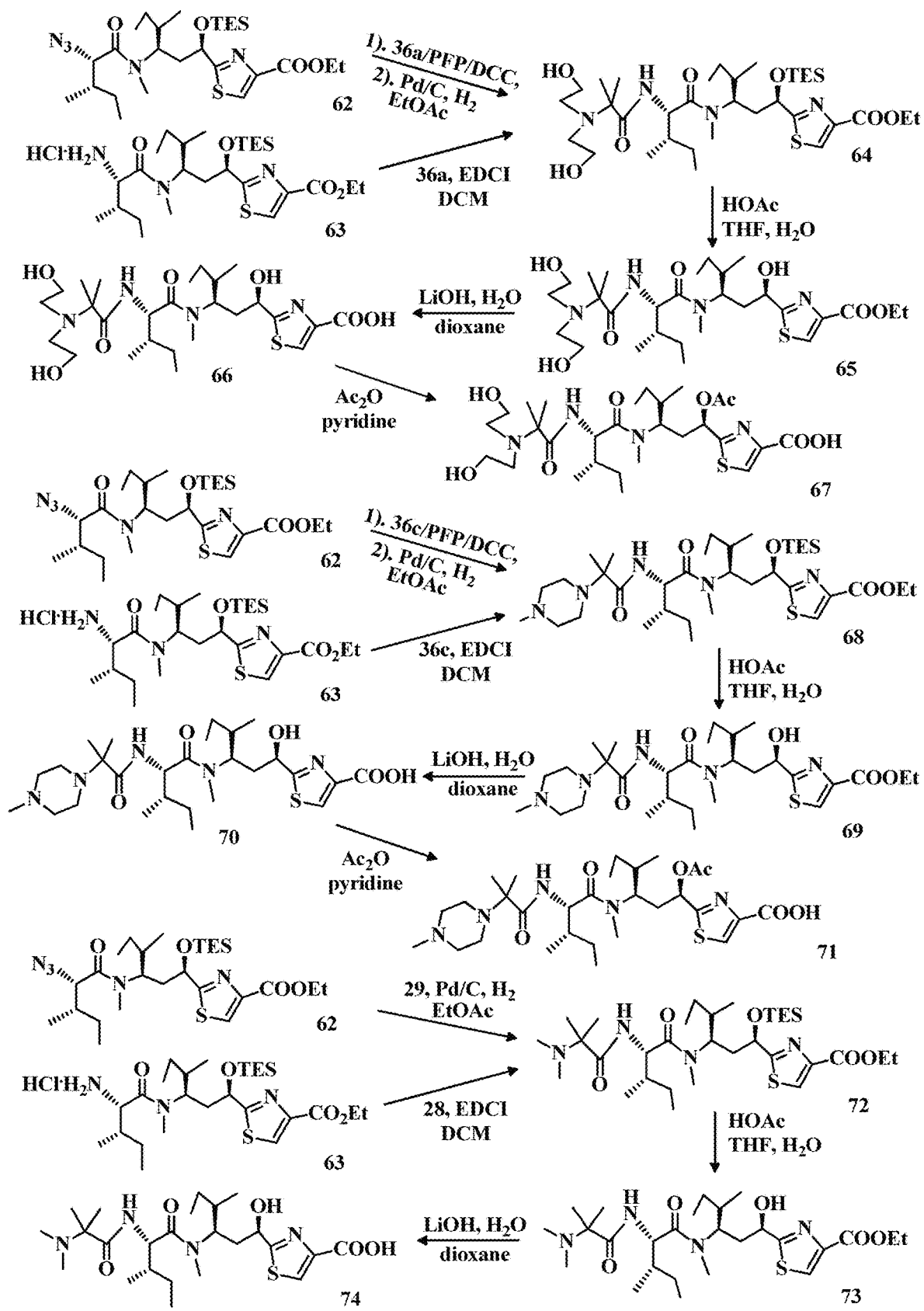
FIG. 5 shows the synthesis of components of tubulysin analogs.
Figure 6:
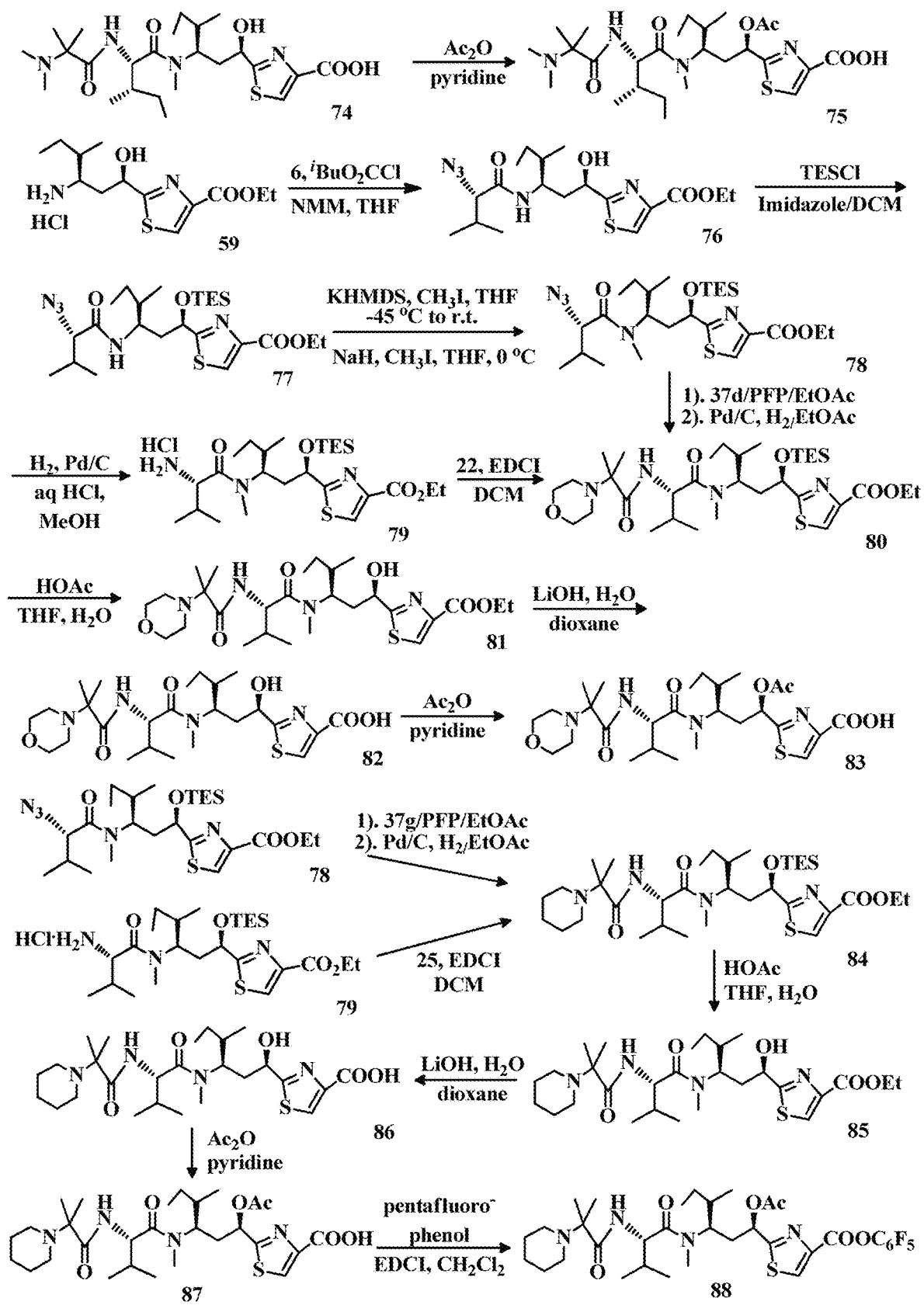
FIG. 6 shows the synthesis of components of tubulysin analogs.
Figure 7:
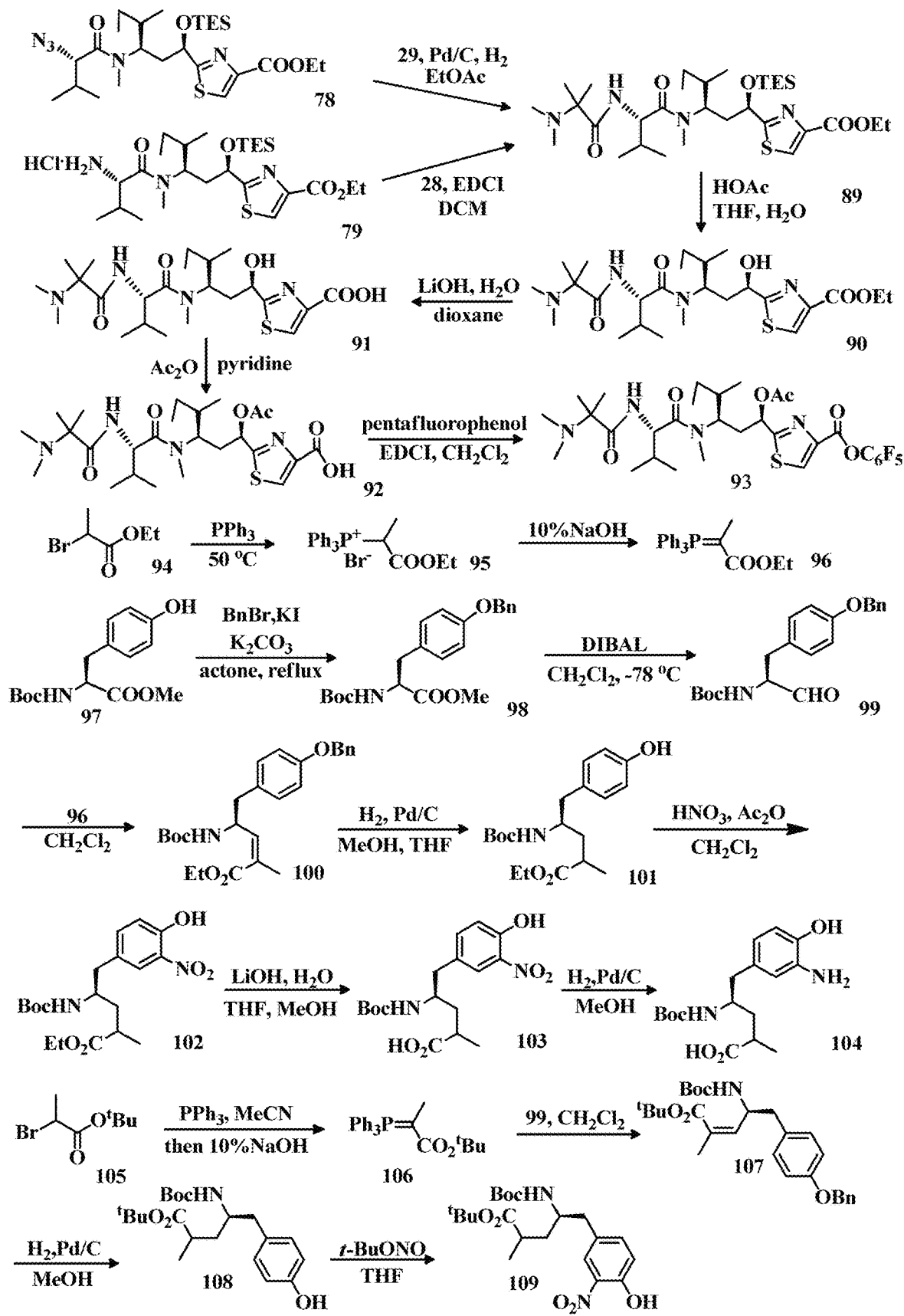
FIG. 7 shows the synthesis of components of tubulysin analogs.
Figure 8:
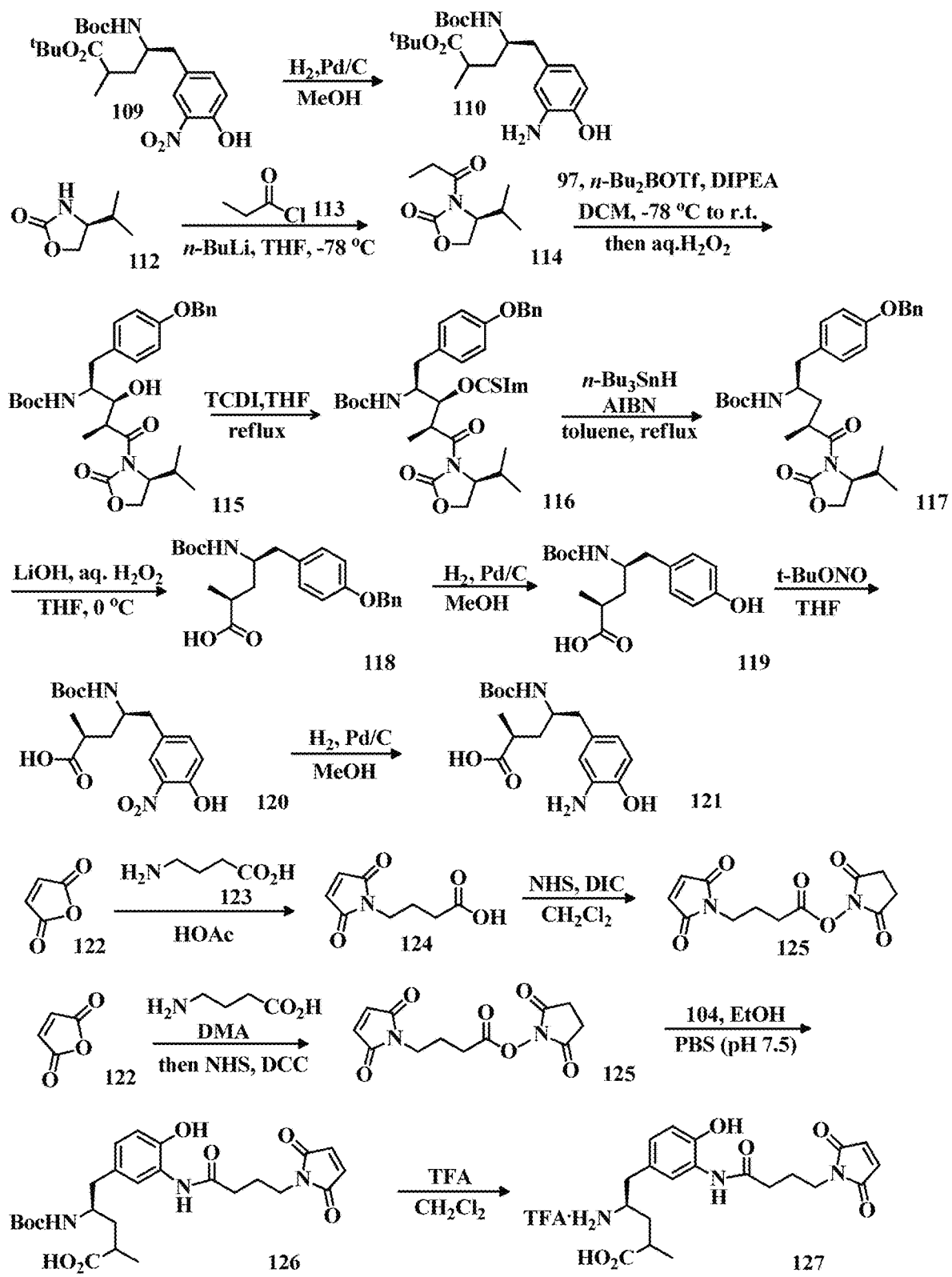
FIG. 8 shows the synthesis of components of tubulysin analogs containing a conjugate linker.
Figure 9:
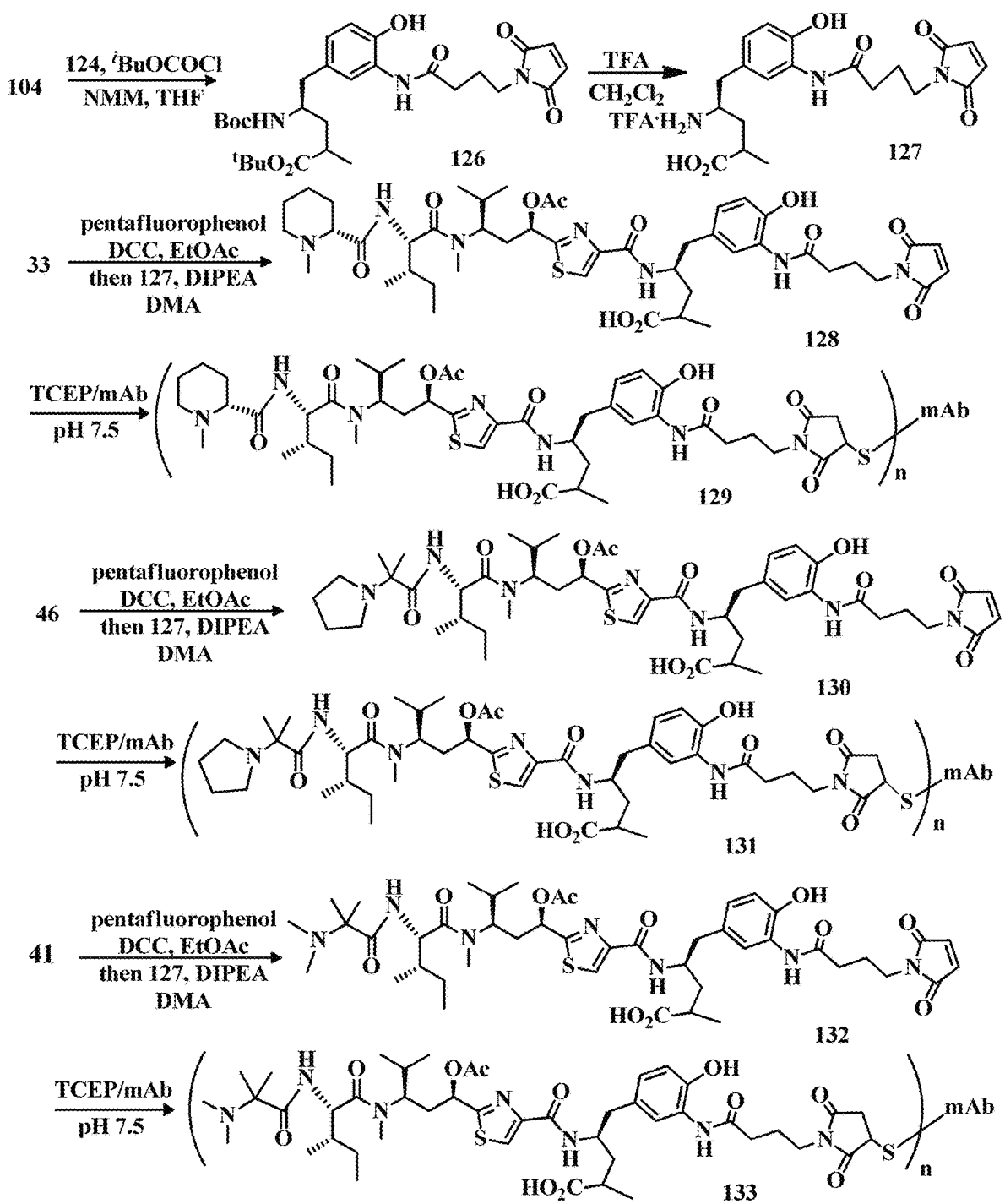
FIG. 9 shows the synthesis of components of tubulysin analogs and their conjugations to an antibody.
Figure 10:
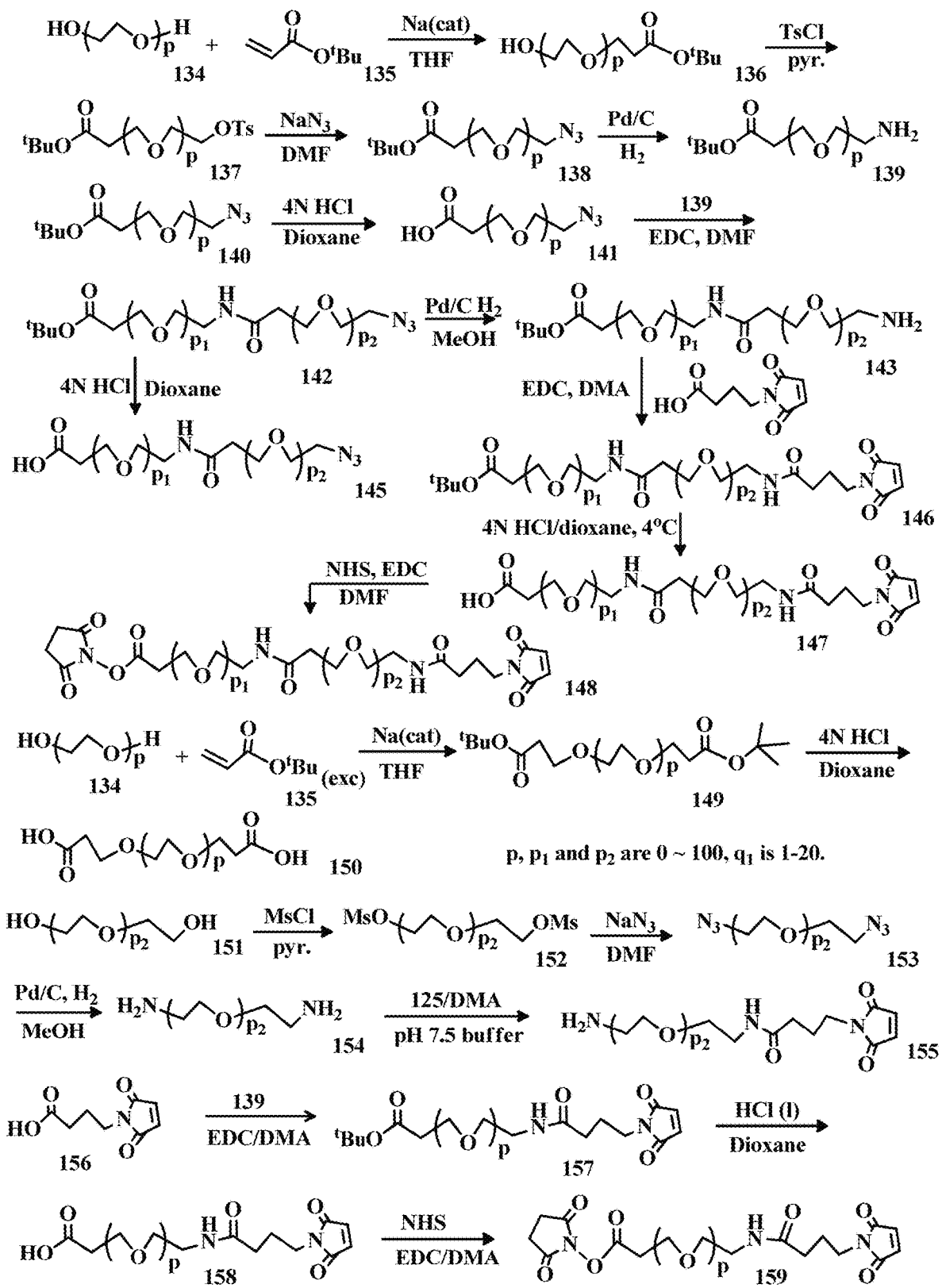
FIG. 10 shows the synthesis of components of a linker.
Figure 11:
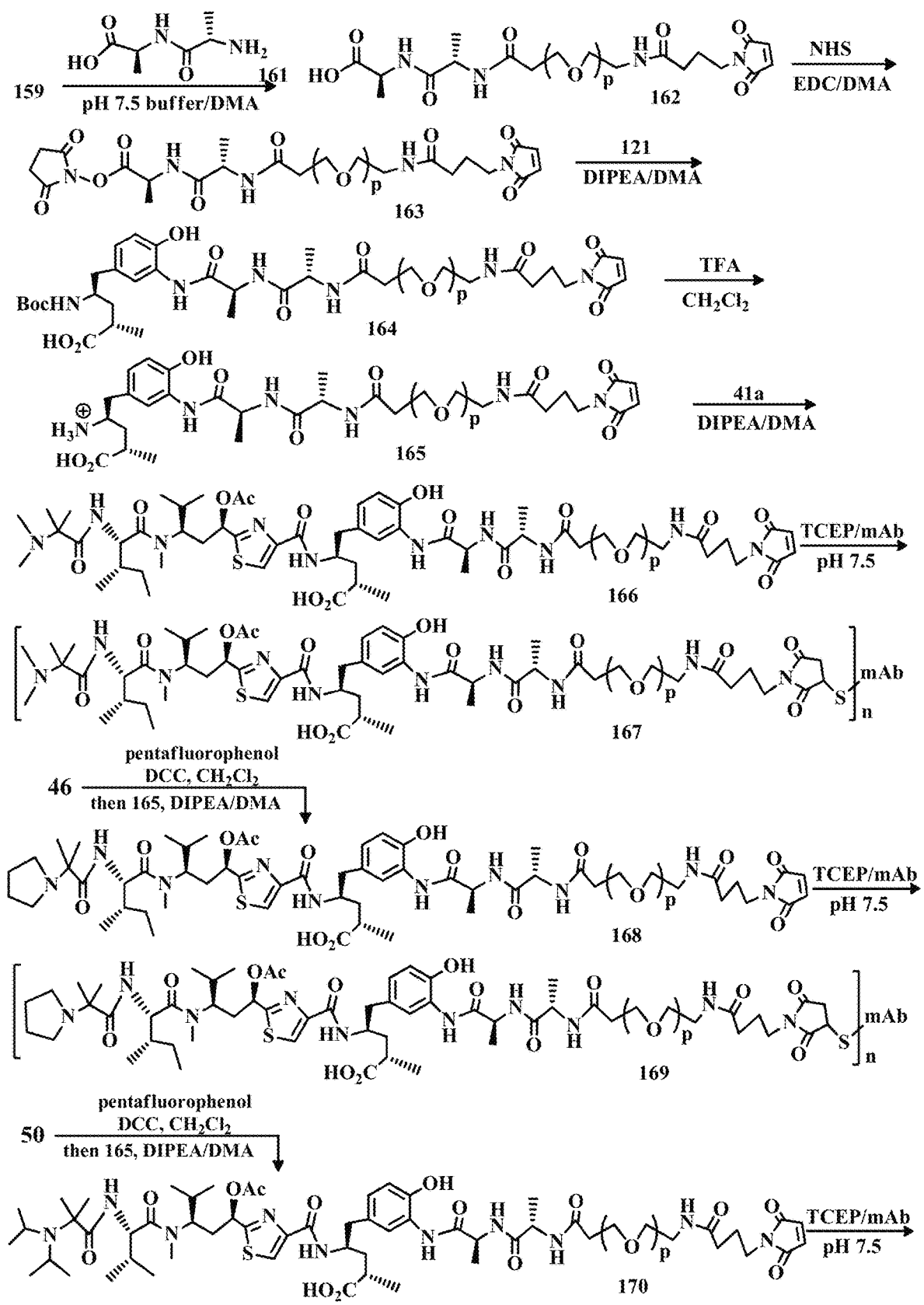
FIG. 11 shows the synthesis of Tubulysin analogs containing a linker and their conjugations to an antibody.
Figure 12:
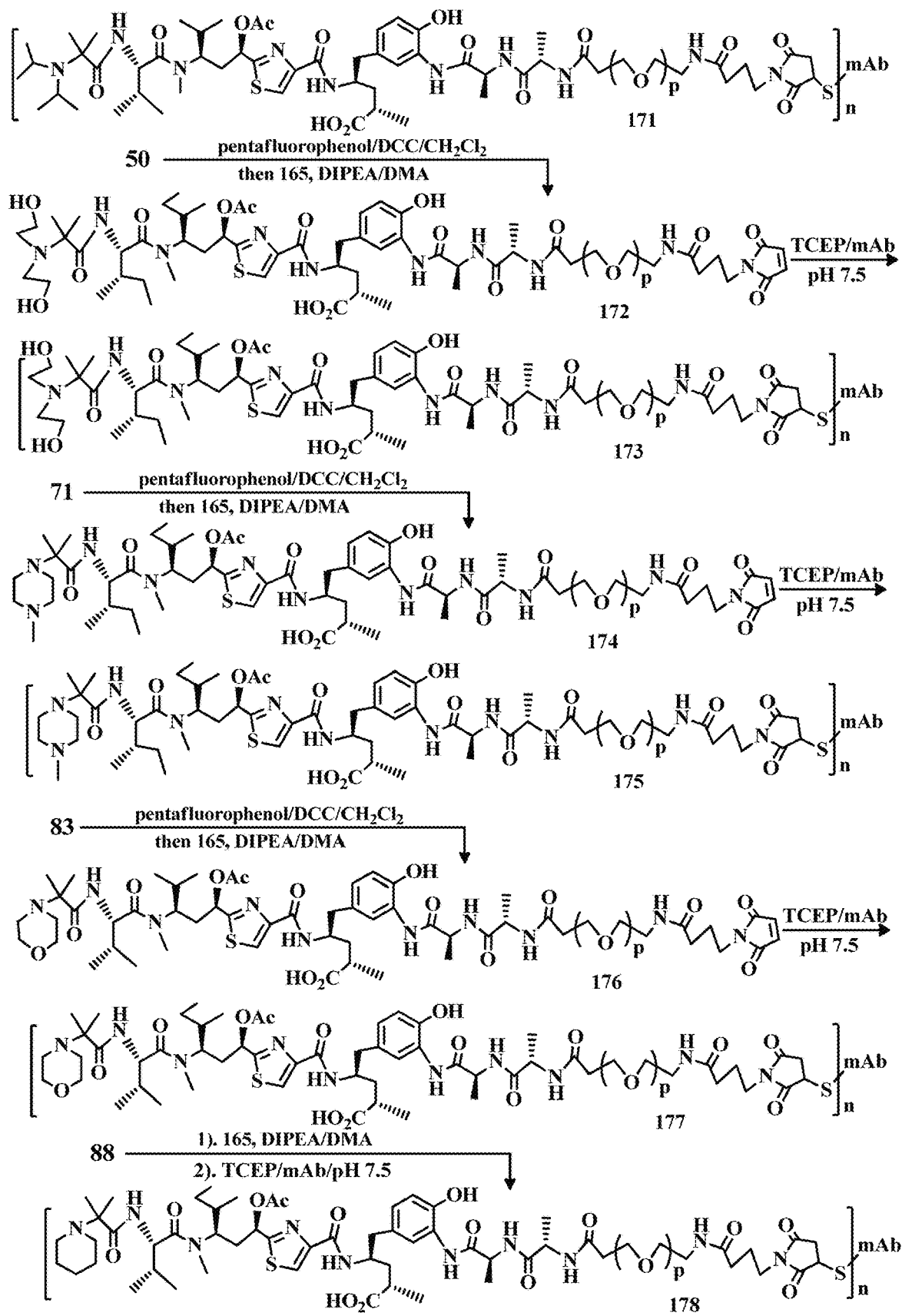
FIG. 12 shows the synthesis of Tubulysin analogs containing a linker and their conjugations to an antibody.
Figure 13:
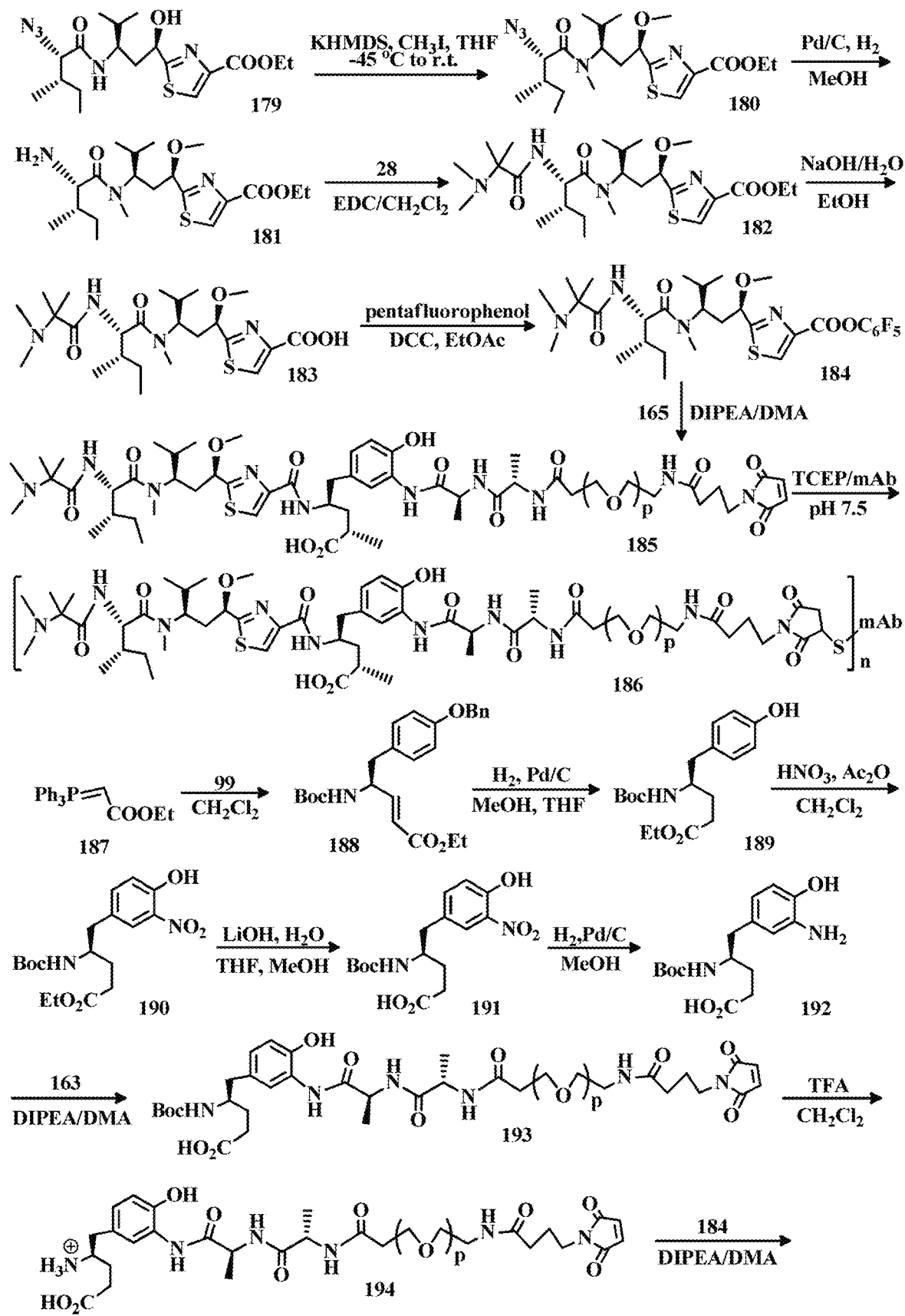
FIG. 13 shows the synthesis of Tubulysin analogs containing a linker and their conjugations to an antibody.
Figure 14:
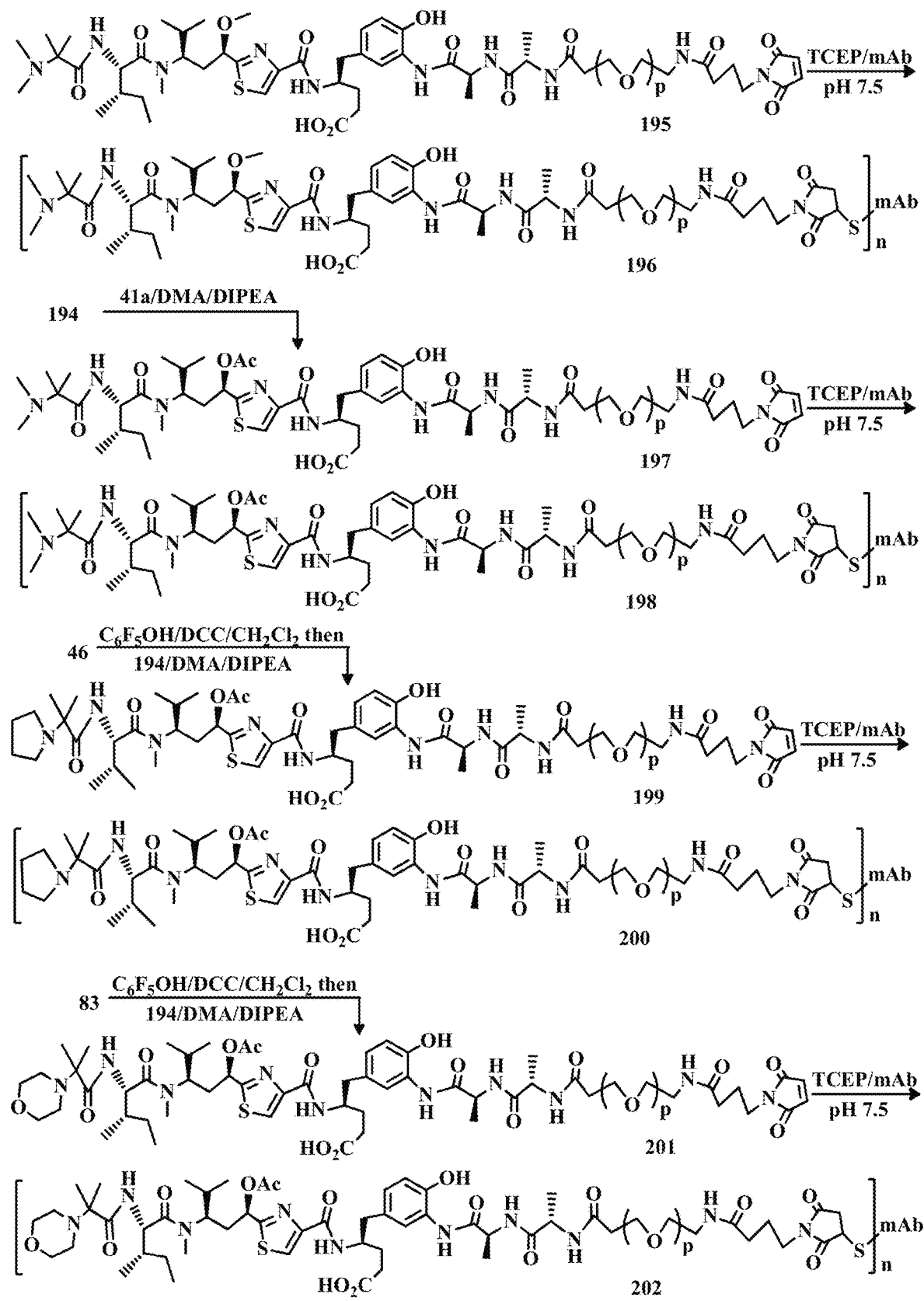
FIG. 14 shows the synthesis of tubulysin analogs containing a linker and their conjugations to an antibody.
Figure 15:
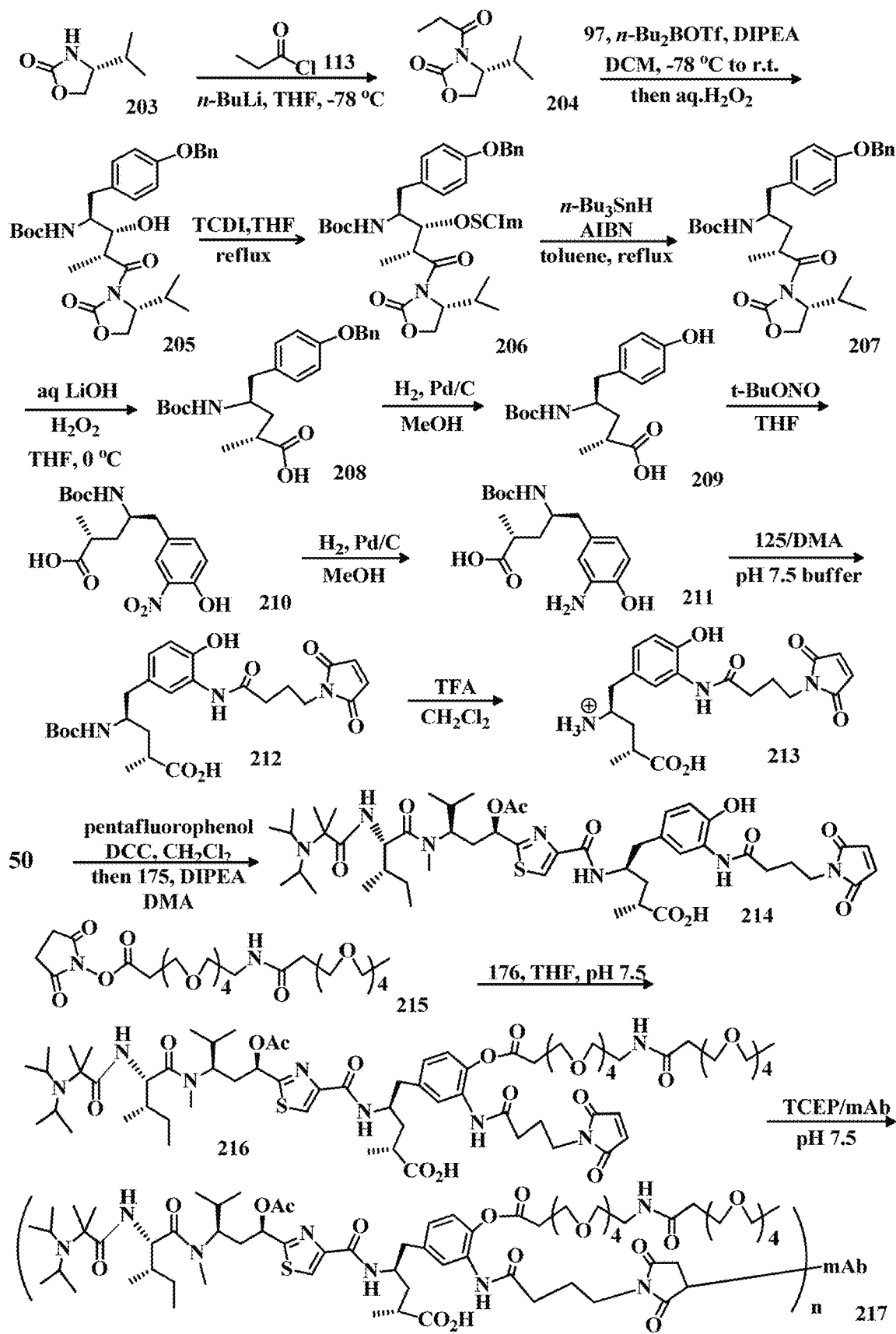
FIG. 15 shows the synthesis of components of a linker and their linkage to Tubulysin analogs containing a linker as well the conjugation to an antibody.
Figure 16:
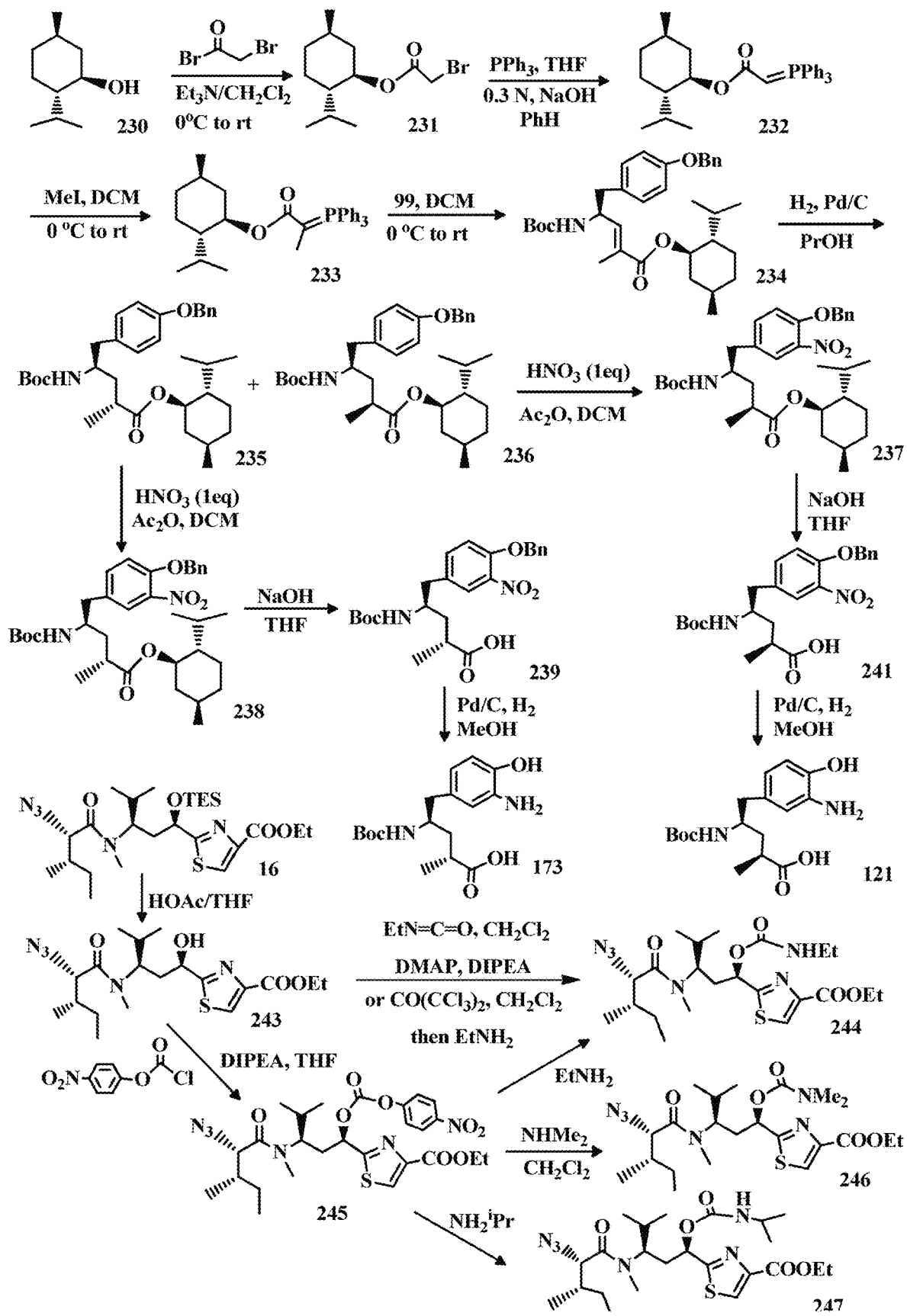
FIG. 16 shows the synthesis of components of Tup and Tuv analogs.
Figure 17:
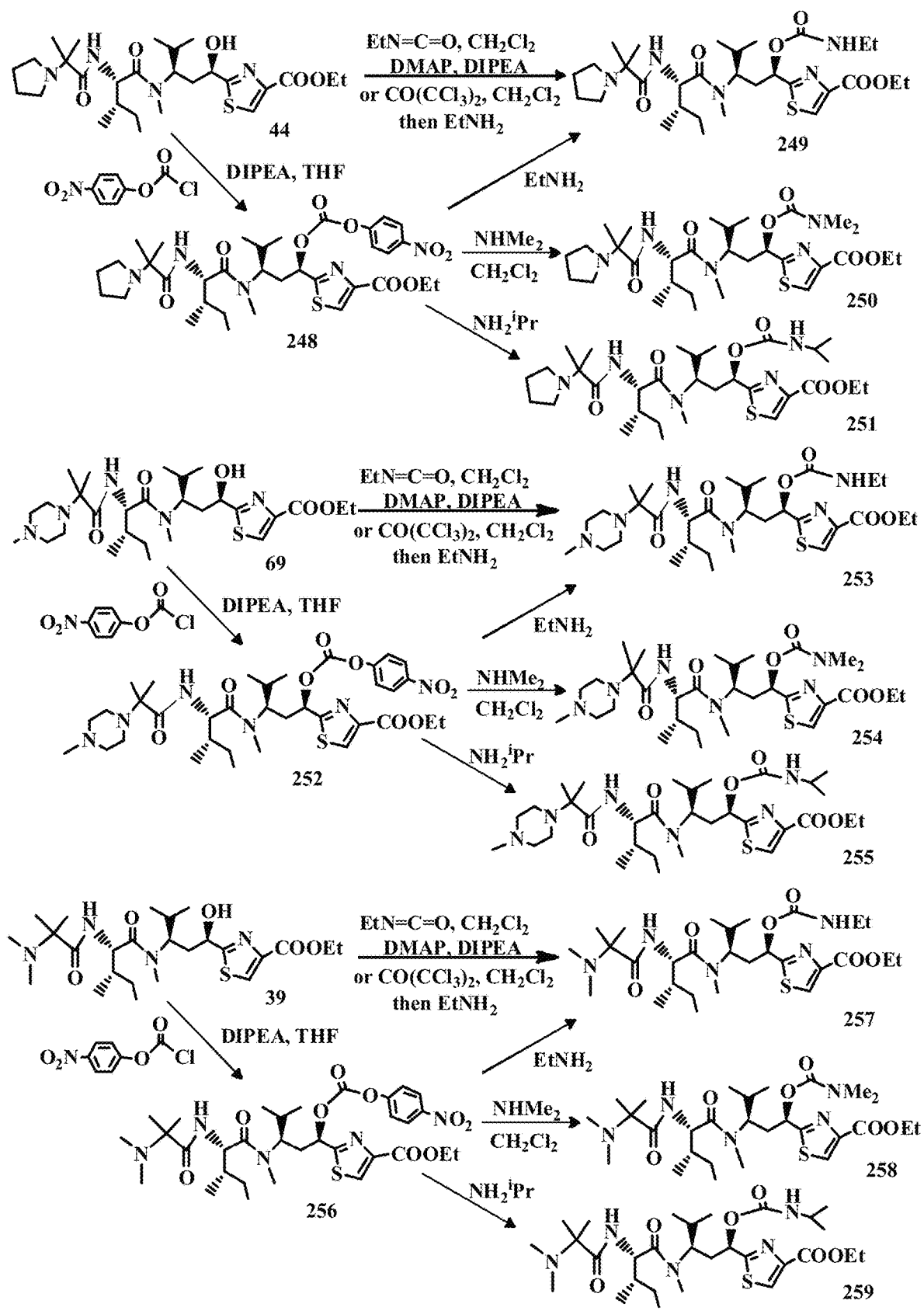
FIG. 17 shows the synthesis of components of Tuv analogs.
Figure 18:
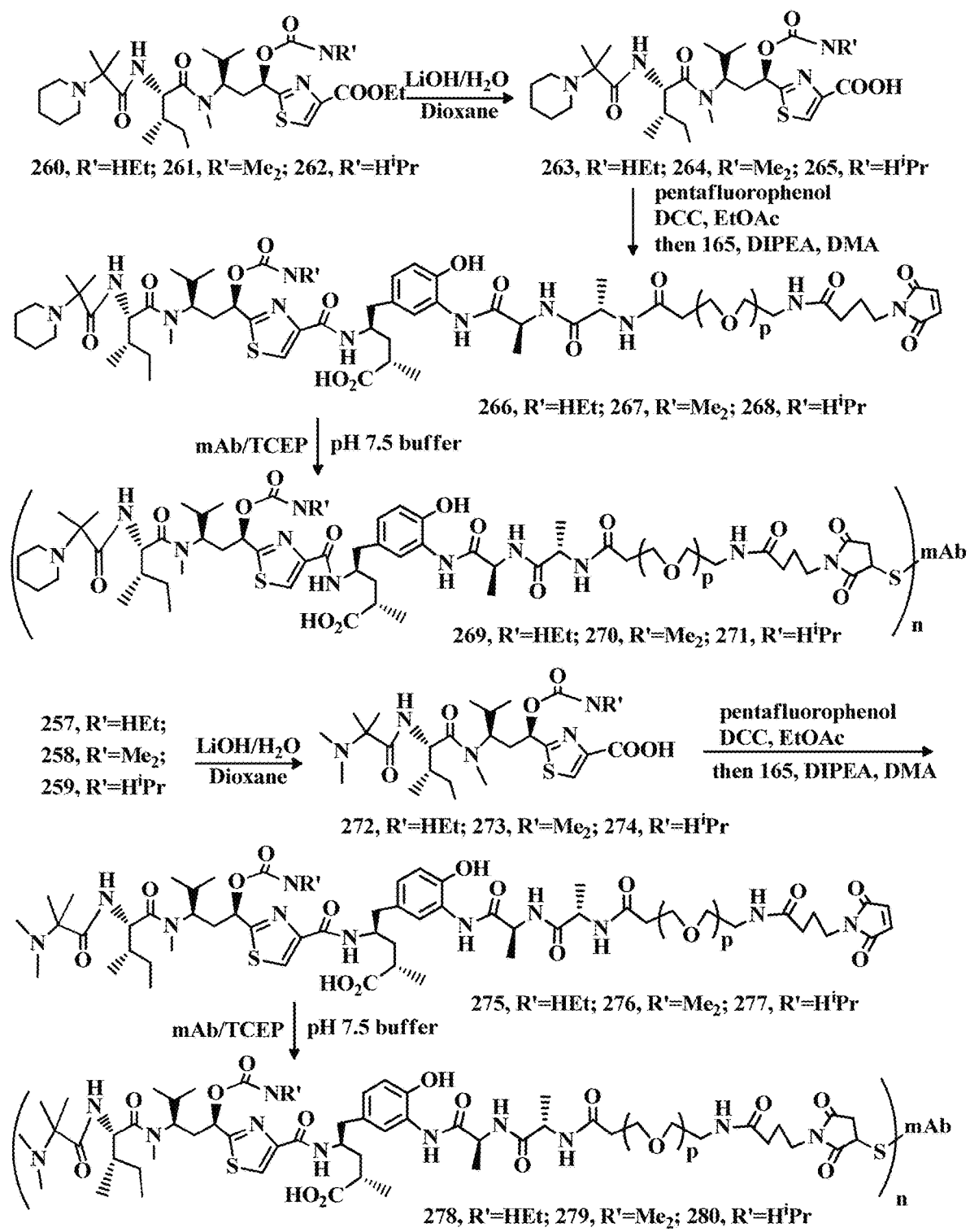
FIG. 18 shows the synthesis of tubulysin analogs containing a linker and their conjugations to an antibody.
Figure 19:
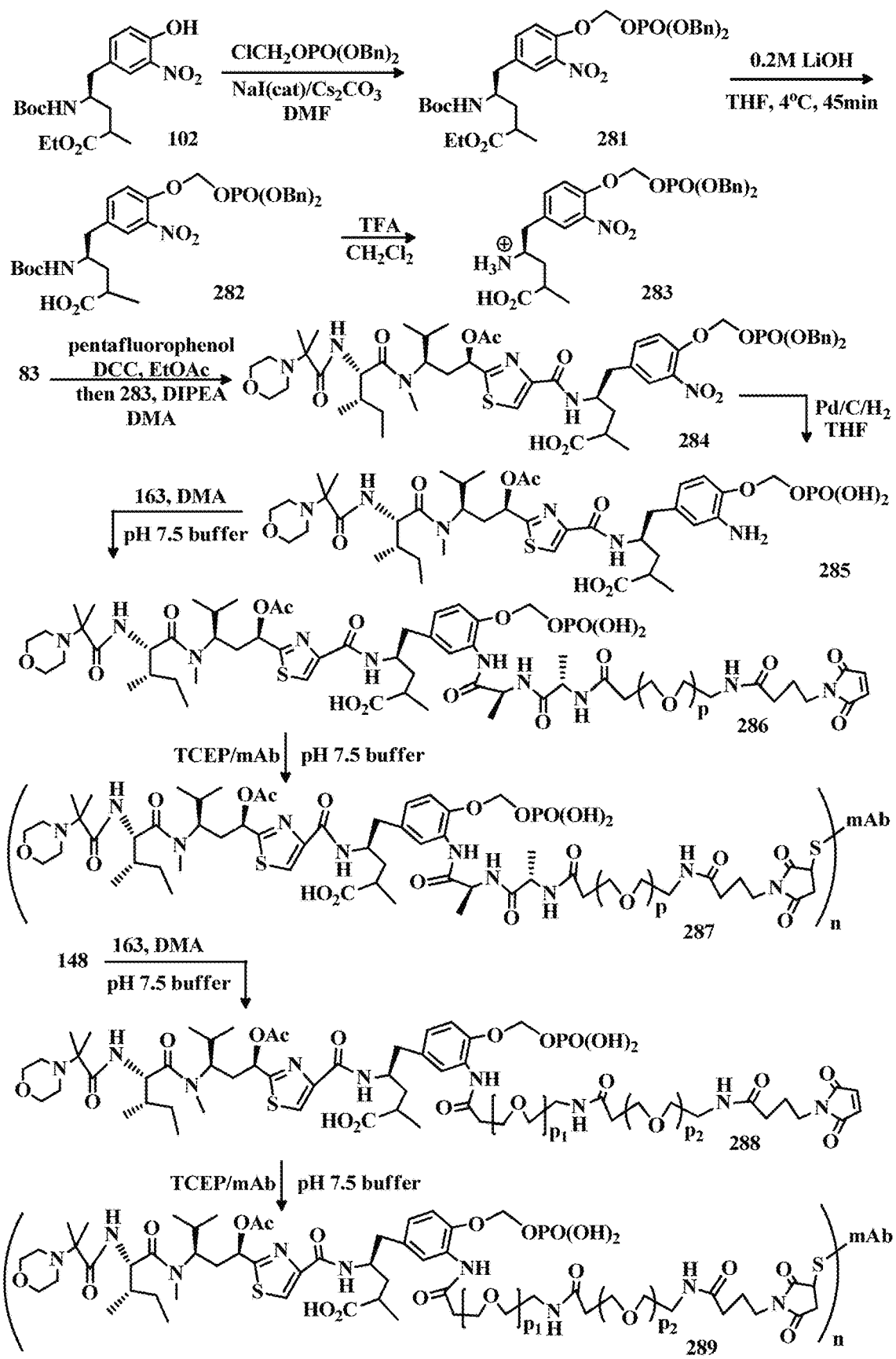
FIG. 19 shows the synthesis of tubulysin analogs containing a linker and their conjugations to an antibody.
Figure 20:
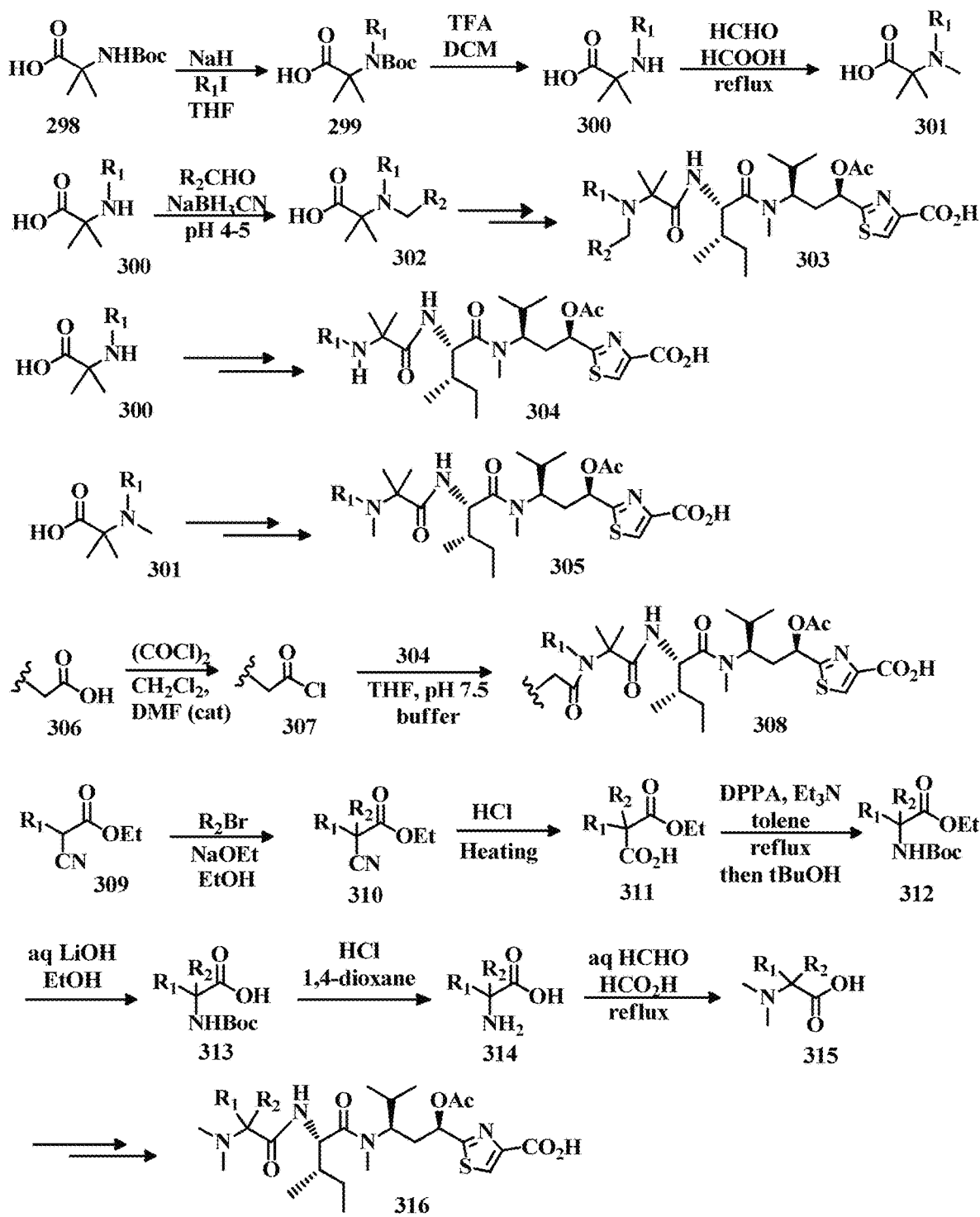
FIG. 20 shows the synthesis of components of Tubulysin analogs.
Figure 21:
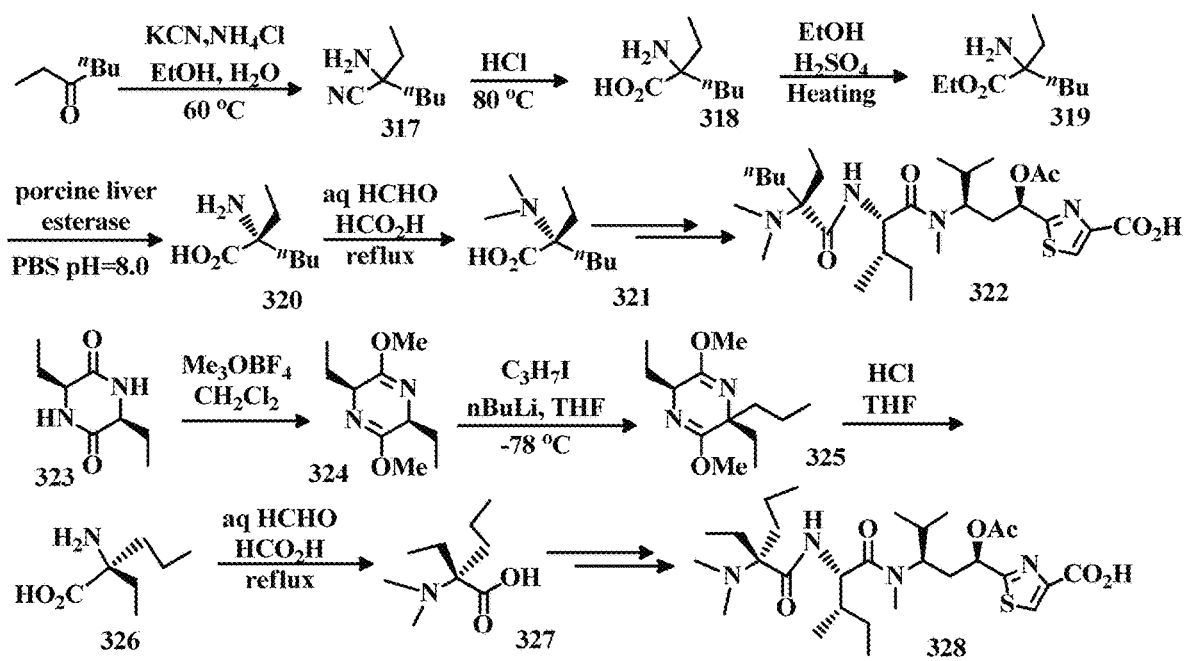
FIG. 21 shows the synthesis of components of Tubulysin analogs.

"Alkyl" refers to an aliphatic hydrocarbon group or univalent groups derived from alkane by removal of one or two hydrogen atoms from carbon atoms. It may be straight or branched having $C_1$-$C_8$ (1 to 8 carbon atoms) in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)$_2$R', —S(O)R', —OH, -halogen, —N$_3$, —NH$_2$, —NH(R'), —N(R')$_2$ and —CN; where each R' is independently selected from —$C_1$-$C_8$ alkyl and aryl.

"Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)R', —S(O)$_2$R', —OH, -halogen, —N$_3$, —NH$_2$, —NH(R'), —N(R')$_2$ and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by O, N, Si, Se, P or S, preferentially by O, S, and N. The term aryl or Ar also refers to an aromatic group, wherein one or several H atoms are replaced independently by —R', -halogen, —OR', or —SR', —NR'R", —N═NR', —N═R', —NR'R", —NO$_2$, —S(O)R', —S(O)$_2$R', —S(O)$_2$OR', —OS(O)$_2$OR', —PR'R", —P(O)R'R", —P(OR')(OR"), —P(O)(OR')(OR") or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference. Preferred nonaromatic heterocyclic include epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrimidinyl, dihydrothiopyranyl, azepanyl, as well as the fused systems resulting from the condensation with a phenyl group.

The term "heteroaryl" or aromatic heterocycles refers to a 3 to 14, preferably 5 to 10 membered aromatic hetero, mono-, bi-, or multi-cyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazolyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, benzyl, 2-phenylethan-1- yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or sp$^3$ carbon atom, is replaced with a heteroaryl radical. Examples of heteroarylalkyl groups are 2-benzimidazolylmethyl, 2-furylethyl.

Examples of a "hydroxyl protecting group" includes, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, a halide (e.g., chloride, bromide, and iodide), methanesulfonyl (mesyl), p-toluenesulfonyl (tosyl), trifluoromethylsulfonyl (triflate), and trifluoromethylsulfonate. A preferred leaving group is selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCE, dichloroethane; DCM, dichloromethane; DEAD is diethyl azodicarboxylate, DIAD, diisopropylazodicarboxylate; DIBAL-H, diisobutyl-aluminium hydride; DIPEA or DEA, diisopropylethylamine; DEPC, diethyl phosphorocyanidate; DMA, N,N-dimethyl acetamide; DMAP, 4-(N, N-dimethylamino)pyridine; DMF, N,N-dimethylformamide; DMSO, dimethylsulfoxide; DTPA is diethylenetriaminepentaacetic acid; DTT, dithiothreitol; EDC, 1-(3-dimethylaminopropyl)-3-ethylcarbodiimide hydrochloride; ESI-MS, electrospray mass spectrometry; EtOAc is ethyl acetate; Fmoc is N-(9-fluorenylmethoxycarbonyl); HATU, O-(7-azabenzotriazol-1-yl)-N, N, N', N'-tetramethyluronium hexafluorophosphate; HOBt, 1-hydroxybenzotriazole; HPLC, high pressure liquid chromatography; NHS, N-Hydroxysuccinimide; MeCN is acetonitrile; MeOH is methanol; MMP, 4-methylmorpholine; PAB, p-aminobenzyl; PBS, phosphate-buffered saline (pH 7.0-7.5); Ph is phenyl; phe is L-phenylalanine; PyBrop is bromo-tris-pyrrolidino-phosphonium hexafluorophosphate; PEG, polyethylene glycol; SEC, size-exclusion chromatography; TCEP, tris(2-carboxyethyl)phosphine; TFA, trifluoroacetic acid; THF, tetrahydrofuran; Val, valine; TLC is thin layer chromatography; UV is ultraviolet.

The "amino acid(s)" can be natural and/or unnatural amino acids, preferably alpha-amino acids. Natural amino acids are those encoded by the genetic code, which are alanine, arginine, asparagine, aspartic acid, cysteine, glutamic acid, glutamine, glycine, histidine, isoleucine, leucine, lysine, methionine, phenylalanine, proline, serine, threonine, tyrosine. tryptophan and valine. The unnatural amino acids are derived forms of proteinogenic amino acids. Examples include hydroxyproline, lanthionine, 2-aminoisobutyric acid, dehydroalanine, gamma-aminobutyric acid (the neurotransmitter), ornithine, citrulline, beta alanine (3-aminopropanoic acid), gamma-carboxyglutamate, selenocysteine (present in many noneukaryotes as well as most eukaryotes, but not coded directly by DNA), pyrrolysine (found only in some archaea and one bacterium), N-formylmethionine (which is often the initial amino acid of proteins in bacteria, mitochondria, and chloroplasts), 5-hydroxytryptophan, L-dihydroxyphenylalanine, triiodothyronine, L-3,4-dihydroxyphenylalanine (DOPA), and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, 3-aminopropanoic acid, 4-aminobutanoic acid, 5-aminopentanoic acid, 6-aminohexanoic acid, 7-aminoheptanoic acid, methionine-sulfoxide, and methionine methyl sulfonium. Preferably, an amino acid mimetic is a compound that has a structure different from the general chemical structure of an alpha-amino acid but functions in a manner similar to one. The term "unnatural amino acid" is intended to represent the "D" stereochemical form, the natural amino acids being of the "L" form. When 1-8 amino acids are used in this patent application, amino acid sequence is then preferably a cleavage recognition sequence for a protease. Many cleavage recognition sequences are known in the art. See, e.g., Matayoshi et al. Science 247: 954 (1990); Dunn et al. Meth. Enzymol. 241: 254 (1994); Seidah et al. Meth. Enzymol. 244: 175 (1994); Thornberry, Meth. Enzymol. 244: 615 (1994); Weber et al. Meth. Enzymol. 244: 595 (1994); Smith et al. Meth. Enzymol. 244: 412 (1994); and Bouvier et al. Meth. Enzymol. 248: 614 (1995); the disclosures of which are incorporated herein by reference. In particular, the sequence is selected from the group consisting of Val-Cit, Ala-Val, Ala-Ala, Val-Val, Val-Ala-Val, Lys-Lys, Ala-Asn-Val, Val-Leu-Lys, Cit-Cit, Val-Lys, Ala-Ala-Asn, Asp-Lys, Asp-Glu, Glu-Lys, Lys, Cit, Ser, and Glu.

The "glycoside" is a molecule in which a sugar group is bonded through its anomeric carbon to another group via a glycosidic bond. Glycosides can be linked by an O- (an O-glycoside), N- (a glycosylamine), S- (a thioglycoside), or C- (a C-glycoside) glycosidic bond. Its core the empirical formula is $C_m(H_2O)_n$ (where m could be different from n, and m and n are <36), Glycoside herein includes glucose (dextrose), fructose (levulose) allose, altrose, mannose, gulose, iodose, galactose, talose, galactosamine, glucosamine, sialic acid, N-acetylglucosamine, sulfoquinovose (6-deoxy-6-sulfo-D-glucopyranose), ribose, arabinose, xylose, lyxose, sorbitol, mannitol, sucrose, lactose, maltose, trehalose, maltodextrins, raffinose, Glucuronic acid (glucuronide), and stachyose. It can be in D form or L form, 5 atoms cyclic furanose forms, 6 atoms cyclic pyranose forms, or acyclic form, α-isomer (the —OH of the anomeric carbon below the plane of the carbon atoms of Haworth projection), or a β-isomer (the —OH of the anomeric carbon above the plane of Haworth projection). It is used herein as a monosaccharide, disaccharide, polyols, or oligosaccharides containing 3-6 sugar units.

The term "antibody," as used herein, refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g. IgG, IgE, IgM, IgD, IgA and IgY), class (e.g., IgG1, IgG2, IgG3, IgG4, IgA1 and IgA2) or subclass of immunoglobulin molecule. The immunoglobulins can be derived from any species. Preferably, however, the immunoglobulin is of human, murine, or rabbit origin. Antibodies useful in the invention are preferably monoclonal, and include, but are not limited to, polyclonal, monoclonal, bispecific, human, humanized or chimeric antibodies, single chain antibodies, Fv, Fab fragments, F(ab') fragments, F(ab')$_2$ fragments, fragments produced by a Fab expression library, anti-idiotypic (anti-Id) antibodies, CDR's, and epitope-binding fragments of any of the above which immunospecifically bind to cancer cell antigens, viral antigens or microbial antigens.

An "enantiomer", also known as an "optical isomer", is one of two stereoisomers that are mirror images of each other that are non-superposable (not identical), much as one's left and right hands are the same except for being reversed along one axis (the hands cannot be made to appear identical simply by reorientation). A single chiral atom or similar structural feature in a compound causes that compound to have two possible structures which are non-superposable, each a mirror image of the other. The presence of multiple chiral features in a given compound increases the number of geometric forms possible, though there may be some perfect-mirror-image pairs. Enantiopure compounds refer to samples having, within the limits of detection, molecules of only one chirality. When present in a symmetric environment, enantiomers have identical chemical and physical properties except for their ability to rotate plane-polarized light (+/−) by equal amounts but in opposite directions (although the polarized light can be considered an asymmetric medium). They are sometimes called optical isomers for this reason. A mixture of equal parts of an optically active isomer and its enantiomer is termed racemic and has zero net rotation of plane-polarized light because the positive rotation of each (+) form is exactly counteracted by the negative rotation of a (−) one. Enantiomer members often have different chemical reactions with other enantiomer substances. Since many biological molecules are enantiomers, there is sometimes a marked difference in the effects of two enantiomers on biological organisms. In drugs, for example, often only one of a drug's enantiomers is responsible for the desired physiologic effects, while the other enantiomer is less active, inactive, or sometimes even productive of adverse effects. Owing to this discovery, drugs composed of only one enantiomer ("enantiopure") can be developed to enhance the pharmacological efficacy and sometimes eliminate some side effects.

Isotopes are variants of a particular chemical element which differs in neutron number. All isotopes of a given element have the same number of protons in each atom. Each atomic number identifies a specific element, but not the isotope; an atom of a given element may have a wide range in its number of neutrons. The number of nucleons (both protons and neutrons) in the nucleus is the atom's mass number, and each isotope of a given element has a different mass number. For example, carbon-12, carbon-13 and carbon-14 are three isotopes of the element carbon with mass numbers 12, 13 and 14 respectively. The atomic number of carbon is 6, which means that every carbon atom has 6 protons, so that the neutron numbers of these isotopes are 6, 7 and 8 respectively. Hydrogen atom has three isotopes of protium ($^1$H), deuterium ($^2$H), and tritium ($^3$H), which deuterium has twice the mass of protium and tritium has three times the mass of protium. Isotopic substitution can be used to determine the mechanism of a chemical reaction and via the kinetic isotope effect. Isotopic substitution can be used to study how the body affects a specific xenobiotic/chemical after administration through the mechanisms of absorption and distribution, as well as the metabolic changes of the substance in the body (e.g. by metabolic enzymes such as cytochrome P450 or glucuronosyltransferase enzymes), and the effects and routes of excretion of the metabolites of the drug. This study is called pharmacokinetics (PK). Isotopic substitution can be used to study of the biochemical and physiologic effects of drugs. The effects can include those manifested within animals (including humans), microorganisms, or combinations of organisms (for example, infection). This study is called pharmacodynamics (PD). The effects can include those manifested within animals (including humans), microorganisms, or combinations of organisms (for example, infection). Both together influence dosing, benefit, and adverse effects of the drug. isotopes can contain a stable (non-radioactive) or an unstable element. Isotopic substitution of a drug may have a different therapeutical efficacy of the original drug.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, PA, 1985, p. 1418, the disclosure of which is hereby incorporated by reference.

"Administering" or "administration" refers to any mode of transferring, delivering, introducing or transporting a pharmaceutical drug or other agent to a subject. Such modes include oral administration, topical contact, intravenous, intraperitoneal, intramuscular, intralesional, intranasal, subcutaneous or intrathecal administration. Also contemplated by the present invention is utilization of a device or instrument in administering an agent. Such device may utilize active or passive transport and may be slow-release or fast-release delivery device.

In the context of cancer, the term "treating" includes any or all of: preventing growth of tumor cells or cancer cells, preventing replication of tumor cells or cancer cells, lessening of overall tumor burden and ameliorating one or more symptoms associated with the disease.

In the context of an autoimmune disease, the term "treating" includes any or all of: preventing replication of cells associated with an autoimmune disease state including, but not limited to, cells capable of producing an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

Examples of a "mammal" or "animal" include, but are not limited to, a human, rat, mouse, guinea pig, monkey, pig, goat, cow, horse, dog, cat, bird and fowl.

Drug-Linker—Binding Ligand Conjugates

As stated above, this invention provides a cell surface binding molecule—antimitotic (cytotoxic) agent conjugate of Formula (I):

carbocyclic, cycloalkyl, heterocyclic, heterocycloalkyl, aromatic or heteroaromatic ring system; Y is N or C; In addition, $R^1$, $R^2$, $R^3$, and $R^4$ can be independently absent;

Wherein $R^5$, $R^6$, $R^8$ and $R^{10}$ are independently selected from H and linear or branched $C_1$-$C_4$ of alkyl or $C_2$-$C_4$ of heteroalkyl;

Wherein $R^7$ is selected from H, $R^{14}$, or —$R^{14}C(=O)X^1R^{15}$; —$R^{14}X^1R^{15}$; $X^1$ is selected from O, S, S—S, NH, or $NR^{14}$;

Wherein $R^9$ is H, —O—, —$OR^{14}$, —$OC(=O)R^{14}$—, —$OC(=O)NHR^{14}$—, —$OC(=O)NR^{14}R^{15}$—, —$OC(=O)$ $R^{14}SSR^{15}$—, $OP(=O)(OR^{14})$—, or $OR^{14}OP(=O)(OR^{15})$;

Wherein $R^{11}$ is H, $R^{14}$, —$R^{14}C(=O)R^{16}$, —$R^{14}C(=O)X^2R^{16}$, —$R^{14}X^2R^{16}$, —$R^{14}C(=O)X^2$, wherein $X^2$ is —O—, —S—, —NH—, —$NHS(O_2)$, —NHS(O), —$N(R^{14})$—, —O—$R^{14}$—, —S—$R^{14}$—, —S(=O)—$R^{14}$—, or —$NHR^{14}$—;

Wherein $R^{12}$ is H, $R^{14}$, —O—, —S—, —N—, =N—, =NNH—, —OH, —SH, —$NH_2$, =NH, =$NNH_2$, —$NH(R^{14})$, —$OR^{14}$, —C(O)O—, —$C(O)OR^{16}$—, —$COR^{16}$, —$COOR^{14}$—, C(O)NH—, $C(O)NH_2$, C(O)$NHR^{14}$, —$SR^{14}$, —$S(=O)R^{14}$, —$P(=O)(OR^{16})_2$, —$OP(=O)(OR^{16})_2$, —$CH_2OP(=O)(OR^{16})_2$, —$SO_2R^{16}$;

Wherein $R^{13}$ is linear or branched $C_1$-$C_{10}$ of alkyl, alkyl acid, alkyl amide, alkyl amine; or $C_2$-$C_{10}$ of heteroalkyl; or $C_3$-$C_{10}$ of Ar; Ar refers to an aromatic or hetero aromatic group, composed of one or several rings, comprising four to ten carbon atoms, preferentially four to six carbon atoms. The term of hetero aromatic group refers to an aromatic group that has one or several carbon atoms replaced by hetero atoms, preferentially one, two or three carbon atoms replaced by O, N, Si, Se, P or S, more preferentially O, S, N. The term aryl or Ar also refers to an aromatic group, wherein one or several H atoms can be replaced independently by $R^{17}$, F, Cl,

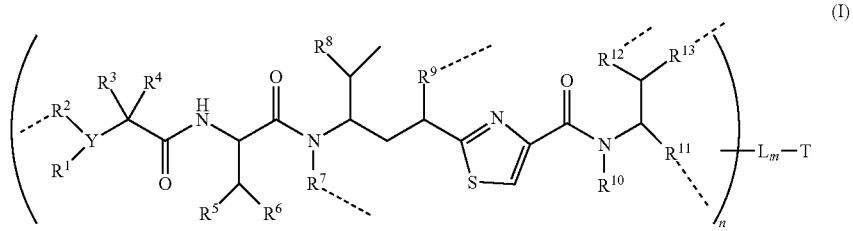

(I)

or their pharmaceutically acceptable salts, hydrates, or hydrated salts; or the polymorphic crystalline structures of these compounds; or their optical isomers, racemates, diastereomers or enantiomers thereof;

Wherein T is a targeting or binding ligand; L is a releasable linker; ----- is a linkage bond that L connects to an atom inside the bracket independently; n is 1~20 and m is 1~10; Inside the bracket is a potent antimitotic agent wherein $R^1$, $R^2$, $R^3$, and $R^4$ are independently linear or branched $C_1$-$C_8$ of alkyl, alkylalcohol; $C_2$-$C_8$ of heteroalkyl, alkylcycloalkyl, heterocycloalkyl, alkyl ether, alkyl carboxylate, alkyl amine, alkyl ester, alkyl amide; $C_3$-$C_8$ of aryl, Ar-alkyl, heterocyclic, carbocyclic, cycloalkyl, heteroalkylcycloalkyl, alkylcarbonyl; or two R's: $R^1R^2$, $R^3R^4$, $R^5R^6$, or $R^{12}R^{13}$ together independently form a 3-7 membered Br, I, $OR^{16}$, $SR^{16}$, $NR^{16}R^{17}$, N=$NR^{16}$, N=$R^{16}$, $NR^{16}R^{17}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, $OP(O)(OR^{17})_2$, $OCH_2OP(O)(OR^{17})_2$, $OC(O)OP(O)(OR^{17})_2$, $PO(OR^{16})(OR^{17})$, $OP(O)(OR^7)OP(O)(OR^{17})_2$, OC(O) $R^{17}$ or $OC(O)NHR^{17}$;

Wherein $R^{14}$ and $R^{15}$ are independently H; linear or branched $C_1$-$C_8$ of alkyl; $C_2$-$C_8$ of alkenyl, alkynyl, heteroalkyl, heterocyclic, carbocyclic; $C_3$-$C_8$ of aryl, cycloalkyl, alkylcycloalkyl, heterocycloalkyl, heteroaralkyl, heteroalkylcycloalkyl, alkylcarbonyl;

Wherein when $R^{14}$ is bivalent, it is a $R^{14}$ that is further connected to an additional functional group of one to four amino acid units, or $(CH_2CH_2O)_r$, r is an integer ranging from 0 to 12, or $C_4$-$C_{12}$ of glycosides, or $C_1$-$C_8$ of carboxylic acid;

Wherein R[16] is H, OH, R[14] or one to four amino acid units;

Wherein R[17] is H, linear or branched $C_1$-$C_8$ of alkyl; $C_2$-$C_8$ of alkenyl, alkynyl, heteroalkyl, heterocyclic; $C_3$-$C_8$ of aryl, carbocyclic, cycloalkyl, alkylcycloalkyl, heterocycloalkyl, heteroalkylcycloalkyl, heteroaralkyl, alkylcarbonyl or $C_4$-$C_{12}$ of glycosides, or pharmaceutical salts.

In another embodiment, conjugates of antimitotic agents have the formula (II)

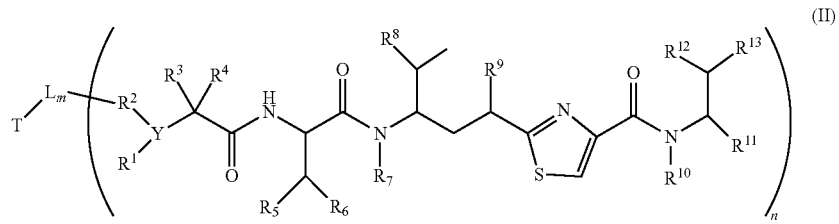

(II)

or their pharmaceutically acceptable salts, hydrates, or hydrated salts; or the polymorphic crystalline structures of these compounds; or their optical isomers, racemates, diastereomers or enantiomers thereof;

Wherein T, L, n, m, Y, R[1], R[2], R[3], R[4], R[5], R[6], R[8], R[10], R[13], R[14], R[15], R[16] and R[17] are defined the same as in the Formula (I);

Wherein R[7] is selected from H, R[14], or —R[14]C(=O)X[1]R[15]; —R[14]X[1]R[15]; X[1] is selected from O, S, S—S, NH, or NR[14];

Wherein R[9] is H, —OH, —OR[14], —OC(=O)R[14], —OC(=O)NHR[14], —OC(=O)NR[14]R[15], —OC(=O)R[14]SSR[15], OP(=O)(OR[14])$_2$, or OR[14]OP(=O)(OR[15]);

Wherein R[11] is H, R[14], —R[14]C(=O)R[16], —R[14]C(=O)X[2]R[16], —R[14]X[2]R[16], —R[14]C(=O)X[2], wherein X[2] is —O—, —S—, —NH—, —NHS($O_2$), —N(R[14])—, —O—R[14]—, —S—R[14]—, —S(=O)—R[14]—, or —NHR[14]—;

Wherein R[12] is H, R[14], —O—, —S—, —N—, =N—, =NNH—, —OH, —SH, —NH$_2$, =NH, =NNH$_2$, —NH(R[14]), —OR[14], —C(O)O—, —C(O)OR[16]—, —COR[16], —COOR[14]—, C(O)NH—, C(O)NH$_2$, C(O)NHR[14], —SR[14], —S(=O)R[14], —P(=O)(OR[16])$_2$, —OP(=O)(OR[16])$_2$, —CH$_2$OP(=O)(OR[16])$_2$, —SO$_2$R[16].

Illustrative compounds inside the bracket of formula (II) have preferred structures below:

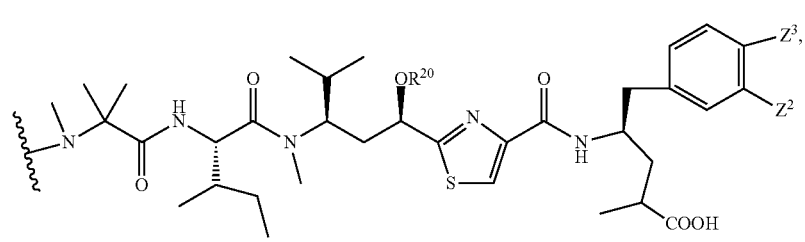

II-01

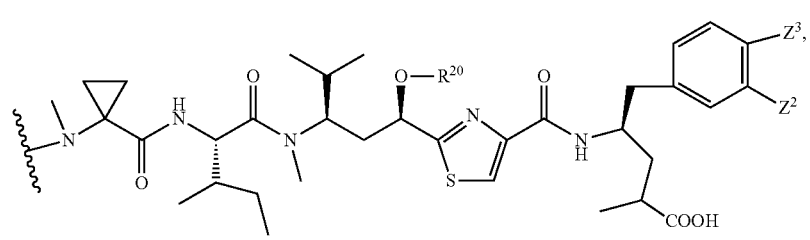

II-02

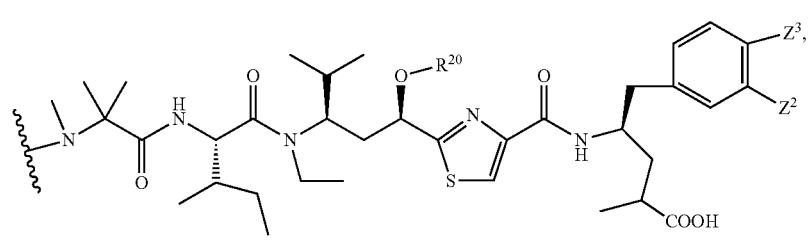

II-03

-continued
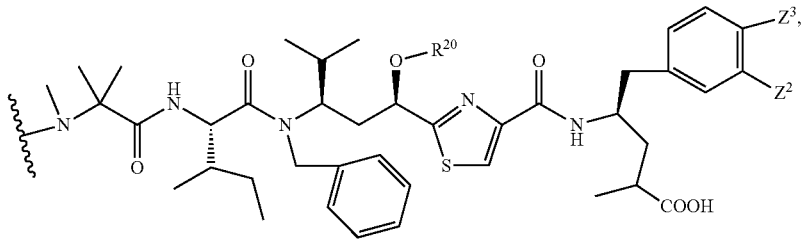
II-04
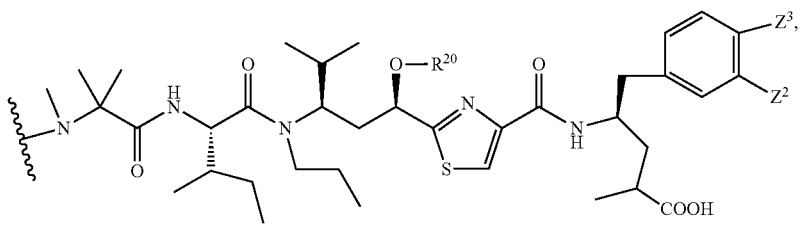
II-05
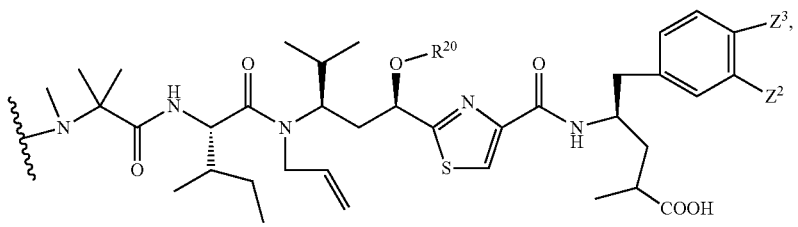
II-06
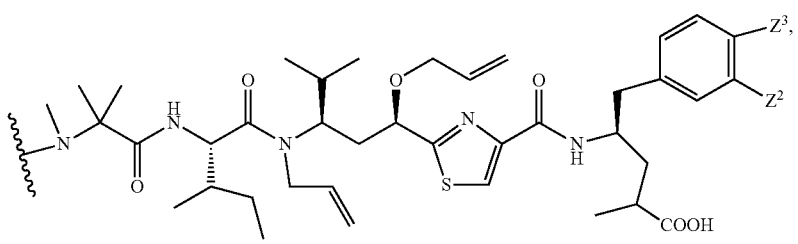
II-07
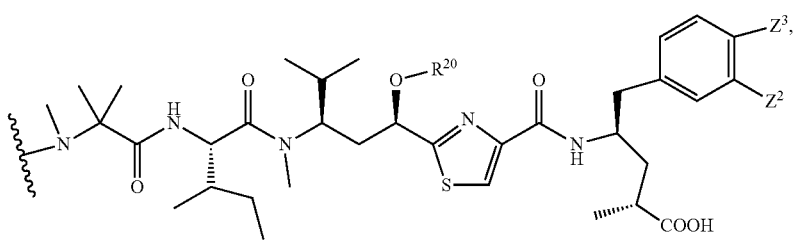
II-08
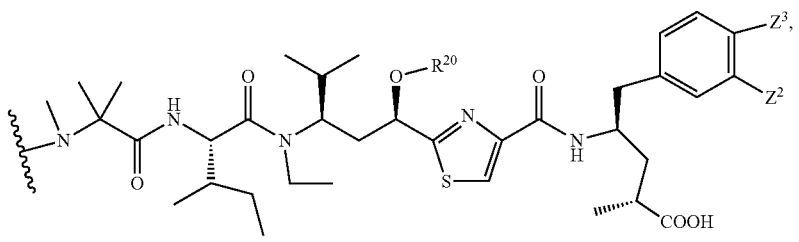
II-09

-continued
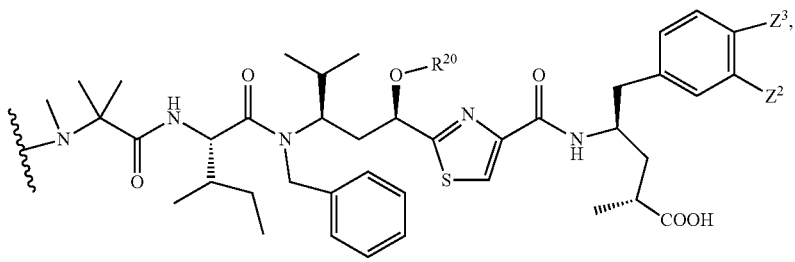
II-10
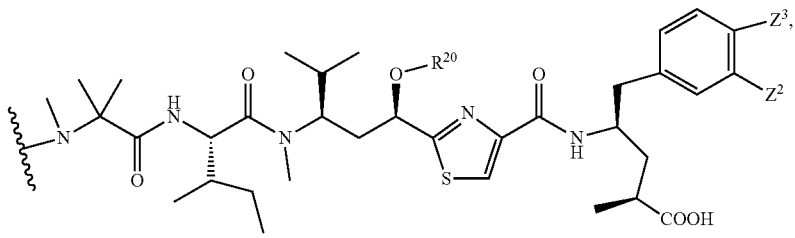
II-11
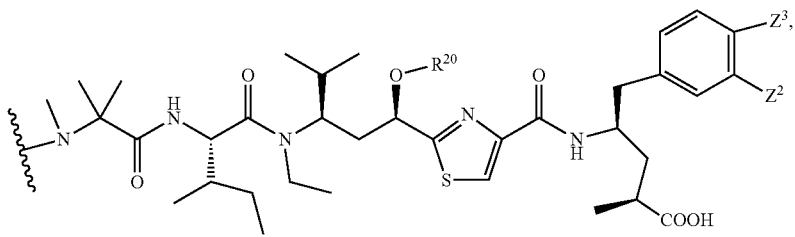
II-12
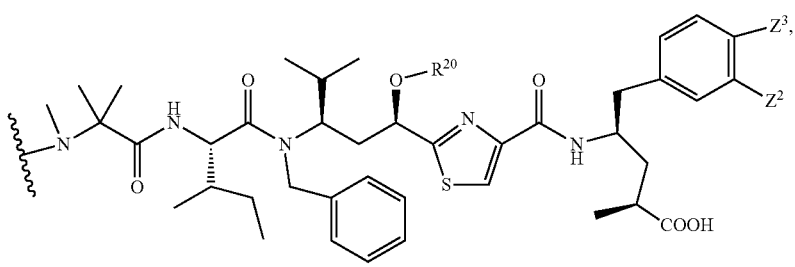
II-13
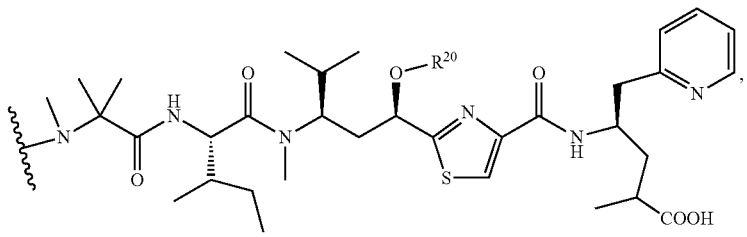
II-14
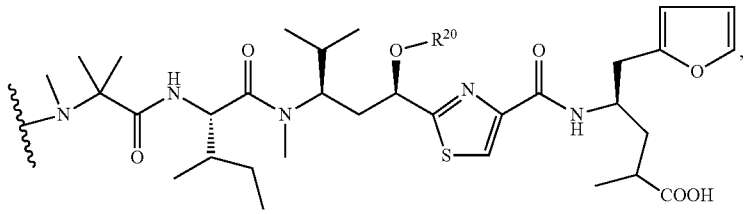
II-15

-continued
II-16
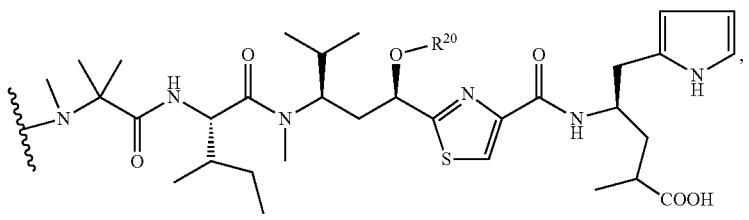
II-17
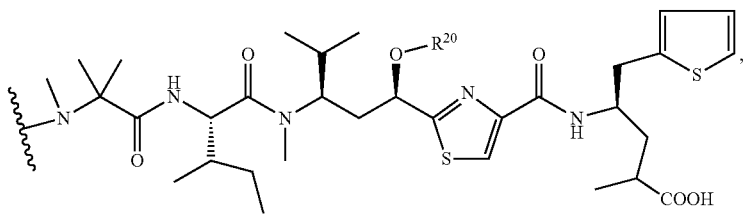
II-18
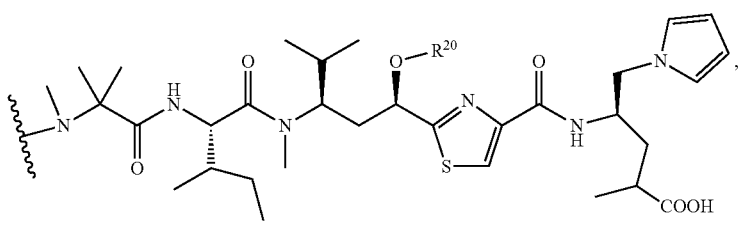
II-19
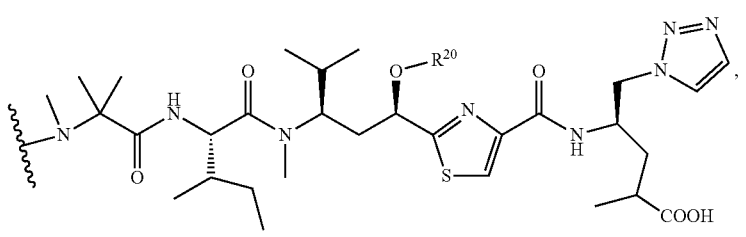
II-20
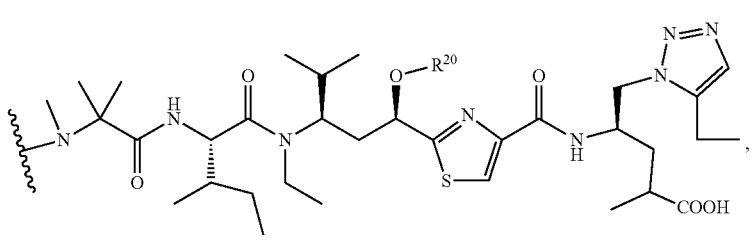
II-21
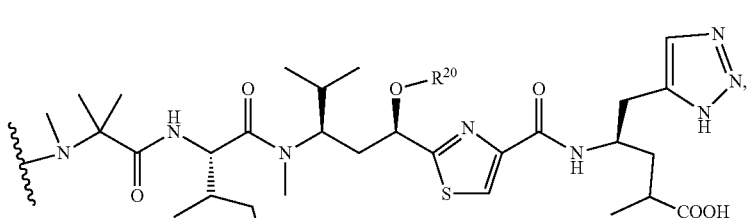
II-22

II-23
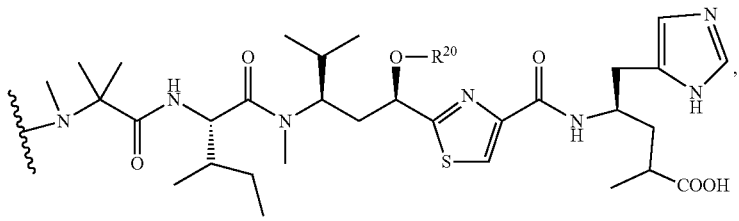
II-24
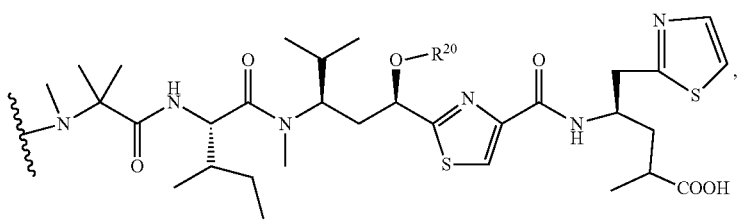
II-25
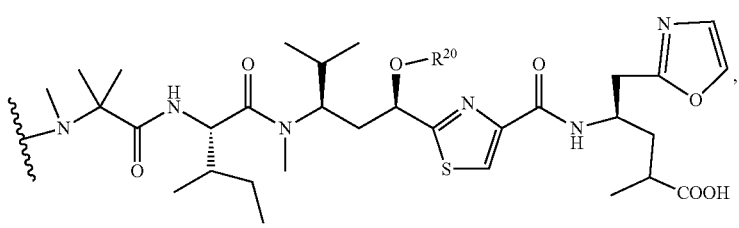
II-26
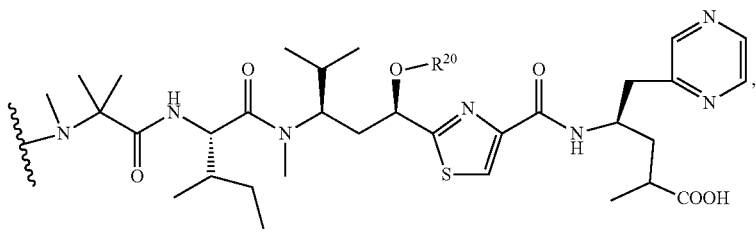
II-27
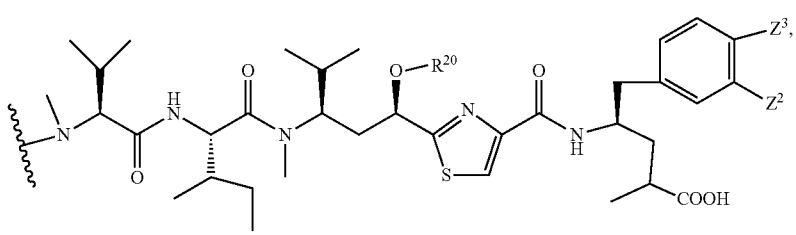
II-28
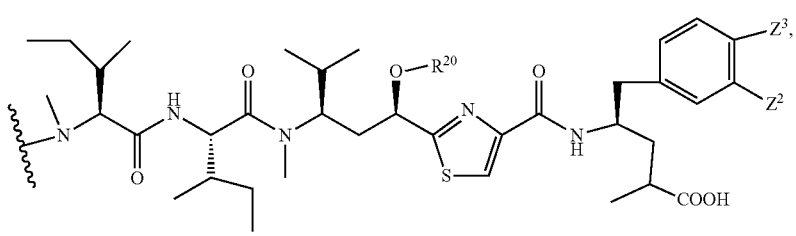
II-29
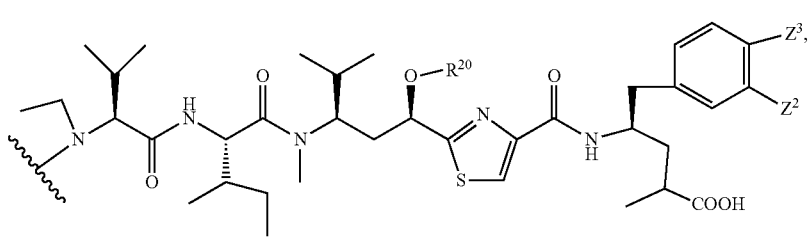

II-30
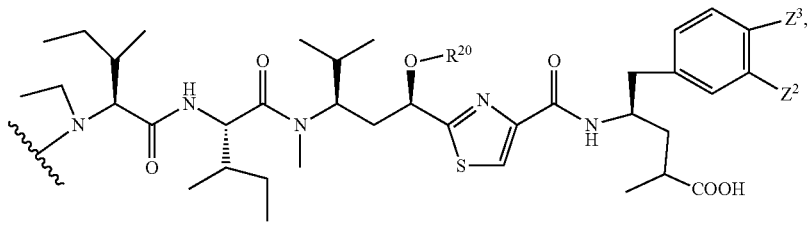
II-31
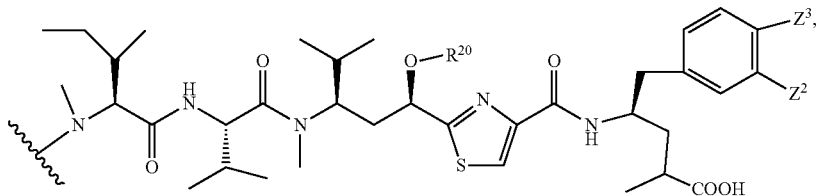
II-32
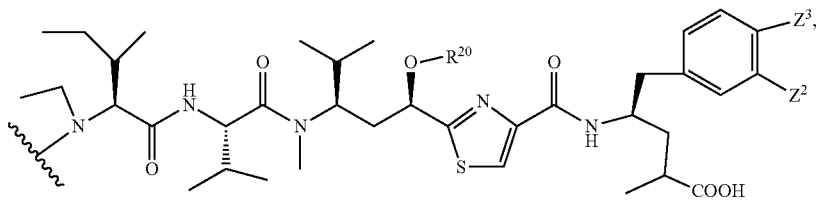
II-33
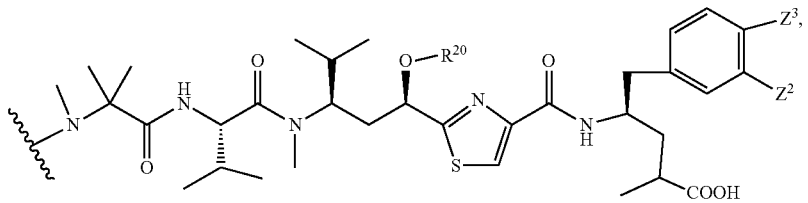
II-34
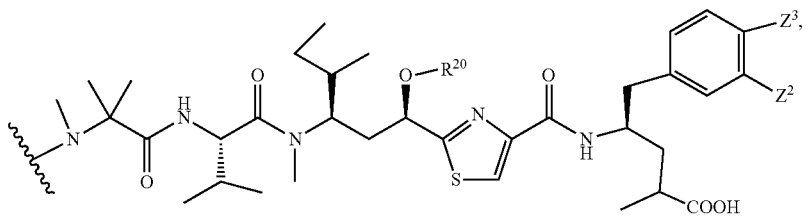
II-35
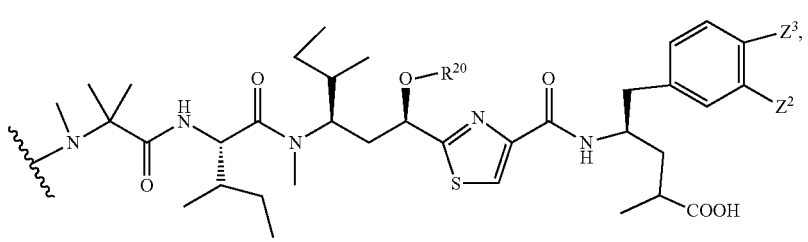
II-36
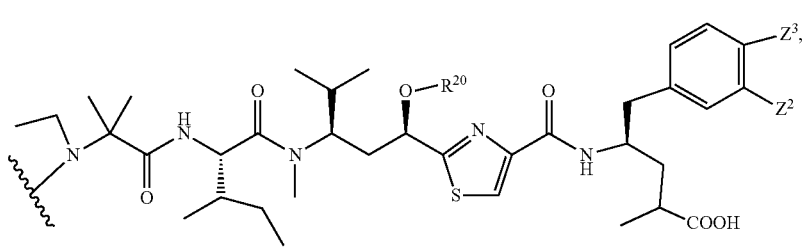

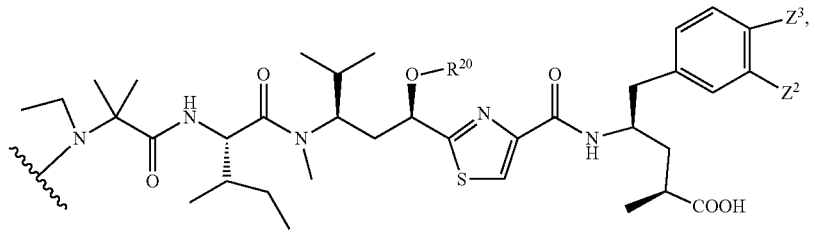
II-37

II-38
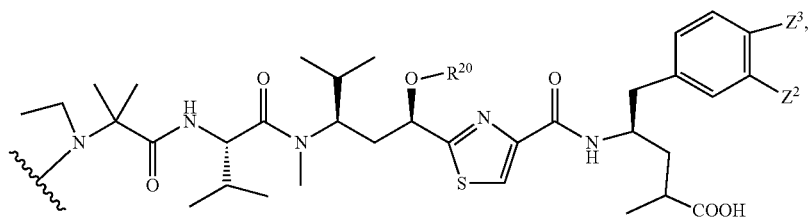
II-39
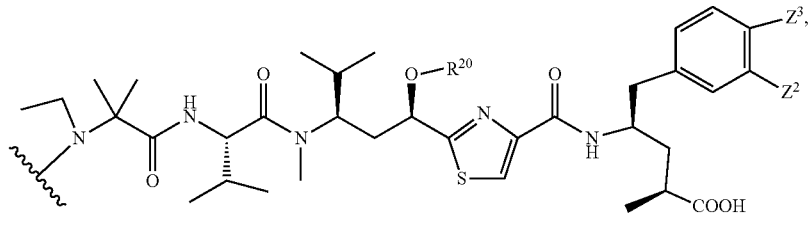
II-40
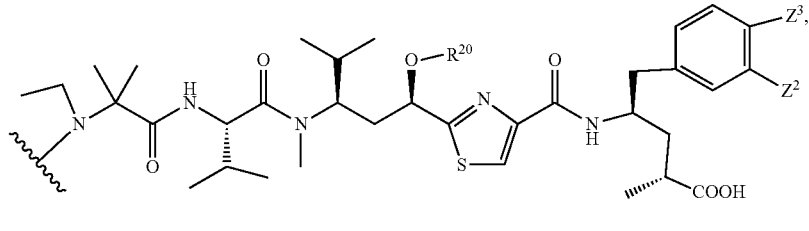
II-41
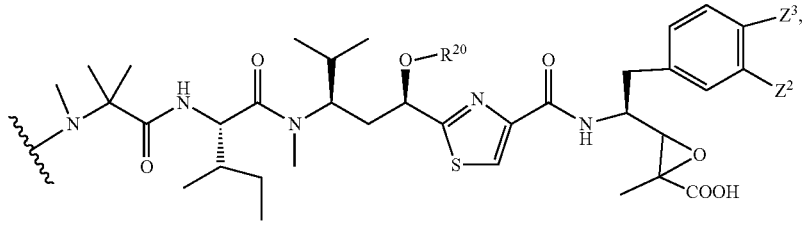
II-42
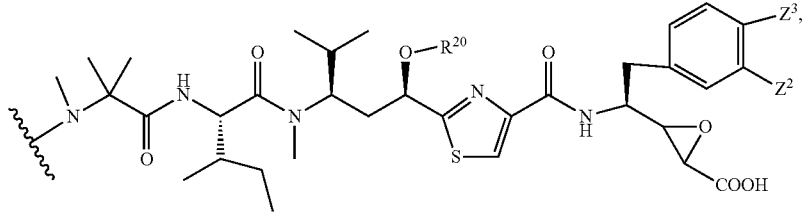
II-43

II-44
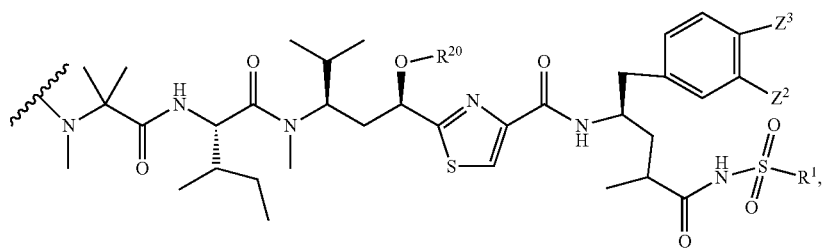
II-45
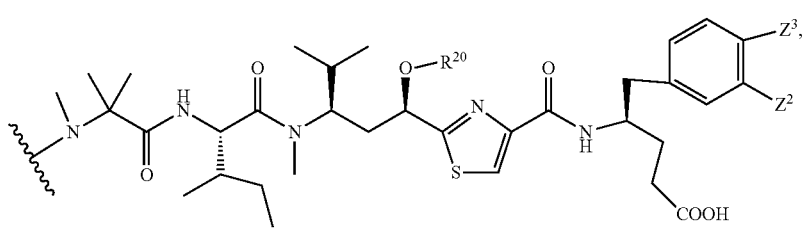
II-46
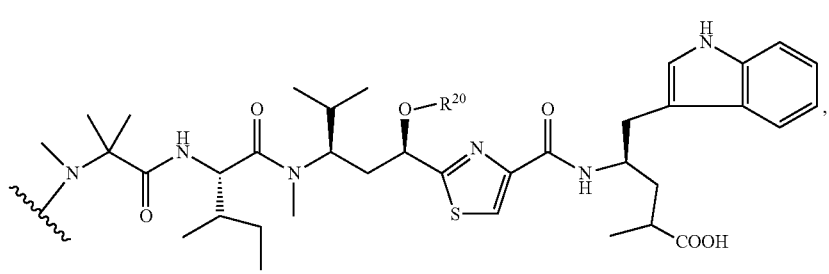
II-47
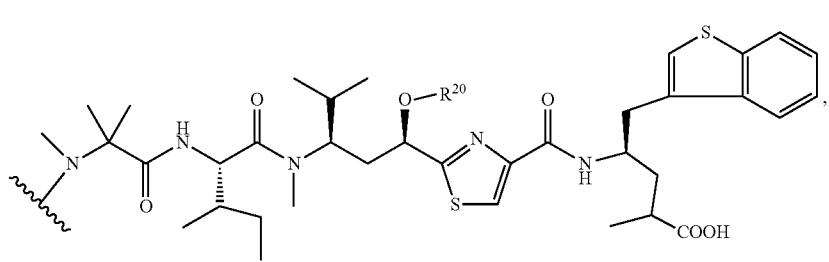
II-48
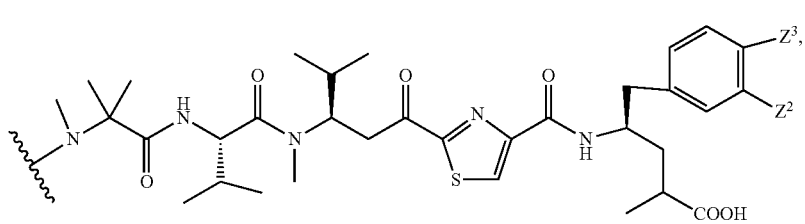
II-49
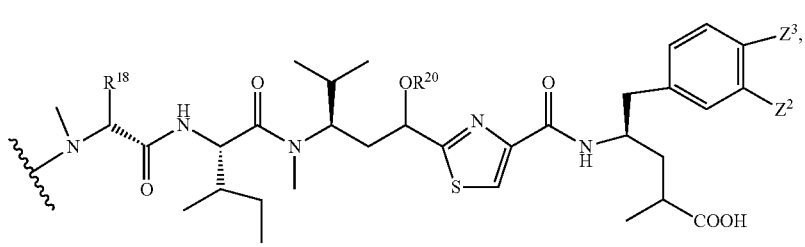

-continued
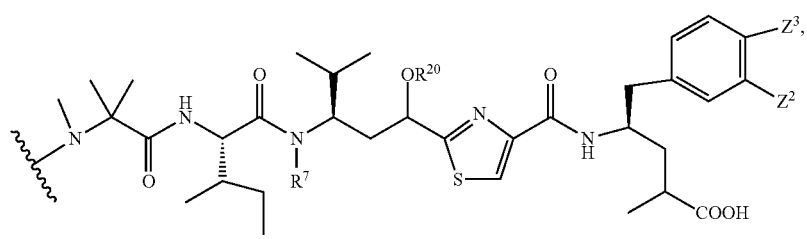
II-50
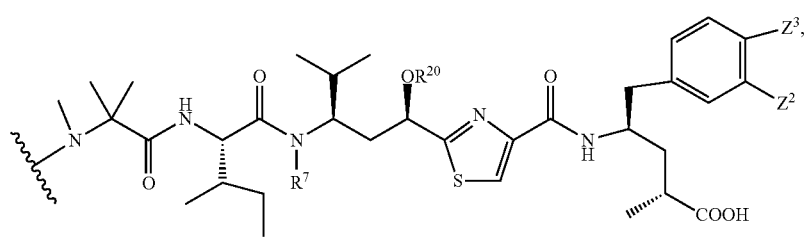
II-51
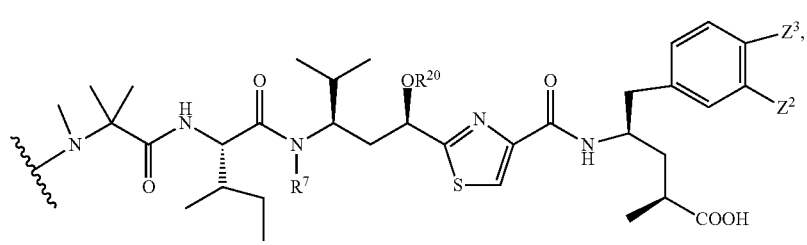
II-52
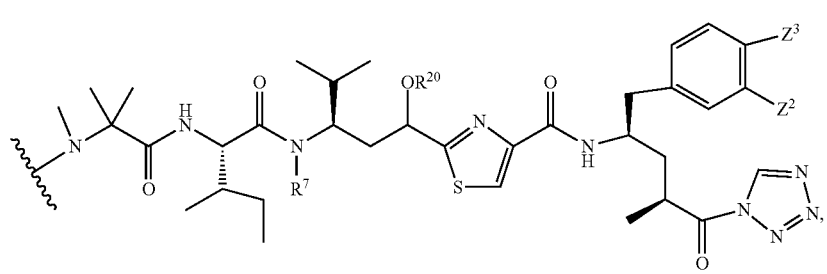
II-53
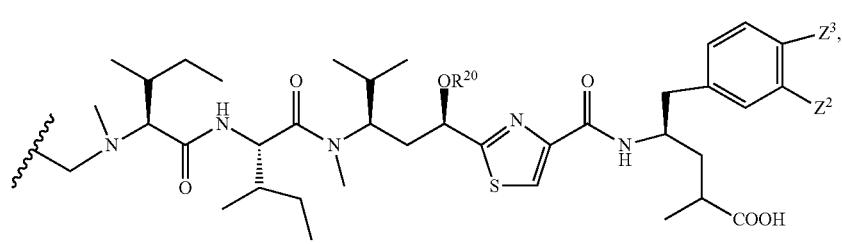
II-54
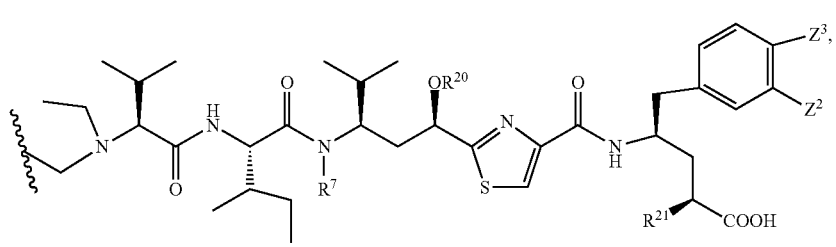
II-55

II-56
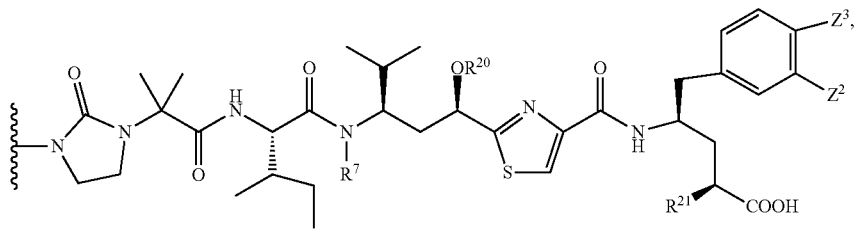
II-57
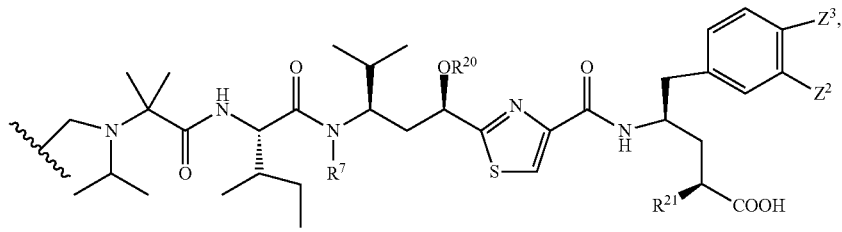
II-58
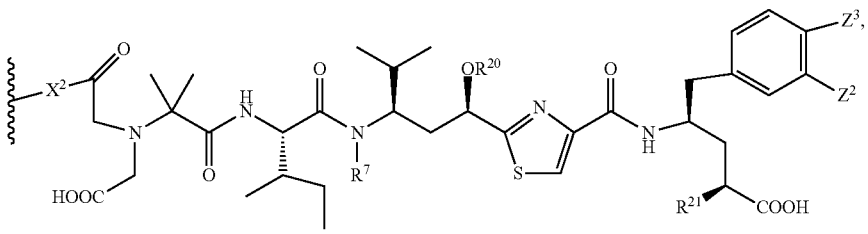
II-59
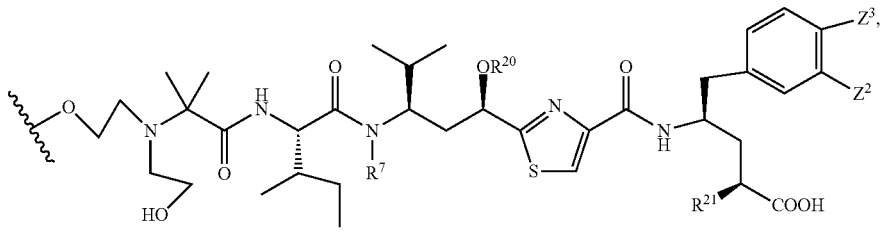
II-60
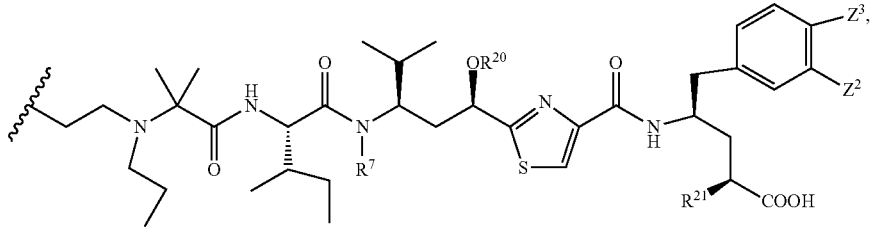
II-61
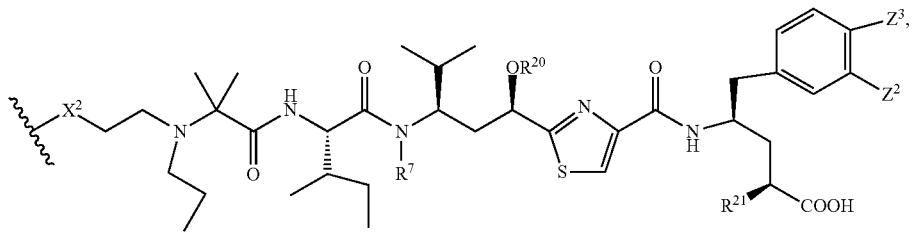

II-62
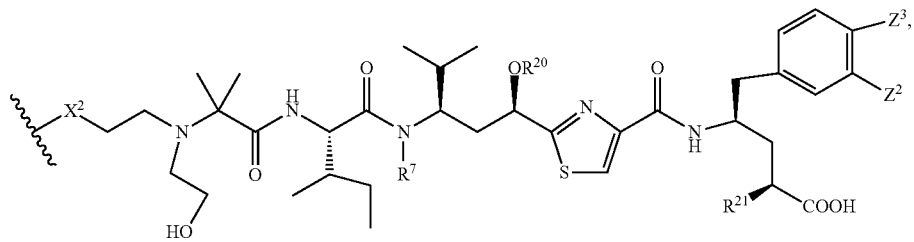
II-63
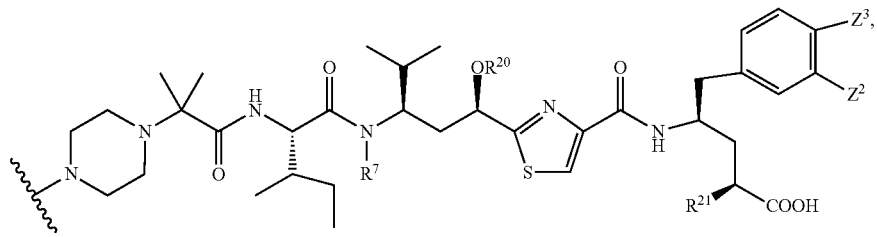
II-64
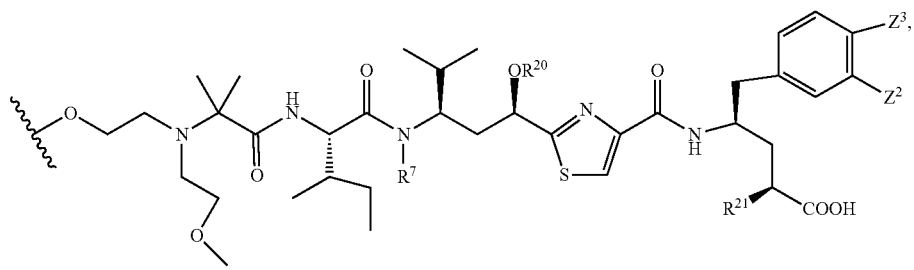
II-65
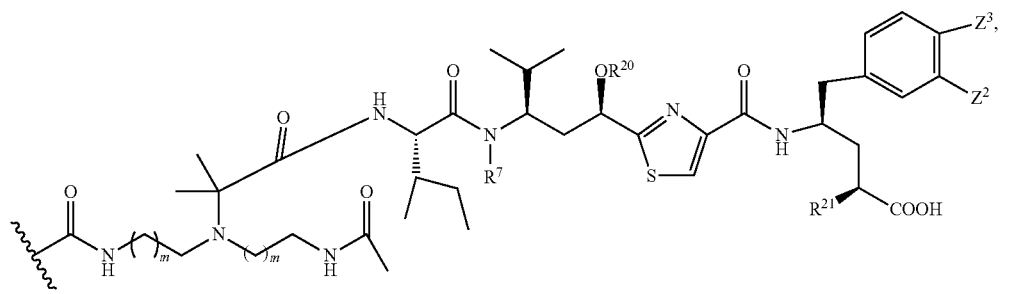
II-66
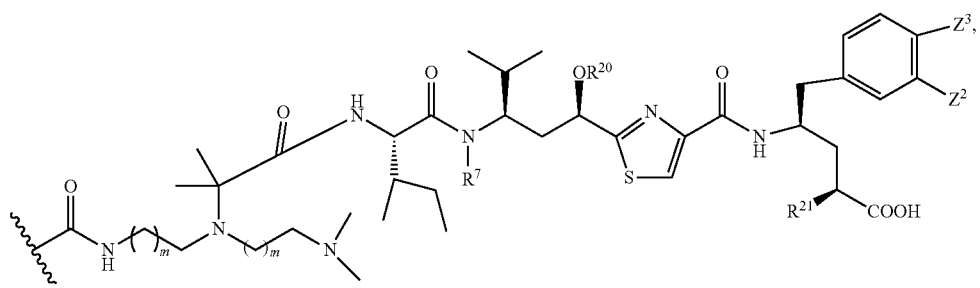
II-67
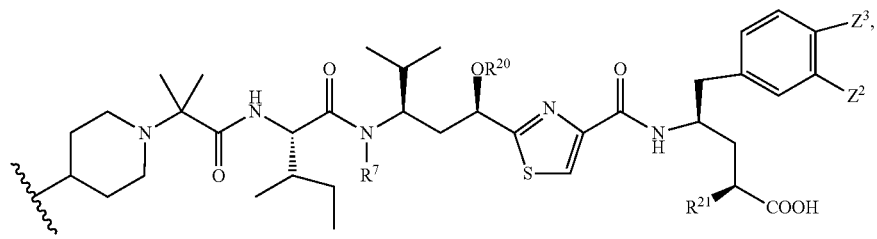

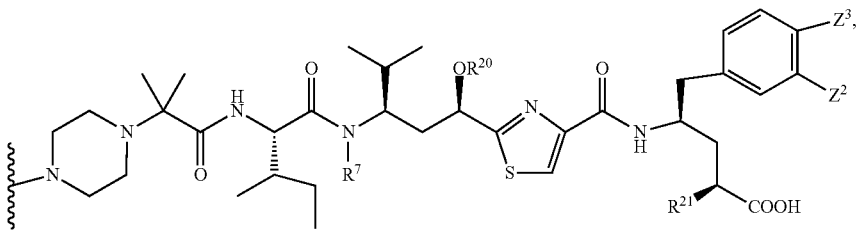

II-68

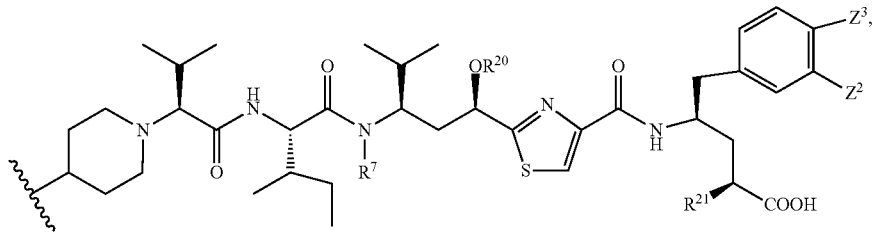

II-69 or their pharmaceutically acceptable salts, hydrates, or hydrated salts; or the polymorphic crystalline structures of these compounds; or their optical isomers, racemates, diastereomers or enantiomers thereof;

wherein $R^{20}$ is H; $C_1$-$C_8$ of linear or branched alkyl, heteroalkyl, or acyl (—C(O)$R^{17}$); $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)O$R^{17}$), carbamate (—C(O)N$R^{17}R^{18}$); or 1-8 carbon atoms of carboxylate, esters, ether, or amide; or 1~8 amino acids; or polyethyleneoxy unit of formula (OCH$_2$CH$_2$)$_p$ or (OCH$_2$CH(CH$_3$))$_p$, wherein p is an integer from 0 to about 1000; or $R^{20}$ is absent and the oxygen forms a ketone, or combination above thereof;

wherein $R^{21}$ is H, $C_1$-$C_8$ of linear or branched alkyl;

wherein $Z^3$ and $Z^3$ are independently H, OH, NH$_2$, O$R^{17}$, NH$R^{17}$, COOH, COO$R^{17}$, C(O)$R^{17}$, C(O)NH$R^{17}$, C(O)NHNH$R^{17}$, C(O)NH$_2$, $R^{18}$, OCH$_2$OP(O)(O$R^{18}$)$_2$, OC(O)OP(O)(O$R^{18}$)$_2$, OPO(O$R^{18}$)$_2$, NHPO(O$R^{18}$)$_2$, OP(O)(O$R^{18}$)OP(O)(O$R^{18}$)$_2$, OC(O)$R^{18}$, OC(O)NH$R^{18}$, OSO$_2$(O$R^{18}$), O—(C$_4$-C$_{12}$ glycoside), C$_1$-C$_8$ of linear or branched alkyl or heteroalkyl; C$_2$-C$_8$ of linear or branched alkenyl, alkynyl, alkylcycloalkyl, heterocycloalkyl; C$_3$-C$_8$ linear or branched of aryl, Ar-alkyl, heterocyclic, carbocyclic, cycloalkyl, heteroalkylcycloalkyl, alkylcarbonyl, heteroaryl; carbonate (—C(O)O$R^{17}$), carbamate (—C(O)N$R^{17}R^{18}$); $R^{17}$ and $R^{18}$ are independently H, C$_1$-C$_8$ linear or branched alkyl or heteroalkyl; C$_2$-C$_8$ of linear or branched alkenyl, alkynyl, alkylcycloalkyl, heterocycloalkyl; C$_3$-C$_8$ linear or branched of aryl, Ar-alkyl, heterocyclic, carbocyclic, cycloalkyl, heteroalkylcycloalkyl, alkylcarbonyl, heteroaryl; carbonate (—C(O)O$R^{17}$), carbamate (—C(O)N$R^{17}R^{18}$); $R^{19}$ is H, OH, NH$_2$, OSO$_2$(O$R^{18}$), XCH$_2$OP(O)(O$R^{18}$)$_2$, XPO(O$R^{18}$)$_2$, XC(O)OP(O)(O$R^{18}$)$_2$, XC(O)$R^{18}$, XC(O)NH$R^{18}$, C$_1$-C$_8$ alkyl or carboxylate; C$_2$-C$_8$ alkenyl, alkynyl, alkylcycloalkyl, heterocycloalkyl; C$_3$-C$_8$ aryl or alkylcarbonyl; or pharmaceutical salts; X is O, S, NH, NHNH, NH$R^{17}$, or CH$_2$; $R^7$ is defined the same above;

wherein "⌇" is the site that linked to a linker L of Formula (II).

In another embodiment, a conjugate of a cell binding molecule-antimitotic agent has the Formula (III):

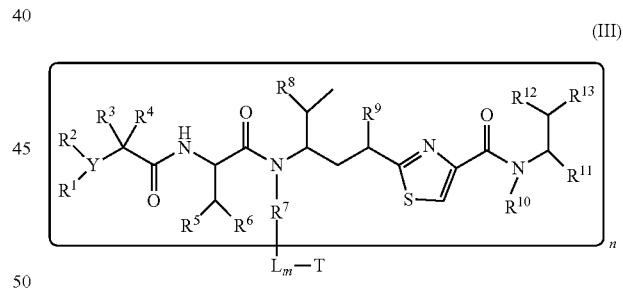

(III)

or their pharmaceutically acceptable salts, hydrates, or hydrated salts; or the polymorphic crystalline structures of these compounds; or their optical isomers, racemates, diastereomers or enantiomers thereof;

wherein T, L, m, Y, $R^1$, $R^2$, $R^3$, $R^4$, $R^5$, $R^6$, $R^8$, $R^9$, $R^{10}$, $R^{11}$, $R^{12}$, $R^{13}$ and n are defined the same as in Formula (I) and (II);

Wherein $R^7$ is independently selected from —$R^{14}$—, or —$R^{14}$C(=O)$X^1R^{15}$— or —$R^{14}X^1R^{15}$—, wherein $R^{14}$ and $R^{15}$ are independently linear or branched C$_1$-C$_8$ of alkyl, heteroalkyl; C$_2$-C$_8$ of alkenyl, alkynyl; C$_3$-C$_8$ of aryl, heterocyclic, carbocyclic, cycloalkyl, heterocycloalkyl, heteroaralkyl heteroalkylcycloalkyl, alkylcarbonyl; $X^1$ is selected from O, S, S—S, NH, or N$R^{14}$.

Illustrative compounds inside the bracket of Formula (III) have the structures:
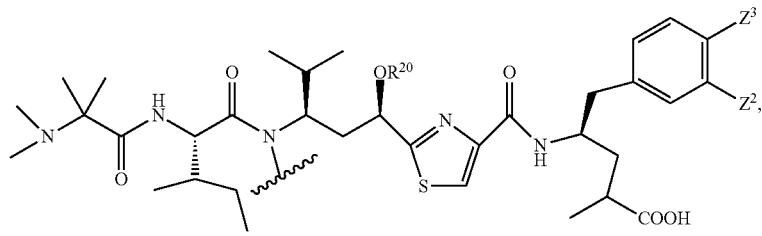
III-01
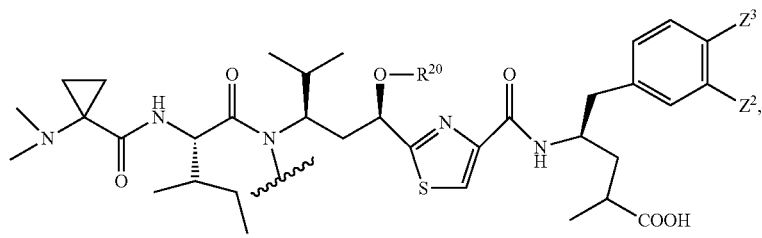
III-02
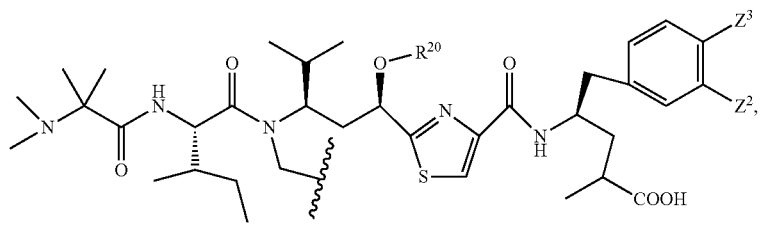
III-03
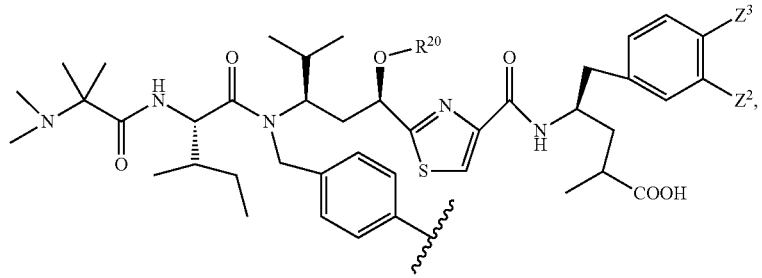
III-04
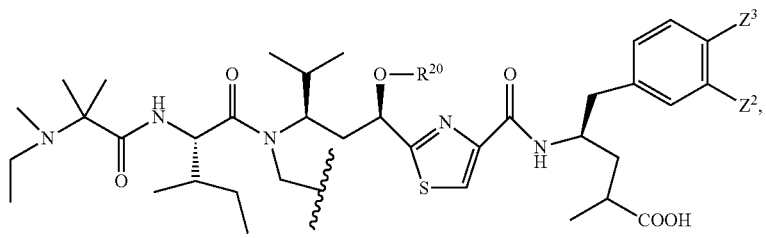
III-05
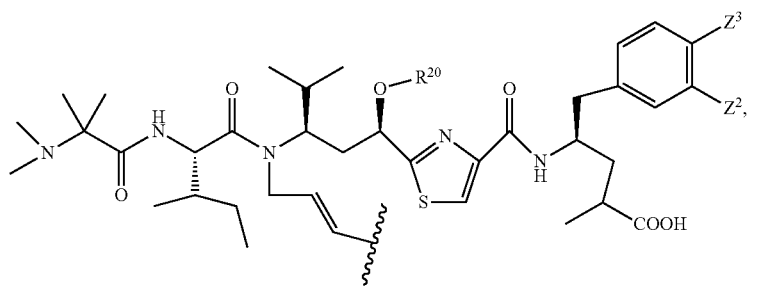
III-06

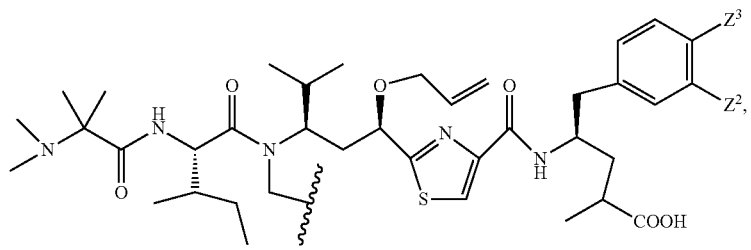
III-07
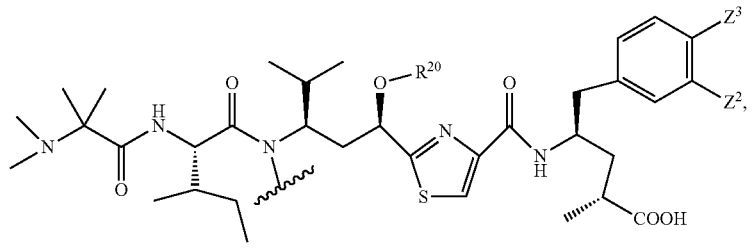
III-08
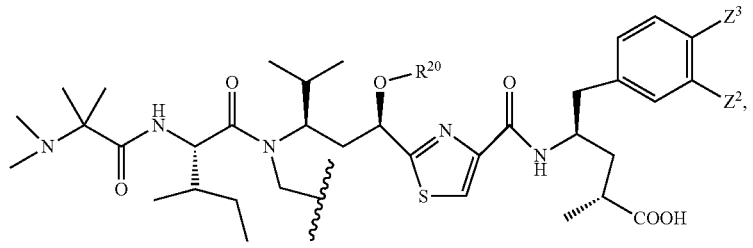
III-09
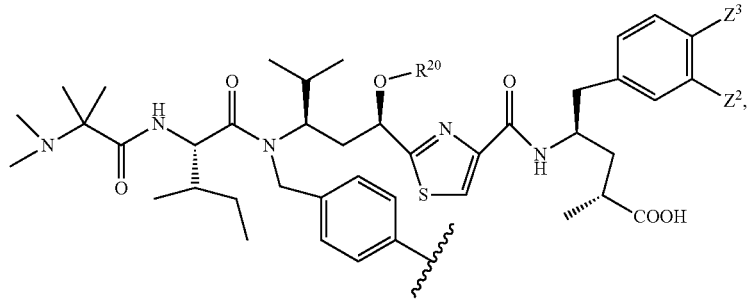
III-10
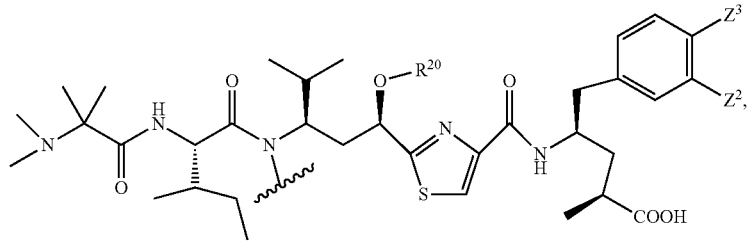
III-11
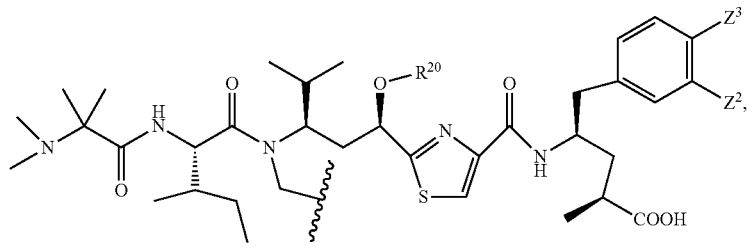
III-12

-continued
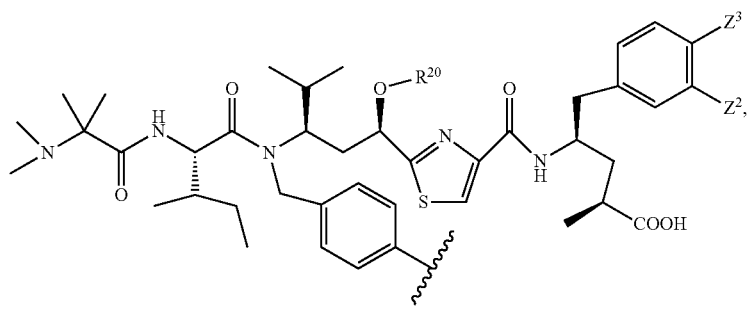
III-13
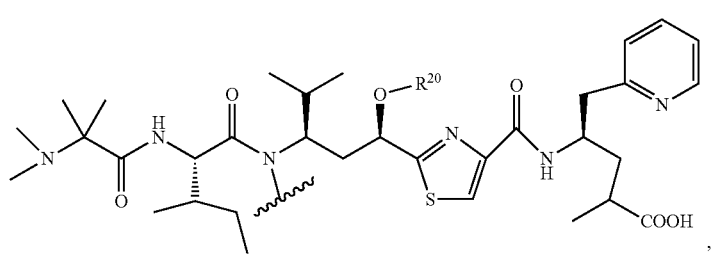
III-14
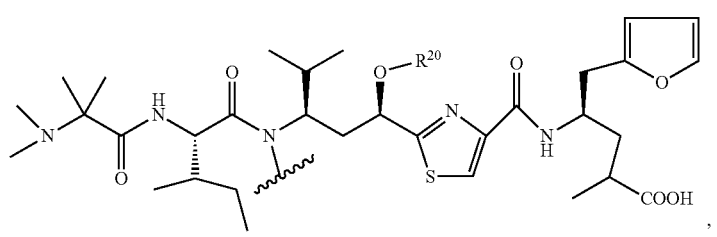
III-15
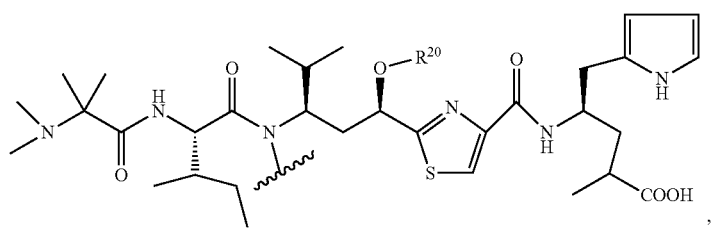
III-16
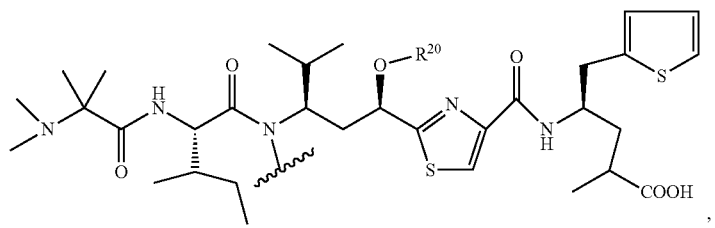
III-17
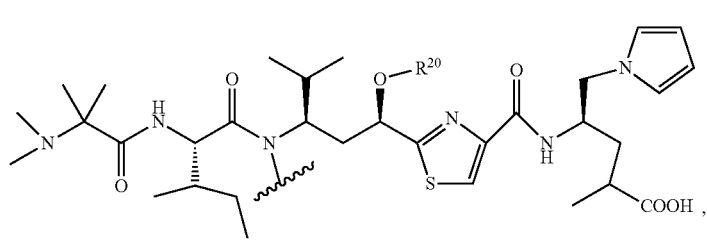
III-18

-continued
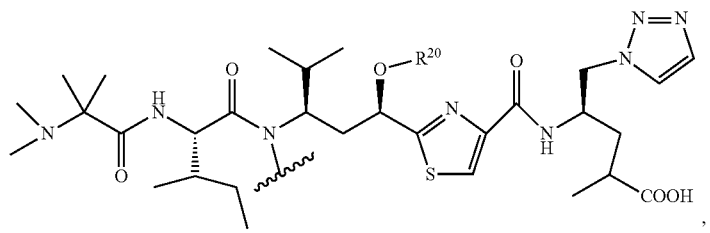
III-19
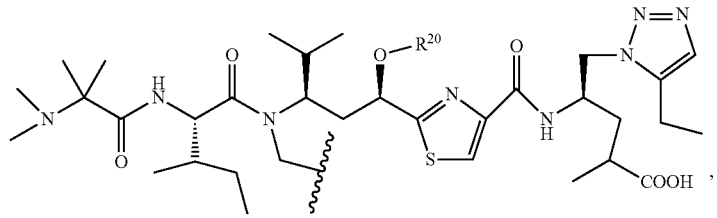
III-20
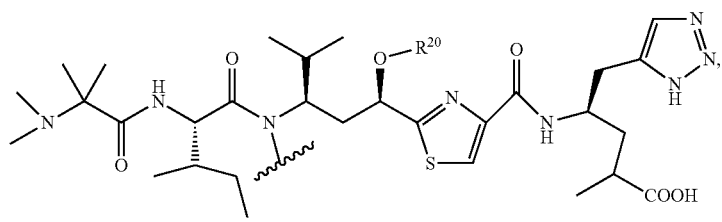
III-21
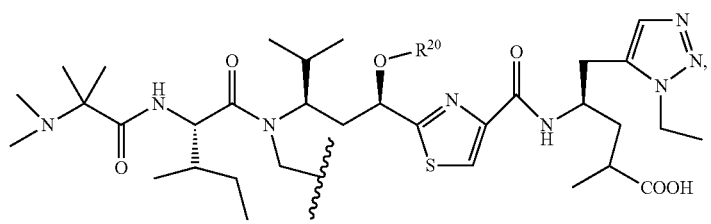
III-22
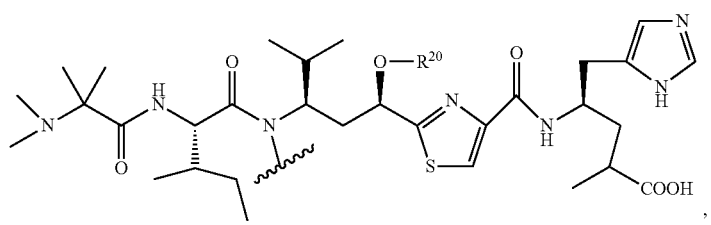
III-23
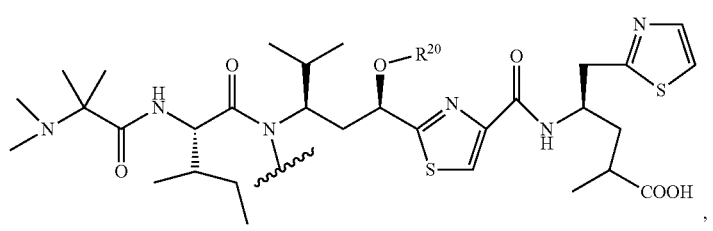
III-24
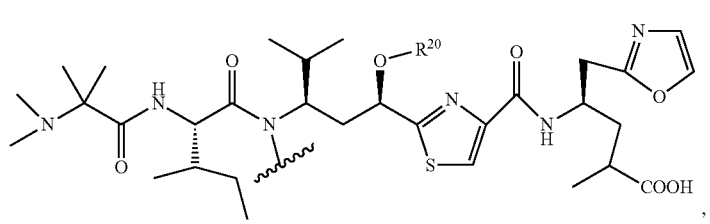
III-25

-continued
III-26
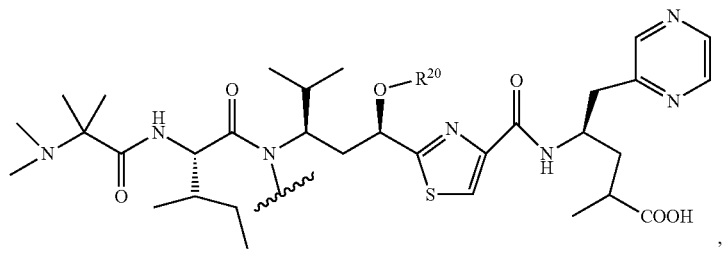
III-27
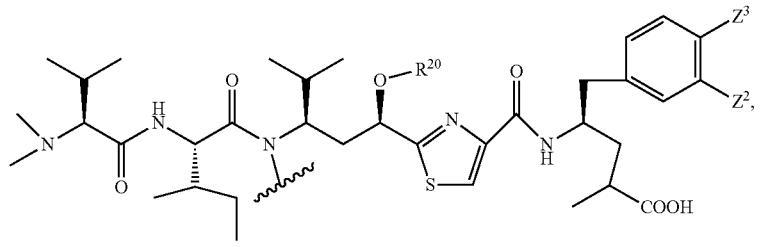
III-28
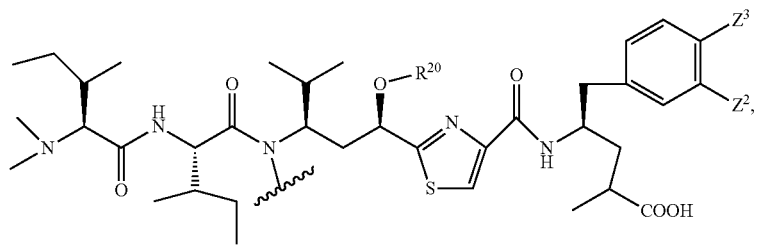
III-29
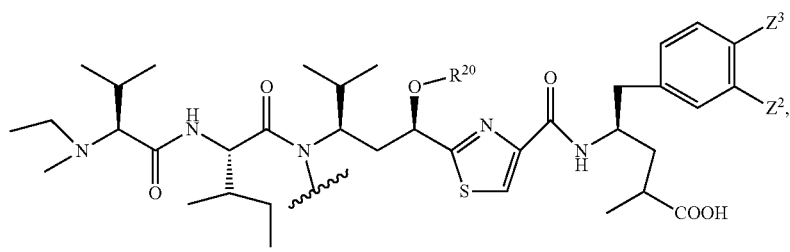
III-30
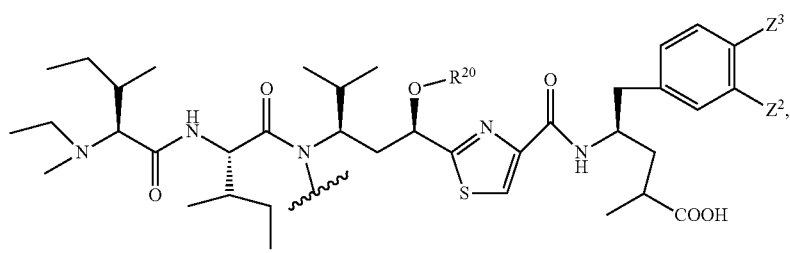
III-31
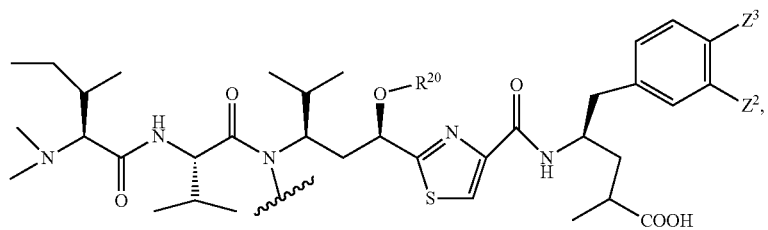

III-32
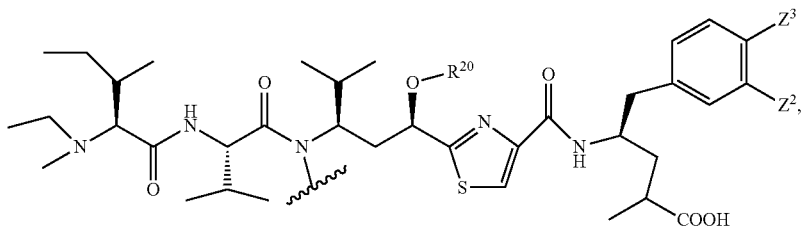
III-33
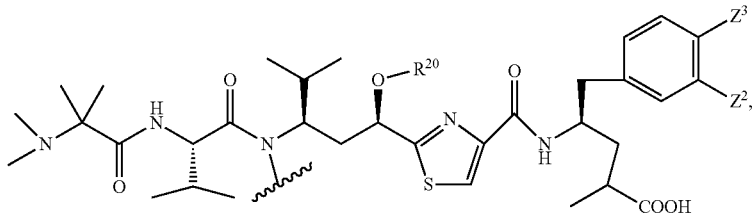
III-34
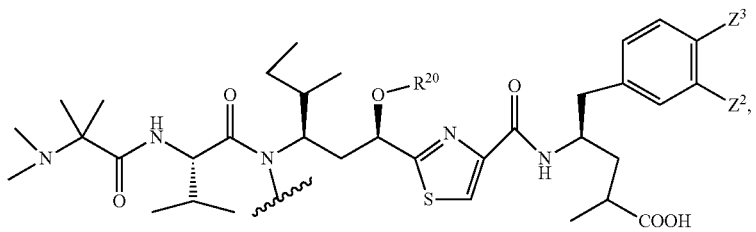
III-35
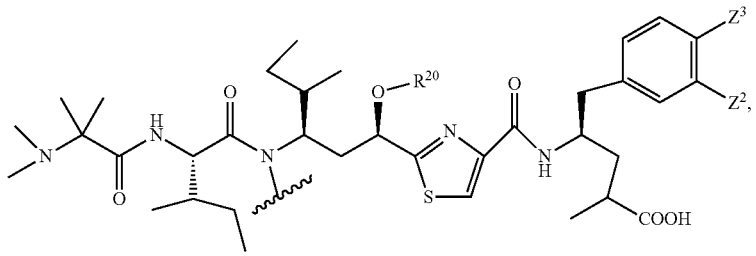
III-36
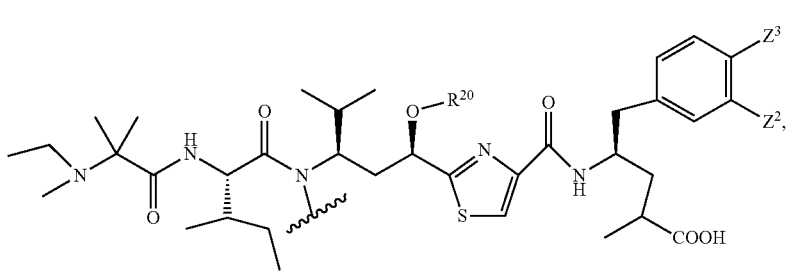
III-37
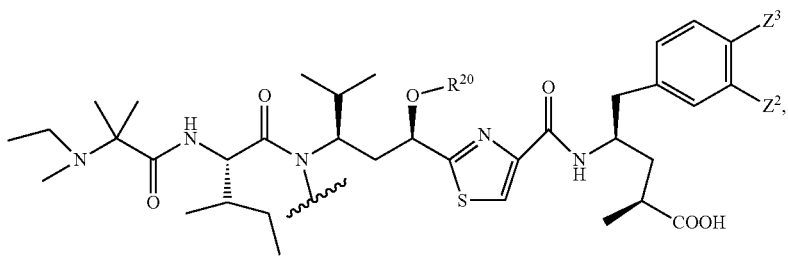

-continued
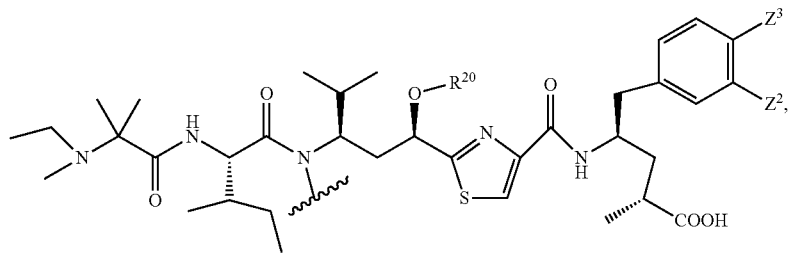
III-38
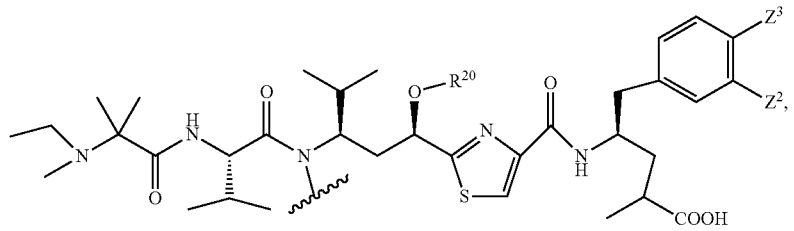
III-39
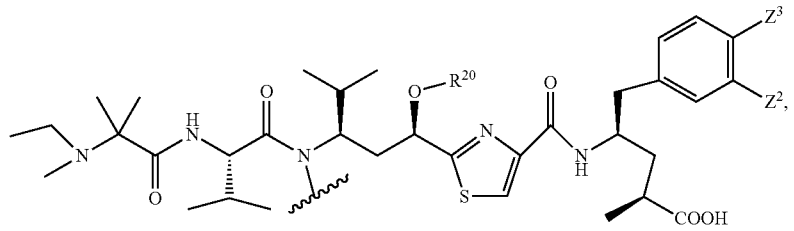
III-40
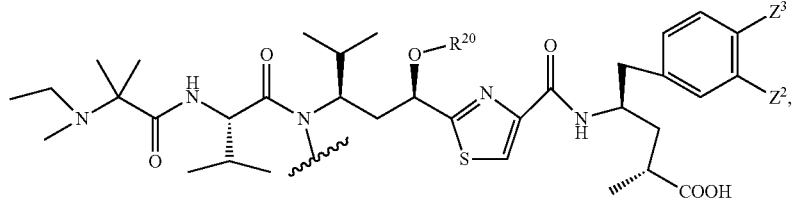
III-41
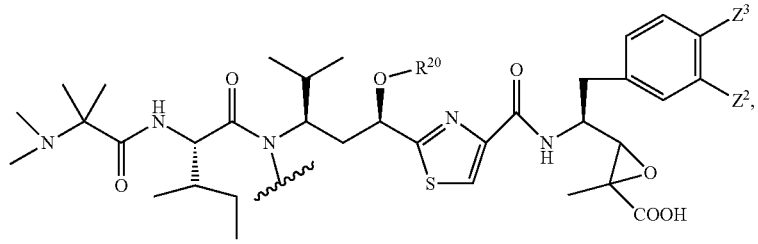
III-42
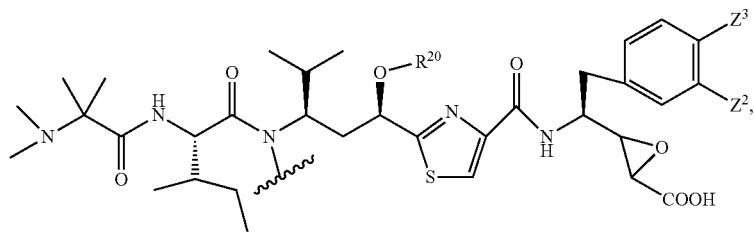
III-43

III-44
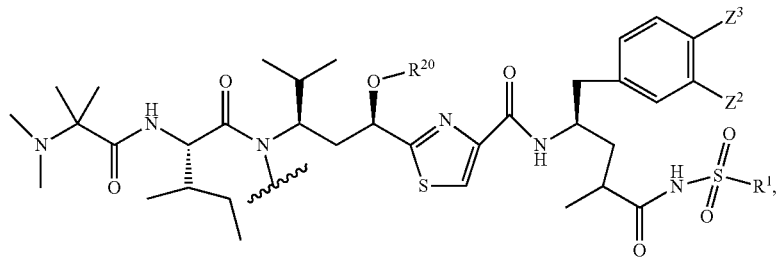
III-45
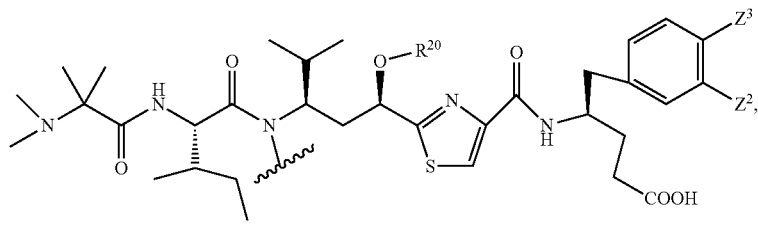
III-46
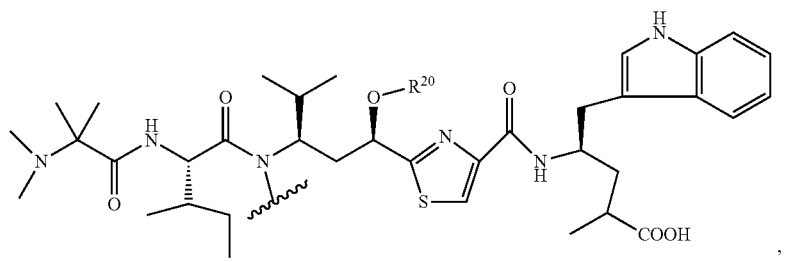
III-47
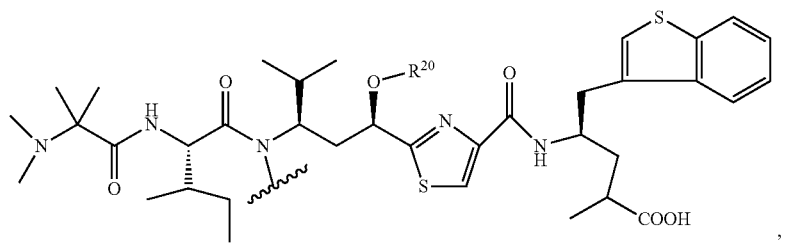
III-48
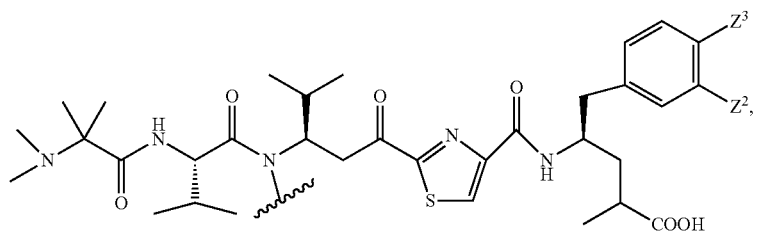
III-49
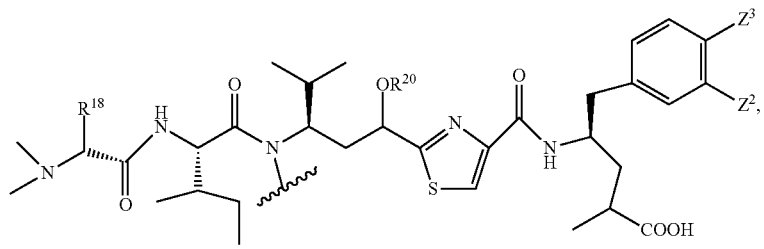

III-50
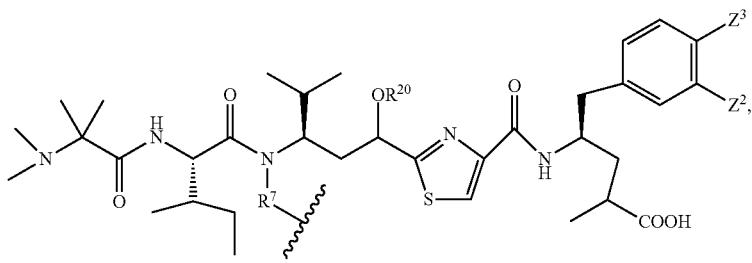
III-51
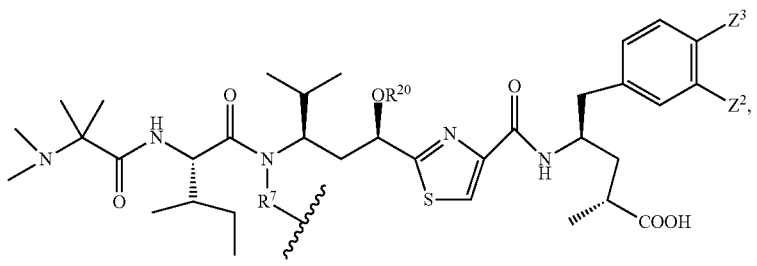
III-52
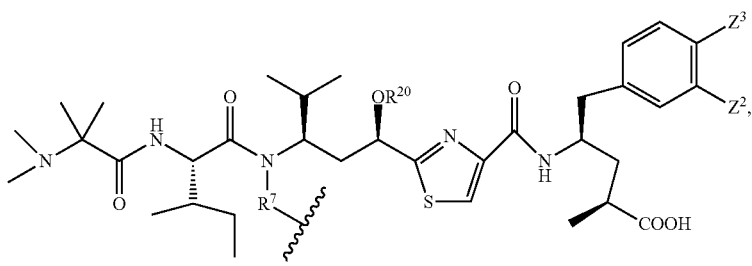
III-53
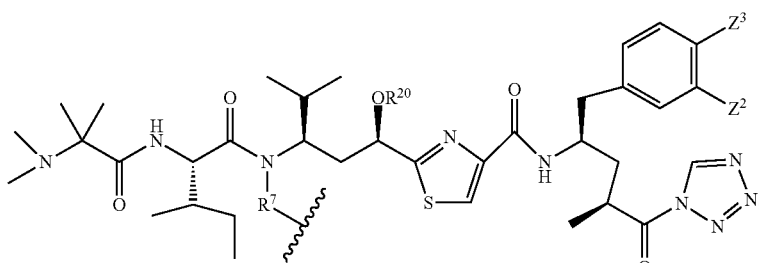
III-54
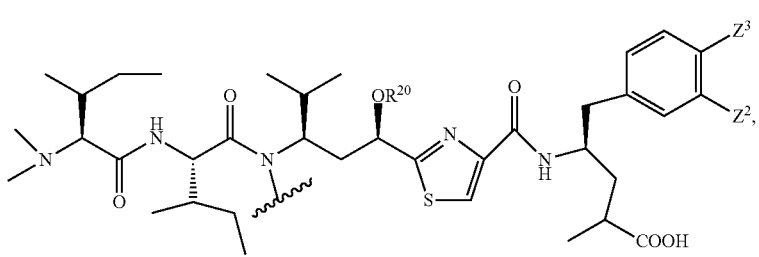
III-55
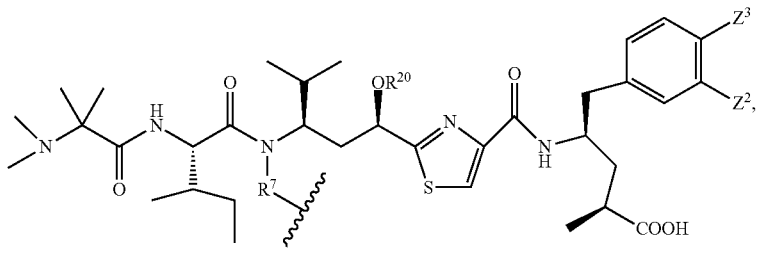

-continued
III-56
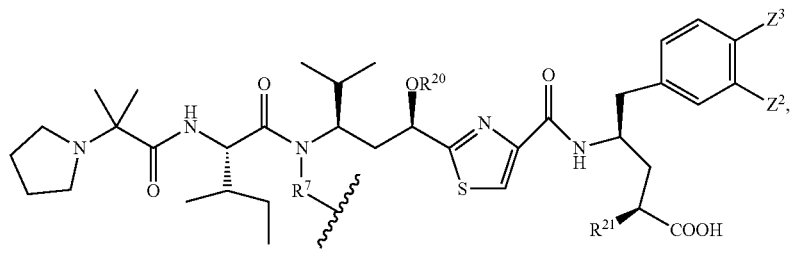
III-57
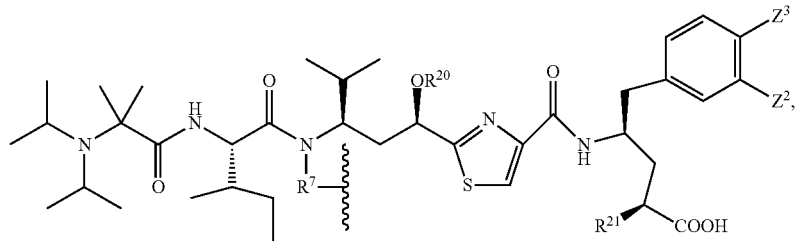
III-58
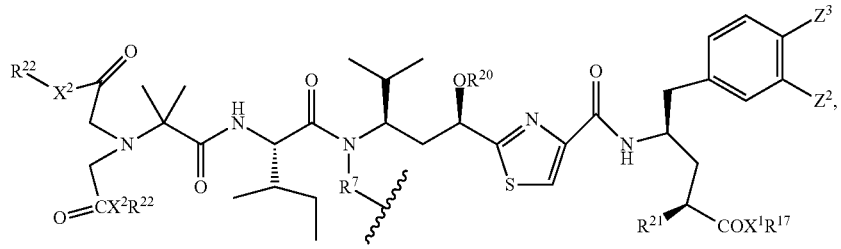
III-59
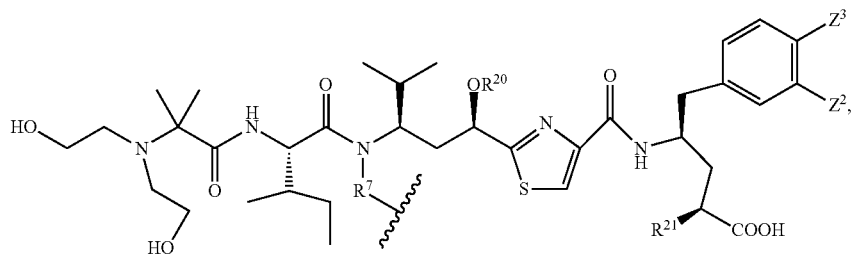
III-60
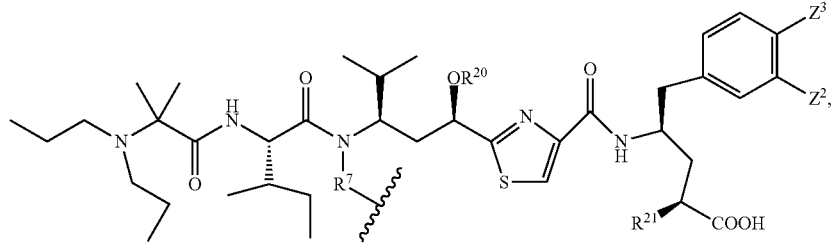
III-61
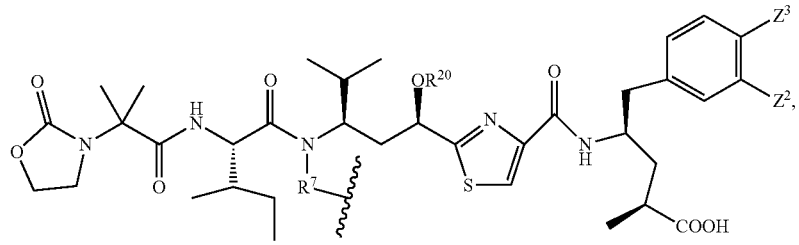

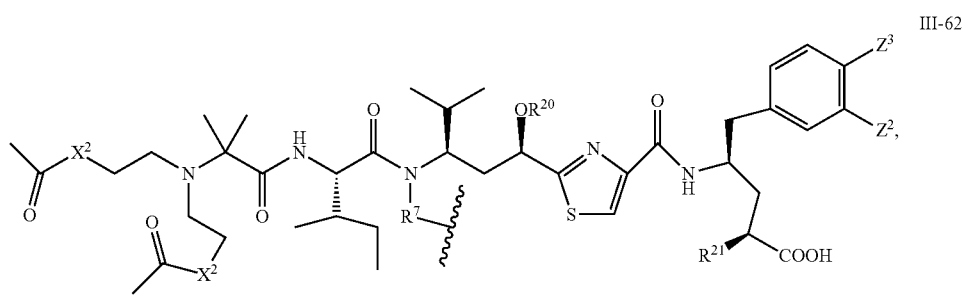
III-62
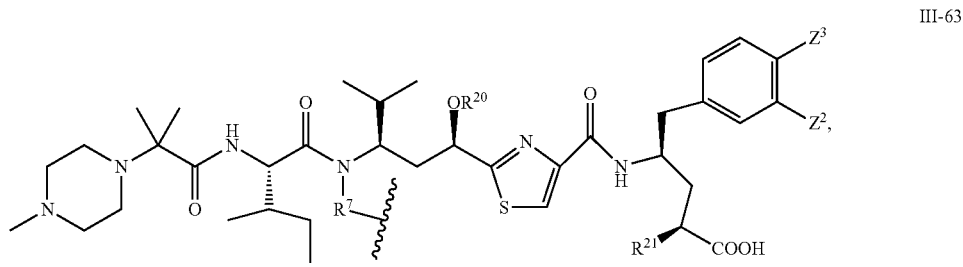
III-63
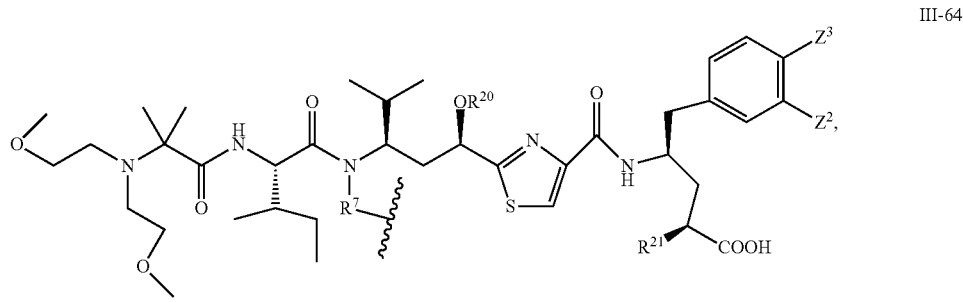
III-64
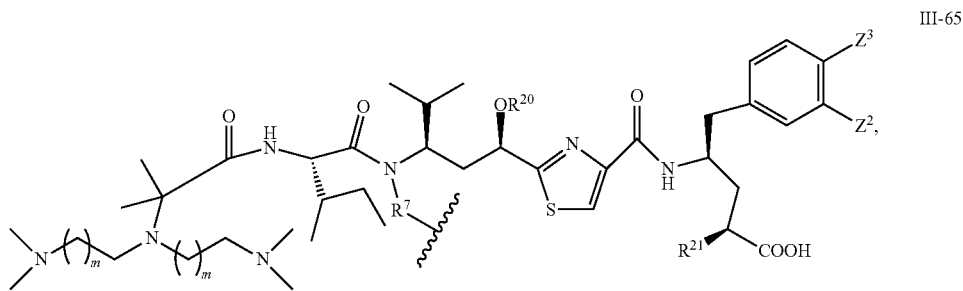
III-65
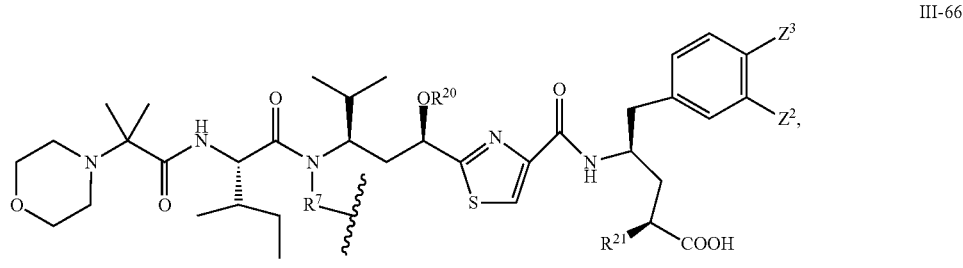
III-66
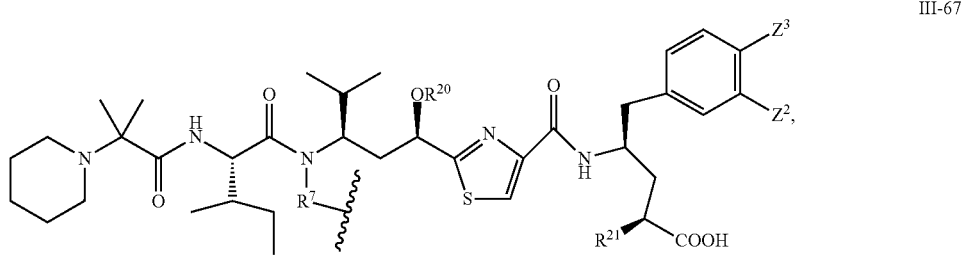
III-67

III-68

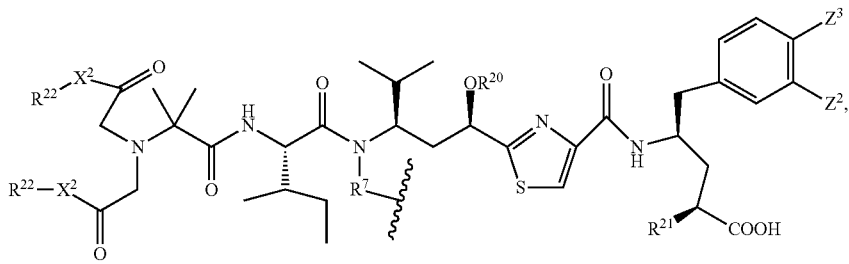

or their pharmaceutically acceptable salts, hydrates, or hydrated salts; or the polymorphic crystalline structures of these compounds; or their optical isomers, racemates, diastereomers or enantiomers thereof;

wherein $R^{20}$ is H; $C_1$-$C_8$ of linear or branched alkyl, heteroalkyl, or acyl (—C(O)$R^{17}$); $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)O$R^{17}$), carbamate (—C(O)N$R^{17}R^{18}$); or 1-8 carbon atoms of carboxylate, esters, ether, or amide; or 1~8 amino acids; or polyethyleneoxy unit of formula (OCH$_2$CH$_2$)$_p$ or (OCH$_2$CH(CH$_3$))$_p$, wherein p is an integer from 0 to about 1000; or $R^{20}$ is absent and the oxygen forms a ketone, or combination above thereof; wherein $R^{21}$ and $R^{22}$ are independently H, $C_1$-$C_8$ of linear or branched alkyl;

$Z^3$ and $Z^3$ are independently H, OH, NH$_2$, O$R^{17}$, NH$R^{17}$, COOH, COO$R^{17}$, C(O)$R^7$, C(O)NH$R^{17}$, C(O)NHNH$R^7$, C(O)NH$_2$, $R^{18}$, OCH$_2$OP(O)(O$R^8$)$_2$, OC(O) OP(O)(O$R^{18}$)$_2$, OPO(O$R^{18}$)$_2$, NHPO(O$R^{18}$)$_2$, OP(O) (O$R^{18}$)OP(O)(O$R^{18}$)$_2$, OC(O)$R^8$, OC(O)NH$R^{18}$, OSO$_2$ (O$R^{18}$), O—(C$_4$-C$_{12}$-glycoside), $C_1$-$C_8$ of linear or branched alkyl or heteroalkyl; $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O) O$R^{17}$), carbamate (—C(O)N$R^{17}R^{18}$); $R^{17}$ and $R^{18}$ are independently H, $C_1$-$C_8$ linear or branched alkyl or heteroalkyl; $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)O$R^{17}$), carbamate (—C(O) N$R^{17}R^{18}$); $R^{19}$ is H, OH, NH$_2$, OSO$_2$(O$R^{18}$), XCH$_2$OP (O)(O$R^{18}$)$_2$, XPO(O$R^{18}$)$_2$, XC(O)OP(O)(O$R^{18}$)$_2$, XC(O)$R^{18}$, XC(O)NH$R^{18}$, $C_1$-$C_8$ alkyl or carboxylate; $C_2$-$C_8$ alkenyl, alkynyl, alkylcycloalkyl, heterocycloalkyl; $C_3$-$C_8$ aryl or alkylcarbonyl; or pharmaceutical salts; X, $X^1$ and $X^2$ are independently O, S, NH, NHNH, or CH$_2$.

In another embodiment, a cell binding molecule-antimitotic agent conjugate has the Formula (IV):

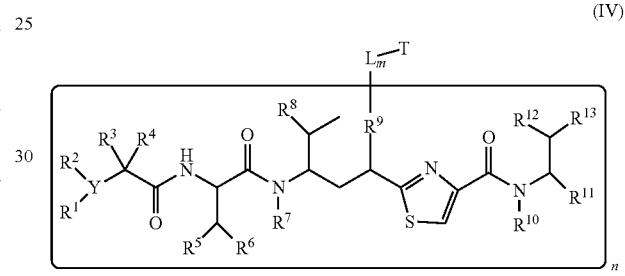

(IV)

or their pharmaceutically acceptable salts, hydrates, or hydrated salts; or the polymorphic crystalline structures of these compounds; or their optical isomers, racemates, diastereomers or enantiomers thereof;

wherein T, L, m, $R^1$, $R^2$, $R^3$, $R^4$, $R^5$, $R^6$, $R^7$, $R^8$, $R^{10}$, $R^{11}$, $R^{12}$, $R^{13}$ and n are defined the same as in Formula (II);

Wherein $R^9$ is independently H, —O—, —O$R^{14}$—, —OC (=O)$R^{14}$—, —OC(=O)NH$R^{14}$—, —OC(=O) N$R^{14}R^{15}$—, —OC(=O)$R^{14}$SS$R^{15}$—, —OP(=O) (O$R^{14}$)O—, wherein $R^{14}$, $R^{15}$ are independently H, $C_1$-$C_8$ of alkyl, heteroalkyl; $C_3$-$C_8$ of aryl, heteroaryl, heterocyclic, carbocyclic, cycloalkyl, alkylcycloalkyl, heterocycloalkyl, heteroalkylcycloalkyl, heteroaralkyl, alkylcarbonyl or pharmaceutical salts.

Illustrative compounds inside the bracket of Formula (IV) have the structures:

IV-01

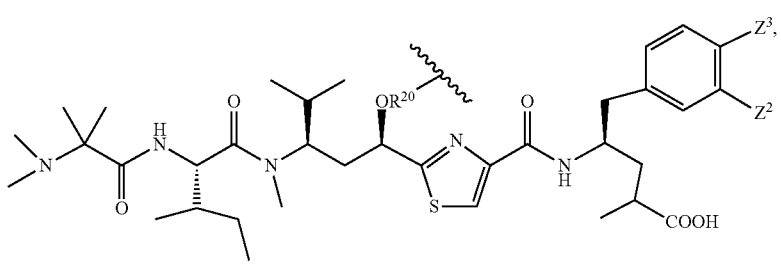

-continued
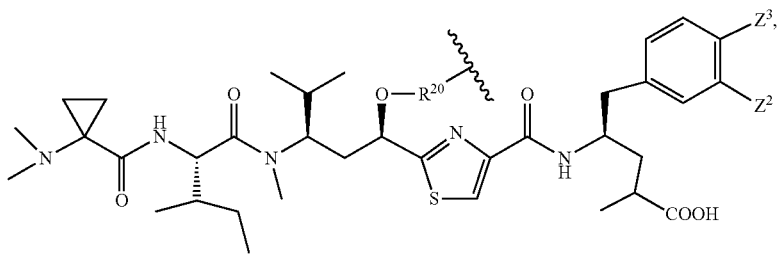
IV-02
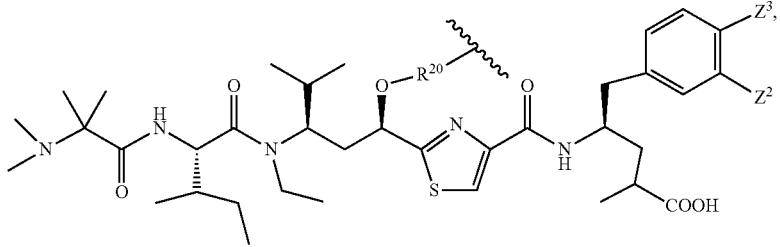
IV-03
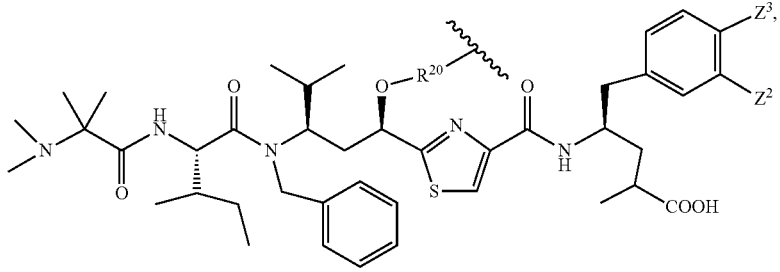
IV-04
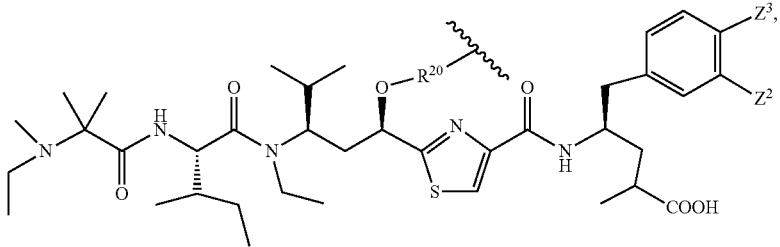
IV-05
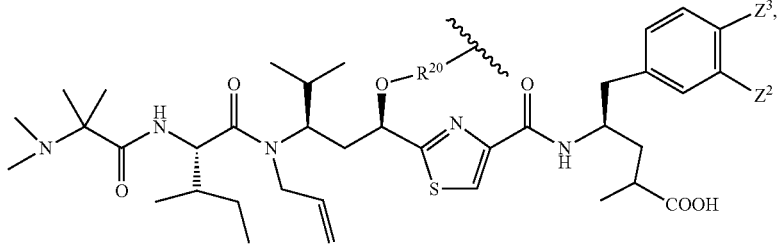
IV-06
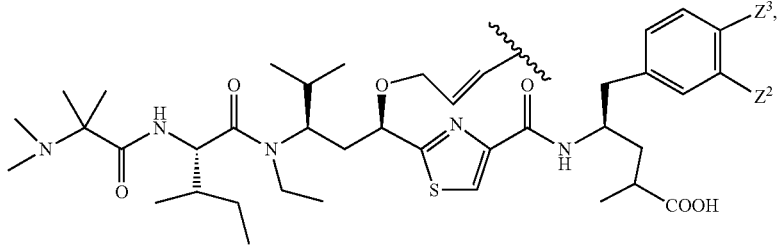
IV-07

-continued
IV-08
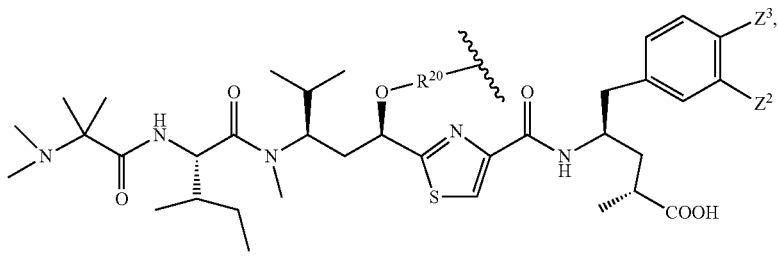
IV-09
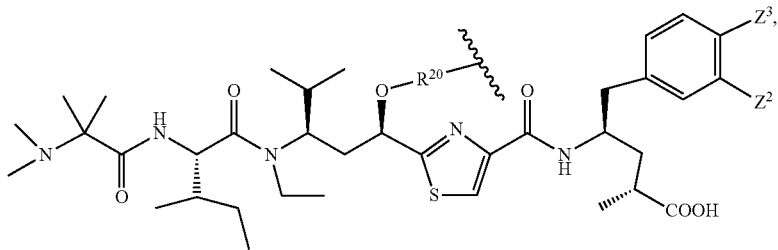
IV-10
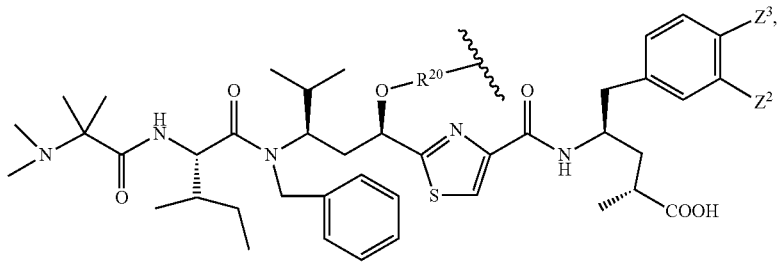
IV-11
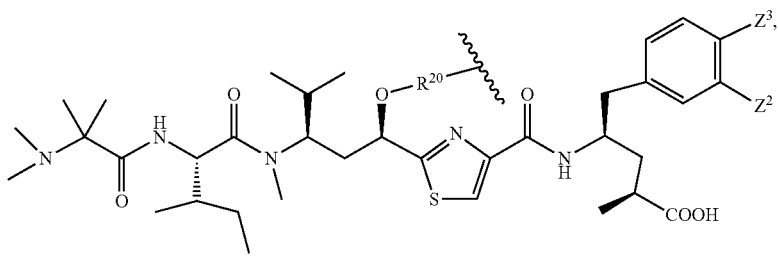
IV-12
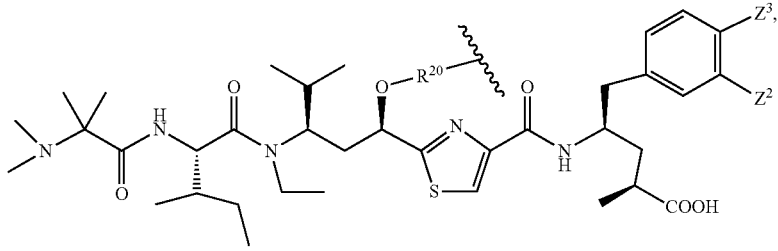
IV-13
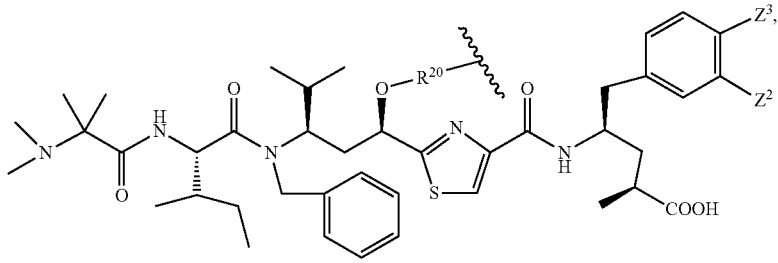

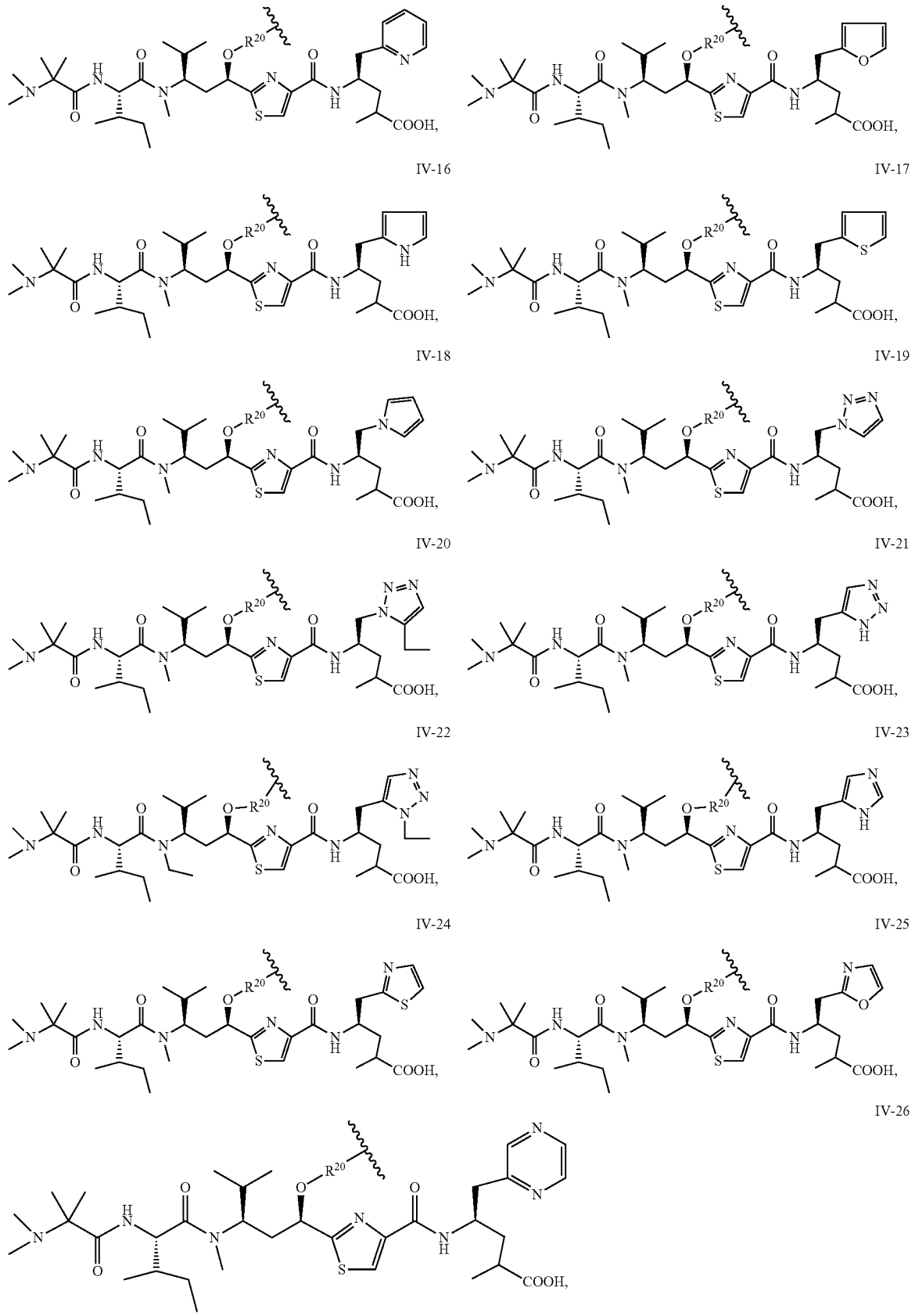

IV-27
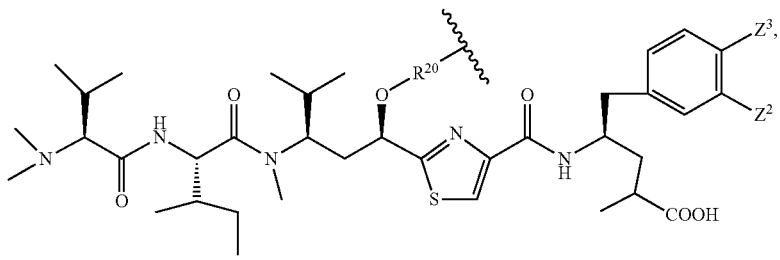
IV-28
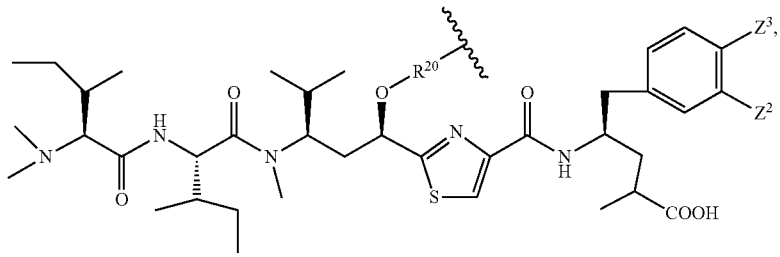
IV-29
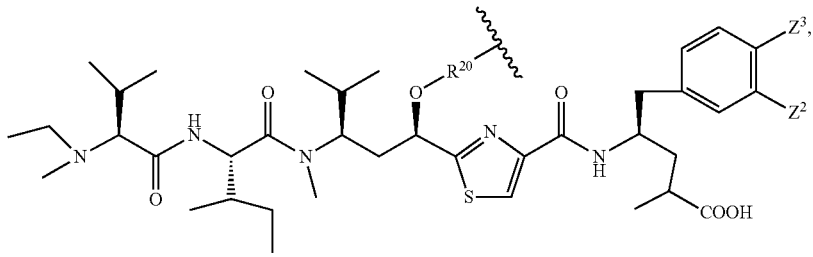
IV-30
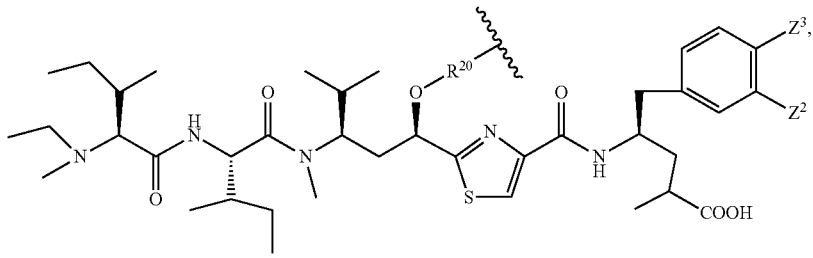
IV-31
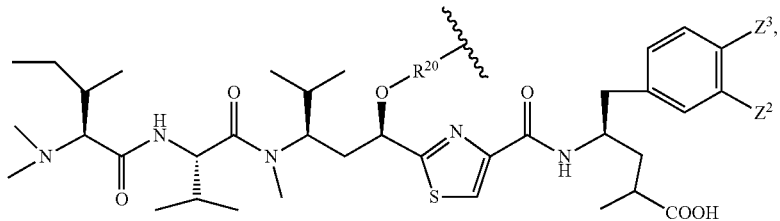
IV-32
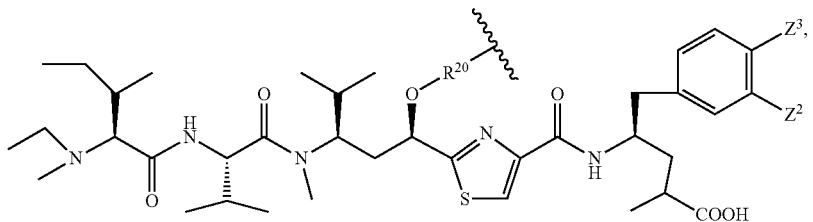

IV-33
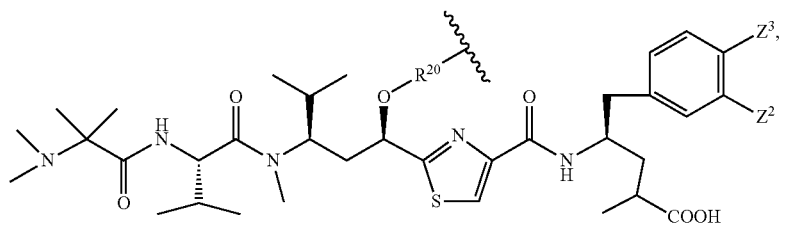
IV-34
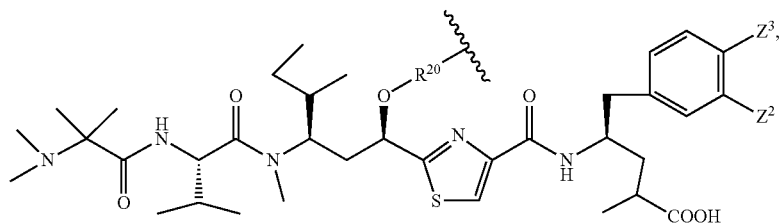
IV-35
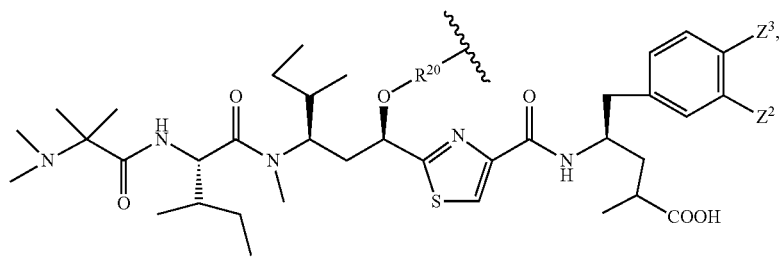
IV-36
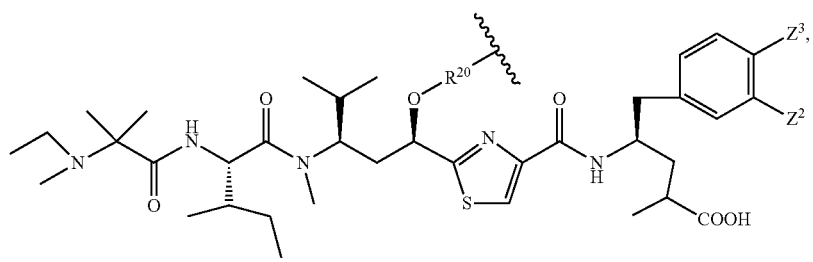
IV-37
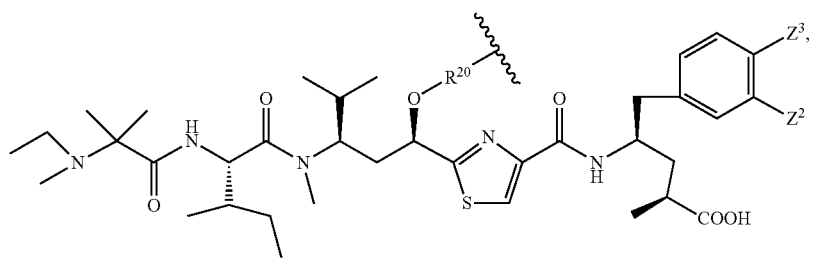
IV-38
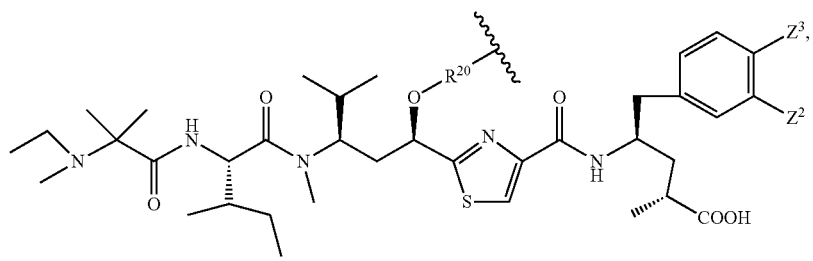

-continued
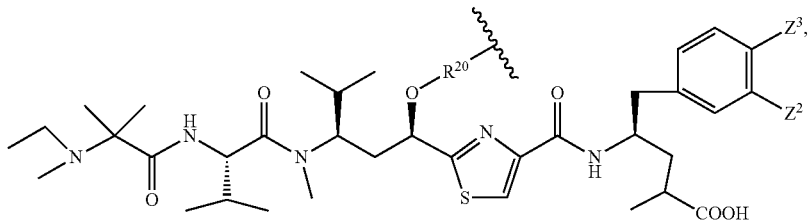
IV-39
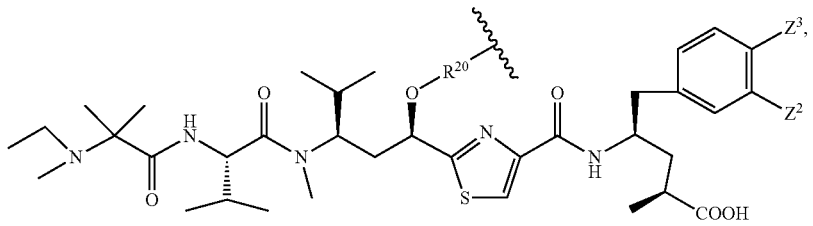
IV-40
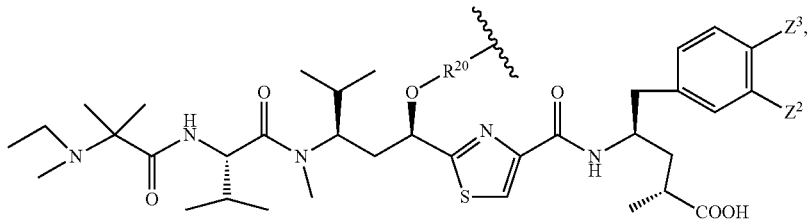
IV-41
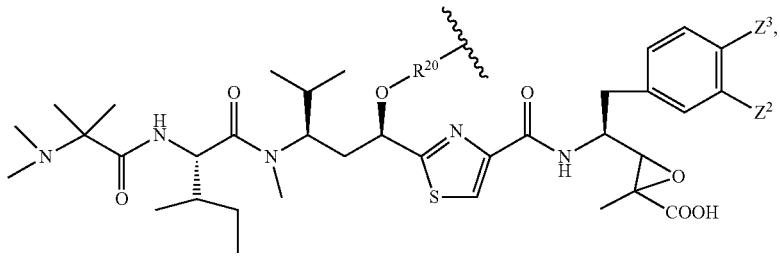
IV-42
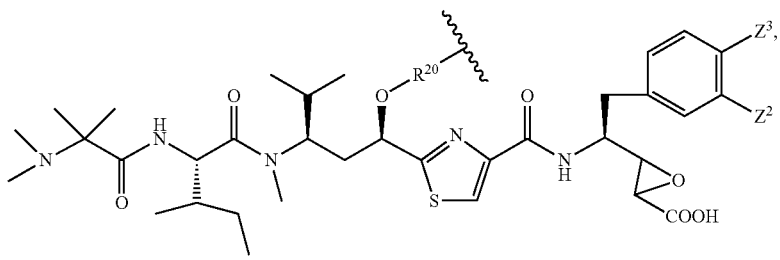
IV-43
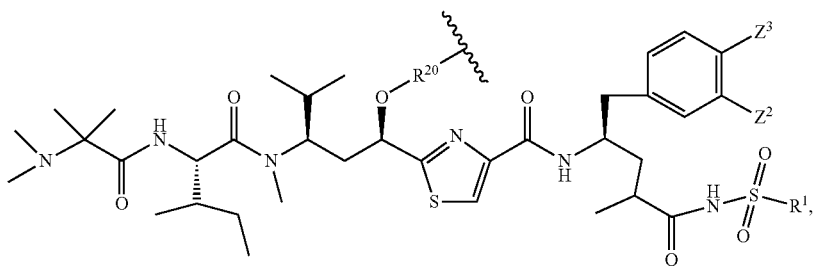
IV-44

-continued
IV-45
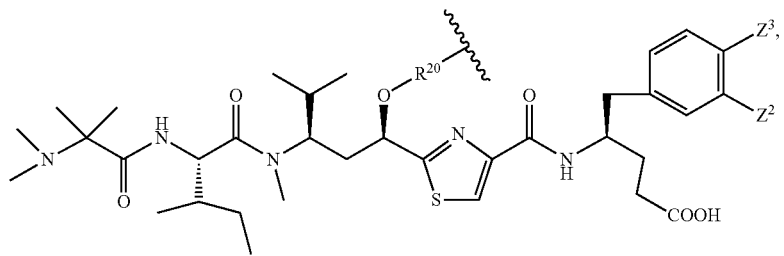
IV-46
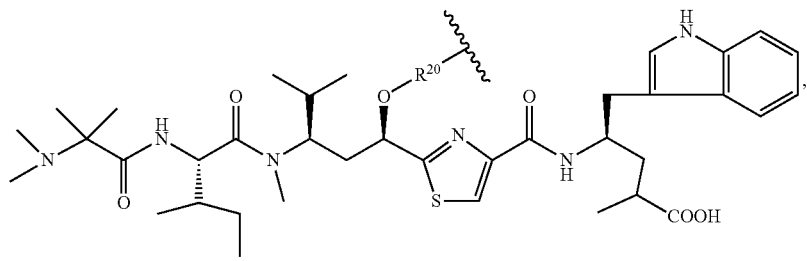
IV-47
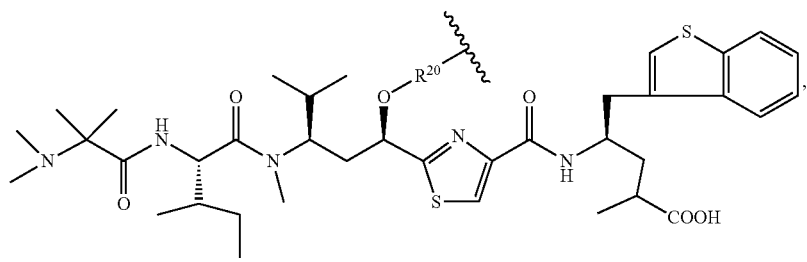
IV-48
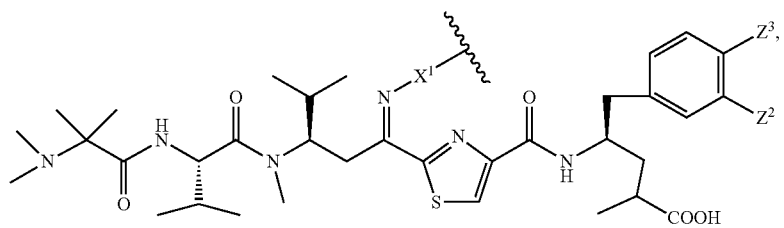
IV-49
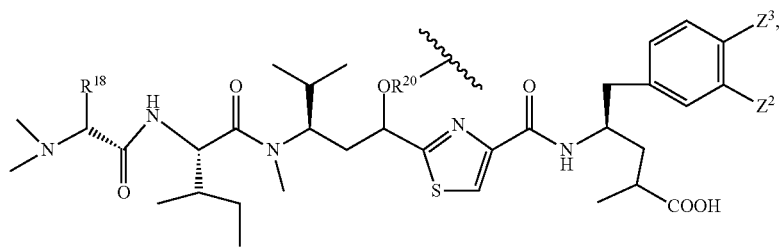
IV-50
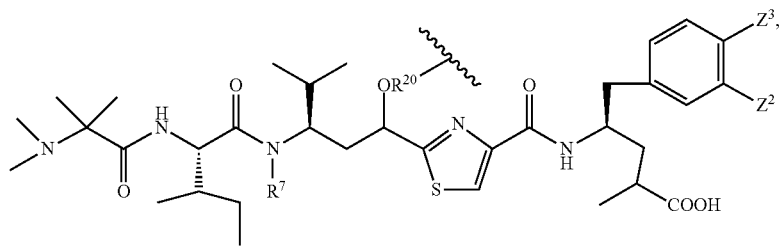

-continued
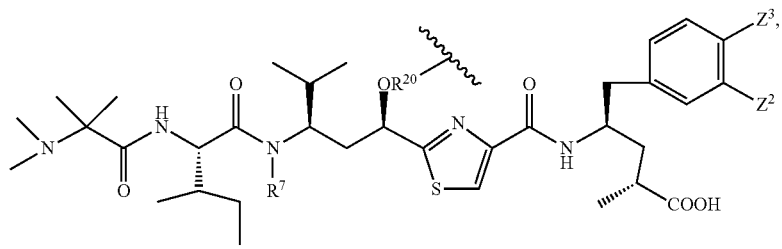
IV-51
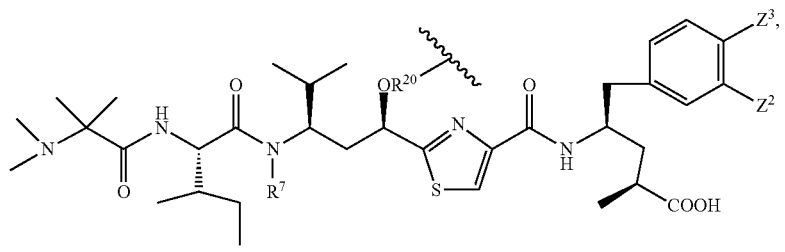
IV-52
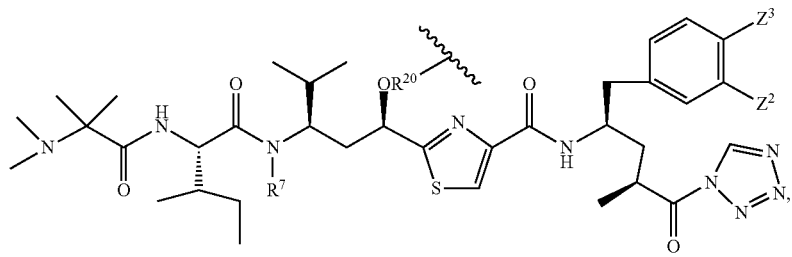
IV-53
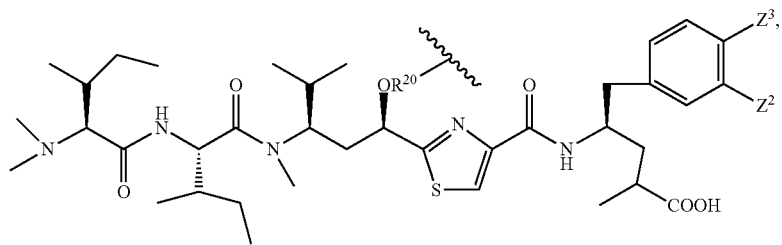
IV-54
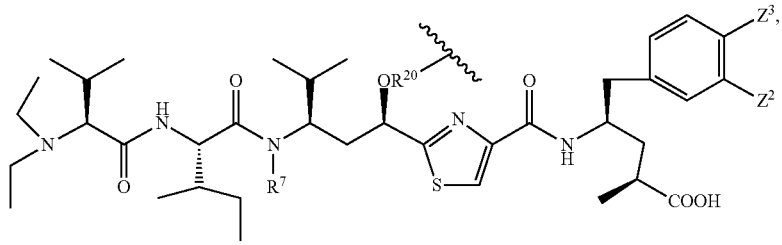
IV-55
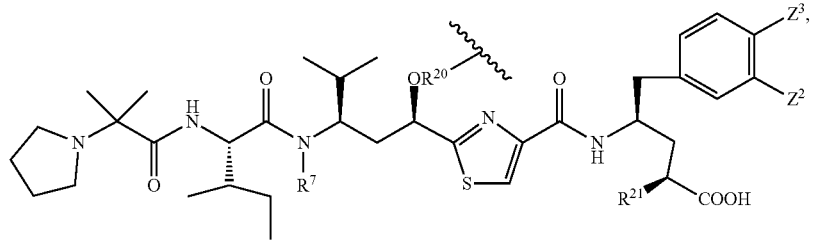
IV-56

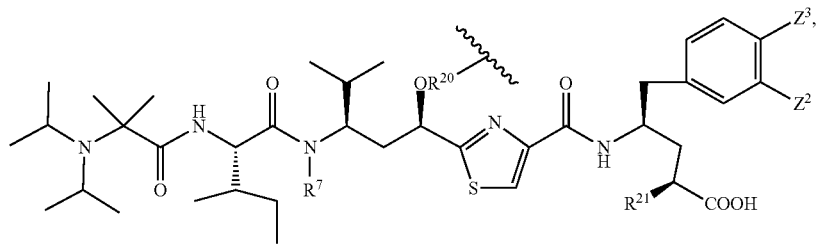
IV-57
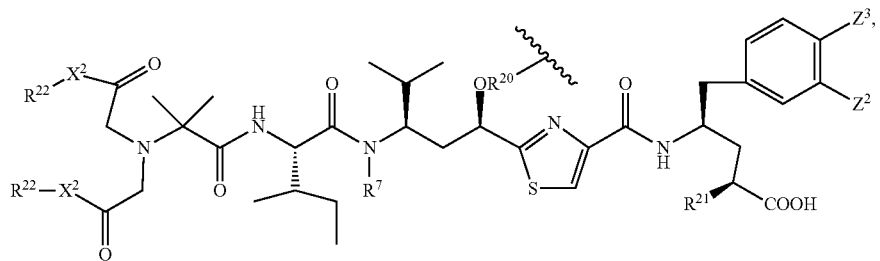
IV-58
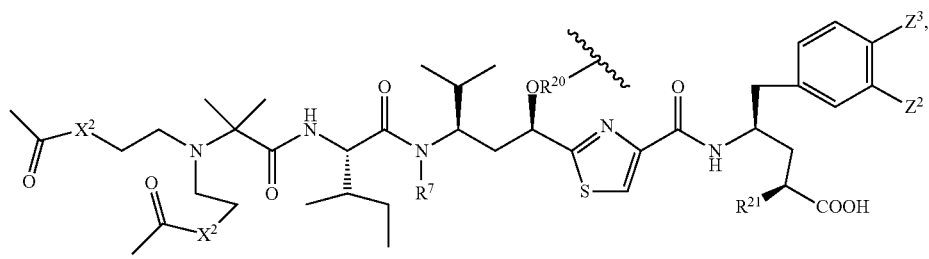
IV-59
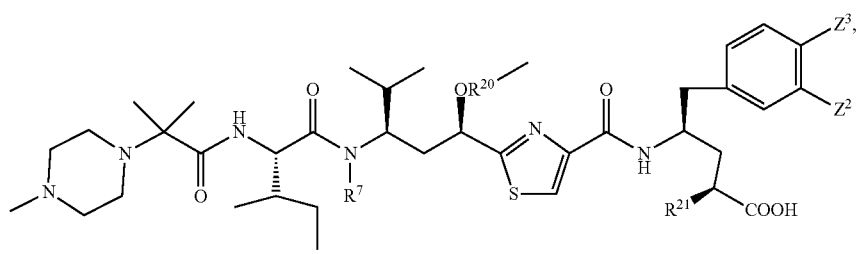
IV-60
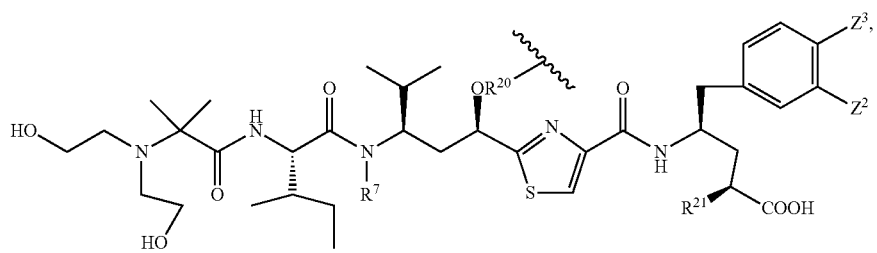
IV-61
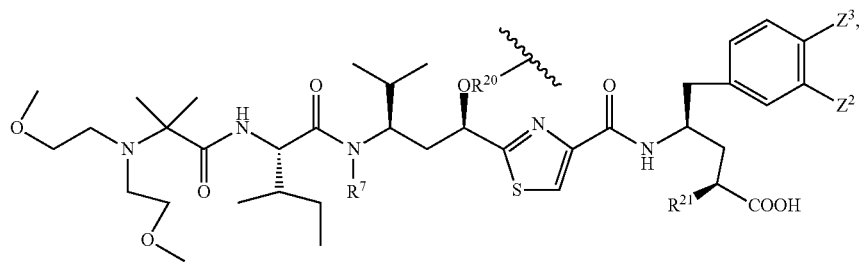
IV-62

-continued

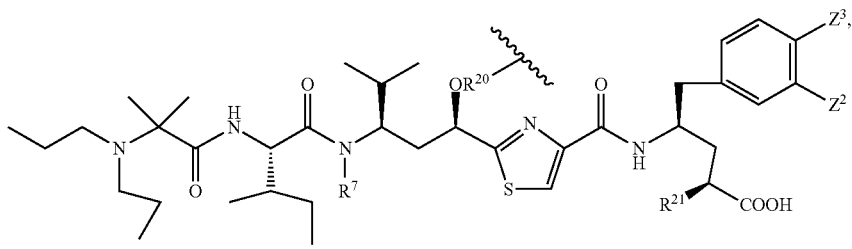
IV-63

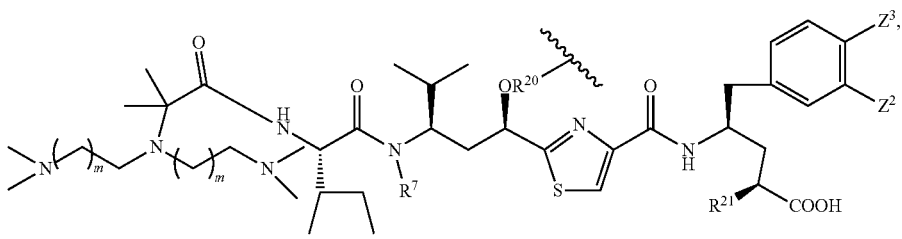
IV-64

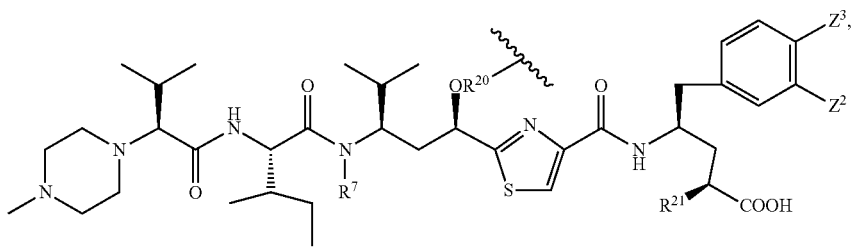
IV-65

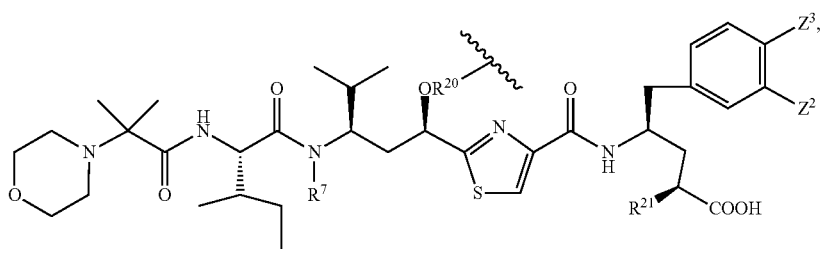
IV-66

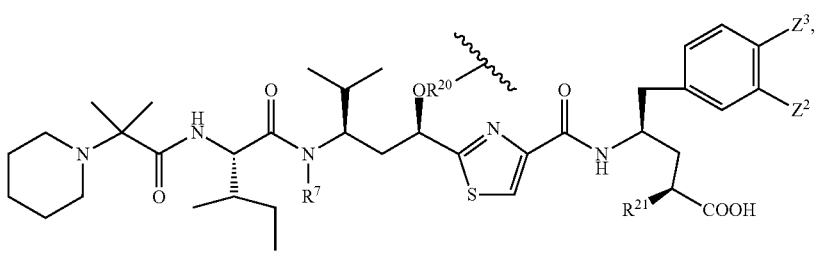
IV-67

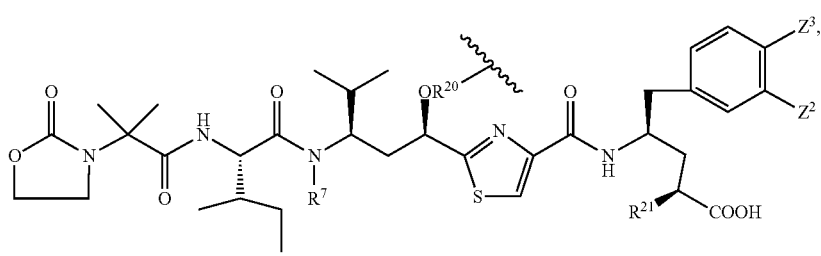
IV-68 or their pharmaceutically acceptable salts, hydrates, or hydrated salts; or the polymorphic crystalline structures of these compounds; or their optical isomers, racemates, diastereomers or enantiomers thereof;

wherein "⸝", $R^7$, $R^{20}$, $R^{21}$, $R^{22}$, $Z^2$, $Z^3$, and $X^2$ are defined the same as above.

In another embodiment, a cell-binding molecule-antimitotic agent conjugate has the formula (V):

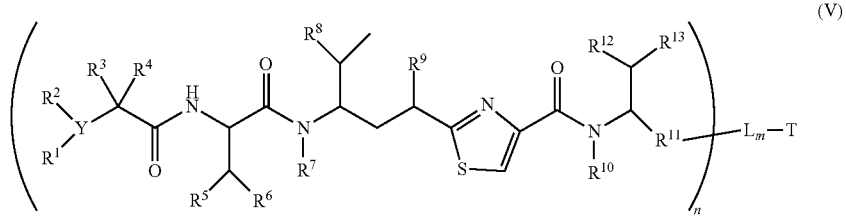

(V)

or their pharmaceutically acceptable salts, hydrates, or hydrated salts; or the polymorphic crystalline structures of these compounds; or their isotopes, optical isomers, racemates, diastereomers or enantiomers thereof;

wherein T, L, m, Y, $R^1$, $R^2$, $R^3$, $R^4$, $R^5$, $R^6$, $R^7$, $R^8$, $R^9$, $R^{10}$, $R^{12}$, $R^{13}$ and n are defined the same as in Formula (II);

Wherein $R^{11}$ is —$R^{14}$—, —$R^{14}$C(=O)$R^{17}$—, —$R^{14}$C(=O)$X^2 R^{17}$—, —$R^{14}X^2 R^{17}$—, —$R^{14}$C(=O)$X^2$—, wherein $R^{17}$ is independently H, OH, $C_1$~$C_8$ of alkyl; $C_2$~$C_8$ of alkenyl, alkynyl, heteroalkyl; $C_3$~$C_8$ of aryl, arylene, heterocyclic, carbocyclic, heterocycloalkyl; or an amino acid, or two amino acid units; $X^2$ is —O—, —S—, —NH—, —NHS($O_2$)—, —NHS(O)—, —N($R^{14}$)—, —O—$R^{14}$—, —S—$R^{14}$—, —S(=O)—$R^{14}$—, or —NH$R^{14}$—; $R^{14}$ is H, $C_1$~$C_8$ of alkyl, heteroalkyl; $C_2$~$C_8$ of alkenyl, alkynyl; $C_3$~$C_8$ of aryl, heterocyclic, carbocyclic, cycloalkyl, alkylcycloalkyl, heterocycloalkyl, heteroalkylcycloalkyl, heteroaralkyl, alkylcarbonyl.

Illustrative compounds inside the bracket of Formula (V) have the structures:

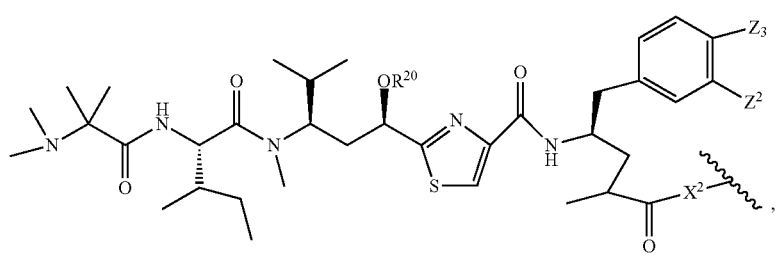

V-01

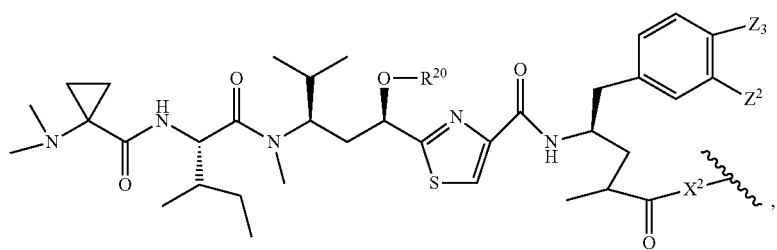

V-02

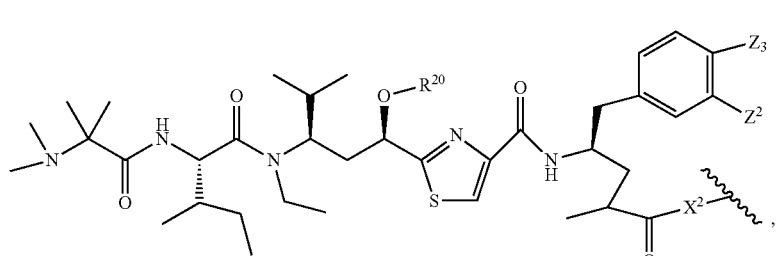

V-03

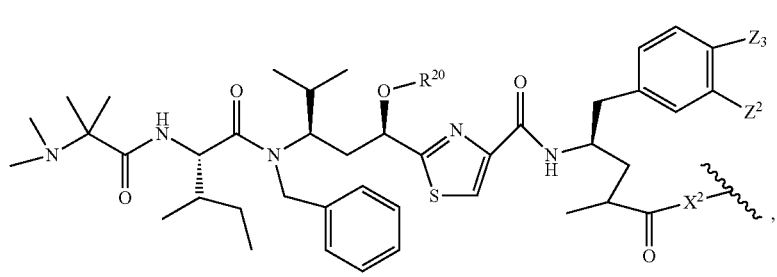

V-04

-continued
V-05
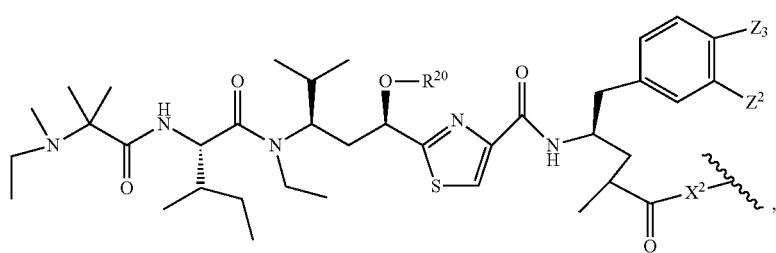
V-06
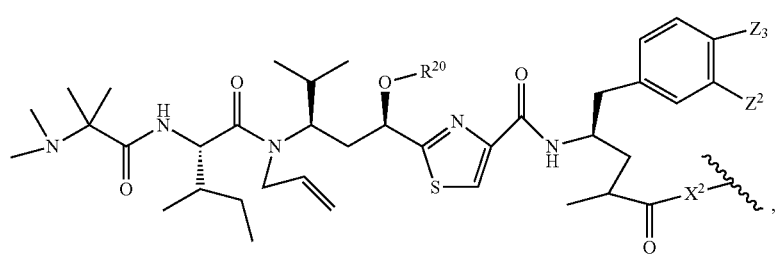
V-07
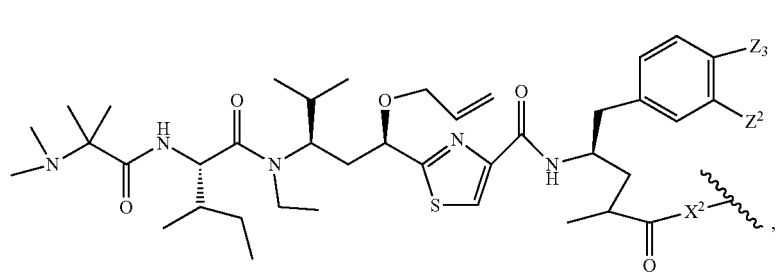
V-08
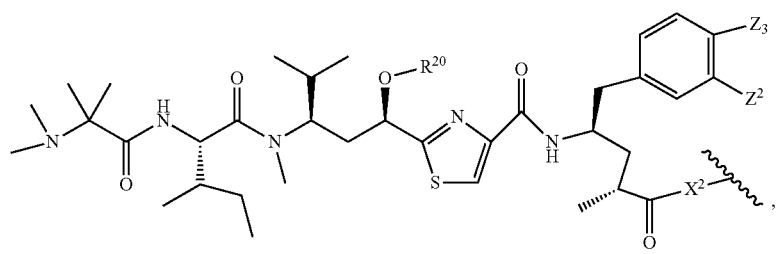
V-09
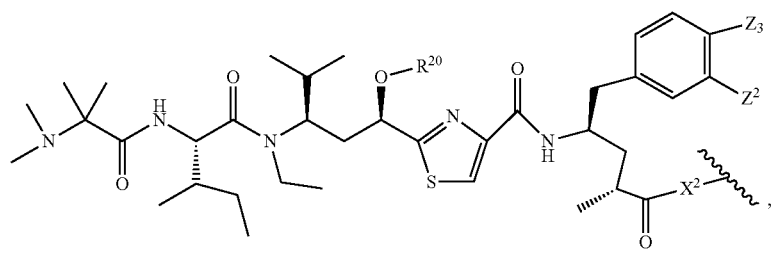
V-10
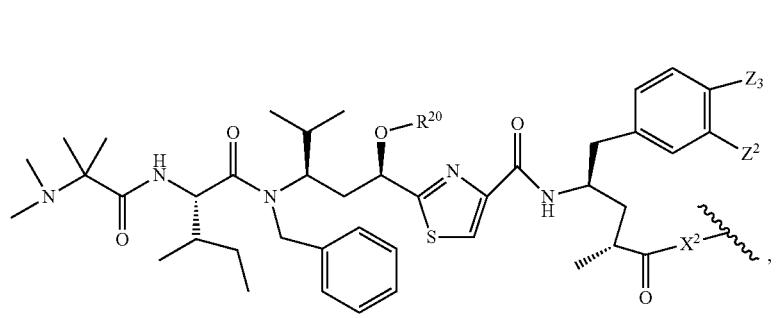

V-11
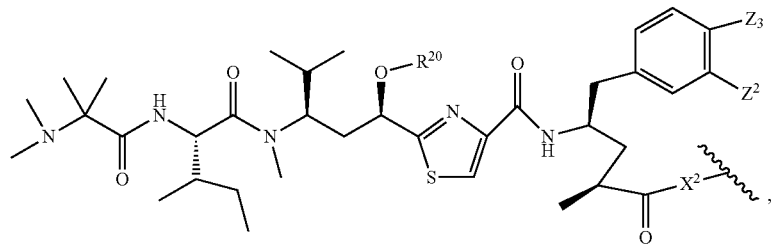
V-12
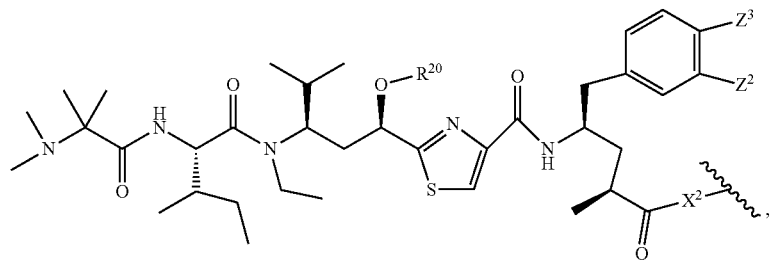
V-13
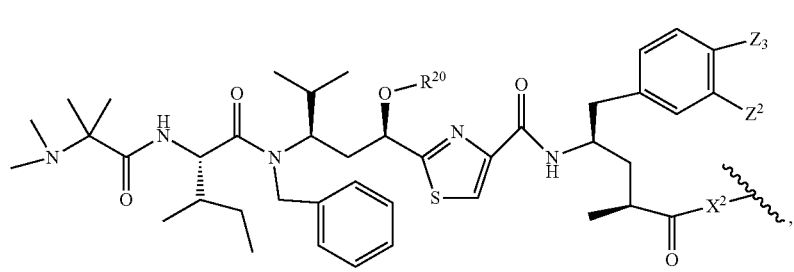
V-14
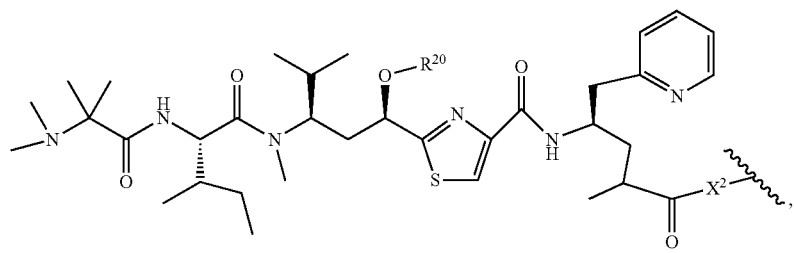
V-15
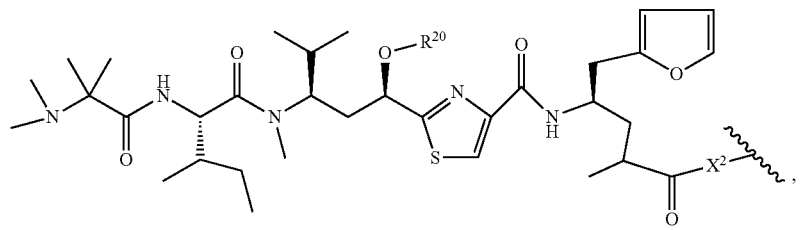
V-16
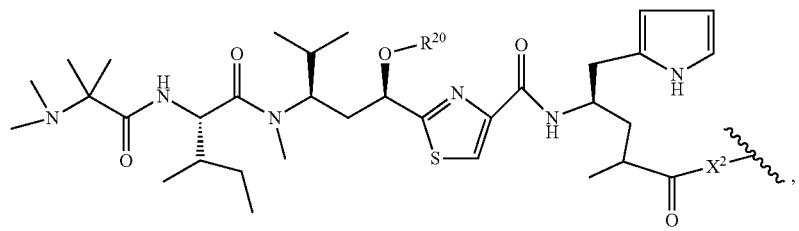

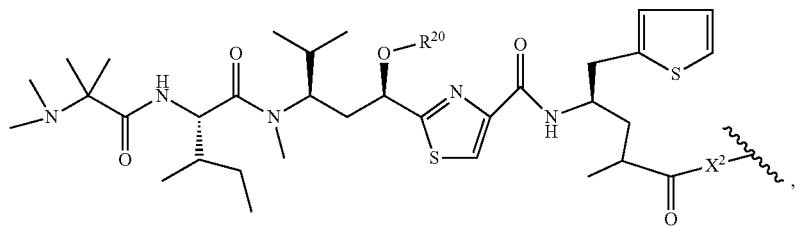
V-17
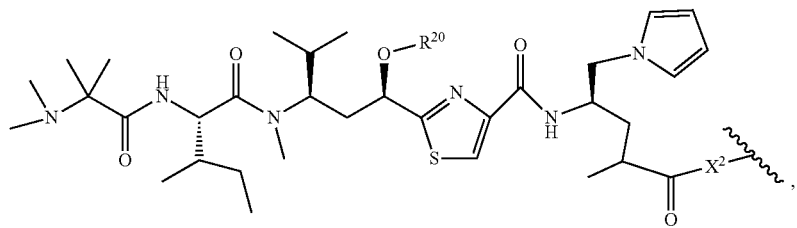
V-18
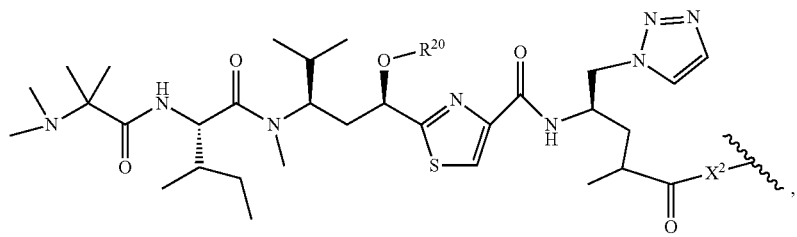
V-19
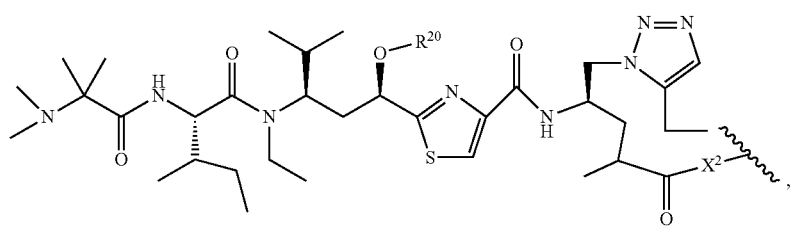
V-20
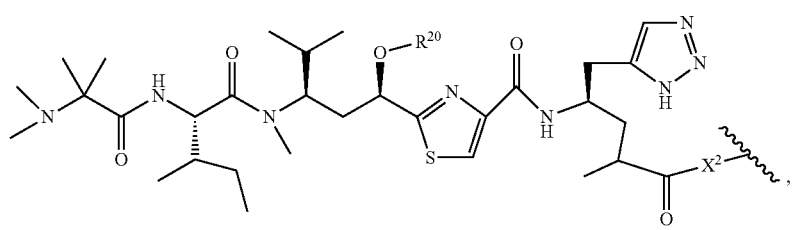
V-21
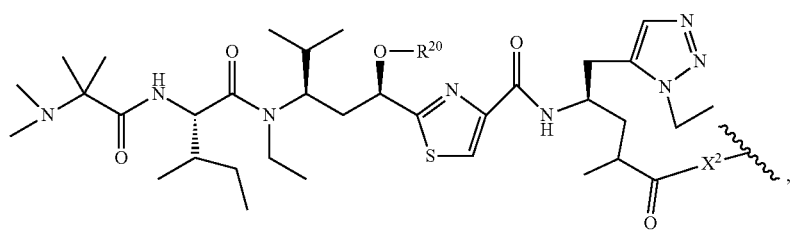
V-22

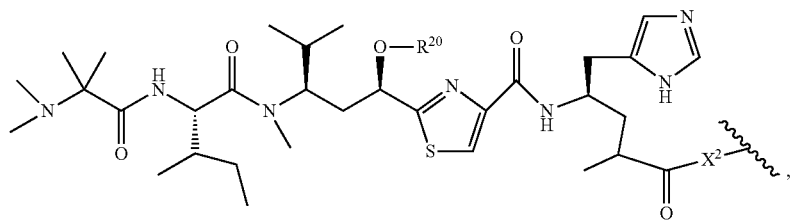
V-23
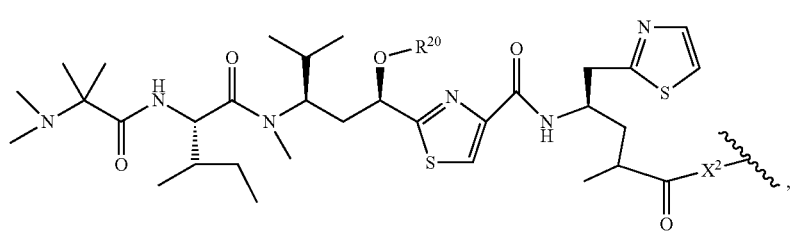
V-24
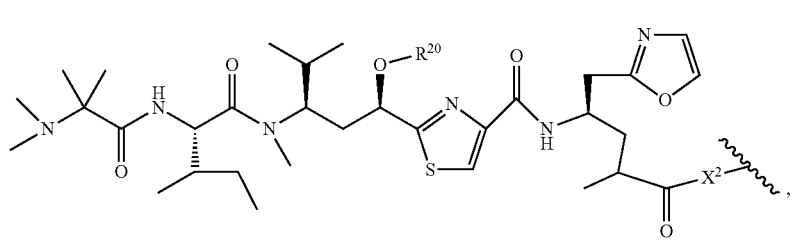
V-25
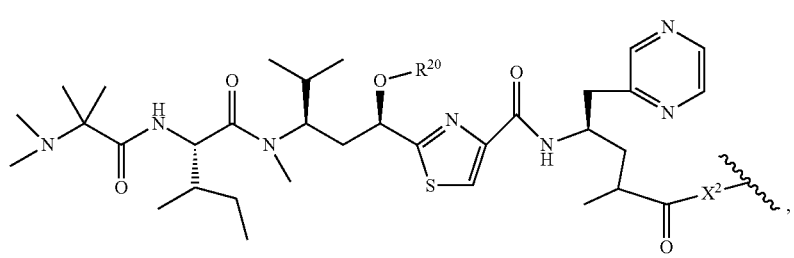
V-26
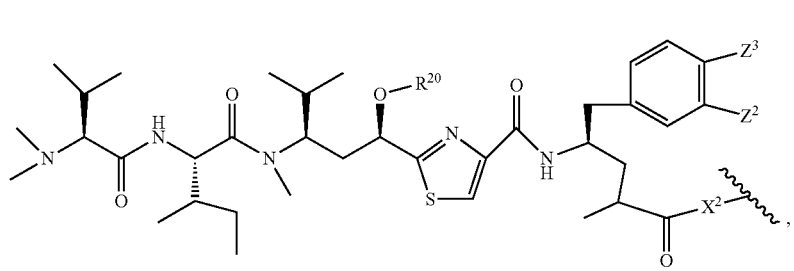
V-27
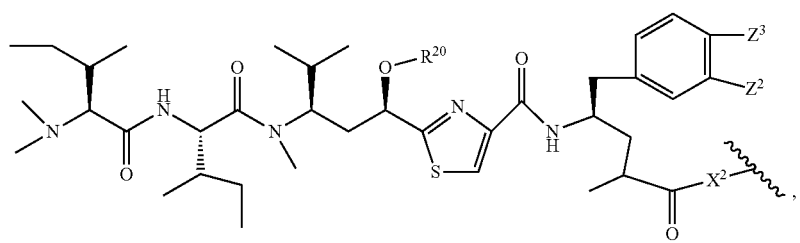
V-28

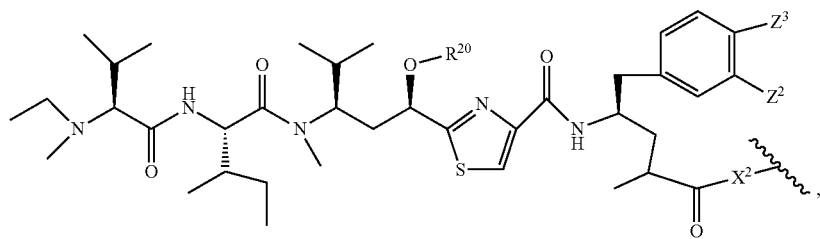
V-29
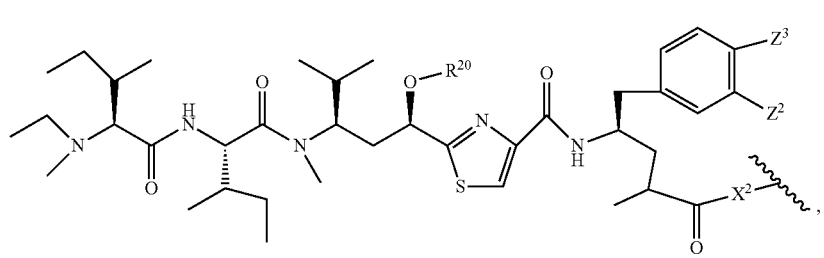
V-30
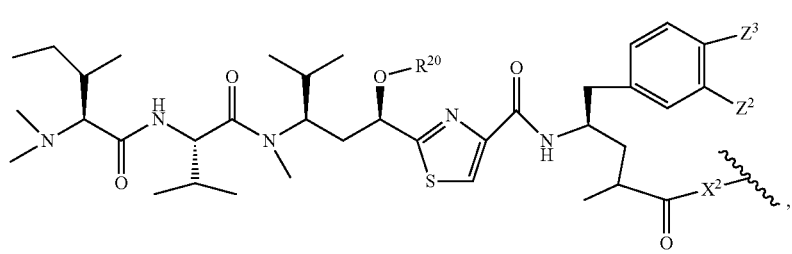
V-31
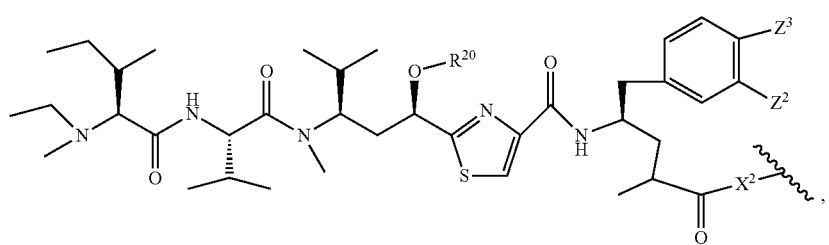
V-32
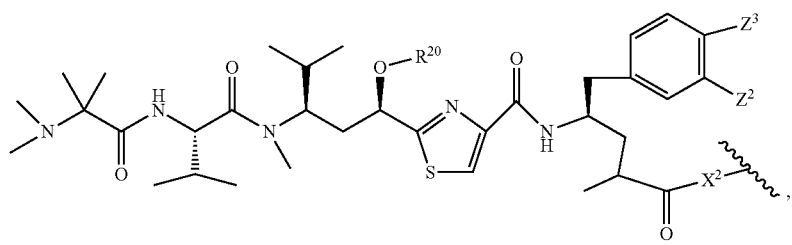
V-33
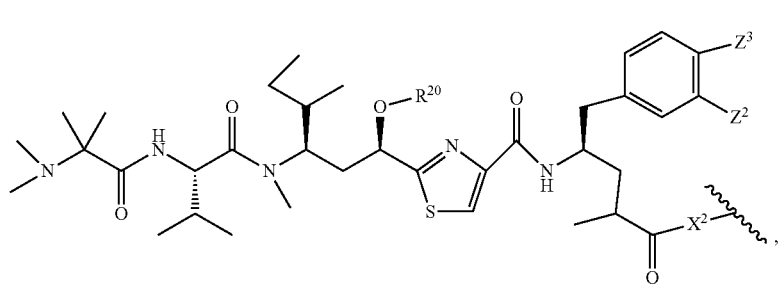
V-34

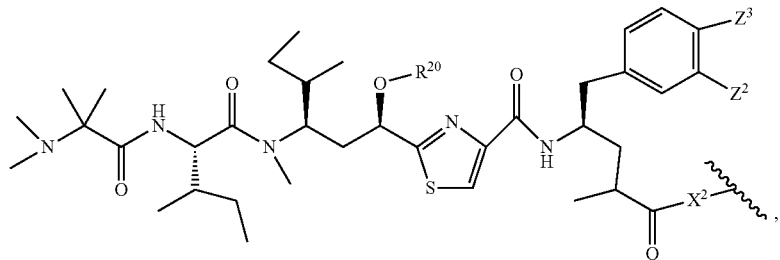
V-35
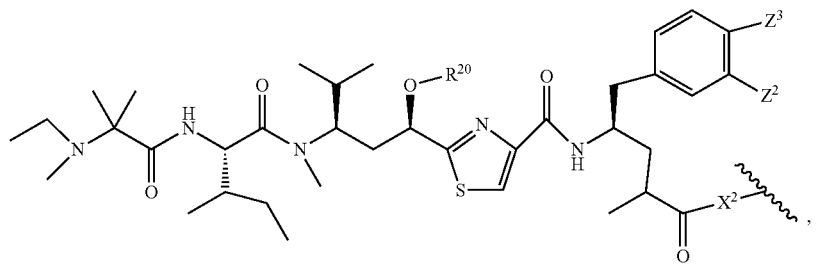
V-36
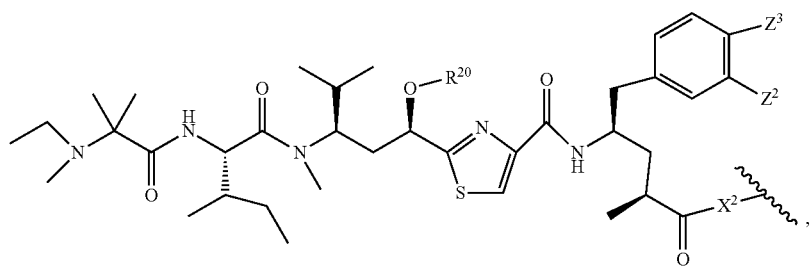
V-37
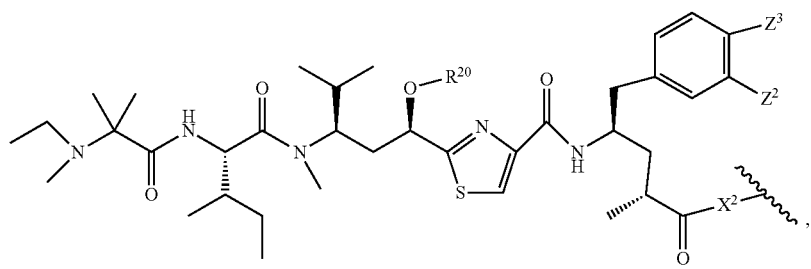
V-38
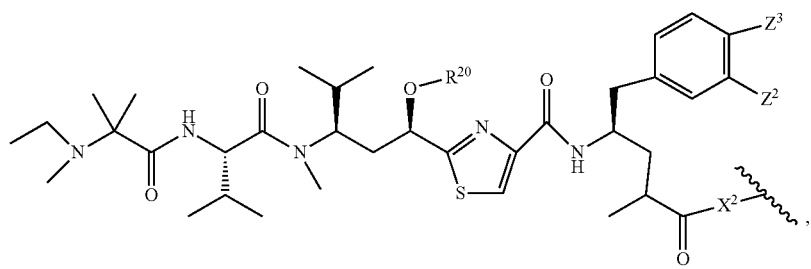
V-39
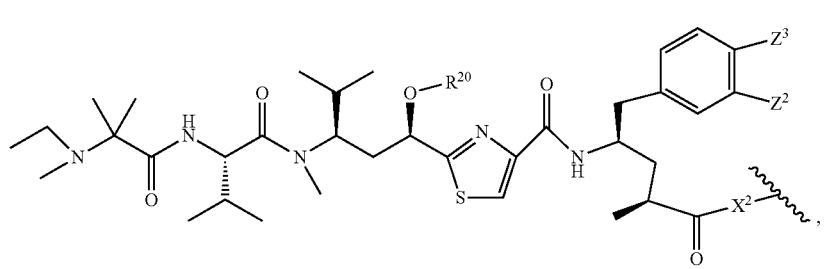
V-40

-continued
V-41
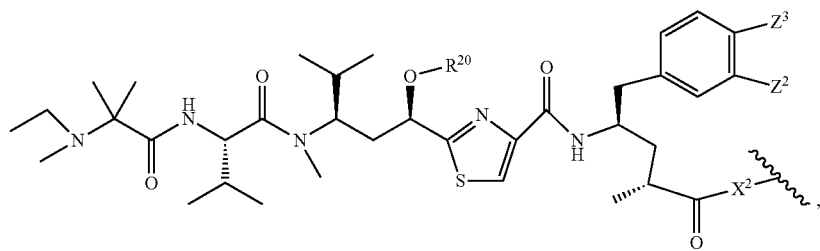
V-42
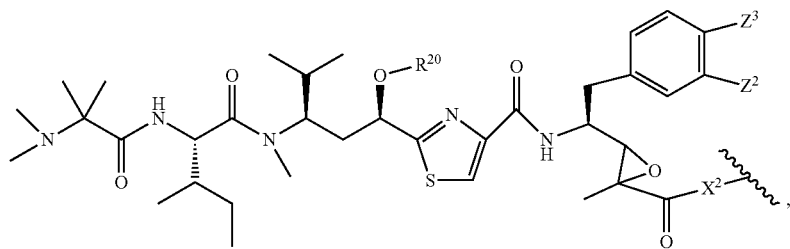
V-43
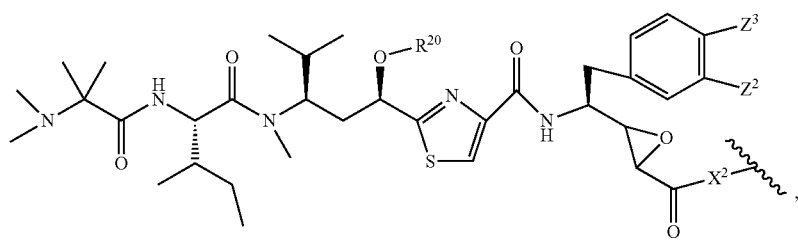
V-44
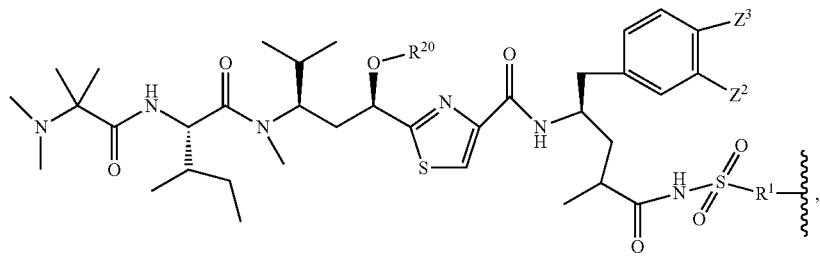
V-45
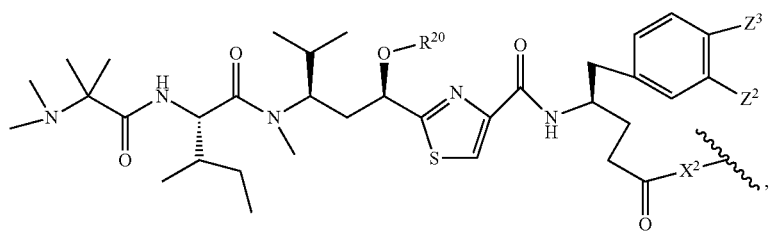
V-46
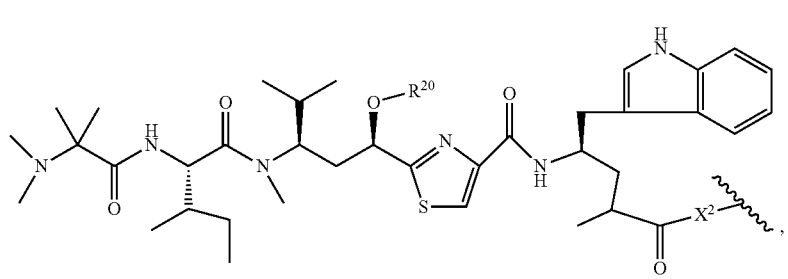

-continued
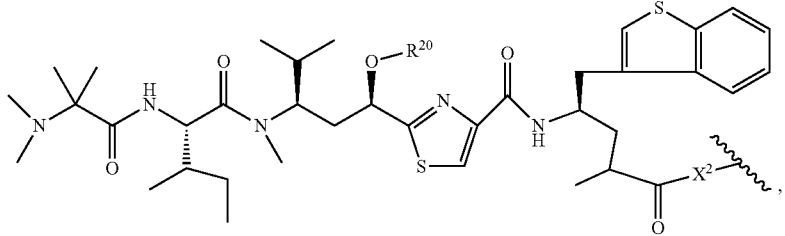
V-47
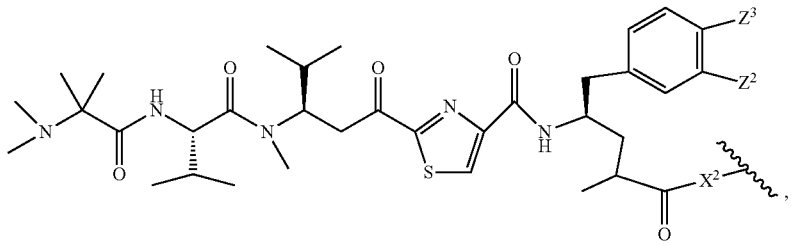
V-48
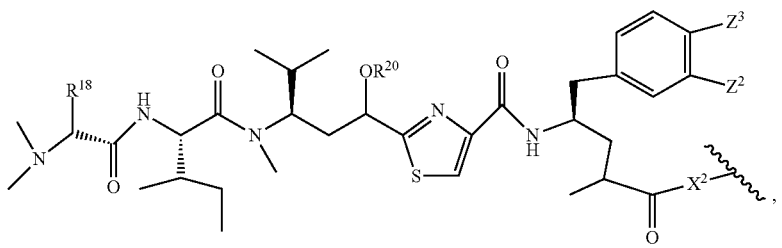
V-49
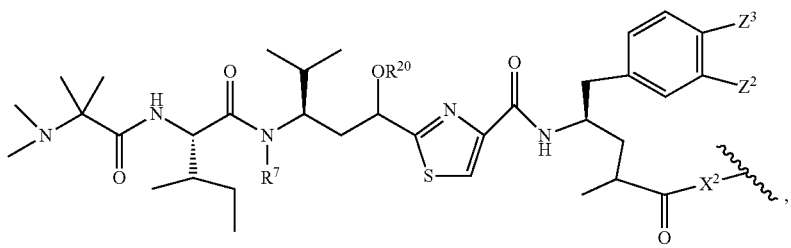
V-50
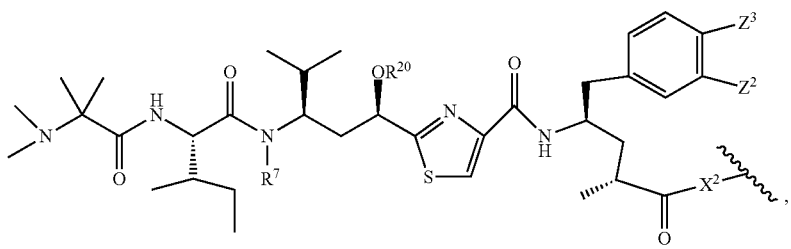
V-51
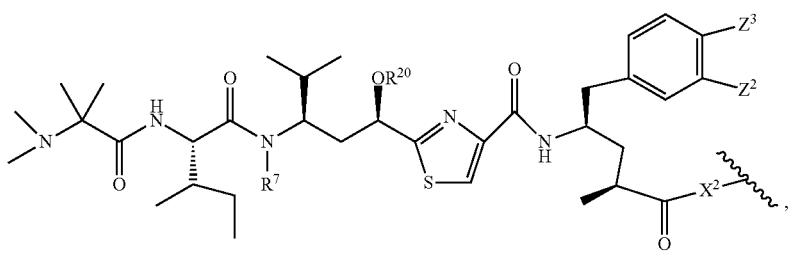
V-52

-continued
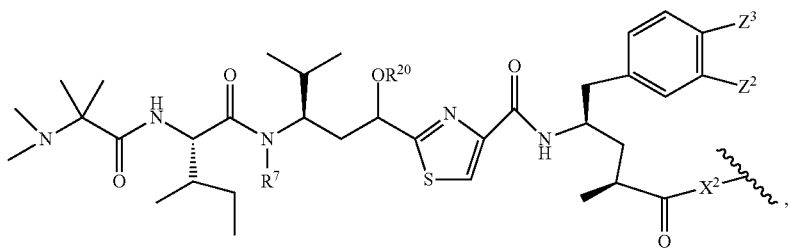
V-53
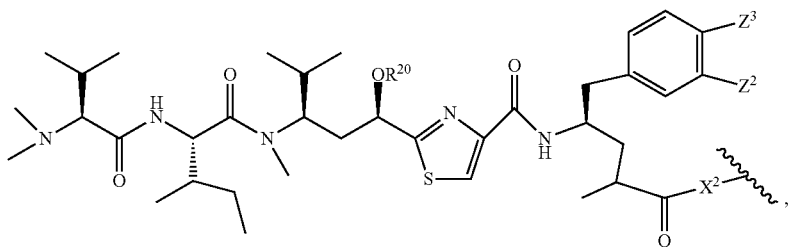
V-54
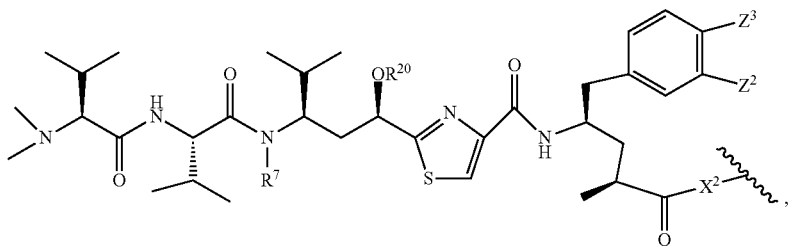
V-55
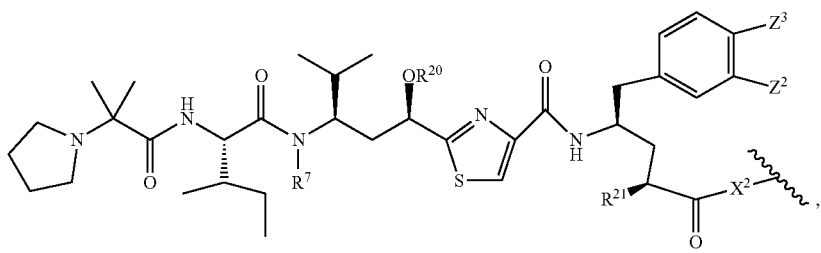
V-56
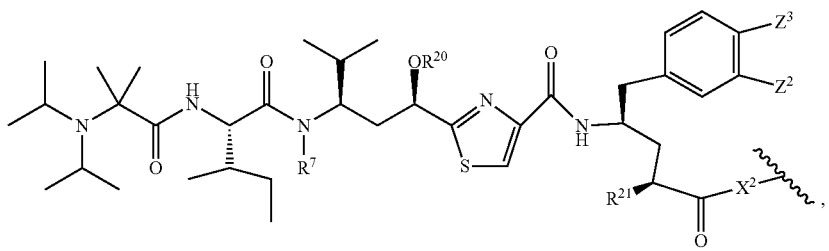
V-57
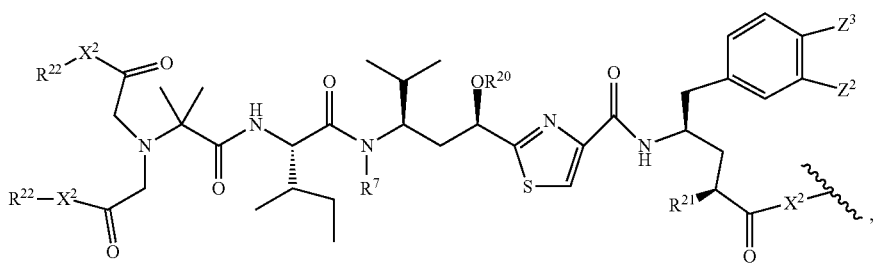
V-58

-continued
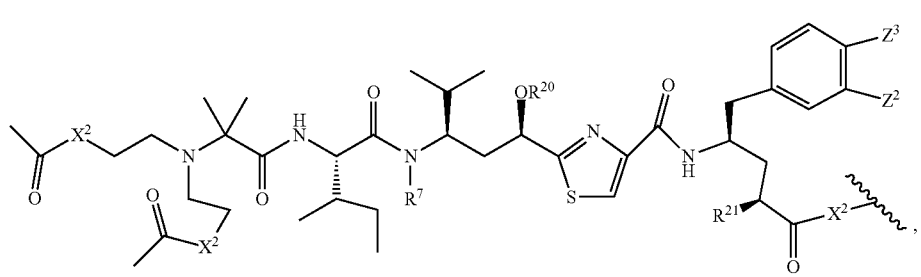
V-59
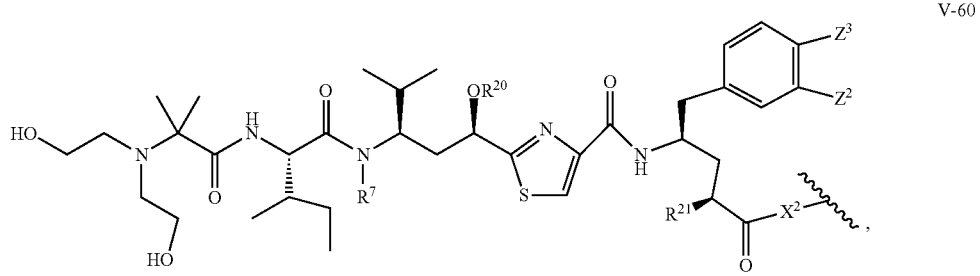
V-60
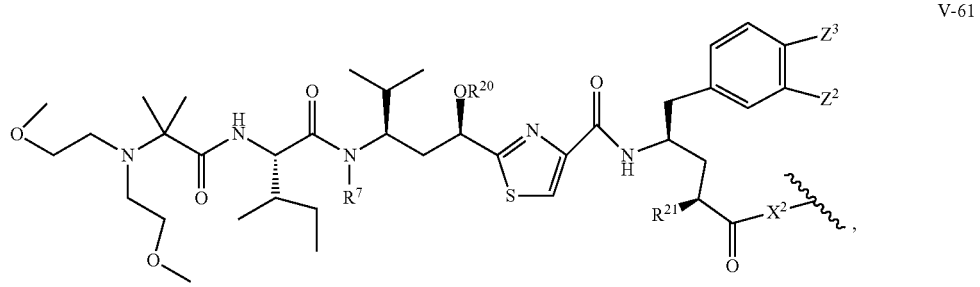
V-61
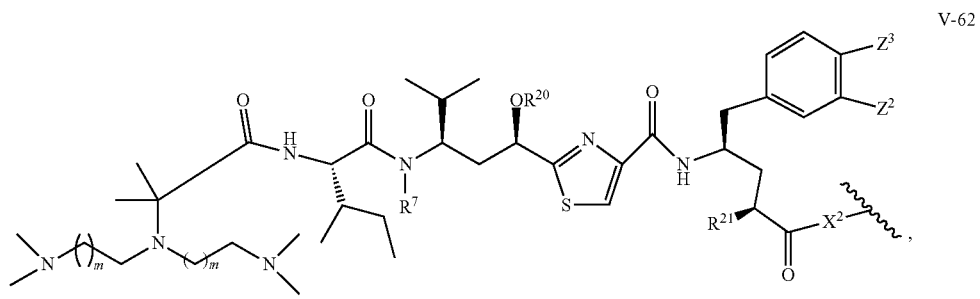
V-62
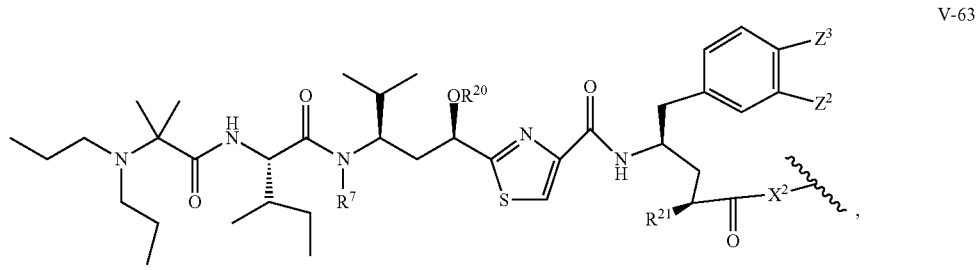
V-63
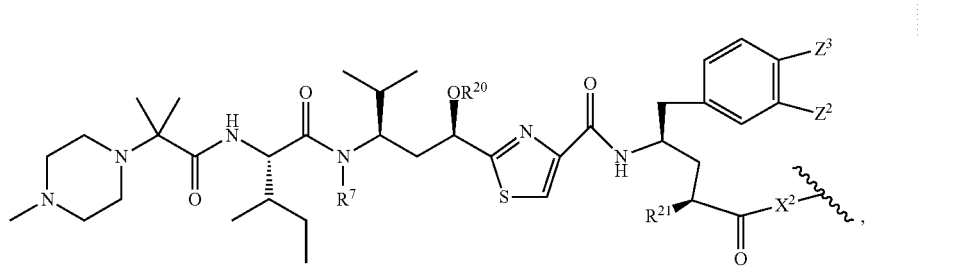
V-64

-continued

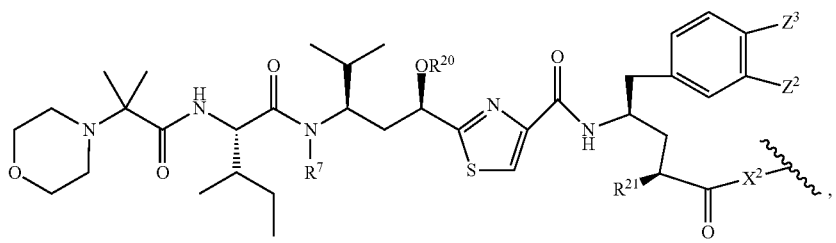
V-65

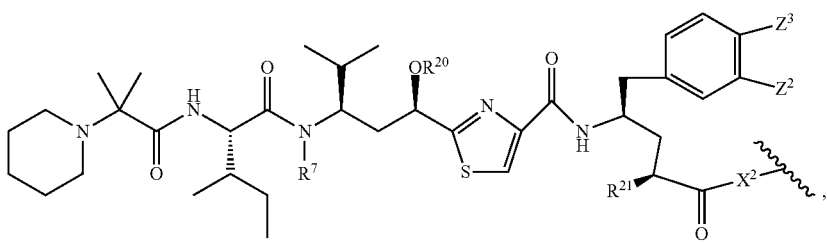
V-66

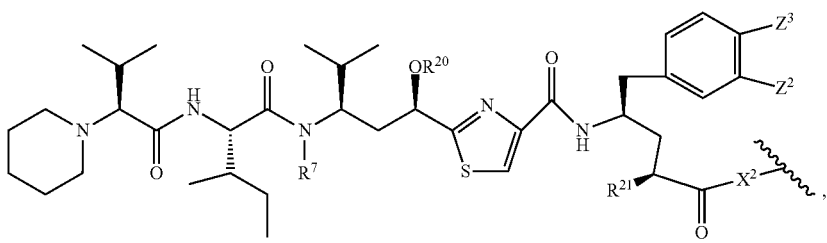
V-67

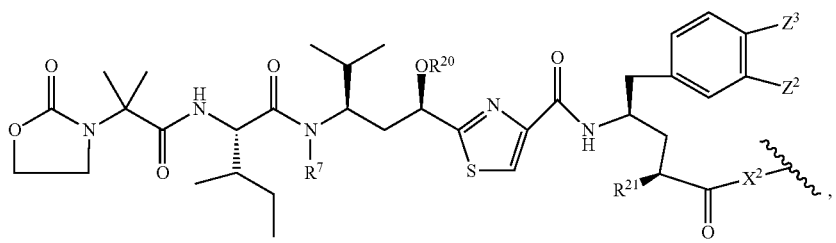
V-68 or their pharmaceutically acceptable salts, hydrates, or hydrated salts; or the polymorphic crystalline structures of these compounds; or their optical isomers, racemates, diastereomers or enantiomers thereof;

wherein " ", $R^7$, $R^{20}$, $R^{21}$, $R^{22}$, $Z^2$, $Z^3$, and $X^2$ are defined the same as above.

In another embodiment, a conjugates of a cell binding-antimitotic agent have the formula (VI)

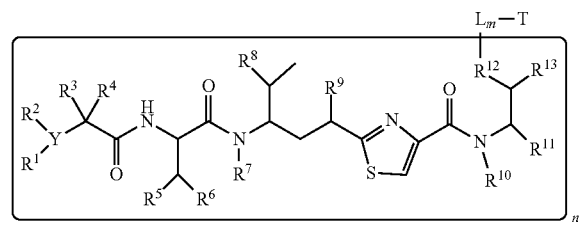
(VI)

or their pharmaceutically acceptable salts, hydrates, or hydrated salts; or the polymorphic crystalline structures of these compounds; or their optical isomers, racemates, diastereomers or enantiomers thereof;

wherein T, L, m, Y, $R^1$, $R^2$, $R^3$, $R^4$, $R^5$, $R^6$, $R^7$, $R^8$, $R^9$, $R^{11}$, $R^{13}$ and n are defined the same as in Formula (II);

wherein $R^{12}$ is independently $R^{14}$, —O—, —S—, —NH—, =N—, =NNH—, —N($R^{14}$)—, —$OR^{14}$—, C(O)O—, C(O)NH—, C(O)$NR^{14}$—, —$SR^{14}$—, —S(=O)$R^{14}$—, —$NHR^{14}$—, —$CH_2OP$(=O)($OR^{15}$)—, —P(=O)($OR^{15}$)—, —OP(=O)($OR^{15}$)O—, —$SO_2R^{14}$, $R^{14}$, $R^{15}$ are independently $C_1$-$C_8$ of alkyl, heteroalkyl; $C_2$-$C_8$ of alkenyl, alkynyl; $C_3$-$C_8$ of aryl, heterocyclic, carbocyclic, cycloalkyl, alkylcycloalkyl, heterocycloalkyl, heteroaralkyl, heteroalkylcycloalkyl, alkylcarbonyl.

Illustrative compounds inside the bracket of Formula (VI) have the structures:

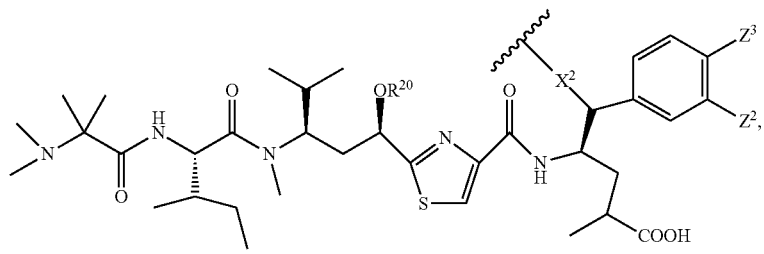
VI-01
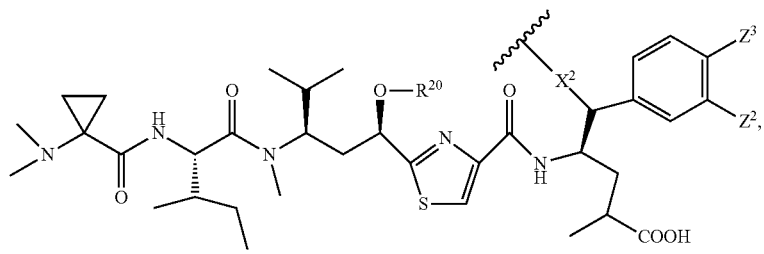
VI-02
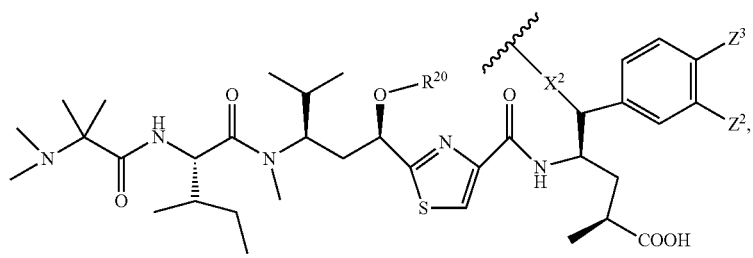
VI-03
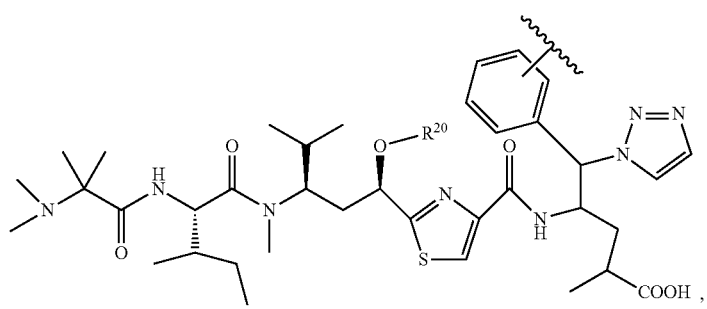
VI-04
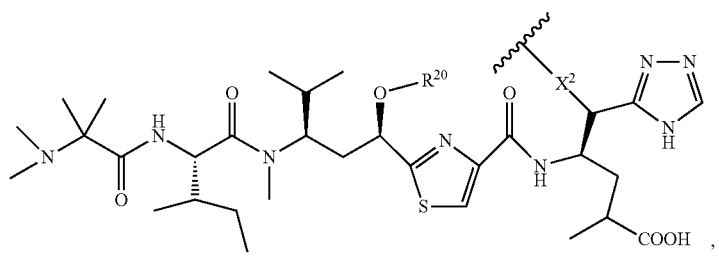
VI-05
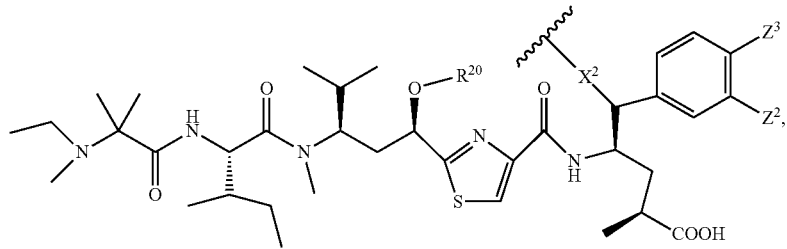
VI-06

-continued
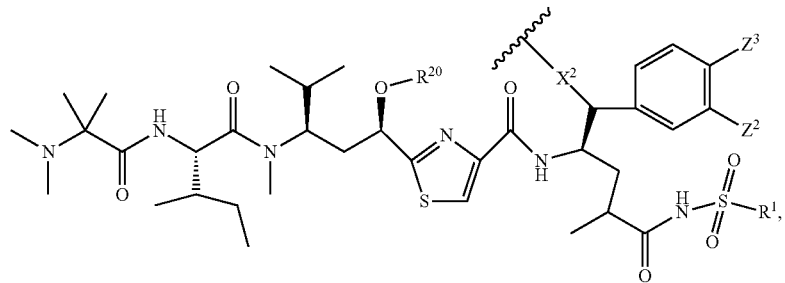
VI-07
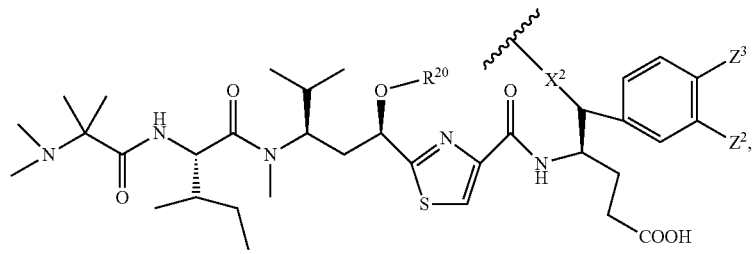
VI-08
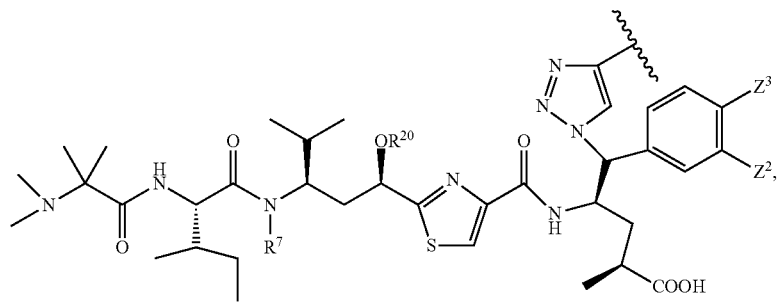
VI-09
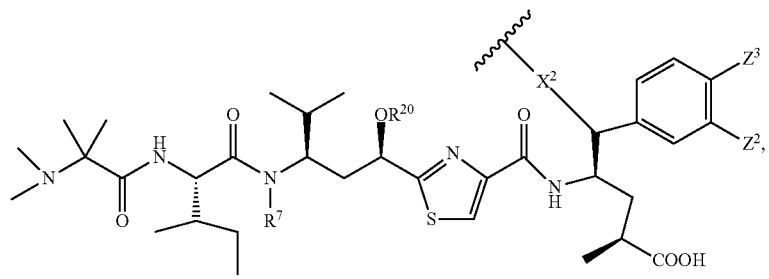
VI-10
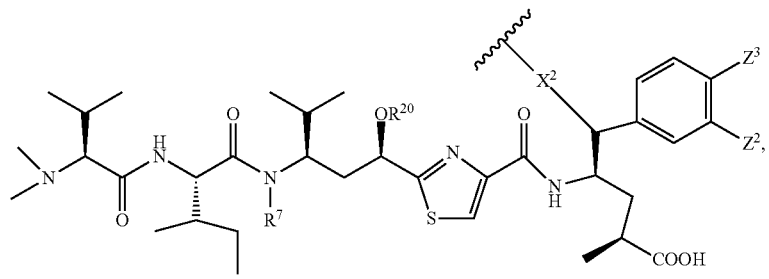
VI-11

VI-12

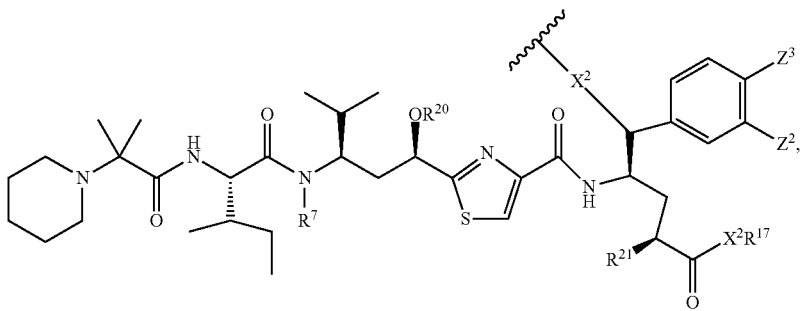

or their pharmaceutically acceptable salts, hydrates, or hydrated salts; or the polymorphic crystalline structures of these compounds; or their optical isomers, racemates, diastereomers or enantiomers thereof;

wherein $R^7$, $R^{17}$, $R^{20}$, $R^{21}$, $Z^2$, $Z^3$, and $X^2$ are defined the same as above.

In another embodiment, the conjugates of the cell-surface binding molecule-antimitotic agents have the Formula (VII):

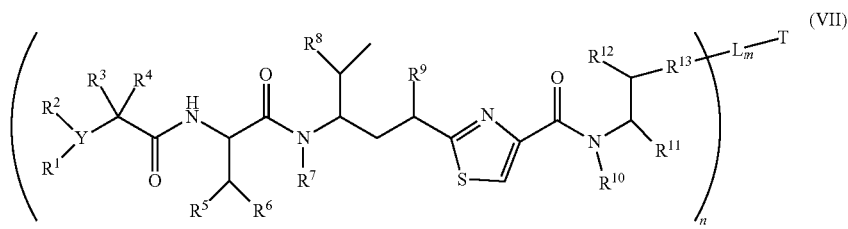

(VII)

or their pharmaceutically acceptable salts, hydrates, or hydrated salts; or the polymorphic crystalline structures of these compounds; or their optical isomers, racemates, diastereomers or enantiomers thereof, Wherein T, L, n, m, Y, $R^1$, $R^2$, $R^3$, $R^4$, $R^5$, $R^6$, $R^8$, $R^{10}$, $R^{11}$, and $R^{12}$ are defined the same as in Formula (II);

Wherein $R^{13}$ is $C_1$~$C_{10}$ of alkyl, heteroalkyl, alkyl acid, alkyl amide, alkyl amine, or Ar; Ar refers to a aromatic or hetero aromatic group, composed of one or several rings, comprising four to ten carbon, preferentially four to six carbon atoms. The term of hetero aromatic group refers one or several carbon on aromatic group, preferentially one, two or three carbon atoms are replaced by O, N, Si, Se, P or S, preferentially O, S, N. The term aryl or Ar also refers to a aromatic group, wherein one or several H atoms are replaced independently by $R^{18}$, F, Cl, Br, I, $OR^{16}$, $SR^{16}$, $NR^{16}R^{18}$, $N=NR^{16}$, $N=R^{16}$, $NR^{16}R^{18}$, $NO_2$, $SOR^{16}R^{18}$, $SO_2R^{16}$, $SO_3R^{16}$, $OSO_3R^{16}$, $PR^{16}R^{18}$, $POR^{16}R^{18}$, $POO_2R^{16}R^{18}$, $OPO_3R^{16}R^{18}$, or $POO_3R^{16}R^{18}$ wherein $R^{16}$, $R^{18}$ are independently H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, alkylcycloalkyl, heterocycloalkyl, heteroaralkyl, heteroalkylcycloalkyl, alkylcarbonyl; or $C_4$~$C_{12}$ glycosides; or pharmaceutical salts.

Illustrative examples of compounds inside the bracket of Formula (VII) have the structures:

VII-01

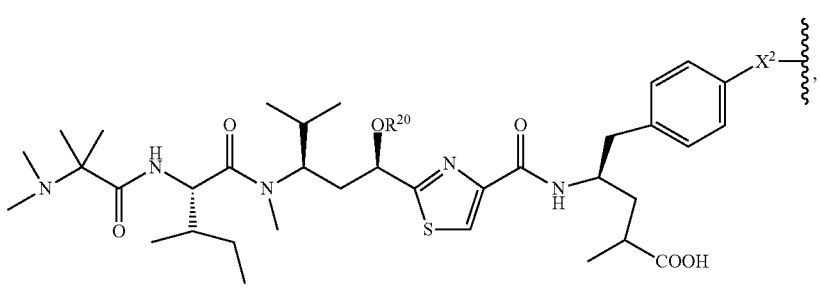

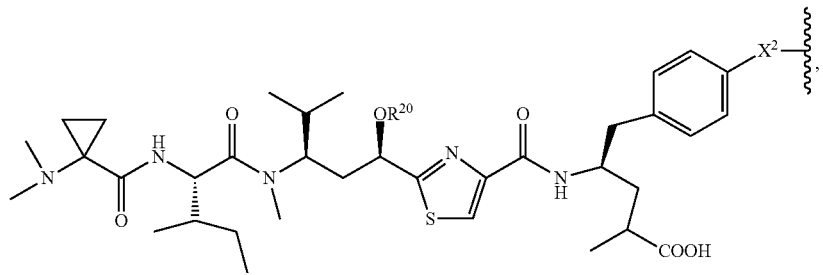
VII-02
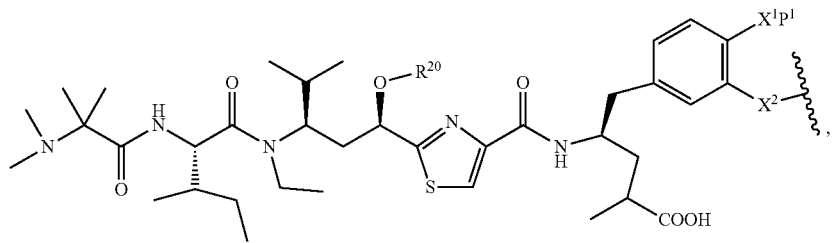
VII-03
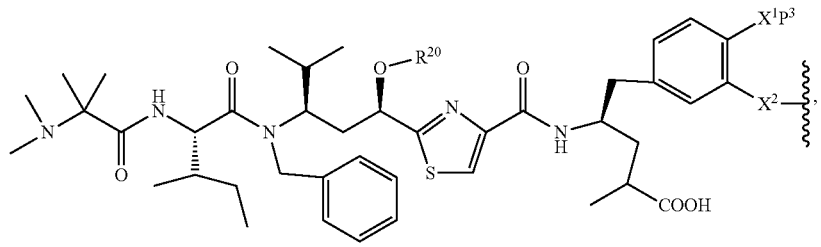
VII-04
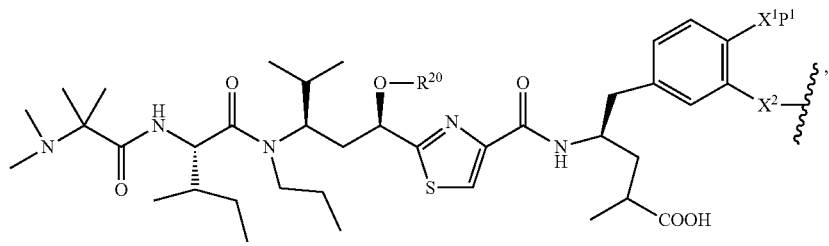
VII-05
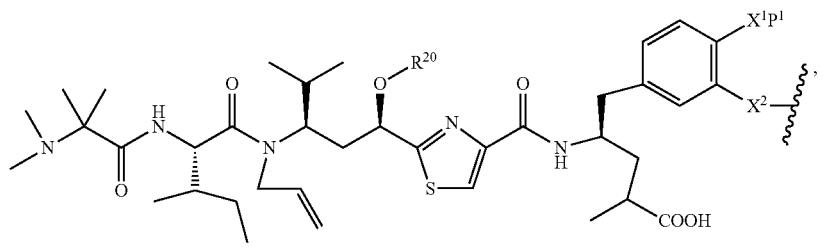
VII-06
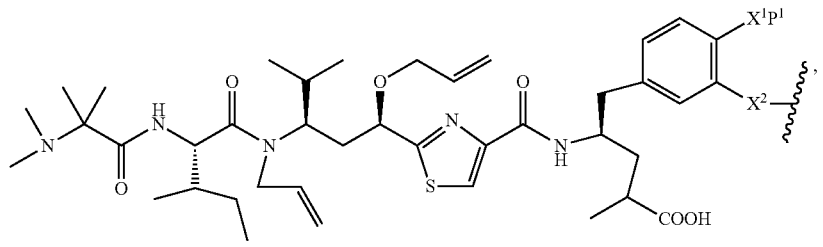
VII-07

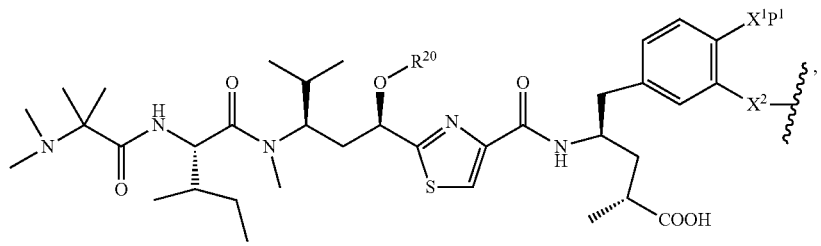
VII-08
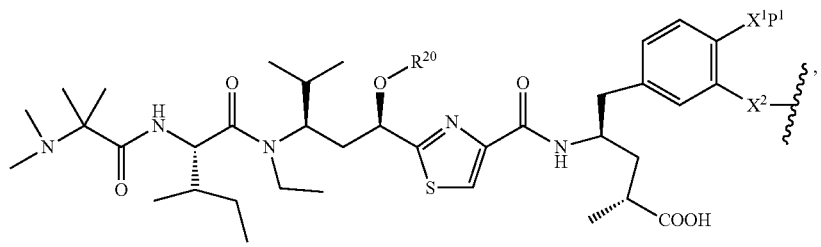
VII-09
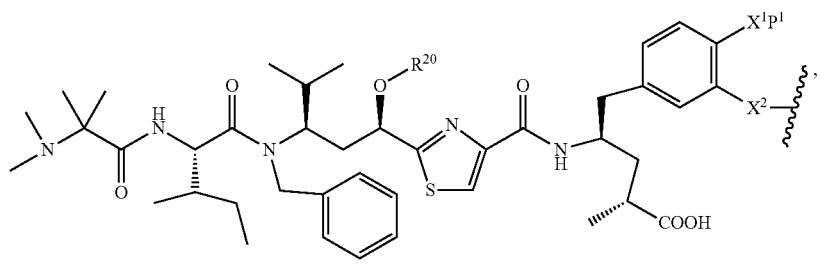
VII-10
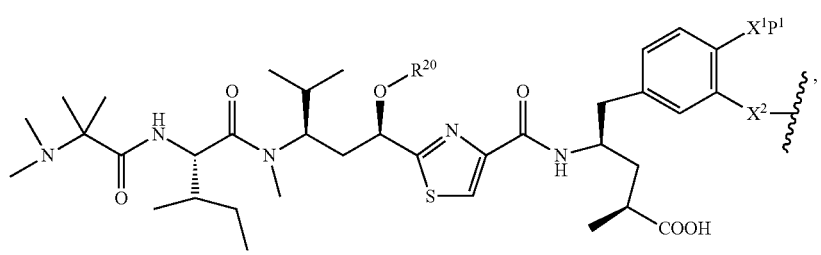
VII-11
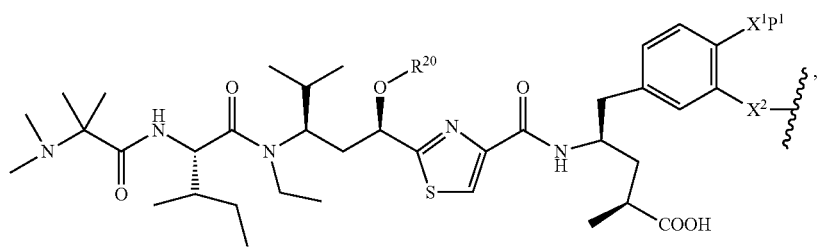
VII-12
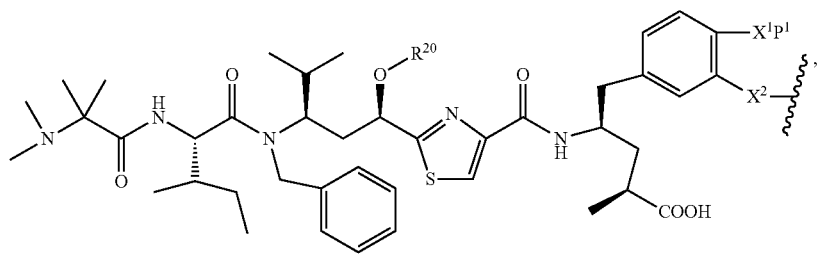
VII-13

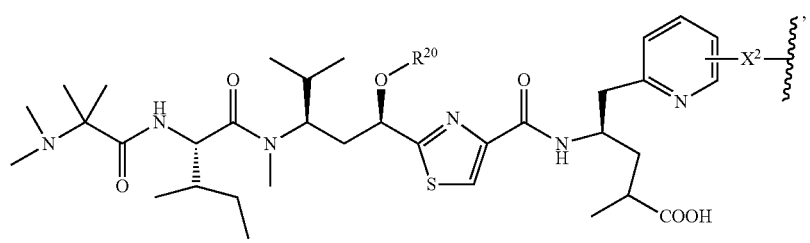
VII-14
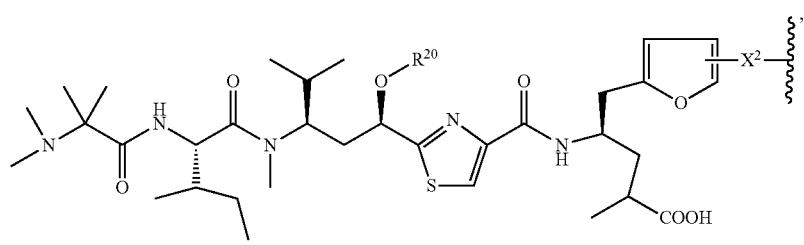
VII-15
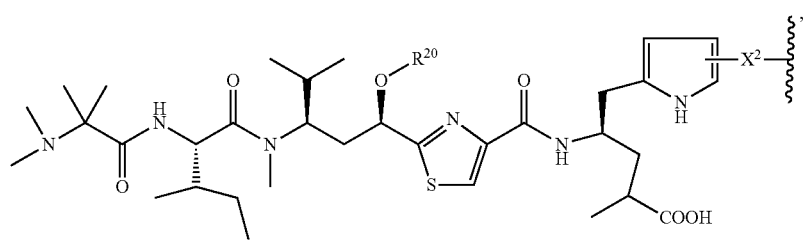
VII-16
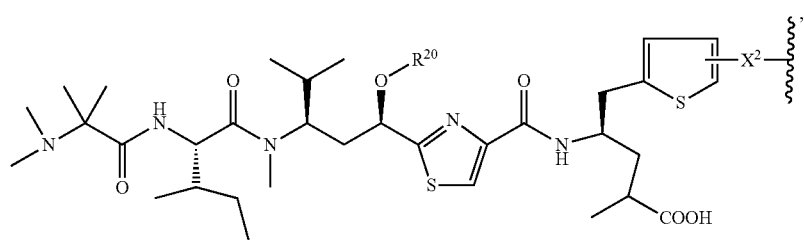
VII-17
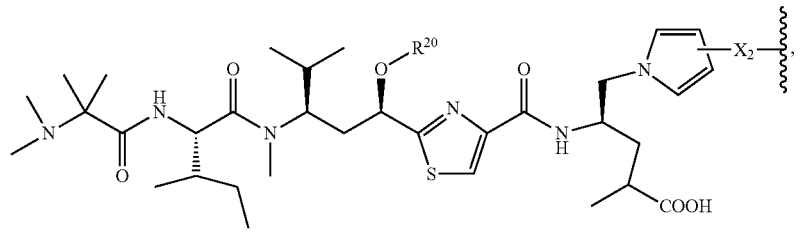
VII-18
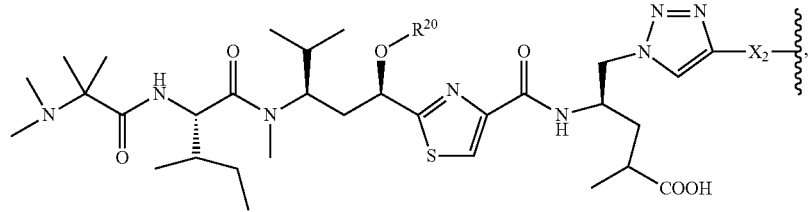
VII-19

-continued
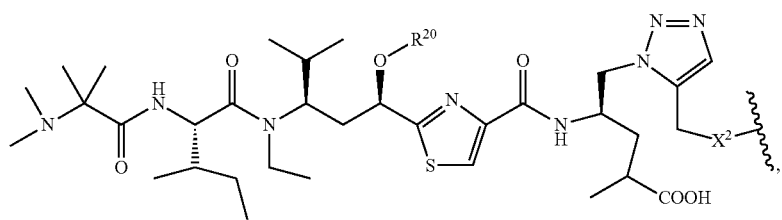
VII-20
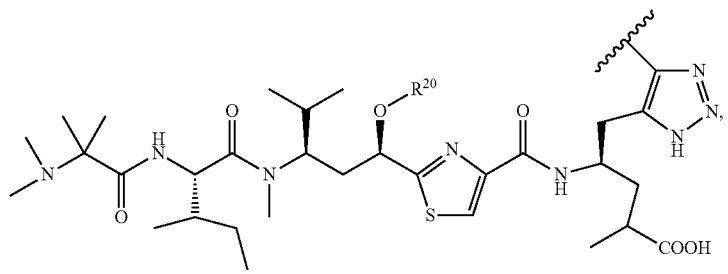
VII-21
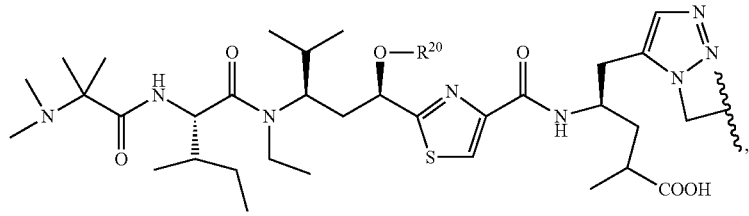
VII-22
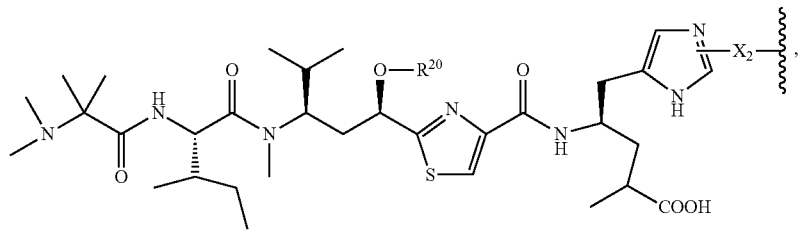
VII-23
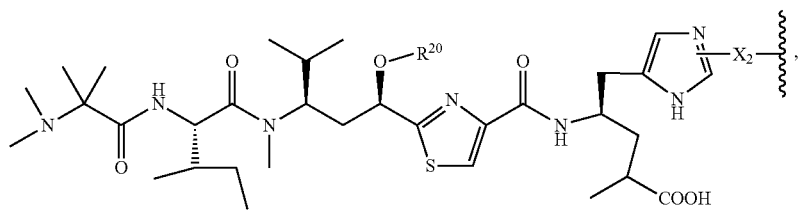
VII-24
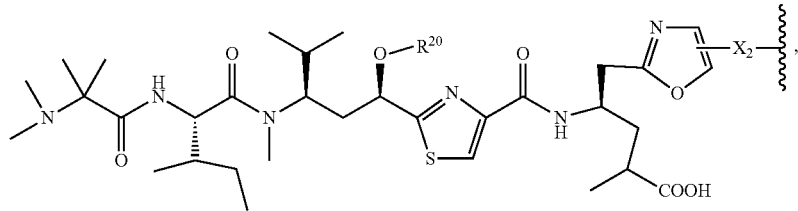
VII-25
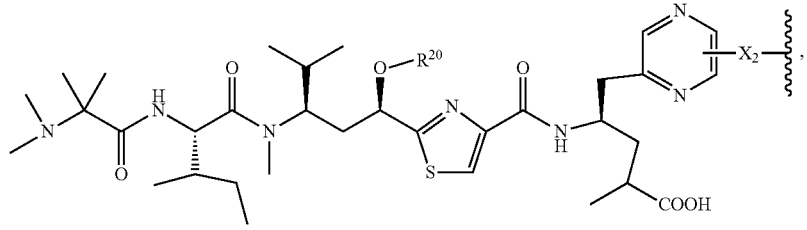
VII-26

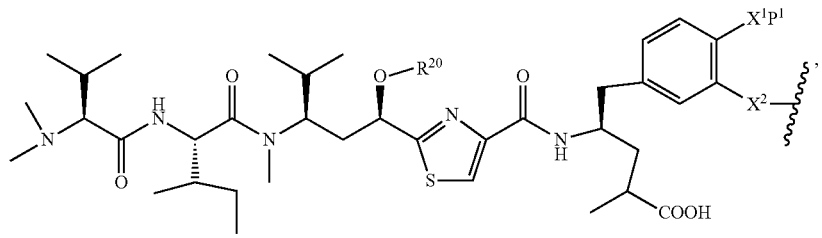
VII-27
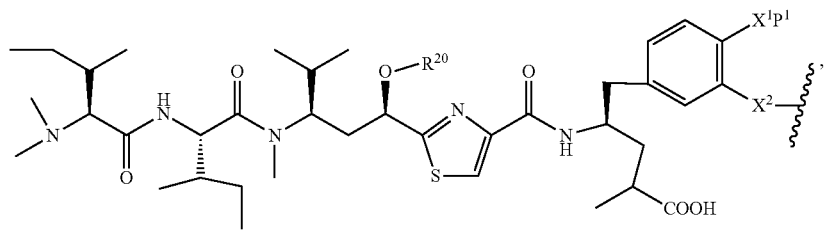
VII-28
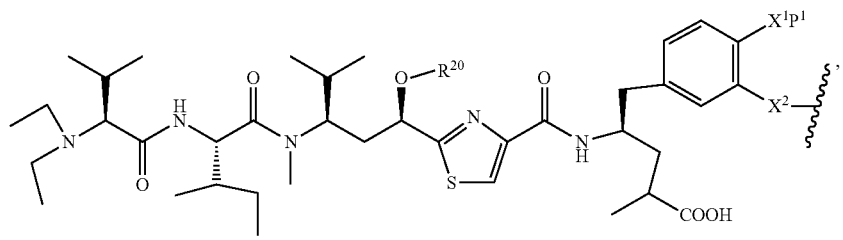
VII-29
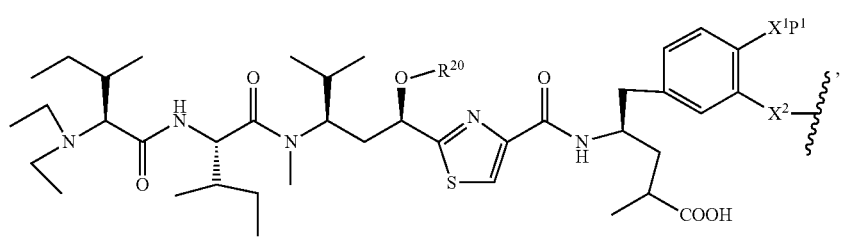
VII-30
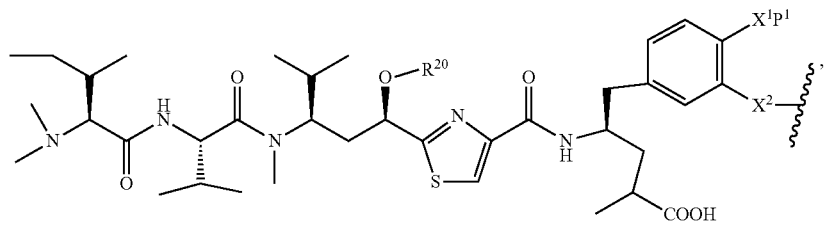
VII-31
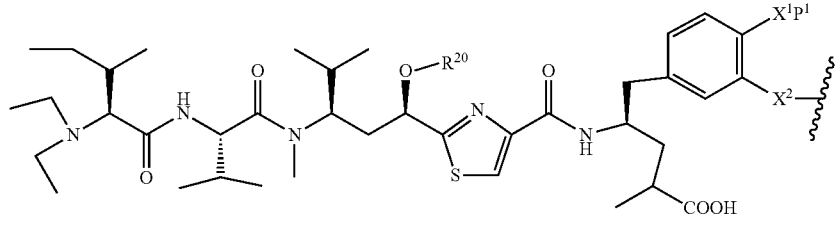
VII-32
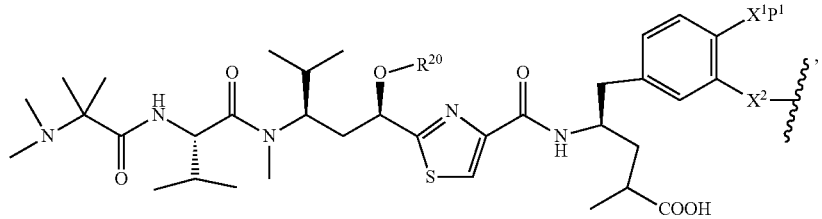
VII-33

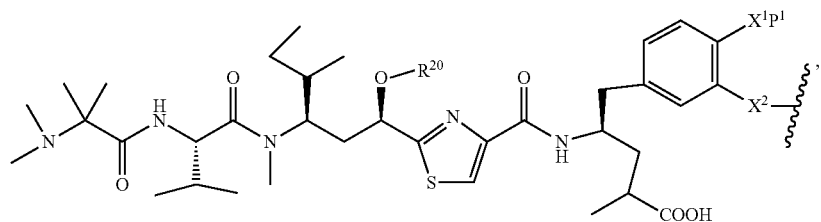
VII-34
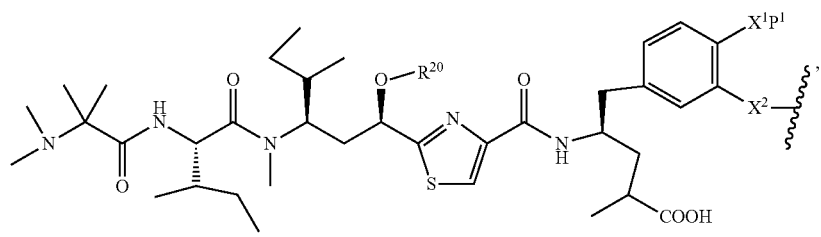
VII-35
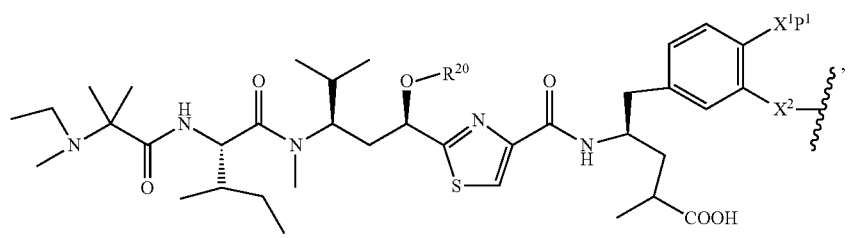
VII-36
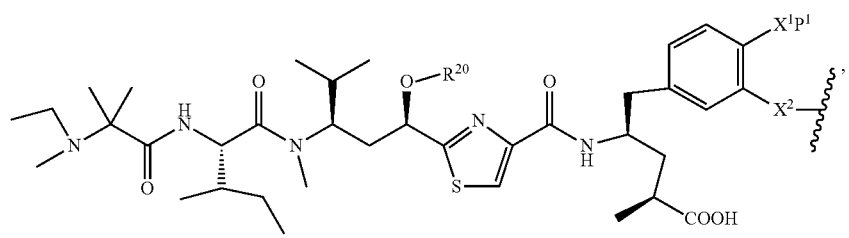
VII-37
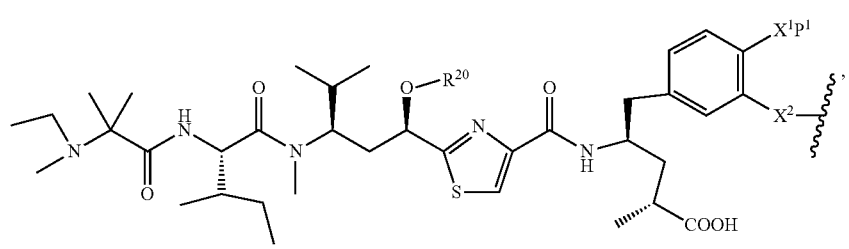
VII-38
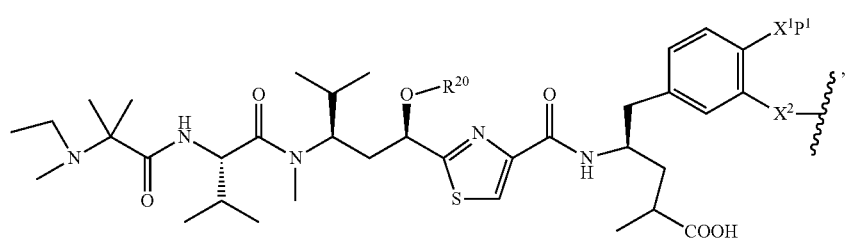
VII-39

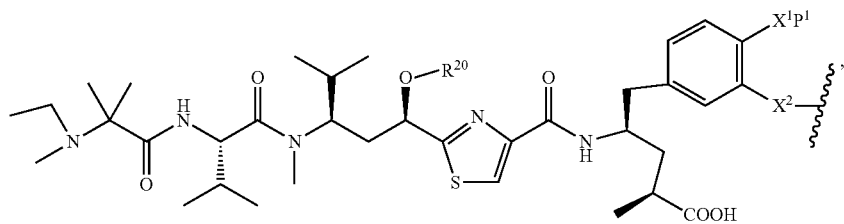
VII-40
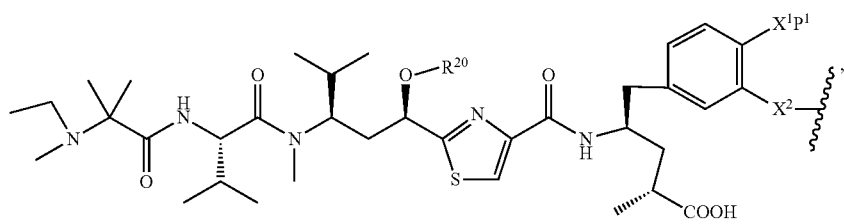
VII-41
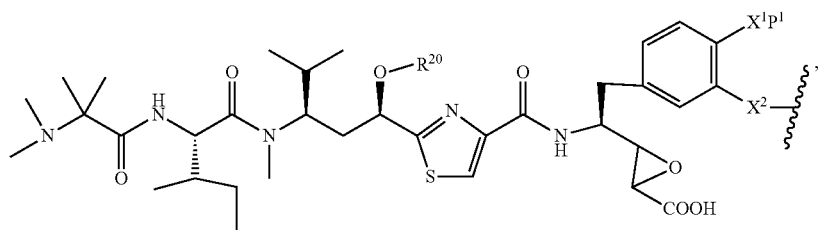
VII-42
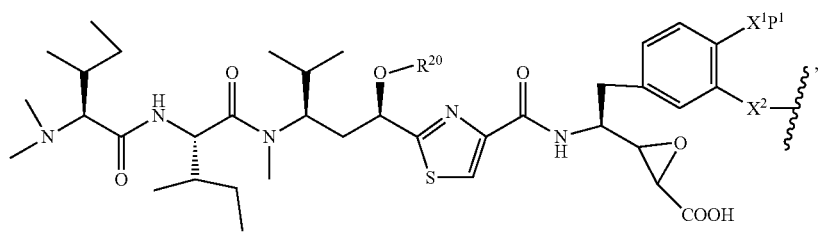
VII-43
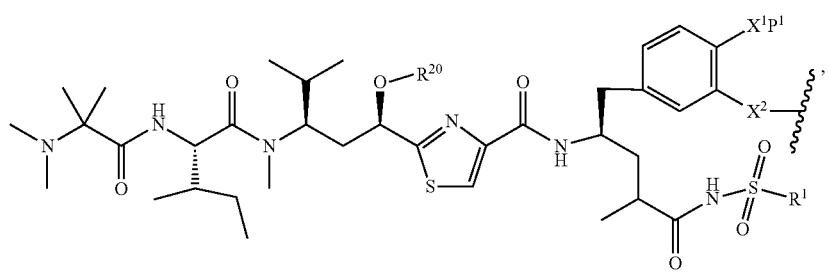
VII-44
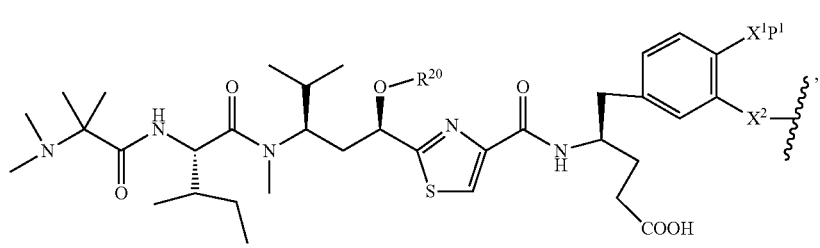
VII-45

VII-46
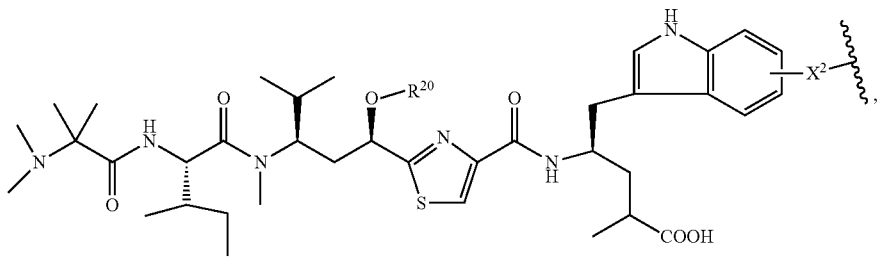
VII-47
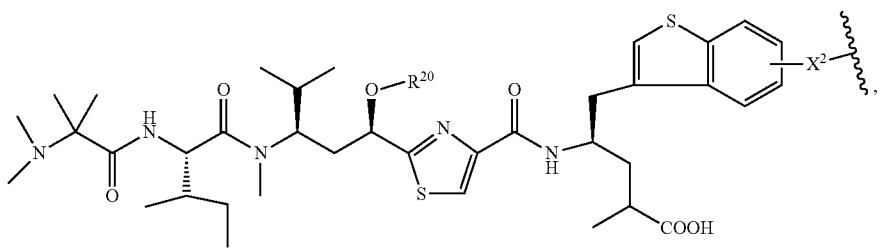
VII-48
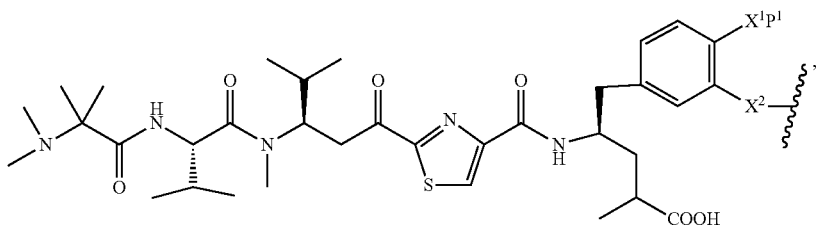
VII-49
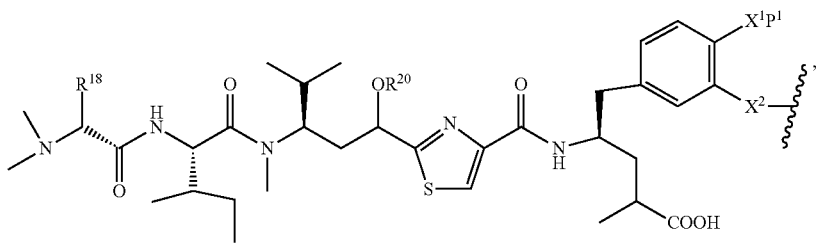
VII-50
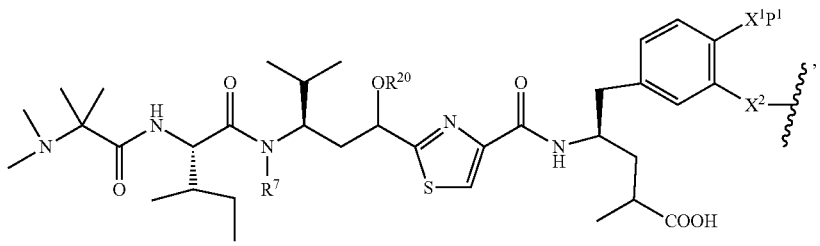
VII-51
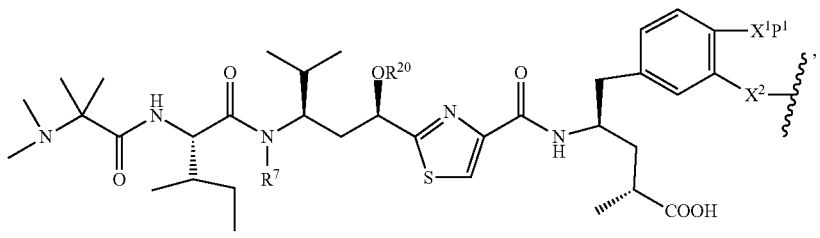

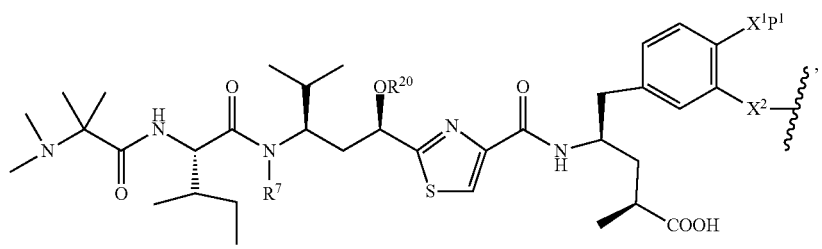
VII-52
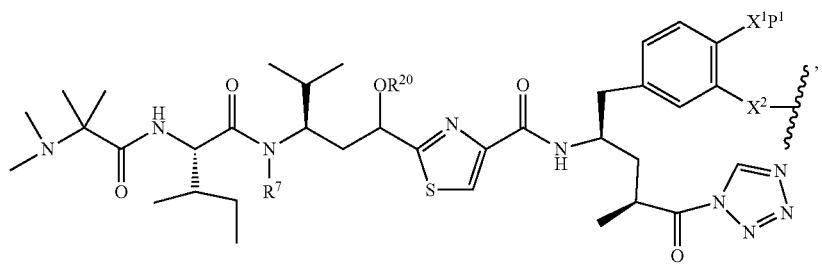
VII-53
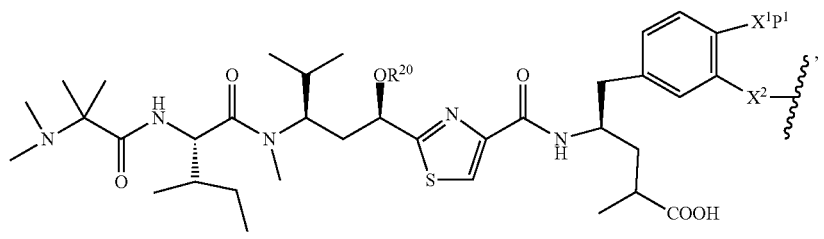
VII-54
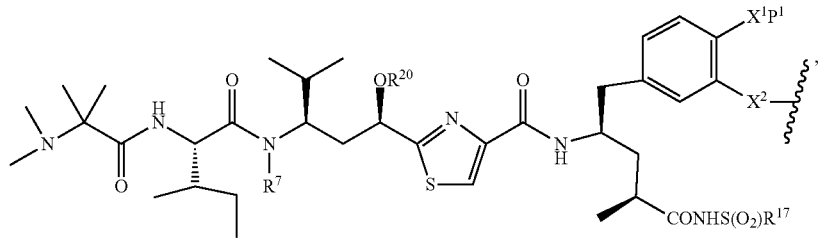
VII-55
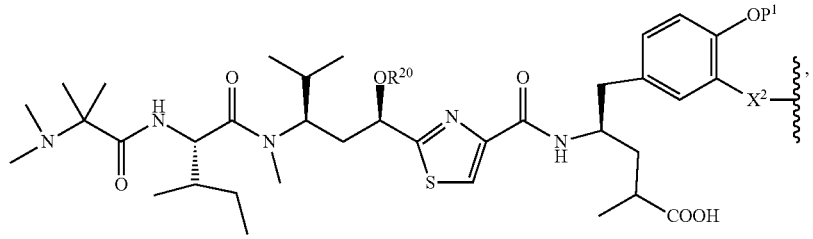
VII-56
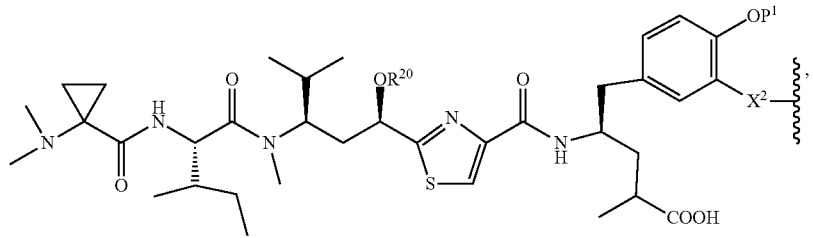
VII-57

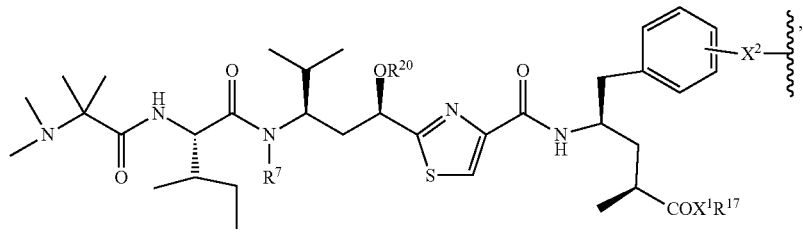
VII-58
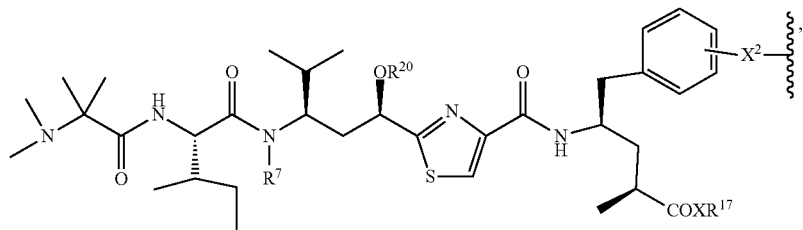
VII-59
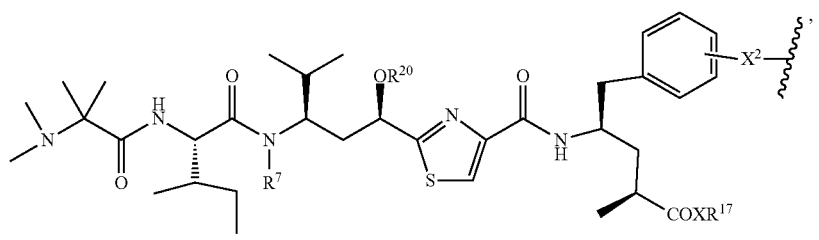
VII-60
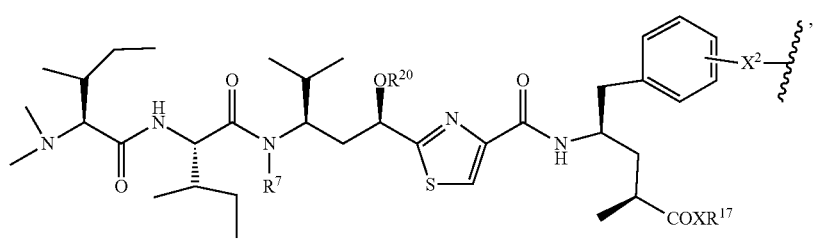
VII-61
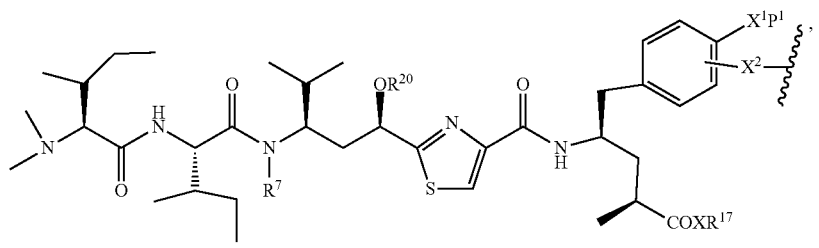
VII-62
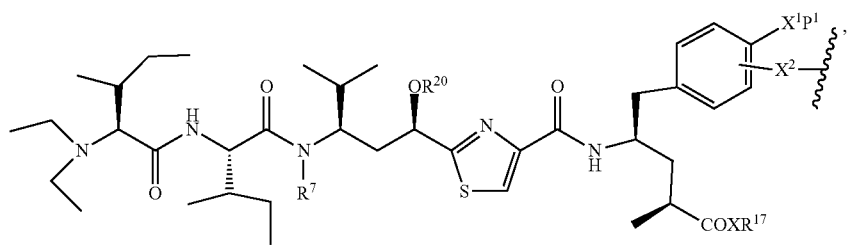
VII-63

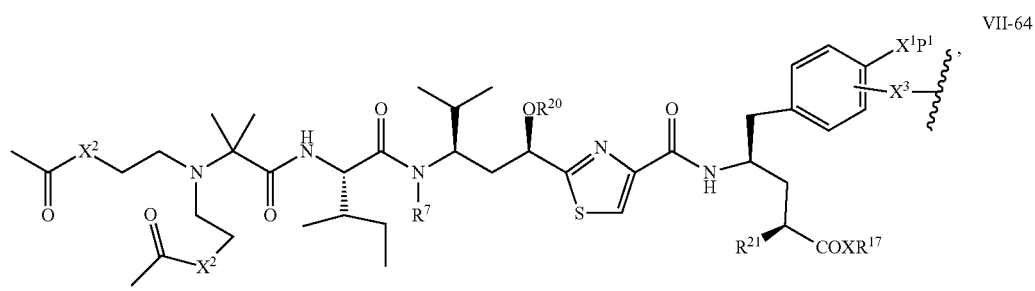
VII-64
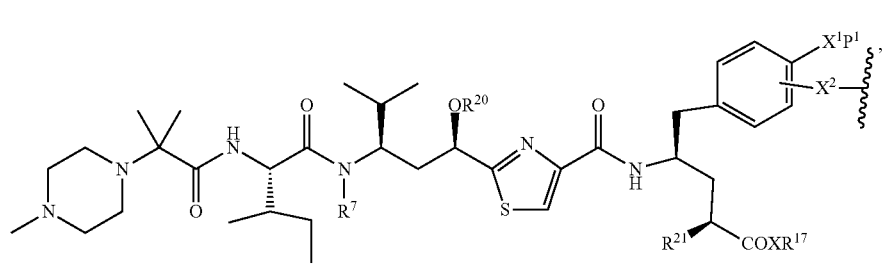
VII-65
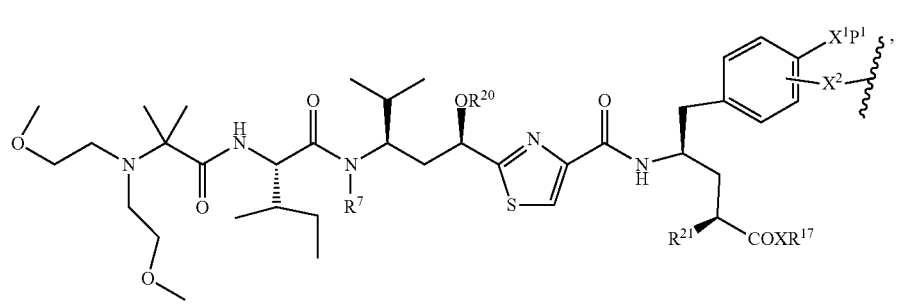
VII-66
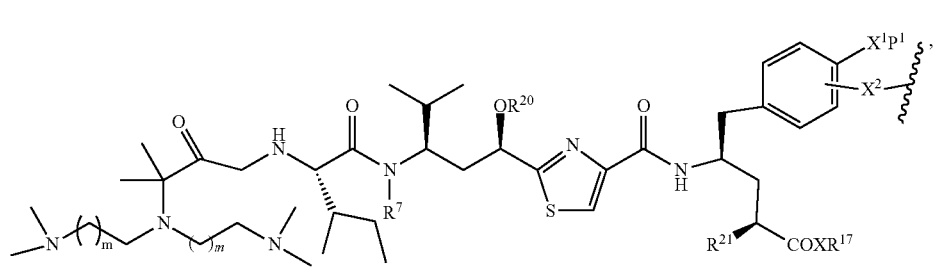
VII-67
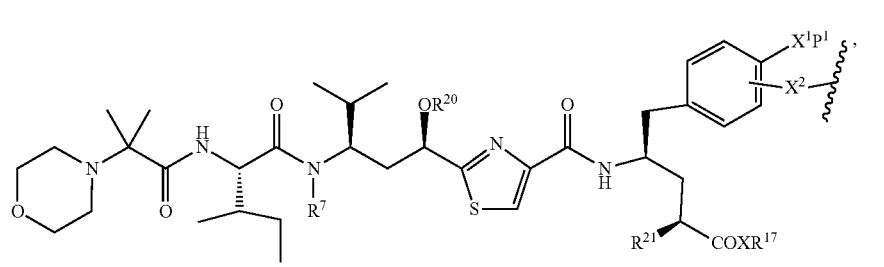
VII-68
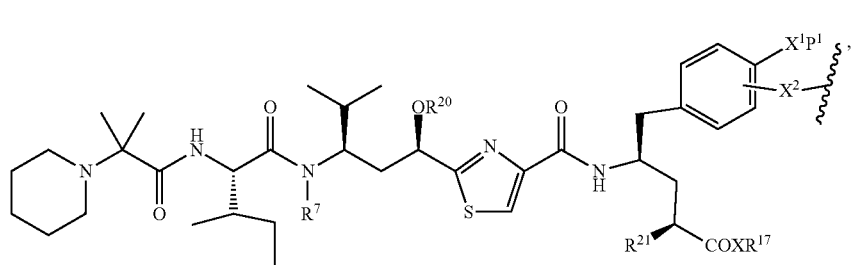
VII-69

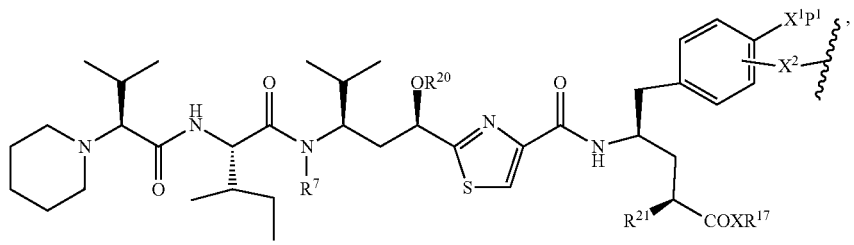
VII-70
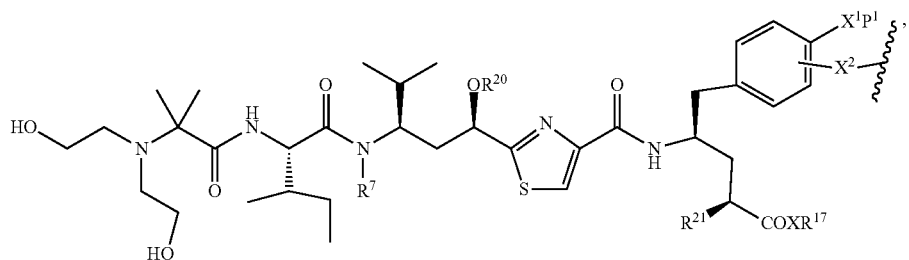
VII-71
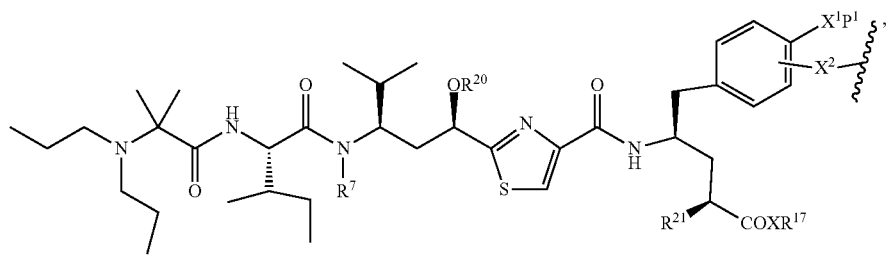
VII-72
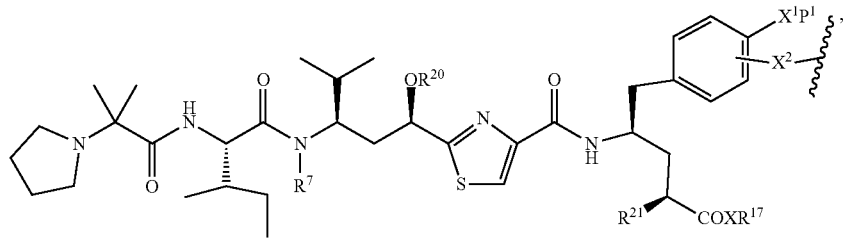
VII-73
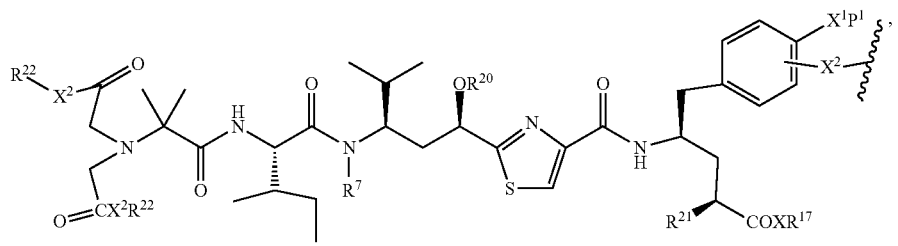
VII-74
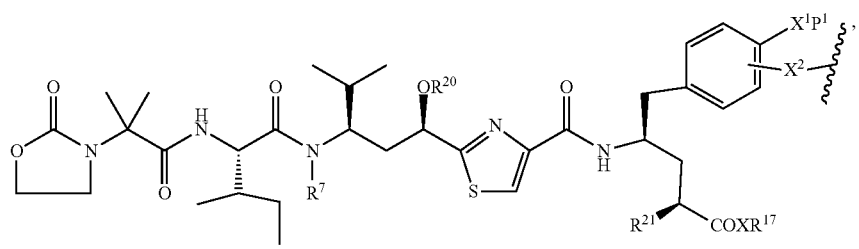
VII-75

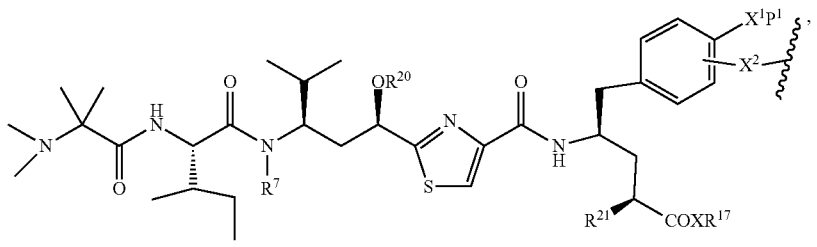

VII-76

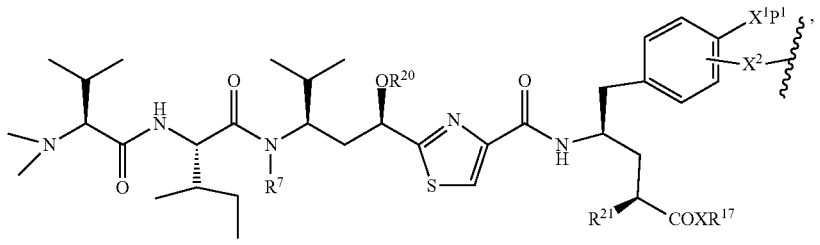

VII-77 or their pharmaceutically acceptable salts, hydrates, or hydrated salts; or the polymorphic crystalline structures of these compounds; or their optical isomers, racemates, diastereomers or enantiomers thereof;

wherein "˛", $R^7$, $R^{20}$, $Z^2$, $Z^3$, and $X^2$ are defined the same as above; X, $X^1$, and $X^3$, are independently O, S, NH, NHNH, $NHR^{17}$, $CH_2$ or absent; $P^1$ is H, $R^{17}$, $P(O)(OH)_2$, $P(O)(X^1R^{17})_2$, $CH_2P(O)(OH)_2$, $S(O^2)$ $(X^1R^{17})$, $C_6H_{12}O_5$ (glycoside), $(CH_2CH_2O)_pR^{17}$, wherein p is selected from 0-100, and $R^{17}$ is defined above; in addition $X^1P^1$ can be absent (together is H).

In another embodiment, the synthetic routes to produce the antimitotic agents and their conjugation to a cell-surface receptor binding molecules of the present invention are exampled, but not limited to, as shown in FIGS. 1-21.

In another embodiment, the releasable linker (L) is a chain of atoms selected from C, N, O, S, Si, and P that covalently connects the cell-surface binding ligand (T) to the potent antimitotic agents. The linker may have a wide variety of lengths, such as in the range from about 2 to about 100 atoms. The atoms used in forming the linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, hydroxamic acids, and many others. In addition, it is to be understood that the atoms forming the releasable linker (L) may be either saturated or unsaturated, or may be radicals, or may be cyclized upon each other to form divalent cyclic structures, including cyclo alkanes, cyclic ethers, cyclic amines, arylenes, heteroarylenes, and the like in the linker.

The term releasable linker refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis or substitution reaction, for example, an endosome having a lower pH than cytosolic pH, and/or disulfide bond exchange reaction with a intracellular thiol, such as the amillimolar range of abundant of glutathione inside the malignant cells.

The releasable linker L of conjugates may have the formula: —Ww-(Aa)r-Vv- wherein: —W— is a Stretcher unit; w is 0 or 1; each -Aa- is independently an Amino Acid unit; r is independently an integer ranging from 0 to 12; —V— is a Spacer unit; and v is 0, 1 or 2. The Stretcher unit (—W—), when present, links a targeted binding molecular unit (T) to an amino acid unit (-Aa-), or links V when an Aa is not present. The Stretcher unit W may independently contain a self-immolative spacer, peptidyl units, a hydrazone bond, disulfide or thioether bonds. In this regard a binding molecular (T) has a functional group that can form a bond with a functional group of a Stretcher. Useful functional groups that can be present on a binding molecular, either naturally or via chemical manipulation include, but are not limited to, sulfhydryl (—SH), amino, hydroxyl, carbonyl, the anomeric hydroxyl group of a carbohydrate, and carboxyl. Preferred functional groups are sulfhydryl, carboxy and amino. Sulfhydryl groups can be generated by reduction of an intramolecular disulfide bond of a Ligand. Alternatively, sulfhydryl groups can be generated by reaction of an amino group of a lysine moiety of a binding molecular using 2-iminothiolane (Traut's reagent) or thiolactone or another sulfhydryl generating reagent, such as modifies T with a disulfide bond linker, or a thiol ester following by reduction or hydrolysis respectively.

Illustrative examples of W linked to T have the structures:

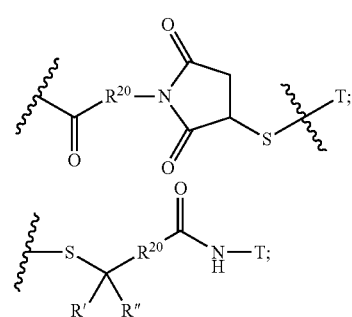

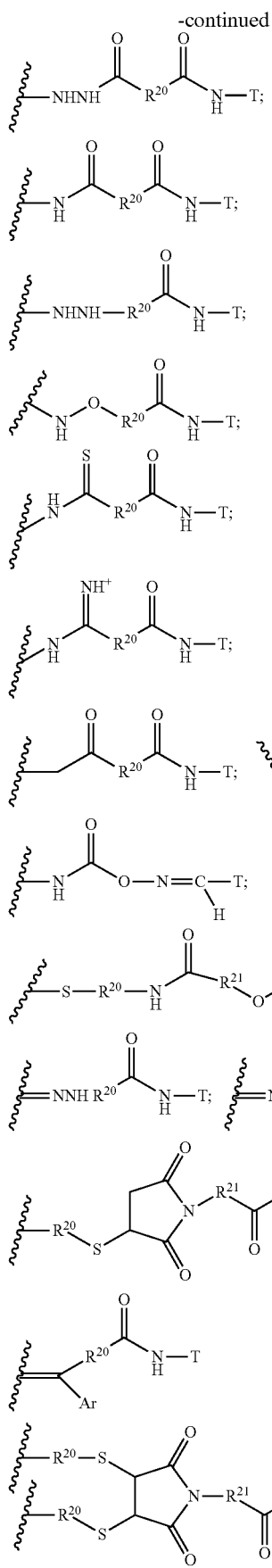
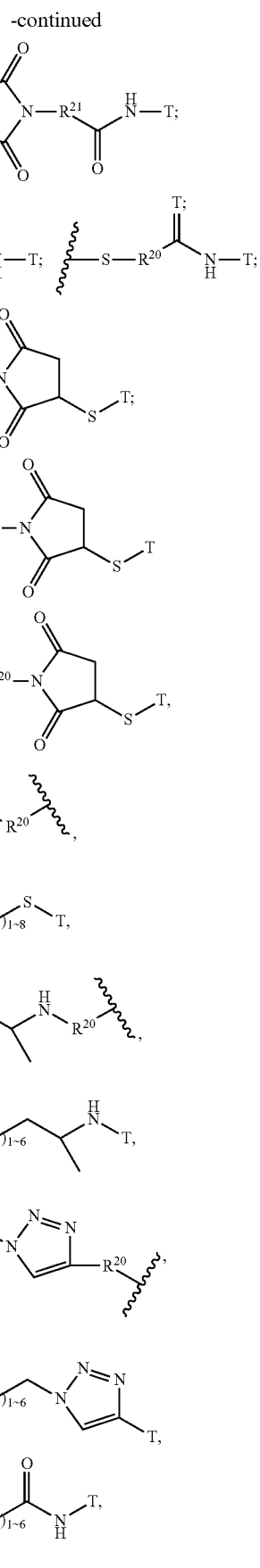

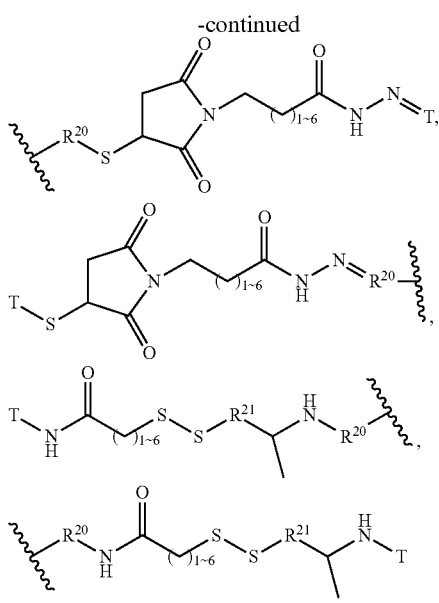

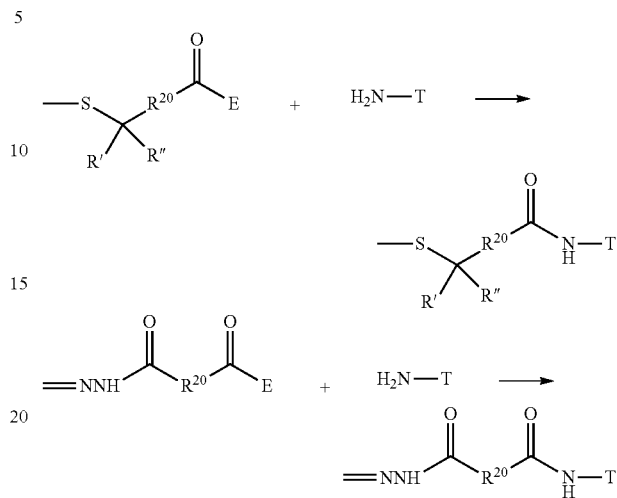

wherein $R^{20}$ and $R^{21}$ are independently selected from —$C_1$~$C_9$ alkylene-, —$C_1$~$C_7$ carbocyclo-, —O—($C_1$~$C_8$ alkyl)-, -arylene-, —$C_1$~$C_9$ alkylene-arylene-, -arylene, —$C_1$~$C_9$ alkylene-, —$C_1$~$C_9$ alkylene-($C_1$~$C_8$ carbocyclo)-, —($C_3$~$C_7$ carbocyclo)-$C_1$~$C_9$ alkylene-, —$C_3$~$C_8$ heterocyclo-, —$C_1$~$C_{10}$ alkylene-($C_3$~$C_8$ heterocyclo)-, —($C_3$~$C_8$ heterocyclo)-$C_1$~$C_9$ alkylene-, —($CH_2CH_2O)_k$—, —(CH($CH_3$)$CH_2O)_k$—, and —($CH_2CH_2O)_k$—$CH_2$—; k is an integer ranging from 1-20; R' and R" are independently H or $CH_3$.

In another embodiment, conjugation of W to T covalently as illustrated above can be via various chemical reactions.

Examples of the Formation of Amide Linkages:

Wherein the Stretcher unit contains a reactive site of E, which can form an amide bond with a primary or secondary amino group of a Ligand. Example of the reactive E, includes, but is not limited to, such as hydroxysuccinimidyl esters (NHS, Sulfo-NHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates.

Examples of Thiol Ether or Disulfide Bond Linkages:

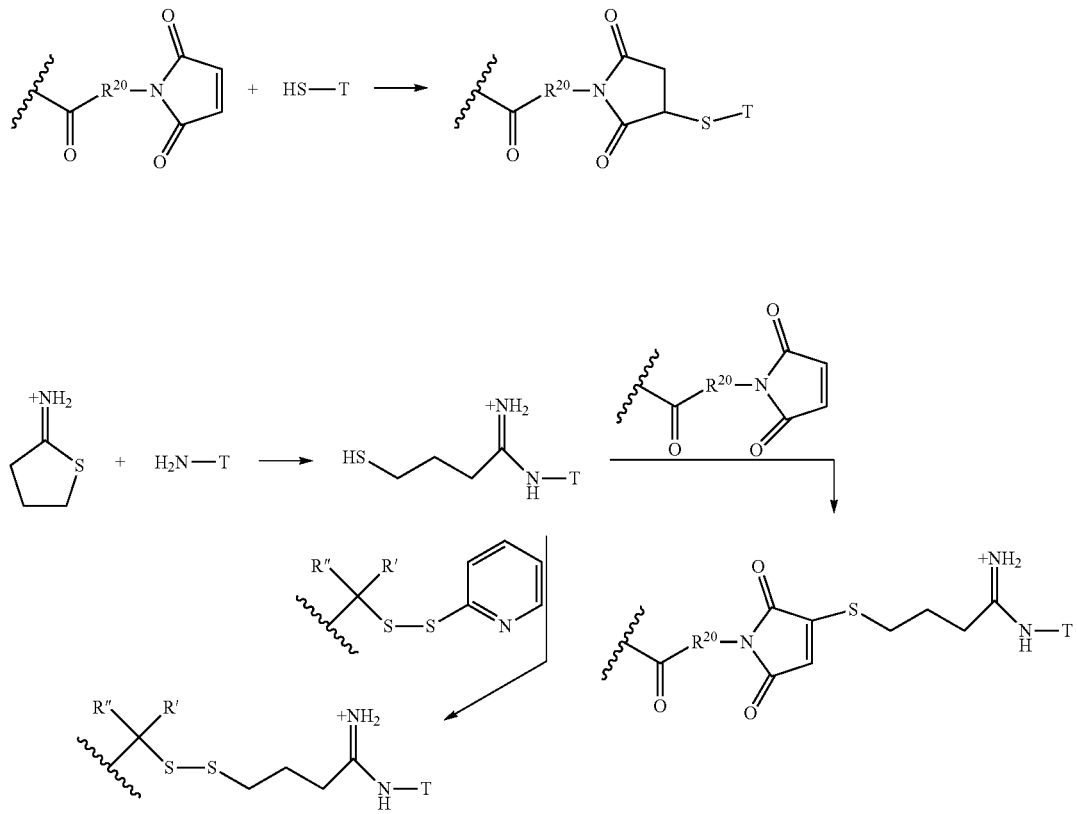

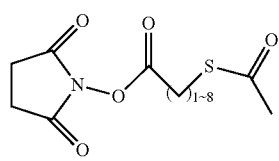
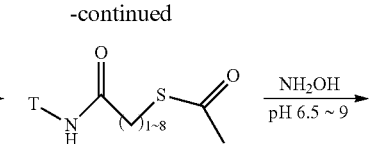
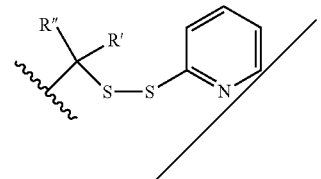
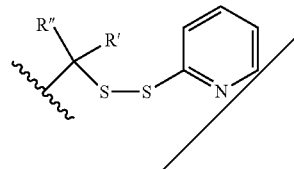
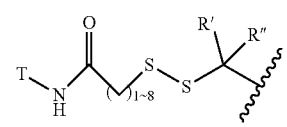
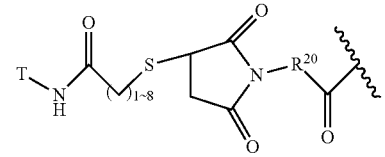
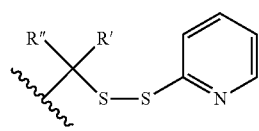
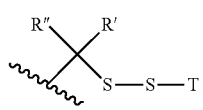

Wherein the Stretcher unit contains a sulfhydryl reactive site, which can form a thiol ether or disulfide bond with a thiol group which is generated by reduction of an intramolecular disulfide bond of the binding ligand T, or generated by a chemical modification on the binding ligand T.

In yet another aspect of the invention, the reactive group of the Stretcher contains a reactive site that is reactive to an aldehyde (—CHO) or a ketone (—C(═O)R) group that can be chemically modified on a binding molecular T. For example, a carbohydrate on a binding molecular T can be mildly oxidized using a reagent such as sodium periodate to generate an aldehyde or a ketone (—C(═O)R) group; or an amine on an amino acid at the N-termini of antibodies (or proteins or peptides) can react with pyridoxal 5′-phosphate (PLP) in a buffer solution to introduce ketone groups (Scheck & Francis, ACS Chem. Biol. 2007, 2, 247-251). The resulting (—C═O) unit can be condensed with a Stretcher that contains a functionality such as a hydrazide, an oxime, a primary or secondary amine, a hydrazine, a thiosemicarbazone, a hydrazine carboxylate, and an arylhydrazide.

Examples of the Conjugation of the Hydrazone, or the Oxime or Imine Linkages:

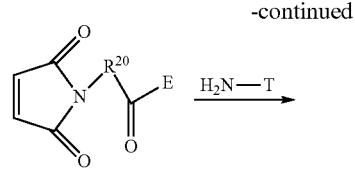
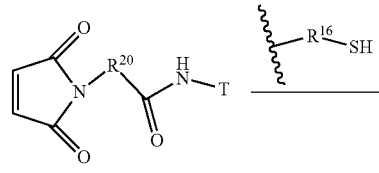
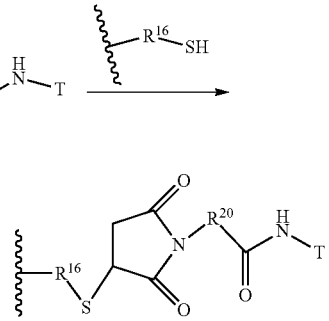

-continued

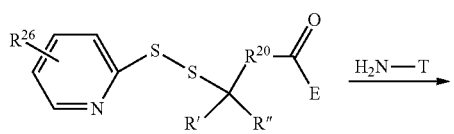
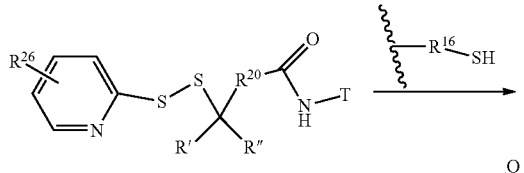
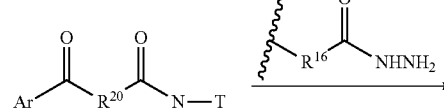
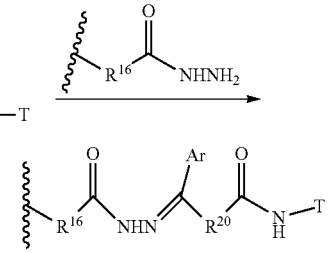
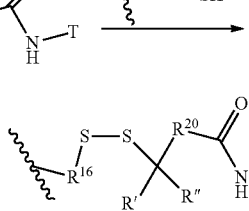
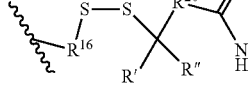

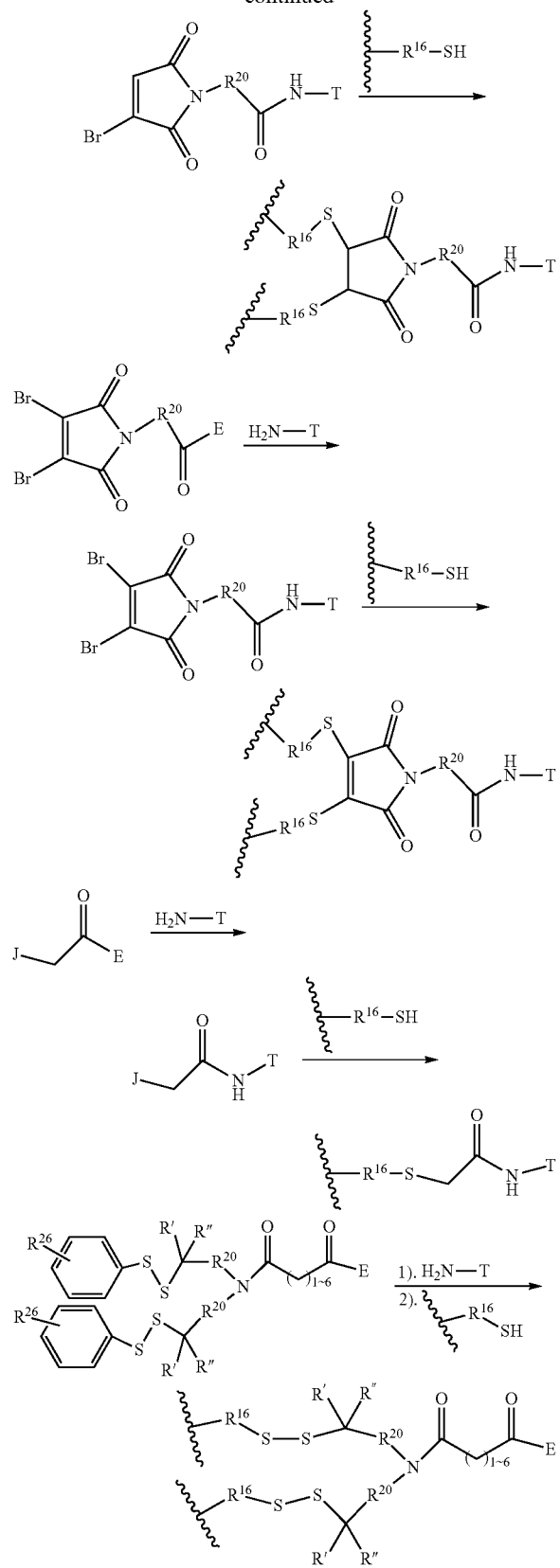

wherein $R^{20}$ and $R^{21}$ are described above, $R^{25}$ is an organic substituent of an amino acid.

In another aspect of the invention, the Stretchers (which may contain a spacer V and/or an amino acid) can be linked to the binding molecules (T), followed by conjugation of a potent antimitotic agent to the binding molecule-stretcher moiety in an aqueous buffered solution. Examples of these kinds of two-step conjugations (a drug linked to $R^{16}$ is omitted here):

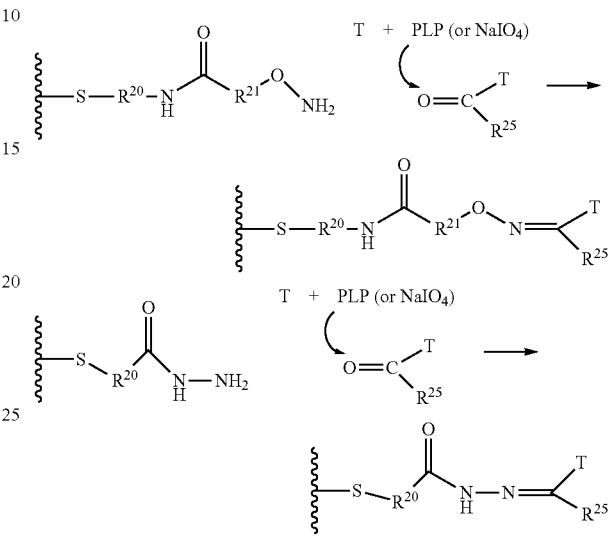

wherein E includes, but is not limited to, such as hydroxysuccinimidyl esters (NHS, Sulfo-NHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates. R' and R" are independently H or $CH_3$; $R^{20}$, $R^{16}$ and Ar are defined in various embodiment throughout this inventions; $R^{26}$ is H, or F, or $NO_2$ independently; J is F, Cl, Br, I, tosylate (TsO) or mesylate (MsO) independently and wherein ⇋-$R_{16}$ bears at least one antimitotic agent/drug $(Drug)_n$ς—$R^{16}$.

In another aspect of the invention, the Stretchers can be linked to a potent antimitotic agent first, followed by conjugation of the binding molecules (T) in an aqueous pH 3~10 (preferably pH 5~8.5) buffered solution containing up to 50% of organic cosolvents. Examples of these kinds of two-step conjugations:

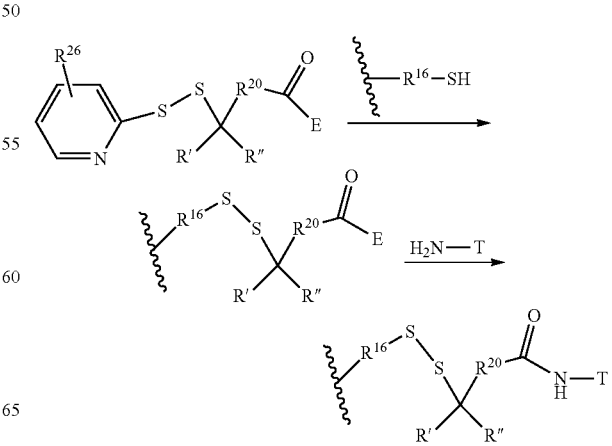

-continued

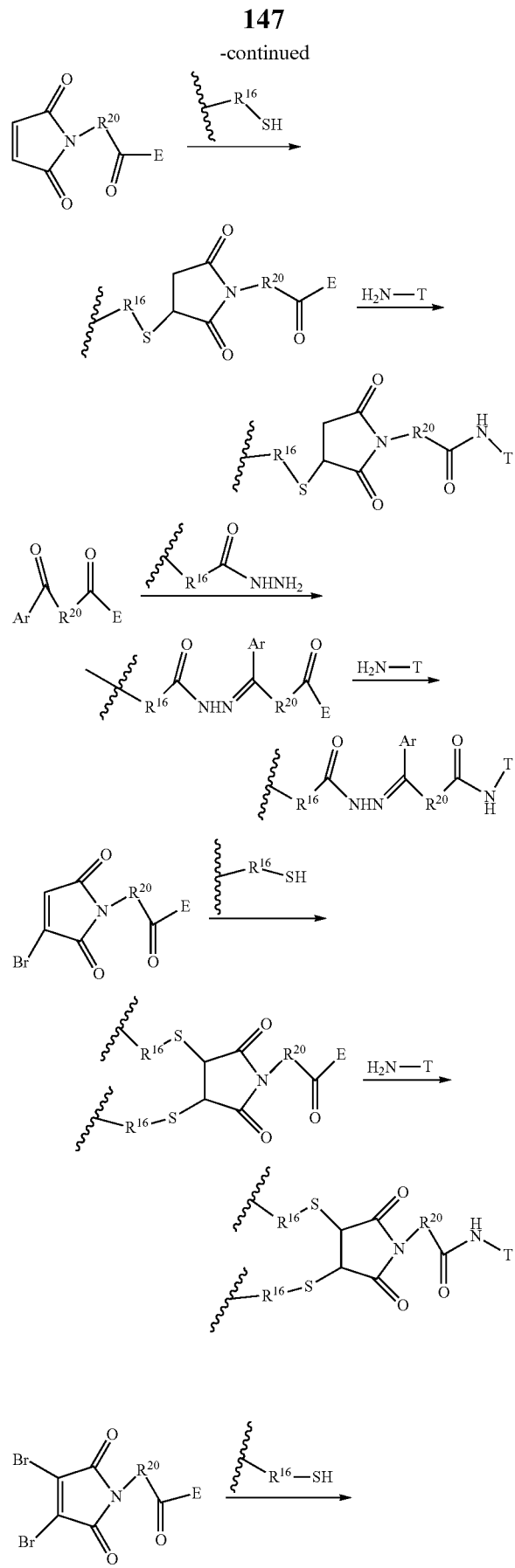

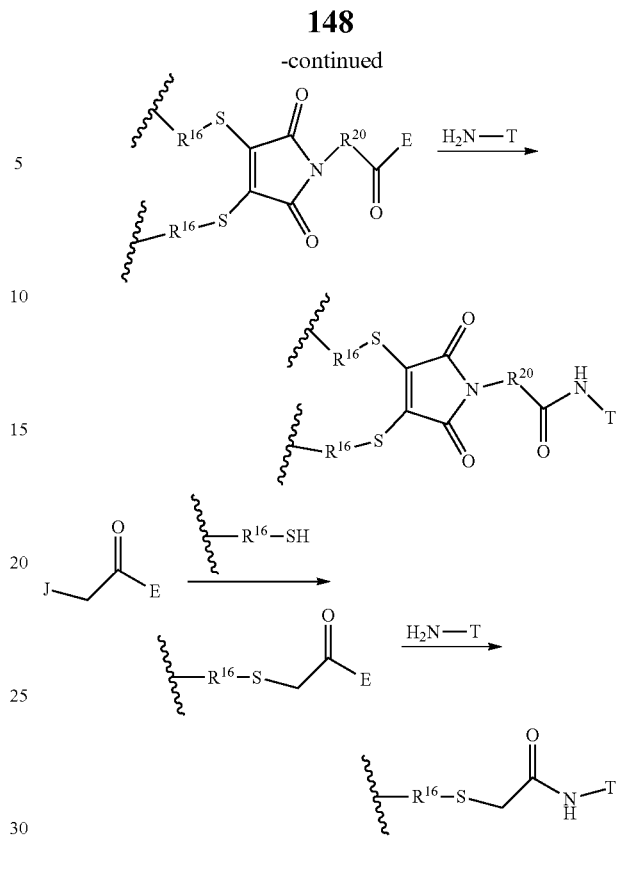

wherein E includes, but is not limited to, such as hydroxysuccinimidyl esters (NHS, Sulfo-NHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates. R' and R" are independently H or $CH_3$; $R^{16}$, $R^{20}$ and Ar are defined in various embodiment throughout this inventions; $R^{26}$ is H, or F, or $NO_2$ independently; J is F, Cl, Br, I, tosylate (TsO) or mesylate (MsO) independently and wherein bears at least one antimitotic agent/drug.

The Amino Acid unit (-Aa-), when present, links the Stretcher unit to the Spacer unit if the Spacer unit is present, links the Stretcher unit to the antimitotic agent unit if the Spacer unit is absent, and links the binding molecule (T) unit to the antimitotic agent unit if the Stretcher unit and Spacer unit are absent. -(Aa)r- is a natural or unnatural amino acid, dipeptide, tripeptide, tetrapeptide, pentapeptide, hexapeptide, heptapeptide, octapeptide, nonapeptide, decapeptide, undecapeptide or dodecapeptide unit, and r is an integer ranging from 0 to 12. The term amino acid as used herein refers generally to aminoalkylcarboxylate, where the alkyl radical is optionally substituted, such as with alkyl, acyl, hydroxy alkyl, sulfhydrylalkyl, aminoalkyl, carboxyalkyl, and the like, The structures of the natural and unnatural amino acids and peptides are described in the book: G. C. Barrett and D. T. Elmore, "Amino Acid and Peptide", Cambridge University Press, 2004. In addition, amino acid refers to beta, gamma, and longer amino acids with intra chain containing methyl, benzyl, hydroxymethyl, thiomethyl, carboxyl, carboxylmethyl, guanidinopropyl, and the like. More preferably the amino acid is selected from asparagine, aspartic acid, cysteine, glycine, glutamic acid, lysine, glutamine, arginine, serine, ornithine, threonine, and the like.

The Amino Acid unit of the Invention can be enzymatically cleaved by one or more enzymes, including a tumor-associated protease, to liberate the antimitotic agent, which in one embodiment is protonated in vivo upon release to provide an antimitotic agent.

The Spacer unit (—V—), when present, links an Amino Acid unit to the antimitotic agent when an Amino Acid unit is present. Alternately, the Spacer unit links the Stretcher unit to antimitotic agent when the Amino Acid unit is absent. The Spacer unit also links antimitotic agent to the binding molecule (T) when both the Amino Acid unit and Stretcher unit are absent. The spacer linkers may contain function groups that substantially increase the water solubility, biological transport, preferential renal clearance, uptake, absorption, biodistribution, and/or bioavailability of the conjugate are described herein. Spacer units are of two general types: self-immolative and non-self-immolative. A non-self-immolative Spacer unit is one in which part or all of the Spacer unit remains bound to antimitotic agent after cleavage, particularly enzymatic, of an Amino Acid unit from the antimitotic agent-Linker- binding molecule conjugate or the antimitotic agent-Linker Compound. The self-immolative unit includes aromatic compounds that are electronically similar to the para-aminobenzyl-carbamoyl (PAB) groups, 2-aminoimidazol-5-methanol derivatives, heterocyclic PAB analogs, beta-glucuronide, and ortho or para-aminobenzylacetals; or one of the following structures:

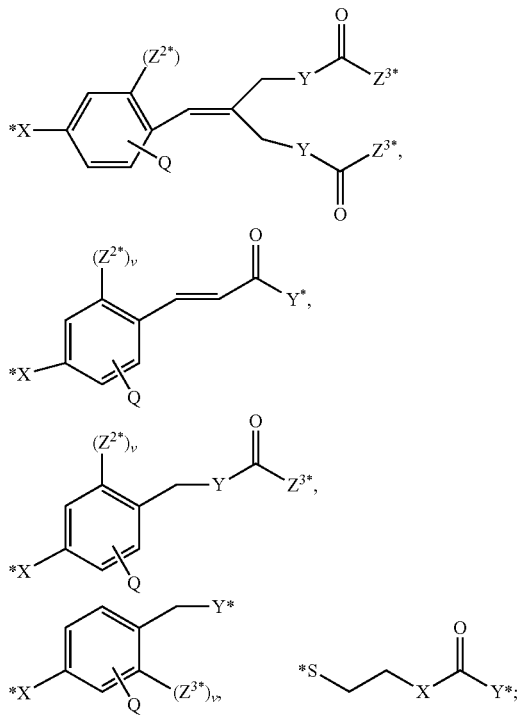

wherein the (*) atom is the point of attachment of additional spacer or releasable linker units, the antimitotic agent, and/or the binding molecule (T); X, Y and $Z^3$ are independently NH, O, or S; $Z^2$ is H, NH, O or S independently. v is 0 or 1; Q is independently H, OH, $C_1$~$C_6$ alkyl, $(OCH_2CH_2)_nF$, Cl, Br, I, $OR^{17}$, or $SR^{17}$, $NR^{17}R^{18}$, $N=NR^{17}$, $N=R^{17}$, $NR^{17}R^{18}$, $NO_2$, $SOR^{17}R^{18}$, $SO_2R^{17}$, $SO_3R^{17}$, $OSO_3R^{17}$, $PR^{17}R^{18}$, $POR^{17}R^{18}$, $PO_2R^{17}R^{18}$, $OPO(OR^{17})(OR^{18})$, or $OCH_2PO(OR^{17}(OR^{18})$ wherein $R^{17}$, $R^{18}$ are independently H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, heterocycloalkyl, heteroaralkyl, alkylcarbonyl; or pharmaceutical cation salts Examples of the Non-Self-Immolative Spacer Linkers:

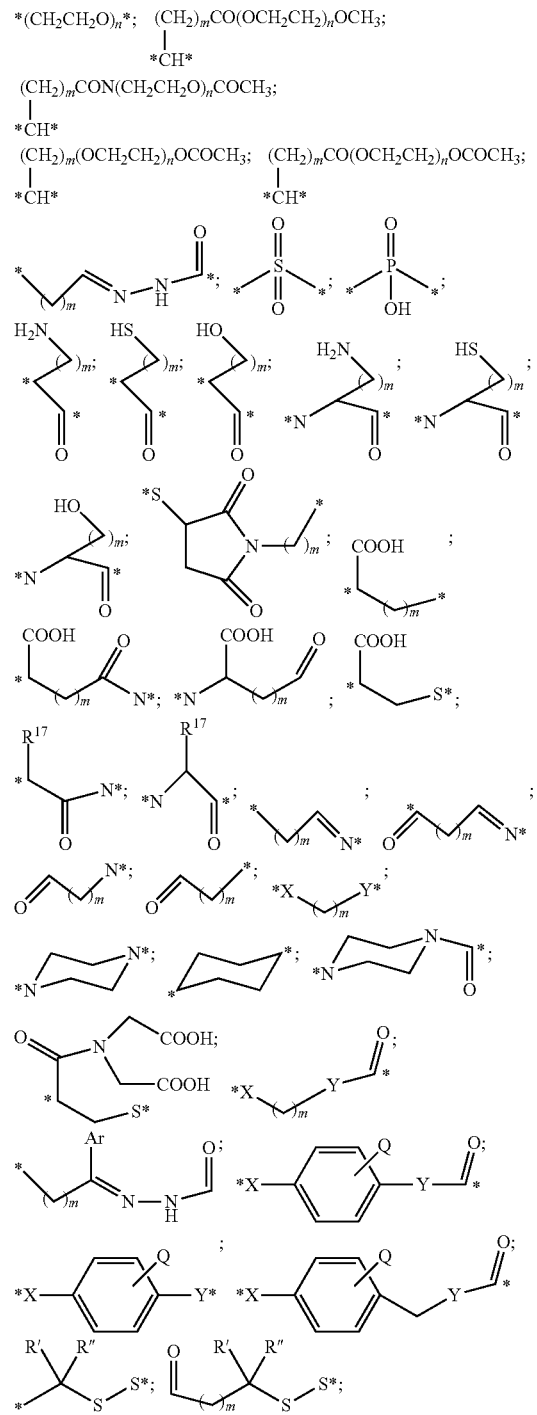

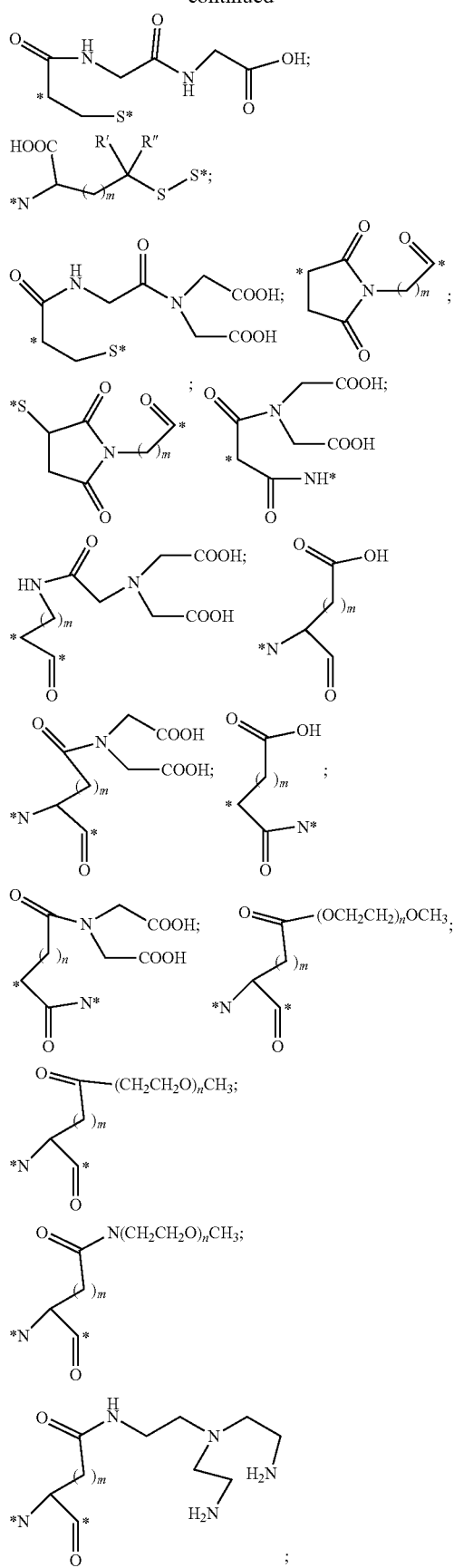
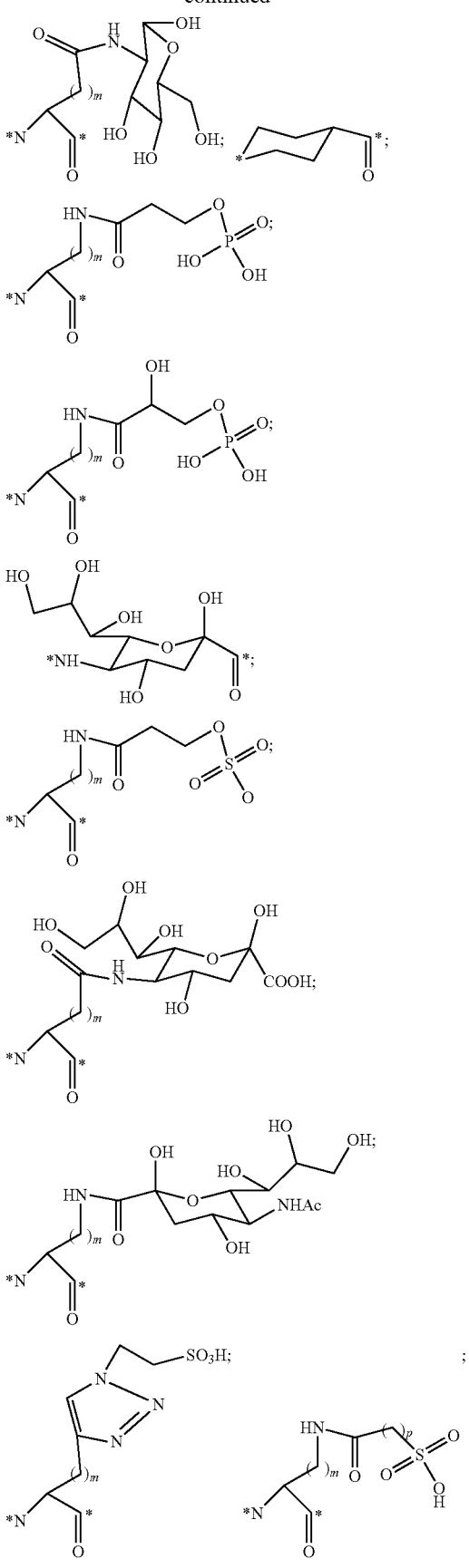

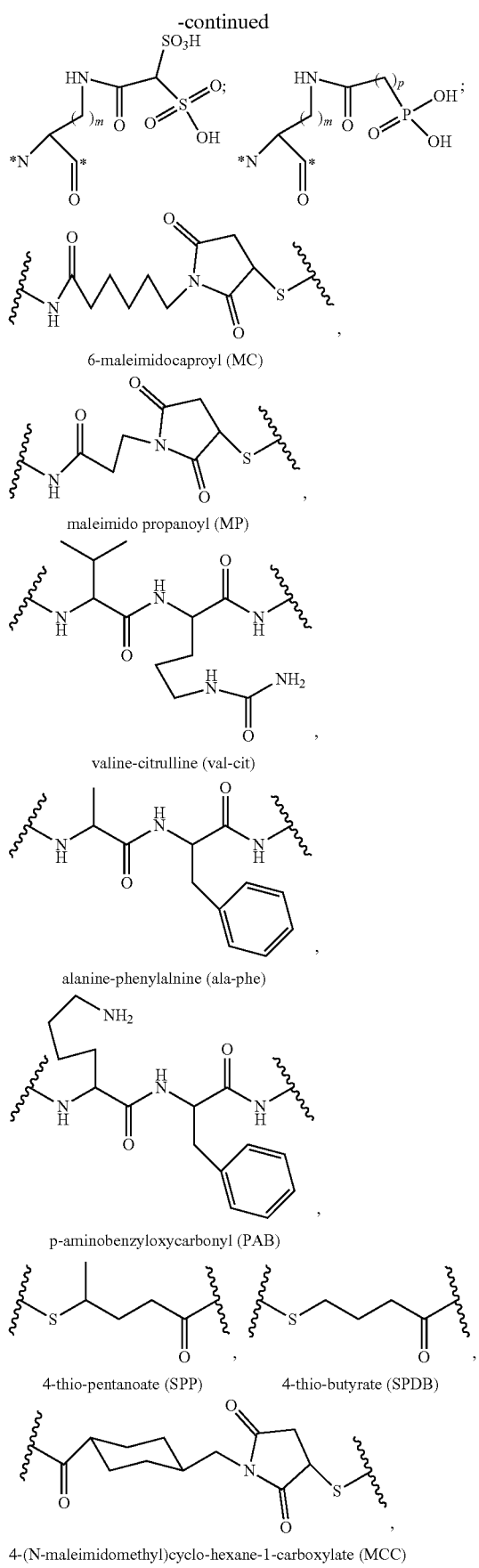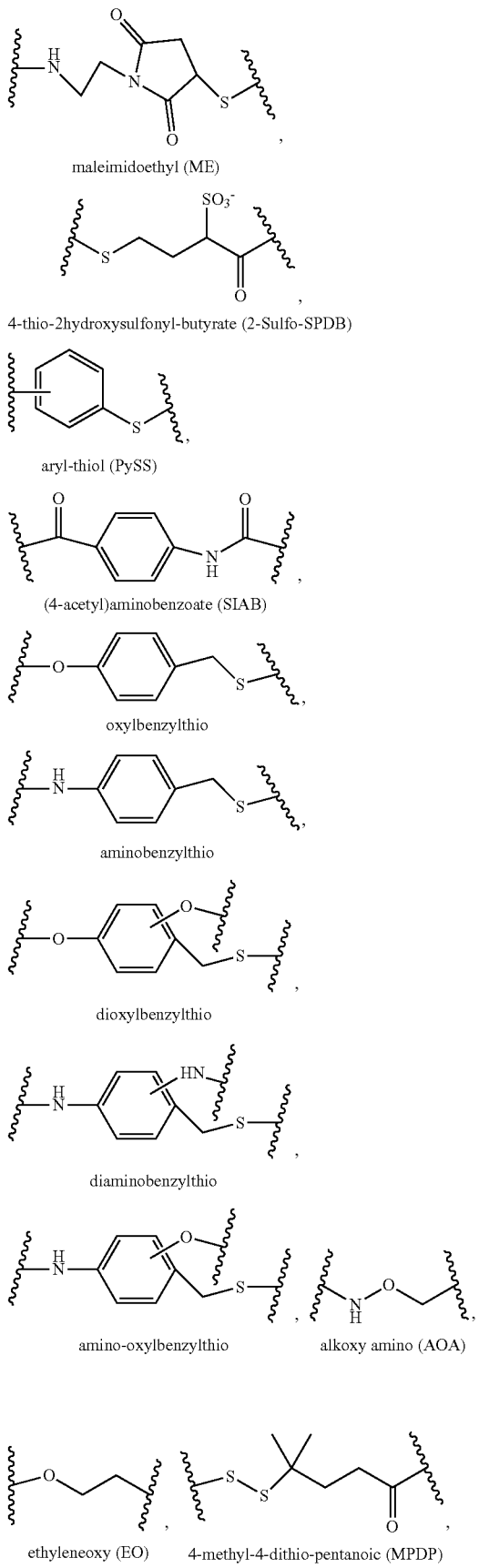

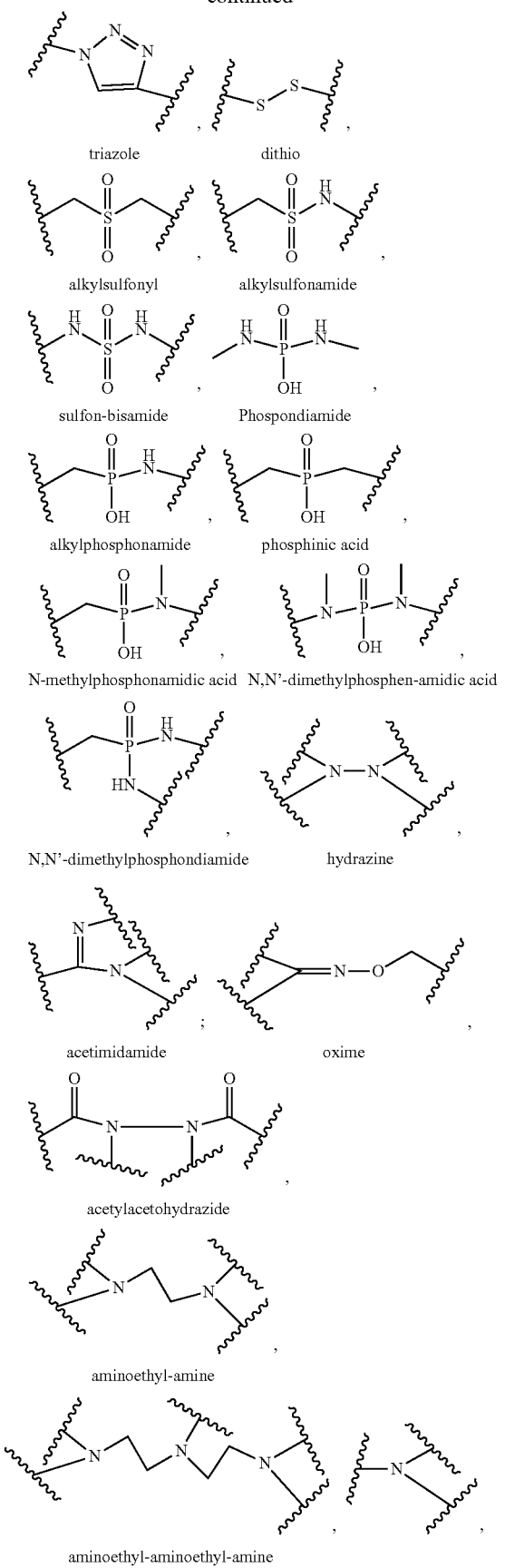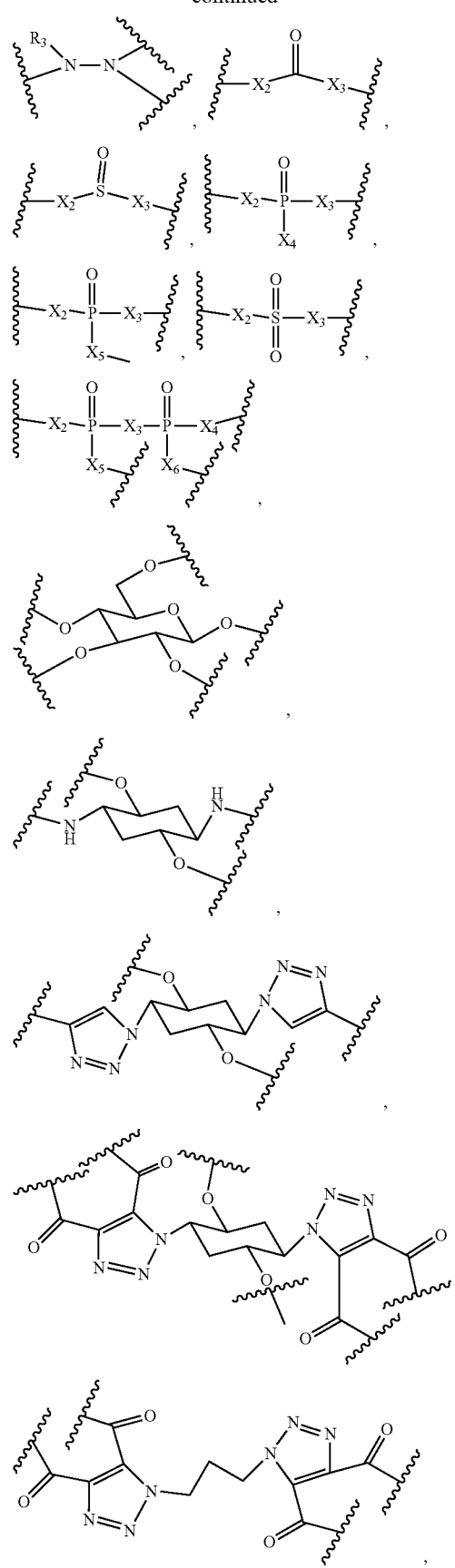

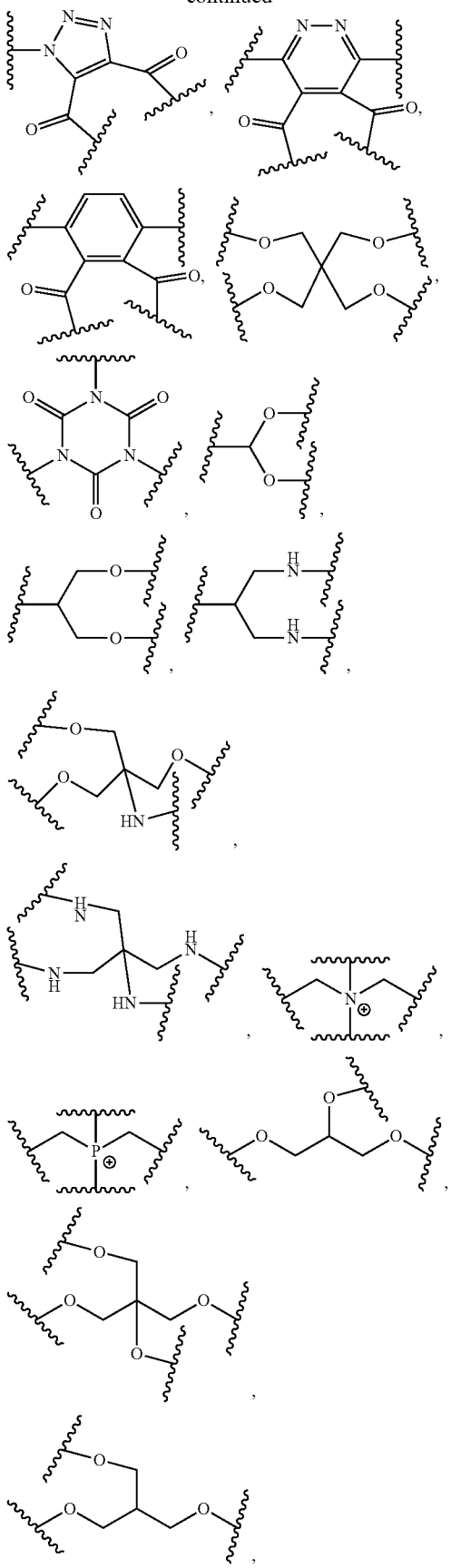

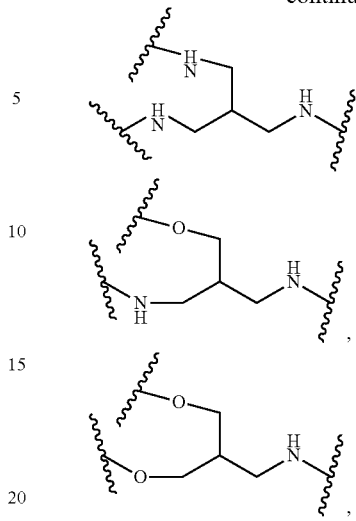

or L- or D-, natural or unnatural peptides containing 1-20 the same or different amino acids;

Wherein the "*" and "~" atom are the point of attachment of additional spacer or releasable linkers, the antimitotic agents, and/or the binding molecules; m is 1~10; n is 1~20; $X_2$, $X_3$, $X_4$, $X_5$, or $X_6$, are independently selected from NH; NHNH; $N(R_{12})$; $N(R_{12})N(R_{12'})$; O; S; $C_1$-$C_6$ of alkyl; $C_2$-$C_6$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; $CH_2OR_{12}$, $CH_2SR_{12}$, $CH_2NHR_{12}$, or 1~8 amino acids; wherein $R_{12}$ and $R_{12'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof.

A releasable component of the linker L that at least one bond in L can be broken under physiological conditions: a pH-labile, acid-labile, base-labile, oxidatively labile, metabolically labile, biochemically labile or enzyme-labile bond, which having one of the following structures:

—$(CR_{15}R_{16})_m(Aa)_r(CR_{17}R_{18})_n(OCH_2CH_2)_t$—,
—$(CR_{15}R_{16})_m(CR_{17}R_{18})_n(Aa)_r(OCH_2CH_2)_t$—, -$(Aa)_r$-$(CR_{15}R_{16})_m(CR_{17}R_{18})_n(OCH_2CH_2)_t$—, —$(CR_{15}R_{16})_m(CR_{17}R_{18})_n(OCH_2CH_2)_r(Aa)_t$-, —$(CR_{15}R_{16})_m(CR_{17}=CR_{18})(CR_{19}R_{20})_n(Aa)_t(OCH_2CH_2)_r$—,
—$(CR_{15}R_{16})_m(NR_{11}CO)(Aa)_t(CR_{19}R_{20})_n$—$(OCH_2CH_2)_r$—, —$(CR_{15}R_{16})_m(Aa)_t(NR_{21}CO)(CR_{19}R_{20})_n(OCH_2CH_2)_r$—, —$(CR_{15}R_{16})_m(OCO)(Aa)_t$-$(CR_{19}R_{20})_n(OCH_2CH_2)_r$—, —$(CR_{15}R_{16})_m(OCNR_{17})(Aa)_t(CR_{19}R_{20})_n(OCH_2CH_2)_r$—, —$(CR_{15}R_{16})_m$—$(CO)(Aa)_t$-$(CR_{19}R_{20})_n(OCH_2CH_2)_r$—, —$(CR_{15}R_{16})_m(NR_{21}CO)(Aa)_t(CR_{19}R_{20})_n(OCH_2CH_2)_r$—, —$(CR_{15}R_{16})_m$—$(OCO)(Aa)_t(CR_{19}R_{20})_n$—$(OCH_2CH_2)_r$—, —$(CR_{15}R_{16})_m(OCNR_{17})(Aa)_t(CR_{19}R_{20})_n$—$(OCH_2CH_2)_r$—, —$(CR_{15}R_{16})_m(CO)(Aa)_t(CR_{19}R_{20})_n$—$(OCH_2CH_2)_r$—, —$(CR_{15}R_{16})_m$-phenyl-CO$(Aa)_t$-$(CR_{17}R_{18})_n$—, —$(CR_{15}R_{16})_m$-furyl-CO$(Aa)_t(CR_{17}R_{18})_n$—, —$(CR_{15}R_{16})_m$-oxazolyl-CO$(Aa)_t(CR_{17}R_{18})_n$—, —$(CR_{15}R_{16})_m$-thiazolyl-CO$(Aa)_t(CCR_{17}R_{18})_n$—, —$(CR_{15}R_{16})_t$-thienyl-CO$(CR_{17}R_{18})_n$—, —$(CR_{15}R_{16})_t$-imidazolyl-CO—$(CR_{17}R_{18})_n$—, —$(CR_{15}R_{16})_t$-morpholino-CO$(Aa)_t$-$(CR_{17}R_{18})_n$—, —$(CR_{15}R_{16})_t$-piperazino-CO$(Aa)_t$ $(CR_{17}R_{18})_n$—, —$(CR_{15}R_{16})_t$—N-methylpiperazin-CO$(Aa)_t$ $(CR_{17}R_{18})_n$—, —$(CR_{15}R_{16})_m$-$(Aa)_t$phenyl-, —$(CR_{15}R_{16})_m$-$(Aa)_t$furyl-, —$(CR_{15}R_{16})_m$-oxazolyl$(Aa)_t$-, —$(CR_{15}R_{16})_m$-thiazolyl$(Aa)_t$-, —$(CR_{15}R_{16})_m$-thienyl-$(Aa)_t$-, —$(CR_{15}R_{16})_m$-imidazolyl$(Aa)_t$-, —$(CR_{15}R_{16})_m$-morpholino-$(Aa)_t$-, —$(CR_{15}R_{16})_m$-piperazino-$(Aa)_t$-, —$(CR_{15}R_{16})_m$—N-methylpiperazino-$(Aa)_t$-, —K$(CR_{15}R_{16})_m$$(Aa)r(CR_{17}R_{18})_n$ $(OCH_2CH_2)_t$—, —K$(CR_{15}R_{16})_m(CR_{17}R_{18})_n(Aa)_r$ $(OCH_2CH_2)_t$—, —K$(Aa)_r$-$(CR_{15}R_{16})_m(CR_{17}R_{18})_n$ $(OCH_2CH_2)_t$—, —K$(CR_{15}R_{16})_m(CR_{17}R_{18})_n(OCH_2CH_2)_r$ $(Aa)_t$-, —K$(CR_{15}R_{16})_m$—$(CR_{17}$=$CR_{18})(CR_{19}R_{20})_n(Aa)_t$ $(OCH_2CH_2)_r$-, —K$(CR_{15}R_{16})_m(NR_{11}CO)(Aa)_t$-$(CR_{19}R_{20})_n$ $(OCH_2CH_2)_r$—, —K$(CR_{15}R_{16})_m(Aa)_t(NR_{21}CO)(CR_{19}R_{20})_n(OCH_2CH_2)_r$—, —K$(CR_{15}R_{16})_m$—(OCO)$(Aa)_t$ $(CR_{19}R_{20})_n$—$(OCH_2H_2CH_2)_r$—, —K$(CR_{15}R_{16})_m$ $(OCNR_{17})(Aa)_t(CR_{19}R_{20})_n$—$(OCH_2CH_2)_r$—, —K$(CR_{15}R_{16})_m(CO)(Aa)_t$-$(CR_{19}R_{20})_n(OCH_2CH_2)_r$—, —K$(CR_{15}R_{16})_m(NR_{21}CO)(Aa)_t$-$(CR_{19}R_{20})_n$—$(OCH_2CH_2)_r$—, —K$(CR_{15}R_{16})_m$—(OCO)$(Aa)_t(CR_{19}R_{20})_n$ $(OCH_2CH_2)_r$—, —K$(CR_{15}R_{16})_m$—$(OCNR_{17})(Aa)_t$-$(CR_{19}R_{20})_n(OCH_2CH_2)_r$—, —K—$(CR_{15}R_{16})_m(CO)(Aa)_t$ $(CR_{19}R_{20})_n(OCH_2C_2)_r$—, —K$(CR_{15}R_{16})_m$-phenyl-CO $(AA)_t(CR_{17}R_{18})_n$—, —K—$(CR_{15}R_{16})_m$-furyl-CO$(AA)_t$ $(CR_{17}R_{18})_n$—, —K$(CR_{15}R_{16})_m$-oxazolyl-CO$(Aa)_t$ $(CR_{17}R_{18})_n$—, —K$(CR_{15}R_{16})_m$-thiazolyl-CO$(Aa)_t$-$(CR_{17}R_{18})_n$—, —K$(CR_{15}R_{16})_t$-thienyl-CO$(CR_{17}R_{18})_n$—, —K$(CR_{15}R_{16})_t$imidazolyl-CO—$(CR_{17}R_{18})_n$—, —K$(CR_{15}R_{15})_t$morpholino-CO$(Aa)_t$-$(CR_{17}R_{18})_n$—, —K$(CR_{15}R_{16})_t$-piperazino-CO$(Aa)_t$-$(CR_{17}R_{18})_n$—, —K$(CR_{15}R_{16})_t$—N-methylpiperazin-CO$(Aa)_t(CR_{17}R_{18})_n$—, —K$(CR_{15}R_{16})_m$-$(Aa)_t$phenyl, —K—$(CR_{15}R_{16})_m$-$(Aa)_t$furyl-, —K$(CR_{15}R_{16})_m$-oxazolyl-$(Aa)_t$-, —K$(CR_{15}R_{16})_m$-thiazolyl$(Aa)_t$-, —K$(CR_{15}R_{16})_m$-thienyl-$(Aa)_t$-, —K$(CR_{15}R_{16})_m$-imidazolyl$(Aa)_t$-, —K$(CR_{15}R_{16})_m$-morpholino$(Aa)_t$-, —K$(CR_{15}R_{16})_m$piperazino$(Aa)_t$G, —K$(CR_{15}R_{16})_m$—N-methyl-piperazino$(Aa)_t$-; wherein m, Aa, m, n, $R_{13}$, $R_{14}$, and $R_{15}$ are described above; t and r here are 0-100 independently; $R_{16}$, $R_{17}$, $R_{18}$, $R_{19}$, and $R_{20}$ are independently chosen from H; halide; $C_1$~$C_8$ of alkyl or heteroalkyl, $C_2$~$C_8$ of aryl, alkenyl, alkynyl, ether, ester, amine or amide, $C_3$-$C_8$ of aryl, which optionally substituted by one or more halide, CN, $NR_{12}R_{12'}$, $CF_3$, $OR_{12}$, Aryl, heterocycle, S(O)$R_{12}$, $SO_2R_{12}$, —$CO_2H$, —$SO_3H$, —$OR_{12}$, —$COO_2R_{12}$, —$CONR_{12}$, —$PO_2R_{12}R_{13}$, —$PO_3H$ or P(O)$R_{12}R_{12'}R_{13}$; K is $NR_{12}$, —SS—, —C(=O)—, —C(=O)NH—, —C(=O)O—, —C=NH—O—, —C=N—NH—, —C(=O)NH—NH—, O, S, Se, B, Het (heterocyclic or heteroaromatic ring having $C_3$-$C_{12}$); or peptides containing the same or different 1-20 amino acids.

The binding molecule (T) may be of any kind presently known, or that become known, molecule that binds to, complexes with or reacts with a moiety of a cell population sought to be therapeutically or otherwise biologically modified. The binding molecule unit acts to deliver the antimitotic agents to the particular target cell population with which the binding molecule (T) reacts.

The cell-binding agents, T include, but are not limited to, large molecular weight proteins such as, for example, full-length antibodies (polyclonal and monoclonal antibodies); single chain antibodies; fragments of antibodies such as Fab, Fab', F(ab')$_2$, $F_v$, [Parham, J. Immunol. 131, 2895-2902 (1983)], fragments produced by a Fab expression library, anti-idiotypic (anti-Id) antibodies, CDR's, and epitope-binding fragments of any of the above which immuno-specifically bind to cancer cell antigens, viral antigens or microbial antigens; interferons (such as type I, II, III); peptides; lymphokines such as IL-2, IL-3, IL-4, IL-6, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin {O'Keefe et al, 260 J. Biol. Chem. 932-937 (1985)}; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93). In general monoclonal antibodies are preferred as a cell-surface binding agent if an appropriate one is available.

Preferably, T is selected from the group consisting of an antibody, a single chain antibody, an antibody fragment that binds to a target cell, a monoclonal antibody, a single chain monoclonal antibody, a monoclonal antibody fragment that binds to the target cell, a chimeric antibody, a chimeric antibody fragment that binds to the target cell, a domain antibody, a domain antibody fragment that binds to the target cell, an adnectin that mimics antibody, DARPins, a lymphokine, a hormone, a vitamin, a growth factor, a colony stimulating factor, a nutrient-transport molecule (a transferrin), and/or a cell-binding peptide, protein, or small molecule attached or coated on an albumin, a polymer, a dendrimer, a liposome, a nanoparticle, a vesicle, or on a (viral) capsid.

In further preferably, the cell binding agent/molecule, T is capable of targeting against a tumor cell, a virus infected cell, a microorganism infected cell, a parasite infected cell, an autoimmune disease cell, an activated tumor cells, a myeloid cell, an activated T-cell, an affecting B cell, or a melanocyte, or any disease cells expressing any one of the following antigens or receptors: CD1, CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD12w, CD13, CD14, CD15, CD16, CD16a, CD16b, CDw17, CD18, CD19, CD20, CD21, CD22, CD23, CD24, CD25, CD26, CD27, CD28, CD29, CD30, CD31, CD32, CD32a, CD32b, CD33, CD34, CD35, CD36, CD37, CD38, CD39, CD40, CD41, CD42, CD42a, CD42b, CD42c, CD42d, CD43, CD44, CD45, CD46, CD47, CD48, CD49b, CD49c, CD49c, CD49d, CD49f, CD50, CD51, CD52, CD53, CD54, CD55, CD56, CD57, CD58, CD59, CD60, CD60a, CD60b, CD60c, CD61, CD62E, CD62L, CD62P, CD63, CD64, CD65, CD65s, CD66, CD66a, CD66b, CD66c, CD66d, CD66e, CD66f, CD67, CD68, CD69, CD70, CD71, CD72, CD73, CD74, CD75, CD75s, CD76, CD77, CD78, CD79, CD79a, CD79b, CD80, CD81, CD82, CD83, CD84, CD85, CD85a, CD85b, CD85c, CD85d, CD85e, CD85f, CD85g, CD85g, CD85i, CD85j, CD85k, CD85m, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121, CD121a, CD121b, CD122, CD123, CD123a, CD124, CD125, CD126, CD127, CD128, CD129, CD130, CD131, CD132, CD133, CD134, CD135, CD136, CD137, CD138, CD139, CD140, CD140a, CD140b, CD141, CD142, CD143, CD144, CD145, CDw145, CD146, CD147, CD148, CD149, CD150, CD151, CD152, CD153, CD154, CD155, CD156, CD156a, CD156b, CD156c, CD156d, CD157, CD158, CD158a, CD158b1, CD158b2, CD158c, CD158d, CD158e1, CD158e2, CD158f2, CD158 g, CD158 h, CD158i, CD158j, CD158k, CD159, CD159a, CD159b, CD159c, CD160, CD161, CD162, CD163, CD164, CD165, CD166, CD167, CD167a, CD167b, CD168, CD169, CD170, CD171, CD172, CD172a, CD172b, CD172 g, CD173, CD174, CD175, CD175s, CD176, CD177, CD178, CD179, CD179a, CD179b, CD180, CD181, CD182, CD183, CD184, CD185, CD186, CDw186, CD187, CD188, CD189, CD190, CD191, CD192, CD193, CD194, CD195, CD196, CD197, CD198, CD199, CDw198, CDw199, CD200, CD201, CD202, CD202(a,b), CD203, CD203c, CD204, CD205, CD206, CD207, CD208, CD209, CD210, CDw210a, CDw210b, CD211, CD212, CD213, CD213a$_1$, CD213a$_2$, CD214, CD215, CD216, CD217, CD218, CD218a, CD218, CD21b9, CD220, CD221, CD222, CD223, CD224, CD225, CD226, CD227, CD228, CD229, CD230, CD231, CD232, CD233, CD234, CD235, CD235a, CD235b, CD236, CD237, CD238, CD239, CD240, CD240ce, CD240d, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD281, CD282, CD283, CD284, CD285, CD286, CD287, CD288, CD289, CD290, CD291, CD292, CD293, CD294, CD295, CD296, CD297, CD298, CD299, CD300, CD300a, CD300b, CD300c, CD301, CD302, CD303, CD304, CD305, CD306, CD307, CD307a, CD307b, CD307c, CD307d, CD307e, CD307f, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD341, CD342, CD343, CD344, CD345, CD346, CD347, CD348, CD349, CD350, CD351, CD352, CD353, CD354, CD355, CD356, CD357, CD358, CD359, CD360, CD361, CD362, CD363, CD364, CD365, CD366, CD367, CD368, CD369, CD370, CD371, CD372, CD373, CD374, CD375, CD376, CD377, CD378, CD379, CD381, CD382, CD383, CD384, CD385, CD386, CD387, CD388, CD389, CRIPTO, CRIPTO, CR, CR1, CRGF, CRIPTO, CXCR5, LY64, TDGF1, 4-1BB, APO2, ASLG659, BMPR1B, 4-1BB, 5AC, 5T4 (Trophoblastic glycoprotein, TPBG, 5T4, Wnt-Activated Inhibitory Factor 1 or WAIF 1), Adenocarcinoma antigen, AGS-5, AGS-22M6, Activin receptor-like kinase 1, AFP, AKAP-4, ALK, Alpha integrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), BCMA, B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, *Canis lupus* familiaris IL31, Carbonic anhydrase IX, Cardiac myosin, CCL11(C—C motif chemokine 11), CCR4 (C—C chemokine receptor type 4), CCR5, CD3E (epsilon), CEA (Carcinoembryonic antigen), CEACAM3, CEACAM5 (carcino-embryonic antigen), CFD (Factor D), Ch4D5, Cholecystokinin 2 (CCK2R), CLDN18 (Claudin-18), CLDN18.1 (Claudin-18.1), CLDN18.2 (Claudin-18.2), Clumping factor A, cMet, CRIPTO, FCSF1R (Colony stimulating factor 1 receptor), CSF2 (colony stimulating factor 2, Granulocyte-macrophage colony-stimulating factor (GM-CSF)), CSP4, CTLA4 (cytotoxic T-lymphocyte-associated protein 4), CTAA16.88 tumor antigen, CXCR4, C—X—C chemokine receptor type 4, cyclic ADP ribose hydrolase, Cyclin B1, CYP1B1, Cytomegalovirus, Cytomegalovirus glycoprotein B, Dabigatran, DLL3 (delta-like-ligand 3), DLL4 (delta-like-ligand 4), DPP4 (Dipeptidyl-peptidase 4), DR5 (Death receptor 5), *E. coli* shiga toxin type-1, *E. coli* shiga toxin type-2, ED-B, EGFL7 (EGF-like domain-containing protein 7), EGFR, EGFRII, EGFRvIII, Endoglin, Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation protein alpha), fibroblast surface antigen, FCGR1, alpha-Fetoprotein, Fibrin II, beta chain, Fibronectin extra domain-B, FOLR (folate receptor), Folate receptor alpha, Folate hydrolase, Fos-related antigen 1F protein of respiratory syncytial virus, Frizzled receptor, Fucosyl GM1, GD2 ganglioside, G-28 (a cell surface antigen glycolipid), GD3 idiotype, GloboH, Glypican 3, N-glycolylneuraminic acid, GM3, GMCSF receptor α-chain, Growth differentiation factor, GP100, GPNMB (Trans-membrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influenza hemagglutinin, IgE, IgE Fc region, IGHE, interleukins (comprising IL-1, IL-2, IL-3, IL-4, IL-5, IL-6, IL-6R, IL-7, IL-8, IL-9, IL-10, IL-11, IL-12, IL-13, IL-15, IL-17, IL-17A, IL-18, IL-19, IL-20, IL-21, IL-22, IL-23, IL-27, or IL-28), IL31RA, ILGF2 (Insulin-like growth factor 2), Integrins (α4, α$_{IIb}$β$_3$, αvβ3, α$_4$β$_7$, α5β1, α6β4, α7β7, α11β3, α5β5, αvβ5), Interferon gamma-induced protein, ITGA2, ITGB2, KIR2D, Kappa Ig, LCK, Le, Legumain, Lewis-Y antigen, LFA-1 (Lymphocyte function-associated antigen 1, CD11a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (mesothelin), MUC1

(Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES1, P21, p53 nonmutant, P97, Page4, PAP, Paratope of anti-(N-glycolyl-neuraminic acid), PAX3, PAX5, PCSK9, PDCD1 (PD-1, Programmed cell death protein 1), PDGF-Ra (Alpha-type platelet-derived growth factor receptor), PDGFR-13, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI)), Rhesus factor, RANKL, RhoC, Ras mutant, RGS5, ROBO4, Respiratory syncytial virus, RON, ROR1, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF-13B (tumor necrosis factor receptor superfamily member 13B), TPBG (trophoblast glycoprotein), TRAIL-R$_1$ (Tumor necrosis apoptosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-1 (Trop1), TRP-2 (Trop2), Tyrosinase, VCAM-1, VEGF, VEGF-A, VEGF-2, VEGFR-1, VEGFR2, or vimentin, WT1, XAGE 1, or cells expressing any insulin growth factor receptors, or any epidermal growth factor receptors.

In the process of the conjugation, prior to conjugating with the antimitotic agents of this invention, the cell-binding molecules can be modified through attachment of a more specific peptide, a protein, or a drug, or the other functional molecules with a heterobifunctional cross linker such as with linkers of Amine-to-Nonselective (succinimidyl (NHS)-diazirine (SDA), NHS ester/Azide), Amine-to-Sulfhydryl (NHS ester/maleimide, NHS ester/pyridyldithiol, NH S esters/haloacetyl), Sulfhydryl-to-Carbohydrate (Maleimide/Hydrazide, Pyridyldithiol/Hydrazide), Hydroxyl-to-Sulfhydryl (Isocyanate/Maleimide), Amine-to-DNA (NHS ester/Psoralen), Amine-to-Carboxyl (Carbodiimide).

In the SDA linkage modification, the NHS ester of a SDA linker reacts with primary an amine group of a binding molecule backbone in pH 6~9 buffer to form a stable amide bond upon release of NHS, Then photoactivation of the diarzirine with long-wave UV light (330-370 nm) creates a reactive carbene intermediate that can react with an amine group of a more specific peptide or a protein or the other functional molecule. The order of these two steps can be different as this: an amine group of a functional molecule reacts with a SDA linker first following by photoactive reaction of a binding molecule with long-wave UV light (330-370 nm). The SDA crosslinkers can be cleavable (with a disulfide bond inside such as SDAD linker).

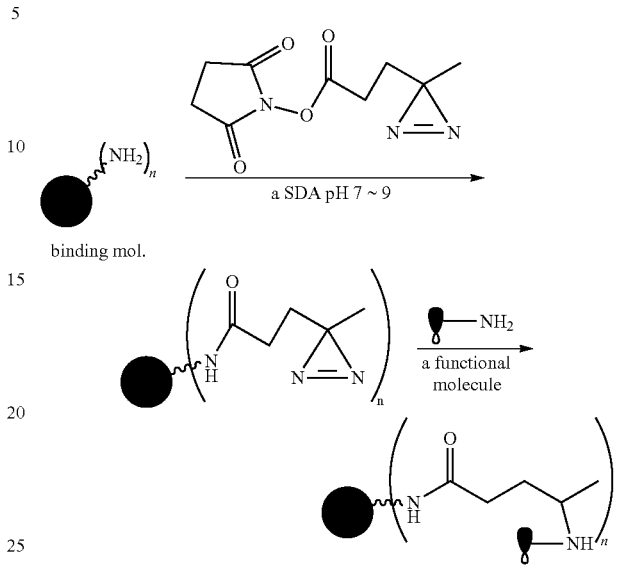

In the NHS ester/Azide linkage modification, the NHS ester of the linker reacts with primary an amine group of a binding molecule backbone in pH 6~9 buffer to form a stable amide. Then an alkynyl group on a more specific peptide or a protein or the other functional molecule reacts to the azide on the other side of the linker via Azide-Alkyne Huisgen Cycloaddition to form a 1,2,3-triazole linkage (click chemistry). Also, the NHS ester of the linker reacts with primary an amine group of a functional molecule in pH 6~9 buffer to form a stable amide. Then n alkynyl group being linked on a binding molecule reacts to the azide on the other side of the linker via 5 Azide-Alkyne Huisgen Cycloaddition to form a 1,2,3-triazole linkage.

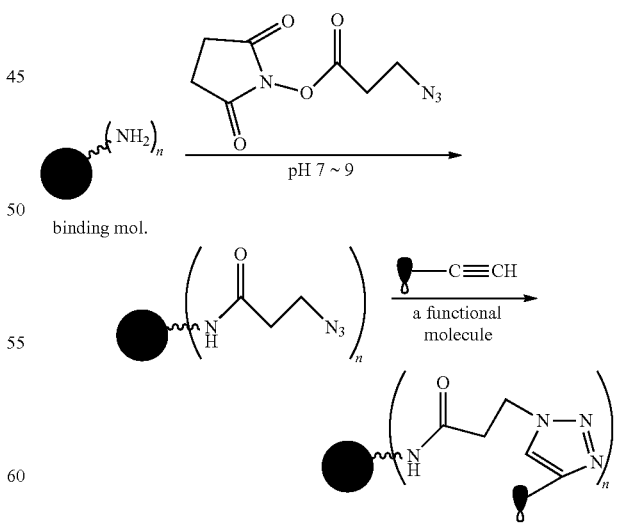

In the Amine-to-Sulfhydryl linkage modification, the NHS ester of the linker reacts with a primary amine group of a binding molecule backbone in pH 6~9 buffer to form a stable amide bond. Then a sulfhydryl on a more specific peptide or a protein or the other functional molecule reacts to the maleimide, or pyridyldithiol, or haloacetyl on the other side of the Amine-tosulfhydryl linker at pH 4.5~8.5 to form a thioether or a disulfide bond. The conjugation with the Amine-to-Sulfhydryl linker can be in different orders. For instance, an amine group of a functional molecule can be reacted with the linker to form an amide bond first, following by reaction with a sulfhydryl on a binding molecule. Also a sulfhydryl group of a functional molecule can be reacted with the linker to form a thioether or a disulfide bond at pH-4.5~7 first, following by reaction with an amine group on a binding molecule at pH 6~9 to form an amide bond.

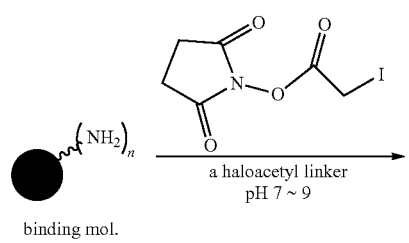

In the Sulfhydryl-to-Carbohydrate linkage modification, the sulfhydryl group of a binding molecule can be reacted with the maleimide or the pyridyldithiol on the linker to form a thioether or a disulfide bond at pH 4.5~8 first, Then a carbonyl (aldehyde/ketone) group on a functional molecule reacts with the hydrazide to form an hydrazone bond. Also the sulfhydryl group on a functional molecule can react with the linker to form a thioether or a disulfide bond at pH 4.5~8 first, following by reaction with a carbohydrate, or an oxidized carbohydrate, or an carbonyl (aldehyde/ketone) group on a binding molecule form an hydrazone bond.

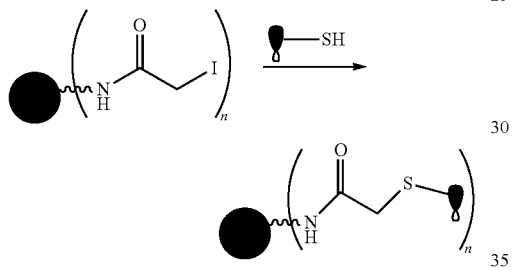

In the Hydroxyl-to-Sulfhydryl linkage modification, the sulfhydryl group of a binding molecule can be reacted with the maleimide or the pyridyldithiol on the linker to form a thioether or a disulfide bond at pH 6~8 first, Then a hydroxy group on a functional molecule reacts with the isocyanate on the linker to form a carbamate bond at pH 8~9. Also the sulfhydryl group on a functional molecule can react with the linker to form a thioether or a disulfide bond at pH 6~8 first, following by reaction with a hydroxy on a binding molecule form a carbamate bond at pH 8~9.

In yet another aspect of the invention, the production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). *Nature* 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after Protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8:396 (1959)) supplemented with 4.5 gm/l glucose, 20 mm glutamine, 20% fetal calf serum and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989).

Monocolonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859,205 and 6,797,492; Liu et al, Immunol Rev. 222:9-27 (2008); Almagro et al, Front Biosci. 1; 13:1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix, Inc.), the HuMAb-Mouse (Medarex/BMS), the VelociMouse (Regeneron), see also U.S. Pat. Nos. 6,596,541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26:39-60 (2004); Houdebine, Curr Opin Biotechnol. 13:625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3:964-70, (2002)); Adams et al, J Immunol Methods. 231:249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 2003; 23(4):307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, as long as such attachment permits the peptide or protein to retain its antigen binding specificity.

Examples of antibodies used for conjugation of antimitotic agents in this prevention for treating cancer, autoimmune disease, and infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R$_2$), CR6261 (anti-Influenza A hemagglutinin), Dacetuzumab (anti-CD40), Daclizumab (Zenapax, anti-CD25 (α chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin α$_v$β$_3$), Exbivirumab (anti-hepatitis B surface antigen), Fanolesomab (Neutro-Spec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), anti-HLA-DR antibody, Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R$_2$), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R$_1$), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin α$_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin α$_{IIb}$β$_3$), Talizumab (anti-IgE), Tanezumab (anti-NGF), Taplitumomab (anti-CD19), Tefibazumab (Aurexis, anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R$_2$), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin α$_4$β$_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin α$_5$β$_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRαβ (T cell receptor alpha/beta), complex, from MedImmune Inc for Graft-versus-host disease], RING SCAN [anti-TAG 72 (tumor associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp.

for Colon, Ovarian, Prostate cancers and NHL]; anti-Trop-2-humanized antibody hRS7, LymphoCide (Immunomedics, NJ), Smart ID 10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone Systems) and Cetuximab (ImClone).

Other antibodies as binding ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (A-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v \beta 3$, $\alpha 5 \beta 1$, $\alpha 6 \beta 4$, $\alpha 11 \beta 3$, $\alpha 5 \beta 5$, $\alpha v \beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76). Examples of these antigens that antibodies against are: Many other Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Annexin A1, Nucleolin, Endoglin (CD105), ROBO4, Amino-peptidase N, Δ-like-4 (DLL4), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 nonmutant, NY-ESO-1, GD2, CEA, MelanA/MART1, Ras mutant, gp100, p53 mutant, Proteinase3 (PR1), bcr-abl, Tyrosinase, Survivin, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-P3, MAD-CT-2, Fos-related antigen 1.

In another specific embodiment, the antimitotic agent-binding molecule conjugates of the invention are used in accordance with the compositions and methods of the invention for the treatment of cancers. The cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metastatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the antimitotic agent-binding molecule conjugates of the invention are used in accordance with the compositions and methods of the invention for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barre syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate for the treatment or prevention of an autoimmune disease includes, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub. RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial (M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to both a receptor or a receptor complex expressed on an activated lymphocyte which is associated with an autoimmune disease. The receptor or receptor complex can comprise an immunoglobulin gene superfamily member (e.g. CD2, CD3, CD4, CD8, CD19, CD22, CD28, CD79, CD90, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The binding molecules-antimitotic agent conjugates of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, Baylisascaris infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Sträussler-Scheinker syndrome, Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, *Kuru*, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis pneumonia*, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever, Rocky mountain spotted fever, Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (*Variola*), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), *Yersinia pseudotuberculosis* infection, Yersiniosis, Yellow fever, Zygomycosis.

The binding molecules, proffered antibodies described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma* genus, *Bacillus* anthracis, Arcanobacterium haemolyticum, Junin virus, Ascaris lumbricoides, Aspergillus genus, Astroviridae family, Babesia genus, Bacillus cereus, multiple bacteria, Bacteroides genus, Balantidium coli, Baylisascaris genus, BK virus, Piedraia hortae, Blastocystis hominis, Blastomyces dermatitides, Machupo virus, Borrelia genus, Clostridium botulinum, Sabia, Brucella genus, usually Burkholderia cepacia and other Burkholderia species, Mycobacterium ulcerans, Caliciviridae family, Campylobacter genus, usually Candida albicans and other Candida species, Bartonella henselae, Group A Streptococcus and Staphylococcus, Trypanosoma cruzi, Haemophilus ducreyi, Varicella zoster virus (VZV), Chlamydia trachomatis, Chlamydophila pneumoniae, Vibrio cholerae, Fonsecaea pedrosoi, Clonorchis sinensis, Clostridium difficile, Coccidioides immitis and Coccidioides posadasii, Colorado tick fever virus, rhinoviruses, coronaviruses, CJD prion, Crimean-Congo hemorrhagic fever virus, Cryptococcus neoformans, Cryptosporidium genus, Ancylostoma braziliense; multiple parasites, Cyclospora cayetanensis, Taenia solium, Cytomegalovirus, Dengue viruses (DEN-1, DEN-2, DEN-3 and DEN-4)—Flaviviruses, Dientamoeba fragilis, Corynebacterium diphtheriae, Diphyllobothrium, Dracunculus medinensis, Ebolavirus, Echinococcus genus, Ehrlichia genus, Enterobius vermicularis, Enterococcus genus, Enterovirus genus, Rickettsia prowazekii, Parvovirus B19, Human herpesvirus 6 and Human herpesvirus 7, Fasciolopsis buski, Fasciola hepatica and Fasciola gigantica, FFI prion, Filarioidea superfamily, Clostridium perfringens, Fusobacterium genus, Clostridium perfringens; other Clostridium species, Geotrichum candidum, GSS prion, Giardia intestinalis, Burkholderia mallei, Gnathostoma spinigerum and Gnathostoma hispidum, Neisseria gonorrhoeae, Klebsiella granulomatis, Streptococcus pyogenes, Streptococcus agalactiae, Haemophilus influenzae, Enteroviruses, mainly Coxsackie A virus and Enterovirus 71, Sin Nombre virus, Helicobacter pylori, Escherichia coli O157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, Histoplasma capsulatum, Ancylostoma duodenale and Necator americanus, Hemophilus influenzae, Human bocavirus, Ehrlichia ewingii, Anaplasma phagocytophilum, Human metapneumovirus, Ehrlichia chaffeensis, Human papillomavirus, Human parainfluenza viruses, Hymenolepis nana and Hymenolepis diminuta, Epstein-Barr Virus, Orthomyxoviridae family, Isospora belli, Kingella kingae, Klebsiella pneumoniae, Klebsiella ozaenas, Klebsiella rhinoscleromotis, Kuru prion, Lassa virus, Legionella pneumophila, Legionella pneumophila, Leishmania genus, Mycobacterium leprae and Mycobacterium lepromatosis, Leptospira genus, Listeria monocytogenes, Borrelia burgdorferi and other Borrelia species, Wuchereria bancrofti and Brugia malayi, Lymphocytic choriomeningitis virus (LCMV), Plasmodium genus, Marburg virus, Measles virus, Burkholderia pseudomallei, Neisseria meningitides, Metagonimus yokagawai, Microsporidia phylum, Molluscum contagiosum virus (MCV), Mumps virus, Rickettsia typhi, Mycoplasma pneumoniae, numerous species of bacteria (Actinomycetoma) and fungi (Eumycetoma), parasitic dipterous fly larvae, Chlamydia trachomatis and Neisseria gonorrhoeae, vCJD prion, Nocardia asteroides and other Nocardia species, Onchocerca volvulus, Paracoccidioides brasiliensis, Paragonimus westermani and other Paragonimus species, Pasteurella genus, Pediculus humanus capitis, Pediculus humanus corporis, Phthirus pubis, Bordetella pertussis, Yersinia pestis, Streptococcus pneumoniae, Pneumocystis jirovecii, Poliovirus, Prevotella genus, Naegleria fowleri, JC virus, Chlamydophila psittaci, Coxiella burnetii, Rabies virus, Streptobacillus moniliformis and Spirillum minus, Respiratory syncytial virus, Rhinosporidium seeberi, Rhinovirus, Rickettsia genus, Rickettsia akari, Rift Valley fever virus, Rickettsia rickettsii, Rotavirus, Rubella virus, Salmonella genus, SARS coronavirus, Sarcoptes scabiei, Schistosoma genus, Shigella genus, Varicella zoster virus, Variola major or Variola minor, Sporothrix schenckii, Staphylococcus genus, Staphylococcus genus, Staphylococcus aureus, Streptococcus pyogenes, Strongyloides stercoralis, Treponema pallidum, Taenia genus, Clostridium tetani, Trichophyton genus, Trichophyton tonsurans, Trichophyton genus, Epidermophyton floccosum, Trichophyton rubrum, and Trichophyton mentagrophytes, Trichophyton rubrum, Hortaea werneckii, Trichophyton genus, Malassezia genus, Toxocara canis or Toxocara cati, Toxoplasma gondii, Trichinella spiralis, Trichomonas vaginalis, Trichuris trichiura, Mycobacterium tuberculosis, Francisella tularensis, Ureaplasma urealyticum, Venezuelan equine encephalitis virus, Vibrio colerae, Guanarito virus, West Nile virus, Trichosporon beigelii, Yersinia pseudotuberculosis, Yersinia enterocolitica, Yellow fever virus, Mucorales order (Mucormycosis) and Entomophthorales order (Entomophthoramycosis), Pseudomonas aeruginosa, Campylobacter (Vibrio) fetus, Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma spp., Rickettsia prowazeki, Rickettsia tsutsugumushi, Clamydia spp.; pathogenic fungi (Aspergillus fumigatus, Candida albicans, Histoplasma capsulatum); protozoa (*Entomoeba histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other antibodies as a binding ligand in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate of the invention together with a pharmaceutically acceptable carrier for treatment of cancer and autoimmune disorders. The method for treatment of cancer and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 15 minutes to about 48 hours at about 37° C. The exact conditions of concentration and time of incubation (=dose) are readily determined by the skilled clinicians. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

Formulation and Application

The conjugates of the patent application are formulated to liquid, or suitable to be lyophilized and subsequently be reconstituted to a liquid formulation. The contemplated excipients, which may be utilized in the aqueous pharmaceutical compositions of the patent application include, for example, flavoring agents, antimicrobial agents, sweeteners, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4$^{th}$ edition, Rowe et al., Eds., American Pharmaceuticals Association (2003); and Remington: the Science and Practice of Pharmacy, 21$^{th}$ edition, Gennaro, Ed., Lippincott Williams & Wilkins (2005).

A pharmaceutical container or vessel is used to hold the pharmaceutical formulation of any of conjugates of the patent application. The vessel is a vial, bottle, pre-filled syringe, pre-filled or auto-injector syringe. The liquid formula can be freeze-dried or drum-dryed to a form of cake or powder in a borosilicate vial or soda lime glass vial. The solid powder can also be prepared by efficient spray drying, and then packed to a vial or a pharmaceutical container for storage and distribution.

In a further embodiment, the invention provides a method for preparing a formulation comprising the steps of: (a) lyophilizing the formulation comprising the conjugates, excipients, and a buffer system; and (b) reconstituting the lyophilized mixture of step (a) in a reconstitution medium such that the reconstituted formulation is stable. The formulation of step (a) may further comprise a stabilizer and one or more excipients selected from a group comprising bulking agent, salt, surfactant and preservative as hereinabove described. As reconstitution media, several diluted organic acids or water, i.e. sterile water, bacteriostatic water for injection (BWFI) or may be used. The reconstitution medium may be selected from water, i.e. sterile water, bacteriostatic water for injection (BWFI) or the group consisting of acetic acid, propionic acid, succinic acid, sodium chloride, magnesium chloride, acidic solution of sodium chloride, acidic solution of magnesium chloride and acidic solution of arginine, in an amount from about 10 to about 250 mM.

A liquid pharmaceutical formulation of the conjugates of the patent application should exhibit a variety of pre-defined characteristics. One of the major concerns in liquid drug products is stability, as proteins/antibodies tend to form soluble and insoluble aggregates during manufacturing and storage. In addition, various chemical reactions can occur in solution (deamidation, oxidation, clipping, isomerization etc.) leading to an increase in degradation product levels and/or loss of bioactivity. Preferably, a conjugate in either liquid or loyphilizate formulation should exhibit a shelf life of more than 6 months at 25° C. More preferred a conjugate in either liquid or loyphilizate formulation should exhibit a shelf life of more than 12 months at 25° C. Most preferred liquid formulation should exhibit a shelf life of about 24 to 36 months at 2-8° C. and the loyphilizate formulation should exhibit a shelf life of about preferably up to 60 months at 2-8° C. Both liquid and loyphilizate formulations should exhibit a shelf life for at least two years at −20° C., or −70° C.

In certain embodiments, the formulation is stable following freezing (e. g., −20° C., or −70° C.) and thawing of the formulation, for example following 1, 2 or 3 cycles of freezing and thawing. Stability can be evaluated qualitatively and/or quantitatively in a variety of different ways, including evaluation of drug/antibody (protein) ratio and aggregate formation (for example using UV, size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis, or matrix-assisted laser desorption ionization/time-of-flight mass spectrometry (MALDI/TOF MS), or HPLC-MS/MS; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

A stable conjugate should also "retains its biological activity" in a pharmaceutical formulation, if the biological activity of the conjugate at a given time, e. g. 12 month, within about 20%, preferably about 10% (within the errors of the assay) of the biological activity exhibited at the time the pharmaceutical formulation was prepared as determined in an antigen binding assay, and/or in vitro, cytotoxic assay, for example.

For clinical in vivo use, the conjugate via the linkers of the invention will be supplied as solutions or as a lyophilized solid that can be redissolved in sterile water for injection. Examples of suitable protocols of conjugate administration are as follows. Conjugates are given daily, weekly, biweekly, triweekly, once every four weeks or monthly for 8~54 weeks as an i.v. bolus. Bolus doses are given in 50 to 1000 ml of normal saline to which human serum albumin (e.g. 0.5 to 1 mL of a concentrated solution of human serum albumin, 100 mg/mL) can optionally be added. Dosages will be about 50 µg to 20 mg/kg of body weight per week, i.v. (range of 10 µg to 200 mg/kg per injection). 4~54 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the linkers of this invention may be provided in an aqueous physiological buffer solution containing 0.1 to 10% w/v conjugates for parenteral administration. Typical dose ranges are from 1 µg/kg to 0.1 g/kg of body weight daily; weekly, biweekly, triweekly, or monthly, a preferred dose range is from 0.01 mg/kg to 20 mg/kg of body weight weekly, biweekly, triweekly, or monthly, an equivalent dose in a human. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the conjugates by the chosen delivery route, and the speed (bolus or continuous infusion) and schedule of administrations (number of repetitions in a given period of time).

The conjugates of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two weeks (biweekly), triweekly, or per month. Preferably the unit dose range is from 1 to 500 mg administered one to four times a month and even more preferably from 1 mg to 100 mg, once a week, or once biweekly, or once triweekly. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches. The compositions may conveniently be administered in unit dosage form and may be prepared by any of the methods well known in the pharmaceutical art, for example, as described in *Remington: The Science and Practice of Pharmacy*, 21$^{th}$ ed.; Lippincott Williams & Wilkins: Philadelphia, PA, 2005.

Preferred formulations include pharmaceutical compositions in which a compound of the present invention is formulated for oral or parenteral administration. For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

In a specific embodiment, a conjugate of the invention is administered concurrently with the other known or will be known therapeutic agents such as the chemotherapeutic agent, the radiation therapy, immunotherapy agents, autoimmune disorder agents, anti-infectious agents or the other antibody-drug conjugates, resulting in a synergistic effect. In another specific embodiment, the synergistic drugs or radiation therapy are administered prior or subsequent to administration of a conjugate, in one aspect at least an hour, 12 hours, a day, a week, biweeks, triweeks, a month, in further aspects several months, prior or subsequent to administration of a conjugate of the invention.

In other embodiments, the synergistic drugs include, but not limited to:

1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocarmycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemel-amine, trietylenephosphoramide, triethylenethio-phosphaoramide and trimethylolomel-amine]; b). Plant Alkaloids: such as Vinca alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, amatoxins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). A poly (ADP-ribose) polymerase (PARP) inhibitors, such as olaparib, niraparib, iniparib, talazoparib, veliparib, veliparib, CEP 9722 (Cephalon's), E7016 (Eisai's), BGB-290 (BeiGene's), 3-aminobenzamide.

h). antibiotics, such as the enediyne antibiotics (e.g. calicheamicins, especially calicheamicin γ1, δ1, α1 and β1, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; i). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Anti-adrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2''-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols:azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; l). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides &nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), l-nucleosides (e.g. β-l-thymidine and β-l-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The radioisotopes for radiotherapy. Examples of radioisotopes (radionuclides) are $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labeled antibodies are useful in receptor targeted imaging experiments or can be for targeted treatment such as with the antibody-radioisotope conjugates (Wu et al (2005) Nature Biotechnology 23(9): 1137-46). The cell binding molecules, e.g. an antibody can be labeled with ligand reagents that bind, chelate or otherwise complex a radioisotope metal, using the techniques described in Current Protocols in Immunology, Volumes 1 and 2, Coligen et al, Ed. Wiley-Interscience, New York, Pubs. (1991). Chelating ligands which may complex a metal ion include DOTA, DOTP, DOTMA, DTPA and TETA (Macrocyclics, Dallas, Tex. USA).

6). Another cell-binding molecule-drug conjugate as a synergy therapy. The preferred synergic conjugate can be a conjugate having a cytotoxic agent of a tubulysin analog, maytansinoid analog, taxanoid (taxane) analog, CC-1065 analog, daunorubicin and doxorubicin compound, amatoxin analog, benzodiazepine dimer (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotic compound, actinomycin, azaserine, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, geldanamycins, methotrexates, thiotepa, vindesines, vincristines, hemiasterlins, nazumamides, microginins, radiosumins, topoisomerase I inhibitors, alterobactins, microsclerodermins, theonellamides, esperamicins, PNU-159682, and their analogues and derivatives above thereof.

7). Other immunotheraphy drugs: e.g. imiquimod, interferons (e.g. c, J3), granulocyte colony-stimulating factors, cytokines, Interleukins (IL-1~IL-35), antibodies (e. g. trastuzumab, pertuzumab, bevacizumab, cetuximab, panitumumab, infliximab, adalimumab, basiliximab, daclizumab, omalizumab, PD-1 or PD-L1), Protein-bound drugs (e.g., Abraxane), an antibody conjugated with drugs selected from calicheamicin derivative, of maytansine derivatives (DM1 and DM4), CC-1065, SN-38, exatecan, topotecan, topoisomerase I inhibitors, duocarmycin, PBD or IGN minor groove binders, potent taxol derivatives, doxorubicin, auristatin antimitotic drugs (e. g. Trastuzumab-DM1, Trastuzumab deruxtecan (DS-8201a), Inotuzumab ozogamicin, Brentuximab vedotin, Sacituzumab govitecan, Glembatumumab vedotin, lorvotuzumab mertansine, AN-152 LMB2, TP-38, VB4-845, Cantuzumab mertansine, AVE9633, SAR3419, CAT-8015 (anti-CD22), IMGN388, Mirvetuximab soravtansine (IMGN853), Enfortumab vedotin, milatuzumab-doxorubicin, SGN-75 (anti-CD70), anti-Her3-exetecan, anti-Trop2-exetecan, nnti-CD79b-MMAE, anti-Her2-MMAE, anti-trop2-MMAE, anti-Her2-MMAF, anti-trop2-MMAF, anti-CD22-calicheamicin derivative, anti-CD22-MMAE, anti-Her2-auristatin derivatives, anti-Muc1-auristatin derivatives, anti-cMet-auristatin derivatives, or anti-Claudin 18.2-auristatin derivatives).

8). The pharmaceutically acceptable salts, acids or derivatives of any of the above drugs.

In another synergistic immunotherapy, an antibody of a checkpoint inhibitor, TCR (T cell receptors) T cells, or CARs (chimeric antigen receptors) T cells, or of B cell receptor (BCR), Natural killer (NK) cells, or the cytotoxic cells, or an antibody of anti-CD3, CD4, CD8, CD16 (FcγRIII), CD19, CD20, CD22, CD25, CD27, CD30, CD33, CD37, CD38, CD40, CD40L, CD45RA, CD45RO, CD56, CD57, CD57$^{bright}$, CD70, CD79, CD79b, CD123, CD125, CD138, TNFβ, Fas ligand, MHC class I molecules (HLA-A, B, C), VEGF, or NKR-Plantigen is preferred to use along with the conjugates of the present patent for synergistic therapy.

In yet another embodiment, a pharmaceutical composition comprising a therapeutically effective amount of the conjugate of Formula (I)~(VII) or any conjugates described through the present patent can be administered concurrently with the other therapeutic agents such as the chemotherapeutic agent, the radiation therapy, immunotherapy agents, autoimmune disorder agents, anti-infectious agents or the other conjugates for synergistically effective treatment or prevention of a cancer, or an autoimmune disease, or an infectious disease.

According to a still further object, the present invention is also concerned with the process of preparation of the conjugate of the invention. The conjugate and process of the present invention may be prepared in a number of ways well known to those skilled in the art. The antimitotic agents used in the conjugate can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, 2$^{nd}$ Edition, Wiley-VCH Publishers, 1999.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see P. G. Wuts and T. W. Greene, Greene's Protective Groups in Organic Synthesis, Wiley-Interscience; 4th edition (2006). Some reactions may be carried out in the presence of a base, or an acid or in a suitable solvent. There is no particular restriction on the nature of the base, acid and solvent to be used in this reaction, and any base, acid or solvent conventionally used in reactions of this type may equally be used here, provided that it has no adverse effect on other parts of the molecule. The reactions can take place over a wide range of temperatures. In general, we find it convenient to carry out the reaction at a temperature of from −80° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The work-up of the reaction can be carried out by conventional means. For example, the reaction products may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography. The synthesis of the antimitotic agents and their conjugates of this invention are illustrated in FIGS. 1-21.

The conjugates of the cell-binding molecules with potent antimitotic agents are further illustrated but not restricted by the description in the following examples.

EXPERIMENTAL MATERIALS

Mass spectra were obtained using a Bruker Esquire 3000 system. NMR spectra were recorded on a Bruker AVANCE300 spectrometer. Chemical shifts are reported in ppm relative to TMS as an internal standard. Ultraviolet spectra were recorded on a Hitachi U1200 spectrophotometer. HPLC was performed using an Agilent 1100 HPLC system equipped with a fraction collector and a variable wavelength detector. Thin layer chromatography was performed on Analtech GF silica gel TLC plates. Aminal acids and their derivatives as well as preloaded resins were either from Merck Chemicals International Co, or Synthetech Co., or Peptides International Inc or Chembridge International Co. or Sigma-Aldrich Co. Some of the linkers, Linkers of NHS ester/Maleimide (AMAS, BMPS, GMBS, MBS, SMCC, EMCS or Sulfo-FMCS, SMPB, SMPH, LC-SMCC, Sulfo-KMUS, SM(PEG)4, SM(PEG)6, SM(PEG)8, SM(PEG)12, SM(PEG)24); NHS ester/Pyridyldithiol (SPDP, LC-SPDP or Sulfo-LC-SPDP, SMPT, Sulfo-LC-SMPT); NHS esters/H-aloacetyl (SIA, SBAP, SIAB or Sulfo-SLAB); NHS ester/Diazirine (SDA or Sulfo-SDA, LC-SDA or Sulfo-LC-SDA, SDAD or Sulfo-SDAD); Maleimide/Hydrazide (BMPH, EMCH, MPBH, KMUH); Pyridyldithiol/Hydrazide (PDPH); Isocyanate/Maleimide (PMPI) were purchased from Thermo Fisher Scientific Co. SPDB, SPP linkers were made according to the references (Cumber, A. et al, *Bioconjugate Chem.*, 1992, 3, 397-401). T-DM1 and Trastuzumab was from Genentech. All other chemicals or anhydrous solvents were from Sigma-Aldrich International or Aladdin Chemical (Shanghai) Ltd.

Example 1. Synthesis of di-tert-butyl-1,2-bis(2-(tert-butoxy)-2-oxoethyl) hydrazine-1,2-dicarboxylate

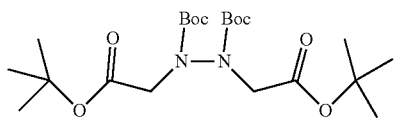 [SMILES: CC(C)(C)OC(=O)CN(C(=O)OC(C)(C)C)N(CC(=O)OC(C)(C)C)C(=O)OC(C)(C)C]

To di-tert-butyl hydrazine-1,2-dicarboxylate (8.01 g, 34.4 mmol) in DMF (150 ml) was added NaH (60% in oil, 2.76 g, 68.8 mmol). After stirred at RT for 30 min, tert-butyl 2-bromoacetate (14.01 g, 72.1 mmol) was added. The mixture was stirred overnight, quenched with addition of methanol (3 ml), concentrated, diluted with EtOAc (100 ml) and water (100 ml), separated, and the aqueous layer was extracted with EtOAc (2×50 ml). The organic layers were combined, dried over MgSO$_4$, filtered, evaporated, and purified by SiO$_2$ column chromatography (EtOAc/Hexane 1:5 to 1:3) to afforded the title compound (12.98 g, 82% yield) as a colorless oil. MS ESI m/z calcd for C$_{22}$H$_{41}$N$_2$O$_8$ [M+H]$^+$ 461.28, found 461.40.

Example 2. Synthesis of 2,2'-(hydrazine-1,2-diyl)diacetic acid

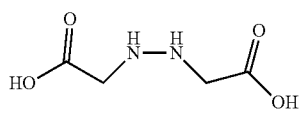

Di-tert-butyl 1,2-bis(2-(tert-butoxy)-2-oxoethyl)hydrazine-1,2-dicarboxylate (6.51 g, 14.14 mmol) in 1,4-dioxane (40 ml) was added HCl (12 M, 10 ml). The mixture was stirred for 30 min, diluted with dioxane (20 ml) and toluene (40 ml), evaporated and co-evaporated with dioxane (20 ml) and toluene (40 ml) to dryness to afford the crude title product for the next step without further production (2.15 g, 103% yield, ~93% pure). MS ESI m/z calcd for C$_4$H$_9$N$_2$O$_4$ [M+H]$^+$ 149.05, found 149.40.

Example 3. Synthesis of 2,2'-(1,2-bis((E)-3-bromoacryloyl)hydrazine-1,2-diyl)diacetic acid

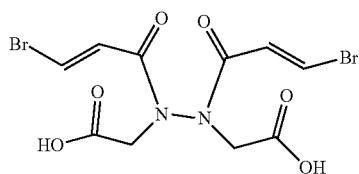 [SMILES: O=C(O)CN(C(=O)/C=C/Br)N(CC(=O)O)C(=O)/C=C/Br]

To a solution of 2,2'-(hydrazine-1,2-diyl)diacetic acid (1.10 g, 7.43 mmol) in the mixture of THF (50 ml) and NaH$_2$PO$_4$ (0.1 M, 80 ml, pH 6.0) was added (E)-3-bromoacryloyl bromide (5.01 g, 23.60 mmol). The mixture was stirred for 6 h, concentrated and purified on SiO$_2$ column eluted with H$_2$O/CH$_3$CN (1:9) containing 3% formic acid to afford the title compound (2.35 g, 77% yield, ~93% pure). MS ESI m/z calcd for C$_{10}$H$_{11}$Br$_2$N$_2$O$_6$ [M+H]$^+$ 412.89, found 413.50.

Example 4. Synthesis of 2,2'-(1,2-bis((E)-3-bromoacryloyl)hydrazine-1,2-diyl)diacetyl chloride

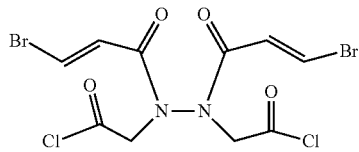 [SMILES: O=C(Cl)CN(C(=O)/C=C/Br)N(CC(=O)Cl)C(=O)/C=C/Br]

2,2'-(1,2-Bis((E)-3-bromoacryloyl)hydrazine-1,2-diyl)diacetic acid (210 mg, 0.509 mmol) in dichloroethane (15 ml) was added (COCl)$_2$ (505 mg, 4.01 mmol), followed by addition of 0.040 ml of DMF. After stirred at RT for 2 h, the mixture was concentrated and co-evaporated with dichloroethane (2×20 ml) and toluene (2×15 ml) to dryness to afford the title crude product (which is not stable) for the next step without further purification (245 mg, 107% yield). MS ESI m/z calcd for C10H9Br2Cl2N2O4 [M+H]+ 448.82, 450.82, 452.82, 454.82, found 448.60, 450.60, 452.60, 454.60.

Example 5. Synthesis of tert-butyl 2,8-dioxo-1,5-oxazocane-5-carboxylate

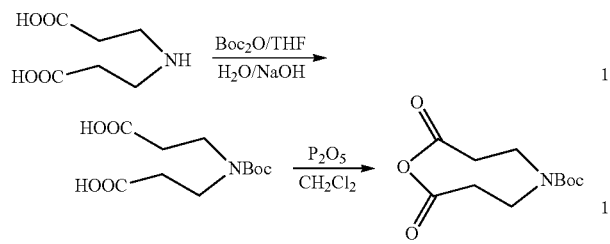

To a solution of 3,3'-azanediyldipropanoic acid (10.00 g, 62.08 mmol) in 1.0 M NaOH (300 ml) at 4° C. was added di-tert-butyl dicarbonate (22.10 g, 101.3 mmol) in 200 ml THF in 1 h. After addition, the mixture was kept to stirring for 2 h at 4° C. The mixture was carefully acidified to pH~4 with 0.2 M H3PO4, concentrated in vacuo, extracted with CH2Cl2, dried over Na2SO4, evaporated and purified with flash SiO2 chromatography eluted with AcOH/MeOH/CH2Cl2 (0.01:1:5) to afford 3,3'-((tert-butoxycarbonyl)azanediyl)dipropanoic acid (13.62 g, 84% yield). ESI MS m/z C11H19NO6 [M+H]+, calcd. 262.27, found 262.40.

To a solution of 3,3'-((tert-butoxycarbonyl)azanediyl)dipropanoic acid (8.0 g, 30.6 mmol) in CH2Cl2 (500 ml) at 0° C. was added phosphorus pentoxide (8.70 g, 61.30 mmol). The mixture was stirred at 0° C. for 2 h and then r.t. for 1 h, filtered through short SiO2 column, and rinsed the column with EtOAc/CH2Cl2 (1:6). The filtrate was concentrated and triturated with EtOAc/hexane to afford the title compound (5.64 g, 74% yield). ESI MS m/z C11H17NO5 [M+H]+, calcd. 244.11, found 244.30.

Example 6. Synthesis of 2,5-dioxopyrrolidin-1-yl propiolate

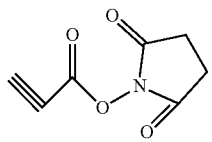

Propiolic acid (5.00 g, 71.4 mmol), NHS (9.01 g, 78.3 mmol) and EDC (20.0 g, 104.1 mmol) in CH2Cl2 (150 ml) and DIPEA (5 ml, 28.7 mmol) was stirred for overnight, evaporated and purified by SiO2 column chromatography (EtOAc/Hexane 1:4) to afforded the title compound (9.30 g, 79% yield) as a colorless oil. 1H NMR (500 MHz, CDCl3) δ 2.68 (s, 1H), 2.61 (s, 4H). MS ESI m/z calcd for C7H5NNaO4 [M+Na]+ 190.02, found 190.20.

Example 7. Synthesis of tert-butyl 2-propioloylhydrazinecarboxylate

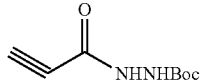

Propiolic acid (5.00 g, 71.4 mmol), tert-butyl hydrazinecarboxylate (9.45 g, 71.5 mmol) and EDC (20.0 g, 104.1 mmol) in CH2Cl2 (150 ml) and DIPEA (5 ml, 28.7 mmol) was stirred for overnight, evaporated and purified by SiO2 column chromatography (EtOAc/Hexane 1:5) to afforded the title compound (7.92 g, 84% yield) as a colorless oil. 1H NMR (500 MHz, CDCl3) δ 8.76 (m, 2H), 2.68 (s, 1H), 1.39 (s, 9H). MS ESI m/z calcd for C5H12NaN2O2 [M+Na]+ 155.09, found 155.26.

Example 8. Synthesis of propiolohydrazide, HCl salt

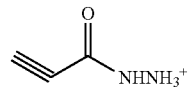

tert-butyl 2-propioloylhydrazinecarboxylate (4.01 g, 30.35 mmol) dissolved in 1,4-dioxane (12 mL) was treated with 4 ml of HCl (conc.) at 4° C. The mixture was stirred for 30 min, diluted with Dioxane (30 ml) and toluene (30 ml) and concentrated under vacuum. The crude mixture was purified on silica gel using a mixture of methanol (from 5% to 10%) and 1% formic acid in methylene chloride as the eluant to give title compound (2.11 g, 83% yield), ESI MS m/z C3H5N2O [M+H]+, calcd. 85.03, found 85.30.

Example 9. Synthesis of Compound 2

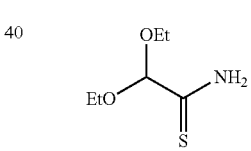

2

In a 10-L reactor 2,2-diethoxyacetonitrile (1.00 kg, 7.74 mol, 1.0 eq.) was mixed with (NH4)2S (48% aqueous solution, 1.41 kg, 9.29 mol, 1.2 eq.) in methanol (6.0 L) at room temperature. The internal temperature increased to 33° C. and then dropped back to r.t. After stirring overnight, the reaction mixture was concentrated under vacuum and the residue was taken up in ethyl acetate (5 L) and washed with saturated NaHCO3 solution (4×1.0 L). The aqueous layer was back-extracted with ethyl acetate (5×1.0 L). The organic phases were combined and washed with brine (3 L), dried over anhydrous Na2SO4 and concentrated. The resulting solid was collected by vacuum filtration and washed with petroleum ether. The filtrate was concentrated and triturated with petroleum ether to yield a few crops of white or light yellow solid. All crops were combined to give 1.1 kg of desired product (87% yields). 1H NMR (500 MHz, CDCl3) δ 7.81 (d, J=71.1 Hz, 2H), 5.03 (s, 1H), 3.73 (dq, J=9.4, 7.1 Hz, 2H), 3.64 (dq, J=9.4, 7.0 Hz, 2H), 1.25 (t, J=7.1 Hz, 6H).

Example 10. Synthesis of Compound 3

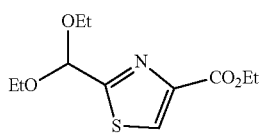

3

In a 5-L 3-neck round bottle flask, equipped with a reflux condenser and an additional funnel, ethyl bromopyruvate (80% purity, 404 mL, 2.57 mol, 1.2 eq.) was added over 30 min. to a mixture of molecular sieves (3 Å, 500 g) and thioamide (350 g, 2.14 mol, 1.0 eq.) in 3 L EtOH. During addition, the internal temperature increased slightly. The reaction mixture was then heated to reflux and stirred for 30 min. After cooling to r.t. the reaction mixture was filter over celite and the filter cake washed with ethyl acetate. The filtrate was concentrated under vacuum. Two batches of the crude product were combined and mixed with silica gel (1.5 kg) and loaded on a silica gel (10 kg packed) column and eluted with ethyl acetate/petroleum ether (10-20%) to give thiazole carboxylate as a brown oil (509 g, 92% yield).

Example 11. Synthesis of Compound 4

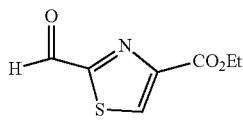

4

A solution of acetal (300 g, 1.16 mol) in acetone (3.0 L) was heated to reflux and 4N HCl (250 mL) was added over 1.0 h to the refluxing solution. TLC analysis indicated complete consumption of the starting material. The reaction mixture was concentrated under reduced pressure and phases were separated. The organic phase was diluted with ethyl acetate (1.5 L) and washed with saturated NaHCO$_3$ solution (1.0 L), water (1.0 L) and brine (1.0 L), and then dried over anhydrous Na$_2$SO$_4$. All of the aqueous phases were combined and extracted with ethyl acetate. The extracts were combined and dried over anhydrous Na$_2$SO$_4$. The organic solutions were filtered and concentrated under reduced pressure. The crude product was triturated with petroleum ether and diethyl ether (5:1) and the resulting solid was collected by vacuum filtration and washed with petroleum ether and ethyl acetate (10:1). The filtrate was concentrated and chromatographed using 0-15% ethyl acetate/petroleum ether to give another crop of desired product. All white to light yellow solids were combined and weighed 40 g (43% yield). $^1$H NMR (500 MHz, CDCl$_3$) δ 10.08-10.06 (m, 1H), 8.53-8.50 (m, 1H), 4.49 (q, J=7.1 Hz, 2H), 1.44 (t, J=7.1 Hz, 3H). MS ESI m/z calcd for C$_7$H$_8$NO$_3$S [M+H]$^+$ 186.01; found 186.01.

Example 12. Synthesis of Compound 6

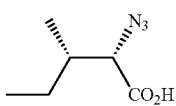

6

NaN$_3$ (740 g, 11.4 mol) was dissolved in water (2.0 L) and dichloromethane (2.0 L) was added and cooled at 0° C., to which Tf$_2$O (700 mL, 4.10 mol, 1.8 eq.) was added over 1.5 h. After addition was completed, the reaction was stirred at 0° C. for 3 h. The organic phase was separated and the aqueous phase was extracted with dichloromethane (2×500 mL). The combined organic phases were washed with saturated NaHCO$_3$ solution (3×1.0 L). This dichloromethane solution of triflyl azide was added to a mixture of (L)-isoleucine (300 g, 2.28 mol, 1.0 eq.), K$_2$CO$_3$ (472 g, 3.42 mol, 1.5 eq.), CuSO$_4$·5H$_2$O (5.7 g, 22.8 mmol, 0.01 eq.) in water (3.0 L) and methanol (3.0 L) at r.t. During addition, the internal temperature increased slightly. And the mixture was then stirred at r.t. for 16 h. The organic solvents were removed under reduced pressure and the aqueous phase was acidified to pH 6-6.5 with concentrated HCl (about 280 mL added) and then diluted with phosphate buffer (0.25 M, pH 6.2, 6.0 L), washed with EtOAc (6×2.0 L) to remove the sulfonamide by-product. The solution was acidified to pH 3 with concentrated HCl (about 400 mL added), extracted with EtOAc (4×2.0 L). The combined organic layers were washed with brine (2.0 L) and dried over anhydrous Na$_2$SO$_4$, filtered and concentrated to give product 6 (320 g, 89% yield) as a light yellow oil. $^1$H NMR (500 MHz, CDCl$_3$) δ 12.01 (s, 1H), 3.82 (d, J=5.9 Hz, 1H), 2.00 (ddd, J=10.6, 8.6, 5.5 Hz, 1H), 1.54 (dqd, J=14.8, 7.5, 4.4 Hz, 1H), 1.36-1.24 (m, 1H), 1.08-0.99 (m, 3H), 0.97-0.87 (m, 3H).

Example 13. Synthesis of Compound 10

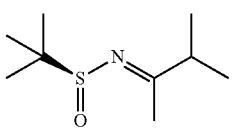

10

To a solution of (S)-2-methylpropane-2-sulfinamide (100 g, 0.825 mol, 1.0 eq.) in 1 L THF was added Ti(OEt)$_4$ (345 mL, 1.82 mol, 2.2 eq.) and 3-methyl-2-butanone (81 mL, 0.825 mol, 1.0 eq.) under N$_2$ at r.t. The reaction mixture was refluxed for 16 h, then cooled to r.t. and poured onto iced water (1 L). The mixture was filtered and the filter cake was washed with EtOAc. The organic layer was separated, dried over anhydrous Na$_2$SO$_4$ and concentrated to give a residue which was purified by vacuum distillation (15-20 torr, 95° C.) to afforded product 10 (141 g, 90% yield) as a yellow oil. $^1$H NMR (500 MHz, CDCl$_3$) δ 2.54-2.44 (m, 1H), 2.25 (s, 3H), 1.17 (s, 9H), 1.06 (dd, J=6.9, 5.1 Hz, 6H). MS ESI m/z calcd for C$_9$H$_{19}$NaNOS [M+Na]$^+$ 212.12; found 212.11.

Example 14. Synthesis of Compound 11

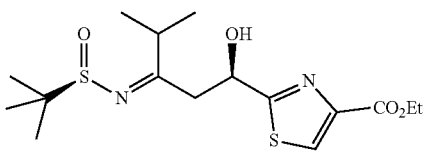

To a solution of diisopropylamine (264 mL, 1.87 mol, 1.65 eq.) in dry THF (1 L) was added n-butyllithium (2.5 M, 681 mL, 1.70 mol, 1.5 eq.) at −78° C. under $N_2$. The reaction mixture was warmed to 0° C. over 30 min and then cooled back to −78°. Compound 10 (258 g, 1.36 mol, 1.2 eq.) was added, and rinsed with THF (50 mL). The reaction mixture was stirred for 1 h before $ClTi(O^iPr)_3$ (834 g, 3.17 mol, 2.8 eq.) in THF (1.05 L) was added dropwise. After stirring for 1 h, compound 4 (210 g, 1.13 mol, 1.0 eq.) dissolved in THF (500 mL) was added dropwise in about 1 hours and the resulting reaction mixture was stirred for 3 h. The completion of the reaction was indicated by TLC analysis. The reaction was quenched by a mixture of acetic acid and THF (v/v 1:1, 300 mL), then poured onto brine (2 L), extracted with EtOAc (8×1 L). The organic phase was washed with water and brine, dried over anhydrous $Na_2SO_4$, filtered and concentrated. The residue was purified by column chromatography (DCM/EtOAc/PE 2:1:2) to afforded the compound 11 (298 g, 74% yield) as a colorless oil. $^1$H NMR (500 MHz, $CDCl_3$) δ 8.13 (s, 1H), 6.63 (d, J=8.2 Hz, 1H), 5.20-5.11 (m, 1H), 4.43 (q, J=7.0 Hz, 2H), 3.42-3.28 (m, 2H), 2.89 (dt, J=13.1, 6.5 Hz, 1H), 1.42 (t, J=7.1 Hz, 3H), 1.33 (s, 9H), 1.25-1.22 (m, 6H). MS ESI m/z calcd for $C_{16}H_{26}NaN_2O_4S_2$ [M+Na]$^+$ 397.13, found 397.11.

Example 15. Synthesis of Compound 12

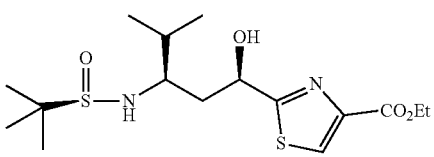

A solution of compound 11 (509 g, 1.35 mol, 1.0 eq.) dissolved in THF (200 mL) was cooled to −78° C. $Ti(OEt)_4$ (570 mL, 2.72 mol, 2.0 eq.) was added slowly. After completion of the addition, the mixture was stirred for 1 h, before $NaBH_4$ (51.3 g, 1.36 mol, 1.0 eq.) was added in portions over 90 min. The reaction mixture was stirred at −78° C. for 3 h. TLC analysis showed starting material still remained. EtOH (50 mL) was added slowly, and the reaction was stirred for 1.5 h and then poured onto brine (2 L, with 250 mL HOAc) and warmed to r.t. After filtration over Celite, the organic phase was separated and washed with water and brine, dried over anhydrous $Na_2SO_4$, filtered, and concentrated. The residue was purified by column chromatography (EtOAc/PE 1:1) to deliver product 12 (364 g, 71% yield) as a white solid. $^1$H NMR (500 MHz, $CDCl_3$) δ 8.10 (s, 1H), 5.51 (d, J=5.8 Hz, 1H), 5.23-5.15 (m, 1H), 4.41 (q, J=7.0 Hz, 2H), 3.48-3.40 (m, 1H), 3.37 (d, J=8.3 Hz, 1H), 2.29 (t, J=13.0 Hz, 1H), 1.95-1.87 (m, 1H), 1.73-1.67 (m, 1H), 1.40 (t, J=7.1 Hz, 3H), 1.29 (s, 9H), 0.93 (d, J=7.3 Hz, 3H), 0.90 (d, J=7.2 Hz, 3H). MS ESI m/z calcd for $C_{16}H_{28}NaN_2O_4S_2$ [M+Na]$^+$ 399.15, found 399.14.

Example 16. Synthesis of Compound 13

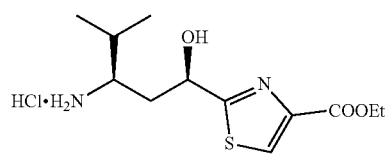

To a solution of compound 12 (600 g, 1.60 mol, 1.0 eq.) in ethanol (590 mL) was added 4 N HCl in dioxane (590 mL) slowly at 0° C. The reaction was allowed to warm to r.t. and stirred for 2.5 h. A white precipitate crushed out and was collected by filtration and washed with EtOAc. The filtrate was concentrated and triturated with EtOAc. Two crops of white solid were combined and weighed 446 g (90% yield).

Example 17. Synthesis of Compound 14

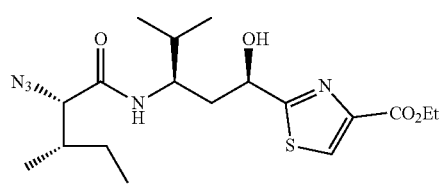

Compound 10: Azido-Ile-OH (6, 153 g, 0.97 mol, 2.0 eq.) was dissolved in THF (1.5 L) and cooled to 0° C., to which NMM (214 mL, 1.94 mol, 4.0 eq.) and isobutylchloroformate (95 mL, 0.73 mol, 2.0 eq.) were added in sequence. The reaction was stirred at 0° C. for 1.0 h. Compound 13 (150 g, 0.49 mmol, 1.0 eq.) was added in portions. After stirring at 0° C. for 30 min, the reaction was warmed to r.t. and stirred for 2 h. Water was added at 0° C. to quench the reaction and the resulting mixture was extracted with EtOAc for three times. The combined organic layers were washed with 1N HCl, saturated $NaHCO_3$ and brine, dried over anhydrous $Na_2SO_4$, filtered and concentrated. The residue was purified by column chromatography (0-30% EtOAc/PE) to give a white solid (140 g, 70% yield). $^1$H NMR (500 MHz, $CDCl_3$) δ 8.14 (s, 1H), 6.57 (d, J=8.9 Hz, 1H), 4.91 (d, J=11.1 Hz, 1H), 4.44 (dd, J=13.2, 6.3 Hz, 2H), 4.08-3.95 (m, 2H), 2.21 (dd, J=24.4, 11.5 Hz, 2H), 1.90-1.79 (m, 3H), 1.42 (t, J=6.6 Hz, 3H), 1.37-1.27 (m, 2H), 1.11 (d, J=6.4 Hz, 3H), 1.01-0.94 (m, 9H). MS ESI m/z calcd for $C18H_{30}N_5O_4S$ [M+H]$^+$ 412.19, found 412.19.

Example 18. Synthesis of Compound 15

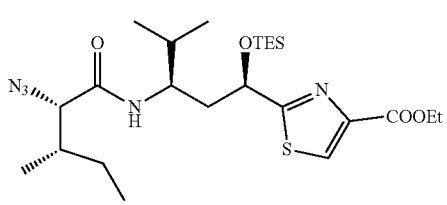

15

Compound 11: To a solution of compound 14 (436 g, 1.05 mol, 1.0 eq.) in CH$_2$Cl$_2$ (50 mL) was added imidazole (94 g, 1.37 mmol, 1.3 eq.), followed by chlorotriethylsilane (222 mL, 1.32 mol, 1.25 eq.) at 0° C. The reaction mixture was allowed to warm to r.t. over 1 hour and stirred for an additional hour. Brine was added to the reaction mixture, the organic layer was separated and the aqueous layer was extracted with EtOAc. The combined organic phases were dried, filtered, concentrated under reduced pressure, and purified by column chromatography with a gradient of 15-35% EtOAc in petroleum ether to afford product 15 (557.4 g, 95% yield) as a colorless oil. $^1$H NMR (500 MHz, CDCl$_3$) δ 8.12 (s, 1H), 6.75 (d, J=8.0 Hz, 1H), 5.20-5.12 (m, 1H), 4.44 (q, J=7.0 Hz, 2H), 4.06-3.97 (m, 1H), 3.87 (d, J=3.8 Hz, 1H), 2.14 (d, J=3.8 Hz, 1H), 2.01-1.91 (m, 3H), 1.42 (t, J=7.1 Hz, 3H), 1.34-1.25 (m, 2H), 1.06 (d, J=6.8 Hz, 3H), 1.00-0.93 (m, 18H), 0.88 (dd, J=19.1, 6.8 Hz, 6H). MS ESI m/z calcd for C$_{24}$H$_{44}$N$_5$O$_4$SSi [M+H]+ 526.28, found 526.28.

Example 19. Synthesis of Compound 16

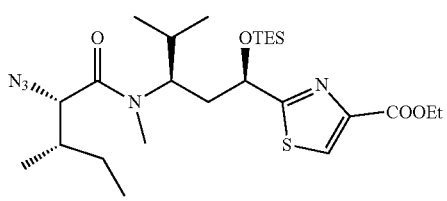

16

To a solution of 15 (408 g, 0.77 mol, 1.0 eq.) and methyl iodide (145 mL, 2.32 mol, 3.0 eq.) in THF (4 L) was added sodium hydride (60% dispersion in mineral oil, 62.2 g, 1.55 mol, 2.0 eq.) at 0° C. The resulting mixture was stirred at 0° C. overnight and then poured onto ice-water cooled saturated ammonium chloride (5 L) with vigorous stirring. The mixture was then extracted with EtOAc (3×500 mL) and the organic layers were dried, filtered, concentrated and purified by column chromatography with a gradient of 15-35% EtOAc in petroleum ether to afford product 16 (388 g, 93% yield) as a light yellow oil. $^1$H NMR (500 MHz, CDCl$_3$) δ 8.09 (s, 1H), 4.95 (d, J=6.6 Hz, 1H), 4.41 (q, J=7.1 Hz, 2H), 3.56 (d, J=9.5 Hz, 1H), 2.98 (s, 3H), 2.27-2.06 (m, 4H), 1.83-1.70 (m, 2H), 1.41 (t, J=7.2 Hz, 3H), 1.29 (ddd, J=8.9, 6.8, 1.6 Hz, 3H), 1.01 (d, J=6.6 Hz, 3H), 0.96 (dt, J=8.0, 2.9 Hz, 15H), 0.92 (d, J=6.6 Hz, 3H), 0.90 (d, J=6.7 Hz, 3H). MS ESI m/z calcd for C$_{25}$H$_{46}$N$_5$O$_4$SSi [M+H]$^+$ 540.30, found 540.30.

Example 20. Synthesis of Compound 17

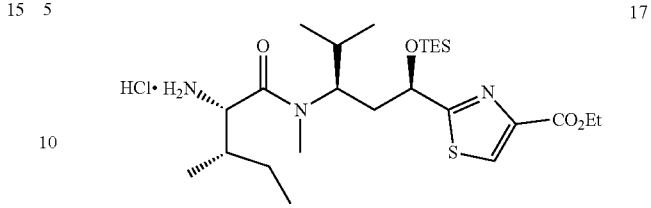

17

To a solution of compound 16 (1.01 g, 1.87 mmol) in methanol (15 mL) was added 0.1N HCl dropwise until a neutral pH was reached. After addition of Pd/C (10 wt %, 583 mg), the mixture was stirred under H$_2$ (1 atm) at room temperature for 16 h. The Pd/C was then removed by filtration, with washing of the filter pad with methanol. The filtrate was concentrated under reduced pressure and the residue was re-dissolved in EtOAc (50 mL), dried over anhydrous Na$_2$SO$_4$, filtered and concentrated to afford compound 17 (900 mg, 94% yield) as a pale yellow oil.

Example 21. Synthesis of Compound 22

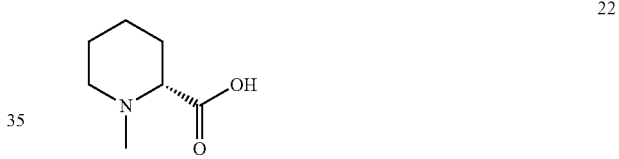

22

To a solution of D-pipecolinic acid (10.0 g, 77.4 mmol, 1.0 eq.) in methanol (100 mL) was added formaldehyde (37% aqueous solution, 30.8 mL, 154.8 mmol, 2.0 eq.), followed by Pd/C (10 wt %, 1.0 g). The reaction mixture was stirred under H$_2$ (1 atm) overnight, and then filtered through Celite, with washing of the filter pad with methanol. The filtrate was concentrated under reduced pressure to afford compound 22 (10.0 g, 90% yield) as a white solid.

Example 22. Synthesis of Compound 23

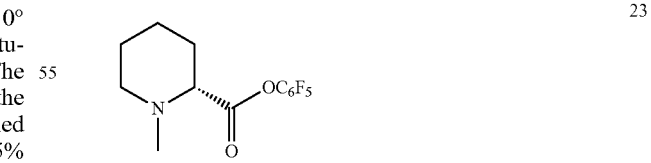

23

To a solution of D-N-methyl pipecolinic acid (2.65 g, 18.5 mmol) in EtOAc (50 mL) were added pentafluorophenol (3.75 g, 20.4 mmol) and DCC (4.21 g, 20.4 mmol). The reaction mixture was stirred at r.t. for 16 h, and then filtered over Celite. The filter pad was washed with 10 mL of EtOAc. The filtrate was used immediately without further purification or concentration.

Example 23. Synthesis of Compound 28

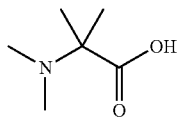

28

A mixture of 2-amino-2-methylpropanoic acid (500 g, 4.85 mol, 1.0 eq.), aqueous formaldehyde (37%, 1.0 L, 12.1 mol, 2.5 eq.) and formic acid (1.0 L) was heated to reflux (80° C.) for 3.0 h. 6 N HCl (850 mL) was then added at r.t. and the reaction mixture was concentrated. The resulting solid was collected by filtration with washing of ethyl acetate for three times (1.0 L). The solid was dissolved in water (1.5 L) and neutralized to pH 7.0 with 4N NaOH (about 1.0 L solution). The solution was concentrated and co-evaporated with ethanol (2.0 L) to remove residual water. MeOH (2.0 L) was added to the residue and the solid (NaCl) was filtered off with washing of ethyl acetate. The filtrate was concentrated under reduced pressure to give a white solid 639.2 g, which contains some NaCl and was used without further treatment.

Example 24. Synthesis of Compound 29

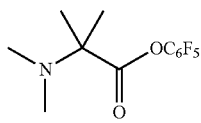

29

To a solution of 2-(dimethylamino)-2-methylpropanoic acid (97 g, 0.74 mol) in EtOAc (1 L) were added pentafluorophenol (163 g, 0.88 mol) and DIC (126 mL, 0.81 mol). The reaction mixture was stirred at r.t. for 24 h, and then filtered over Celite. The filter pad was washed with 10 mL of EtOAc. The filtrate was used immediately without further purification or concentration.

Example 25. Synthesis of Compound 30

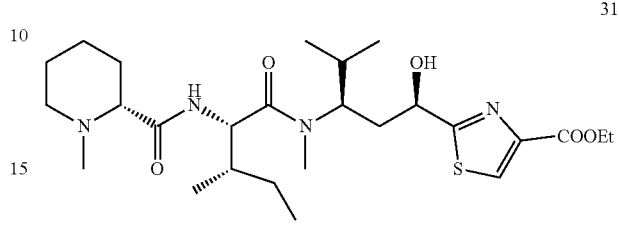

30

Dry Pd/C (10 wt %, 300 mg) and azide compound 16 (3.33 g, 6.61 mmol) were added to pentafluorophenyl ester 23 in EtOAc. The reaction mixture was stirred under hydrogen atmosphere for 27 h, and then filtered through a plug of Celite, with washing of the filter pad with EtOAc. The combined organic portions were concentrated and purified by column chromatography with a gradient of 0-5% methanol in EtOAc to deliver compound 30 (3.90 g, 86% yield). MS ESI m/z calcd for $C_{32}H_{59}N_4O_5SSi$ [M+H]$^+$ 639.39, found 639.39.

Example 26. Synthesis of Compound 31

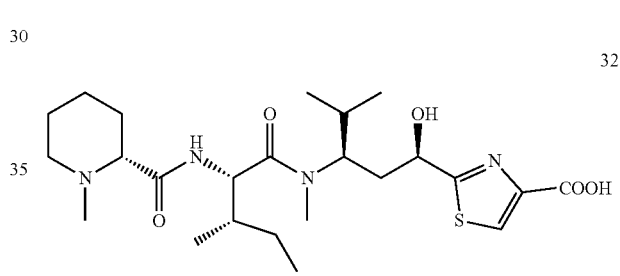

31

The coupled product compound 30 (3.90 g, 6.1 mmol) was dissolved in AcOH/water/THF (v/v/v 3:1:1, 100 mL), and stirred at r.t. for 48 h. The reaction was then concentrated and purified by column chromatography (2:98 to 15:85 MeOH/EtOAc) to afford compound 31 (2.50 g, 72% yield over 2 steps). MS ESI m/z calcd for $C_{26}H_{45}N_4O_5S$ [M+H]$^+$ 525.30, found 525.33.

Example 27. Synthesis of Compound 32

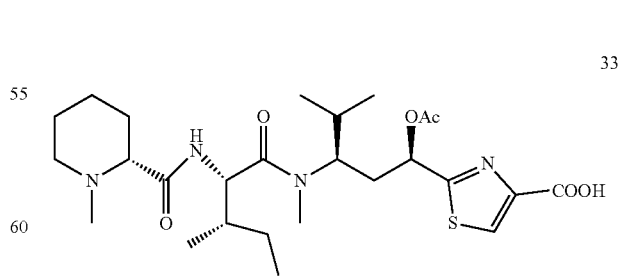

32

An aqueous solution of LiOH (0.4 N, 47.7 mL, 19.1 mmol, 4.0 eq.) was added to a solution of compound 31 (2.50 g, 4.76 mmol, 1.0 eq.) in dioxane (47.7 mL) at 0° C. The reaction mixture was stirred at r.t. for 2 h and then concentrated. Column chromatography (100% $CH_2Cl_2$ to $CH_2Cl_2$/MeOH/$NH_4OH$ 80:20:1) afforded compound 32 (2.36 g, 99% yield) as an amorphous solid. MS ESI m/z calcd for $C_{24}H_{41}N_4O_5S$ [M+H]$^+$ 497.27, found 497.28.

Example 28. Synthesis of Compound 33

33

To a solution of compound 32 (2.36 g, 4.75 mmol) in pyridine (50 mL) at 0° C., acetic anhydride (2.25 mL, 24 mmol) was added slowly. The reaction mixture was allowed to warm to r.t. over 2 h and stirred at r.t. for 24 h. The reaction was concentrated and then treated with dioxane/water (v/v 1:1, 10 mL) for 1 h to destroy possible anhydride. After concentration the residue was purified by column chromatography (100% CH$_2$Cl$_2$ to CH$_2$Cl$_2$/MeOH/NH$_4$OH 50:50:1) to afford compound 33 (2.25 g, 88% yield) as an amorphous white solid. MS ESI m/z calcd for C$_{26}$H$_{43}$N$_4$O$_6$S [M+H]$^+$ 539.28, found 539.28.

Example 29. Synthesis of Compound 38

38

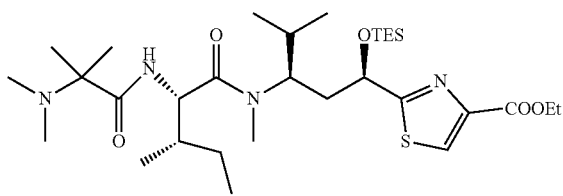

To the EtOAc solution of pentafluorophenyl ester 29, compound 16 (200 g, 0.37 mol) and dry Pd/C (10 wt %, 10 g) were added. The reaction mixture was stirred under hydrogen atmosphere (1 atm) for 27 h, and then filtered through a plug of Celite, with washing of the filter pad with EtOAc. The combined organic portions were concentrated and purified by column chromatography with a gradient of 0-5% methanol in EtOAc to deliver compound 38 (184 g, 79% yield). MS ESI m/z calcd for C$_{31}$H$_{58}$N$_4$O$_5$SSi [M+H]$^+$ 627.39, found 627.39.

Example 30. Synthesis of Compound 39

39

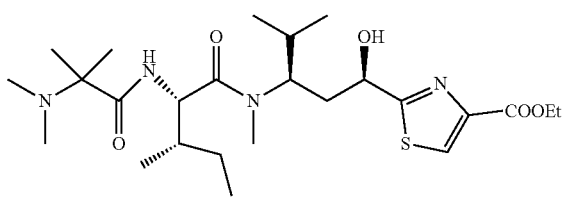

Compound 38 (200 g, 0.32 mmol) was dissolved in AcOH/water/THF (v/v/v 3:1:1, 638 mL), and stirred at r.t. for 4 days. After the reaction was concentrated, toluene was added and concentrated again; this step was repeated two times to afford compound 39, which was used directly in the next step. MS ESI m/z calcd for C$_{25}$H$_{45}$N$_4$O$_5$S [M+H]$^+$ 513.30, found 513.30.

Example 31. Synthesis of Compound 40

40

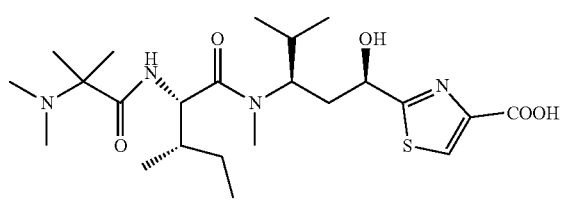

An aqueous solution of LiOH (0.4 N, 600 mL, 2.55 mol, 8.0 eq.) was added to a solution of compound 39 (160 g, 0.319 mol, 1.0 eq.) in MeOH (1.2 L) at 0° C. The reaction mixture was stirred at r.t. for 2 h and then concentrated. Column chromatography (pure CH$_2$Cl$_2$ to 80:20:1 CH$_2$Cl$_2$/MeOH/NH$_4$OH) afforded compound 40 (140 g, 91% yield for two steps) as an amorphous solid. MS ESI m/z calcd for C$_{23}$H$_{40}$N$_4$O$_5$S [M+H]$^+$ 485.27, found 485.27.

Example 32. Synthesis of Compound 41

41

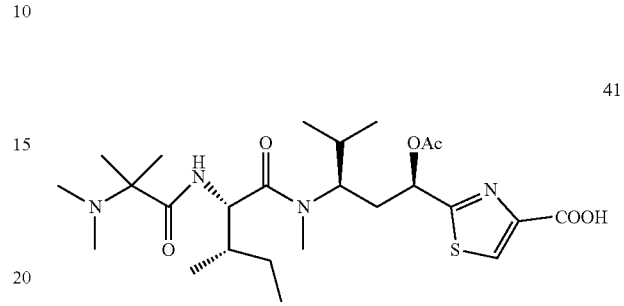

A solution of compound 27 (143 g, 0.30 mol, 1.0 eq.) and DMAP (0.36 g, 2.95 mmol, 0.01 eq.) in anhydrous THF (1.4 L) and anhydrous DMF (75 mL) was cooled to 0° C., to which TEA (82.2 mL, 0.59 mmol, 2.0 eq.) and acetic anhydride (56 mL, 0.59 mmol, 2.0 eq.) were added. The reaction mixture was allowed to warm to r.t. and stirred for 24 h, and then concentrated. Column chromatography (5-50% MeOH/DCM) delivered compound 41 (147 g, 95% yield) as an amorphous solid. MS ESI m/z calcd for C$_{25}$H$_{44}$N$_4$O$_6$S [M+H]$^+$ 527.28, found 527.28.

Example 33. Synthesis of Compound 41a

41a

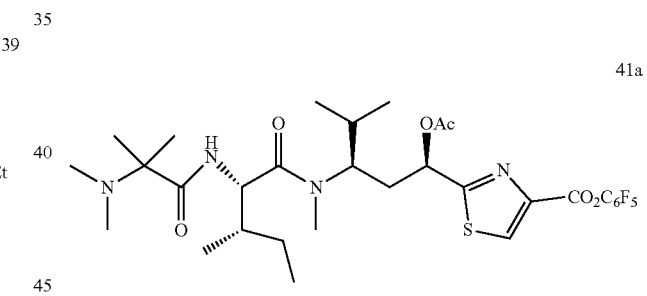

To a solution of compound 41 (5.0 g, 9.5 mmol, 1.0 eq) in anhydrous DCM (100 mL) was added EDC (4.6 g, 23.8 mmol, 2.5 eq) and pentafluorophenol (4.4 g, 23.8 mmol, 2.5 eq) at room temperature under N$_2$. The mixture was stirred at room temperature for 2 h, and then diluted in DCM (100 mL), washed with water (2×200 mL) and brine (200 mL), dried over anhydrous sodium sulfate, filtered, concentrated and purified by SiO$_2$ column chromatography (50% EtOAc/PE) to give compound 41a as a white solid (5.2 g, 79% yield) MS ESI m/z calcd for C$_{31}$H$_{42}$F$_5$N$_4$O$_6$S [M+H]$^+$: 693.27, found: 693.27.

Example 34. Synthesis of Compound 95

95

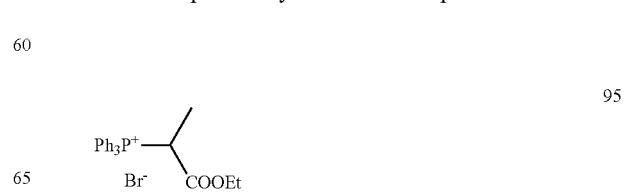

In a 500 mL round-bottomed flask equipped with a magnetic stir bar was added triphenylphosphine (100 g, 381 mmol, 1.0 eq.) and ethyl 2-bromopropionate (100 mL, 762 mmol, 2.0 eq.). The mixture was then heated to 50° C. under $N_2$ atmosphere overnight. After the white solid ($PPh_3$) was dissolved, a large amount of white solid was generated. Trituration with petroleum ether/EtOAc and filtration gave compound 95 as a white solid (135 g, 80% yield). MS ESI m/z calcd for $C_{23}H_{24}O_2P$ [M-Br]$^+$ 363.15, found 363.13.

Example 35. Synthesis of Compound 96

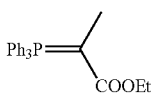

96

A solution of compound 95 (135.42 g, 305.7 mmol) in dichloromethane (500 mL) was added slowly into 10% NaOH solution (450 mL) with vigorous stirring. The organic solution rapidly turned bright yellow. After 30 minutes, TLC analysis showed that the reaction was completed. Layers were separated and the aqueous layer was further extracted with $CH_2Cl_2$ (2×200 mL). Combined organic layers were washed with brine, dried over anhydrous $Na_2SO_4$ and concentrated to give a yellow solid 96 (104 g, 94% yield). MS ESI m/z calcd for $C_{23}H_{24}O_2P$ [M+H]$^+$ 362.14, found 363.13. The crude product was used directly in the next step.

Example 36. Synthesis of Compound 98

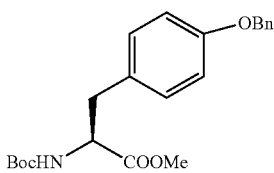

98

To a mixture of Boc-L-Tyr-OMe (670 g, 2.27 mol, 1.0 eq.), $K_2CO_3$ (358 g, 2.5 mol, 1.1 eq.) and KI (38 g, 0.227 mol, 0.1 eq.) in acetone (3 L) was added benzyl bromide (283 mL, 2.38 mol, 1.05 eq.) slowly. The mixture was then refluxed overnight. Water (6 L) was added and the reaction mixture was extracted with EtOAc (5×100 L). The combined organic layers were washed with brine (2 L), dried over anhydrous $Na_2SO_4$, filtered, concentrated and purified by $SiO_2$ column chromatography (4:1 hexanes/EtOAc) to give a white solid 98 (795 g, 91% yield). $^1$H NMR (500 MHz, $CDCl_3$) δ 7.43 (d, J=7.0 Hz, 2H), 7.38 (t, J=7.4 Hz, 2H), 7.32 (t, J=7.2 Hz, 1H), 7.04 (d, J=8.5 Hz, 2H), 6.91 (d, J=8.6 Hz, 2H), 5.04 (s, 2H), 4.55 (d, J=6.9 Hz, 1H), 3.71 (s, 3H), 3.03 (qd, J=14.0, 5.8 Hz, 2H), 1.43 (s, 9H). ESI: m/z: calcd for $C_{22}H_{28}NO_5$ [M+H]$^+$: 386.19, found 386.19.

Example 37. Synthesis of Compound 99

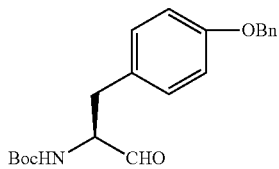

99

To a solution of ester 98 (380 g, 987 mmol, 1.0 eq.) in anhydrous dichloromethane (1 L) at −78° C. was added DIBAL (1.0 M in hexanes, 2.9 L, 2.9 eq.) over 3 h. After the addition was completed, the mixture was quenched with 3 L of ethanol. 1N HCl was added dropwise until pH 4 was reached. The resulting mixture was allowed to warm to 0° C. Layers were separated and the aqueous layer was further extracted with EtOAc (3×3 L). The combined organic solution was washed with brine, dried over anhydrous $Na_2SO_4$, and concentrated. Trituration with PE/EtOAc and filtration gave a white solid 99 (263 g, 75% yield). $^1$H NMR (500 MHz, $CDCl_3$) δ 9.65 (s, 1H), 7.45 (d, J=7.1 Hz, 2H), 7.41 (t, J=7.4 Hz, 2H), 7.35 (t, J=7.1 Hz, 1H), 7.11 (d, J=8.6 Hz, 2H), 6.95 (d, J=8.6 Hz, 2H), 5.07 (s, 2H), 4.42 (dd, J=12.4, 6.1 Hz, 1H), 3.09 (d, J=6.2 Hz, 2H), 1.46 (s, 9H). ESI: m/z: calcd for $C_{21}H_{26}NO_4$ [M+H]$^+$: 356.18, found 356.19.

Example 38. Synthesis of Compound 100

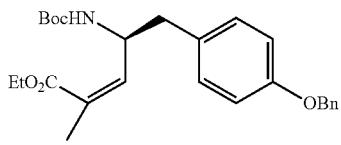

100

To a solution of aldehyde 99 (81.4 g, 229 mmol, 1.0 eq.) in anhydrous dichloromethane (800 mL) at room temperature was added ylide 96 (2.0 eq.) in anhydrous dichloromethane (800 mL) over 30 min. The mixture was stirred at room temperature overnight then concentrated and purified by $SiO_2$ column chromatography (6:1 petroleum ether/EtOAc) to give a white solid 100 (63.4 g, 63% yield). $^1$H NMR (500 MHz, $CDCl_3$) δ 7.45-7.41 (m, 2H), 7.40-7.35 (m, 2H), 7.33 (d, J=7.2 Hz, 1H), 7.10-7.06 (m, 2H), 6.92-6.88 (m, 2H), 6.50 (dd, J=8.8, 1.3 Hz, 1H), 5.04 (s, 2H), 4.57 (s, 2H), 4.18 (q, J=7.1 Hz, 2H), 2.86 (d, J=8.5 Hz, 1H), 2.72 (dd, J=13.6, 6.8 Hz, 1H), 1.71 (d, J=1.4 Hz, 3H), 1.41 (d, J=2.2 Hz, 9H), 1.28 (td, J=7.5, 5.1 Hz, 4H). MS ESI m/z calcd for $C_{26}H_{33}NaNO_5$ [M+Na]$^+$ 462.24, found 462.22.

Example 39. Synthesis of Compound 101

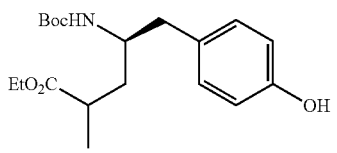

101

In a hydrogenation bottle, Pd/C (1.83 g, 10 wt %, 50% water) was added to a solution of compound 100 (30.2 g, 68.9 mmol) in THF (100 mL) and methanol (300 mL). The mixture was shaken under 1 atm $H_2$ overnight, filtered through Celite (filter aid), and the filtrate was concentrated to afford compound 101 (25.0 g, theoretical yield) as a colorless oil. $^1$H NMR (500 MHz, CDCl$_3$) δ 6.99 (d, J=7.0 Hz, 2H), 6.72 (d, J=7.6 Hz, 2H), 4.39 (s, 1H), 4.18-4.04 (m, 2H), 3.82 (s, 1H), 2.60 (dd, J=37.2, 20.9 Hz, 4H), 1.95-1.81 (m, 1H), 1.39 (s, 11H), 1.24 (dd, J=9.5, 4.3 Hz, 3H), 1.13 (t, J=8.9 Hz, 3H). MS ESI m/z calcd for $C_{19}H_{31}NO_5$ [M+H]$^+$ 352.20, found 352.19.

Example 40. Synthesis of Compound 102

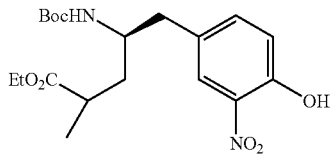

To a solution of compound 101 (5.96 g, 35.9 mmol, 1.0 eq.) in anhydrous dichloromethane (200 mL) was added Ac$_2$O (3.2 mL, 33.9 mmol, 2.0 eq.) and HNO$_3$ (65%-68%, 3.5 mL, 50.79 mmol, 3.0 eq.) at room temperature. The mixture was stirred at room temperature for 30 min, and TLC analysis showed that the reaction was completed. The reaction solution was washed with water (3×200 mL), and the aqueous layer was back-extracted with dichloromethane (3×100 mL). The combined dichloromethane solution was washed with brine, dried over anhydrous Na$_2$SO$_4$, filtered, concentrated and purified by SiO$_2$ column chromatography (5:1 hexanes/EtOAc) to give compound 102 as a yellow solid (4.18 g, 72% yield). $^1$H NMR (500 MHz, CDCl$_3$) δ 10.49 (s, 1H), 7.89 (s, 1H), 7.44 (d, J=8.4 Hz, 1H), 7.09 (d, J=8.6 Hz, 1H), 4.32 (d, J=8.3 Hz, 1H), 4.12 (dd, J=14.0, 7.0 Hz, 2H), 3.80 (s, 1H), 2.76 (dd, J=13.0, 6.8 Hz, 2H), 2.59 (s, 1H), 1.88 (s, 1H), 1.37 (t, J=8.7 Hz, 9H), 1.25 (dd, J=13.5, 6.9 Hz, 4H), 1.16 (t, J=8.0 Hz, 3H). MS ESI m/z calcd for $C_{19}H_{28}NaN_2O_7$ [M+Na]$^+$ 419.19, found 419.17.

Example 41. Synthesis of Compound 103

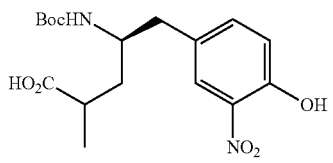

To a solution of ester 102 (15.3 g, 38.6 mmol, 1.0 eq.) in THF (100 mL) and methanol (100 mL) was added LiOH·H$_2$O (16.3 g, 389 mmol, 10.0 eq.) in water (190 mL) at room temperature. The mixture was stirred at room temperature for 40 min. and then diluted with water (400 mL) and 1N KHSO$_4$ was added dropwise until pH 3-4 was reached. After extraction with EtOAc (3×300 mL), the organic phase was washed with brine, dried over anhydrous Na$_2$SO$_4$, filtered, concentrated to give 103 as a yellow solid (14.4 g, theoretical yield). $^1$H NMR (500 MHz, CDCl$_3$) δ 10.48 (s, 1H), 7.98-7.88 (m, 1H), 7.42 (dd, J=18.4, 8.2 Hz, 1H), 7.14-7.03 (m, 1H), 4.48 (d, J=8.6 Hz, 1H), 3.90 (s, 1H), 2.82-2.53 (m, 3H), 1.97-1.82 (m, 2H), 1.42-1.27 (m, 10H), 1.21 (d, J=6.7 Hz, 4H). MS ESI m/z calcd for $C_{17}H_{23}N_2O_7$ [M−H]$^−$ 367.16, found 367.14.

Example 42. Synthesis of Compound 104

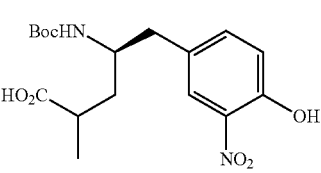

In a hydrogenation bottle, Pd/C (2.60 g, 10 wt %, 50% water) was added to a solution of compound 103 (26.0 g, 70.6 mmol, 1.0 eq.) in methanol (260 mL). The mixture was shaken overnight under 1 atm $H_2$ then filtered through Celite (filter aid), the filtrate was concentrated to afford compound 104 as a green oil (24.0 g, >100% yield).

Example 43. Synthesis of Compound 106

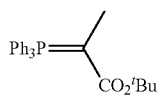

A mixture of tert-butyl-2-bromopropanoate (255 g, 1.22 mol, 1.0 eq.) and triphenyl phosphine (320 g, 1.22 mol, 1.0 eq.) in dry acetonitrile (1 L) was stirred at room temperature for 18 h. Acetonitrile was removed under reduced pressure and toluene was added to crash out a white precipitate. Toluene was then decanted off and the white solid was dissolved in dichloromethane (1 L) and transferred to a separatory funnel. 10% NaOH (1 L) was added to the funnel, and the organic layer immediately turned yellow after shaking. The organic layer was separated and the aqueous layer was extracted with dichloromethane (1 L) once. The dichloromethane layers were combined and washed with brine (400 mL) once, then dried over Na$_2$SO$_4$, filtered and concentrated, giving the ylide 106 as a yellow solid (280 g, 58%).

Example 44. Synthesis of Compound 107

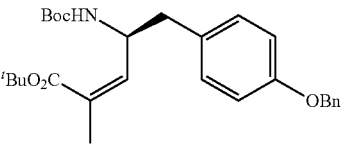

Aldehyde 99 (450 g, 1.27 mol, 1.0 eq.) was dissolved in dry dichloromethane (3 L), to which tert-butyl ester ylide 106 (546 g, 1.40 mmol, 1.1 eq.) was added and the solution was stirred at r.t. overnight as determined complete by TLC. Purification by column chromatography (10-50% EtOAc/ hexanes) afforded compound 107 (444 g, 75% yield) as a white solid. ESI m/z calcd for $C_{28}H_{38}NO_5$ [M+H]$^+$: 468.27, found 468.22.

Example 45. Synthesis of Compound 108

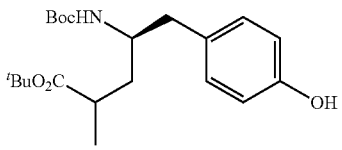

108

Compound 107 (63 g, 0.13 mol) was dissolved in methanol (315 mL) and hydrogenated (1 atm $H_2$) with Pd/C catalyst (10 wt %, 6.3 g) at r.t. overnight. The catalyst was filtered off and the filtrate were concentrated under reduced pressure to afford compound 108 (45.8 g, 93% yield).

Example 46. Synthesis of Compound 109

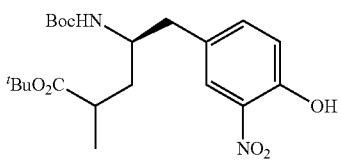

109

To a solution of compound 108 (390 g, 1.03 mol, 1.0 eq.) in THF (4 L) tert-butyl nitrite (1.06 kg, 10.3 mol, 10 eq.) was added at r.t. and the reaction was stirred overnight. After removal of THF, the residue was purified by column chromatography (10-50% EtOAc/hexanes) to afford compound 109 (314 g, 72% yield) as a light yellow solid.

Example 47. Synthesis of Compound 110

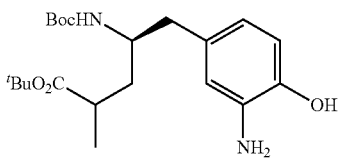

110

To a solution of 109 (166 g, 0.392 mol, 1.0 eq.) in EtOAc (500 mL) was added Pd/C (10 wt %, 16 g) under nitrogen, and the reaction flask was evacuated and purged with hydrogen for 3 times. The reaction mixture was stirred under hydrogen (1 atm) at r.t. for 16 h and then filtered over Celite and concentrated to afford product 110 (146 g, 97% yield) as a light yellow foam. $^1$H NMR (400 MHz, CDCl$_3$) δ 6.62 (d, J=7.9 Hz, 1H), 6.55 (s, 1H), 6.43 (d, J=7.3 Hz, 1H), 4.39 (dd, J=53.0, 44.2 Hz, 1H), 3.77 (s, 4H), 2.72-2.29 (m, 3H), 1.83-1.58 (m, 1H), 1.40 (d, J=7.6 Hz, 18H), 1.24 (s, 1H), 1.06 (t, J=5.7 Hz, 3H). MS ESI m/z calcd for $C_{21}H_{35}N_2O_5$ [M+H]$^+$394.25, found 395.25.

Example 48. Synthesis of Compound 114

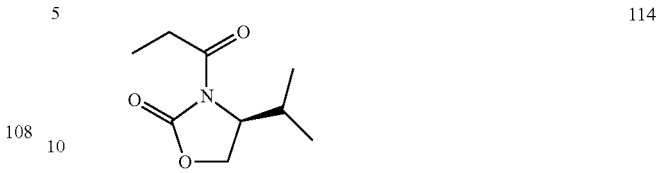

114

To a solution of (S)-4-isopropyloxazolidin-2-one (5.00 g, 38.7 mmol, 1.0 eq.) in anhydrous THF (200 mL) at −78° C. was added n-BuLi (2.5 M in hexanes, 17.0 mL, 1.2 eq.) in 30 min under $N_2$. The mixture was stirred at −78° C. for 1 h, and then propionyl chloride (4.0 mL, 42.58 mmol, 1.1 eq.) was added dropwise. After the mixture was stirred at −78° C. for another 1 h, TLC analysis indicated the reaction completed. Saturated ammonium chloride solution (250 mL) was added and extracted with EtOAc (3×100 mL). The combined organic layers were washed with 1N NaOH solution (200 mL) and brine (300 mL), dried over anhydrous Na$_2$SO$_4$, filtered, concentrated and purified by column chromatography (7:1 hexanes/EtOAc) to give compound 114 as a colourless oil (6.36 g, 89% yield). MS ESI m/z calcd for $C_9H_{16}NO_3$ [M+H]$^+$ 186.10, found 186.10. $^1$H NMR (400 MHz, CDCl$_3$) δ 4.48-4.39 (m, 1H), 4.27 (t, J=8.7 Hz, 1H), 4.21 (dd, J=9.1, 3.1 Hz, 1H), 3.06-2.82 (m, 2H), 2.38 (dtd, J=14.0, 7.0, 4.0 Hz, 1H), 1.17 (t, J=7.4 Hz, 3H), 0.90 (dd, J=17.0, 7.0 Hz, 6H).

Example 49. Synthesis of Compound 115

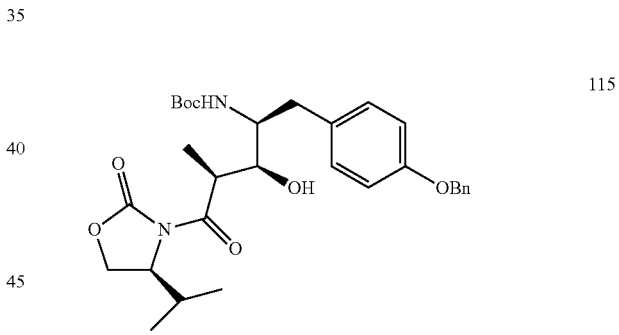

115

To a solution of (S)-4-isopropyl-3-propionyloxazolidin-2-one (2.00 g, 11.9 mmol, 1.1 eq.) in anhydrous dichloromethane (20 mL) at 0° C. was added DIPEA (2.3 mL, 12.9 mmol, 1.2 eq.) and n-Bu$_2$BOTf (1.0 M in dichloromethane, 12.0 mL, 1.1 eq.) under $N_2$. The mixture was stirred at 0° C. for 45 min, then cooled to −78° C., to which a solution of compound 99 (4.24 mL, 10.8 mmol, 1.0 eq.) in dichloromethane was added dropwise. The mixture was stirred at −78° C. for 1 h and then warmed slowly to room temperature. The mixture was stirred at room temperature overnight, and PBS (0.1M, pH 7.0, 100 mL) was added. After phase separation, the aqueous phase was further extracted with dichloromethane (3×50 mL). The combined organic layers were washed with brine (200 mL), dried over anhydrous Na$_2$SO$_4$, filtered and concentrated. The crude product was re-dissolved in methanol (100 mL) and treated with H$_2$O$_2$ (30% aqueous solution, 26 mL, 23 eq.) at 0° C. for 3 h. The methanol was removed by rotary evaporation and water (100 mL) was added. The resulting mixture was extracted with EtOAc (3×100 mL). The combined organic layers were washed with brine (300 mL), dried over anhydrous Na$_2$SO$_4$, filtered, concentrated and purified by SiO$_2$ column chromatography (3:1 hexanes/EtOAc) to give compound 115 as a foamy solid (2.70 g, 49% yield). $^1$H NMR (400 MHz, CDCl$_3$) δ7.52-7.26 (m, 5H), 7.15 (d, J=7.4 Hz, 2H), 6.93 (d, J=7.3 Hz, 2H), 5.05 (s, 2H), 4.69 (d, J=7.0 Hz, 1H), 4.47 (s, 1H), 4.36 (t, J=7.8 Hz, 1H), 4.17 (d, J=8.5 Hz, 1H), 3.93 (d, J=7.1 Hz, 1H), 3.85 (s, 2H), 2.84 (d, J=6.9 Hz, 2H), 2.31 (s, 1H), 1.40-1.37 (m, 9H), 1.31 (s, 3H), 0.92 (dd, J=13.4, 6.6 Hz, 6H). MS ESI m/z calcd for C$_{30}$H$_{41}$N$_2$O$_7$ [M+H]+ 541.28, found 541.30.

Example 50. Synthesis of Compound 116

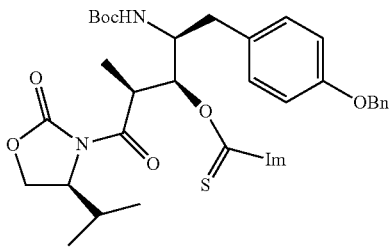

A mixture of compound 115 (2.50 g, 4.63 mmol, 1.0 eq.) and 1,1'-thiocarbonyl-diimidazole (2.48 g, 13.89 mmol, 3.0 eq.) in anhydrous THF (46 mL) was refluxed overnight. Water (100 mL) was added and the resulting mixture was extracted with EtOAc (3×50 mL). The combined organic layers were washed with brine (200 mL), dried over anhydrous Na$_2$SO$_4$, filtered, concentrated and purified by SiO$_2$ column chromatography (3:1 hexanes/EtOAc) to give compound 116 as a yellow foam (2.33 g, 77% yield). $^1$H NMR (400 MHz, CDCl$_3$) δ 8.41 (s, 1H), 7.67 (s, 1H), 7.36 (dt, J=16.0, 6.9 Hz, 6H), 7.09 (s, 1H), 7.05 (d, J=8.4 Hz, 2H), 6.86 (d, J=8.4 Hz, 2H), 6.32 (d, J=9.5 Hz, 1H), 5.01 (s, 2H), 4.56-4.43 (m, 2H), 4.32 (ddd, J=16.2, 15.6, 7.8 Hz, 3H), 4.19 (d, J=8.7 Hz, 1H), 2.96 (dd, J=14.6, 4.4 Hz, 1H), 2.49 (dd, J=14.5, 10.5 Hz, 1H), 2.29 (td, J=13.4, 6.7 Hz, 1H), 1.31 (s, 3H), 1.29 (s, 9H), 0.91 (dd, J=13.9, 6.9 Hz, 6H). MS ESI m/z calcd for C$_{34}$H$_{43}$N$_4$O$_7$S [M+H]$^+$ 651.27, found 651.39.

Example 51. Synthesis of Compound 117

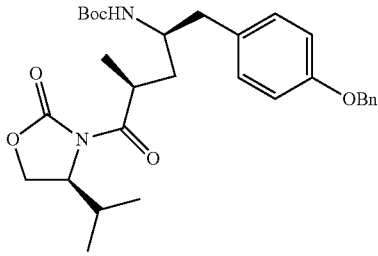

To a solution of compound 116 (1.90 g, 2.92 mmol, 1.0 eq.) in anhydrous toluene (30 mL) was added n-Bu$_3$SnH (1.6 mL, 5.84 mmol, 2.0 eq.) and azodiisobutyronitrile (0.05 g, 0.584 mmol, 0.1 eq.) in sequence. The mixture was refluxed for 2.5 h and then concentrated and purified by SiO$_2$ column chromatography (5:1 hexanes/EtOAc) to give compound 117 as a white foam (1.21 g, 79% yield). $^1$H NMR (400 MHz, CDCl$_3$) δ 7.36 (ddd, J=24.5, 14.5, 7.1 Hz, 5H), 7.08 (d, J=8.5 Hz, 2H), 6.90 (d, J=8.5 Hz, 2H), 5.04 (d, J=5.1 Hz, 2H), 4.48 (d, J=4.2 Hz, 1H), 4.33 (t, J=8.4 Hz, 1H), 4.22 (d, J=9.7 Hz, 1H), 4.15 (d, J=8.8 Hz, 1H), 3.81 (s, 2H), 2.73 (dd, J=14.1, 5.9 Hz, 1H), 2.61 (dd, J=14.0, 7.2 Hz, 1H), 2.29 (dq, J=13.5, 6.8 Hz, 1H), 2.11-2.00 (m, 1H), 1.35 (s, 9H), 1.20 (d, J=6.9 Hz, 3H), 0.89 (dd, J=14.0, 6.9 Hz, 6H). MS ESI m/z calcd for C$_{30}$H$_{41}$N$_2$O$_6$ [M+H]$^+$ 525.28, found 525.37.

Example 52. Synthesis of Compound 118

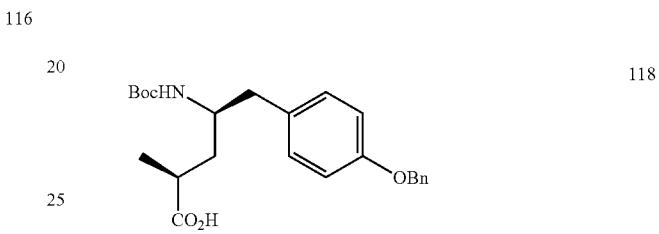

To a solution of compound 117 (1.20 g, 2.29 mmol, 1.0 eq) in THF (30 mL) were added LiOH (0.192 g, 4.58 mmol, 2.0 eq.) in water (6 mL) and H$_2$O$_2$ (30% aqueous solution, 1.4 mL, 6.0 eq.). After 3 h of stirring at 0° C., sodium bisulfite solution (1.5 M, 30 mL) was added to quench the reaction. After 30 min, 1 N KHSO$_4$ was added dropwise until pH 4 was reached. The reaction mixture was then extracted with EtOAc (3×50 mL). The EtOAc solution was washed with brine, dried over anhydrous Na$_2$SO$_4$, filtered, concentrated and purified by SiO$_2$ column chromatography (3:1 hexanes/EtOAc, containing 1% HOAc) to give compound 118 as a white solid (0.78 g, 82% yield). $^1$H NMR (400 MHz, CDCl$_3$) δ 7.46-7.28 (m, 5H), 7.07 (d, J=7.7 Hz, 2H), 6.91 (d, J=7.8 Hz, 2H), 4.52 (d, J=8.5 Hz, 1H), 3.87 (d, J=41.8 Hz, 1H), 2.82-2.43 (m, 3H), 1.85 (t, J=12.2 Hz, 1H), 1.41 (s, 9H), 1.17 (d, J=6.9 Hz, 3H). MS ESI m/z calcd for C$_{24}$H$_{32}$NO$_5$ [M+H]$^+$ 414.22, found 414.21.

Example 53. Synthesis of Compound 119

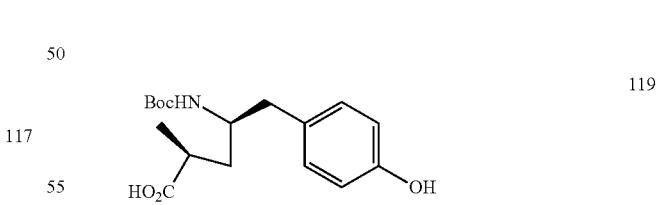
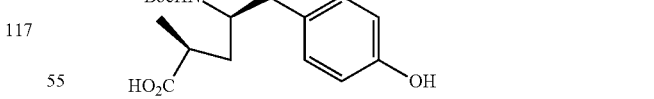

A mixture of compound 118 (0.77 g, 1.86 mmol, 1.0 eq.) and Pd/C (10%0, 0.25 g) in methanol (15 mL) was hydrogenated under 1 atm H$_2$ pressure for 16 h and then filtered through Celite (filter aid). The filtrate was concentrated to afford compound 119 as a white solid (0.58 g, 96% yield). $^1$H NMR (400 MHz, CDCl$_3$) δ 7.00 (d, J=7.5 Hz, 2H), 6.80 (s, 2H), 4.51 (d, J=9.0 Hz, 1H), 3.88 (s, 1H), 2.66 (dd, J=65.6, 22.6 Hz, 4H), 1.88 (t, J=12.2 Hz, 1H), 1.42 (s, 9H), 1.14 (d, J=6.6 Hz, 3H). MS ESI m/z calcd for C$_{17}$H$_{26}$NO$_5$ [M+H]$^+$: 324.17, found 324.16.

Example 54. Synthesis of Compound 120

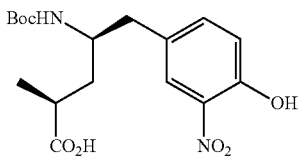

To a solution of compound 119 (0.57 g, 1.76 mmol, 1.0 eq.) in THF (10 mL) was added t-BuONO (0.63 mL, 5.28 mmol, 3.0 eq.) at 0° C. The reaction was stirred at 0° C. for 1 hr then room temperature 1 h. After water (50 mL) was added, the reaction mixture was extracted with EtOAc (3×30 mL). The combined organic layers were washed with brine (100 mL), dried over anhydrous $Na_2SO_4$, filtered, concentrated and purified by $SiO_2$ column chromatography (2:1 hexanes/EtOAc, containing 1% HOAc) to give compound 120 as a yellow solid (0.50 g, 77% yield). $^1$H NMR (400 MHz, DMSO) δ7.92 (s, 1H), 7.47 (d, J=8.3 Hz, 1H), 7.05 (d, J=8.5 Hz, 1H), 3.73 (s, 1H), 2.78 (dd, J=13.6, 5.3 Hz, 1H), 2.69-2.47 (m, 2H), 1.87 (t, J=11.9 Hz, 1H), 1.47-1.37 (m, 1H), 1.32 (s, 9H), 1.17 (d, J=7.2 Hz, 3H). MS ESI m/z calcd for $C_{17}H_{25}N_2O_7$ [M+H]$^+$ 369.15, found 369.14.

Example 55. Synthesis of Compound 121

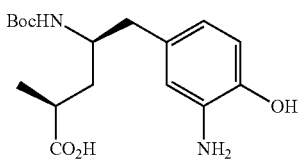

A mixture of compound 120 (0.50 g, 1.36 mmol, 1.0 eq.) and Pd/C (10 wt %, 0.02 g) in methanol (10 mL) was hydrogenated (1 atm $H_2$) at r.t. for 1 h, and then filtered through Celite (filter aid). The filtrate was concentrated to afford compound 121 as white foam (0.43 g, 93% yield). MS ESI m/z calcd for $C_{17}H_{27}N_2O_5$ [M+H]+ 339.18, found 339.17. $^1$H NMR (400 MHz, MeOD) δ 6.60 (d, J=7.9 Hz, 2H), 6.44 (d, J=7.3 Hz, 1H), 3.71 (d, J=6.3 Hz, 1H), 2.62-2.37 (m, 3H), 1.83 (ddd, J=13.7, 9.9, 3.7 Hz, 1H), 1.39 (s, 9H), 1.13 (d, J=7.1 Hz, 3H).

Example 56. Synthesis of Compound 124

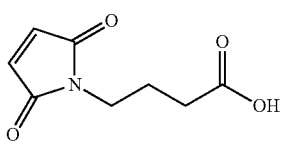

To a solution of maleic anhydride (268 g, 2.73 mol) in acetic acid (1 L) was added 4-aminobutanoic acid (285 g, 2.76 mol). After stirring at r.t. for 30 min, the reaction was refluxed for 1.5 h, cooled to r.t. and evaporated under vacuum to give a residue, which was taken up in EA, washed with water and brine, and dried over anhydrous $Na_2SO_4$, filtered and concentrated. The crude product was crystallized from EtOAc and PE to give a white solid (400 g, 80% yield). $^1$H NMR (500 MHz, CDCl$_3$) δ 6.71 (s, 2H), 3.60 (t, J=6.7 Hz, 2H), 2.38 (t, J=7.3 Hz, 2H), 2.00-1.84 (m, 2H).

Example 57. Synthesis of Compound 125

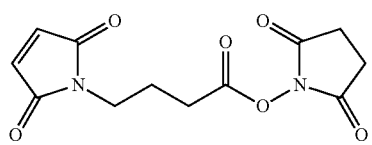

Compound 124 (400 g, 2.18 mol, 1.0 eq.) was dissolved in $CH_2Cl_2$ (1.5 L), to which N-hydroxysuccinimide (276 g, 2.40 mmol, 1.1 eq.) and DIC (303 g, 2.40 mol, 1.1 eq.) were added at r.t. and stirred overnight. The reaction was concentrated and purified by column chromatography (1:2 petroleum ether/EtOAc) to give NHS ester 125 as a white solid (382 g, 63% yield). $^1$H NMR (500 MHz, CDCl$_3$) δ 6.74 (s, 2H), 3.67 (t, J=6.8 Hz, 2H), 2.85 (s, 4H), 2.68 (t, J=7.5 Hz, 2H), 2.13-2.03 (m, 2H).

Example 58. Synthesis of Compound 126

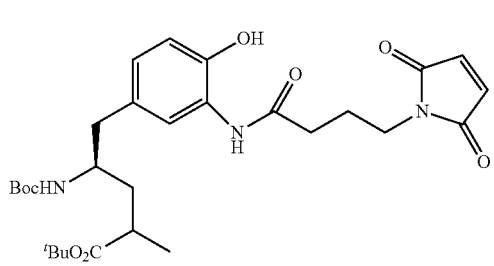

To a solution of 124 (60 g, 328 mmol, 1.3 eq.) in THF (600 mL) was added NMM (85.3 mL, 984 mmol, 3.0 eq.) at 0° C. with stirring, followed by isobutyl chloroformate (44.6 mL, 426 mmol, 1.3 eq.) dropwise. After stirring at 0° C. for 2 h, the resulting mixture was added dropwise to a solution of 104 (102 g, 259 mmol, 1.0 eq.) in THF (400 mL) while keeping the temperature at 0° C. After the addition was completed, the reaction was stirred for additional 30 min. and then quenched with water (300 mL), extracted with EtOAc (3×300 mL). The combined organic layers were dried, filtered, concentrated and purified by column chromatography with a gradient of 9-35% EtOAc/PE to afford compound 126 (104 g, 73% yield) as a light yellow solid. $^1$H NMR (400 MHz, CDCl$_3$) δ 8.86 (s, 1H), 8.40 (d, J=17.3 Hz, 1H), 6.87 (s, 3H), 6.70 (s, 2H), 4.53-4.16 (m, OH), 3.79 (s, 1H), 3.62 (t, J=6.1 Hz, 1H), 2.63 (s, 1H), 2.40 (t, J=6.9 Hz, 1H), 2.12-1.88 (m, 4H), 1.84-1.64 (m, 1H), 1.38 (t, J=9.6 Hz, 6H), 1.06 (t, J=6.0 Hz, 3H).

Example 59. Synthesis of Compound 127

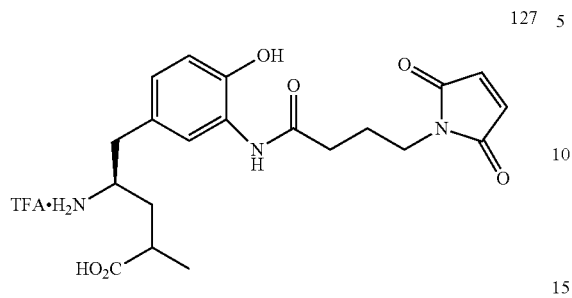

127

Compound 126 (12.7 g, 22.7 mmol) dissolved in CH$_2$Cl$_2$ (20 mL) was treated with TFA (40 mL) at 0° C. and the reaction was warmed to r.t. and stirred for 3 h. The mixture was concentrated and co-evaporated with toluene three times. The residue was triturated with diethyl ether and a light yellow solid 127 was collected (11.4 g, theoretical yield).

Example 60. Synthesis of Compound 128

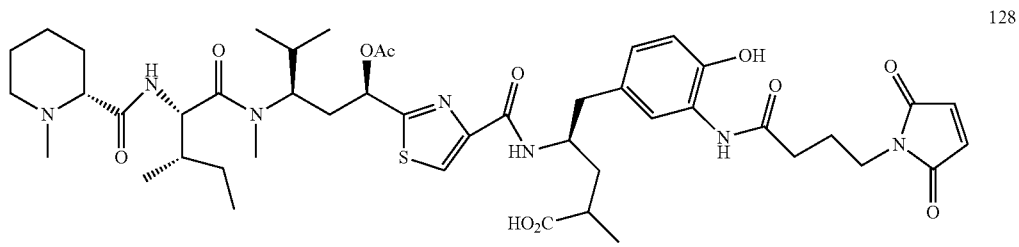 [SMILES: CC[C@H](C)[C@H](NC(=O)[C@H]1CCCCN1C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)O)cs1)C(C)C]

128

To a solution of carboxylic acid 33 (40 mg, 0.074 mmol, 1.0 eq.) in EtOAc was added pentafluorophenol (27 mg, 0.148 mmol, 2.0 eq.) and DCC (23 mg, 0.111 mmol, 1.5 eq.). The reaction mixture was stirred at r.t. for 16 h and then filtered over a Celite pad, with washing of the pad with EtOAc. The filtrate was concentrated and re-dissolved in DMA (6 mL), then compound 127 (56.6 mg, 0.13 mmol) and DIPEA (47.4 µL, 0.18 mmol) were added. The reaction mixture was stirred at r.t. for 24 h and then concentrated and purified by reverse phase HPLC (C$_{18}$ column, 10-100% acetonitrile/water) to afford compound 128 (43 mg, 63% yield) as a white solid. MS ESI m/z calcd for C$_{46}$H$_{66}$N7O$_{11}$S [M+H]$^+$ 924.45, found 924.45.

Example 61. Synthesis of Compound 132

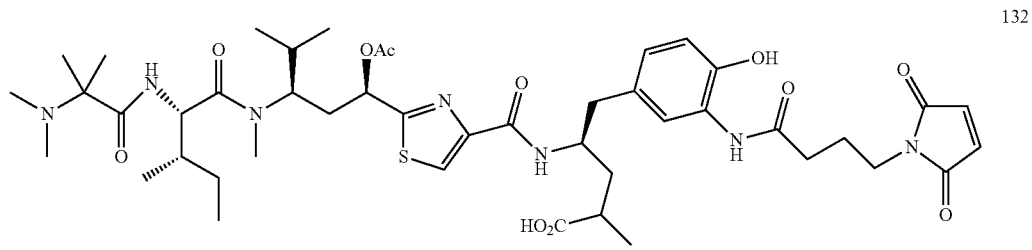 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)O)cs1)C(C)C]

132

To a solution of compound 41a (11 g, 15.9 mmol, 1.0 eq.) and compound 127 (12.3 g, 23.8 mmol, 1.5 eq.) in DMF (100 mL) was added DIPEA (6.9 mL, 39.7 mmol, 2.5 eq.) at 0° C. The reaction mixture was warmed to r.t. and stirred for 1 h. The mixture was concentrated under vacuum and purified on silica gel column (100% DCM to 10% MeOH/DCM) to give compound 132 (10 g, 69% yield) as an amorphous solid. MS ESI m/z calcd for $C_{45}H_{65}N_7O_{11}S$ [M+H]$^+$ 912.45, found 912.45.

Example 62. Synthesis of Compound 204

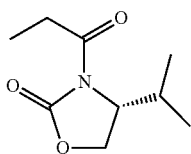

204

To a solution of (R)-4-isopropyloxazolidin-2-one (203) (25.0 g, 0.194 mol, 1.0 eq) in anhydrous THF (1150 mL) was added n-BuLi (85.0 mL, 0.213 mol, 1.1 eq) at −78° C. under $N_2$ and the mixture was stirred at the same temperature for 1 h, a large number of white solids formed. Then propionyl chloride (20.0 mL, 0.232 mol, 1.2 eq) was added at −78° C. and the mixture was stirred at the same temperature for 1 h. After the consumption of (S)-4-isopropyloxazolidin-2-one monitored by TLC, the solution was poured into saturated ammonium chloride solution (1.2 L) and the mixture was extracted with EA (700 mL, 350 mL×2). The organic extract was washed with 1.0 N NaOH solution (1.0 L) and brine (1.0 L), dried over anhydrous sodium sulfate, filtered, concentrated in vacuo and purified by $SiO_2$ column chromatography (PE:EA=10:1) to give the title compound as a colorless oil (32.6 g, 90.8%). ESI m/z: calcd for $C_9H_{17}NO_3$ [M+H]$^+$: 186.1, found 186.1. $^1$H NMR (400 MHz, CDCl$_3$) δ 4.48-4.37 (m, 1H), 4.27 (t, J=8.7 Hz, 1H), 4.21 (dd, J=9.1, 3.1 Hz, 1H), 3.04-2.82 (m, 2H), 2.45-2.30 (m, 1H), 1.17 (t, J=7.4 Hz, 3H), 0.90 (dd, J=17.1, 7.0 Hz, 6H).

Example 63. Synthesis of Compound 205

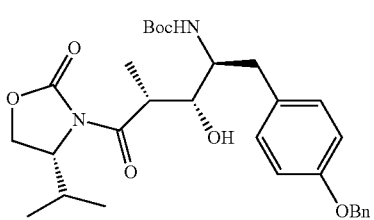

205

To a solution of (R)-4-isopropyl-3-propionyloxazolidin-2-one (18.4 g, 99.5 mmol, 1.1 eq) in anhydrous DCM (200 mL) were added Bu$_2$BOTf (1 M dichloromethane solution, 100 mL, 100 mmol, 1.1 eq) and DIPEA (19 mL, 108.6 mmol, 1.2 eq) at 0° C. under $N_2$, and the mixture was stirred at the same temperature for 45 min. A solution of aldehyde 99 (32.2 g, 90.5 mmol, 1.0 eq) in dichloromethane (320 mL) was added at −78° C. and stirred at the same temperature for 1 h, then the solution was allowed to slowly warm to room temperature for 15 hours. The mixture was poured into 700 mL of potassium phosphate buffer (pH 7.0) and extracted with ethyl acetate. The organic extract was washed with brine, dried over anhydrous sodium sulfate, filtered, and then concentrated in vacuo. The residue was dissolved in methanol (730 mL) and cooled to 0° C., then 30% H$_2$O$_2$ aqueous solution (225 mL) was added slowly, and the mixture was stirred at the same temperature for 3 hours. After addition of water (750 mL), the mixture was concentrated in vacuo to remove methanol. The resulting aqueous solution was extracted with ethyl acetate (500 mL, 150 mL×2), and the organic extract was washed with 5% sodium hydrogen carbonate solution and brine, dried over anhydrous sodium sulfate, filtered, concentrated in vacuo and purified by SiO$_2$ column chromatography (PE:EA=3:1) to give the title compound as a white foam (31.7 g, 64.8%). ESI m/z: calcd for $C_{30}H_{41}N_2O_7$ [M+H]$^+$: 541.3, found 541.3. $^1$H NMR (400 MHz, CDCl$_3$) δ 7.49-7.29 (m, 5H), 7.17 (t, J=10.7 Hz, 2H), 6.93 (d, J=7.0 Hz, 2H), 5.06 (s, 2H), 4.28 (dd, J=44.4, 36.4 Hz, 3H), 4.04-3.52 (m, 3H), 3.11-2.73 (m, 2H), 2.35 (s, 1H), 1.41 (t, J=16.3 Hz, 9H), 0.91 (dd, J=15.6, 6.4 Hz, 5H).

Example 64. Synthesis of Compound 206

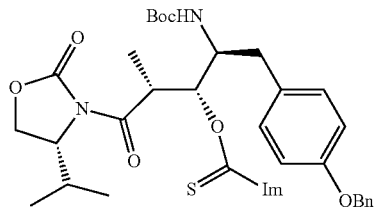

206

To a solution of compound 205 (28.3 g, 52.3 mmol, 1.0 eq) in anhydrous THF (350 mL) was added 1,1-thiocarbonyl diimidazole (TCDI) (35.1 g, 157.0 mmol, 3.0 eq), and the mixture was heated under reflux overnight. After the consumption of starting material monitored by TLC, the mixture was concentrated in vacuo and purified by SiO$_2$ column chromatography (PE:EA=3:1) to give the title compound as a pale yellow foam (26.1 g, 76.8%). ESI m/z: calcd for $C_{34}H_{43}N_4O_7S$ [M+H]$^+$: 651.3, found 651.3. $^1$H NMR (400 MHz, CDCl$_3$) δ 8.21 (s, 1H), 7.43 (d, J=11.8 Hz, 1H), 7.42-7.28 (m, 5H), 7.06 (d, J=8.3 Hz, 2H), 7.01 (s, 1H), 6.80 (d, J=8.3 Hz, 2H), 6.17 (dd, J=8.5, 2.9 Hz, 1H), 4.96 (s, 2H), 4.42-4.04 (m, 5H), 2.83 (dd, J=14.2, 6.2 Hz, 1H), 2.69 (dd, J=14.2, 7.1 Hz, 1H), 2.32 (dd, J=6.8, 4.2 Hz, 1H), 1.37 (s, 9H), 1.30 (d, J=6.9 Hz, 3H), 0.87 (dd, J=9.9, 7.0 Hz, 6H).

Example 65. Synthesis of Compound 207

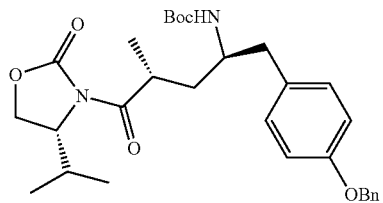

207

To a solution of compound 206 (26.0 g, 40.0 mmol, 1.0 eq) in anhydrous toluene (350 mL) was added n-Bu₃SnH (21.5 mL, 80.0 mmol, 2.0 eq) and 2,2'-azobis(2-methylpropionitrile) (AIBN) (0.066 g, 0.01 eq) under N₂, and the mixture was heated under reflux for 1 hour. After the consumption of starting material monitored by TLC, the mixture was concentrated in vacuo and purified by SiO₂ column chromatography (PE:EA=5:1) to give the title compound as a white foam (6.0 g, 37.3%). ESI m/z: calcd for $C_{30}H_{41}N_2O_6$ [M+H]⁺: 525.3, found 525.3. ¹H NMR (400 MHz, CDCl₃) δ 7.37 (ddd, J=25.1, 15.1, 7.1 Hz, 5H), 7.08 (d, J=7.9 Hz, 2H), 6.89 (d, J=8.4 Hz, 2H), 5.03 (s, 2H), 4.61 (d, J=8.4 Hz, 1H), 4.40 (s, 1H), 4.32-4.08 (m, 2H), 3.91-3.66 (m, 2H), 2.83 (d, J=8.4 Hz, 1H), 2.60 (t, J=10.1 Hz, 1H), 2.33 (s, 1H), 1.71 (s, 1H), 1.41 (s, 9H), 1.15 (d, J=6.5 Hz, 3H), 0.87 (dd, J=17.0, 7.0 Hz, 6H).

Example 66. Synthesis of Compound 208

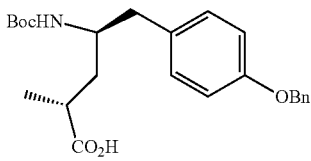

208

To a solution of compound 207 (7.84 g, 15.0 mmol, 1.0 eq) in THF (90 mL) and water (30 mL) was added LiOH·H₂O (1.57 g, 37.5 mmol, 2.5 eq) in 30% H₂O₂ aqueous solution (11.4 mL, 112.5 mmol, 7.5 eq) at 0° C., and the mixture was stirred at the same temperature for 3 hours. After addition of 1.5M Na₂SO₃ solution (160 mL) at 0° C., the mixture was stirred at the same temperature for 30 min. then 1N KHSO₄ was added slowly until pH 4. The resulting aqueous solution was extracted with EA (200 mL, 75 mL×2), and the organic extract was washed with brine, dried over anhydrous sodium sulfate, filtered, concentrated in vacuo and purified by SiO₂ column chromatography (PE: EA=2:1) to give the title compound as a white solid (6.18 g, 100%). ESI m/z: calcd for $C_{24}H_{32}N_1O_5$ [M+H]⁺: 414.2, found 414.2. ¹H NMR (400 MHz, CDCl₃) δ 7.39 (ddd, J=24.5, 15.0, 7.2 Hz, 5H), 7.11 (d, J=7.8 Hz, 2H), 6.93 (d, J=8.3 Hz, 2H), 5.06 (s, 2H), 4.44 (t, J=8.3 Hz, 1H), 3.83 (d, J=69.4 Hz, 1H), 2.85-2.61 (m, 2H), 2.61-2.40 (m, 1H), 1.99-1.70 (m, 1H), 1.39 (d, J=26.1 Hz, 9H), 1.19 (s, 3H).

Example 67. Synthesis of Compound 209

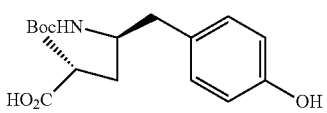

209

To a solution of compound 208 (6.18 g, 15.0 mmol, 1.0 eq) in MeOH (50 mL) was added Pd/C (0.6 g, 10% Pd/C) in a hydrogenation bottle. The mixture was shaken under 1 atm hydrogen atmosphere overnight, then filtered. The filtrate was concentrated to give the title compound as colourless oil (4.8 g, 99% yield). ESI m/z: calcd for $C_{17}H_{26}N_1O_5$ [M+H]⁺: 324.2, found 324.2. ¹H NMR (400 MHz, CDCl₃) δ 6.97 (d, J=6.5 Hz, 2H), 6.74 (d, J=8.2 Hz, 2H), 3.93-3.66 (m, 1H), 2.58 (tdd, J=19.5, 12.9, 7.4 Hz, 3H), 1.75 (ddd, J=20.1, 16.3, 7.7 Hz, 1H), 1.37 (d, J=21.5 Hz, 9H), 1.11 (d, J=7.0 Hz, 3H).

Example 68. Synthesis of Compound 210

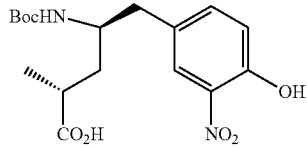

210

To a solution of compound 209 (4.8 g, 15.0 mmol, 1.0 eq) in anhydrous THF (75 mL) was added slowly t-BuONO (18.0 mL, 150 mmol, 10.0 eq) at 0° C. under N₂, and the mixture was stirred at the same temperature for 3 hours. After the consumption of starting material monitored by TLC, 1N KHSO₄ was added slowly to the mixture until pH 4. The resulting aqueous solution was extracted with EA (150 mL, 75 mL×2), and the organic extract was washed with brine, dried over anhydrous sodium sulfate, filtered, concentrated in vacuo and the residue was purified by SiO₂ column chromatography (PE:EA=3:1) to give the title compound as a yellow solid (3.6 g, 65.4%). ESI m/z: calcd for $C_{17}H_{25}N_2O_7$ [M+H]⁺: 369.2, found 369.2. ¹H NMR (400 MHz, MeOD) δ 7.93 (d, J=2.0 Hz, 1H), 7.48 (dd, J=8.6, 2.1 Hz, 1H), 7.06 (d, J=8.5 Hz, 1H), 3.83-3.71 (m, 1H), 2.82 (dd, J=13.6, 5.0 Hz, 1H), 2.66-2.41 (m, 2H), 1.84 (ddd, J=14.0, 10.6, 5.6 Hz, 1H), 1.65-1.51 (m, 1H), 1.28 (d, J=24.9 Hz, 9H), 1.15 (d, J=7.0 Hz, 3H).

Example 69. Synthesis of Compound 211

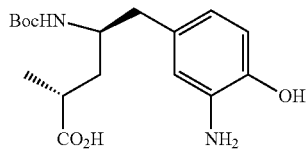

211

To a solution of compound 210 (3.2 g, 7.74 mmol, 1.0 eq) in MeOH (20 mL) was added Pd/C (0.2 g, 10% Pd/C) in a hydrogenation bottle. The mixture was shaken under 1 atm H₂ atmosphere for 3 h. After consumption of starting material monitored by TLC, the mixture was filtered and the filtrate was concentrated to give the title compound as white foam (2.3 g, 92.0% yield). ESI m/z: calcd for $C_{17}H_{27}N_2O_5$ [M+H]⁺: 339.2, found 339.2. ¹H NMR (400 MHz, MeOD) δ 6.61 (d, J=8.0 Hz, 2H), 6.45 (d, J=6.3 Hz, 1H), 3.72 (d, J=7.3 Hz, 1H), 2.68-2.34 (m, 3H), 1.81-1.66 (m, 1H), 1.56-1.45 (m, 1H), 1.36 (d, J=29.0 Hz, 9H), 1.08 (d, J=6.9 Hz, 3H).

Example 70. Synthesis of Compound 390

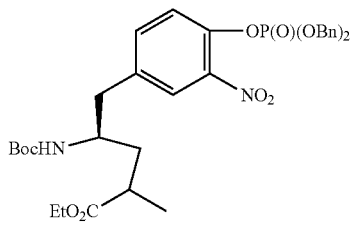

To a solution of compound 102 (1.00 g, 2.52 mmol) in acetonitrile (10 mL) was added CCl$_4$ (2.2 mL, 22.7 mmol, 9.0 eq.) at −25 OC. After stirring for 10 min, diisopropylethylamine (0.88 mL, 5.04 mmol, 2.0 eq.) and DMAP (0.03 g, 0.252 mmol, 0.1 eq.) were added, followed by dibenzyl phosphite (0.84 mL, 3.78 mmol, 1.5 eq.). The reaction mixture was allowed to reach r.t. over 1.5 h, and then quenched by a solution of KH$_2$PO$_4$ (0.5 M, 50 mL). The reaction mixture was extracted with EtOAc (3×50 mL). The combined organic extracts were dried over anhydrous Na$_2$SO$_4$ and concentrated under reduced pressure. The residue was purified by flash column chromatography (10-50% EtOAc/PE) to afford compound 390 (1.60 g, 96% yield) as a colorless oil. MS ESI m/z calcd for C$_{33}$H$_{41}$N$_2$O$_{10}$P [M+H]$^+$ 657, found 657.

Example 71. Synthesis of Compound 391

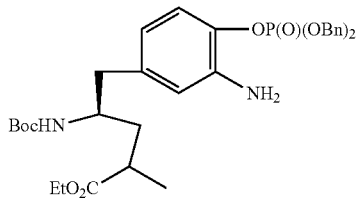

To a solution of compound 390 (1.60 g, 2.43 mmol) in methanol (20 mL) was added Pd/C (10 wt %, 160 mg). The reaction mixture was stirred under H$_2$ atmosphere (1 atm) at r.t. for 3 h, then filtered through Celite and concentrated under reduced pressure to afford compound 391 (1.00 g, 91% yield) as a white solid. MS ESI m/z calcd for C$_{19}$H$_{31}$N$_2$O$_8$P [M−H]$^−$ 447, found 447.

Example 72. Synthesis of Compound 392

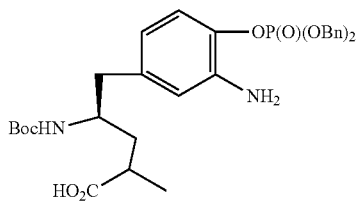

A solution of compound 391 (730 mg, 1.63 mmol) in ethanol (10 mL) was treated with 1 N NaOH (16 mL, 16.3 mmol, 10 eq.) at r.t. overnight, and then concentrated under reduced pressure. The residue was taken up in water (20 mL) and acidified to pH 6 by 1 N HCl. The aqueous solution was concentrated under reduced pressure and the residue was triturated with MeOH/EtOAc (80:20, 5 mL), compound 392 (0.68 g, 990% yield) was collected from filtration as a white solid. MS ESI m/z calcd for C$_{17}$H$_{27}$N$_2$O$_8$P [M−H]$^−$ 417, found 417.

Example 73. Synthesis of Compound 399

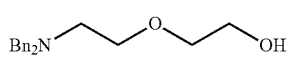

2-(2-aminoethoxy)ethanol (21.00 g, 200 mmol, 1.0 eq.) and K$_2$CO$_3$ (83.00 g, 600 mmol, 3.0 eq.) in acetonitrile (350 mL) was added BnBr (57.0 mL, 480 mmol, 2.4 eq.). The mixture was refluxed overnight. Water (1 L) was added and extracted with EtOAc (3×300 mL). The combined organic layers were washed with brine (1000 mL), dried over anhydrous Na$_2$SO$_4$, filtered, concentrated and purified by SiO$_2$ column chromatography (4:1 hexanes/EtOAc) to give a colourless oil (50.97 g, 89.2% yield). MS ESI m/z calcd for C$_{18}$H$_{23}$NO$_2$Na [M+Na]$^+$ 309.17, found 309.19.

Example 74. Synthesis of Compound 400

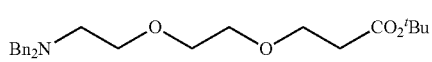

To a mixture of 2-(2-(dibenzylamino)ethoxy)ethanol (47.17 g, 165.3 mmol, 1.0 eq.), tert-butyl acrylate (72.0 mL, 495.9 mmol, 3.0 eq.) and n-Bu$_4$NI (6.10 g, 16.53 mmol, 0.1 eq.) in DCM (560 mL) was added sodium hydroxide solution (300 mL, 50%). The mixture was stirred overnight. The organic layer was separated and the water layer was extracted with EtOAc (3×100 mL). The organic layers were washed with water (3×3000 mL) and brine (3000 mL), dried over anhydrous Na$_2$SO$_4$, filtered, concentrated and purified by SiO$_2$ column chromatography (7:1 hexanes/EtOAc) to give a colourless oil (61.08 g, 89.4% yield). MS ESI m/z calcd for C$_{25}$H$_{36}$NO$_4$ [M+H]$^+$ 414.2566, found 414.2384.

Example 75. Synthesis of Compound 401

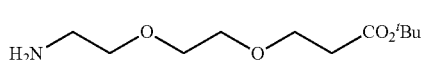

To a solution of tert-butyl 3-(2-(2-(dibenzylamino)ethoxy)ethoxy) propanoate (20.00 g, 48.36 mmol, 1.0 eq.) in THF (30 mL) and MeOH (60 mL) was added Pd/C (2.00 g, 10 wt %, 50% wet) in a hydrogenation bottle. The mixture was shaken overnight, filtered through Celite (filter aid), and the filtrate was concentrated to afford a colourless oil (10.58 g, 93.8% yield). MS ESI m/z calcd for C$_{11}$H$_{24}$NO$_4$ [M+H]$^+$ 234.1627, found 234.1810.

Example 76. Synthesis of Compound 402

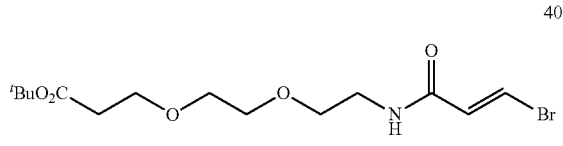

To a solution of (E)-3-bromoacrylic acid (0.15 g, 1 mmol), DMAP (0.15 g, 1.2 mmol) and DCC (0.21 g, 1 mmol) in DCM (10 ml), compound 401 (0.23 g, 1 mmol) were added at 0° C. The reaction mixture was allowed to warm to r.t. and stirred overnight. The crude product was concentrated and purified by SiO$_2$ column chromatography with a gradient of EA/DCM to give the title product 402 (0.31 g, 85% yield). ESI MS m/z: calcd for $C_{14}H_{25}BrNO_5$ [M+H]$^+$: 366.08, found 366.08.

Example 77. Synthesis of Compound 403

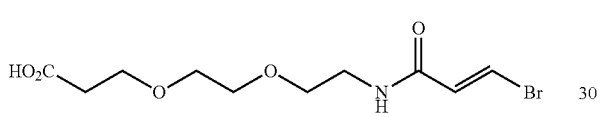

Compound 402 (0.31 g, 0.84 mmol) was dissolved in fomic acid (4 mL) at 0° C. then H$_2$O (2 mL) was added. The reaction mixture was allowed to warm to r.t. and stirred overnight. The crude product was concentrated and used for the next step without further purification. ESI MS m/z: calcd for $C_{10}H_{17}BrNO_5$ [M+H]$^+$: 310.02, found 310.03.

Example 78. Synthesis of Compound 404

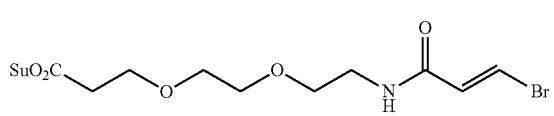

Compound 303 (0.12 g, 0.39 mmol), NHS (0.067 g, 0.58 mmol) and EDCI (0.11 g, 0.58 mmol) were dissolved in DCM (10 mL) and the mixture was stirred at r.t. overnight, concentrated and purified by SiO$_2$ column chromatography to give the title product 404 (0.13 g, 82% yield). ESI MS m/z: calcd for $C_{14}H_{20}BrN_2O_7$ [M+H]$^+$: 407.04, found 407.04.

Example 79. Synthesis of Compound 426

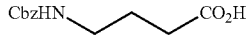

A solution of 4-aminobutyric acid (7.5 g, 75 mmol) and NaOH (6 g, 150 mmol) in H$_2$O (40 mL) was cooled to 0° C. and treated with a solution of CbzCl (16.1 g, 95 mmol) in THF (32 ml) dropwise. After 1 h, the reaction was allowed to warm to r.t. and stirred for 3 h. THF was removed under vacuum, the pH of the aqueous solution was adjusted to 1.5 by addition of 6 N HCl. The solution was extracted with ethyl acetate, and the organic layer was washed with brine, dried and concentrated to give compound 426 (16.4 g, 92% yield). MS ESI m/z calcd for $C_{12}H_{16}NO_5$ [M+H]$^+$ 238.10, found 238.08.

Example 80. Synthesis of Compound 427

DMAP (0.8 g, 6.56 mmol) and DCC (17.1 g, 83 mmol) were added to a solution of 4-(((benzyloxy)carbonyl)amino)butanoic acid (16.4 g, 69.2 mmol) and t-BuOH (15.4 g, 208 mmol) in DCM (100 mL). After stirring at r.t. overnight, the reaction was filtered and filtrate concentrated. The residue was dissolved in ethyl acetate and the washed with 1N HCl, brine and dried over Na$_2$SO$_4$. Concentration and purification by column chromatography (10 to 50% EtOAc/hexanes) yielded compound 427 (7.5 g, 37% yield). MS ESI m/z calcd for $C_{16}H_{23}NO_4Na$ [M+Na]$^+$ 316.16, found 316.13.

Example 81. Synthesis of Compound 428

Tert-Butyl 4-(((benzyloxy)carbonyl)amino)butanoate (560 mg, 1.91 mmol) was dissolved in MeOH (50 mL), and mixed with Pd/C catalyst (10 wt %, 100 mg) then hydrogenated (1 atm) at r.t. for 3 h. The catalyst was filtered off and all volatiles were removed under vacuum to afford compound 428 (272 mg, 90% yield). MS ESI m/z calcd for $C_8H_{18}NO_2$ [M+H]$^+$ 160.13, found 160.13.

Example 82. Synthesis of Compound 430

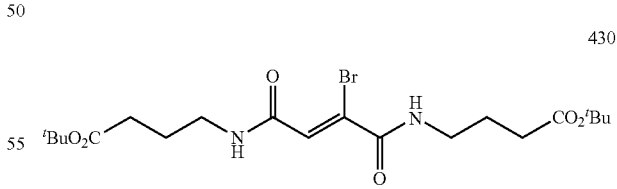

Tert-Butyl 4-aminobutanoate (477 mg, 3 mmol) and 2,3-dibromosuccinic acid (414 mg, 1.5 mmol) was dissolved in DCM (35 mL), to which DIPEA (1.16 g, 9 mmol) and EDC (0.86 g, 4.5 mmol) were added. The resulting solution was stirred at r.t. overnight and then washed with brine, dried over Na$_2$SO$_4$. Filtration, concentration and purification by column chromatography (pure DCM to 10% MeOH/DCM) yielded compound 430 (160 mg, 22% yield). MS ESI m/z calcd for $C_{20}H_{34}BrN_2O_6$ [M+H]+ 477.15, found 477.16.

Example 83. Synthesis of Compound 431

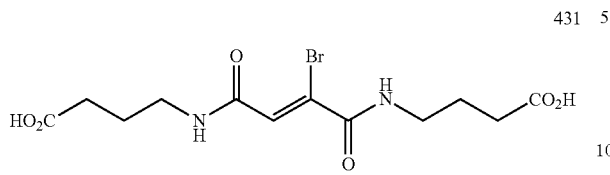

Compound 430 (80 mg, 0.168 mmol) was dissolved in DCM (5 mL) and treated with formic acid (8 mL) at 38° C. overnight. All volatiles were removed under vacuum to afford compound 431 (61 mg, 99% yield). MS ESI m/z calcd for $C_{12}H_{18}BrN_2O_6$ [M+H]$^+$ 365.03, found 365.05.

Example 84. Synthesis of Compound 432

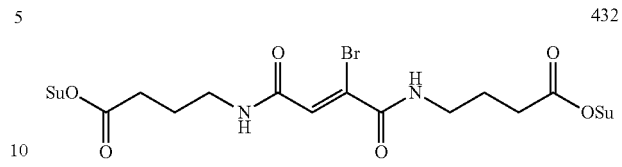

NHS (60 mg, 0.504 mmol) and EDCI (97 mg, 0.504 mmol) were added to a solution of compound 431 (61 mg, 0.168 mmol) in DCM (10 mL). After stirring at r.t. overnight, the reaction mixture was concentrated and purified by column chromatography (0 to 10% MeOH/DCM) to afford compound 432 (72 mg, 77% yield). MS ESI m/z calcd for $C_{20}H_{24}BrN_4O_{10}$ [M+H]$^+$ 559.06, found 559.78.

Example 85. Synthesis of Compound 433

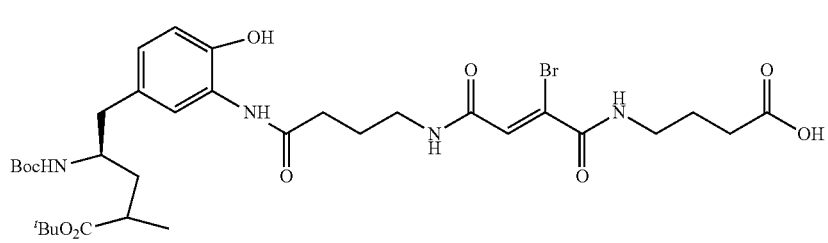

NaH$_2$PO$_4$ (0.1M in water, 1 mL) was added to a solution of compound 432 (36 mg, 0.065 mmol) and compound 110 (25 mg, 0.063 mmol) in EtOH (5 mL). The resulting solution was stirred at r.t. overnight. All volatiles were removed under vacuum and the residue was purified by column chromatography (0 to 10% MeOH/DCM) to yield compound 433 (19.7 mg, 41% yield). MS ESI m/z 741.35 ([M+H]$^+$).

Example 86. Synthesis of Compound 435

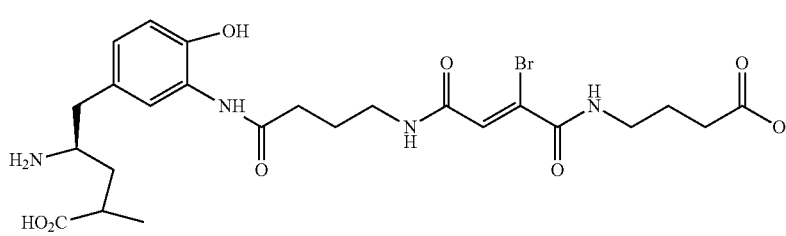

Compound 433 (18 mg, 0.024 mmol) was dissolved in DCM (2 mL) and treated with TFA (2 mL) at r.t. for 2 h. All volatiles were removed under vacuum to afford compound 435 (14 mg, 98% yield), which was use directly in the next step. MS ESI m/z 585.22 ([M+H]$^+$).

Example 87. Synthesis of Compound 437

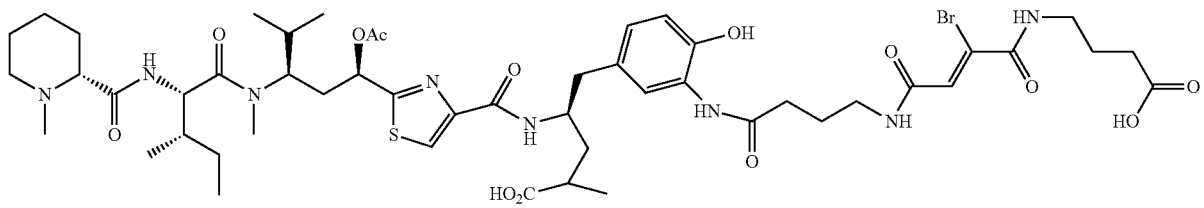

Compound 435 (14 mg, 0.0239 mmol) and perfluorophenyl ester 33a (18 mg, 0.0255 mmol) were dissolved in DMA (5 mL). To the mixture, DIPEA (10 mg, 0.077 mmol) was added. The resulting mixture was stirred at r.t. overnight, concentrated and purified by preparative HPLC ($C_{18}$ column, 10-90% MeCN/$H_2O$) to afford compound 437 (12.8 mg, 48% yield). MS ESI m/z 1105.50 ([M+H]$^+$).

Example 88. Synthesis of Compound 441

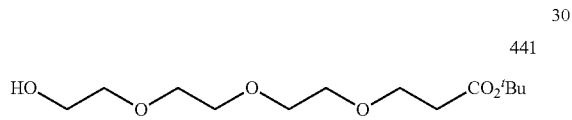

To a solution of 2,2'-(ethane-1,2-diylbis(oxy))diethanol (55.0 mL, 410.75 mmol, 3.0 eq.) in anhydrous THF (200 mL) was added sodium (0.1 g). The mixture was stirred until Na disappeared and then tert-butyl acrylate (20.0 mL, 137.79 mmol, 1.0 eq.) was added dropwise. The mixture was stirred overnight and then quenched by HCl solution (20.0 mL, 1N) at 0° C. THF was removed by rotary evaporation, brine (300 mL) was added and the resulting mixture was extracted with EtOAc (3×100 mL). The organic layers were washed with brine (3×300 mL), dried over anhydrous $Na_2SO_4$, filtered and concentrated to afford a colourless oil (30.20 g, 79.0% yield), which was used without further purification. MS ESI m/z calcd for $C_{13}H_{27}O_6$ [M+H]$^+$ 278.1729, found 278.1730.

Example 89. Synthesis of Compound 442

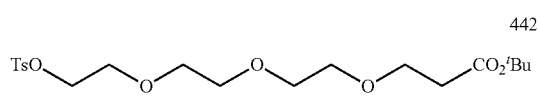 [SMILES: Cc1ccc(S(=O)(=O)OCCOCCOCCOCCC(=O)OC(C)(C)C)cc1]

To a solution of tert-butyl 3-(2-(2-(2-hydroxyethoxy)ethoxy)ethoxy) propanoate (30.20 g, 108.5 mmol, 1.0 eq.) and TsCl (41.37 g, 217.0 mmol, 2.0 eq.) in anhydrous DCM (220 mL) at 0° C. was added TEA (30.0 mL, 217.0 mmol, 2.0 eq.). The mixture was stirred at room temperature overnight, and then washed with water (3×300 mL) and brine (300 mL), dried over anhydrous $Na_2SO_4$, filtered, concentrated and purified by $SiO_2$ column chromatography (3:1 hexanes/EtOAc) to give a colourless oil (39.4 g, 84.0% yield). MS ESI m/z calcd for $C_{20}H_{33}O_8S$ [M+H]$^+$ 433.1818, found 433.2838.

Example 90. Synthesis of Compound 443

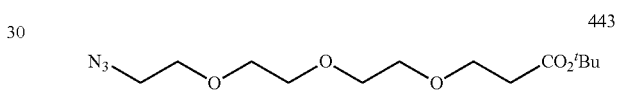

To a solution of tert-butyl 3-(2-(2-(2-(tosyloxy)ethoxy)ethoxy)ethoxy) propanoate (39.4 g, 91.1 mmol, 1.0 eq.) in anhydrous DMF (100 mL) was added $NaN_3$ (20.67 g, 316.6 mmol, 3.5 eq.). The mixture was stirred at room temperature overnight. Water (500 mL) was added and extracted with EtOAc (3×300 mL). The combined organic layers were washed with water (3×900 mL) and brine (900 mL), dried over anhydrous $Na_2SO_4$, filtered, concentrated and purified by $SiO_2$ column chromatography (5:1 hexanes/EtOAc) to give a light yellow oil (23.8 g, 85.53% yield). MS ESI m/z calcd for $C_{13}H_{25}O_3N_5Na$ [M+Na]$^+$ 326.2, found 326.2.

Example 91. Synthesis of Compound 444

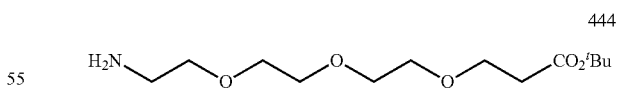

Raney-Ni (7.5 g, suspended in water) was washed with water (three times) and isopropyl alcohol (three times) and mixed with compound 443 (5.0 g, 16.5 mmol) in isopropyl alcohol. The mixture was stirred under a $H_2$ balloon at r.t. for 16 h and then filtered over a Celite pad, with washing of the pad with isopropyl alcohol. The filtrate was concentrated and purified by column chromatography (5-25% MeOH/DCM) to give light yellow oil (2.60 g, 57% yield). MS ESI m/z calcd for $C_{13}H_{28}NO_5$ [M+H]$^+$ 279.19; found 279.19.

Example 92. Synthesis of Compound 445

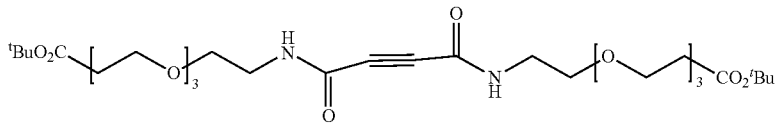

445

Acetylenedicarboxylic acid (0.35 g, 3.09 mmol, 1.0 eq.) was dissolved in NMP (10 mL) and cooled to 0° C., to which compound 444 (2.06 g, 7.43 mmol, 2.4 eq.) was added, followed by DMTMM (2.39 g, 8.65 mmol, 2.8 eq.) in portions. The reaction was stirred at 0° C. for 6 h and then diluted with ethyl acetate and washed with water and brine. The organic solution was concentrated and triturated with a mixture solvent of ethyl acetate and petroleum ether. The solid was filtered off and the filtrate was concentrated and purified by column chromatography (80-90% EA/PE) to give a light yellow oil (2.26 g, >100% yield), which was used without further purification. MS ESI m/z calcd for $C_{30}H_{53}N_2O_{12}$ $[M+H]^+$ 633.35; found 633.30.

Example 93. Synthesis of Compound 446

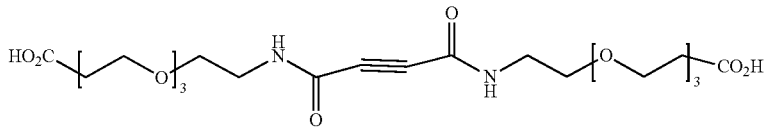

446

Compound 445 (2.26 g) was dissolved in dichloromethane (15 mL) and cooled to 0° C. then treated with TFA (15 mL). The reaction was warmed to r.t. and stirred for 45 min, and then the solvent and residual TFA was removed on rotovap. The crude product was purified by column chromatography (0-15% MeOH/DCM) to give light yellow oil (1.39 g, 86% yield for two steps). MS ESI m/z calcd for $C_{22}H_{37}N_2O_{12}$ $[M+H]^+$ 521.23; found 521.24.

Example 94. Synthesis of Compound 480

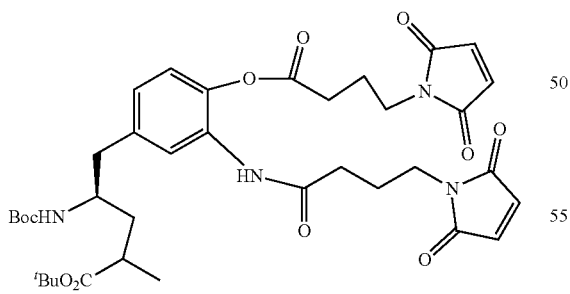

480

Compound 110 (68 mg, 0.17 mmol), compound 124 (94.5 mg, 0.52 mmol) and HATU (162 mg, 0.425 mmol) were dissolved in DCM (50 mL). TEA (73 ul, 0.52 mmol) was then added. The reaction mixture was stirred at r.t. overnight. Then the solvent was removed under reduced pressure and the residue was purified by $SiO_2$ column to give the title product 480 (98 mg, 80% yield). ESI m/z calcd for $C_{37}H_{49}N_4O_{11}$ $[M+H]^+$: 725.33, found 725.34.

Example 95. Synthesis of Compound 481

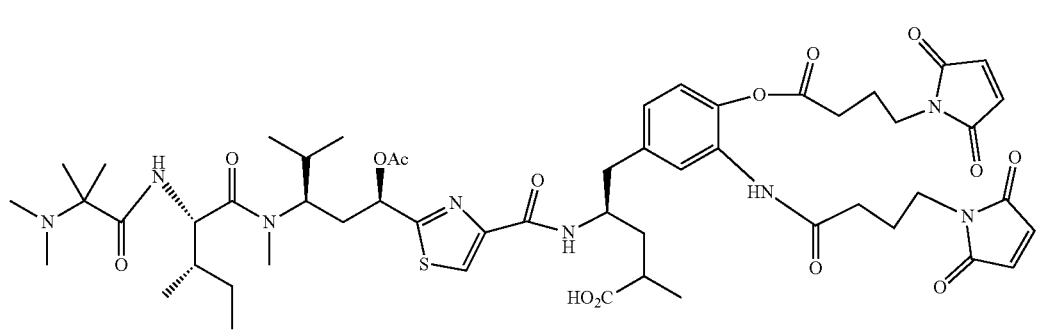

Compound 480 (98 mg, 0.135 mmol) dissolved in DCM (1.0 mL) was treated with TFA (1.0 mL) at r.t. for 2 h, then concentrated and redissolved in DMA (1 mL), to which pentafluorophenyl ester 41a (44 mg, 0.06 mmol) and DIPEA (45.8 µL, 0.27 mmol) were added. The reaction was stirred overnight and then concentrated. The residue was purified by prep-HPLC with a gradient of MeCN/H$_2$O to give the title product 481 (37 mg, 55% yield). ESI m/z calcd for C$_{53}$H$_{73}$N$_8$O$_{14}$S [M+H]$^+$: 1077.49, found 1077.50.

Example 96. Synthesis of Compound 484

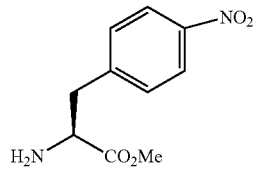

To a solution of (S)-2-amino-3-(4-nitrophenyl)propanoic acid (13.2 g, 62.8 mmol) in methanol (120 mL) was added thionyl chloride (9 mL, 125.6 mmol) at 0° C. The reaction mixture was heated to reflux and stirred for 1 h, then concentrated under vacuum and suspended in ethyl acetate (50 mL). The mixture was then filtered to afford the title compound as a white solid (14.5 g, 91% yield). ESI m/z calcd for C$_{10}$H$_{13}$N$_2$O$_4$ [M+H]$^+$: 225.08, found 225.08.

Example 97. Synthesis of Compound 485

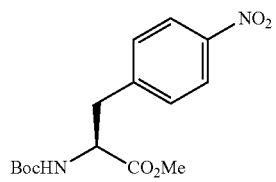

To a solution of compound 484 (9.5 g, 36.4 mmol) in THF (200 mL) was added triethylamine (12.6 mL, 91.1 mmol). After the mixture was stirred for 30 minutes, di-tert-butyl dicarbonate (12.5 mL, 54.7 mmol) was added, and the reaction mixture was stirred for 1 h, then diluted with ethyl acetate (200 mL), washed with 1 N HCl (30 mL), water (30 mL), dried over sodium sulfate, filtered and concentrated under vacuum to afford the title compound as a white solid (11.4 g, 97% yield). ESI m/z calcd for C$_{15}$H$_{21}$N$_2$O$_6$ [M+H]$^+$: 325.13, found 325.13.

Example 98. Synthesis of Compound 486

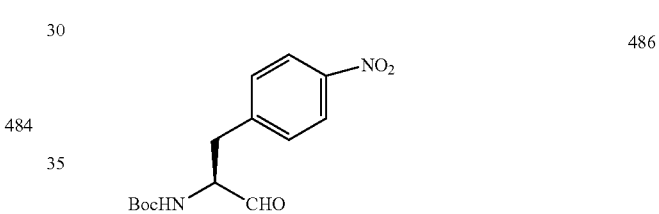

To a solution of compound 485 (14 g, 43.2 mmol) in anhydrous dichloromethane (150 mL) was added DIBAL-H (108 mL, 108 mmol) at −78° C. The reaction mixture was stirred at −78° C. for 30 min., then poured into ice water (200 mL), extracted with ethyl acetate (3×80 mL). The combined organic phase was washed with 1N HCl (2×50 mL), water (50 mL), dried over sodium sulfate, filtered, concentrated under vacuum, and purified by silica gel column chromatography to afford the title compound (8.6 g, 68% yield). ESI m/z calcd for C$_{14}$H$_{19}$N$_2$O$_5$ [M+H]$^+$: 295.12, found 295.12.

Example 99. Synthesis of Compound 487

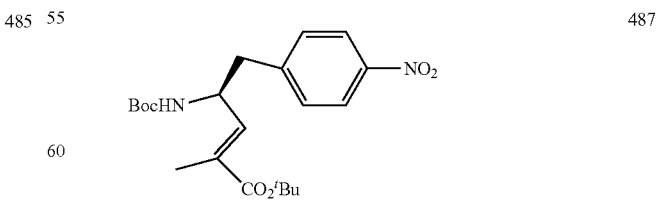

To a solution of compound 106 (8.1 g, 20.8 mmol) in DCM (100 mL) was added compound 486 (5.2 g, 17.8 mmol) at 0° C. The reaction mixture was warmed to r.t. and stirred for 30 min. then concentrated under vacuum and purified by silica gel column to afford the title compound as a yellow solid (5.9 g, 82% yield). ESI m/z calcd for $C_{21}H_{31}N_2O_6$ [M+H]$^+$: 406.21, found 406.21.

Example 100. Synthesis of Compound 488

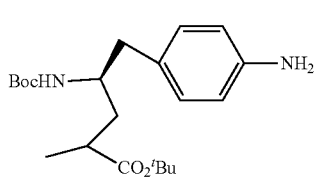

488

To a solution of compound 487 (4 g, 9.85 mmol) in MeOH (40 mL) was added Pd/C (0.4 g, 10 wt %) in a hydrogenation bottle. The mixture was stirred under 1 atm $H_2$ overnight, filtered through Celite (filter aid), and the filtrate was concentrated to afford compound 488 (3.6 g, yield-100%). ESI m/z: calcd for $C_{21}H_{35}N_2O_4$ [M+H]$^+$: 379.25, found 379.25.

Example 101. Synthesis of Compound 489

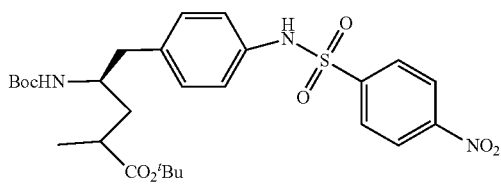

489

To a solution of compound 488 (3.6 g, 9.52 mmol) and triethylamine (1.3 mL, 9.52 mmol) in dichloromethane (50 mL) was added 4-nitrobenzenesulfonyl chloride (2.1 g, 9.52 mmol) at 0° C. The reaction mixture was warmed to r.t. and stirred for 1 h, then diluted with DCM (50 mL), washed with 1N HCl (20 mL), water (20 mL), dried over sodium sulfate, filtered and concentrated under vacuum, then purified by silica gel column chromatography to afford the title compound as a yellow solid (4 g, 75% yield). ESI m/z calcd for $C_{27}H_{38}N_3O_8S$ [M+H]$^+$: 564.23, found 564.23.

Example 102. Synthesis of Compound 490

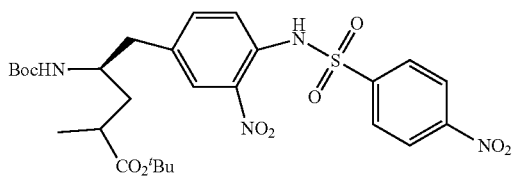

490

To a solution of compound 489 (3.6 g, 6.39 mmol) in acetonitrile (40 mL) was added tert-butyl nitrite (2.29 mL, 19.1 mmol). The reaction mixture was warmed to 45° C. and stirred for 6 hours. The reaction was then concentrated under vacuum and purified by silica gel column chromatography to afford the title compound (3 g, 79% yield). ESI m/z calcd for $C_{27}H_{37}N_4O_{10}S$ [M+H]$^+$: 609.22, found 609.22.

Example 103. Synthesis of Compound 491

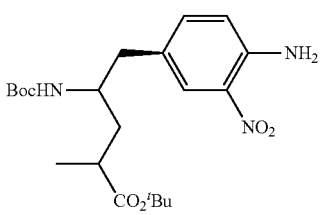

491

To a solution of compound 490 (3.0 g, 4.92 mmol) in acetonitrile/DMSO (30 mL/1 mL) were added 4-methoxy thiophenol (2.76 g, 19.7 mmol) and potassium carbonate (2.7 g, 19.7 mmol). The reaction mixture was stirred at the room temperature overnight, then diluted with ethyl acetate (100 mL), washed with water (20 mL), brine (20 mL), dried over sodium sulfate, filtered and concentrated under vacuum, and purified by silica gel column chromatography to afford the title compound (1.7 g, 85% yield). ESI m/z calcd for $C_{21}H_{34}N_3O_6$ [M+H]$^+$: 424.24, found 424.24.

Example 104. Synthesis of Compound 492

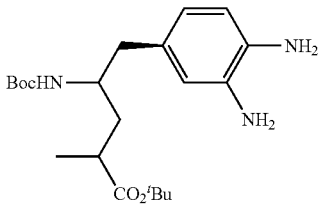

492

To a solution of compound 491 (100 mg, 0.236 mmol) in MeOH (4 mL) was added Pd/C (10 mg, 10 wt %) in a hydrogenation bottle. The mixture was stirred under 1 atm $H_2$ overnight, filtered through Celite (filter aid), and the filtrate was concentrated to afford the title compound (92.9 mg, —100% yield). ESI m/z calcd for $C_{21}H_{36}N_3O_4$ [M+H]$^+$: 394.26, found 394.26.

Example 105. Synthesis of Compound 493

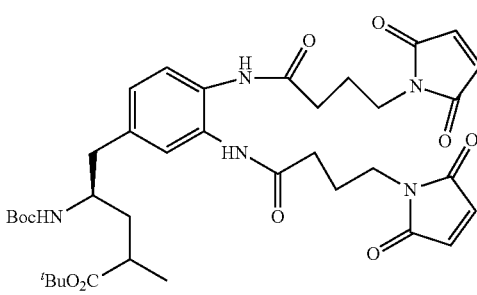

493

Compound 492 (66 mg, 0.17 mmol), compound 124 (94.5 mg, 0.52 mmol) and HATU (162 mg, 0.425 mmol) were dissolved in DCM (50 mL). TEA (73 ul, 0.52 mmol) was then added. The reaction mixture was stirred at r.t. overnight, the solvent was removed under reduced pressure and the residue was purified by SiO$_2$ column to give the title product 493 (98 mg, 80% yield). ESI m/z calcd for $C_{37}H_{50}N_5O_{10}$ [M+H]$^+$: 724.35, found 724.35.

Example 106. Synthesis of Compound 494

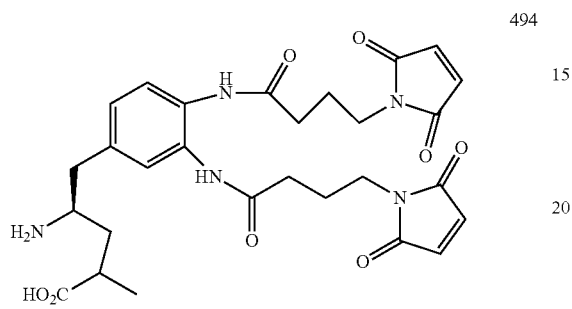

Compound 493 (98 mg, 0.135 mmol) dissolved in DCM (1.0 mL) was treated with TFA (1.0 mL) at r.t. for 2 h, then concentrated to give compound 494, which was used in the next step without further purification.

Example 107. Synthesis of Compound 495

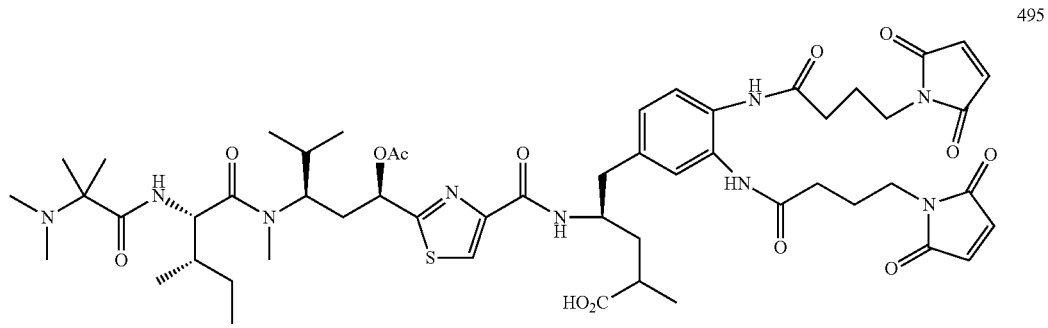 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(NC(=O)CCCN3C(=O)C=CC3=O)c(NC(=O)CCCN3C(=O)C=CC3=O)c2)CC(C)C(=O)O)cs1)C(C)C]

To a solution of compound 494 (76.9 mg, 0.135 mmol) in DMA (1 mL) was added pentafluorophenyl ester 41a (44 mg, 0.06 mmol) and DIPEA (45.8 µL, 0.27 mmol). The reaction was stirred overnight, then concentrated and the residue was purified by prep-HPLC with a gradient of MeCN/H$_2$O to give the title product 495 (37 mg, 55% yield). ESI m/z calcd for $C_{53}H_{74}N_9O_{13}S$ [M+H]$^+$: 1076.50, found 1076.50.

Example 108. Synthesis of Compound 509

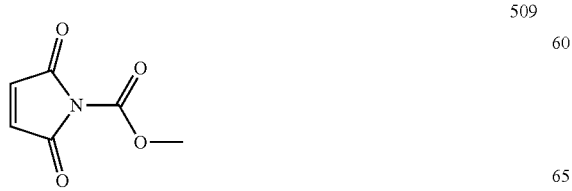

To a solution of maleimide (6.35 g, 65.4 mmol, 1.0 eq.) in EtOAc (120 mL) were added N-methyl morpholine (8.6 mL, 78.5 mmol, 1.2 eq.) and methyl chloroformate (6.0 mL, 78.5 mmol, 1.2 eq.) at 0° C. The reaction was stirred at 0° C. for 30 min and r.t. 1 h. The solid was filtered off and filtrate concentrated. The residue was dissolved in CH$_2$Cl$_2$ and filtered through a silica gel plug and eluted with CH$_2$Cl$_2$ to remove the color. The appropriate fractions were concentrated and resulted solid was triturated with 10% EtOAc/PE to give a white solid (9.00 g, 89% yield).

Example 109. Synthesis of Compound 510

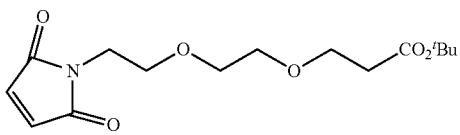

510

A mixture of compound 401 (8.16 g, 35.0 mmol, 1.0 eq.) and saturated NaHCO$_3$ (40 mL) was cooled to 0° C., to which compound 509 (5.43 g, 35.0 mmol, 1.0 eq.) was added in portions. After stirring at 0° C. for 1 h, the reaction was warmed to r.t. and stirred for 1 h. The reaction was extracted with DCM (3×100 mL) and the organic extract was washed with brine, dried over anhydrous Na$_2$SO$_4$, concentrated and purified by SiO$_2$ column chromatography to give a white solid (6.76 g, 62% yield). MS ESI m/z calcd for C$_{15}$H$_{23}$NO$_6$ [M+H]$^+$ 314.15, found 314.15.

Example 110. Synthesis of Compound 511

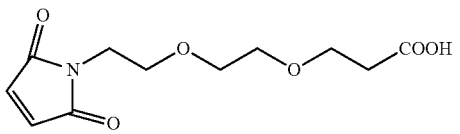

511

A solution of compound 510 (1.85 g, 5.9 mmol) was dissolved in DCM (20 mL) and treated with TFA (7 mL) at r.t. for 16 h, then concentrated and purified by SiO$_2$ column chromatography (11:1 DCM/MeOH) to give a white foam (1.47 g, 97% yield). MS ESI m/z calcd for C$_{11}$H$_{15}$NO$_6$ [M+H]$^+$ 258.09, found 258.09.

Example 111. Synthesis of Compound 519

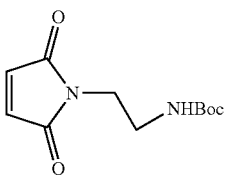

519

A mixture of N-Boc-ethylenediamine (5.6 mL, 35.4 mmol, 1.1 eq.) and saturated NaHCO$_3$ (60 mL) was cooled to 0° C., to which compound 509 (5.00 g, 32.2 mmol, 1.0 eq.) was added in portions. After stirring at 0° C. for 30 min, the reaction was warmed to r.t. and stirred for 1 h. The precipitate was collected by filtration and washed with cold water, then dissolved in EtOAc and washed with brine, dried over anhydrous Na$_2$SO$_4$ and concentrated to give a white solid (6.69 g, 87% yield).

Example 112. Synthesis of Compound 520

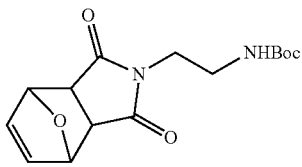

520

A solution of compound 519 (6.00 g, 25.0 mmol), furan (18.0 mL) in toluene (120 mL) in a high pressure tube was heated to reflux and stirred for 16 h. The colorless solution turned yellow during reaction. The mixture was then cooled to r.t. and concentrated. The resulting white solid was triturated with ethyl ether to give compound 520 (6.5 g, 84% yield).

Example 113. Synthesis of Compound 521

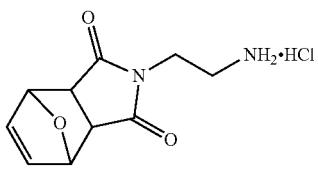

521

A solution of compound 520 (9.93 g, 32.2 mmol) was dissolved in dioxane (15 mL) and treated with concentrated HCl (15 mL) at r.t. for 3 h. The reaction was concentrated and the resulting solid was collected by filtration, with washing of the filter cake with EtOAc. The solid was dried in an oven (50° C.) overnight to give compound 521 (6.94 g, 88% yield).

Example 114. Synthesis of Compound 522

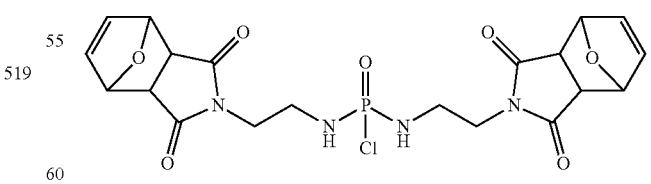

522

To a solution of compound 521 (0.85 g, 3.47 mmol) in THF (10 mL) was added POCl$_3$ (162 µL, 1.73 mmol) at −10 OC, followed by TEA (966 µL, 6.95 mmol). The reaction was stirred at −10° C. for 3 h, and then the solution was diluted with DCM (20 mL) and filtered over Celite, the filtrate was concentrated to give compound 522, which was used in the next step directly. ESI m/z calcd for C$_{20}$H$_{23}$ClN$_4$O$_7$P [M+H]$^+$: 497.09, found 497.09.

Example 115. Synthesis of Compound 523

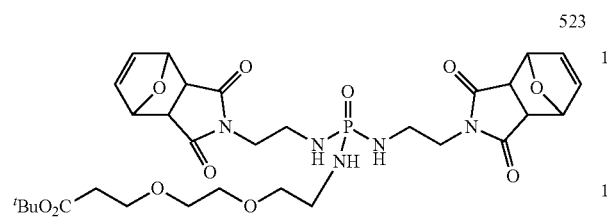

Compound 522 (0.50 g, 1.0 mmol) and DIPEA (0.4 mL, 2.4 mmol) were dissolved in DCM (5.0 mL) at 0° C., and then compound 401 (0.23 g, 1.0 mmol) was added. The reaction was stirred at 0° C. for 2.5 h, then concentrated and purified by SiO$_2$ column to give the title product 523 (0.30 g, 43%). ESI m/z calcd for C$_{31}$H$_{45}$N$_5$O$_{11}$P [M+H]$^+$: 694.28, found 694.28.

Example 116. Synthesis of Compound 524

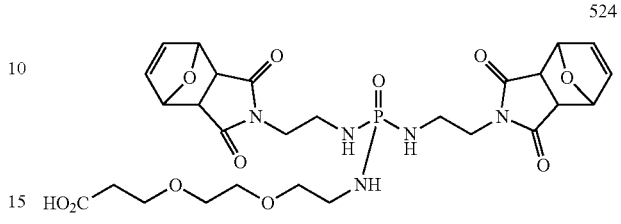

Compound 523 (0.30 g, 0.5 mmol) was dissolved in DCM (3 mL), and treated with TFA (3 mL) at r.t. for 2 h, then concentrated to give compound 524, which was used in the next step without further purification.

Example 117. Synthesis of Compound 525

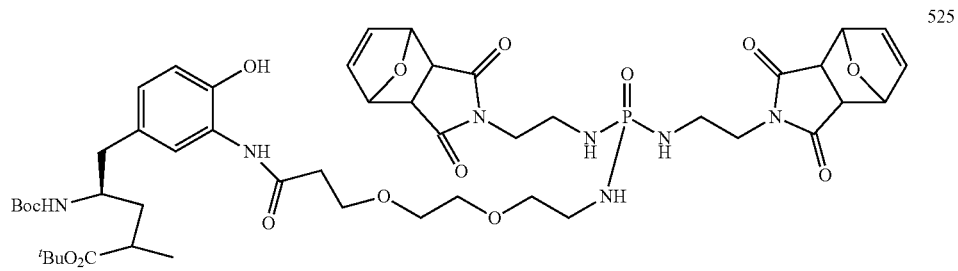 [SMILES: CC(C[C@H](Cc1ccc(O)c(NC(=O)CCOCCOCCNP(=O)(NCCN2C(=O)C3C4C=CC(O4)C3C2=O)NCCN2C(=O)C3C4C=CC(O4)C3C2=O)c1)NC(=O)OC(C)(C)C)C(=O)OC(C)(C)C]

Compound 524 (40 mg, 0.063 mmol), compound 110 (40 mg, 0.10 mmol), HATU (24 mg, 0.063 mmol) were dissolved in DCM (5 mL), and then TEA (27.8 μL, 0.2 mmol) was added. The reaction mixture was stirred at r.t. overnight. Then the solvent was removed under reduced pressure and the residue was purified by SiO$_2$ column to give the title product 525 (53.4 mg, 84% yield). ESI m/z calcd for C$_{48}$H$_{69}$N$_7$O$_{15}$P [M+H]$^+$: 1014.45, found 1014.45.

Example 118. Synthesis of Compound 526

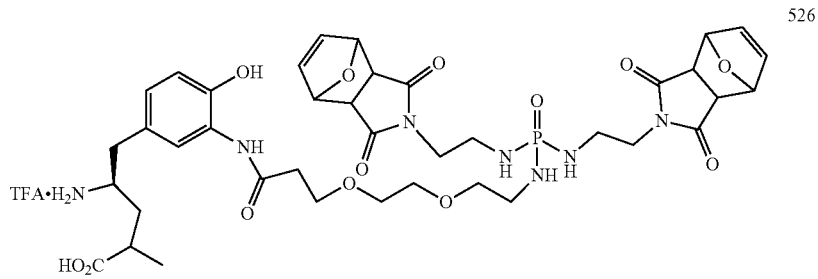

Compound 525 (53.4 mg, 0.053 mmol) was dissolved in DCM (2 mL), and treated with TFA (2 mL) at r.t. for 2 h, then concentrated to give compound 526, which was used in the next step without further purification.

Example 119. Synthesis of Compound 527

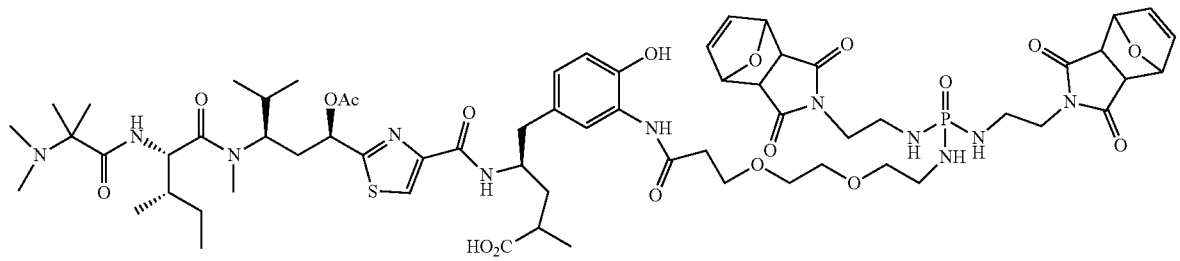
527

To a solution of compound 526 (45.0 mg, 0.053 mmol) in DMA (1 mL) were added pentafluorophenyl ester 41a (37.0 mg, 0.053 mmol) and DIPEA (17 μL, 0.1 mmol). The reaction was stirred overnight and concentrated. The residue was purified by prep-HPLC with a gradient of MeCN/H$_2$O to give the title product 527 (26.2 mg, 36% yield). ESI m/z calcd for C$_{64}$H$_{93}$N$_{11}$O$_{18}$PS [M+H]$^+$: 1366.61, found 1366.61.

Example 120. Synthesis of Compound 528

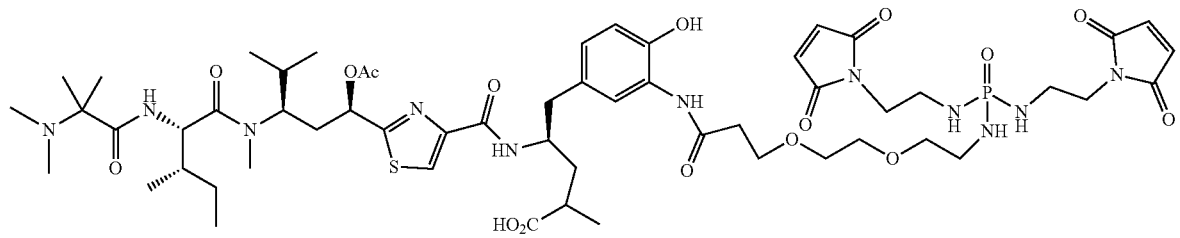
528

Compound 527 (8.0 mg, 0.0058 mmol) was dissolved in toluene (5.0 mL) and heated to reflux overnight, then concentrated and purified by prep-HPLC with a gradient of MeCN/H$_2$O to give the title product 528 (6.4 mg, 90% yield). ESI m/z calcd for C$_{56}$H$_{85}$N$_{11}$O$_{16}$PS [M+H]$^+$: 1230.56, found 1230.56.

Example 121. Synthesis of Compound 529

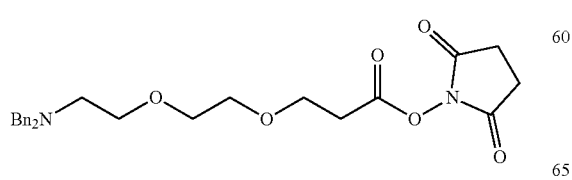
529

To a solution of tert-butyl 3-(2-(2-(dibenzylamino)ethoxy)ethoxy)propanoate (5.00 g, 12.1 mmol) in 10 mL DCM was added 5 mL of TFA. The reaction mixture was stirred at r.t. for 1 h, and then concentrated. The crude product was dissolved in DCM (50 mL), to which NHS (4.25 g, 37 mmol) and EDCI (7.10 g, 37 mmol) were added. The reaction mixture was stirred at r.t. overnight, then concentrated and purified by $SiO_2$ column with a gradient of DCM/MeOH to give the title compound 529 (5.00 g, 91%). ESI m/z calcd for $C_{25}H_{31}N_2O_6$ [M+H]$^+$: 455.21, found 455.21.

Example 122. Synthesis of Compound 530

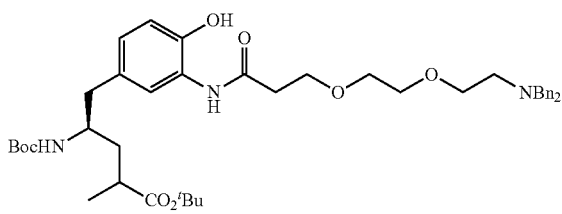

To a solution of compound 110 (1.00 g, 2.5 mmol, 1.0 eq.) in EtOH (10 mL) were added compound 529 (1.80 g, 3.9 mmol, 1.5 eq.) and 0.1M $NaH_2PO_4$ (2 mL) at r.t. The reaction mixture was stirred at r.t. overnight, and then concentrated. The residue was diluted with $H_2O$ (100 mL), then extracted with EtOAc (3×50 mL). The combined the organic layers were dried over $Na_2SO_4$, filtered and concentrated, purified by $SiO_2$ column with a gradient of DCM/MeOH to give the title compound 530 (0.93 g, 50%). ESI m/z calcd for $C_{42}H_{60}N_3O_8$ [M+H]$^+$: 734.43, found 734.43.

Example 123. Synthesis of Compound 531

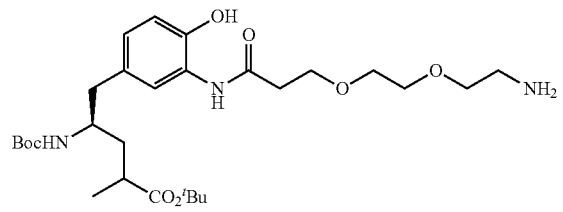

In a hydrogenation bottle, Pd/C (0.093 g, 10 wt %) was added to a solution of compound 530 (0.93 g, 1.27 mmol) in EtOAc (20 mL). The mixture was shaken overnight under 1 atm $H_2$ then filtered through Celite (filter aid), the filtrate was concentrated to afford compound 531 (0.57 g, 81%) and used in the next step without further purification. ESI m/z calcd for $C_{28}H_{48}N_3O_8$ [M+H]$^+$: 554.34, found 554.34.

Example 124. Synthesis of Compound 537

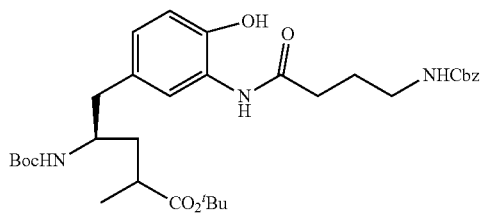

HATU (39.9 g, 105 mmol) was added to a solution of 4-(((benzyloxy)carbonyl)amino) butanoic acid (26.1 g, 110 mmol) in DMF (300 mL). After stirring at r.t. for 30 min, the mixture was added to a solution of compound 110 (39.4 g, 100 mmol) and TEA (20.2 g, 200 mmol) in DMF (300 mL). The resulting mixture was stirred at r.t. for 2 h. Water was then added, extracted with EtOAc, the organic layer was washed with brine, dried over $Na_2SO_4$. Purification by column chromatography (20% to 70% EA/PE) yielded the title product as a white solid (45 g, 73% yield). ESI m/z calcd for $C_{33}H_{48}N_3O_8$ [M+H]$^+$: 614.34, found 614.15.

Example 125. Synthesis of Compound 538

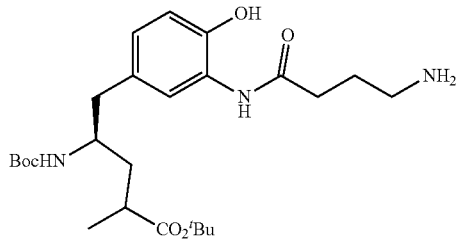

Compound 537 (100 g, 163 mmol) was dissolved in methanol (500 mL) and hydrogenated (1 atm) with Pd/C catalyst (10 wt %, 10 g) at r.t. overnight. The catalyst was filtered off and the filtrate were concentrated under reduced pressure to afford compound 538 (75.8 g, 97% yield) as a brown foamy solid. $^1$H NMR (400 MHz, CDCl3) δ 7.11 (s, 1H), 6.83 (d, J=10.3 Hz, 2H), 5.04-4.52 (m, 6H), 3.90-3.56 (m, 1H), 2.81 (d, J=5.3 Hz, 2H), 2.63 (dd, J=12.5, 6.1 Hz, 2H), 2.54-2.26 (dd, J=14.0, 7.6 Hz, 4H), 1.94-1.64 (m, 3H), 1.44-1.36 (m, 18H), 1.08 (d, J=6.9 Hz, 3H). ESI m/z calcd for $C_{25}H_{42}N_3O_6$ [M+H]$^+$: 480.30, found 480.59.

Example 126. Synthesis of Compound 539

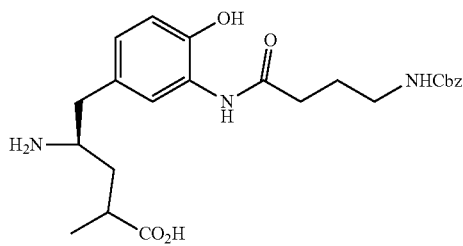

To a solution of compound 537 (1.00 g, 1.63 mmol) in 1 mL DCM was added 2 mL TFA, the reaction mixture was stirred at r.t. for 1. h, and then concentrated. The resulting crude product 539 was used in the next step without further purification. ESI m/z calcd for $C_{24}H_{32}N_3O_6$ [M+H]$^+$: 458.22, found 458.22.

Example 127. Synthesis of Compound 540

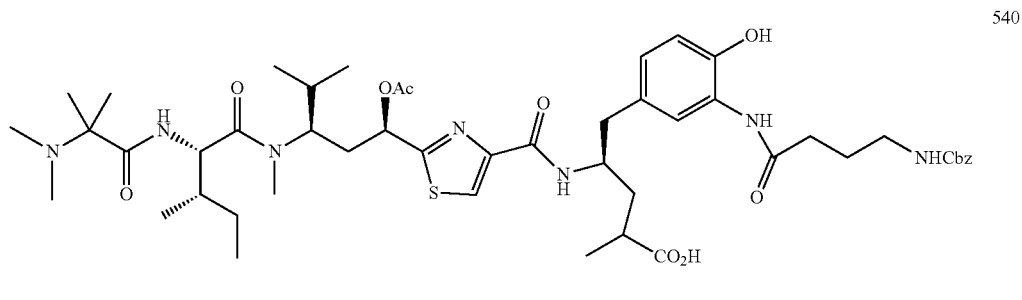 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCNC(=O)OCc3ccccc3)c2)CC(C)C(=O)O)cs1)C(C)C]

540

To a solution of compound 539 (0.42 g, 0.92 mmol) in DMF (3 mL) were added pentafluorophenyl ester 41a (0.63 g, 0.91 mmol) and DIPEA (0.46 mL, 2.73 mmol). The reaction was stirred at r.t. overnight, then concentrated and purified by SiO$_2$ column with a gradient of DCM/MeOH to give the title compound 540 (0.67 g, 75% yield) as a yellow oil. ESI m/z calcd for $C_{49}H_{72}N_7O_{11}S$ [M+H]$^+$: 966.49, found 966.49.

Example 128. Synthesis of Compound 541

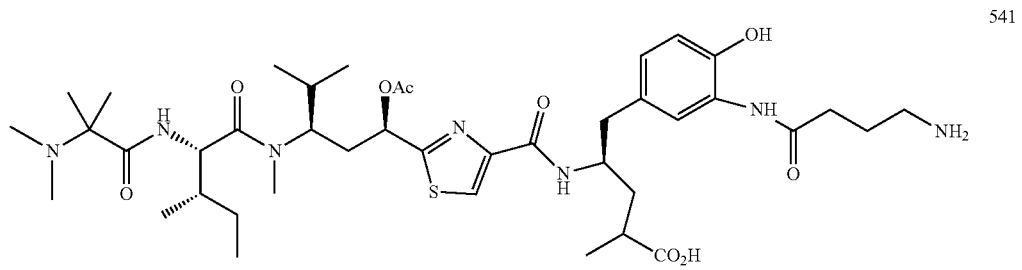 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN)c2)CC(C)C(=O)O)cs1)C(C)C]

541

In a hydrogenation bottle, Pd/C (0.02 g, 10 wt %) was added to a solution of compound 540 (0.40 g, 0.41 mmol) in MeOH (15 mL). a drop of 1N HCl was then added to adjust pH to around 4. The mixture was shaken overnight under 1 atm H$_2$ then filtered through Celite (filter aid), the filtrate was concentrated to afford compound 541, which was used in the next step without further purification. ESI m/z calcd for $C_{41}H_{66}N_7O_9S$ [M+H]$^+$: 832.46, found 832.46.

Example 129. Synthesis of Compound 587

587

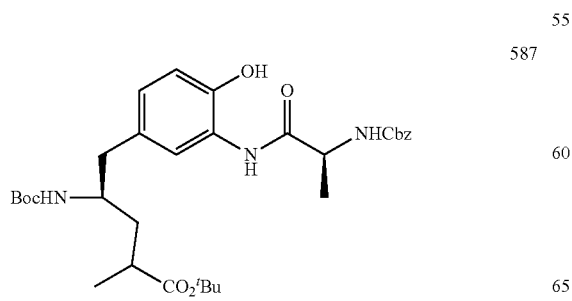

Compound 110 (0.30 g, 0.76 mmol), compound Z-L-Ala-OH (0.17 g, 0.76 mmol) and HATU (0.29 g, 0.76 mmol) were dissolved in DCM (20 mL), to which TEA (110 μL, 0.8 mmol) was added. The reaction mixture was stirred at r.t. overnight. Then the solvent was removed under reduced pressure and the residue was purified by $SiO_2$ column to give the title product 587 (0.43 g, 95% yield). ESI m/z calcd for $C_{32}H_{46}N_3O_8$ [M+H]$^+$: 600.32, found 600.32.

Example 130. Synthesis of Compound 627

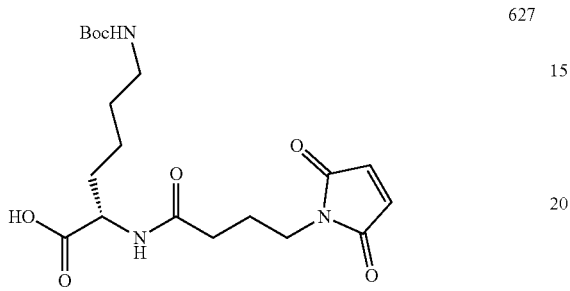

627

To a solution of H-Lys(Boc)-OH (1.00 g, 3.8 mmol, 1.0 eq.) in EtOH (16 mL) was added compound 125 (1.00 g, 5.6 mmol, 1.5 eq.) at r.t. After 0.1 M $NaH_2PO_4$ (3 mL) was added, the reaction mixture was stirred at r.t. overnight. The reaction was concentrated under vacuum, and the residues was purified by $SiO_2$ column with a gradient of DCM/MeOH to give the title compound 627 (1.62 g, theoretical yield). ESI m/z calcd for $C_{19}H_{30}N_3O_7$ [M+H]$^+$: 412.20, found 412.20.

Example 131. Synthesis of Compound 628

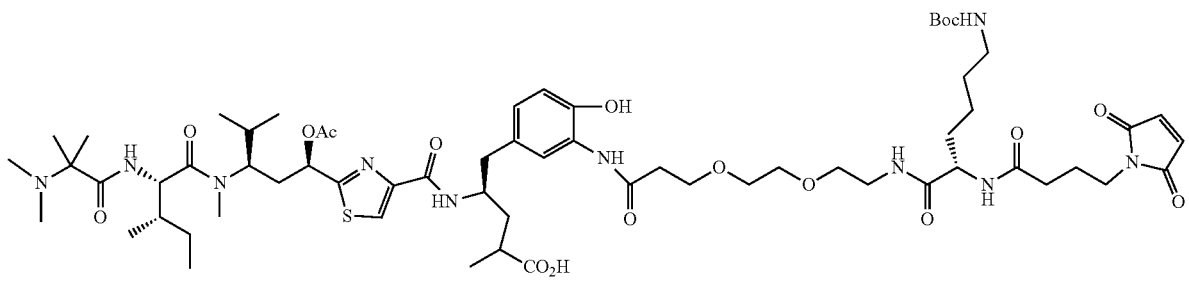

628

To a solution of carboxylic acid 627 (0.24 g, 0.58 mmol) in EtOAc (10 mL) were added pentafluorophenol (0.21 g, 1.17 mmol) and DCC (0.24 g, 1.17 mmol). The reaction mixture was stirred at r.t. overnight, and then filtered with washing of the filter cake with EtOAc, and the filtrate was concentrated. The resulting PFP-ester (32 mg, 0.056 mmol) was dissolved in 1 mL DMF, to which compound 531 (50 mg, 0.056 mmol) and i-$Pr_2$EtN (29 μL, 0.168 mmol) were added. The reaction mixture was stirred at r.t. for 2 h and concentrated. The residue was purified by HPLC with a gradient of MeCN/$H_2O$ to give the title compound 628 (3 mg, 4% yield). ESI m/z calcd for $C_{63}H_{99}N_{10}O_{17}S$ [M+H]$^+$: 1299.68, found 1299.68.

Example 132. Synthesis of Compound 629

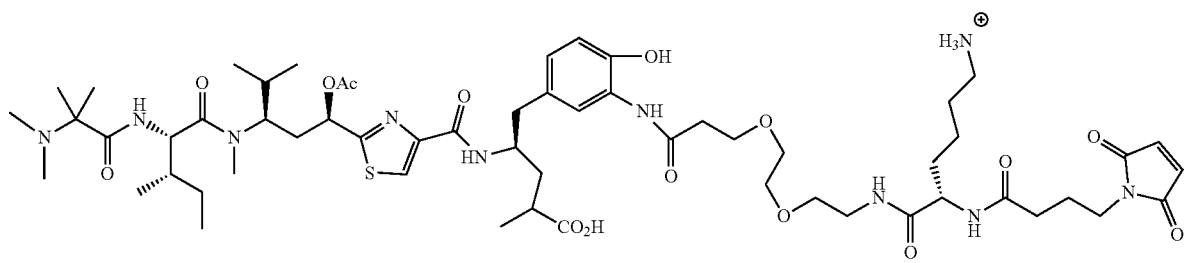

629

To a solution of compound 628 (3 mg, 0.002 mmol) in 0.5 mL DCM was added 1 mL TFA, the reaction mixture was stirred at r.t. for 1 h, then concentrated. The crude product was purified by HPLC with a gradient of MeCN/H$_2$O to give the title compound 629 (1.43 mg, 52% yield). ESI m/z calcd for C$_{58}$H$_{91}$N$_{10}$O$_{15}$S [M+H]$^+$: 1199.63, found 1199.62.

Example 133. Synthesis of Compound 632

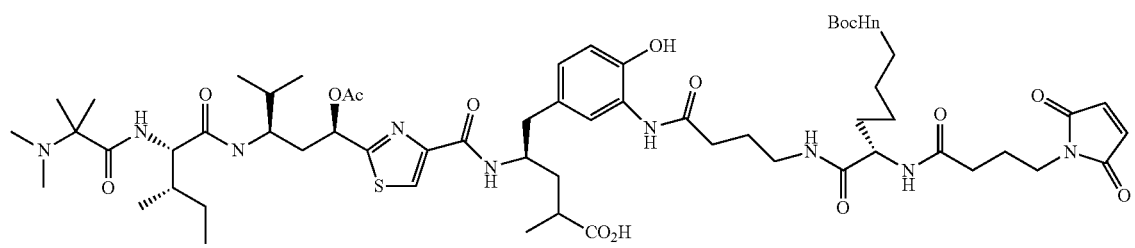

632

The pentafluorophenyl ester of compound 627 (0.11 g, 0.19 mmol) was dissolved in 1 mL DMF, to which compound 541 (0.21 g, 0.25 mmol) and i-Pr$_2$EtN (86 uL, 0.5 mmol) were added. The reaction mixture was stirred at r.t. for 2 h and concentrated. The residue was purified by prep-HPLC with a gradient of MeCN/H$_2$O to give the title product 632 (20 mg, 9%). ESI m/z calcd for C$_{60}$H$_{93}$N$_{10}$O$_{15}$S [M+H]$^+$: 1225.65, found 1225.66.

Example 134. Synthesis of Compound 633

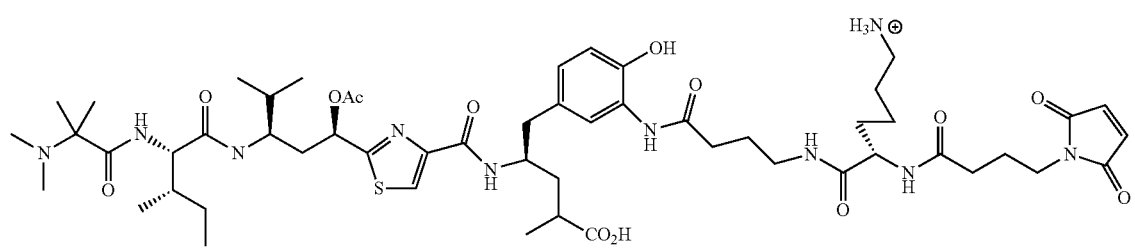

633

To a solution of compound 632 (20 mg, 0.016 mmol) in 1 mL DCM was added 2 mL TFA. The reaction mixture was stirred at r.t. for 1 h, then concentrated, and the crude product was purified by prep-HPLC with a gradient of MeCN/H$_2$O to give the title compound 633 (8.9 mg, 18% yield). ESI m/z calcd for C$_{55}$H$_{85}$N$_{10}$O$_{13}$S [M+H]$^+$: 1125.59, found 1125.59.

Example 135. Synthesis of Compound 636

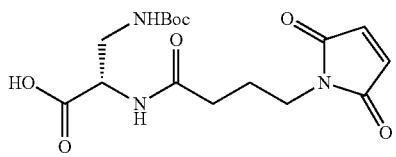

636

To a solution of H-Dap(Boc)-OH (1.00 g, 4.9 mmol, 1.0 eq.) in EtOH (30 mL) was added compound 125 (2.00 g, 7.3 mmol, 1.5 eq.) at r.t. Then 0.1M NaH$_2$PO$_4$ (6 mL) was added, and the reaction mixture was stirred at r.t. overnight. The solvents were removed under vacuum, and the residues was purified by SiO$_2$ column with a gradient of DCM/MeOH to give the title compound 636 (1.41 g, 78%). ESI m/z calcd for C$_{16}$H$_{24}$N$_3$O$_7$ [M+H]$^+$: 370.15, found 370.15.

Example 136. Synthesis of Compound 637

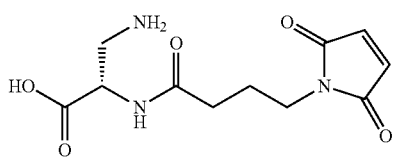

637

To a solution of compound 636 (1.41 g, 3.8 mmol) in 2 mL DCM was added 5 mL TFA. The reaction mixture was stirred at r.t. for 1 h, and then concentrated. The crude product 637 was used in the next step without further purification. ESI m/z calcd for C$_{11}$H$_{16}$N$_3$O$_5$ [M+H]$^+$: 270.10, found 270.10.

Example 137. Synthesis of Compound 638

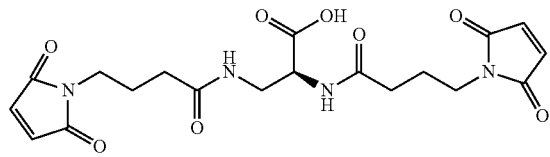

638

To a solution of above compound 637 in EtOH (20 mL) was added compound 125 (1.90 g, 6.9 mmol, 1.5 eq.) at r.t. Then 0.1M NaH$_2$PO$_4$ (4 mL) was added, and the reaction mixture was stirred at r.t. overnight. After the solvents were removed under vacuum, then the residues was purified by HPLC with a gradient of H$_2$O/MeCN to give the title compound 638 (0.45 g, 22% yield). ESI m/z calcd for C$_{19}$H$_{23}$N$_4$O$_8$ [M+H]$^+$: 435.14, found 435.14.

Example 138. Synthesis of Compound 639

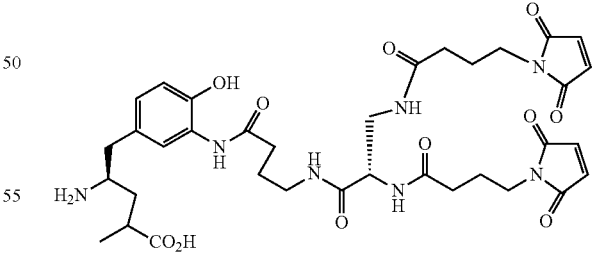

639

To a solution of compound 638 (0.15 g, 0.34 mmol), compound 538 (0.17 g, 0.34 mmol) and HATU (0.16 g, 0.41 mmol) in DMF (2 mL), TEA (95 μL, 0.68 mmol) was added. After stirring at r.t. for 1 h, the reaction was concentrated under reduced pressure and the residue was purified by prep-HPLC with a gradient of MeCN/H$_2$O to give the title compound 639 (34 mg, 11% yield). ESI m/z calcd for C$_{44}$H$_{62}$N$_7$O$_{13}$ [M+H]$^+$: 896.43, found 896.42.

Example 139. Synthesis of Compound 640

640

To a solution of compound 639 (34 mg, 0.04 mmol) in 0.5 mL DCM was added 1 mL TFA. The reaction mixture was stirred at r.t. for 2 h, and then concentrated to afford the title compound 640, which was used in the next step without further purification. ESI m/z calcd for C$_{35}$H$_{46}$N$_7$O$_{11}$ [M+H]$^+$: 740.30, found 740.32.

Example 140. Synthesis of Compound 641

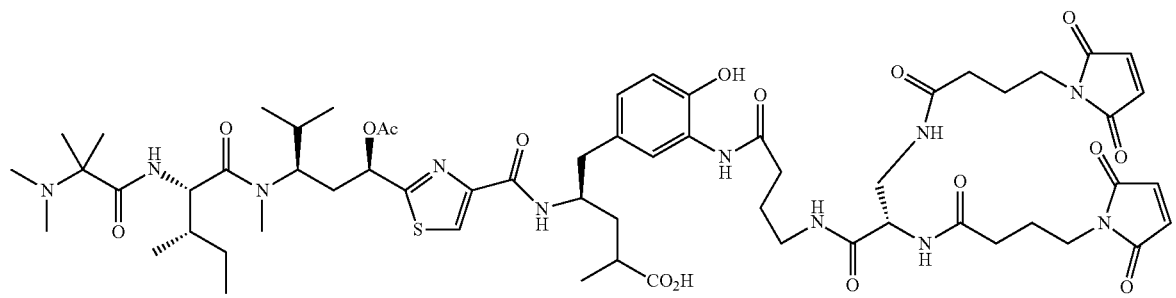

641

To the solution of compound 640 in DMA (2 mL) was added pentafluorophenyl ester 41a (28 mg, 0.04 mmol), followed by DIPEA (21 µL, 0.12 mmol). The reaction was stirred overnight and then concentrated and purified by prep-HPLC with a gradient of MeCN/H$_2$O to give the title compound 641 (14.4 mg, 29%). ESI m/z calcd for $C_{60}H_{86}N_{11}O_{16}S$ [M+H]$^+$: 1248.59, found 1248.60.

Example 141. Synthesis of Compound 644

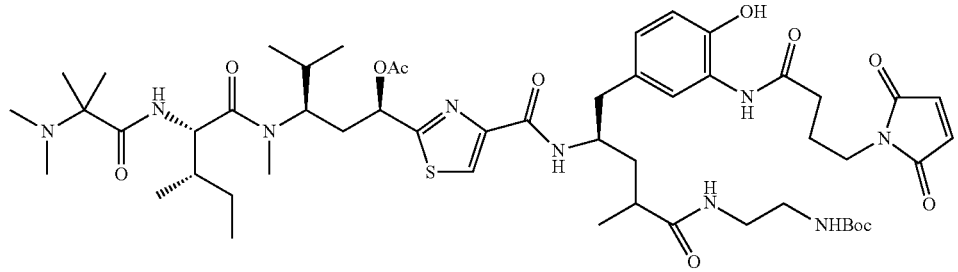

644

To a solution of compound 132 (0.300 g, 0.329 mmol, 1.0 eq.) and tert-butyl (2-aminoethyl)carbamate hydrochloride (0.063 g, 0.395 mmol, 1.2 eq.) in anhydrous DCM (30 mL) at 0° C. was added EDCI (0.189 g, 0.988 mmol, 3.0 eq.). After stirring for 10 minutes, the reaction was warmed to room temperature and stirred overnight. The reaction was diluted with DCM and washed with water and brine, dried over anhydrous Na$_2$SO$_4$, concentrated and purified by SiO$_2$ column chromatography (DCM/MeOH) to give compound 644 as a yellow foamy solid (0.132 g, 54% yield). ESI m/z calcd for $C_{52}H_{80}N_9O_{12}S$ [M+H]$^+$: 1054.6, found: 1054.6.

Example 142. Synthesis of Compound 645

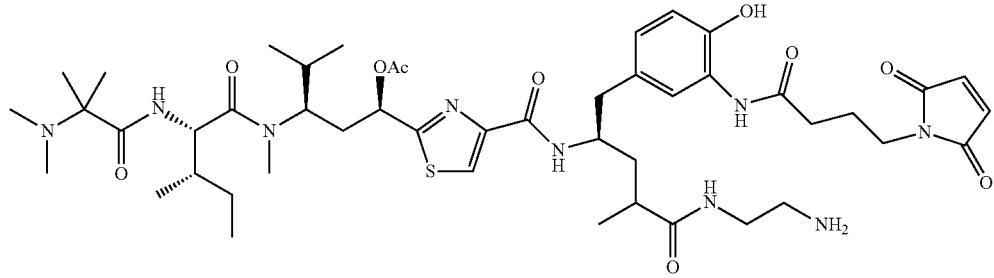

645

To a solution of compound 644 (0.132 g, 0.125 mmol, 1.0 eq.) in DCM (4.5 mL) at r.t. was added TFA (1.5 mL) and stirred for 1 h. The reaction was diluted with anhydrous toluene and concentrated, and this operation was repeated for three times to give yellow oil which was purified on prep-HPLC ($C_{18}$ column, mobile phase A: water, mobile phase B: acetonitrile, from 10% of B to 80% of B in 60 min). The fractions were pooled and lyophilized to give compound 645 (111 mg, 93% yield). ESI m/z calcd for $C_{47}H_{72}N_{9O}O_{10}S$ [M+H]$^+$: 954.5, found: 954.5.

Example 143. Synthesis of Compound 648

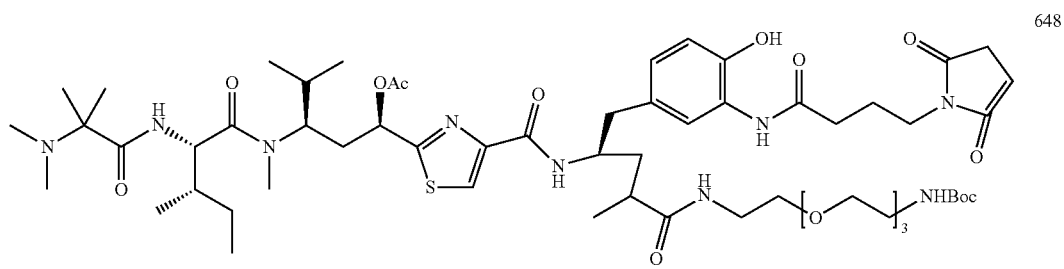

To a solution of compound 645 (0.050 g, 0.0549 mmol, 1.0 eq.) and tert-butyl (2-(2-(2-(2-aminoethoxy)ethoxy)ethoxy)ethyl)carbamate (0.024 g, 0.0824 mmol, 1.5 eq.) in anhydrous DCM (10 mL) at 0° C. was added EDCI (0.032 g, 0.1647 mmol, 3.0 eq.). After stirring for 10 minutes, the reaction was warmed to r.t. and stirred overnight. The mixture was then diluted with DCM and washed with water and brine, dried over anhydrous $Na_2SO_4$, concentrated and purified by $SiO_2$ column chromatography (DCM/MeOH) to give the title compound as a yellow foamy solid (0.030 g, 46% yield). ESI m/z calcd for $C_{58}H_{92}N_9O_{15}S$ [M+H]$^+$: 1186.6, found: 1186.6.

Example 144. Synthesis of Compound 649

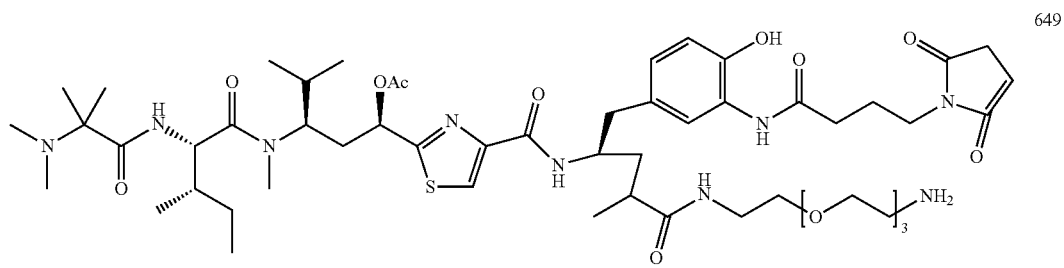

To a solution of compound 648 (0.030 g, 0.0253 mmol, 1.0 eq.) in DCM (3.0 mL) at r.t was added TFA (1.0 mL). The reaction was stirred for 1 h and then diluted with anhydrous toluene and concentrated, this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give compound 649 (11.7 mg, 43% yield). ESI m/z calcd for $C_{53}H_{84}N_9O_{13}S$ [M+H]$^+$: 1086.6, found: 1086.6.

Example 145. Synthesis of Compound 652

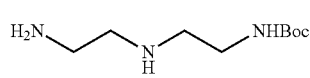
652

To a solution of N-(2-aminoethyl)ethane-1,2-diamine (28.7 g, 275 mmol, 10.0 eq.) and DMAP (0.034 g, 0.000275 mmol, 0.01 eq.) in anhydrous DCM (350 mL) at 0° C. was added Boc$_2$O (6.0 g, 0.0275 mmol, 1.0 eq.) in anhydrous DCM (100 mL) over 3 h. The reaction was then warmed to r.t. and stirred overnight, concentrated and purified by SiO$_2$ column chromatography (DCM/MeOH) to give the title compound as a yellow oil (4.5 g, 80% yield). ESI m/z calcd for C$_9$H$_{22}$N$_3$O$_2$ [M+H]$^+$: 204.2, found: 204.2.

Example 146. Synthesis of Compound 653

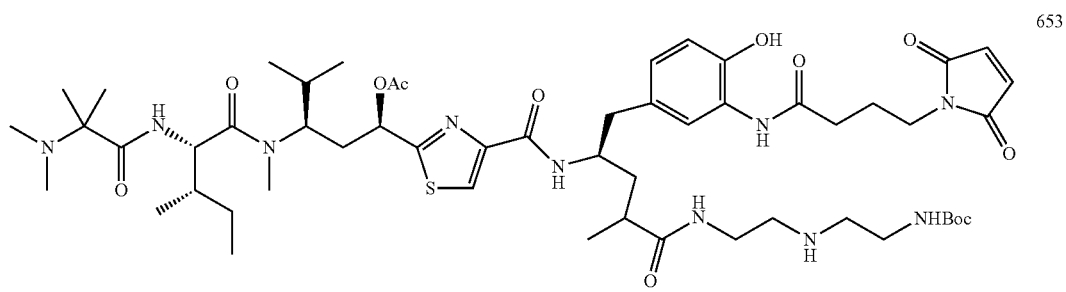 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)NCCNCCNC(=O)OC(C)(C)C)cs1)C(C)C]
653

To a solution of compound 645 (0.060 g, 0.0658 mmol, 1.0 eq.) and tert-butyl (2-((2-aminoethyl)amino)ethyl)carbamate (0.016 g, 0.0790 mmol, 1.2 eq.) in anhydrous DCM (6 mL) at 0° C. was added EDCI (0.038 g, 0.1974 mmol, 3.0 eq.). After stirring for 10 minutes, the reaction was warmed to r.t. and stirred overnight. The mixture was concentrated and purified on prep-HPLC (C$_{18}$ column, mobile phase A: water, mobile phase B: acetonitrile, from 10% of B to 80% of B in 60 min). The fractions were pooled and lyophilized to give the title compound 653 (48 mg, 66% yield). ESI m/z calcd for C$_{54}$H$_{85}$N$_{10}$O$_{12}$S [M+H]$^+$: 1097.6, found: 1097.6.

Example 147. Synthesis of Compound 654

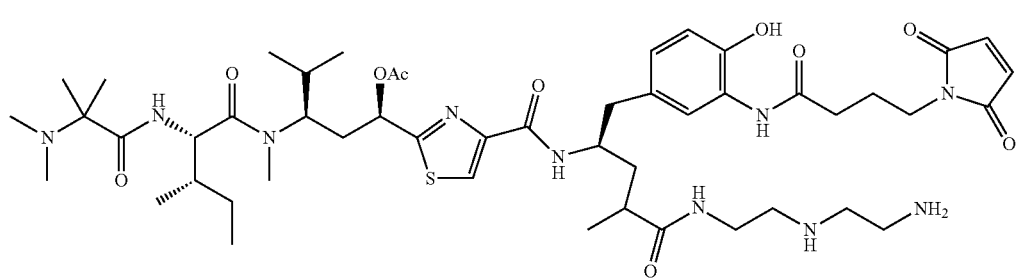
654

To a solution of compound 653 (0.048 g, 0.0437 mmol, 1.0 eq.) in DCM (3.0 mL) at r.t. was added TFA (1.0 mL). After stirring for 1 h, the reaction was diluted with anhydrous toluene and concentrated, and this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give the title compound 654 (111 mg, 93% yield). ESI m/z calcd for $C_{49}H_{77}N_{10}O_{10}S$ [M+H]$^+$: 997.5, found: 997.5.

Example 148. Synthesis of Compound 658

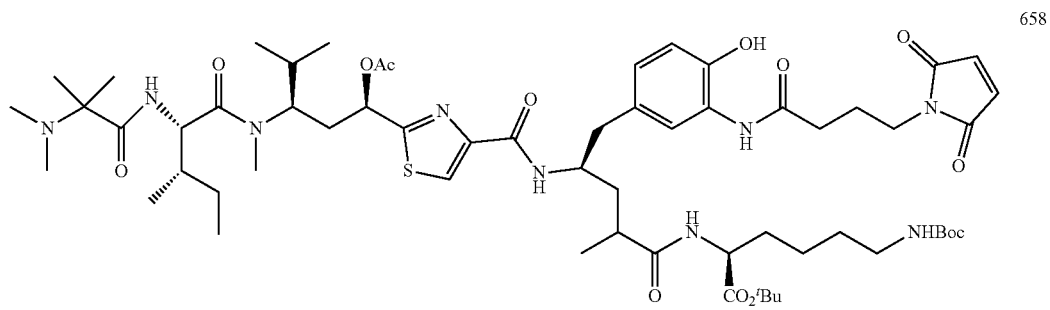 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)N[C@@H](CCCCNC(=O)OC(C)(C)C)C(=O)OC(C)(C)C)cs1)C(C)C]

To a solution of compound 645 (0.400 g, 0.439 mmol, 1.0 eq.) and H-Lys(Boc)-O$^t$Bu·HCl (0.135 g, 0.528 mmol, 1.2 eq.) in anhydrous DCM (40 mL) at 0° C. was added EDCI (0.189 g, 1.317 mmol, 3.0 eq.). After stirring for 10 min, the reaction was warmed to r.t. and stirred overnight. The mixture was diluted with DCM and washed with water and brine, dried over anhydrous $Na_2SO_4$, concentrated and purified by $SiO_2$ column chromatography (DCM/MeOH) to give compound 658 as a yellow oil (0.43 g, 82% yield). ESI m/z calcd for $C_{60}H_{94}N_9O_{14}S$ [M+H]$^+$: 1196.7, found: 1196.7.

Example 149. Synthesis of Compound 559

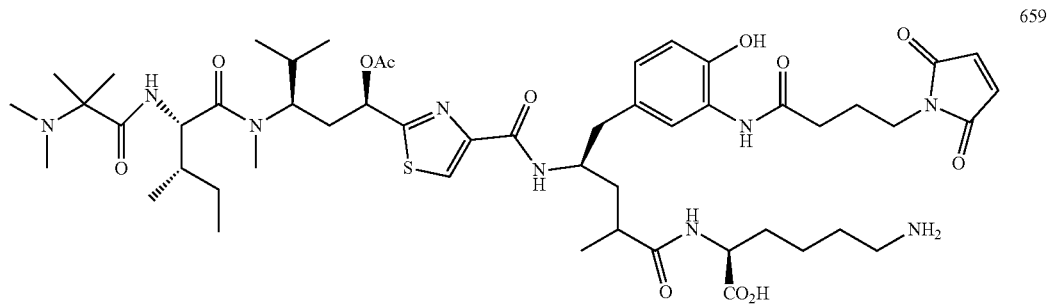 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)N[C@@H](CCCCN)C(=O)O)cs1)C(C)C]

To a solution of compound 658 (0.230 g, 0.192 mmol, 1.0 eq.) in DCM (6.0 mL) at r.t. was added TFA (2.0 mL) and the reaction was stirred for 3 h and then diluted with toluene and concentrated, this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give the title compound (153 mg, 76% yield). ESI m/z calcd for $C_{51}H_{78}N_9O_{12}S$ [M+H]$^+$: 1040.5, found: 1040.5.

Example 150. Synthesis of Compound 662

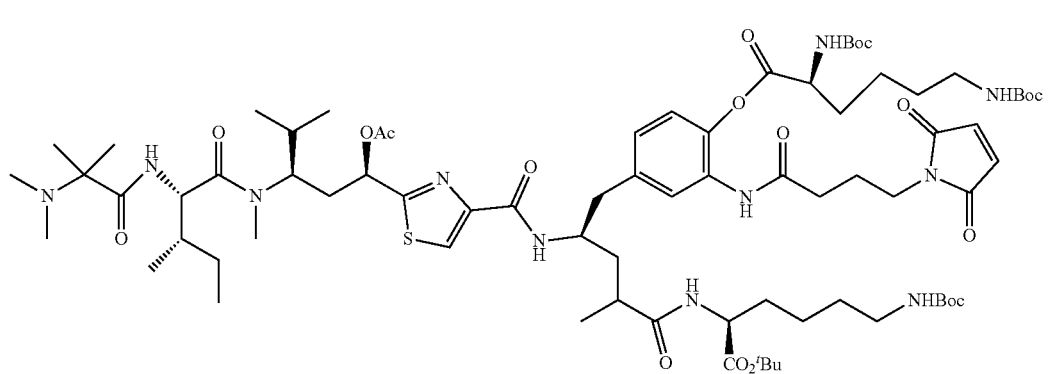

To a solution of compound 658 (0.200 g, 0.167 mmol, 1.0 eq.) and Boc-L-Lys(Boc)-OH (0.070 g, 0.200 mmol, 1.2 eq.) in anhydrous DCM (10 mL) at 0° C. was added HATU (0.095 g, 0.250 mmol, 1.5 eq.) and TEA (46 µL, 0.334 mmol, 2.0 eq.). The reaction was stirred for 10 min at 0° C. and stirred for 10 minutes, then warmed to r.t. and stirred overnight. The mixture was diluted with DCM and washed with water and brine, dried over anhydrous $Na_2SO_4$, concentrated and purified by $SiO_2$ column chromatography (DCM/MeOH) to give compound 662 as a colourless oil (0.270 g, theoretical yield). ESI m/z calcd for $C76H_{122}N_{11}O_{19}S$ $[M+H]^+$: 1524.9, found: 1524.9.

Example 151. Synthesis of Compound 663

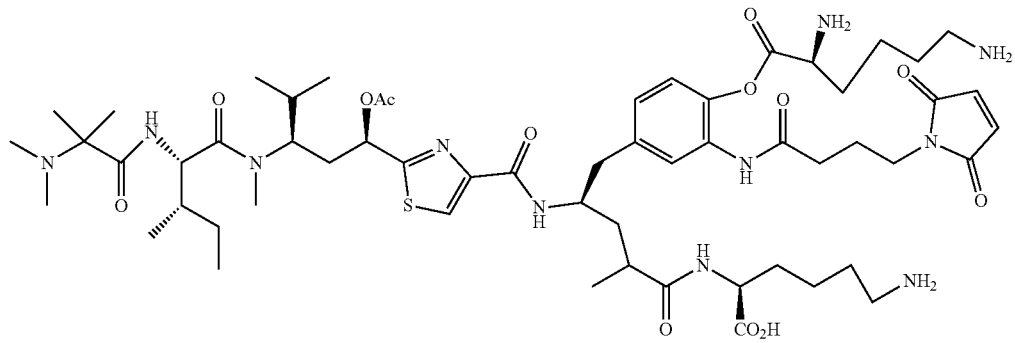

To a solution of compound 662 (0.270 g, 0.177 mmol, 1.0 eq.) in DCM (6.0 mL) at r.t. was added TFA (2.0 mL) and stirred for 4 h. The mixture was diluted with anhydrous toluene and concentrated, this operation was repeated for three times to give yellow oil, which was purified on prep-HPLC ($C_{18}$ column, mobile phase A: water, mobile phase B: acetonitrile, from 10% of B to 80% of B in 60 min). The fractions were pooled and lyophilized to give the title compound (172 mg, 83% yield). ESI m/z calcd for $C_{57}H_{90}N_{11}O_{13}S$ $[M+H]^+$: 1168.6, found: 1168.6.

Example 152. Synthesis of Compound 666

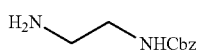
666

To a solution of ethane-1,2-diamine (30.0 g, 0.5 mol, 10.0 eq.) in anhydrous DCM (500 mL) at 0° C. was added CbzCl (8.53 g, 0.050 mol, 1.0 eq.) in anhydrous DCM (250 mL) over 7 h. The reaction was then warmed to r.t. and stirred overnight. The mixture was washed with water and brine, dried over anhydrous $Na_2SO_4$, and concentrated to give benzyl (2-aminoethyl)carbamate as a white solid (7.0 g, 94% yield). ESI m/z calcd for $C_{10}H_{14}N_2O_2$ $[M+H]^+$: 195.1, found: 195.2.

Example 153. Synthesis of Compound 667

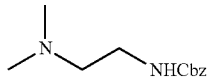
667

To a solution of compound 666 (7.0 g, 35.8 mmol, 1.0 eq.) and 37% HCHO (aq) (14 mL, 0.1772 mmol, 5.0 eq.) in MeOH (120 mL) at 0° C. was added $NaBH_3CN$ (3.9 g, 0.0620 mol, 1.6 eq.), then HOAc (3 mL) was added to adjust pH~7.0. The mixture was warmed to r.t. and stirred overnight, then concentrated. The residue was dissolved in DCM (200 mL), and washed with water and brine, dried over anhydrous $Na_2SO_4$, concentrated and purified by $SiO_2$ column chromatography (DCM/MeOH) to give the title compound as a light yellow oil (6.4 g, 80% yield). ESI m/: calcd for $C_{12}H_{18}N_2O_2$ $[M+H]^+$: 224.1, found: 224.1.

Example 154. Synthesis of Compound 668

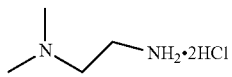
668

Compound 667 (3.0 g, 13.4 mmol, 1.0 eq.) and Pd/C (0.3 g, 10% Pd/C, 50% wet) were mixed with HCl (3 mL) and MeOH (100 mL) in a hydrogenation bottle and shaken at 100 psi $H_2$ atmosphere for 5 h. Then the mixture was filtered over Celite and the filtrate was concentrated to give the title compound as a yellow solid (2.1 g, 98% yield). $^1$H NMR (400 MHz, $D_2O$) δ 3.33 (d, J=4.6 Hz, 2H), 3.27 (s, 2H), 2.79 (s, 6H).

Example 155. Synthesis of Compound 669

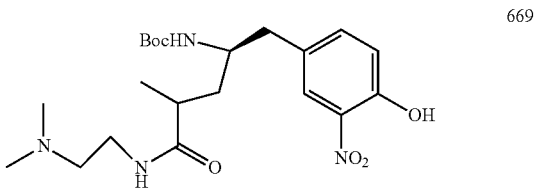 [SMILES: CC(C[C@H](Cc1ccc(O)c([N+](=O)[O-])c1)NC(=O)OC(C)(C)C)C(=O)NCCN(C)C]
669

To a solution of compound 103 (0.58 g, 1.58 mmol, 1.0 eq.) and compound 668 (0.051 g, 3.15 mmol, 2.0 eq.) in anhydrous DMF (10 mL) at 0° C. were added HATU (0.090 g, 2.37 mmol, 1.5 eq.) and TEA (0.656 mL, 4.74 mmol, 3.0 eq.). After stirring for 10 minutes, the reaction was warmed to r.t. and stirred for 90 minutes. The mixture was diluted with $H_2O$ and extracted with EA (3×100 mL). The combined organic layers were washed with water and brine, dried over anhydrous $Na_2SO_4$, concentrated to give the title compound as a yellow foamy solid (0.67 g, 97% yield). ESI m/z calcd for $C_{21}H_{35}N_4O_6$ $[M+H]^+$: 439.2, found: 439.2.

Example 156. Synthesis of Compound 670

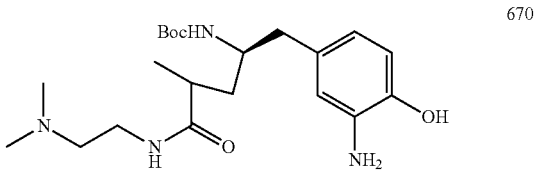 [SMILES: CC(C[C@H](Cc1ccc(O)c(N)c1)NC(=O)OC(C)(C)C)C(=O)NCCN(C)C]
670

Pd/C (0.2 g, 10% Pd/C, 50% wet) was added to a solution of compound 669 (0.60 g, 13.7 mmol, 1.0 eq.) in EA (10 mL). The mixture was shaken at 100 psi $H_2$ atmosphere for 4 h. Then the mixture was filtered over Celite and the filtrate was concentrated to give the title compound as green oil (5.50 g, 98% yield). ESI m/z calcd for $C_{21}H_{37}N_4O_{64}$ $[M+H]^+$: 409.3, found: 409.3.

Example 157. Synthesis of Compound 671

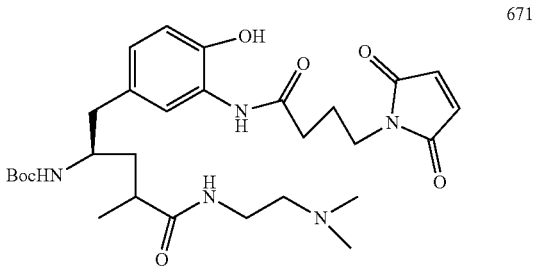 [SMILES: CC(C[C@H](Cc1ccc(O)c(NC(=O)CCCN2C(=O)C=CC2=O)c1)NC(=O)OC(C)(C)C)C(=O)NCCN(C)C]
671

To a solution of compound 670 (0.50 g, 1.22 mmol, 1.0 eq.) in 95% EtOH (10 mL) and 0.1M $NaH_2PO_4$ (2 mL) was added compound 125 (0.683 g, 2.44 mmol, 2.0 eq.) and the reaction was stirred overnight and then concentrated and purified by $SiO_2$ column chromatography (DCM/MeOH) to give the title compound as a light yellow oil (0.624 g, 89% yield). ESI m/z calcd for $C_{29}H_{44}N_5O_7$ $[M+H]^+$: 574.3, found: 574.3.

Example 158. Synthesis of Compound 672

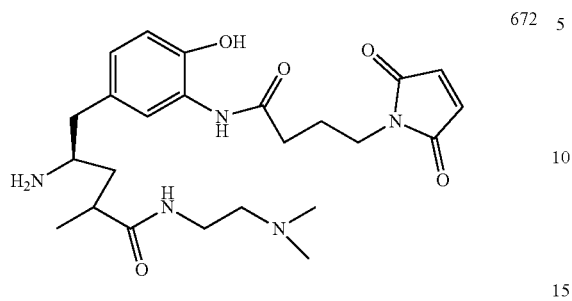

To a solution of compound 671 (0.20 g, 0.349 mmol, 1.0 eq) in DCM (6.0 mL) at r.t. was added TFA (2.0 mL) and the reaction was stirred for 2 h, then diluted with anhydrous toluene and concentrated, this operation was repeated for three times to give the title compound as a yellow oil (165 mg, theoretical yield). ESI m/z calcd for $C_{24}H_{36}N_5O_5$ [M+H]$^+$: 474.3, found: 474.3.

Example 159. Synthesis of Compound 673

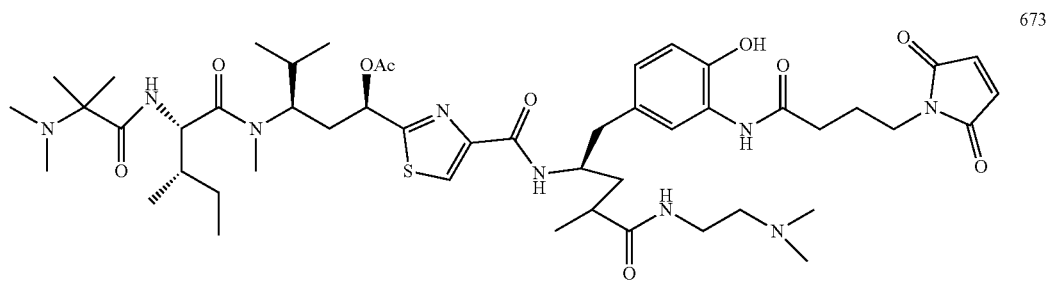 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)NCCN(C)C)cs1)C(C)C]

To a solution of compound 672 (0.165 g, 0.349 mmol, 1.0 eq.) in anhydrous DMF (2 mL) at 0° C. was added compound 41a (0.290 g, 1.047 mmol, 1.2 eq.) in anhydrous DMF (3 mL) and the reaction was stirred for 10 minutes, then warmed to r.t. and stirred for 1 h. The reaction mixture was concentrated and purified on prep-HPLC ($C_{18}$ column, mobile phase A: water, mobile phase B: acetonitrile, from 10% of B to 80% of B in 60 min). The fractions were pooled and lyophilized to give the title compound (58 mg, 17% yield) as a light yellow foamy solid. ESI m/z calcd for $C_{49}H_{76}N_9O_{10}S$ [M+H]$^+$: 982.5, found: 982.5.

Example 160. Synthesis of Compound 704

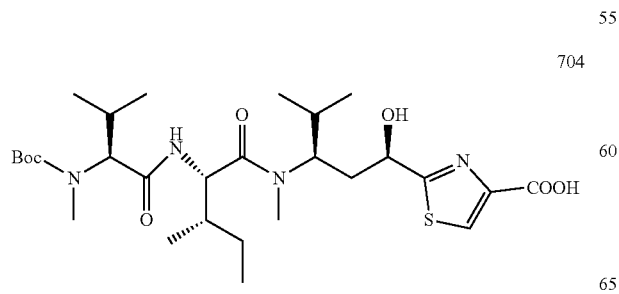

(S)-2-((tert-butoxycarbonyl)(methyl)amino)-3-methylbutanoic acid (33 mg, 0.14 mmol), DCC (32 mg, 0.154 mmol) and pentafluorophenol (39 mg, 0.21 mmol) were dissolved in ethyl acetate (20 mL) and the reaction was stirred at room temperature overnight. The reaction was then concentrated to dryness to give compound (S)-perfluorophenyl 2-((tert-butoxycarbonyl) (methyl)amino)-3-methylbutanoate, which was dissolved in 2 mL of DMA, and a solution of compound 2-((1R,3R)-3-((2 S,3 S)-2-amino-N,3-dimethylpentanamido)-1-hydroxy-4-methylpentyl)thiazole-4-carboxylic acid (52 mg, 0.14 mmol) in 3 mL of DMA and DIPEA (48.5 µL, 0.28 mmol) were added. The reaction was stirred at room temperature overnight and then concentrated. The residue was diluted with 1 mL of acetonitrile and purified by reverse phase HPLC with a gradient of MeCN/H$_2$O to afford compound 704 (40.2 mg, 49% yield). ESI: m/z: calcd for C$_{28}$H$_{49}$N$_4$O$_7$S [M+H]$^+$: 585.32, found 585.32.

Example 161. Synthesis of Compound 705

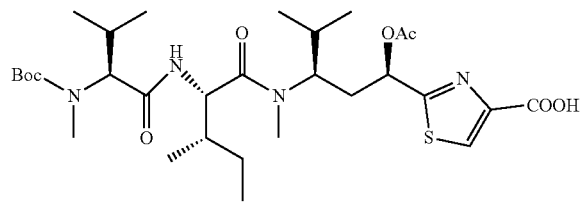

To a solution of compound 704 (40 mg, 0.069 mmol) in pyridine (8 mL) at 0° C. was added acetic anhydride (20.4 mg, 0.2 mmol), and the reaction was warmed to room temperature and stirred overnight, then concentrated. The residue was purified by column chromatography (MeOH/DCM) to afford the title compound 705 (48.1 mg, —100% yield). ESI: m/z: calcd for C$_{30}$H$_{51}$N$_4$O$_8$S [M+H]$^+$: 627.33, found 627.33.

Example 162. Synthesis of Compound 708

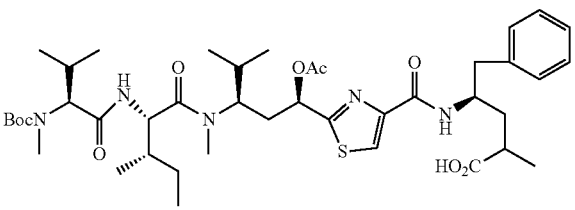

Compound 705 (48.1 mg, 0.077 mmol) DCC (17.4 mg, 0.085 mmol) and pentafluorophenol (21.2 mg, 0.115 mmol) were dissolved in ethyl acetate (10 mL) and the reaction was stirred overnight at room temperature, then concentrated to dryness to give compound perfluorophenyl 2-((6S,9S,12R,14R)-9-((S)-sec-butyl)-6,12-diisopropyl-2,2,5,11-tetramethyl-4,7,10,16-tetraoxo-3,15-dioxa-5,8,11-triazaheptadecan-14-yl)thiazole-4-carboxylate, which was dissolved in 4 mL of DMA, and a solution of compound (4R)-4-amino-2-methyl-5-phenylpentanoic acid, trifluoroacetic acid salt (20.7 mg, 0.1 mmol) in 3 mL of DMA and DIPEA (26.8 µL, 0.154 mmol) were added. The reaction was stirred at room temperature overnight and then concentrated. The residue was diluted with 1 mL of acetonitrile and purified by reverse phase HPLC with a gradient of MeCN/H$_2$O to afford compound 708 (33 mg, 84% yield). ESI: m/z: calcd for C$_{42}$H$_{66}$N$_5$O$_9$S [M+H]$^+$: 816.45, found 816.45.

Example 163. Synthesis of Compound 709

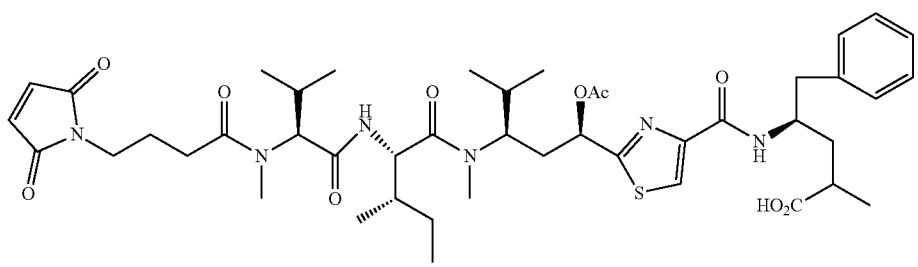

Compound 708 from previous step was dissolved in DCM (1 mL) and treated with TFA (1 mL) at r.t. for 2 h. The reaction was concentrated and the residue was dissolved in EtOH (20 mL). Compound 125 (30.8 mg, 0.11 mmol) and 0.1 M NaH$_2$PO$_4$ (4 mL) were added and the resulting mixture was stirred at r.t. overnight, then concentrated and the residue was purified by column chromatography (MeOH/DCM) to afford the title compound 709 (28.5 mg, 42% yield). ESI m/z: calcd for C$_{45}$H$_{65}$N$_6$O$_{10}$S [M+H]$^+$: 881.44, found 881.44.

Example 164. Synthesis of Compound 712

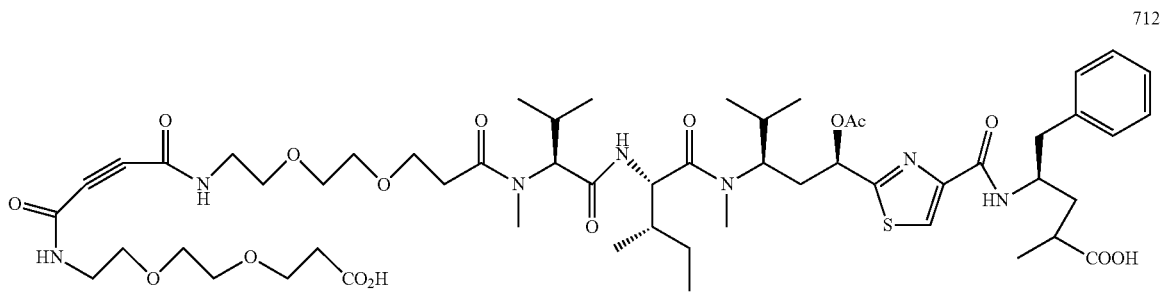 [SMILES: CC[C@H](C)[C@H](NC(=O)[C@H](C(C)C)N(C)C(=O)CCOCCOCCNC(=O)C#CC(=O)NCCOCCOCCC(=O)O)C(=O)N(C)[C@H](C[C@@H](OC(C)=O)c1nc(C(=O)N[C@@H](Cc2ccccc2)CC(C)C(=O)O)cs1)C(C)C]

712

To a solution of compound 708 (63 mg, 0.077 mmol) in DCM (1 mL) was treated with TFA (1 mL) at room temperature for 2 h, then concentrated and the residue was dissolved in DMA (4 mL). Compound 711 (65.8 mg, 0.11 mmol) and DIPEA (27 µL, 0.154 mmol) were added and the reaction was stirred at room temperature overnight, then concentrated and the residue was purified by reverse phase HPLC with a gradient of MeCN/H$_2$O to afford compound 712 (14 mg, 16% yield). ESI: m/z: calcd for C$_{55}$H$_{84}$N$_7$O$_{16}$S [M+H]$^+$: 1130.56, found 1130.57.

Example 165. Synthesis of tert-butyl 17-(2,5-dioxo-2,5-dihydro-1H-pyrrol-1-yl)-14-oxo-4,7,10-trioxa-13-azaheptadecan-1-oate (compound 157a)

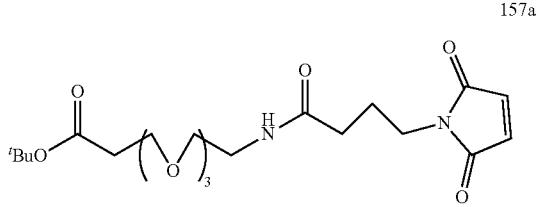

157a

Compound 444 (27.92 g, 0.1 mol) and compound 124 (18.3 g, 0.1 mol) was dissolved in DCM (300 mL), to which DIPEA (12.9 g, 0.1 mol) and EDC (38.6 g, 0.2 mol) were added. The resulting solution was stirred at r.t. overnight and then washed with brine, dried over Na$_2$SO$_4$. Filtration, concentration and purification by column chromatography (5% EtOAc/DCM to 20% EtOAc/DCM) yielded compound 157a (38.03 g, 86% yield). MS ESI m/z calcd for C$_{21}$H$_{35}$N$_2$O$_8$ [M+H]$^+$ 443.2394, found 443.2412.

Example 166. Synthesis of 17-(2,5-dioxo-2,5-dihydro-1H-pyrrol-1-yl)-14-oxo-4,7,10-trioxa-13-azaheptadecan-1-oic acid (compound 158a)

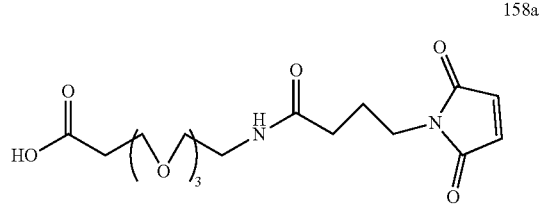

158a

To a solution of compound 157a (38.0 g, 85.9 mmol) in 150 mL DCM was added 50 mL TFA. The reaction mixture was stirred at r.t. for 1 h, and then diluted with toluene (50 ml), concentrated in vacuo and purification by column chromatography (10% MeOH/DCM to 20% MeOH/DCM) yielded compound 158a (27.53 g, 83% yield). MS ESI m/z calcd for C$_{17}$H$_{27}$N$_2$O$_8$ [M+H]$^+$ 387.1768, found 387.1792.

Example 167. Synthesis of 2,5-dioxopyrrolidin-1-yl 17-(2,5-dioxo-2,5-dihydro-1H-pyrrol-1-yl)-14-oxo-4,7,10-trioxa-13-azaheptadecan-1-oate (compound 159a)

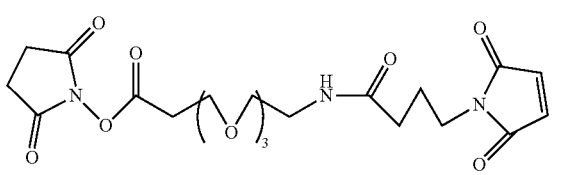

159a

NHS (3.20 g, 27.82 mmol) and EDCI (9.70 g, 50.4 mmol) were added to a solution of compound 158a (10.10 g, 26.15 mmol) in DCM (80 mL). After stirring at r.t. overnight, the reaction mixture was concentrated and purified by column chromatography (5 to 20% EtOAc/DCM) to afford compound 159a (10.73 g, 85% yield). MS ESI m/z calcd for $C_{21}H_{30}N_3O_{10}$ [M+H]$^+$ 484.1942, found 484.1978.

Example 168. Synthesis of (2S,5S)-23-(2,5-dioxo-2,5-dihydro-1H-pyrrol-1-yl)-2,5-dimethyl-4,7,20-trioxo-10,13,16-trioxa-3,6,19-triazatricosan-1-oic acid (compound 162a)

Compound 161 ((S)-Ala-(S)-Ala, 5.01 g, 31.2 mmol) in the mixture of ethanol (100 ml) and pH 7.5 buffer (0.1 M $NaH_2PO_4/Na_2HPO_4$, 100 ml), was added compound 159a (15.08 g, 31.20 mmol) in four portions in 2 hours. After addition, the mixture was continued to stir for 4 hours, concentrated in vacuo, and purified by column chromatography (10 to 20% MeOH/DCM) to afford compound 162a (13.18 g, 80% yield). MS ESI m/z calcd for $C_{23}H_{37}N_4O_{10}$ [M+H]$^+$ 529.2511, found 529.2545.

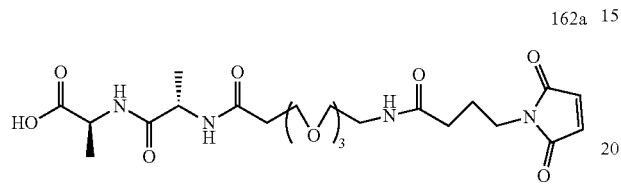

162a

Example 169. Synthesis of (2S,5S)-2,5-dioxopyrrolidin-1-yl 23-(2,5-dioxo-2,5-dihydro-1H-pyrrol-1-yl)-2,5-dimethyl-4,7,20-trioxo-10,13,16-trioxa-3,6,19-triazatricosan-1-oate (163a)

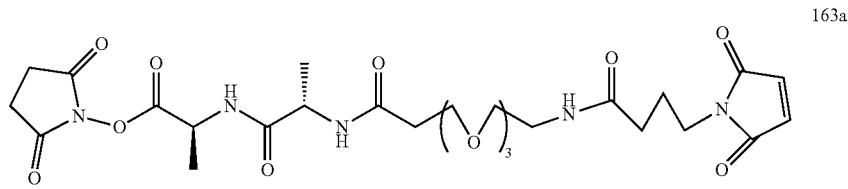

163a

NHS (1.60 g, 13.91 mmol) and EDCI (5.90 g, 30.7 mmol) were added to a solution of compound 162a (6.50 g, 12.30 mmol) in DCM (70 mL). After stirring at r.t. overnight, the reaction mixture was concentrated and purified by column chromatography (5 to 20% EtOAc/DCM) to afford compound 163a (6.61 g, 86% yield). MS ESI m/z calcd for $C_{27}H_{40}N_5O_{12}$ [M+H]$^+$ 626.2672, found 626.2698.

Example 170. Synthesis of (2S,4R)-4-((tert-butoxycarbonyl)amino)-5-(3-((2S,5S)-23-(2,5-dioxo-2,5-dihydro-1H-pyrrol-1-yl)-2,5-dimethyl-4,7,20-trioxo-10,13,16-trioxa-3,6,19-triazatricosanamido)-4-hydroxyphenyl)-2-methylpentanoic acid (164a)

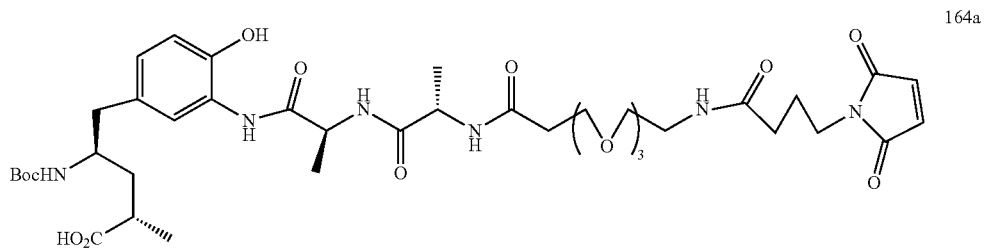

164a

Compound 121 (3.57 g, 10.55 mmol) in the mixture of ethanol (70 ml) and pH 7.5 buffer (0.1 M NaH$_2$PO$_4$/Na$_2$HPO$_4$, 60 ml), was added compound 163a (6.60 g, 10.55 mmol) in four portions in 2 hours. After addition, the mixture was continued to stir for 4 hours, concentrated in vacuo, and purified by column chromatography (15 to 25% MeOH/DCM) to afford compound 164a (7.25 g, 81% yield). MS ESI m/z calcd for C$_{40}$H$_{61}$N$_6$O$_{14}$ [M+H]$^+$ 849.4267, found 849.4295.

Example 171. Synthesis of (2R,4S)-4-carboxy-1-(3-((2S,5 S)-23-(2,5-dioxo-2,5-dihydro-1H-pyrrol-1-yl)-2,5-dimethyl-4,7,20-trioxo-10,13,16-trioxa-3,6,19-triazatricosanamido)-4-hydroxyphenyl)pentan-2-aminium, trifluoroacetate (165a)

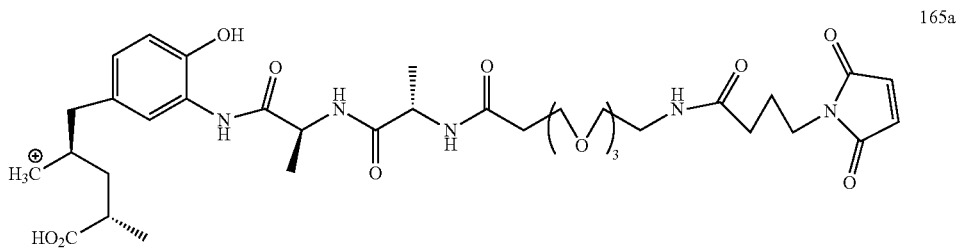

165a

To a solution of compound 164a (0.20 g, 0.349 mmol, 1.0 eq) in DCM (6.0 mL) at r.t. was added TFA (2.0 mL) and the reaction was stirred for 2 h, then diluted with anhydrous toluene and concentrated, this operation was repeated for three times to give the title compound as a yellow oil (165 mg, theoretical yield) for the next step without further purification. ESI m/z calcd for C$_{35}$H$_{54}$N$_6$O$_{12}$ [M+H]$^+$: 750.3795, found: 750.3825.

Example 172. Synthesis of (2S,4R)-4-(2-((6S,9R,11R)-6-((S)-sec-butyl)-9-isopropyl-2,3,3,8-tetramethyl-4,7,13-trioxo-12-oxa-2,5,8-triazatetradecan-11-yl)thiazole-4-carboxamido)-5-(3-((2S,5 S)-23-(2,5-dioxo-2,5-dihydro-1H-pyrrol-1-yl)-2,5-dimethyl-4,7,20-trioxo-10,13,16-trioxa-3,6,19-triazatricosanamido)-4-hydroxyphenyl)-2-methylpentanoic acid (166a)

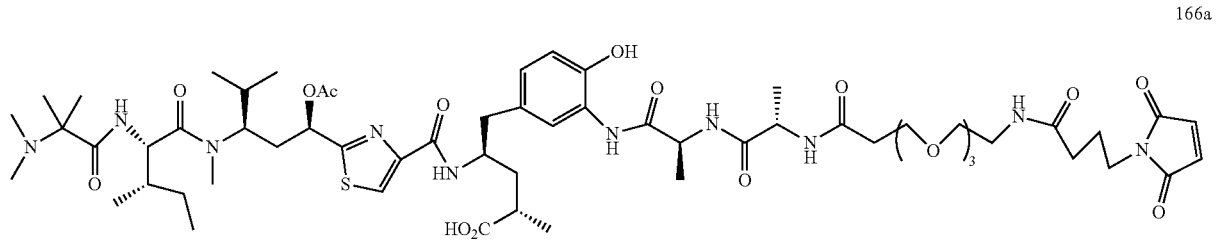

166a

Compound 165a (45 mg, 0.0600 mmol) and perfluorophenyl ester 41a (45 mg, 0.0650 mmol) were dissolved in DMA (5 mL). To the mixture, DIPEA (20 mg, 0.154 mmol) was added. The resulting mixture was stirred at r.t. overnight, concentrated and purified by preparative HPLC (C$_{18}$ column, 10-90% MeCN/H$_2$O) to afford compound 166a (49.1 mg, 65% yield). ESI m/z calcd for C$_{60}$H$_{93}$N$_{10}$O$_{17}$S [M+H]$^+$: 1256.6442, found: 1256.6510.

Example 173. Synthesis of perfluorophenyl 2-methyl-2-(pyrrolidin-1-yl)propanoate 713

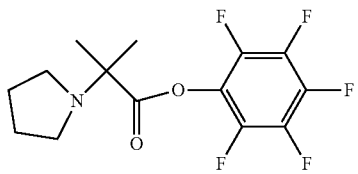

713

2-Methyl-2-(pyrrolidin-1-yl)propanoic acid 25 (401 mg, 2.50 mmol), EDC (654 mg, 3.40 mmol) and pentafluorophenol (480 mg, 2.60 mmol) were dissolved in dichloromethane (45 mL) and the reaction was stirred overnight at room temperature, then concentrated to dryness to give compound perfluorophenyl 2-methyl-2-(pyrrolidin-1-yl)propanoate 713 (662 mg, 82% yield). MS ESI m/z calcd for $C_{14}H_{15}F_5NO_2$ [M+H]$^+$ 324.1024, found 324.1045.

Example 174. Synthesis of ethyl 2-((5R,7R,10S)-10-((S)-sec-butyl)-3,3-diethyl-7-isopropyl-8,13-dimethyl-9,12-dioxo-13-(pyrrolidin-1-yl)-4-oxa-8,11-diaza-3-silatetradecan-5-yl)thiazole-4-carboxylate 714

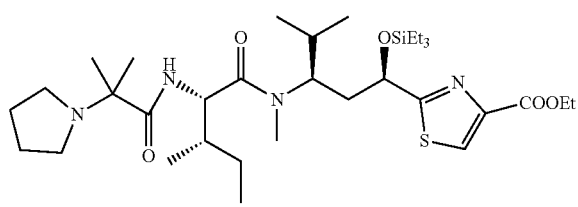

714

To the EtOAc solution (40 ml) of pentafluorophenyl ester 713 (650 mg, 2.01 mmol), compound 16 (1.085 g, 2.01 mmol) and dry Pd/C (10 wt %, 100 mg) were added. The reaction mixture was stirred under hydrogen atmosphere (1 atm) for 24 h, and then filtered through a plug of Celite, with washing of the filter pad with EtOAc. The combined organic portions were concentrated and purified by column chromatography with a gradient of 0-5% methanol in $CH_2Cl_2$ to deliver compound 714 (1.10 g, 84% yield). MS ESI m/z calcd for $C_{33}H_{61}N_4O_5SSi$ [M+H]$^+$ 653.4133, found 653.4148.

Example 175. Synthesis of ethyl 2-((1R,3R)-3-((2S,3S)—N,3-dimethyl-2-(2-methyl-2-(pyrrolidin-1-yl)propanamido)pentanamido)-1-hydroxy-4-methylpentyl)thiazole-4-carboxylate, 715

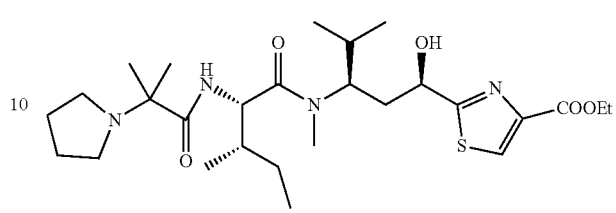

715

Compound 714 (1.10 g, 1.68 mmol) was dissolved in AcOH/water/THF (v/v/v 3:1:1, 25 mL), and stirred at r.t. for 2 days. After the reaction was concentrated, toluene was added and concentrated again; this step was repeated two times to afford compound 715, which was used directly in the next step. MS ESI m/z calcd for $C_{27}H_{47}N_4O_5S$ [M+H]$^+$ 539.3268, found 539.3295.

Example 176. Synthesis of 2-((1R,3R)-3-((2S,3S)—N,3-dimethyl-2-(2-methyl-2-(pyrrolidin-1-yl)propanamido)pentanamido)-1-hydroxy-4-methylpentyl)thiazole-4-carboxylic acid, 716

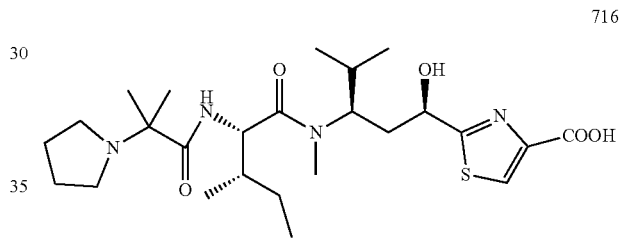

716

An aqueous solution of LiOH (0.4 N, 5 mL) was added to a solution of compound 715 (0.85 g, 1.65 mmol) in MeOH (20 mL) at 0° C. The reaction mixture was stirred at r.t. for 2 h and then concentrated. Column chromatography (pure $CH_2Cl_2$ to 80:20:1 $CH_2Cl_2$/MeOH/NH$_4$OH) afforded compound 716 (773 mg, 90% yield for two steps) as an amorphous solid. MS ESI m/z calcd for $C_{25}H_{43}N_4O_5S$ [M+H]$^+$ 511.2955, found 511.2980.

Example 177. Synthesis of 2-((1R,3R)-1-acetoxy-3-((2S,3S)—N,3-dimethyl-2-(2-methyl-2-(pyrrolidin-1-yl)propanamido)pentanamido)-4-methylpentyl)thiazole-4-carboxylic acid, 717

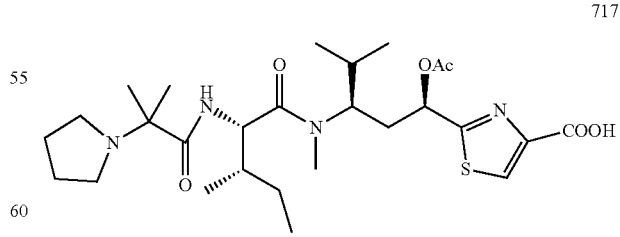

717

A solution of compound 716 (765 mg, 1.50 mmol) and DMAP (180 mg, 1.48 mmol) in anhydrous THF (30 mL) and anhydrous DMF (15 mL) was cooled to 0° C., to which DIPEA (3.0 mL, 17.2 mmol) and acetic anhydride (1.0 g, 9.79 mmol) were added. The reaction mixture was allowed to warm to r.t. and stirred for 4 h, and then concentrated. Column chromatography (5-50% MeOH/DCM) delivered compound 717 (785 mg, 95% yield) as an amorphous solid. MS ESI m/z calcd for $C_{27}H_{45}N_4O_6S$ [M+H]$^+$ 553.3061, found 553.3095.

Example 178. Synthesis of perfluorophenyl 2-((1R, 3R)-1-acetoxy-3-((2S,3 S)—N,3-dimethyl-2-(2-methyl-2-(pyrrolidin-1-yl)propanamido)pentanamido)-4-methylpentyl)thiazole-4-carboxylate, 718

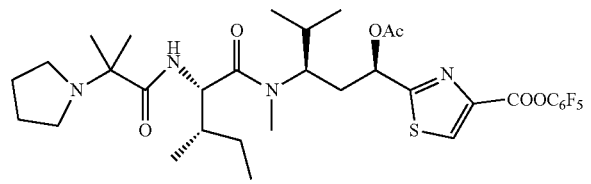

718

To a solution of compound 717 (775 mg, 1.40 mmol) in anhydrous DCM (10 mL) was added EDC (805 mg, 4.19 mmol) and pentafluorophenol (276 mg, 1.50 mmol) at room temperature under $N_2$. The mixture was stirred at room temperature for 4 h, and then diluted in DCM (100 mL), washed with water (2×200 mL) and brine (200 mL), dried over anhydrous sodium sulfate, filtered, concentrated and purified by $SiO_2$ column chromatography (50% EtOAc/PE) to give compound 718 as a white solid (815 mg, 81% yield) MS ESI m/z calcd for $C_{33}H_{44}F_5N_4O_6S$ [M+H]$^+$: 719.2901, found: 719.2945.

Example 179. Synthesis of (2S,4R)-4-(2-((1R,3R)-1-acetoxy-3-((2S,3 S)—N,3-dimethyl-2-(2-methyl-2-(pyrrolidin-1-yl)propanamido)pentanamido)-4-methylpentyl)thiazole-4-carboxamido)-5-(3-((2S,5 S)-23-(2,5-dioxo-2,5-dihydro-1H-pyrrol-1-yl)-2,5-dimethyl-4,7,20-trioxo-10,13,16-trioxa-3,6,19-triazatricosanamido)-4-hydroxyphenyl)-2-methylpentanoic acid

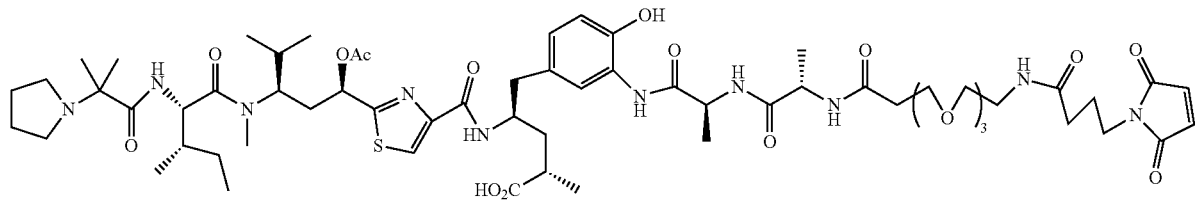

719

In a solution of compound 718 (153 mg, 0.213 mmol) and compound 165a (160 mg, 0.213 mmol) in 7 mL of DMA, DIPEA (100 µL, 0.575 mmol) were added. The reaction was stirred at room temperature overnight and then concentrated. The residue was diluted with 1 mL of acetonitrile and purified by reverse phase HPLC with a gradient of MeCN/ $H_2O$ (10% MeCN to 40% MeCN in 45 min, d2 cm×L25 cm, C-18 column, 8 ml/min) to afford compound 719 (166.1 mg, 61% yield). ESI: m/z: calcd for $C_{62}H_{95}N_{10}O_{17}S$ [M+H]$^+$: 1282.6598, found 1282.6630.

Example 180. Synthesis of (2S,4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-((2S,5 S)-23-(2,5-dioxo-2,5-dihydro-1H-pyrrol-1-yl)-2,5-dimethyl-4,7,20-trioxo-10,13,16-trioxa-3,6,19-triazatricosanamido)-4-hydroxyphenyl)-2-methylpentanoic acid, 720

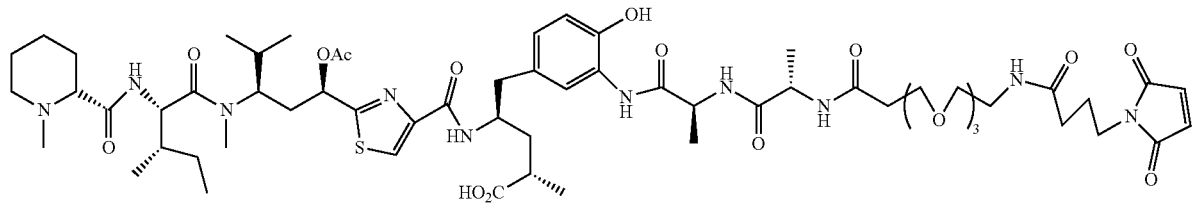

720

Compound 33 (30.2 mg, 0.056 mmol), EDC (25.0 mg, 0.130 mmol) and pentafluorophenol (11 mg, 0.060 mmol) were dissolved in dichloromethane (4 mL) and the reaction was stirred overnight at room temperature, then concentrated to dryness to give compound perfluorophenyl 2-((1R, 3R)-1-acetoxy-3-((2S,3 S)—N,3-dimethyl-2-((R)-1-methylpiperidine-2-carboxamido)pentanamido)-4-methylpentyl) thiazole-4-carboxylate, 33a, which was dissolved in 4 mL of DMA, and a solution of compound 165a (160 mg, 0.213 mmol) in 3 mL of DMA and DIPEA (26.8 µL, 0.154 mmol) were added. The reaction was stirred at room temperature overnight and then concentrated. The residue was diluted with 1 mL of acetonitrile and purified by reverse phase HPLC with a gradient of MeCN/H$_2$O (10% MeCN to 40% MeCN in 45 min, d2 cm×L25 cm, C-18 column, 8 ml/min) to afford compound 720 (133.1 mg, 48% yield). ESI: m/z: calcd for $C_{61}H_{93}N_{10}O_{17}S$ [M+H]$^+$: 1269.6442, found 1282.6630.

Example 181. Synthesis of (2S,4R)-tert-butyl 4-((tert-butoxycarbonyl)amino)-5-(4-((2S,5 S)-23-(2,5-dioxo-2,5-dihydro-1H-pyrrol-1-yl)-2,5-dimethyl-4,7,20-trioxo-10,13,16-trioxa-3,6,19-triazatricosanamido)phenyl)-2-methylpentanoate, 721

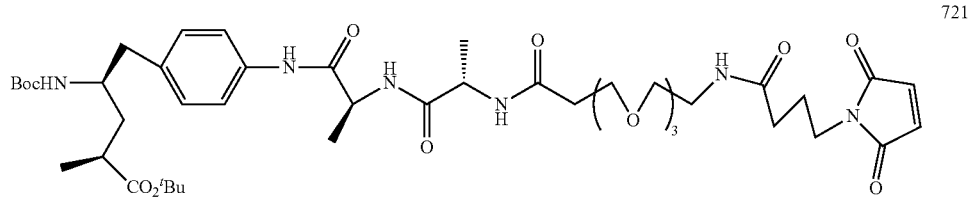

721

Compound 488 (310 mg, 0.82 mmol) in the mixture of ethanol (70 ml) and pH 7.5 buffer (0.1 M NaH$_2$PO$_4$/Na$_2$HPO$_4$, 60 ml), was added compound 163a (660 mg, 1.055 mmol) in four portions in 2 hours. After addition, the mixture was continued to stir for 4 hours, concentrated in vacuo, and purified by column chromatography (15 to 25% EtOAc/DCM) to afford compound 714 (604.5 mg, 83% yield). MS ESI m/z calcd for $C_{44}H_{69}N_6O_{13}$ [M+H]+ 889.4923, found 889.4965.

Example 182. Synthesis of (2S,4R)-4-amino-5-(4-((2S,5 S)-23-(2,5-dioxo-2,5-dihydro-1H-pyrrol-1-yl)-2,5-dimethyl-4,7,20-trioxo-10,13,16-trioxa-3,6,19-triazatricosanamido)phenyl)-2-methylpentanoic acid, trifluoroacetic acid Salt

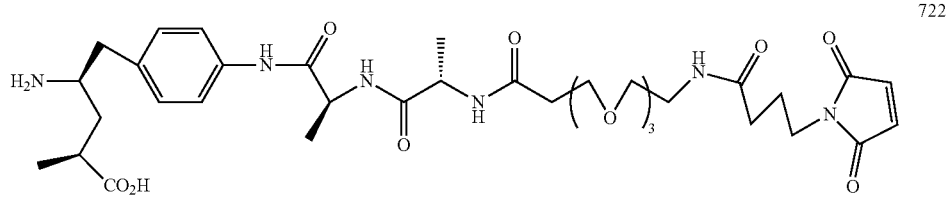

722

To a solution of compound 721 (0.20 g, 0.225 mmol, 1.0 eq) in DCM (6.0 mL) at r.t. was added TFA (2.0 mL) and the reaction was stirred for 2 h, then diluted with anhydrous toluene and concentrated, this operation was repeated for three times to give the title compound as a yellow oil (165 mg, theoretical yield) for the next step without further purification. ESI m/z calcd for $C_{35}H_{53}N_6O_{11}$ $[M+H]^+$: 732.3773, found: 732.3795.

Example 183. Synthesis of (2S,4R)-4-(2-((1R,3R)-1-acetoxy-3-((2S,3 S)—N,3-dimethyl-2-((R)-1-methylpiperidine-2-carboxamido)pentanamido)-4-methylpentyl)thiazole-4-carboxamido)-5-(4-((2S,5 S)-23-(2,5-dioxo-2,5-dihydro-1H-pyrrol-1-yl)-2,5-dimethyl-4,7,20-trioxo-10,13,16-trioxa-3,6,19-triaza-tricosanamido)phenyl)-2-methylpentanoic acid (723, as a reference control)

followed by addition of 4-(azidomethyl)benzoic acid (14-50 µL, 20 mM in pH 7.5, PBS buffer). The mixture was incubated at RT for 4~18 h, then DHAA (135 µL, 50 mM) was added in. After continuous incubation at RT overnight, the mixture was purified on G-25 column eluted with 100 mM $NaH_2PO_4$, 50 mM NaCl pH 6.0~7.5 buffer to afford 12.2~18.6 mg of the conjugate compounds C-128, C-132, C-437, C-481, C-495, C-528, C-629, C-633, C-641, C-644, C-645, C-649, C-654, C-659, C-663, C-673, C-709, C-712, C-166a, C-719, C-720 and C-723, (80%-93% yield) accordingly in 13.4~15.8 ml of the $NaH_2PO_4$ buffer. The drug/antibody ratio (DAR) was 3.4~3.9 for the conjugates, wherein DAR was determined via UPLC-QTOF mass spectrum. It was 94-99% monomer analyzed by SEC HPLC (Tosoh Bioscience, Tskgel G3000SW, 7.8 mm ID×30 cm, 0.5 ml/min, 100 min) and a single band measured by SDS-PAGE gel.

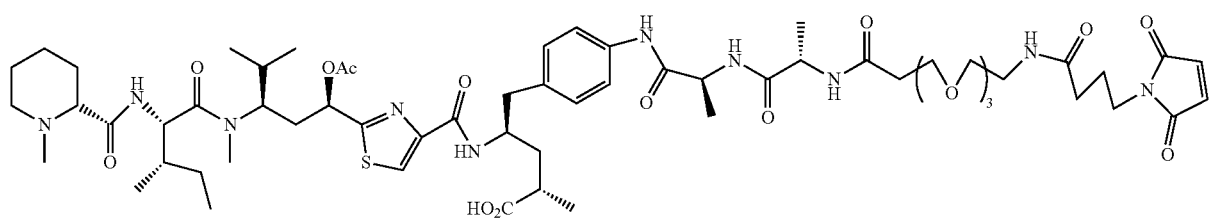

723

Compound 33 (30.2 mg, 0.056 mmol), EDC (25.0 mg, 0.130 mmol) and pentafluorophenol (11 mg, 0.060 mmol) were dissolved in dichloromethane (4 mL) and the reaction was stirred overnight at room temperature, then concentrated to dryness to give compound perfluorophenyl 2-((1R, 3R)-1-acetoxy-3-((2S,3 S)—N,3-dimethyl-2-((R)-1-methylpiperidine-2-carboxamido)pentanamido)-4-methylpentyl)thiazole-4-carboxylate, which was dissolved in 4 mL of DMA, and a solution of compound 722 (160 mg, 0.213 mmol) in 3 mL of DMA and DIPEA (26.8 µL, 0.154 mmol) were added. The reaction was stirred at room temperature overnight and then concentrated. The residue was diluted with 1 mL of acetonitrile and purified by reverse phase HPLC with a gradient of MeCN/H₂O (10% MeCN to 40% MeCN in 45 min, d2 cm×L25 cm, C-18 column, 8 ml/min) to afford compound 723 (47.7 mg, 68% yield). ESI: m/z: calcd for $C_{61}H_{93}N_{10}O_{16}S$ $[M+H]^+$: 1253.6492, found 1253.6540.

Example 184. General method of preparation of antibody conjugates of compounds 128, 132, 437, 481, 495, 528, 629, 633, 641, 645, 649, 654, 659, 663, 673, 709, 712, 166a, 719, 720 and 723

To a mixture of 2.0 mL of 10 mg/ml Herceptin in pH 6.0~8.0, were added of 0.70~2.0 mL PBS buffer of 100 mM $NaH_2PO_4$, pH 6.5~8.5 buffers, TCEP (14-35 µL, 20 mM in water) and the compounds 128, 132, 437, 481, 495, 528, 629, 633, 641, 645, 649, 654, 659, 663, 673, 709, 712, 166a, 719, 720 and 723 (14-28 µL, 20 mM in DMA independently, Example 185. In vitro cytotoxicity evaluation of conjugate C-128, C-132, C-437, C-481, C-495, C-528, C-629, C-633, C-641, C-644, C-645, C-649, C-654, C-659, C-663, C-673, C-709, C-712, C-166a, C-719, C-720 and C-723, in comparison with T-DM1

The cell line used in the cytotoxicity assays was NCI-N87, a human gastric carcinoma cell line; the cells were grown in RPMI-1640 with 10% FBS. To run the assay, the cells (180 µl, 6000 cells) were added to each well in a 96-well plate and incubated for 24 hours at 37° C. with 5% $CO_2$. Next, the cells were treated with test compounds (20 µl) at various concentrations in appropriate cell culture medium (total volume, 0.2 mL). The control wells contain cells and the medium but lack the test compounds. The plates were incubated for 120 hours at 37° C. with 5% $CO_2$. MTT (5 mg/ml) was then added to the wells (20 µl) and the plates were incubated for 1.5 hr at 37° C. The medium was carefully removed and DMSO (180 µl) was added afterward. After it was shaken for 15 min, the absorbance was measured at 490 nm and 570 nm with a reference filter of 620 nm. The inhibition % was calculated according to the following equation: inhibition %=[1-(assay-blank)/(control-blank)]×100. The results are listed in Table 1.

TABLE 1.
The Structures of the Her2-tubulysin analog conjugates of the patent application along with their results of the IC$_{50}$ cytotoxicity against NCI-N87 cells:
| Compound # | Structures and its IC50 against NCI-N87 cells |
|---|---|
| 129 (C-128) | 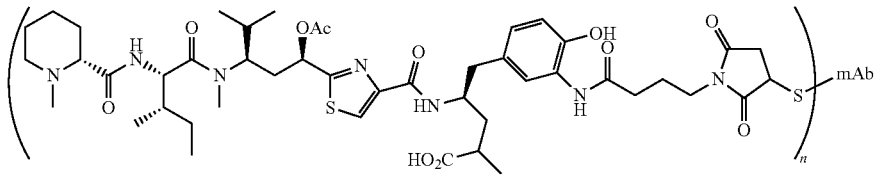 IC$_{50}$ = 0.14 nM, (n = 3.5) |
| 133 (C-132) | 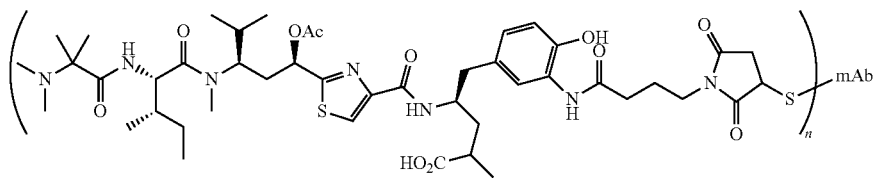 IC$_{50}$ = 0.17 nM, (n = 3.6). |
| C-437 | 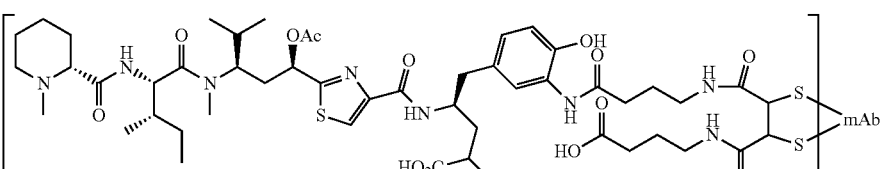 IC$_{50}$ = 3.67 nM, (n = 3.8). |
| C-481 | 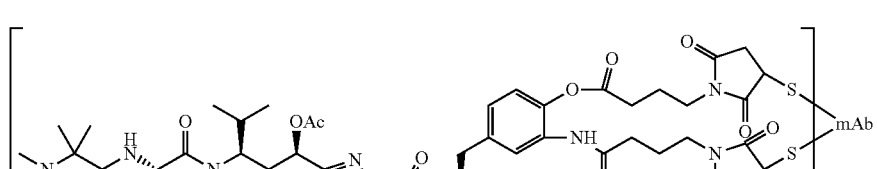 IC$_{50}$ = 0.73 nM, (n = 3.8). |
| C-495 | 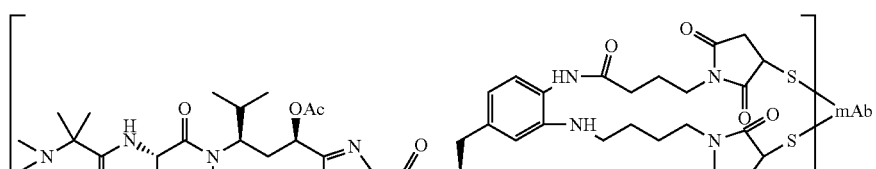 IC$_{50}$ = 13.06 nM, (n = 3.9). |

TABLE 1.-continued
The Structures of the Her2-tubulysin analog conjugates of the patent application along with their results of the $IC_{50}$ cytotoxicity against NCI-N87 cells:
| Compound # | Structures and its IC50 against NCI-N87 cells |
|---|---|
| C-528 | 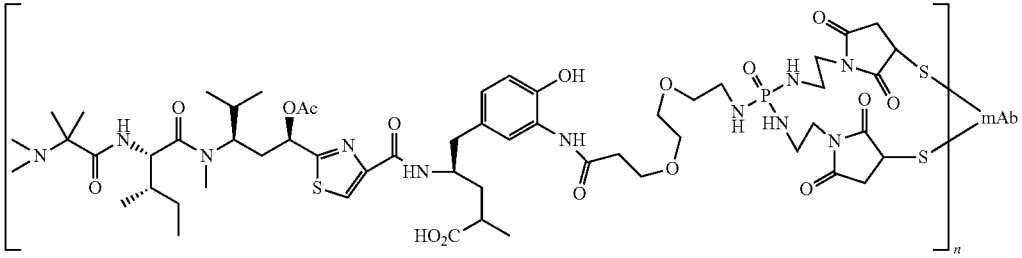<br>$IC_{50}$ = 1.35 nM, (n = 3.8). |
| C-629 | 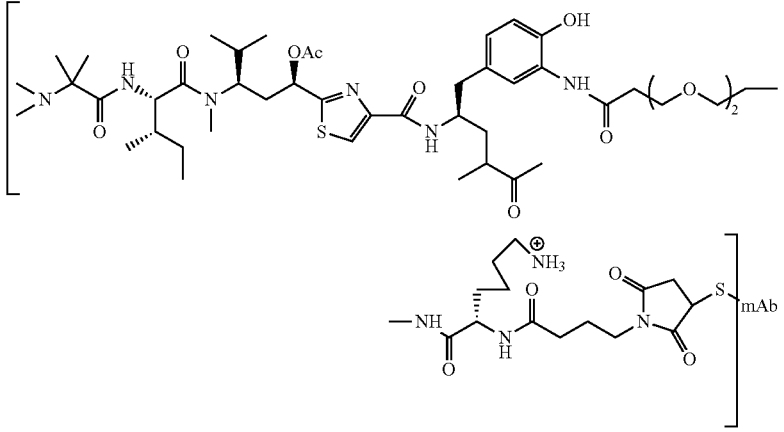<br>$IC_{50}$ = 0.18 nM, (n = 3.7). |
| C-633 | 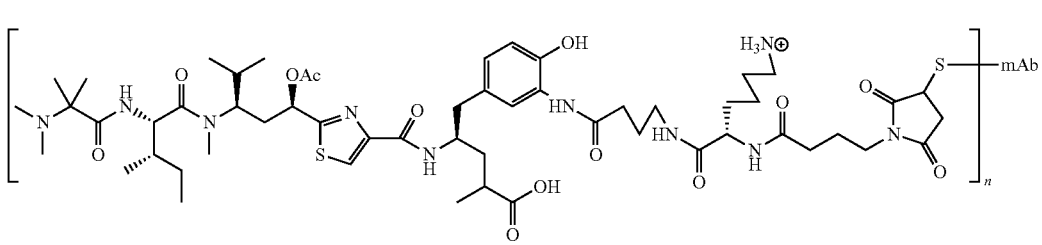<br>$IC_{50}$ = 0.11 nM, (n = 3.6). |
| C-641 | 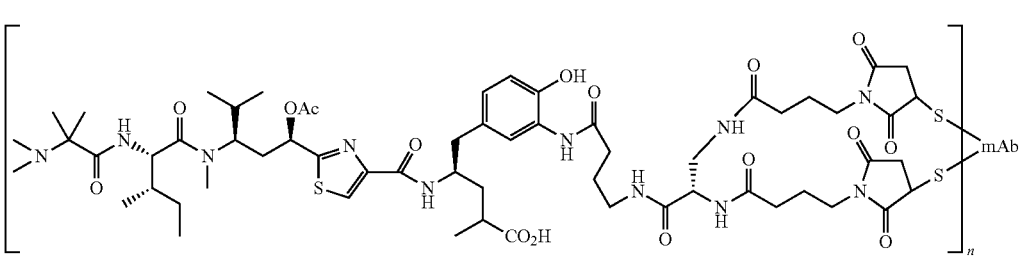<br>$IC_{50}$ = 0.15 nM, (n = 3.6). |

TABLE 1.-continued
The Structures of the Her2-tubulysin analog conjugates of the patent application along with their results of the IC$_{50}$ cytotoxicity against NCI-N87 cells:
| Compound # | Structures and its IC50 against NCI-N87 cells |
|---|---|
| C-645 | 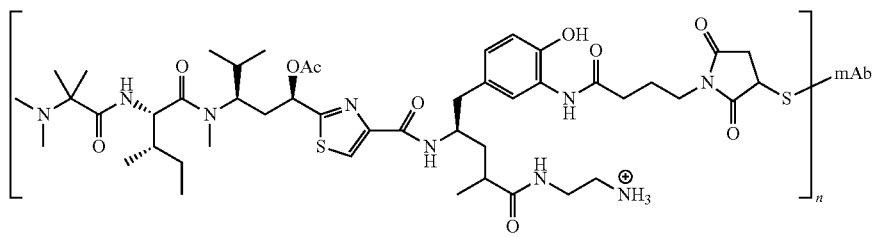 IC$_{50}$ = 3.56 nM, (n = 3.8). |
| C-649 | 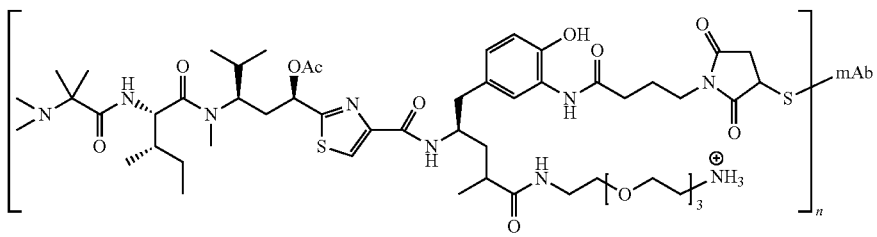 IC$_{50}$ = 9.01 nM, (n = 3.8). |
| C-654 | 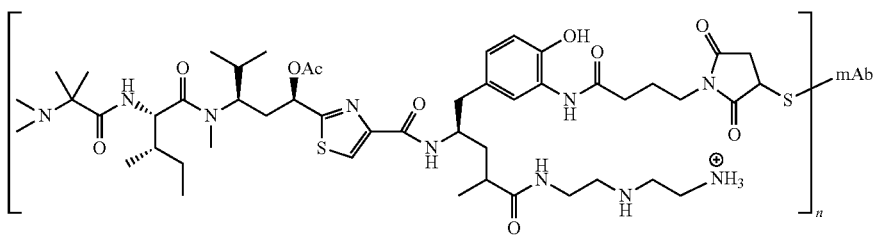 IC$_{50}$ = 3.51 nM, (n = 3.6). |
| C-659 | 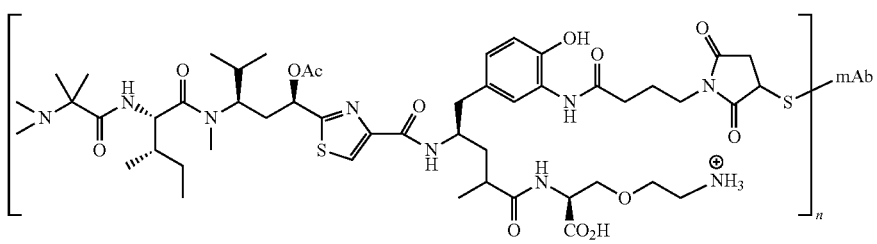 IC$_{50}$ = 2.3 nM, (n = 3.8). |
| C-663 | 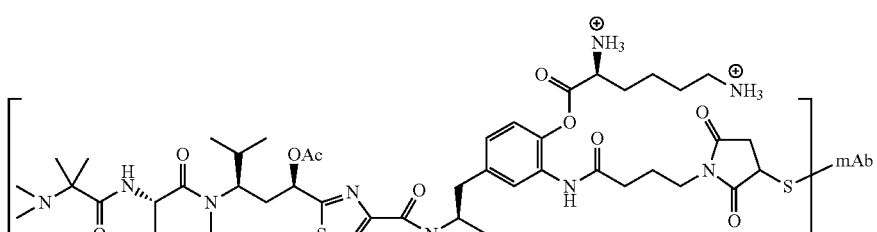 IC$_{50}$ = 4.21 nM, (n = 3.8). |

TABLE 1.-continued
The Structures of the Her2-tubulysin analog conjugates of the patent application along with their results of the $IC_{50}$ cytotoxicity against NCI-N87 cells:
| Compound # | Structures and its IC50 against NCI-N87 cells |
|---|---|
| C-673 | 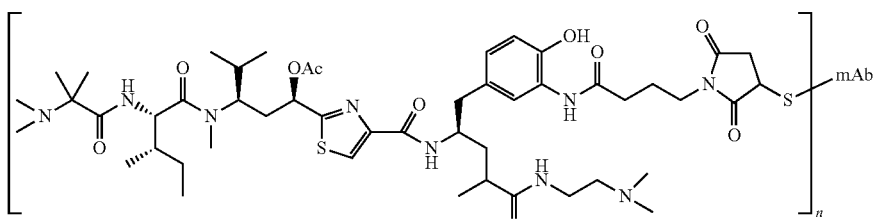 $IC_{50}$ = 1.35 nM, (n = 3.7). |
| C-709 | 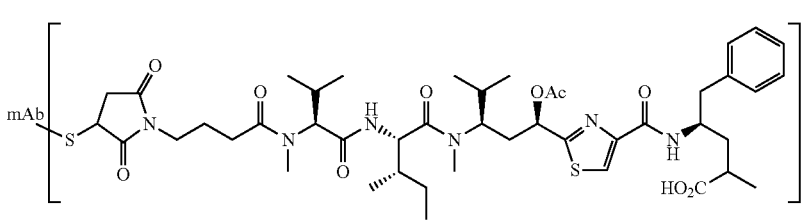 $IC_{50}$ = 9.6 nM, (n = 3.6). |
| C-712 | 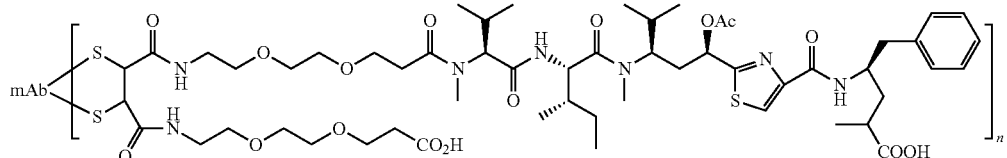 $IC_{50}$ = 11.2 nM, (n = 3.6). |
| C-166a | 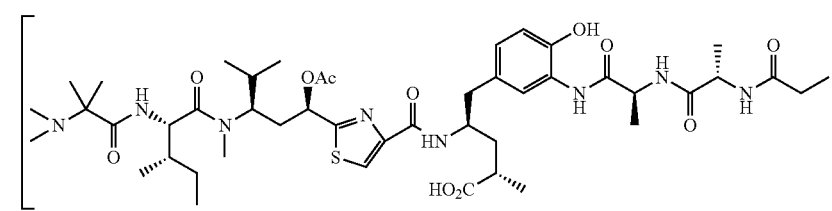 $IC_{50}$ = 0.12 nM, (n = 3.6) |

TABLE 1.-continued
The Structures of the Her2-tubulysin analog conjugates of the patent application along with their results of the IC$_{50}$ cytotoxicity against NCI-N87 cells:
| Compound # | Structures and its IC50 against NCI-N87 cells |
|---|---|
| C-719 | 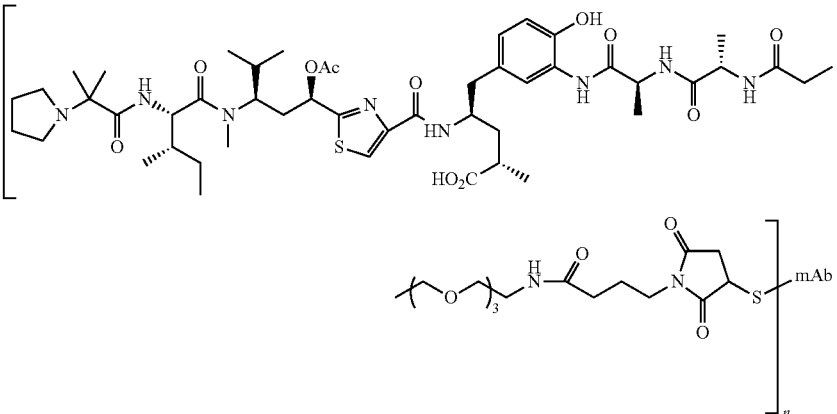<br>IC$_{50}$ = 0.10 nM, (n = 3.6). |
| C-720 | 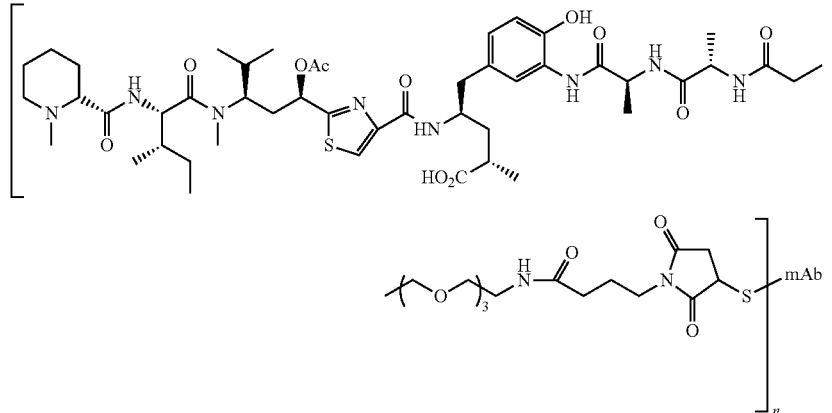<br>IC$_{50}$ = 0.08 nM, (n = 3.6). |
| C-723 | 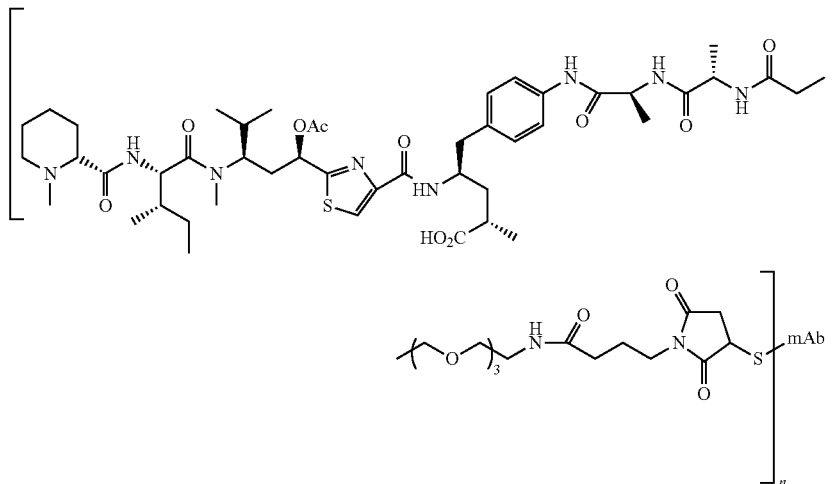<br>IC$_{50}$ = 0.07 nM, (n = 3.6). |

Example 186. Antitumor Activity In Vivo (BALB/c Nude Mice Bearing NCI-N87 Xenograft Tumor)

Figure 22:
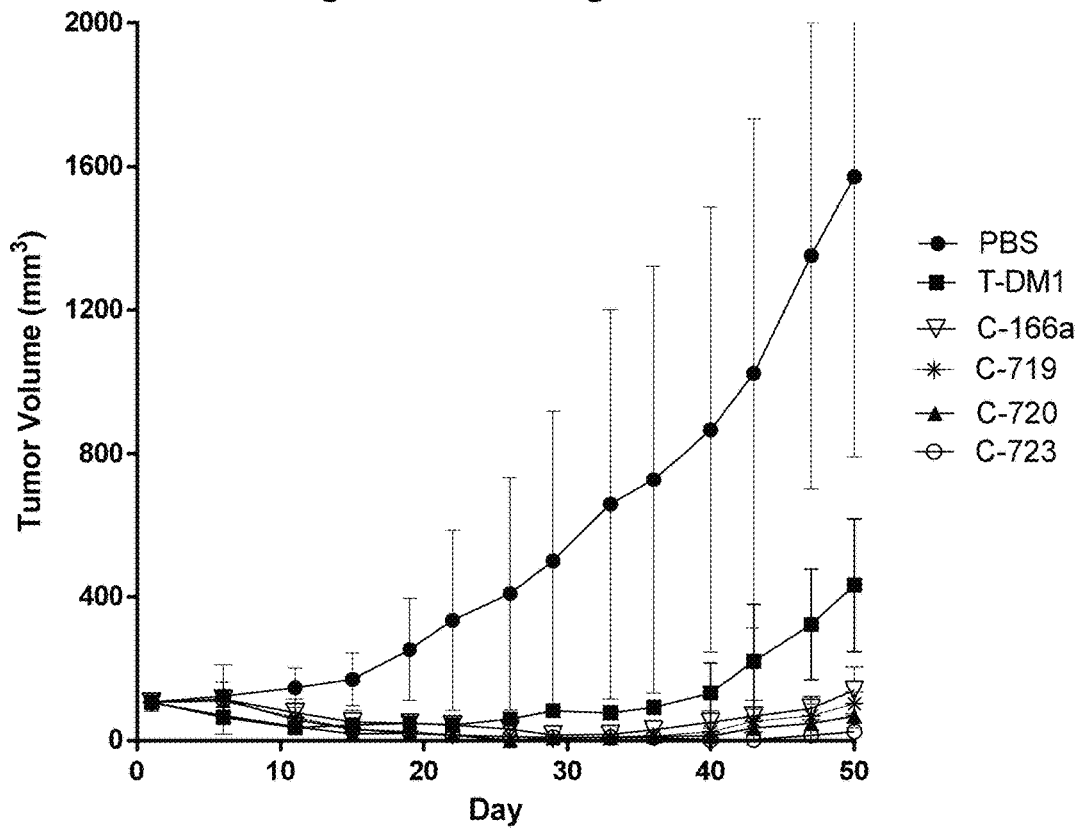
FIG. 22 shows the comparison of the anti-tumor effect of conjugate compounds C-166a, C-719, C-720, and C-723 with T-DM1 using human gastric tumor N87 cell model, i.v., one injection at dosing of 6 mg/kg for conjugates C-166a, C-719, C-720, C-723 and T-DM1. Four conjugates tested here demonstrated better anti-tumor activity than T-DM1. All 6/6 animals at the groups of compounds C-166a, C-719, C-720, and C-723 had completely no tumor measurable at day 22 till day 36, and all of them can inhibit the tumor growth for over 48 days. In contrast T-DM1 at dose of 6 mg/Kg was not able to eliminate the tumors and it only inhibited the tumor growth for 31 days.

The in vivo efficacy of conjugates C-166a, C-719, C-720, C-723 along with T-DM1 were evaluated in a human gastric carcinoma N-87 cell line tumor xenograft models. Five-week-old female BALB/c Nude mice (40 animals) were inoculated subcutaneously in the area under the right shoulder with N-87 carcinoma cells ($5 \times 10^6$ cells/mouse) in 0.1 mL of serum-free medium. The tumors were grown for 7 days to an average size of 125 mm³. The animals were then randomly divided into 6 groups (6 animals per group). The first group of mice served as the control group and was treated with the phosphate-buffered saline (PBS) vehicle. Five groups were treated with conjugates C-166a, C-719, C-720, C-723 and T-DM1 respectively at dose of 6 mg/Kg administered intravenously. Three dimensions of the tumor were measured every 3 or 4 days (twice a week) and the tumor volumes were calculated using the formula tumor volume=½ (length×width×height). The weight of the animals was also measured at the same time. A mouse was sacrificed when any one of the following criteria was met: (1) loss of body weight of more than 20% from pretreatment weight, (2) tumor volume larger than 1500 mm³, (3) too sick to reach food and water, or (4) skin necrosis. A mouse was considered to be tumor-free if no tumor was palpable. The results were plotted in FIG. 22.

Example 187

The toxicity study of the conjugate in comparison with conjugates C-166a, C-719, C-720, C-723 and T-DM1. 66 female ICR mice, 6-7 weeks old, were separated into 11 groups. Each group included 6 mice for the liver toxicity study. The first group of mice served as the control group and was treated with the phosphate-buffered saline (PBS) vehicle. 10 groups were treated with conjugates C-166a, C-719, C-720, C-723 and T-DM1 respectively at dose of 75 mg/Kg and 150 mg/Kg administered intravenously. The body weight changes for each animal were measured every day for 12 days. The blood collection was followed the NCI's Guidelines for Rodent Blood Collection. Basically, Blood samples were collected through retro-orbital sinuses of the mice, and centrifuged to obtain the sera on Day 5 after administration. The levels of aspartate aminotransferase (AST), alanine aminotransferase (ALT) and alkaline phosphatase (ALP) were analyzed using PUS-2018 semi-automatic biochemistry analyzer with a commercial kid (using aspartate and alanine as substrates, respectively). Reference values were established by following reactive dynamics, according to manufacturer's recommendations. After blood collection, the mice were sacrificed and the mice livers were sliced for pathogen studies. The results of AST and ALT on average were shown in Table 2, and the results of the animal body weight changes on average and the pathogen pictures were shown in FIGS. 23A and 23B and FIGS. 24A-24F, respectively.

Figure 23A:
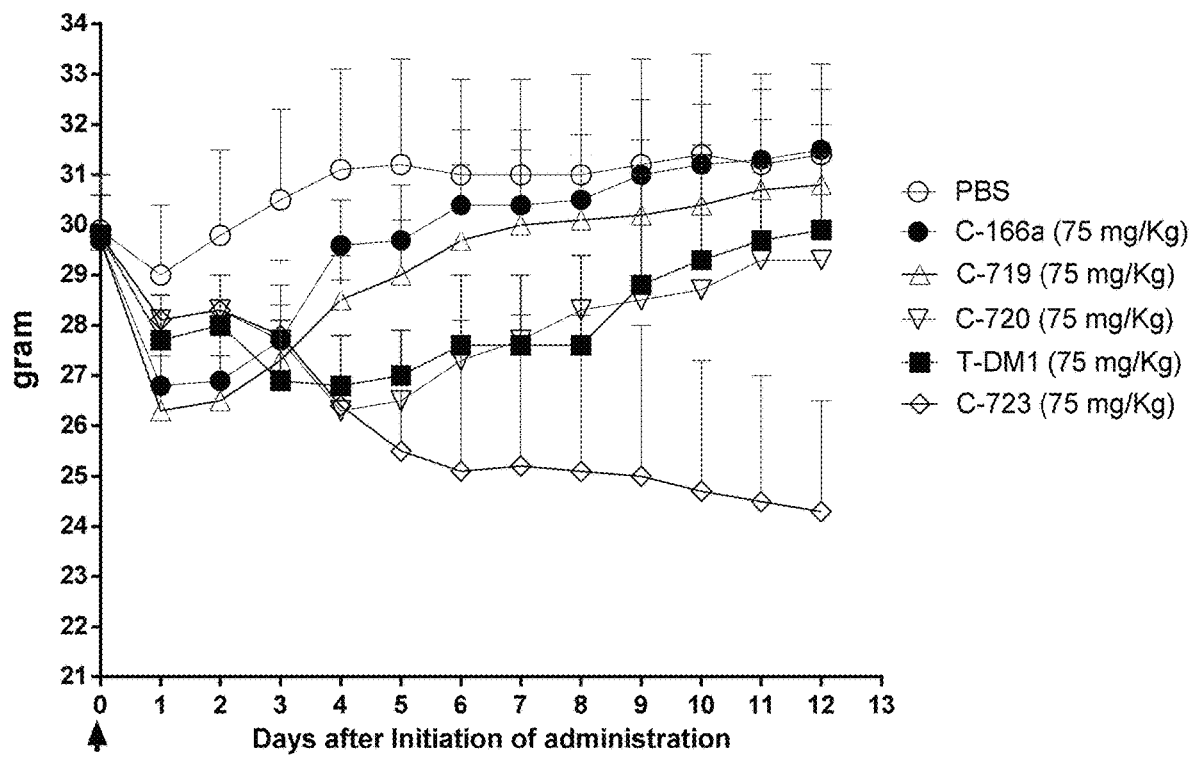
FIGS. 23A and 23B shows an acute toxicity study on ADC conjugates T-DM1, C-166a, C-719, C-720, and C-723 through observing changes in body weight (BW) of mice treated with dose of 75 mg/Kg (FIG. 23A) and 150 mg/Kg (FIG. 23B) in 12 days. The body weight changes demonstrated that conjugate C-723 was more toxic at both doses than T-DM1; conjugate C-720 was similar toxic to T-DM1 at dose of 75 mg/Kg and less toxic than T-DM1 at dose of 150 mg/Kg; and both conjugate C-166a and conjugate C-719 are much less toxic than T-DM1 at both the tested doses.
Figure 23B:
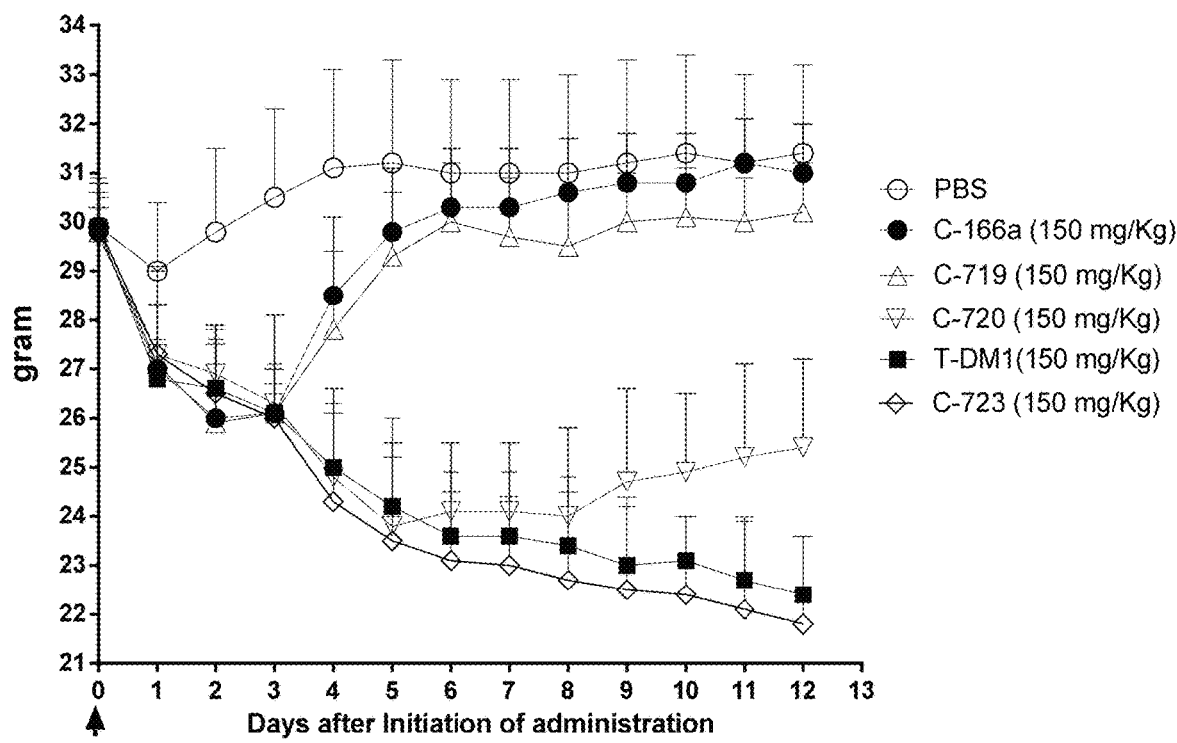
Figure 24A:
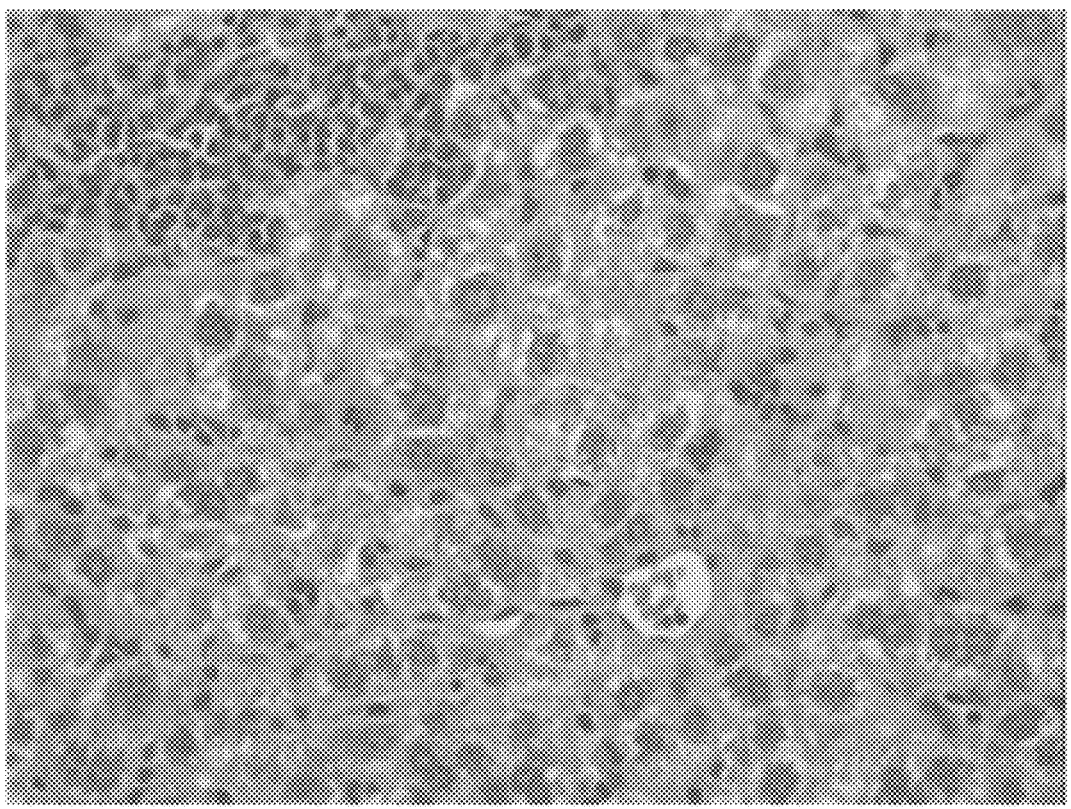
FIGS. 24A and 24B show the liver pathogen of the mice treated with dose of 75 mg/Kg of conjugate compounds T-DM1, C-166a, C-719, C-720, and C-723 in comparison with PBS buffer on day 5. The pictures were enlarged by 40 fold. As the pictures indicated: (1). T-DM1 group (in FIG. 24A), pathology of T-DM1 75 mg/kg group indicated hepatocyte swelling and multifocal necrosis. The lobule structures were not clear. The central venules contained the swollen hepatocytes, red blood cells and red-colored remaining. The nucleuses of hepatocyte were in different sizes and stains. Hepatocytes exhibited the blurred boundaries, increased volume, and eosinophilic-stained plasma. Part of the liver nucleus disappeared. An obvious proliferative phase was seen; (2) In C-723 group (in FIG. 24B), scattered single cell necrosis and water-degeneration are main pathological behaviors. In swelling area, hepatic lobule structure is lost, and a large number of red blood cells are congested in the central venules. Hepatocytes are swollen, borderline unclear and eosinophilic staining. The nuclei vary in sizes and colors. Mild proliferation is observed. (3). Pathology in C-720 group (in FIG. 24C) exhibits the exudate in the central vein of the lobule, disorder in plates arrangement of hepatocytes and hepatocyte hyperplasia. Hypertrophies of Kupffer's cells were occasionally observed. (4). in both C-719 ((in FIG. 24D) and C-166a (in FIG. 24E) groups, hepatic lobular structure was slightly disordered. Hepatic sinuses were visible. Inflammatory cell infiltration was observed in the wall of the bile ducts. Hypertrophy of Kupffer's cells was rare. Hepatocytes were mildly swollen. The microscopic structure is similar to what was seen in the control PBS group (in FIG. 24F).
Figure 24B:
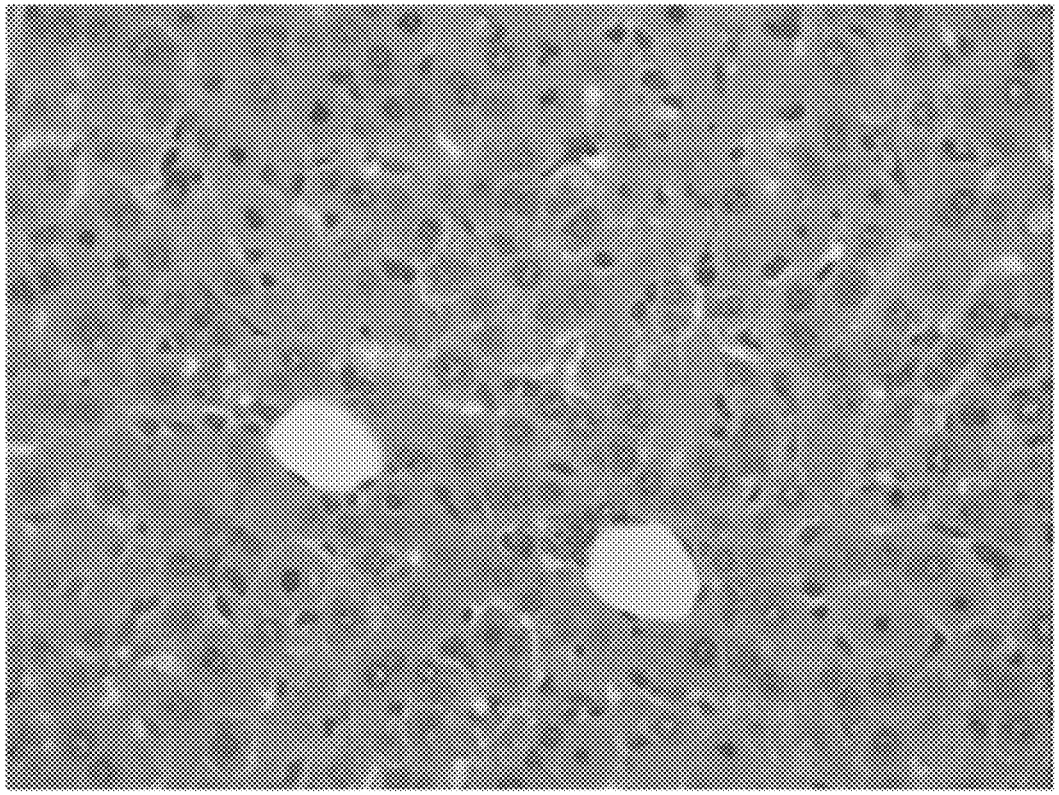
Figure 24C:
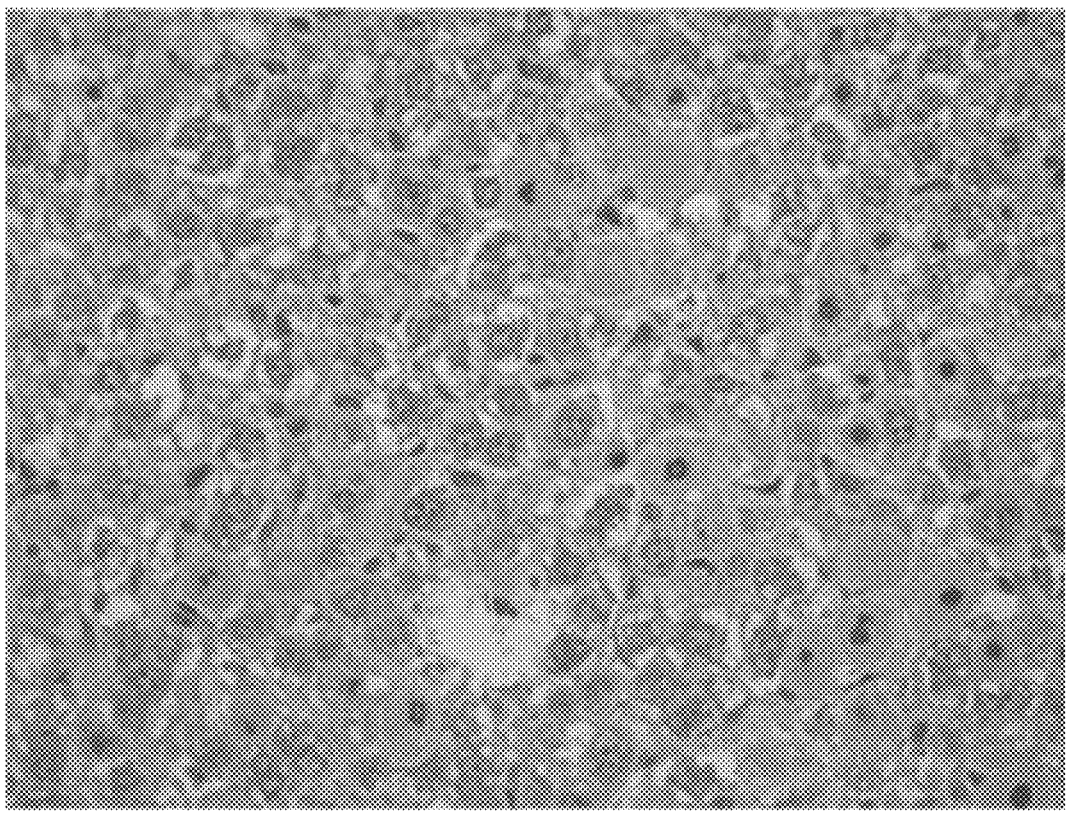
Figure 24D:
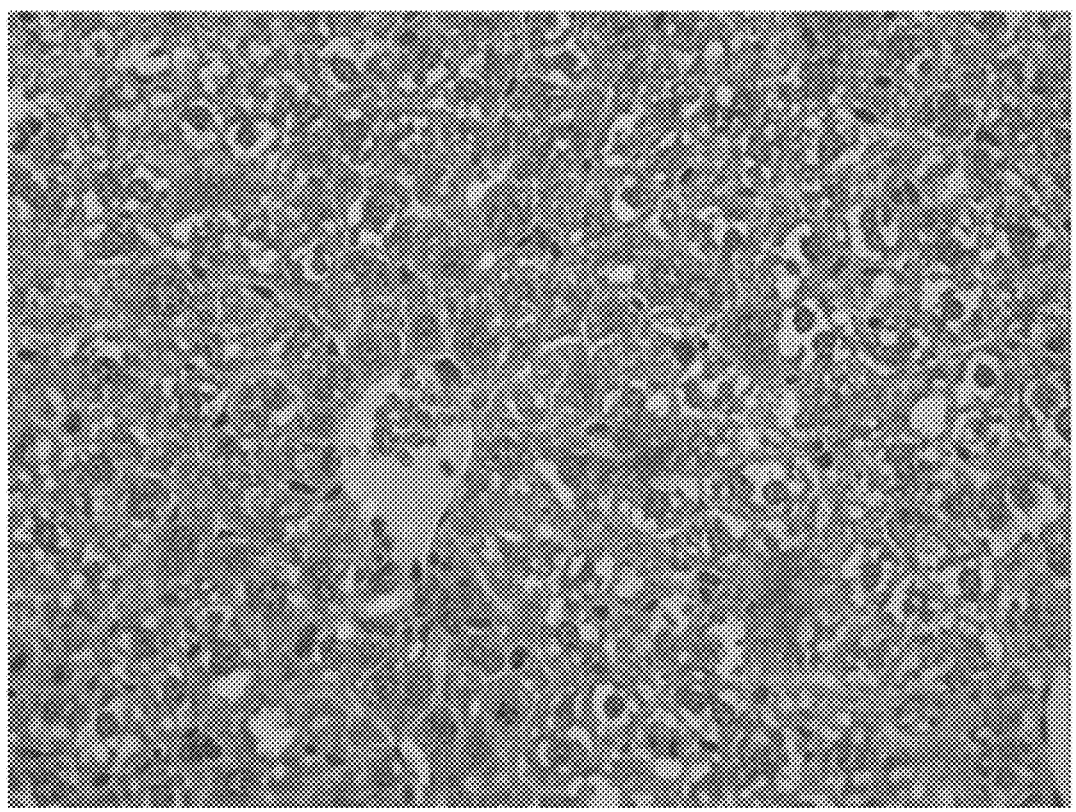
Figure 24E:
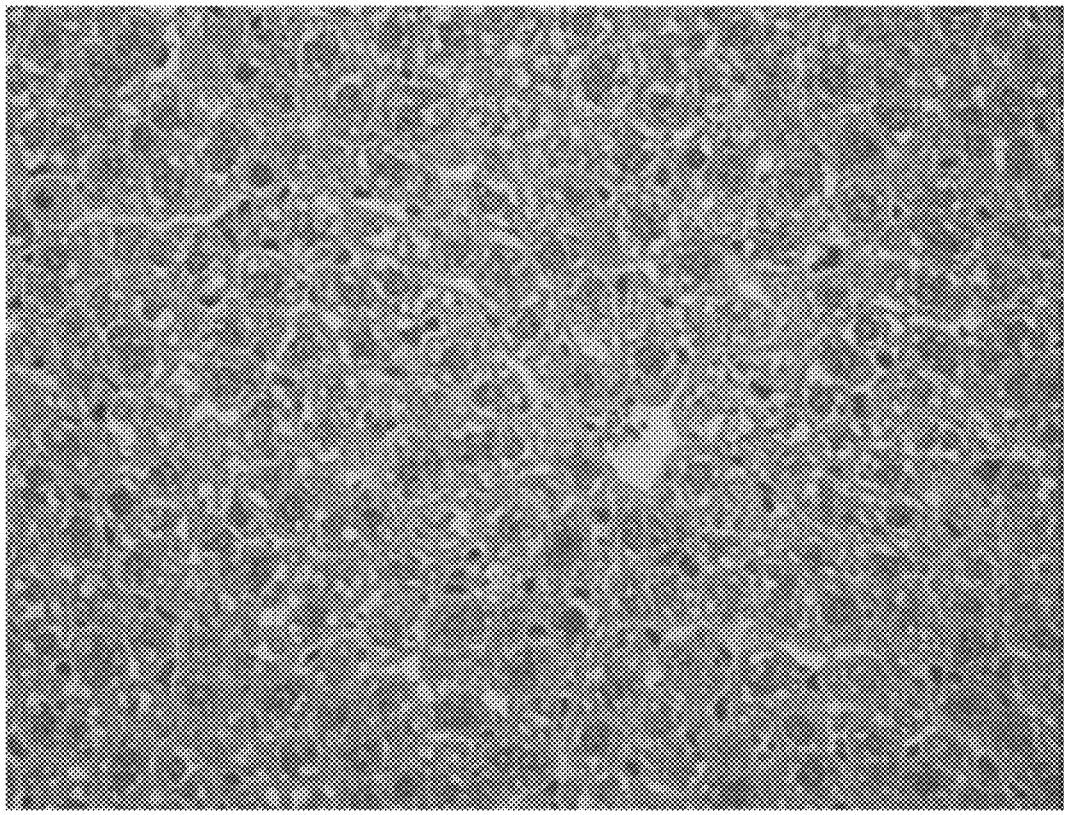
Figure 24F:
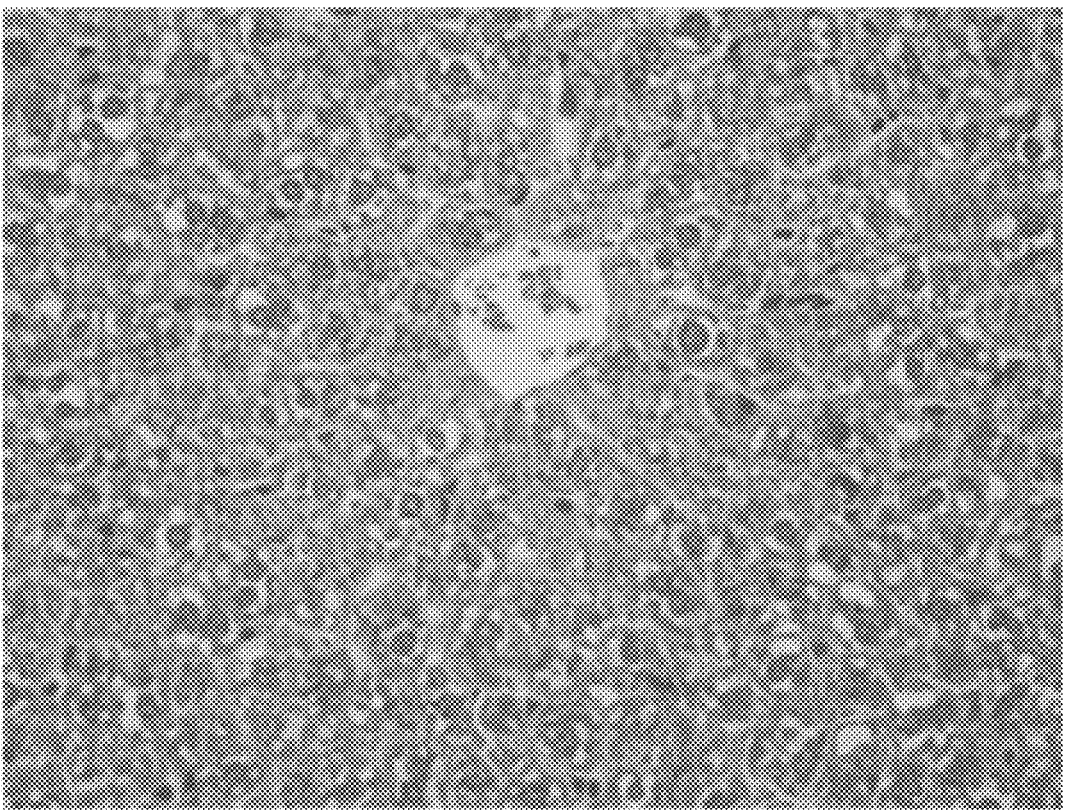

The results of liver toxicity plus the body weight changes indicated that at the much higher dose of 75 mg/Kg and 150 mg/Kg, the conjugates C-166a, and C-719 were less toxic than T-DM1, the conjugate C-720 had somehow the similar toxicity to T-DM1, and the conjugate C-723 was much more toxic than T-DM1. The toxicity order at the tested doses was: C-723>T-DM1≥C-720>C-719>C-166a >PBS. Since conjugates C-166a, C-719, C-720, and C-723 had a similar in vivo activities and all of them had better in vivo activity than T-DM1 as indicated in FIGS. 23A and 23B, therefore the therapeutical windows for conjugates C-166a and C-719 would be much better than T-DM1. In summary, the replacement of N-alkyl-piperidine-2-carboxylic group on the left side of tubulysin by 2-N-alkyl-2,2-dialkyl-acetic group can dramatically reduce animal side toxicity while maintaining the in vivo activities of the tubulysin analogs.

TABLE 2

The results of AST and ALT on average of the tested animals.

| | AST (IU/L) | | ALT (IU/L) | |
|---|---|---|---|---|
| | Day 5 | Day 12 | Day 5 | Day 12 |
| PBS | 91.3 ± 11.4 | 95.9 ± 11.0 | 36.3 ± 18.5 | 27.9 ± 8.0 |
| T-DM1, 75 mg/Kg | 1349.7 ± 321.5 | 303.2 ± 157.8 | 154.4 ± 96.5 | 164.6 ± 61.4 |
| T-DM1, 150 mg/Kg | 3276.6 ± 724.4 | 1509.6 ± 399.3 | 305.9 ± 142.9 | 407.3 ± 53.8 |
| C-166a, 75 mg/Kg | 173.6 ± 13.1 | 100.5 ± 16.1 | 56.8 ± 13.3 | 48.3 ± 9.5 |
| C-166a, 150 mg/Kg | 480.3 ± 50.5 | 131.5 ± 29.3 | 126.5 ± 38.1 | 71.7 ± 15.3 |
| C-719, 75 mg/Kg | 185.6 ± 14.8 | 111.5 ± 19.2 | 62.8 ± 14.8 | 52.7 ± 11.9 |
| C-719, 150 mg/Kg | 543.5 ± 67.5 | 159.5 ± 38.5 | 137.5 ± 43.7 | 83.4 ± 19.2 |
| C-720, 75 mg/Kg | 904.5 ± 231.8 | 264.4 ± 49.6 | 145.6 ± 60.7 | 139.8 ± 28.9 |
| C-720, 150 mg/Kg | 3083.1 ± 803.0 | 1576.6 ± 34.9 | 401.8 ± 59.0 | 335.9 ± 41.5 |
| C-723, 75 mg/Kg | 1673.4 ± 335.5 | 1093.1 ± 351.6 | 206.8 ± 84.1 | 196.0 ± 41.6 |
| C-723, 150 mg/Kg | 4083.4 ± 353.9 | 1861.8 ± 787.1 | 587.6 ± 111.2 | 483.9 ± 220.9 |

What is claimed is:

1. A conjugate of a cell binding molecule with a cytotoxic agent having a structure of Formula (I):

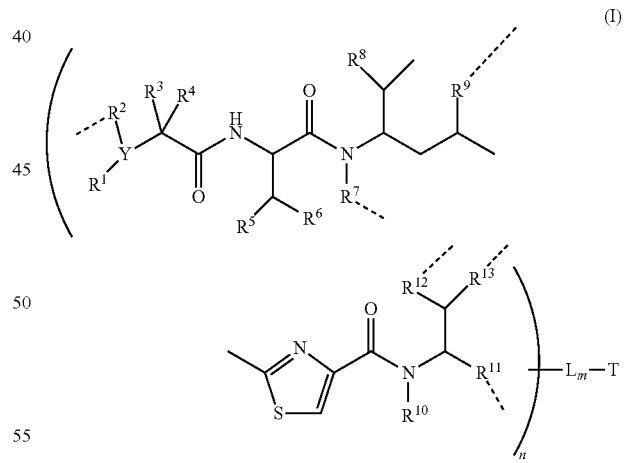

or a pharmaceutically acceptable salt, hydrate, or hydrated salt thereof; or a polymorphic crystalline structure thereof, or an optical isomer, racemate, diastereomer or enantiomer thereof;

wherein T is a targeting or cell-binding molecule; L is a releasable linker; ----- is a linkage bond that L connects to an atom inside the bracket independently; n is 1~20 and m is 1~10;

wherein T is an antibody; a single chain antibody; an antibody fragment that binds to the target cell; a monoclonal antibody; a single chain monoclonal antibody; or a monoclonal antibody fragment that binds the target cell; a chimeric antibody; a chimeric antibody fragment that binds to the target cell; a domain antibody; a domain antibody fragment that binds to the target cell; lymphokine; a hormone; a vitamin; a growth factor; a colony stimulating factor; or a transferrin; a binding peptide, or protein, or antibody, or molecule attached on an albumin, a polymer, a dendrimer, a liposome, a nanoparticle, a vesicle, or a capsid;

wherein the linker L has the formula: —Ww-(Aa)r-Vv-; wherein: —W— is a Stretcher unit; w is 0 or 1; each -Aa-is independently an Amino Acid unit; r is independently an integer ranging from 0 to 12; —V— is a Spacer unit; and v is 0, 1 or 2; the Stretcher unit (—W—), when present, links a targeted binding molecular unit (T) to an amino acid unit (-Aa-), or links V when an Aa is not present; the Stretcher unit W independently contains a self-immolative spacer, peptide unit, a hydrazone bond, disulfide or thiolether bond; W linked to T has a structure of:

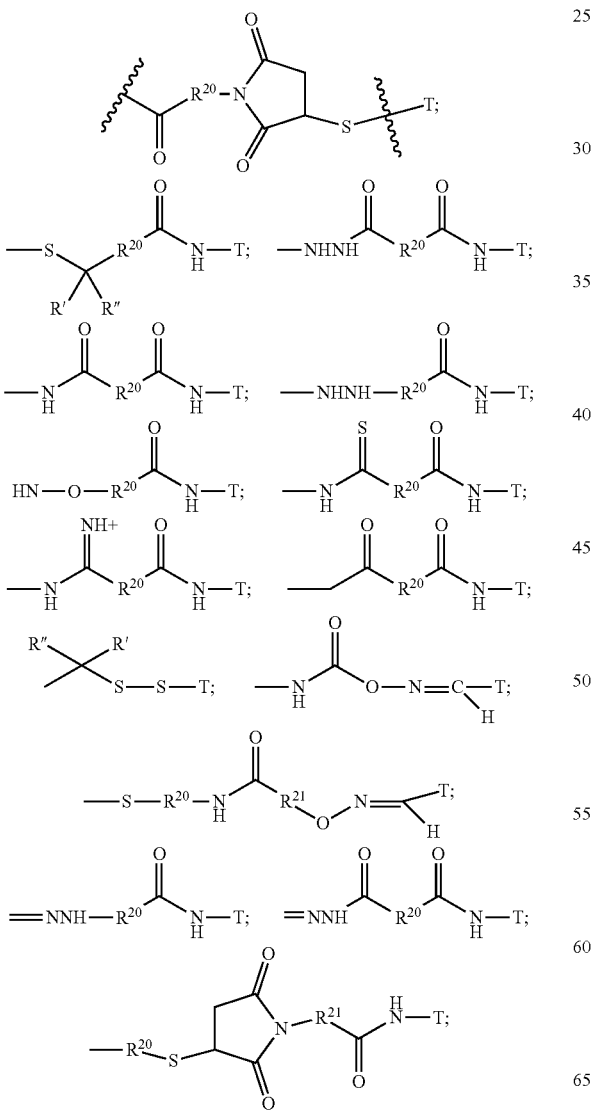

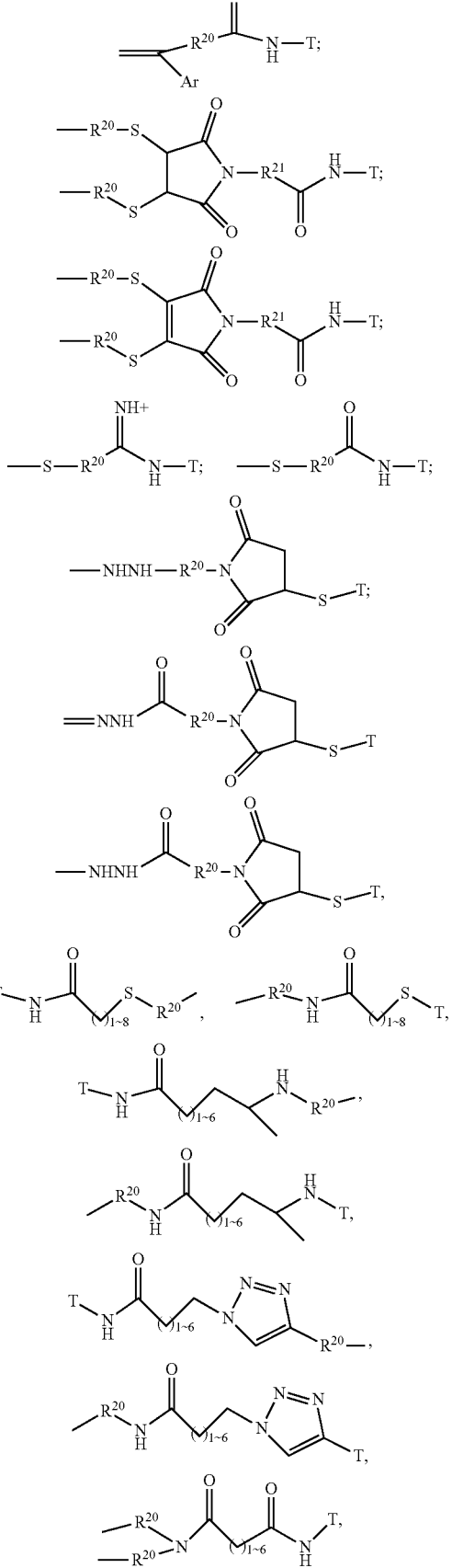

-continued

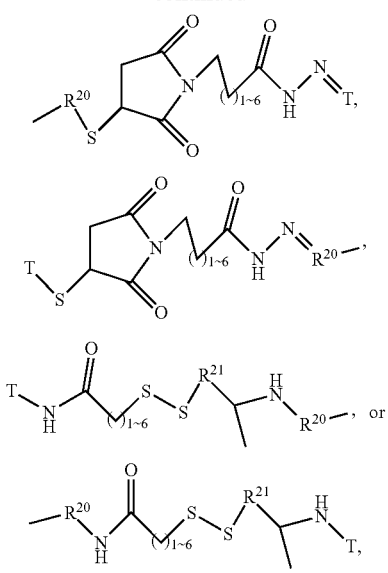

wherein $R^{20}$ and $R^{21}$ are selected from $-C_1\sim C_9$ alkylene-, $-C_1\sim C_7$ carbocyclo-, $-O-(C_1\sim C_8$ alkyl)-, -arylene-, $-C_1\sim C_9$ alkylene-arylene-, -arylene-, $-C_1\sim C_9$ alkylene-, $-C_1\sim C_9$ alkylene-$(C_1\sim C_8$ carbocyclo)-, $-(C_3\text{-}C_7$ carbocyclo)-$C_1\sim C_9$ alkylene-, $-C_3\text{-}C_8$ heterocyclo-, $-C_1\sim C_{10}$ alkylene-$(C_3\sim C_8$ heterocyclo)-, $-(C_3\text{-}C_8$ heterocyclo)-$C_1\sim C_9$ alkylene-, $-(CH_2CH_2O)_k-$, $-(CH(CH_3)CH_2O)_k-$, and $-(CH_2CH_2O)_k-CH_2-$; k is an integer ranging from 1~20; R' and R" are independently H or $CH_3$;

the Spacer unit (—V—), when present, links an Amino Acid unit to the antimitotic agent when an Amino Acid unit is present or the Spacer unit links the Stretcher unit to antimitotic agent when the Amino Acid unit is absent, or the Spacer unit links antimitotic agent to the binding molecule (T) when both the Amino Acid unit and Stretcher unit are absent; the spacer unit contains a function group that substantially increases the water solubility, biological transport, preferential renal clearance, uptake, absorption, biodistribution, and/or bioavailability of the conjugate; the Spacer unit includes a self-immolative or non-self-immolative; the non-self-immolative Spacer unit is one in which part or all of the Spacer unit remains bound to the antimitotic agent after cleavage of the Amino Acid unit from the conjugate; the self-immolative unit includes an aromatic compound that is electronically similar to a para-aminobenzyl-carbamoyl (PAB) group, 2-aminoimidazol-5-methanol group, heterocyclic PAB group, beta-glucuronide, or ortho or para-aminobenzylacetal; or one of the following structures:

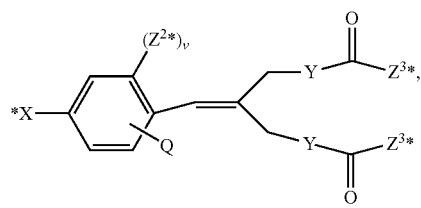

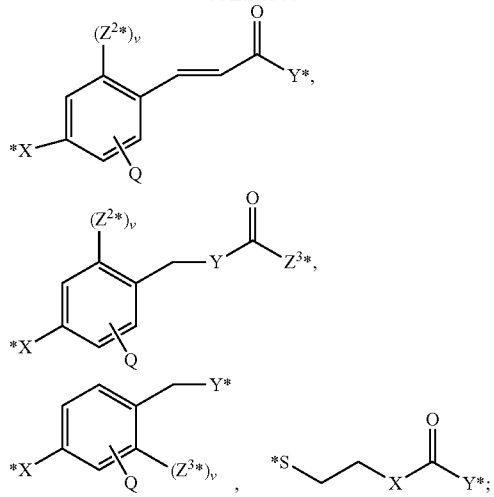

wherein the (*) atom is the point of attachment of additional spacer or releasable linker unit, the antimitotic agent, and/or the binding molecule (T); X, Y and $Z^3$ are independently NH, O, or S; $Z^2$ is H, NH, O or S independently; v is 0 or 1; Q is independently H, OH, $C_1\sim C_6$ alkyl, $(OCH_2CH_2)_n$ F, Cl, Br, I, $OR^{17}$, or $SR^{17}$, $NR^{17}R^{18}$, $N=NR^{17}$, $N=R^{17}$, $NR^{17}R^{18}$, $NO_2$, $SOR^{17}R^{18}$, $SO_2R^{17}$, $SO_3R^{17}$, $OSO_3R^{17}$, $PR^{17}R^{18}$, $POR^{17}R^{18}$, $PO_2R^{17}R^{18}$, $OPO(OR^{17})(OR^{18})$, or $OCH_2PO(OR^{17}(OR^{18})$ wherein $R^{17}$ and $R^{18}$ are independently H, $C_1\sim C_8$ alkyl; $C_2\text{-}C_8$ alkenyl, alkynyl, or heteroalkyl; $C_3\sim C$ aryl, heterocyclic, carbocyclic, cycloalkyl, heterocycloalkyl, heteroaralkyl, or alkylcarbonyl; or a pharmaceutical cation salt thereof;

the non-self-immolative spacer unit having a structure of:

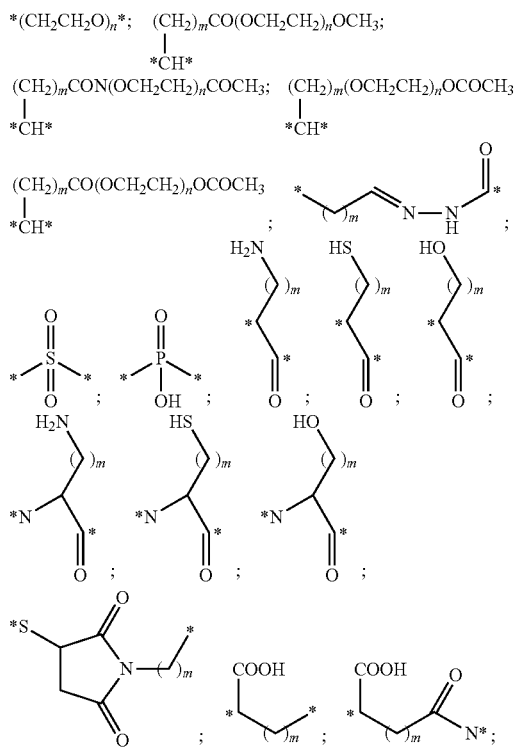

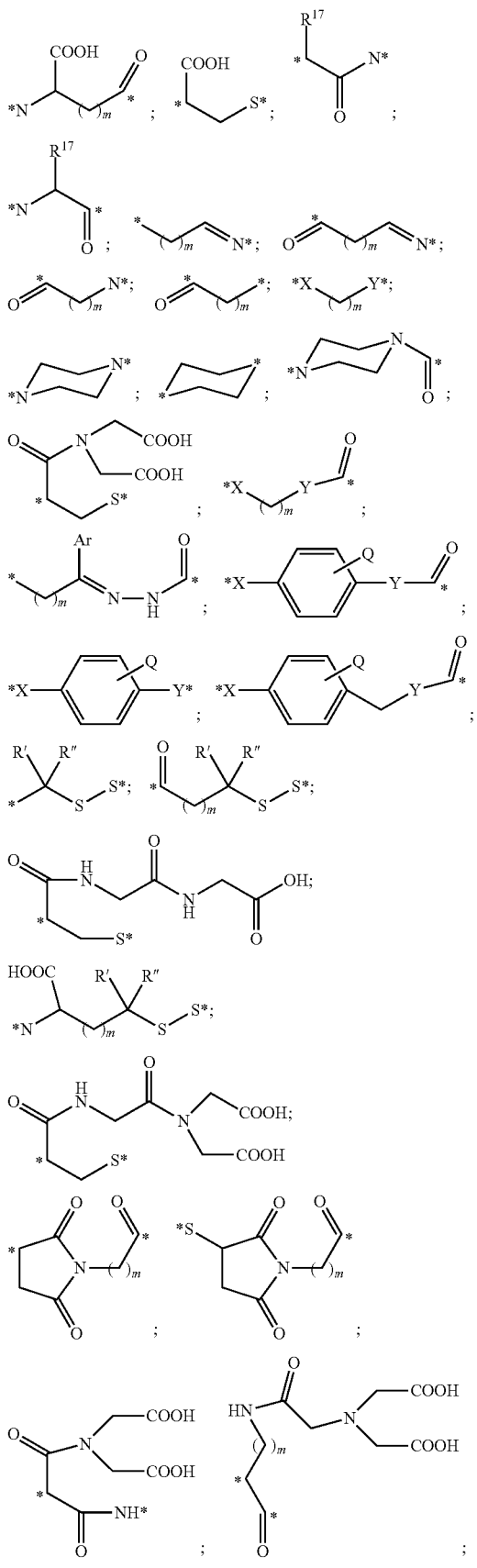
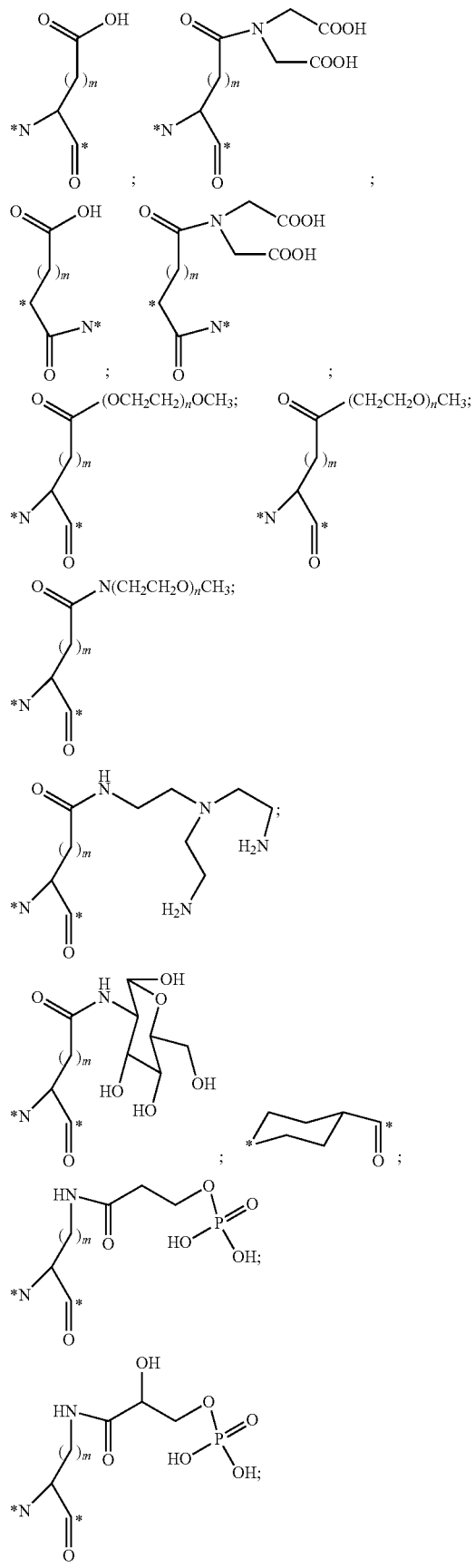

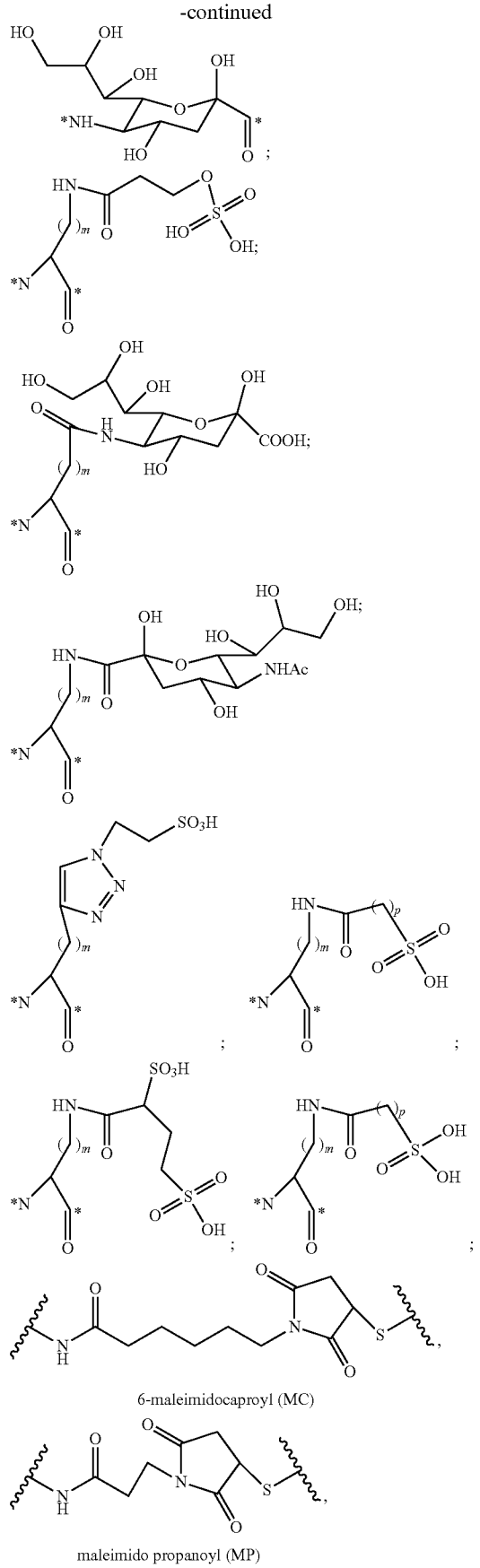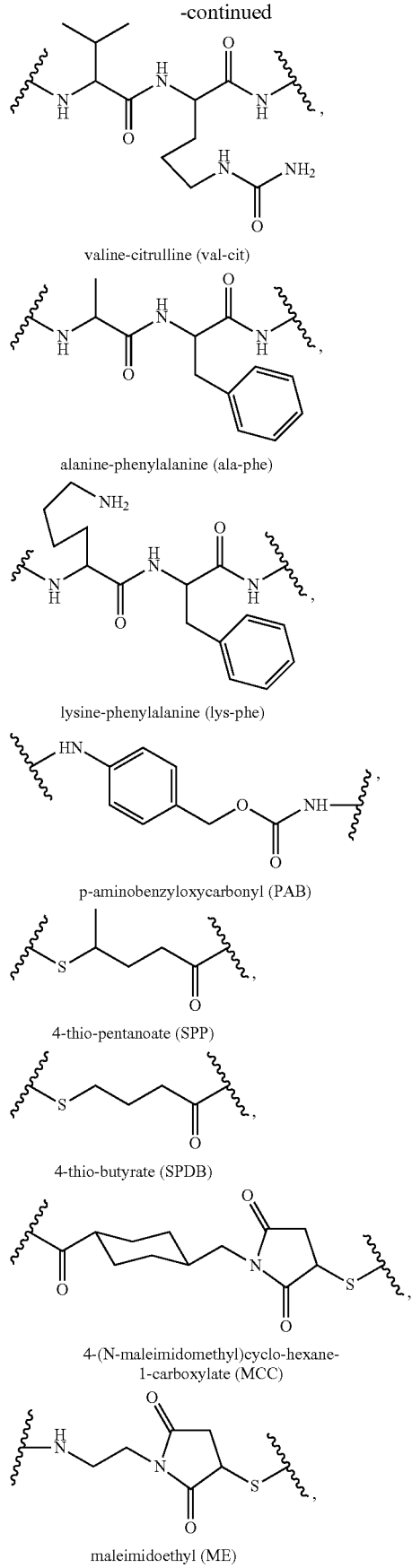

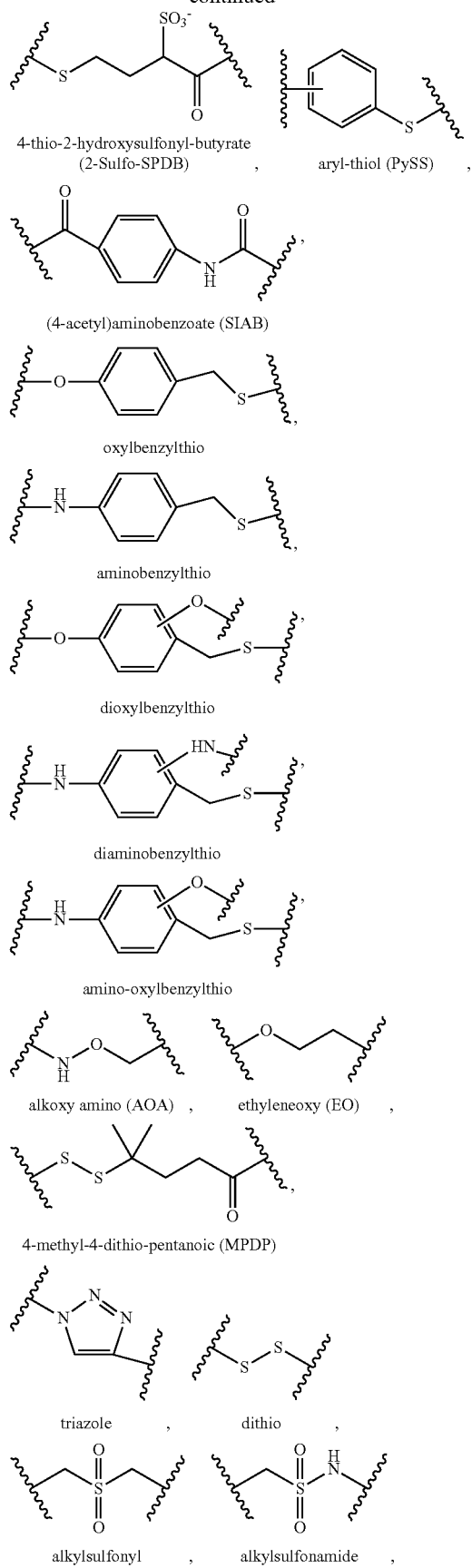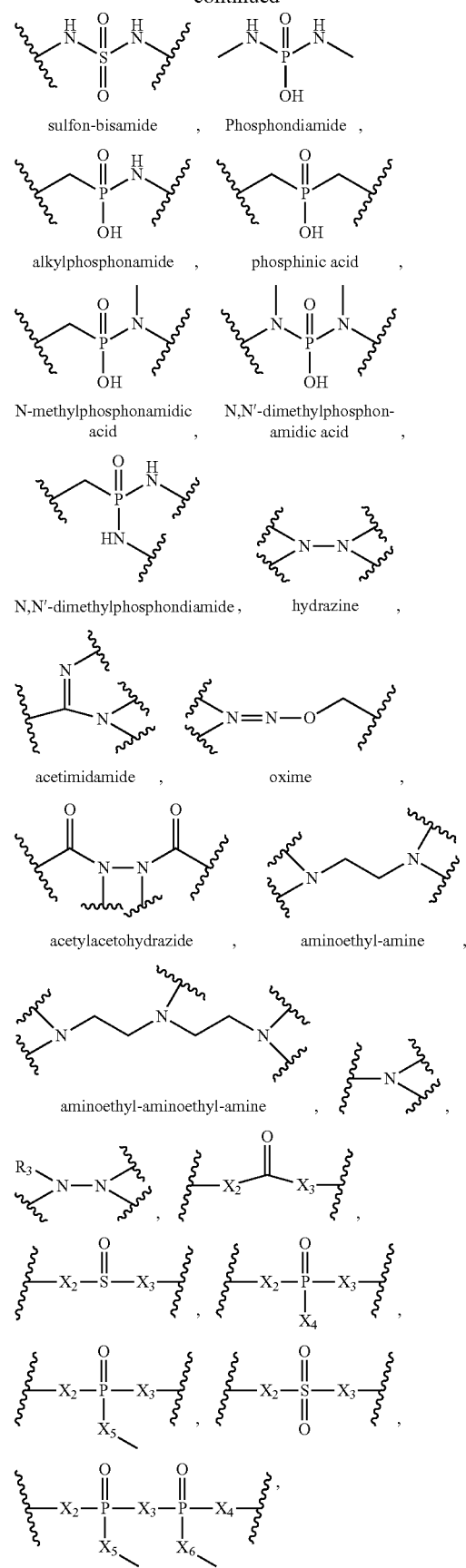

303
-continued
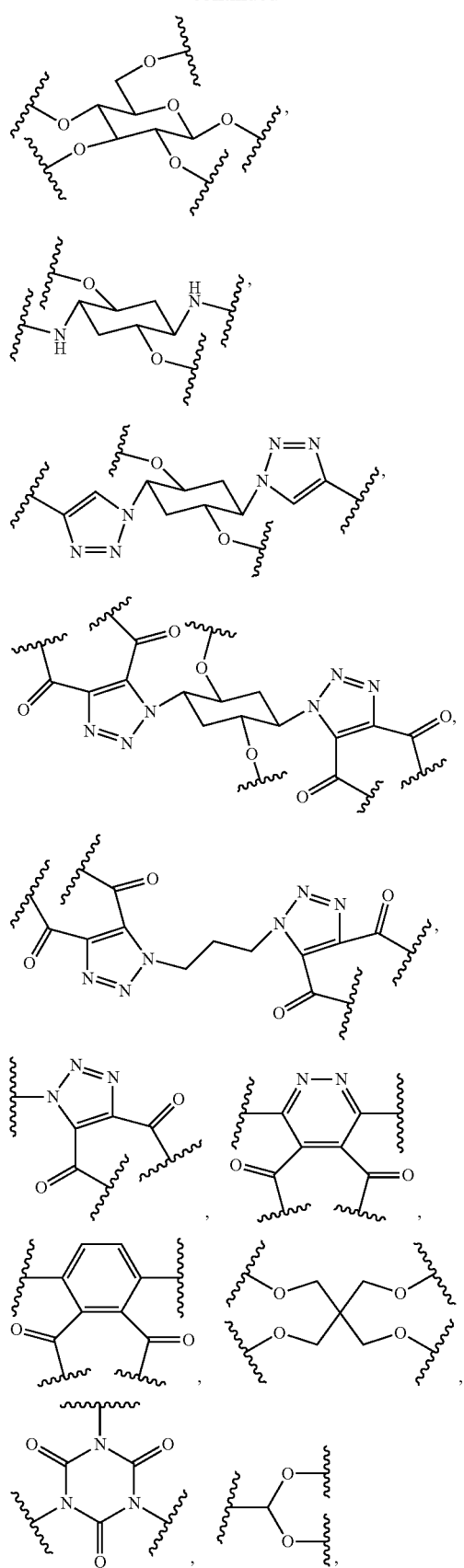
304
-continued
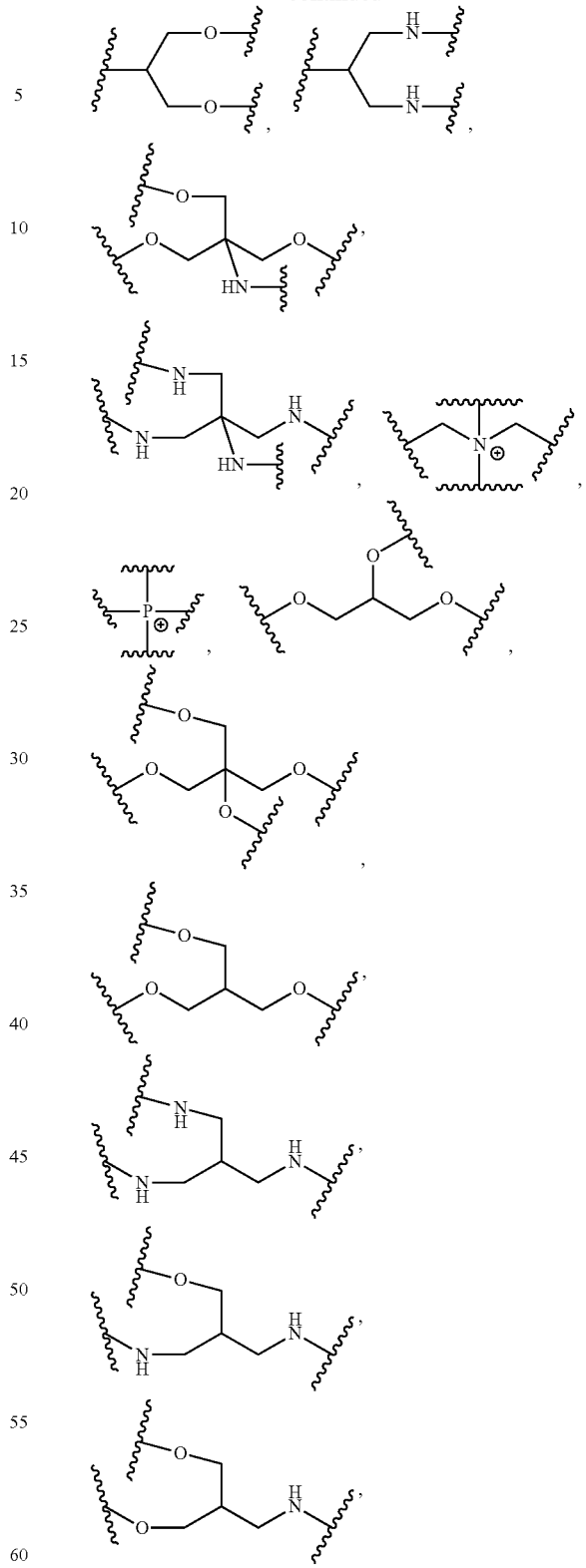
or L- or D-, natural or unnatural peptides containing 1~20 the same or different amino acids;
wherein the "*" and "⸺" atom are the point of attachment of additional spacer or releasable linker, the antimitotic agent, and/or the binding molecule; m is 1~10; n is 1~20; $X_2$, $X_3$, $X_4$, $X_5$, or $X_6$ are independently NH; NHNH; $N(R_{12})$; $N(R_{12})N(R_{12'})$; O; S; $C_1$~$C_6$ alkyl; $C_2$~$C_6$ of heteroalkyl, alkylcycloalkyl, or heterocycloalkyl; $C_3$~$C_8$ aryl, Ar-alkyl, heterocyclic, carbocyclic, cycloalkyl, heteroalkylcycloalkyl, alkylcarbonyl, or heteroaryl; $CH_2OR_{12}$, $CH_2SR_{12}$, $CH_2NHR_{12}$, or 1~8 amino acids; wherein $R_{12}$ and $R_{12'}$ are independently H; $C_1$~$C_8$ alkyl; $C_2$~$C_8$ hetero-alkyl, alkylcycloalkyl, or heterocycloalkyl; $C_3$~$C_8$ aryl, Ar-alkyl, heterocyclic, carbocyclic, cycloalkyl, heteroalkylcycloalkyl, alkylcarbonyl, or heteroaryl; or $C_1$~$C_8$ ester, ether, or amide; or polyethyleneoxy unit of formula $(OCH_2CH_2)_p$ or $(OCH_2CH(CH_3))_p$, wherein p is an integer from 0 to about 1000, or a combination of two or more thereof;

a releasable component of the linker L that at least one bond in L can be broken under physiological conditions: a pH-labile, acid-labile, base-labile, oxidatively labile, metabolically labile, biochemically labile or enzyme-labile bond, which having one of the following structures: $—(CR_{15}R_{16})_m(Aa)r(CR_{17}R_{18})_n(OCH_2C_{12})_t—$, $—(CR_{15}R_{16})_m(CR_{17}R_{18})_n(Aa)_r(OCH_2CH_2)_t—$, $-(Aa)_r$-$(CR_{15}R_{16})_m(CR_{17}R_{18})_n(OCH_2CH_2)_t—$, $—(CR_{15}R_{16})_m(CR_{17}R_{18})_n(OCH_2CH_2)_r$-$(Aa)_t$-, $—(CR_{15}R_{16})_m(CR_{17}=CR_{18})(CR_{19}R_{20})_n(Aa)_t(OCH_2CH_2)_r—$, $—(CR_{15}R_{16})_m(NR_{21}CO)(Aa)_t(CR_{19}R_{20})_n—(OCH_2CH_2)_r—$, $—(CR_{15}R_{16})_m(Aa)_t(NR_{21}CO)(CR_{19}R_{20})_n(OCH_2CH_2)_r—$, $—(CR_{15}R_{16})_m(OCO)(Aa)_t$-$(CR_{19}R_{20})_n(OCH_2CH_2)_r—$, $—(CR_{15}R_{16})_m(OCNR_{17})(Aa)_t(CR_{19}R_{20})_n(OCH_2CH_2)_r—$, $—(CR_{15}R_{16})_m—(CO)(Aa)_t$-$(CR_{19}R_{20})_n(OCH_2CH_2)_r—$, $—(CR_{15}R_{16})_m(NR_{21}CO)(Aa)_t(CR_{19}R_{20})_n(OCH_2CH_2)_r—$, $—(CR_{15}R_{16})_m—(OCO)(Aa)_t(CR_{19}R_{20})_n—(OCH_2CH_2)_r—$, $—(CR_{15}R_{16})_m(OCNR_{17})(Aa)_t(CR_{19}R_{20})_n—(OCH_2CH_2)_r—$, $—(CR_{15}R_{16})_m(CO)(Aa)_t(CR_{19}R_{20})_n—(OCH_2CH_2)_r—$, $—(CR_{15}R_{16})_m$-phenyl-$CO(Aa)_t$-$(CR_{17}R_{18})_n—$, $—(CR_{15}R_{16})_m$-furyl-$CO(Aa)_t(CR_{17}R_{18})_n—$, $—(CR_{15}R_6)_m$-oxazolyl-$CO(Aa)_t(CR_{17}R_{18})_n—$, $—(CR_{15}R_{16})_m$-thiazolyl-$CO(Aa)_t(CCR_{17}R_{18})_n—$, $—(CR_{15}R_{16})_t$-thienyl-$CO(CR_{17}R_{18})_n—$, $—(CR_{15}R_{16})_t$-imidazolyl-$CO—(CR_{17}R_{18})_n—$, $—(CR_{15}R_{16})_t$-morpholino-$CO(Aa)_t$-$(CR_{17}R_{18})_n—$, $—(CR_{15}R_{16})_t$-piperazino-$CO(Aa)_t(CR_{17}R_{18})_n—$, $—(CR_{15}R_{16})_t$-N-methylpiperazin-$CO(Aa)_t(CR_{17}R_{18})_n—$, $—(CR_{15}R_{16})_m$-$(Aa)_t$phenyl-, $—(CR_{15}R_{16})_m$-$(Aa)_t$furyl-, $—(CR_{15}R_{16})_m$-oxazolyl$(Aa)_t$-, $—(CR_{15}R_{16})_m$-thiazolyl$(Aa)_t$-, $—(CR_{15}R_{16})_m$-thienyl-$(Aa)_t$-, $—(CR_{15}R_{16})_m$-imidazolyl$(Aa)_t$-, $—(CR_{15}R_{16})_m$-morpholino-$(Aa)_t$-, $—(CR_{15}R_{16})_m$-piperazino-$(Aa)_t$-, $—(CR_{15}R_{16})_m$-N-methylpiperazino-$(Aa)_t$-, $—K(CR_{15}R_{16})_m(Aa)_r(CR_{17}R_{18})_n(OCH_2CH_2)_t—$, $—K(CR_{15}R_{16})_m(CR_{17}R_{18})_n(Aa)_r(OCH_2CH_2)_t—$, $—K(Aa)_r$-$(CR_{15}R_{16})_m(CR_{17}R_{18})_n(OCH_2CH_2)_t—$, $—K(CR_{15}R_{16})_m(CR_{17}R_{18})_n(OCH_2CH_2)_t(Aa)_r$-, $—K(CR_{15}R_{16})_m—(CR_{17}=CR_{18})(CR_{19}R_{20})_n(Aa)_t(OCH_2CH_2)_r$-, $—K(CR_{15}R_{16})_m(NR_{11}CO)(Aa)_t$-$(CR_{19}R_{20})_n(OCH_2CH_2)_r—$, $—K(CR_5R_6)_m(Aa)_t(NR_{21}CO)(CR_{19}R_{20})_n(OCH_2CH_2)_r—$, $—K(CR_{15}R_{16})_m—(OCO)(Aa)_t(CR_{19}R_{20})_n—(OCH_2CH_2)_r—$, $—K(CR_{15}R_{16})_m(OCNR_{17})(Aa)_t(CR_{19}R_{20})_n—(OCH_2CH_2)_r—$, $—K(CR_{15}R_{16})_m(CO)(Aa)_t$-$(CR_{19}R_{20})_n(OCH_2CH_2)_r—$, $—K(CR_{15}R_{16})_m(NR_{21}CO)(Aa)_t$-$(CR_{19}R_{20})_n—(OCH_2CH_2)_r—$, $—K(CR_{15}R_{16})_m—(OCO)(Aa)_t(CR_{19}R_{20})_n(OCH_2CH_2)_r—$, $—K(CR_{15}R_{16})_m—(OCNR_{17})(Aa)_t$-$(CR_{19}R_{20})_n(OCH_2CH_2)_r—$, $—K—(CR_{15}R_{16})_m(CO)(Aa)_t(CR_{19}R_{20})_n(OCH_2CH_2)_r—$, $—K(CR_{15}R_{16})_m$-phenyl-$CO(Aa)_t(CR_{17}R_{18})_n—$, $—K—(CR_{15}R_{16})_m$-furyl-$CO(Aa)_t(CR_{17}R_{18})_n—$, $—K(CR_{15}R_{16})_m$-oxazolyl-$CO(Aa)_t(CR_{17}R_{18})_n—$, $—K(CR_{15}R_{16})_m$-thiazolyl-$CO(Aa)_t$-$(CR_{17}R_{18})_n—$, $—K(CR_{15}R_{16})_t$-thienyl-$CO(CR_{17}R_{18})_n—$, $—K(CR_{15}R_{16})_t$imidazolyl-$CO—(CR_{17}R_{18})_n—$, $—K(CR_5R_6)_t$morpholino-$CO(Aa)_t$-$(CR_{17}R_{18})_n—$, $—K(CR_{15}R_{16})_t$-piperazino-$CO(Aa)_t$-$(CR_{17}R_{18})_n—$, $—K(CR_{15}R_{16})_t—$N-methylpiperazin-$CO(Aa)_t(CR_{17}R_{18})_n—$, $—K(CR_{15}R_{16})_m$-$(Aa)_t$phenyl, $—K—(CR_{15}R_{16})_m$-$(Aa)_t$furyl-, $—K(CR_{15}R_{16})_m$-oxazolyl-$(Aa)_t$-, $—K(CR_{15}R_{16})_m$-thiazolyl$(Aa)_t$-, $—K(CR_{15}R_{16})_m$-thienyl-$(Aa)_t$-, $—K(CR_{15}R_{16})_m$-imidazolyl$(Aa)_t$-, $—K(CR_{15}R_{16})_m$-morpholino$(Aa)_t$-, $—K(CR_{15}R_{16})_m$piperazino$(Aa)_t$G, $—K(CR_5R_6)_m—$N-methyl-piperazino$(Aa)_t$-; wherein m, Aa, $R_{13}$, $R_{14}$, and $R_{15}$ are described above; t and r here are 0-100 independently; $R_{16}$, $R_{17}$, $R_{18}$, $R_{19}$, and $R_{20}$ are independently H; halide; $C_1$~$C_8$ alkyl or heteroalkyl, $C_2$~$C_8$ aryl, alkenyl, alkynyl, ether, ester, amine or amide, $C_3$~$C_8$ aryl, which optionally substituted by one or more halide, CN, $NR_{12}R_{12'}$, $CF_3$, $OR_{12}$, Aryl, heterocycle, $S(O)R_{12}$, $SO_2R_{12}$, $—CO_2H$, $—SO_3H$, $—OR_{12}$, $—CO_2R_{12}$, $—CONR_{12}$, $—PO_2R_{12}R_{13}$, $—PO_3H$ or $P(O)R_{12}R_{12'}R_{13}$; K is $NR_{12}$, $—SS—$, $—C(=O)—$, $—C(=O)NH—$, $—C(=O)O—$, $—C=NH—O—$, $—C=N—NH—$, $—C(=O)NH—NH—$, O, S, Se, B, Het (heterocyclic or heteroaromatic ring having $C_3$~$C_{12}$); or a peptide containing the same or different 1-20 amino acids;

inside the bracket of the Formula (I) is an antimitotic agent wherein $R^1$, $R^2$, $R^3$, and $R^4$ are independently linear or branched $C_1$-$C_8$ alkyl, or alkylalcohol; $C_2$-$C_8$ heteroalkyl, alkylcycloalkyl, heterocycloalkyl, alkyl ether, alkyl carboxylate, alkyl amine, alkyl ester, or alkyl amide; $C_3$-$C_8$ aryl, Ar-alkyl, heterocyclic, carbocyclic, cycloalkyl, heteroalkylcycloalkyl, or alkylcarbonyl; or two R's: $R^1R^2$, $R^3R^4$, $R^5R^6$, or $R^{12}R^{13}$ together form a 3~7 membered carbocyclic, cycloalkyl, heterocyclic, heterocycloalkyl, aromatic or heteroaromatic ring system; Y is N or C; $R^1$, $R^2$, $R^3$, and $R^4$ may optionally be independently absent;

wherein $R^5$, $R^6$, $R^8$ and $R^{10}$ are independently H, linear or branched $C_1$-$C_4$ alkyl or $C_2$-$C_4$ heteroalkyl;

wherein $R^7$ is H, $R^{14}$, $—R^{14}C(=O)X^1R^{15}$; or $—R^{14}X^1R^{15}$; $X^1$ is O, S, S—S, NH, or $NR^{14}$;

wherein $R^9$ is H, $—O—$, $—OR^{14}$, $—OC(=O)R^{14}—$, $—OC(=O)NHR^{14}—$, $—OC(=O)NR^{14}R^{15}—$, $—OC(=O)R^{14}SSR^{15}—$, $OP(=O)(OR^{14})—$, or $OR^{14}OP(=O)(OR^{15})$;

wherein $R^{11}$ is H, $R^{14}$, $—R^{14}C(=O)R^{16}$, $—R^{14}C(=O)X^2R^{16}$, $—R^{14}X^2R^{16}$, or $—R^{14}C(=O)X^2$, wherein $X^2$ is $—O—$, $—S—$, $—NH—$, $—NHS(O_2)$, $—NHS(O)$, $—N(R^{14})—$, $—O—R^{14}—$, $—S—R^{14}—$, $—S(=O)—R^{14}—$, or $—NHR^{14}—$, provided that when $R^{11}$ is $—R^{14}C(=O)X^2—$ and connects to L, wherein $X^2$ is $—O—$, $R^{14}$ is not $C_1$-$C_8$ alkyl;

wherein $R^{12}$ is H, $R^{14}$, $—O—$, $—S—$, $—N—$, $=N—$, $=NNH—$, $—OH$, $—SH$, $—NH_2$, $=NH$, $=NNH_2$, $—NH(R^{14})$, $—OR^{14}$, $—C(O)O—$, $—C(O)OR^{16}—$, $—COR^{16}$, $—COOR^{14}—$, $C(O)NH—$, $C(O)NH_2$, $C(O)NHR^{14}$, $—SR^{14}$, $—S(=O)R^{14}$, $—P(=O)(OR^{16})_2$, $—OP(=O)(OR^{16})_2$, $—CH_2OP(=O)(OR^{16})_2$, or $—SO_2R^{16}$;

wherein $R^{13}$ is linear or branched $C_1$~$C_{10}$ alkyl, alkyl acid, alkyl amide, or alkyl amine; or $C_2$-$C_{10}$ heteroalkyl; or $C_3$-$C_{10}$ Ar; Ar is an aromatic or hetero aromatic group, composed of one or several rings, comprising four to ten carbon atoms, the hetero aromatic group is an aromatic group that has one or several carbon atoms replaced by hetero atoms, the aryl or Ar is an aromatic group, wherein one or several H atoms can be replaced independently by $R^{17}$, F, Cl, Br, I, $OR^{16}$, $SR^{16}$, $NR^{16}R^{17}$, $N=NR^{16}$, $N=R^{16}$, $NR^{16}R^{17}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, $OP(O)(OR^{17})_2$, $OCH_2OP(O)(OR^{17})_2$, $OC(O)OP(O)(OR^{17})_2$, $PO(OR^{16})(OR^{17})$, $OP(O)(OR^{17})OP(O)(OR^{17})_2$, $OC(O)R^{17}$ or $OC(O)NHR^{17}$;

wherein $R^{14}$ and $R^{15}$ are independently H; linear or branched $C_1$-$C_8$ alkyl; $C_2$-$C_8$ alkenyl, alkynyl, heteroalkyl, heterocyclic, or carbocyclic; $C_3$-$C_8$ aryl, cycloalkyl, alkylcycloalkyl, heterocycloalkyl, heteroaralkyl, heteroalkylcycloalkyl, or alkylcarbonyl;

wherein when $R^{14}$ is bivalent, $R^{14}$ is further connected to an additional functional group of one to four amino acid units, or $(CH_2CH_2O)_r$, r is an integer ranging from 0 to 12, or $C_4$-$C_{12}$ glycoside, or $C_1$-$C_8$ carboxylic acid;

wherein $R^{16}$ is H, OH, $R^{14}$ or one to four amino acid units;

wherein $R^{17}$ is H, linear or branched $C_1$-$C_8$ alkyl; $C_2$-$C_8$ alkenyl, alkynyl, heteroalkyl, or heterocyclic; $C_3$-$C_8$ aryl, carbocyclic, cycloalkyl, alkylcycloalkyl, heterocycloalkyl, heteroalkylcycloalkyl, heteroaralkyl, or alkylcarbonyl, or $C_4$-$C_{12}$ glycoside, or a pharmaceutical salt.

2. The conjugate according to claim 1 having Formula (II):

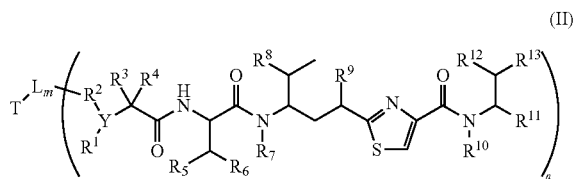

or a pharmaceutically acceptable salt, hydrate, or hydrated salt thereof; or a polymorphic crystalline structure thereof; or an optical isomer, racemate, diastereomer or enantiomer thereof;

wherein T, L, n, m, Y, $R^1$, $R^2$, $R^3$, $R^4$, $R^5$, $R^6$, $R^8$, $R^{10}$, $R^{13}$, $R^{14}$, $R^{15}$, $R^{16}$ and $R^{17}$ are defined the same as in the Formula (I);

wherein $R^7$ is H, $R^{14}$, —$R^{14}C(=O)X^1R^{15}$; or —$R^{14}X^1R^{15}$; $X^1$ is O, S, S—S, NH, or $NR^{14}$;

wherein $R^9$ is H, —OH, —$OR^{14}$, —$OC(=O)R^{14}$, —$OC(=O)NHR^{14}$, —$OC(=O)NR^{14}R^{15}$, —$OC(=O)R^{14}SSR^{15}$, $OP(=O)(OR^{14})_2$, or $OR^{14}OP(=O)(OR^{15})$;

wherein $R^{11}$ is H, $R^{14}$, —$R^{14}C(=O)R^{16}$, —$R^{14}C(=O)X^2R^{16}$, —$R^{14}X^2R^{16}$, or —$R^{14}C(=O)X^2$, wherein $X^2$ is —O—, —S—, —NH—, —NHS(O$_2$), —N($R^{14}$)—, —O—$R^{14}$—, —S—$R^{14}$—, —S(=O)—$R^{14}$—, or —$NHR^{14}$—;

wherein $R^{12}$ is H, $R^{14}$, —O—, —S—, —N—, =N—, =NNH—, —OH, —SH, —$NH_2$, =NH, =$NNH_2$, —NH($R^{14}$), —$OR^{14}$, —C(O)O—, —C(O)$OR^{16}$—, —$COR^{16}$, —$COOR^{14}$, C(O)NH—, C(O)$NH_2$, C(O)$NHR^{14}$, —$SR^{14}$, —S(=O)$R^{14}$, —P(=O)(O$R^{16}$)$_2$, —OP(=O)(O$R^{16}$)$_2$, —$CH_2OP(=O)(OR^{16})_2$, or —$SO_2R^{16}$.

3. The conjugate according to claim 1 having Formula (III):

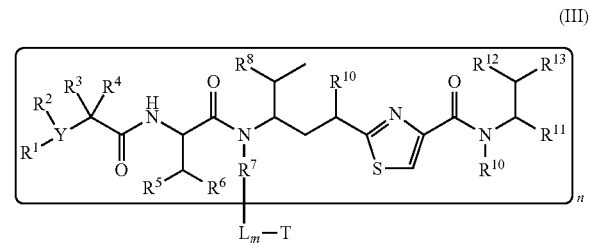

or a pharmaceutically acceptable salt, hydrate, or hydrated salt thereof; or a polymorphic crystalline structure thereof; or an optical isomer, racemate, diastereomer or enantiomer thereof;

wherein T, L, m, Y, $R^1$, $R^2$, $R^3$, $R^4$, $R^5$, $R^6$, $R^8$, $R^9$, $R^{10}$, $R^{11}$, $R^1$, $R^{13}$ and n are defined the same as in Formula (I);

wherein $R^7$ is independently —$R^{14}$—, or —$R^{14}C(=O)X^1R^{15}$— or —$R^{14}X^1R^{15}$—, wherein $R^{14}$ and $R^{15}$ are independently linear or branched $C_1$~$C_8$ alkyl, or heteroalkyl; $C_2$~$C_8$ alkenyl, or alkynyl; $C_3$~$C_8$ aryl, heterocyclic, carbocyclic, cycloalkyl, heterocycloalkyl, heteroaralkyl heteroalkylcycloalkyl, or alkylcarbonyl; $X^1$ is O, S, S—S, NH, or $NR^{14}$.

4. The conjugate according to claim 1 having Formula (IV):

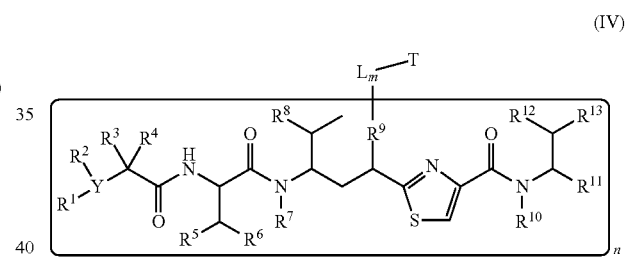

or a pharmaceutically acceptable salt, hydrate, or hydrated salt thereof; or a polymorphic crystalline structure thereof; or an optical isomer, racemate, diastereomer or enantiomer thereof;

wherein T, L, m, $R^1$, $R^2$, $R^3$, $R^4$, $R^5$, $R^6$, $R^7$, $R^8$, $R^{10}$, $R^{11}$, $R^{12}$, $R^{13}$ and n are defined the same as in Formula (I);

wherein $R^9$ is independently H, —O—, —$OR^{14}$—, —$OC(=O)R^{14}$—, —$OC(=O)NHR^{14}$—, —$OC(=O)NR^{14}R^{15}$—, —$OC(=O)R^{14}SSR^{15}$—, or —$OP(=O)(OR^{14})O$—, wherein $R^{14}$ and $R^{15}$ are independently H, $C_1$~$C_8$ alkyl, or heteroalkyl; $C_3$~$C_8$ aryl, heteroaryl, heterocyclic, carbocyclic, cycloalkyl, alkylcycloalkyl, heterocycloalkyl, heteroalkylcycloalkyl, heteroaralkyl, or alkylcarbonyl, or a pharmaceutical salt.

5. The conjugate according to claim 1 having Formula (V):

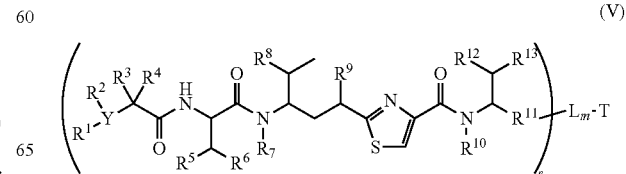

or a pharmaceutically acceptable salt, hydrate, or hydrated salt thereof; or a polymorphic crystalline structure thereof; or an optical isomer, racemate, diastereomer or enantiomer thereof;

wherein T, L, m, Y, $R^1$, $R^2$, $R^3$, $R^4$, $R^5$, $R^6$, $R^7$, $R^8$, $R^9$, $R^{10}$, $R^{12}$, $R^{13}$ and n are defined the same as in Formula (I);

wherein $R^{11}$ is —$R^{14}$—, —$R^{14}$C(=O)$R^{17}$—, —$R^{14}$C(=O)$X^2R^{17}$—, —$R^{14}X^2R^{17}$—, or —$R_{14}$C(=O)$X^2$—, wherein $R^{17}$ is independently H, OH, $C_1$~$C_8$ alkyl; $C_2$~$C_8$ alkenyl, alkynyl, or heteroalkyl; $C_3$~$C_8$ aryl, arylene, heterocyclic, carbocyclic, or heterocycloalkyl; or an amino acid, or two amino acid units; $X^2$ is —O—, —S—, —NH—, —NHS($O_2$)—, —NHS(O)—, —N($R^{14}$)—, —O—$R^{14}$—, —S—$R^{14}$—, —S(=O)—$R^{14}$—, or —NH$R^{14}$—; —$R^{14}$ is H, $C_1$~$C_8$ alkyl, or heteroalkyl; $C_2$~$C_8$ alkenyl, or alkynyl; $C_3$~$C_8$ aryl, heterocyclic, carbocyclic, cycloalkyl, alkylcycloalkyl, heterocycloalkyl, heteroalkylcycloalkyl, heteroaralkyl, or alkylcarbonyl.

6. The conjugate according to claim 1 having Formula (VI):

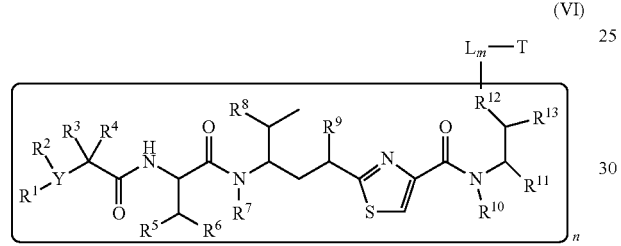

(VI)

or a pharmaceutically acceptable salt, hydrate, or hydrated salt thereof; or a polymorphic crystalline structure thereof; or an optical isomer, racemate, diastereomer or enantiomer thereof;

wherein T, L, m, Y, $R^1$, $R^2$, $R^3$, $R^4$, $R^5$, $R^6$, $R^7$, $R^8$, $R^9$, $R^{11}$, $R^{13}$ and n are defined the same as in Formula (I);

wherein $R^{12}$ is independently $R^{14}$, —O—, —S—, —NH—, =N—, =NNH—, —N($R_{14}$)—, —$OR^{14}$—, C(O)O—, C(O)NH—, C(O)$NR^{14}$—, —$SR^{14}$—, —S(=O)$R^{14}$—, —$NHR^{14}$—, —$CH_2$OP(=O)($OR^{15}$)—, —P(=O)($OR^{18}$)—, —OP(=O)($OR^{15}$)O—, or —$SO_2R^{14}$, $R^{14}$ and $R^{15}$ are independently $C_1$~$C_8$ alkyl, or heteroalkyl; $C_2$~$C_8$ alkenyl, or alkynyl; $C_3$~$C_8$ aryl, heterocyclic, carbocyclic, cycloalkyl, alkylcycloalkyl, heterocycloalkyl, heteroaralkyl, heteroalkylcycloalkyl, or alkylcarbonyl.

7. The conjugate according to claim 1 having Formula (VII):

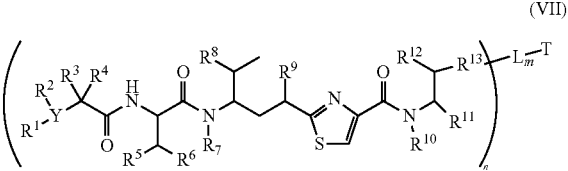

(VII)

or a pharmaceutically acceptable salt, hydrate, or hydrated salt; or a polymorphic crystalline structure thereof, or an optical isomer, racemate, diastereomer or enantiomer thereof, wherein T, L, n, m, Y, $R^1$, $R^{1'}$, $R^2$, $R^3$, $R^4$, $R^6$, $R^8$, $R^{10}$, $R^{11}$, and $R^{12}$ are defined the same as in Formula (I);

wherein $R^{13}$ is $C_1$~$C_{10}$ alkyl, heteroalkyl, alkyl acid, alkyl amide, alkyl amine, or Ar; Ar refers to a aromatic or hetero aromatic group, composed of one or several rings, comprising four to ten carbon atoms; the hetero aromatic group is an aromatic group wherein one, or more carbon atoms are replaced by O, N, Si, Se, P or S, the aryl or Ar is an aromatic group, wherein one or several H atoms are replaced independently by $R^{18}$, F, Cl, Br, I, $OR^{16}$, $SR^{16}$; $NR^{16}R^{18}$, N=$NR^{16}$, N=$R^{16}$, $NR^{16}R^{18}$, $NO_2$, $SOR^{16}R^{18}$, $SO_2R^{16}$, $SO_3R^{16}$, $OSO_3R^{16}$, $PR^{16}R^{18}$, $POR^{16}R^{18}$, $PO_2R^{16}R^{18}$, $OPO_3R^{16}R^{18}$, or $PO_3R^{16}R^{18}$ wherein $R^{16}$ and $R^{18}$ are independently H, $C_1$~$C_8$ alkyl; $C_2$~$C_8$ alkenyl, alkynyl, or heteroalkyl; $C_3$~$C_8$ aryl, heterocyclic, carbocyclic, cycloalkyl, alkylcycloalkyl, heterocycloalkyl, heteroaralkyl, heteroalkylcycloalkyl, or alkylcarbonyl; or $C_4$~$C_{12}$ glycoside; or a pharmaceutical salt.

8. The conjugate according to claim 1, wherein the cytotoxic compound inside the bracket of Formula (I) has a structure represented by one of the following Formulae II-01~II-69, III-01~II-68, IV-01~IV-68, V-01~V-68, VI-01~VI-12, and VII-01~VII-77:

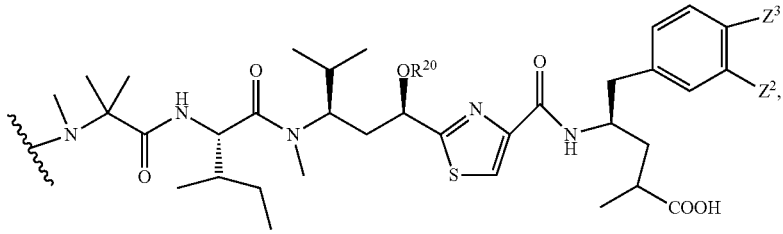

II-01

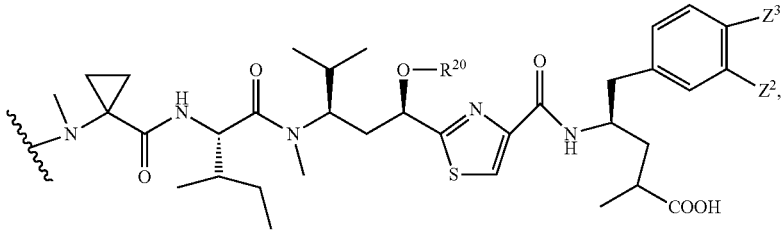

II-02

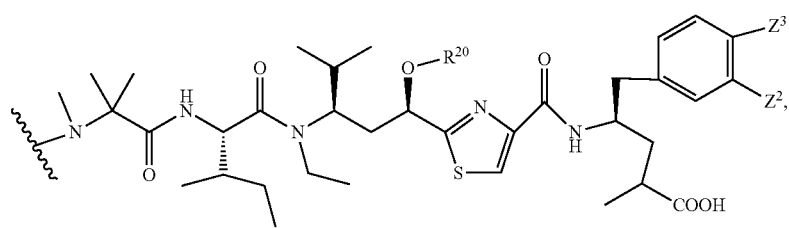
II-03
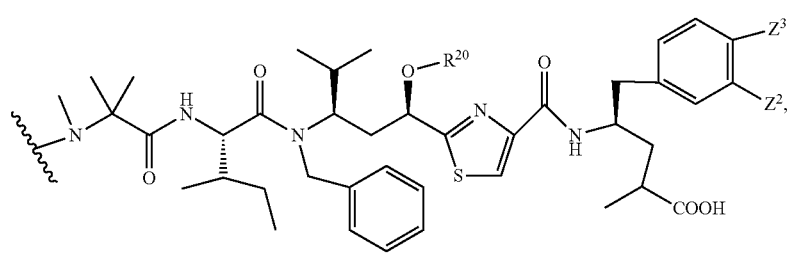
II-04
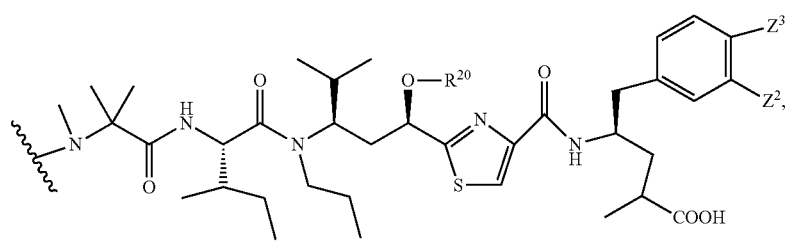
II-05
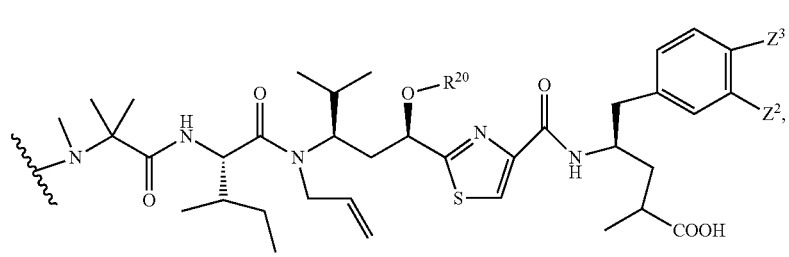
II-06
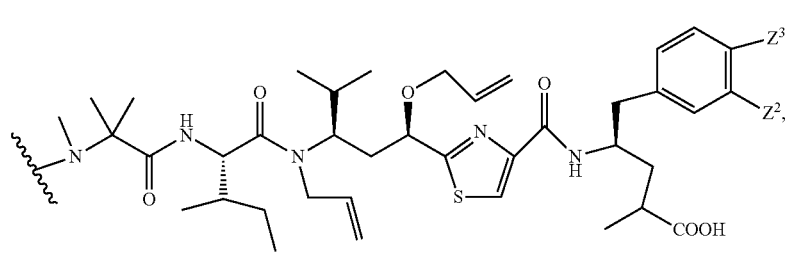
II-07
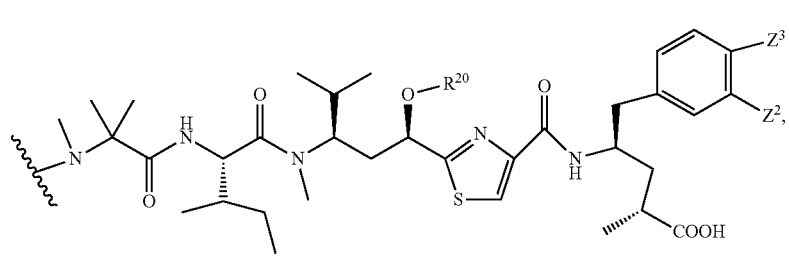
II-08

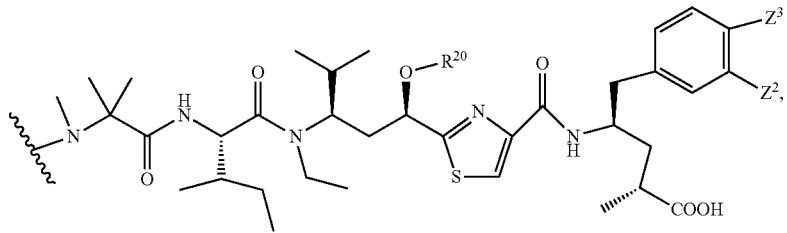
II-09
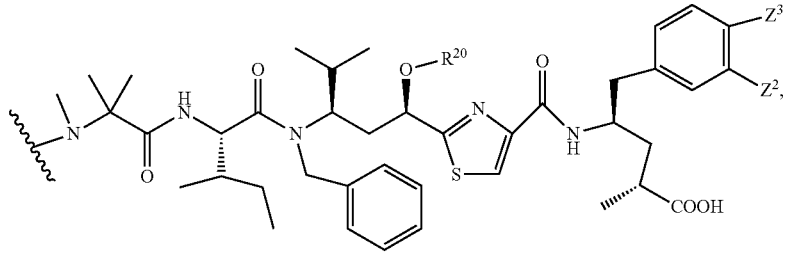
II-10
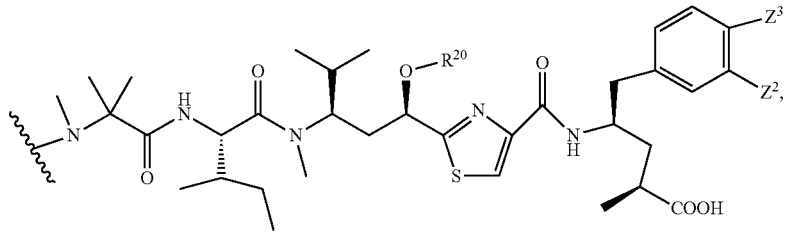
II-11
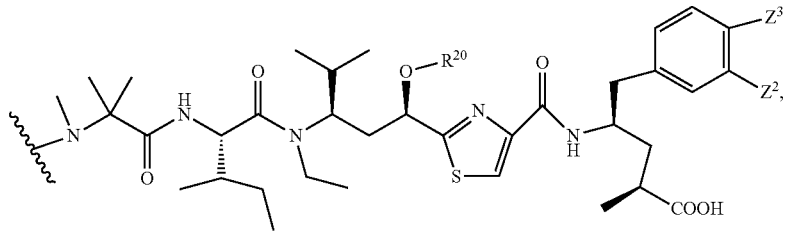
II-12
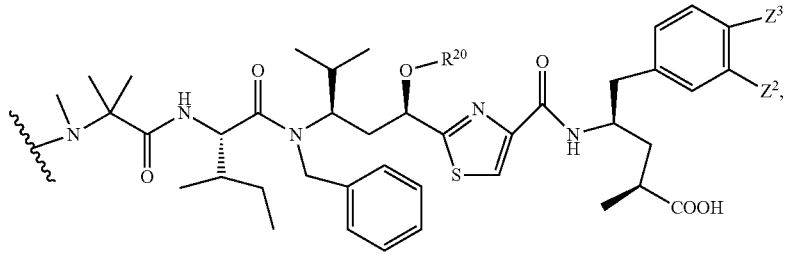
II-13
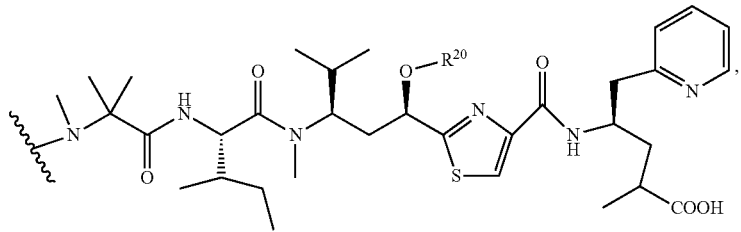
II-14

-continued
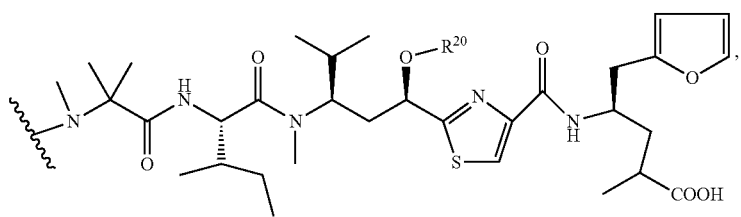
II-15
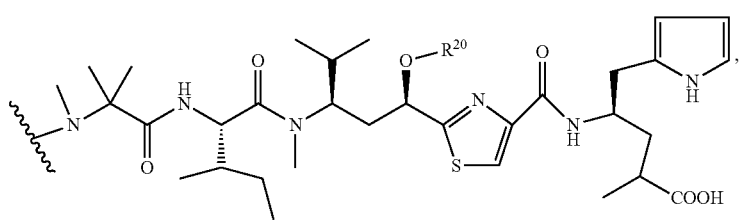
II-16
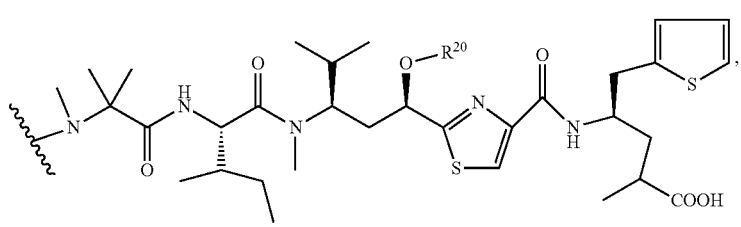
II-17
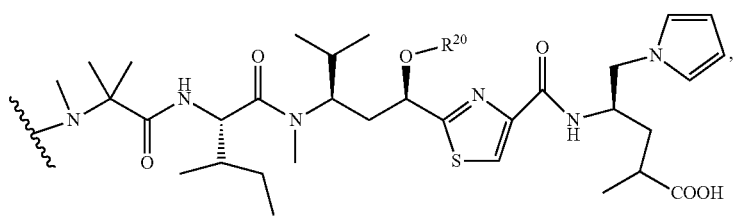
II-18
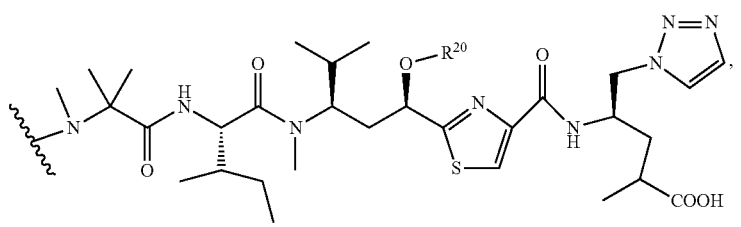
II-19
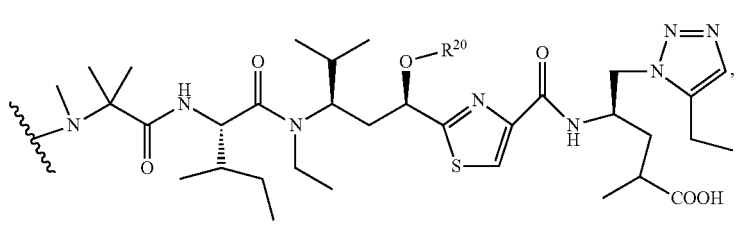
II-20
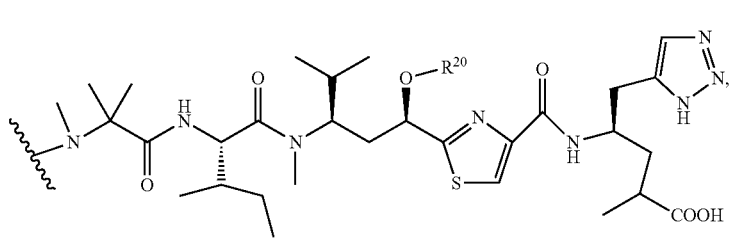
II-21

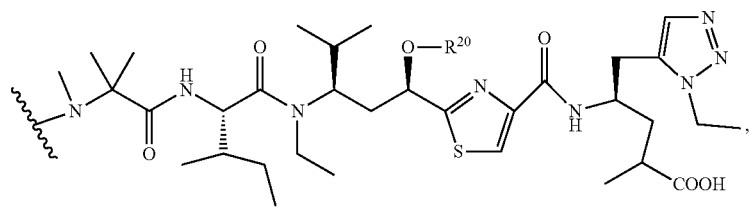
II-22
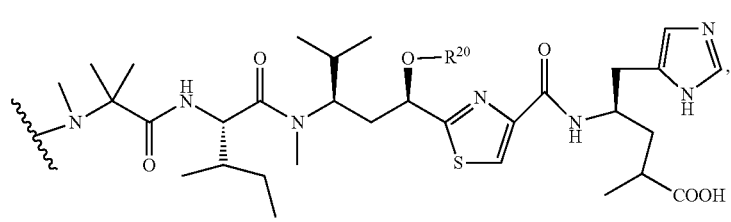
II-23
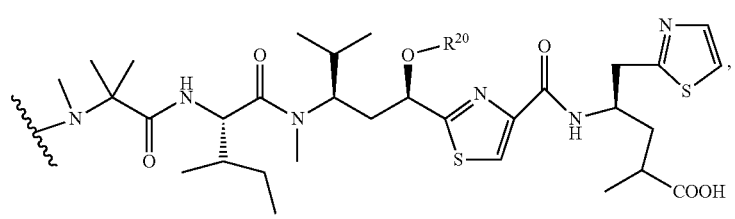
II-24
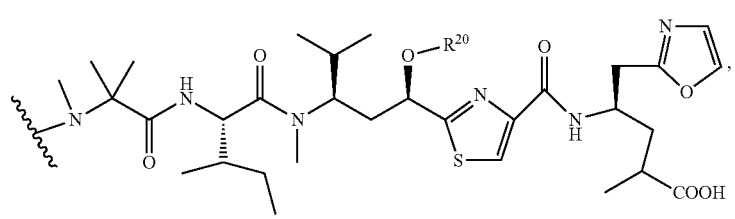
II-25
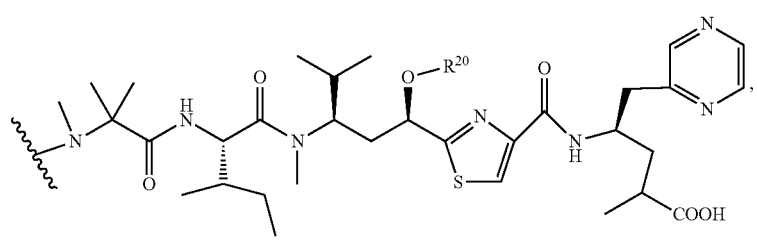
II-26
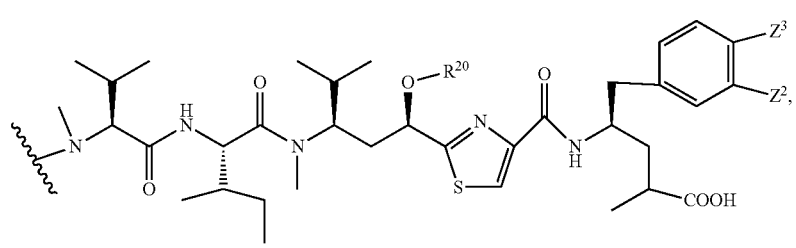
II-27
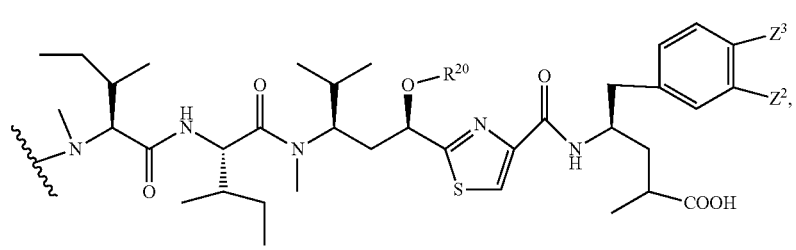
II-28

II-29
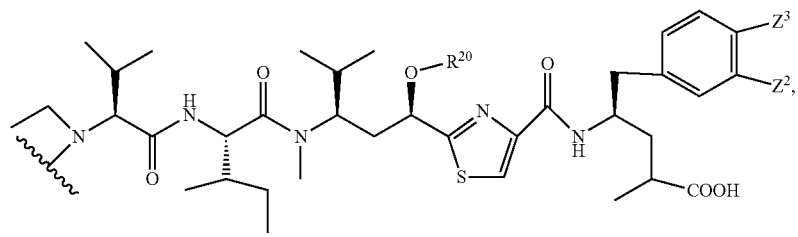
II-30
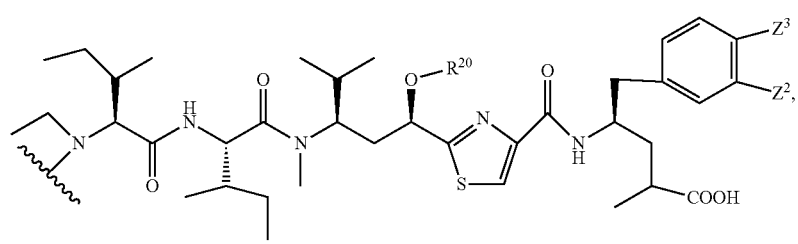
II-31
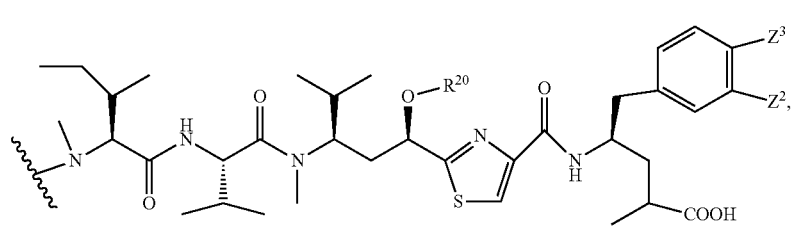
II-32
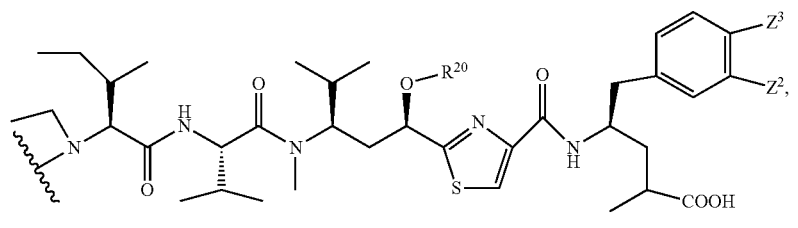
II-33
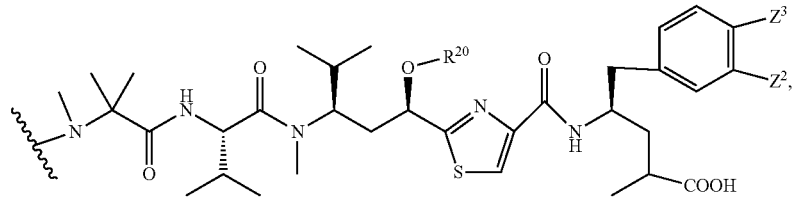
II-34
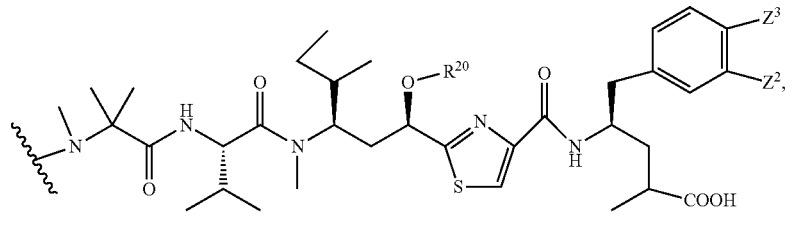
II-35
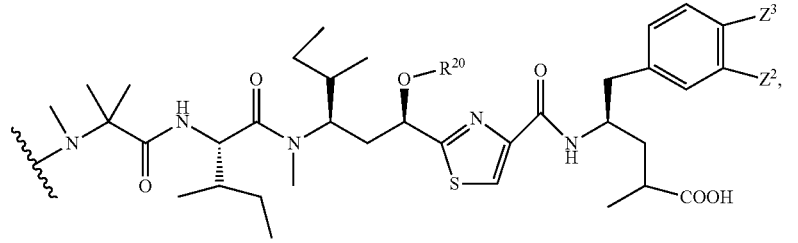

-continued
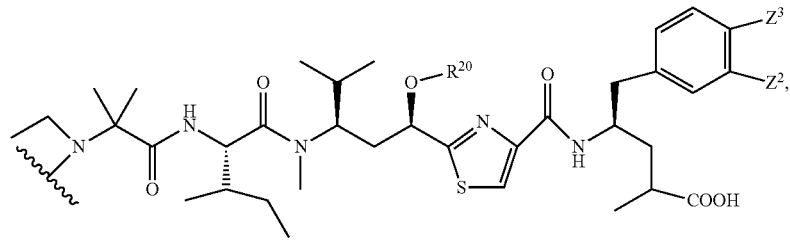
II-36
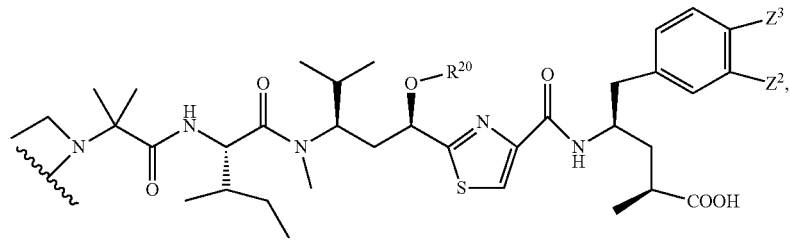
II-37
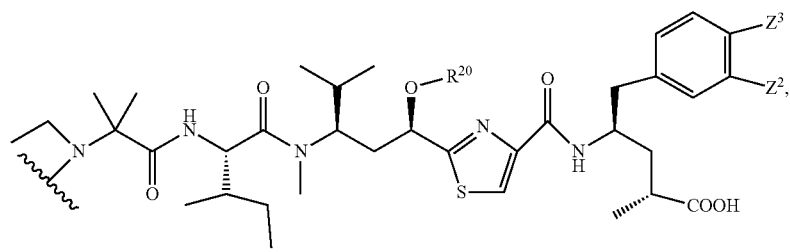
II-38
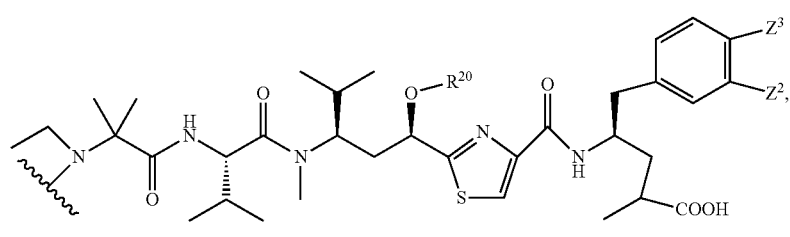
II-39
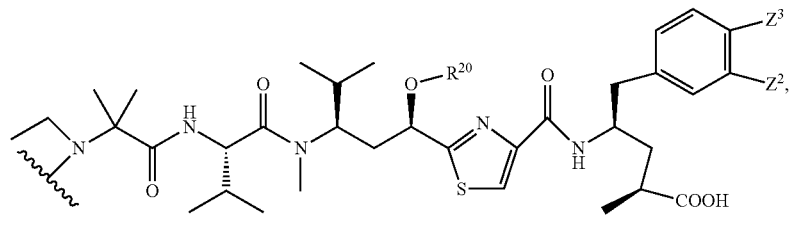
II-40
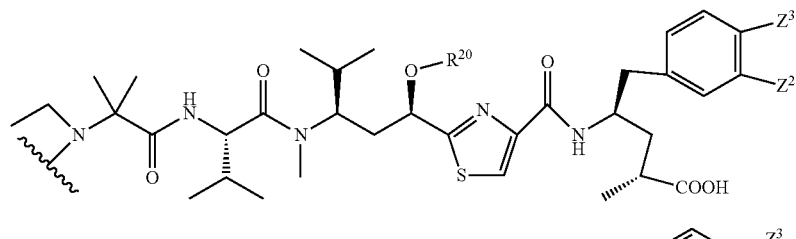
II-41
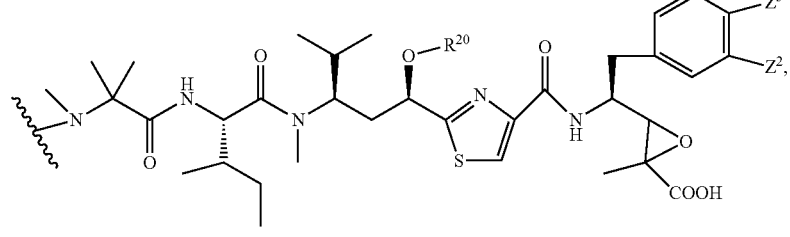
II-42

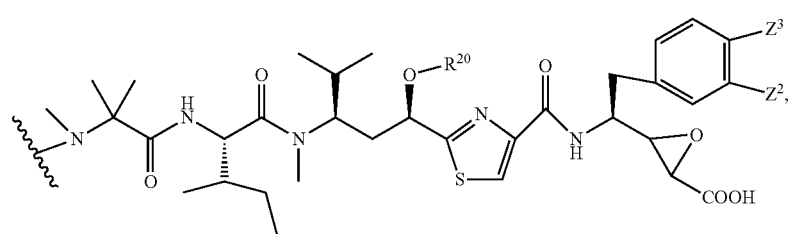
II-43
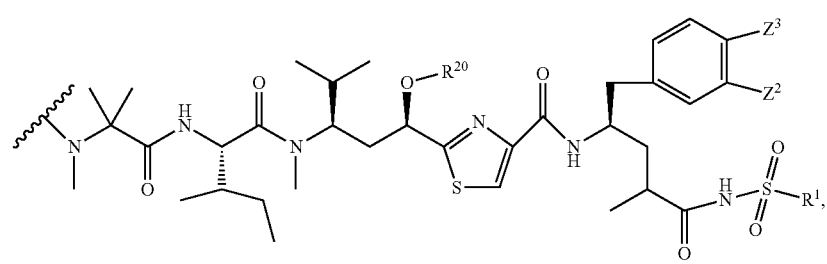
II-44
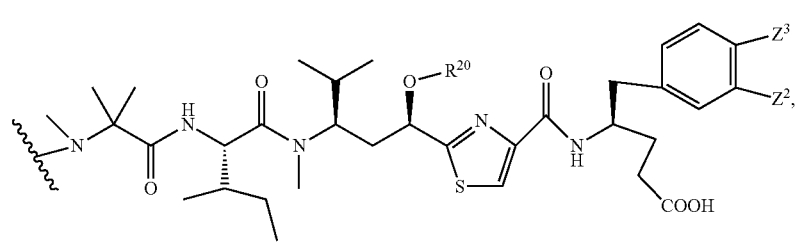
II-45
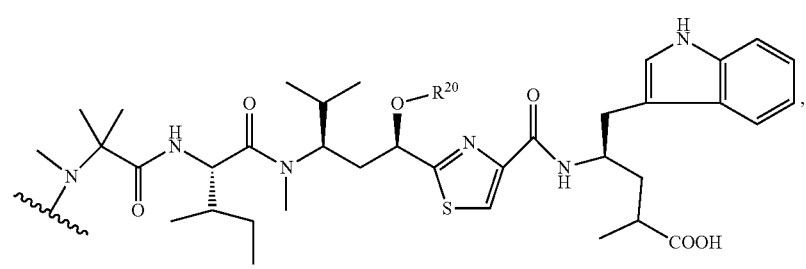
II-46
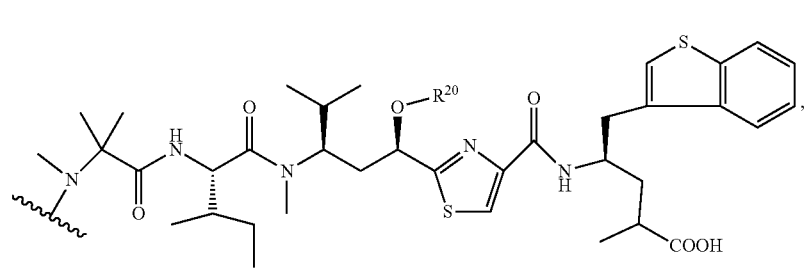
II-47
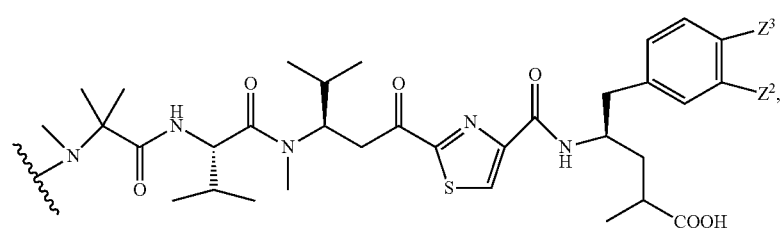
II-48

-continued
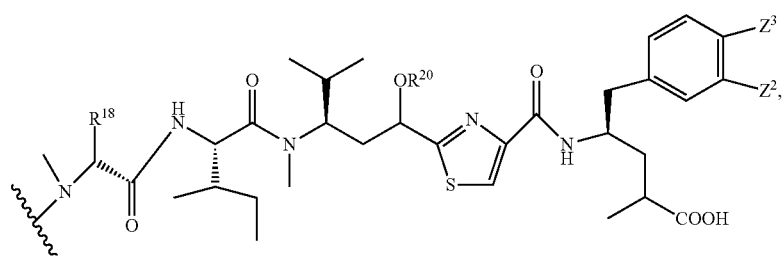
II-49
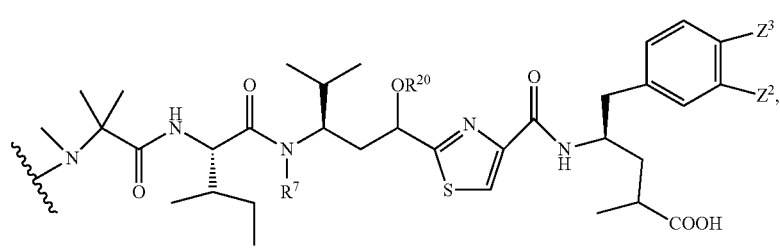
II-50
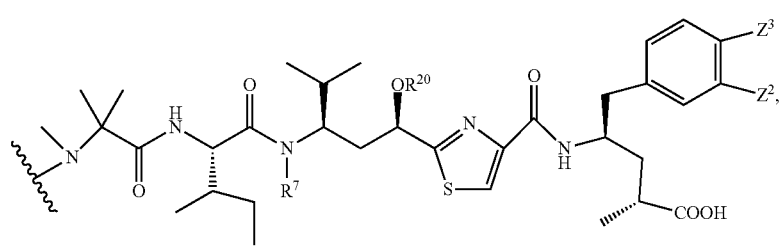
II-51
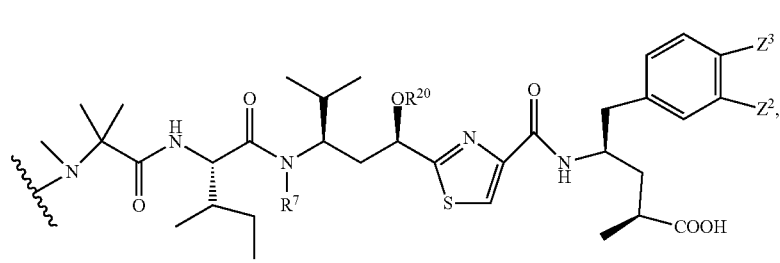
II-52
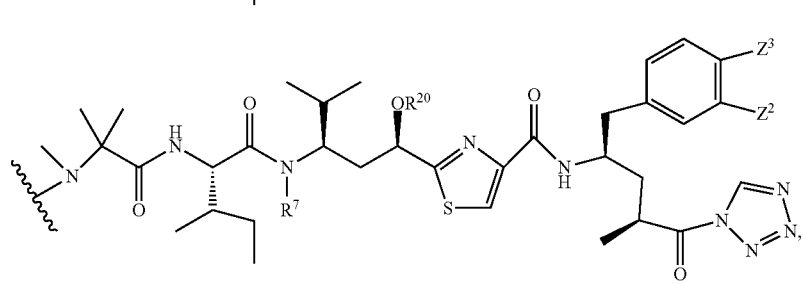
II-53
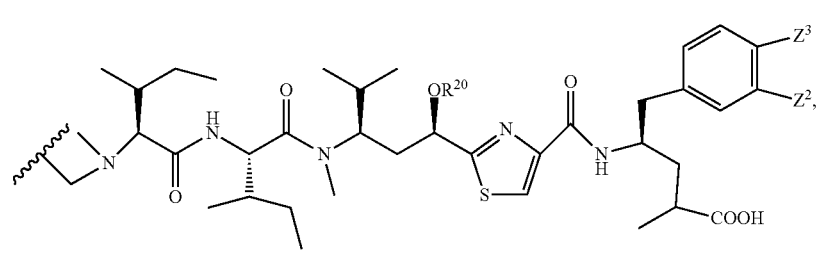
II-54

-continued
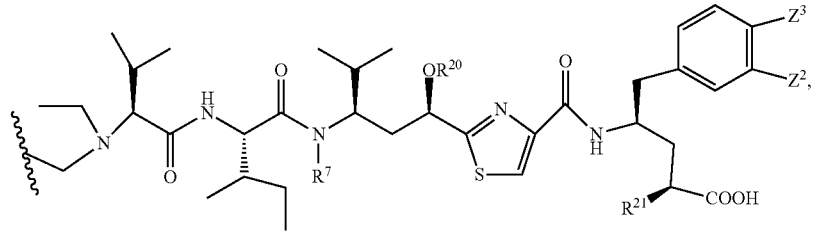
II-55
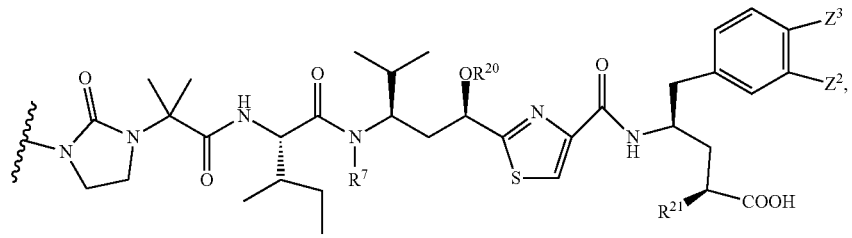
II-56
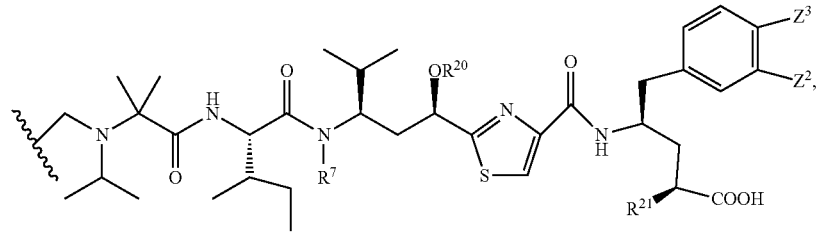
II-57
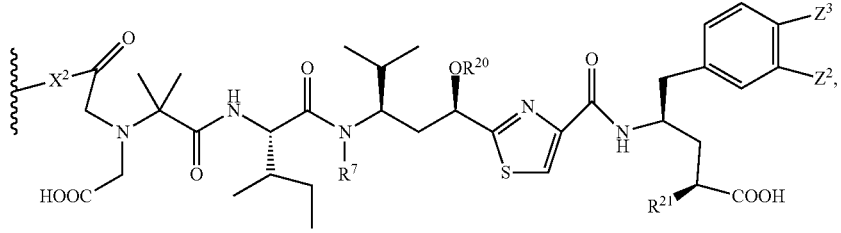
II-58
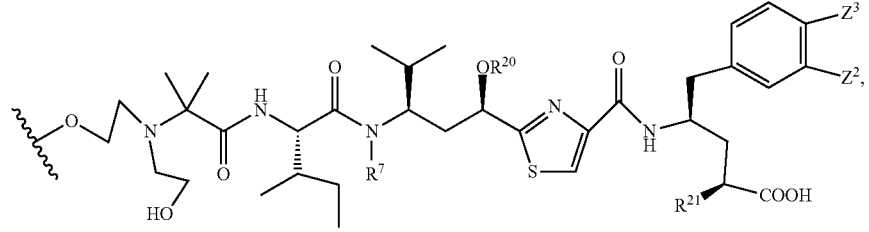
II-59
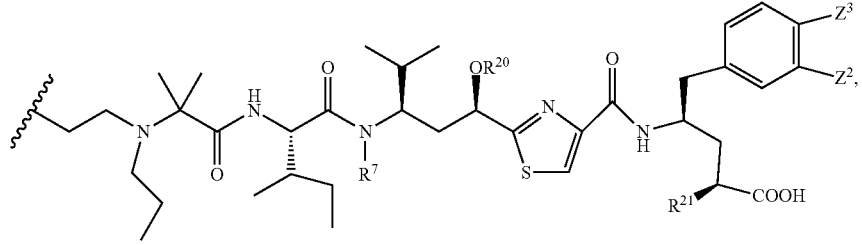
II-60

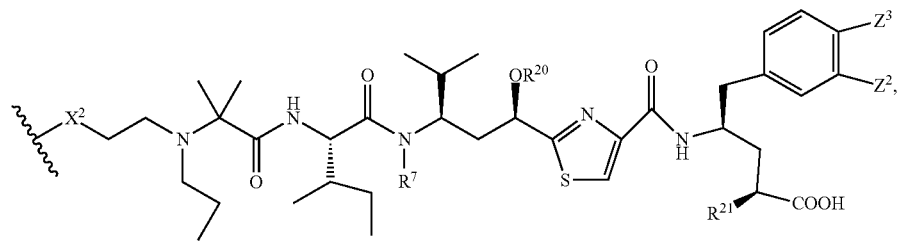
II-61
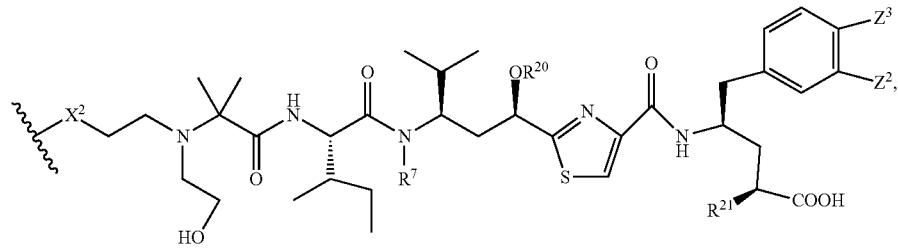
II-62
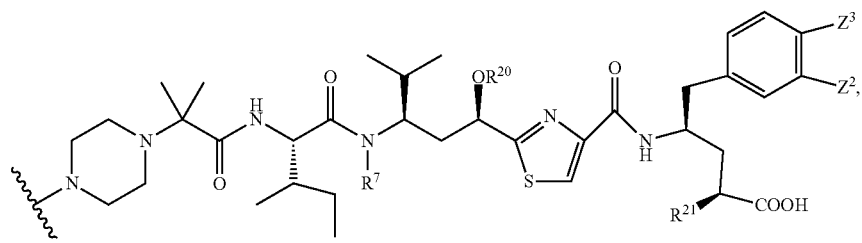
II-63
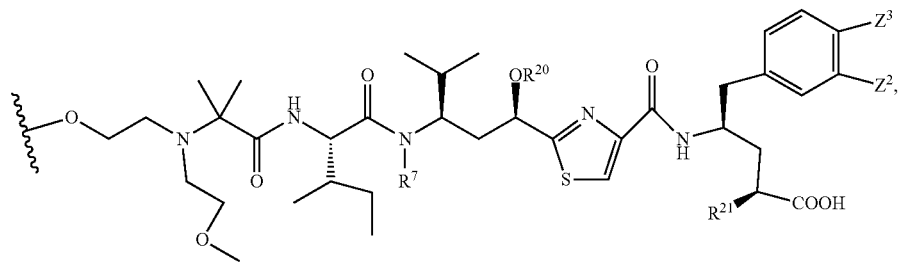
II-64
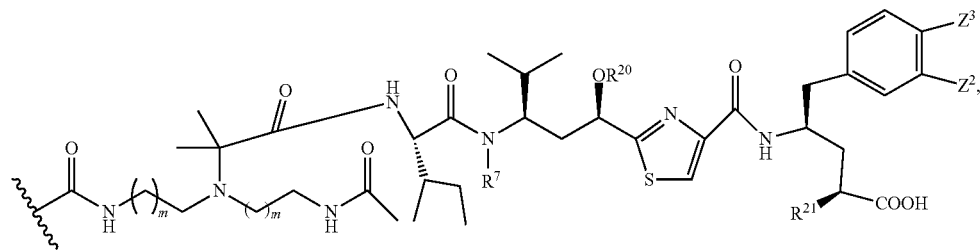
II-65
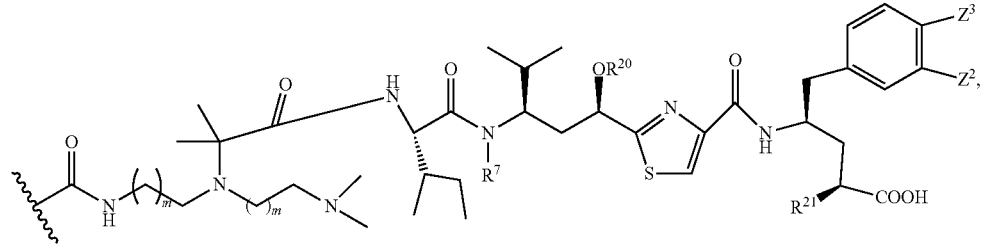
II-66

-continued
II-67
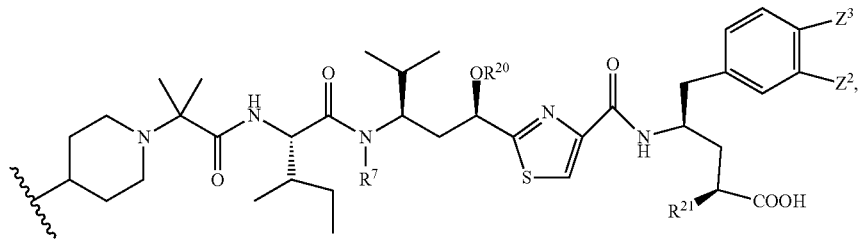
II-68
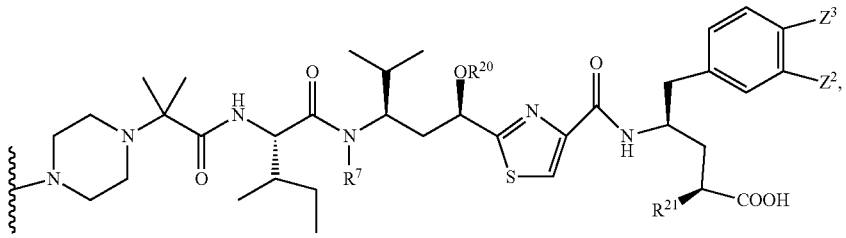
II-69
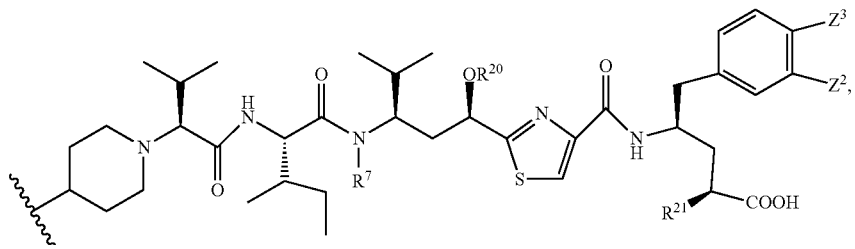
III-01
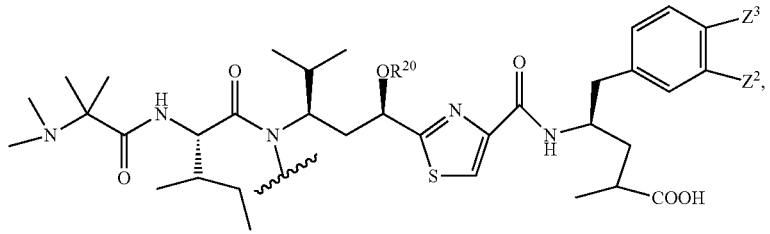
III-02
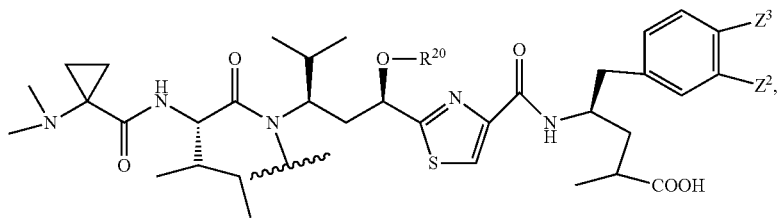
III-03
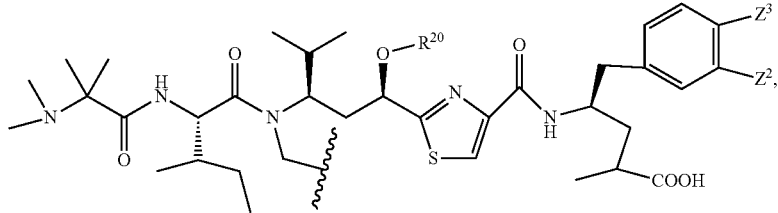

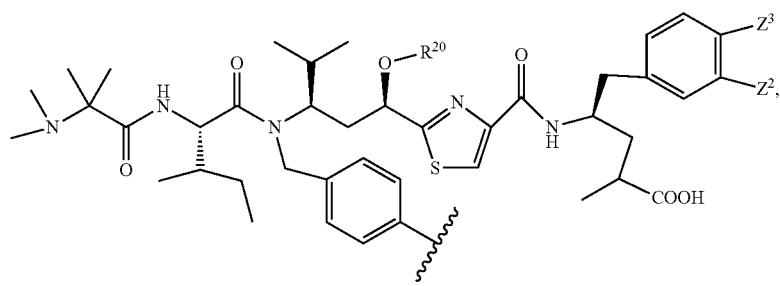
III-04
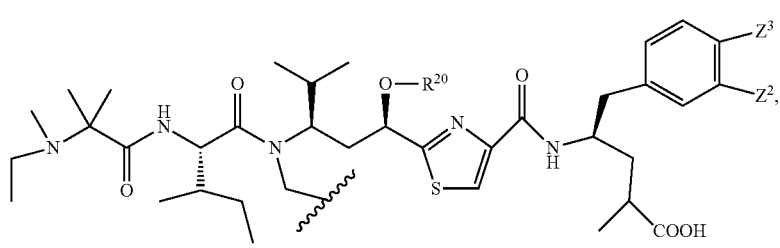
III-05
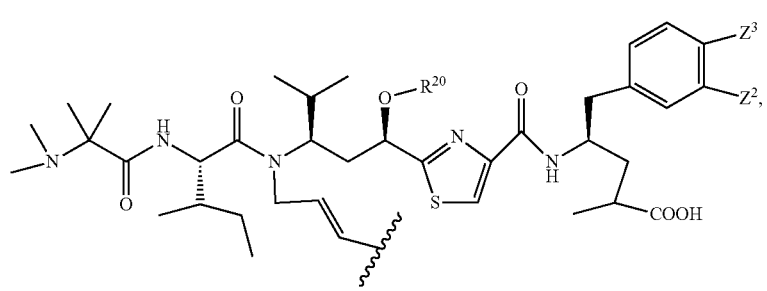
III-06
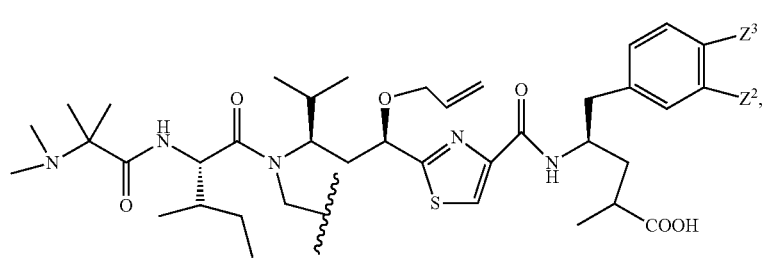
III-07
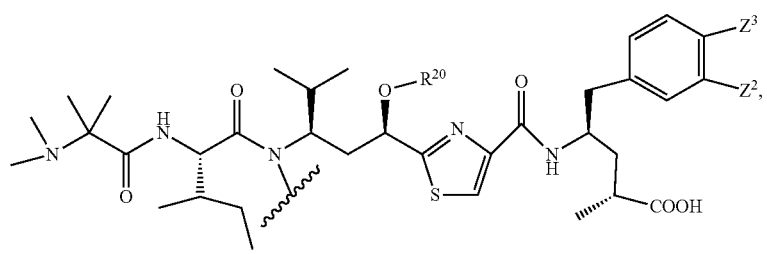
III-08
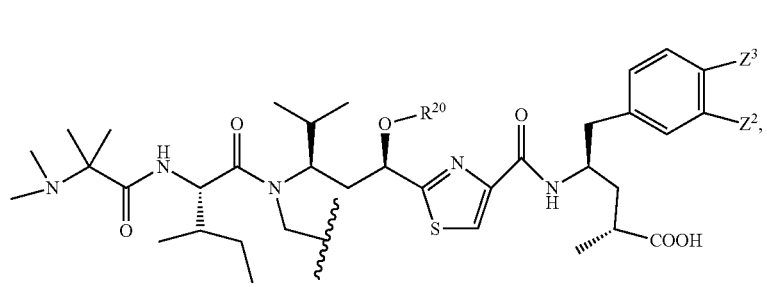
III-09

-continued
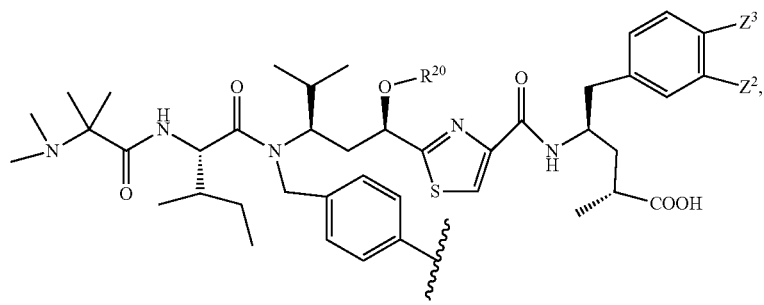
III-10
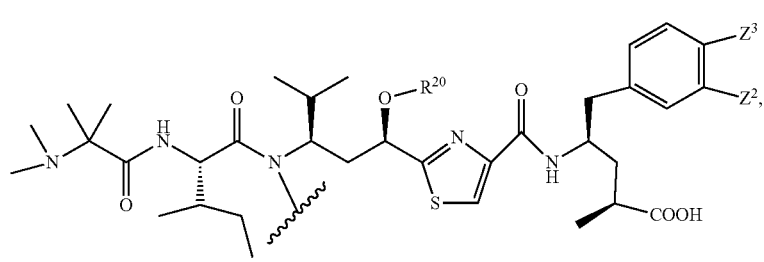
III-11
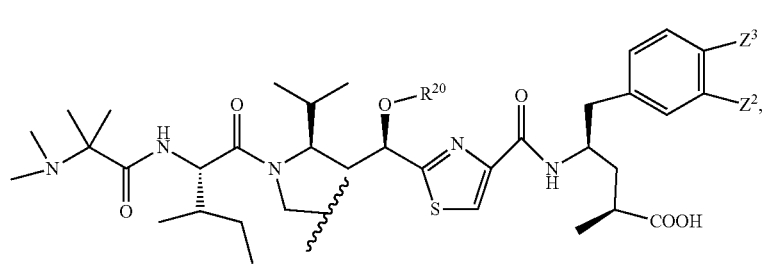
III-12
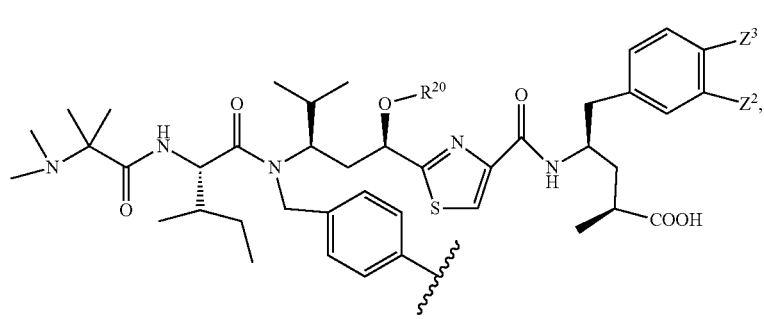
III-13
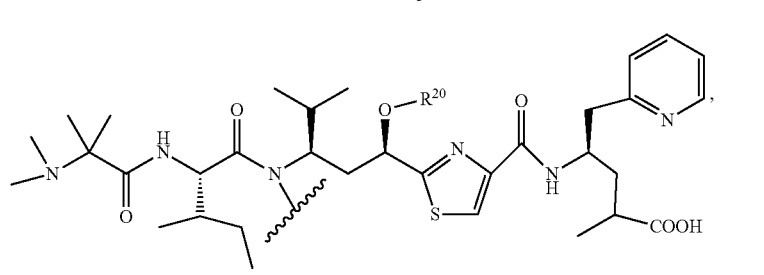
III-14
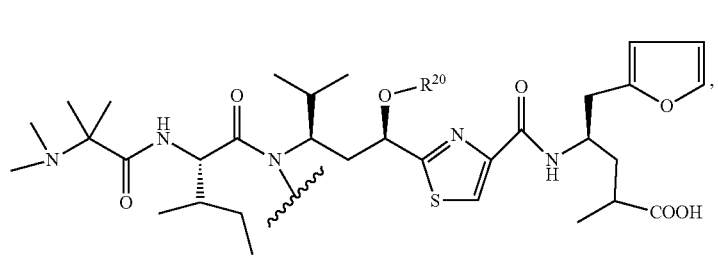
III-15

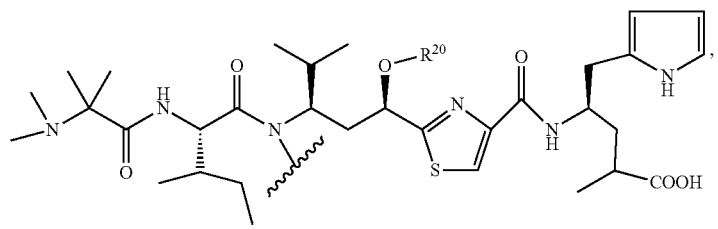
III-16
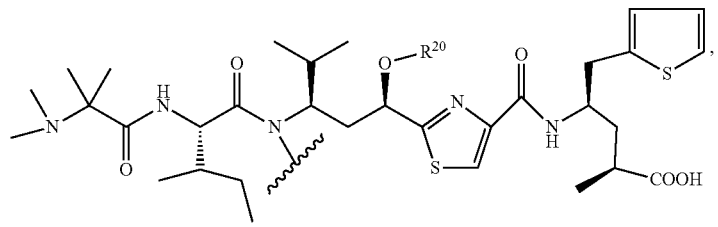
III-17
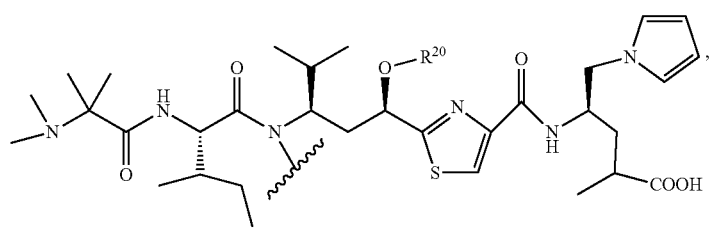
III-18
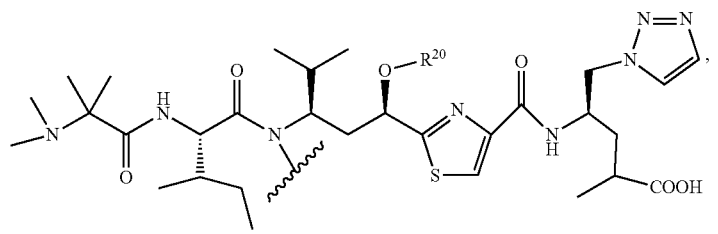
III-19
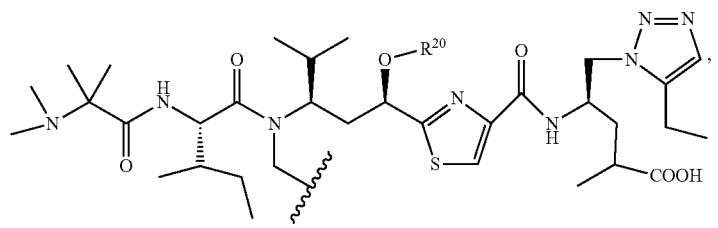
III-20
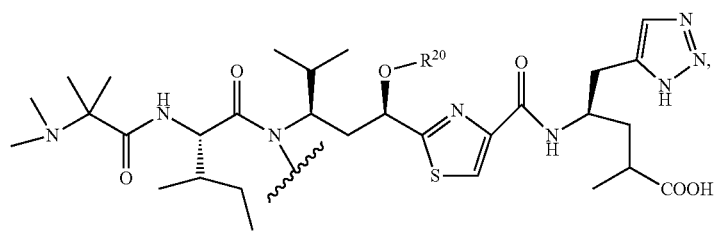
III-21
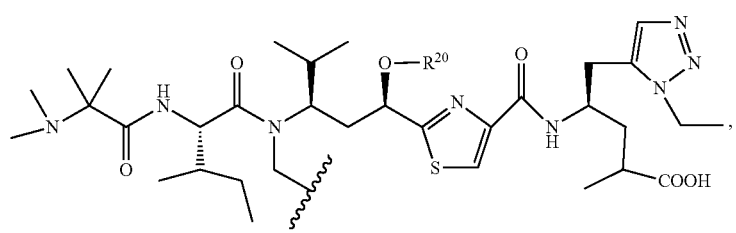
III-22

-continued
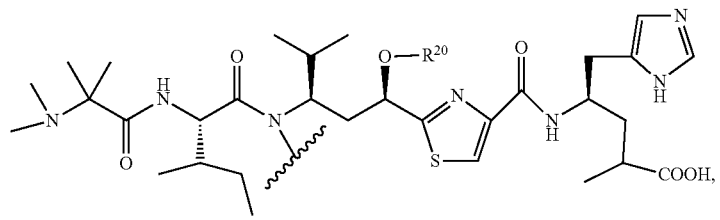
III-23
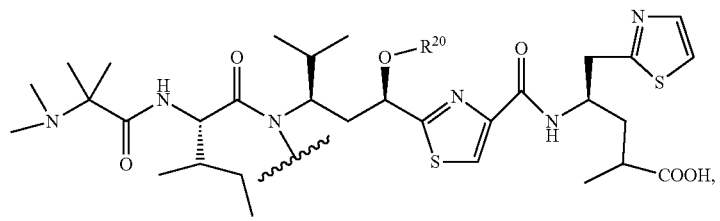
III-24
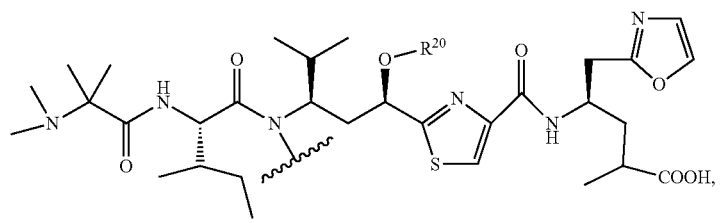
III-25
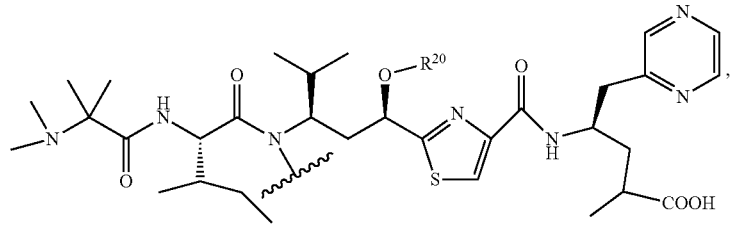
III-26
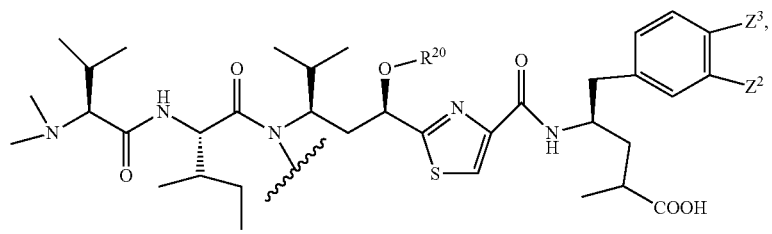
III-27
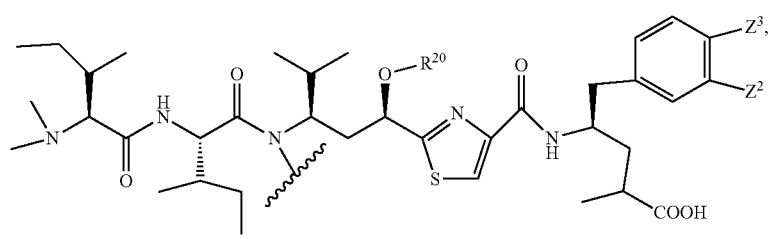
III-28
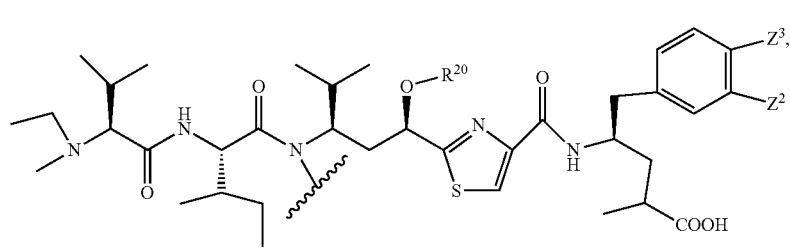
III-29

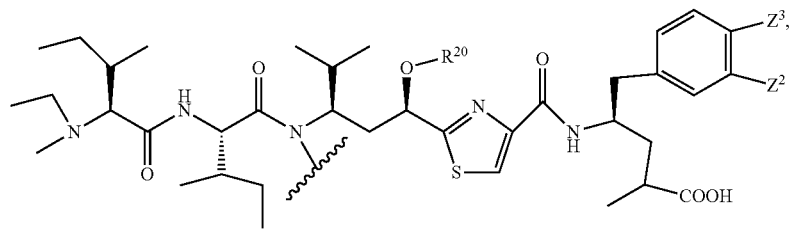
III-30
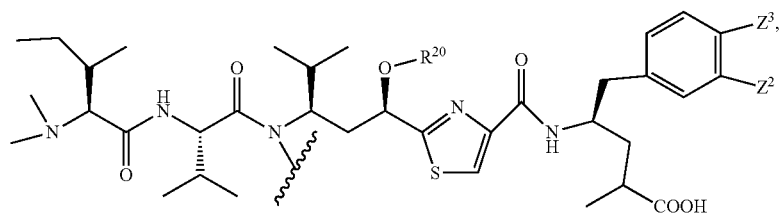
III-31
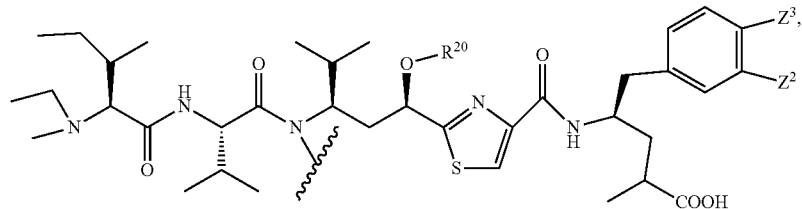
III-32
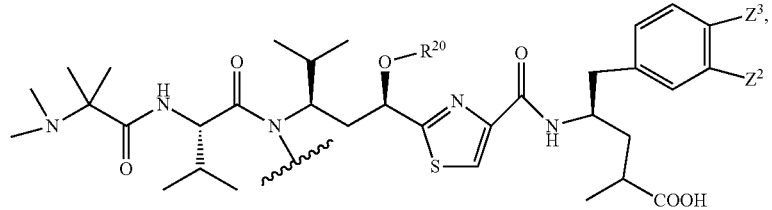
III-33
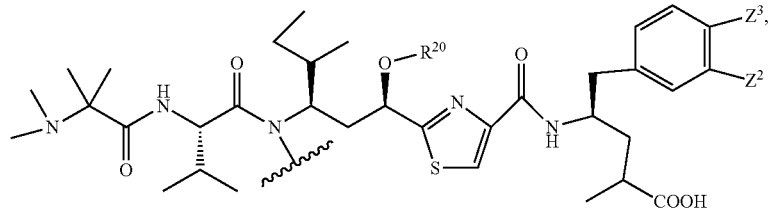
III-34
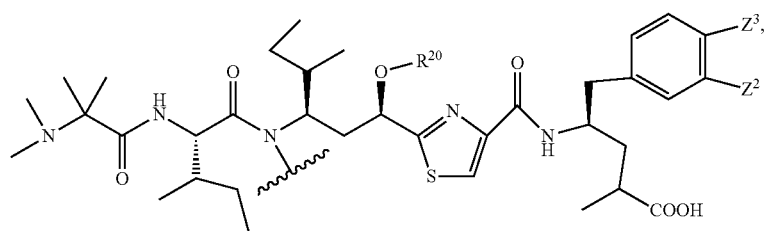
III-35
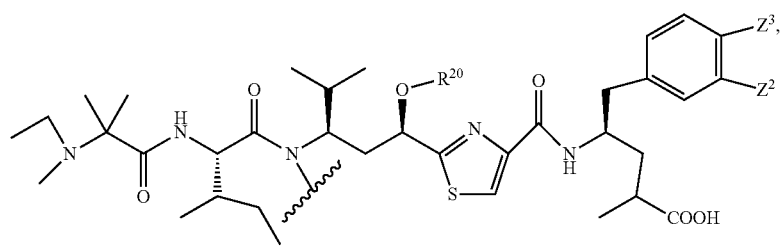
III-36

-continued
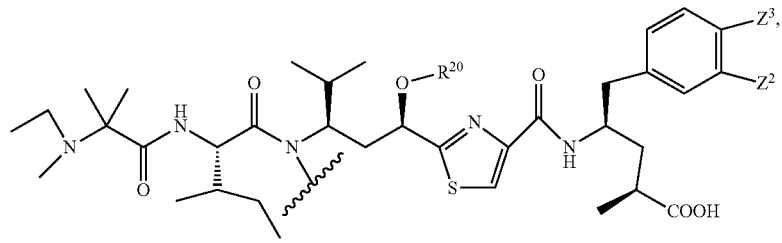
III-37
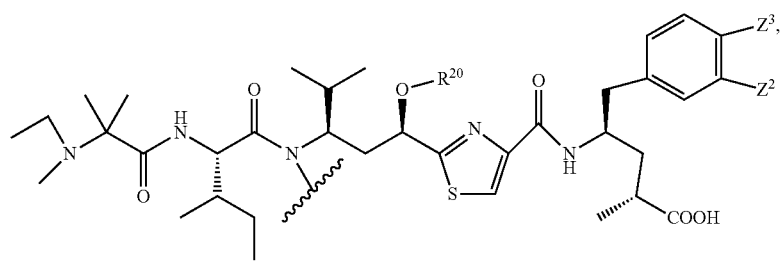
III-38
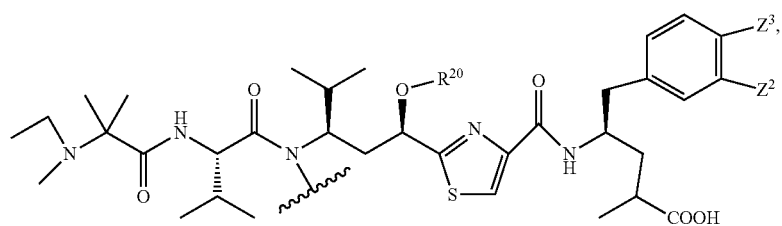
III-39
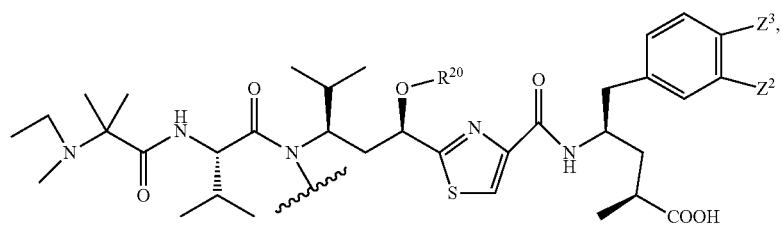
III-40
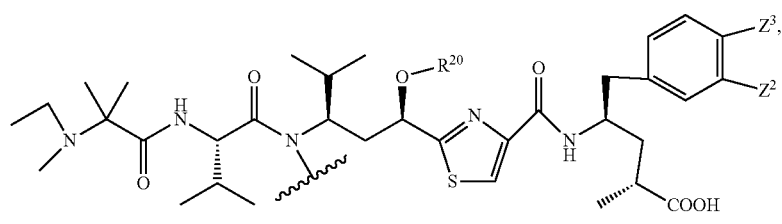
III-41
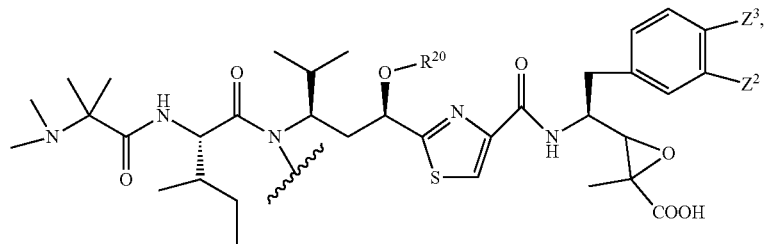
III-42
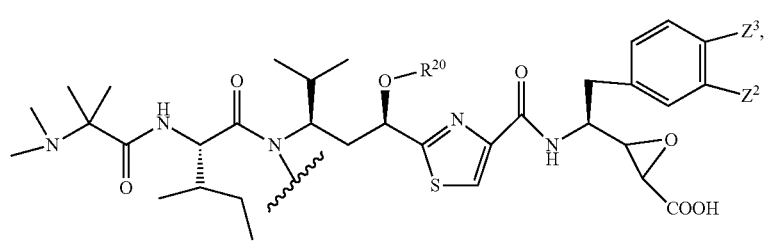
III-43

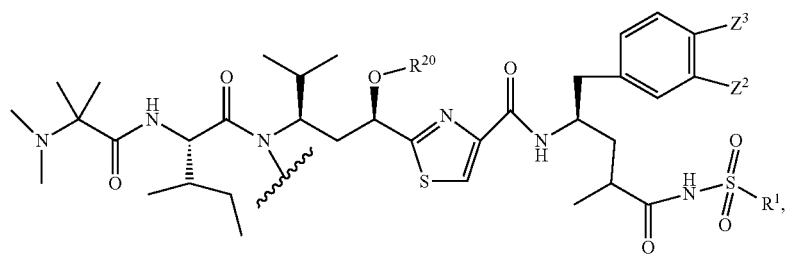
III-44
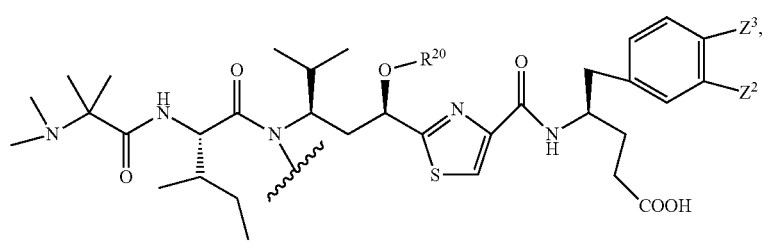
III-45
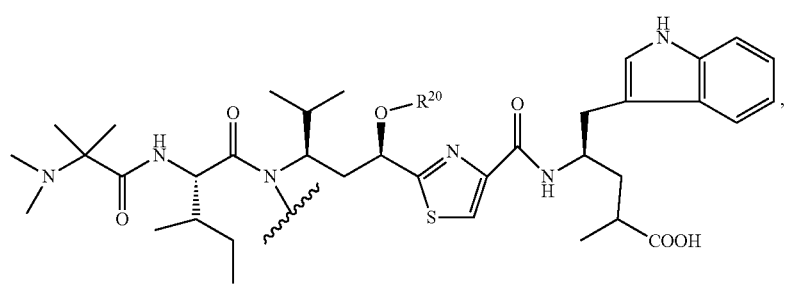
III-46
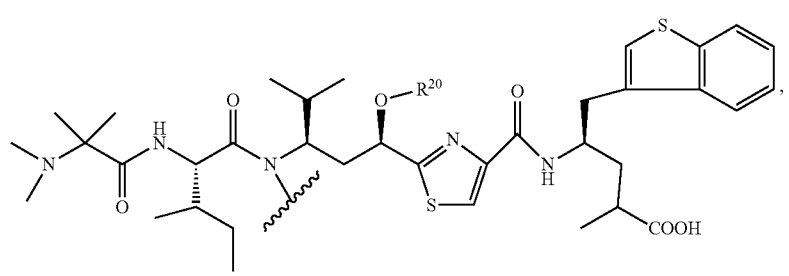
III-47
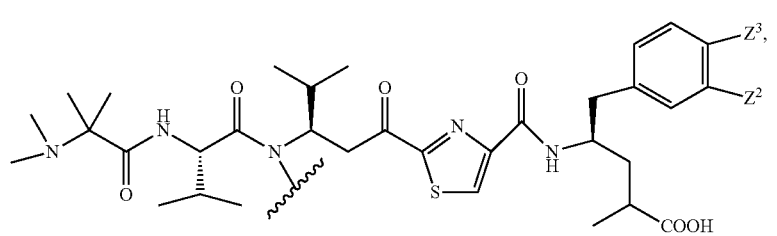
III-48
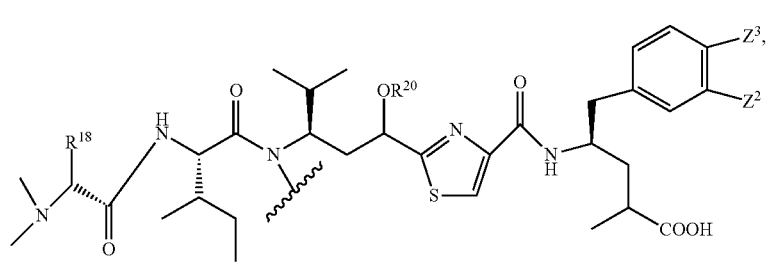
III-49

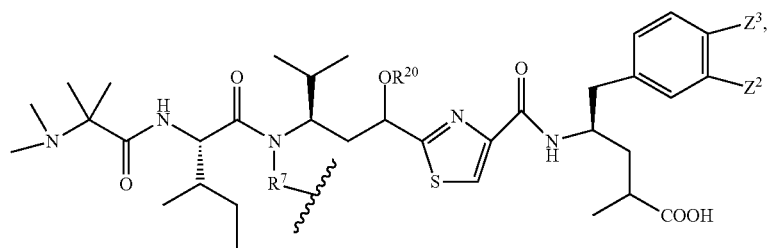
III-50
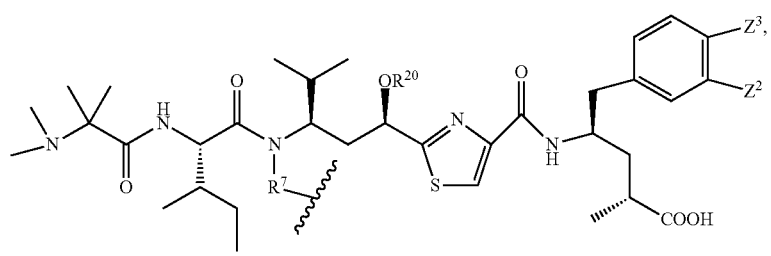
III-51
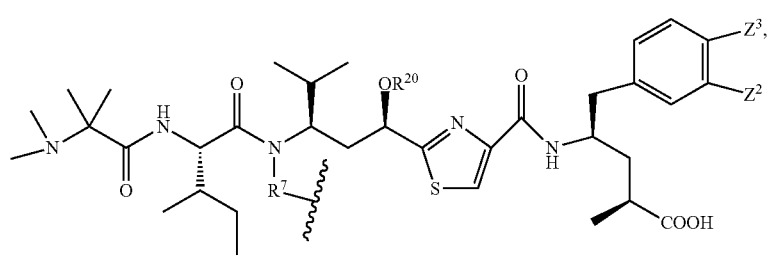
III-52
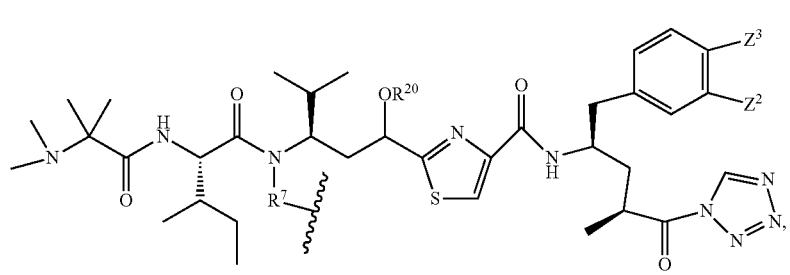
III-53
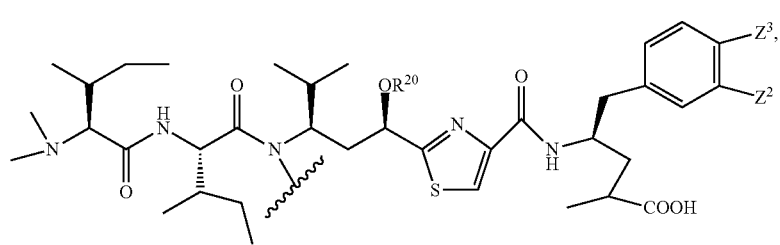
III-54
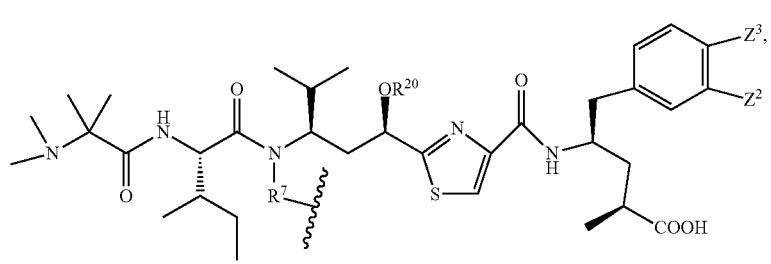
III-55

-continued
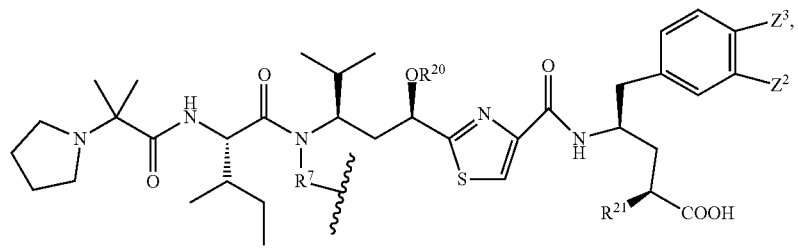
III-56
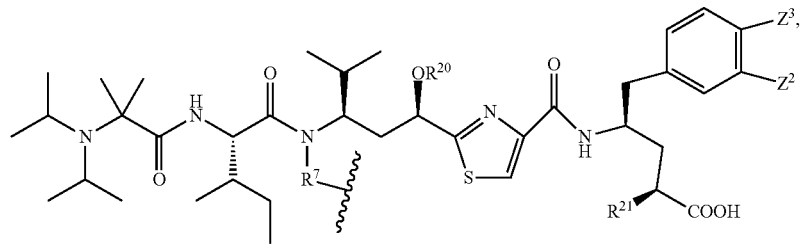
III-57
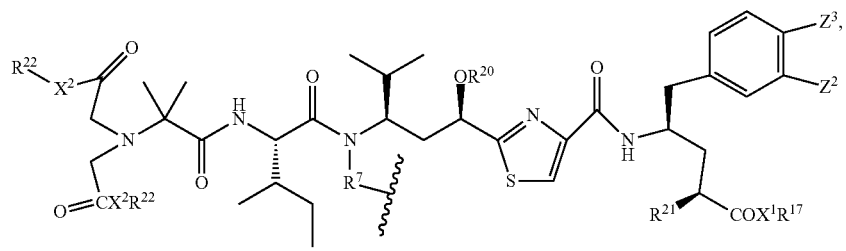
III-58
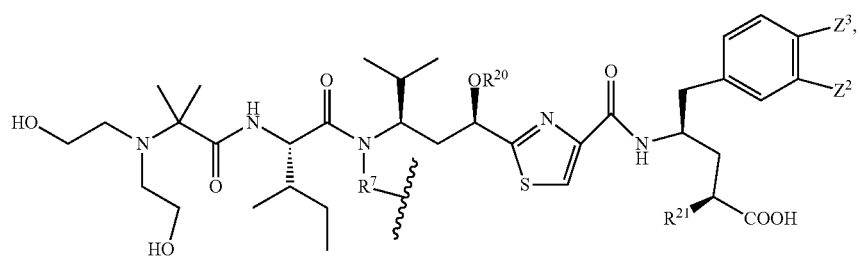
III-59
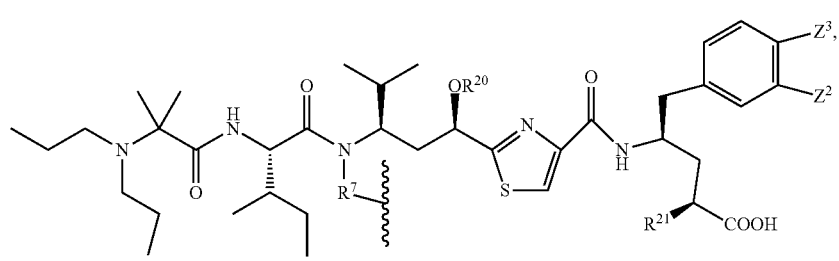
III-60
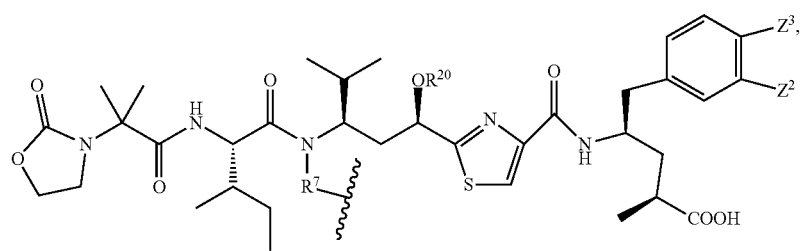
III-61

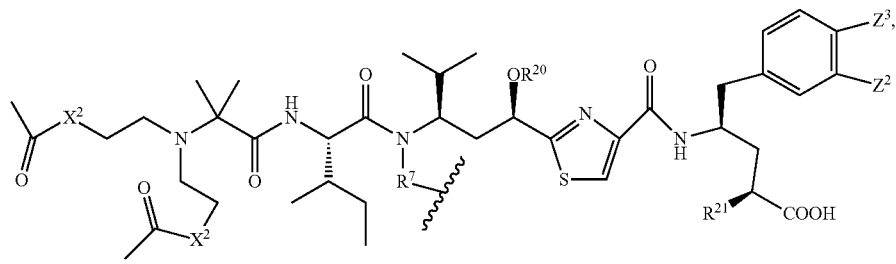
III-62
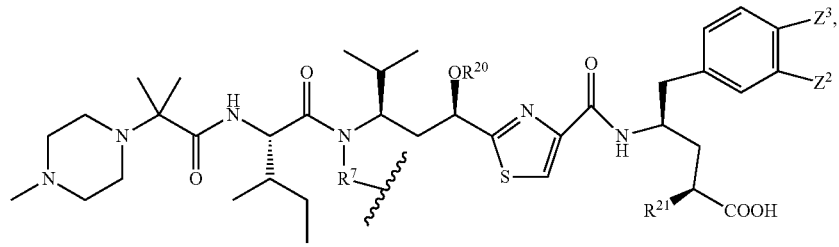
III-63
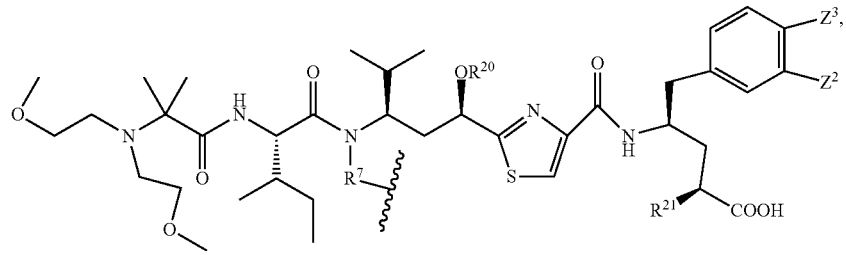
III-64
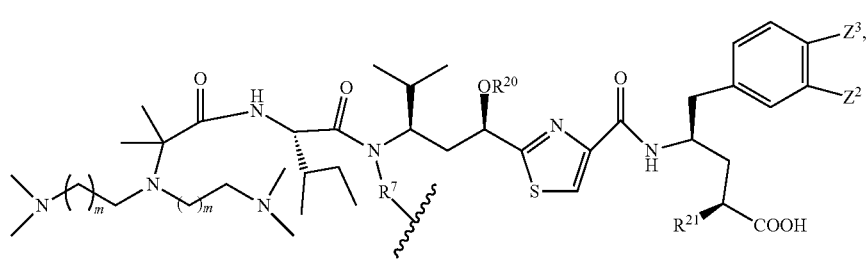
III-65
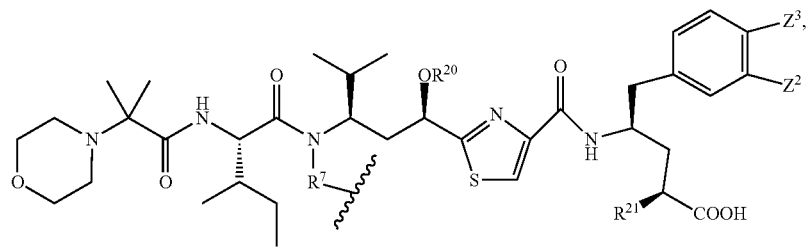
III-66
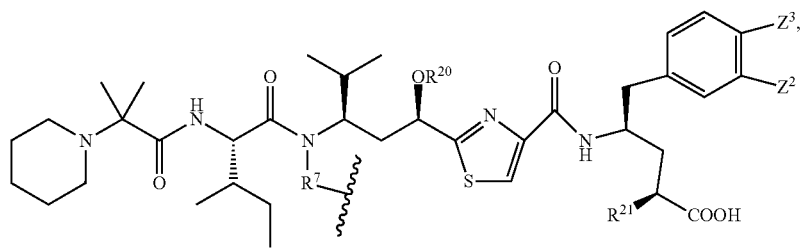
III-67

-continued
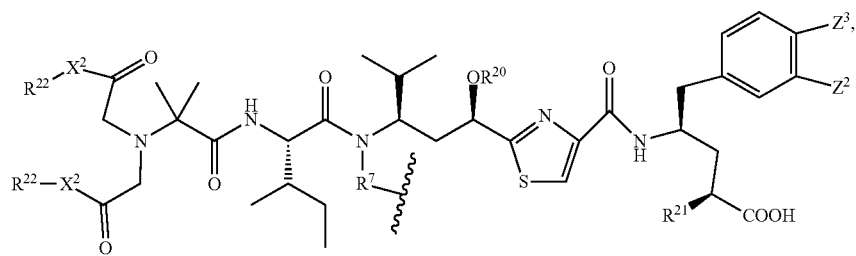 III-68
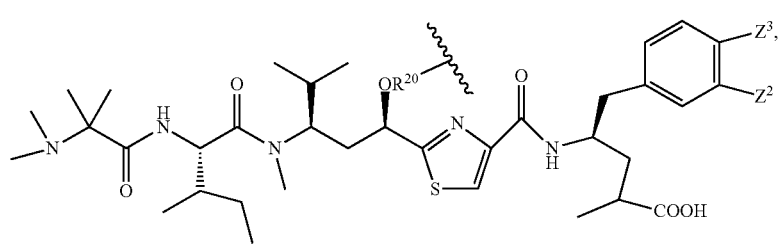 IV-01
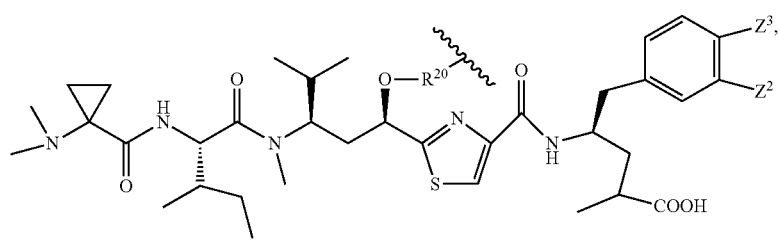 IV-02
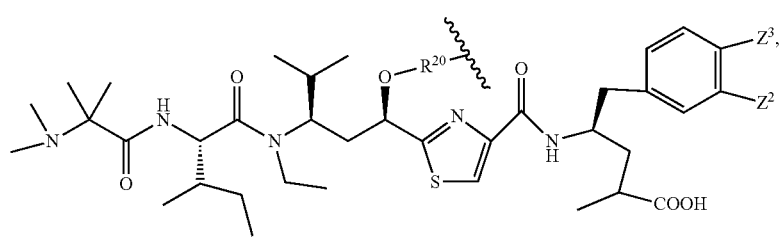 IV-03
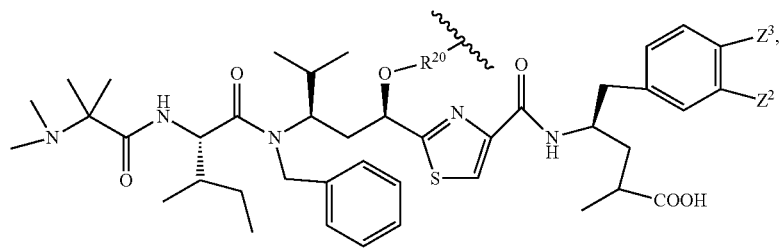 IV-04
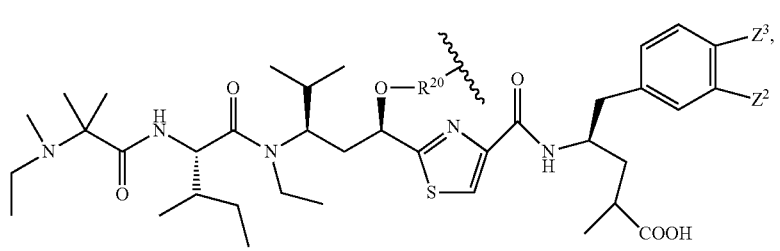 IV-05

-continued
IV-06
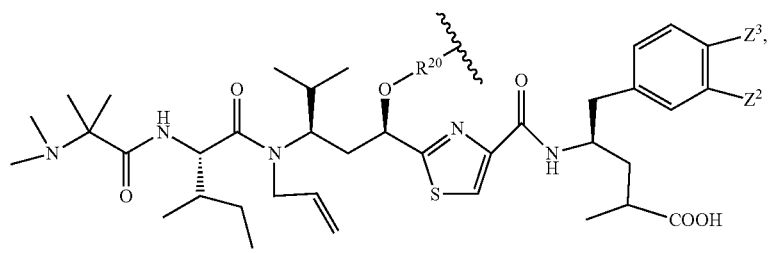
IV-07
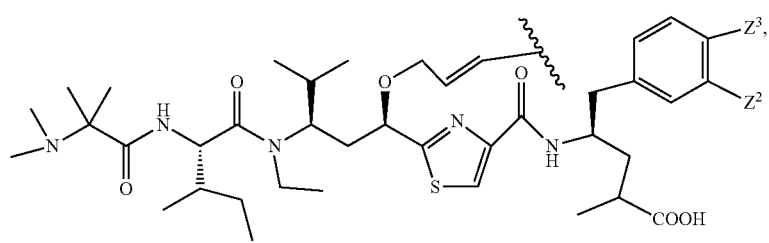
IV-08
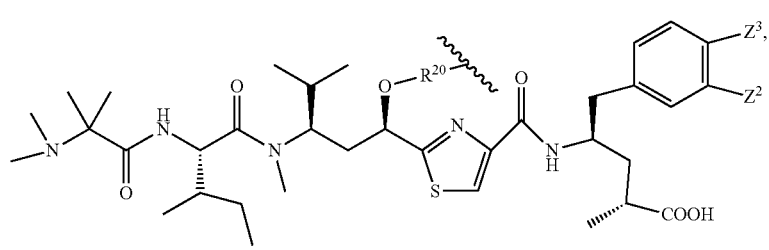
IV-09
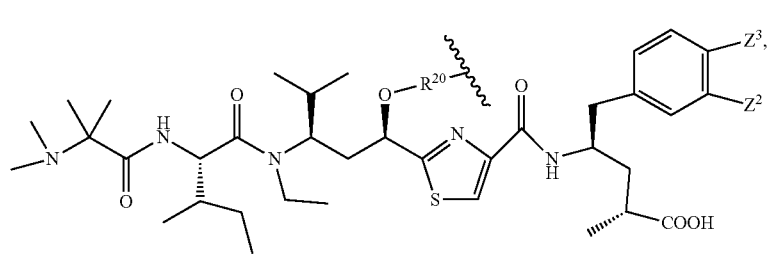
IV-10
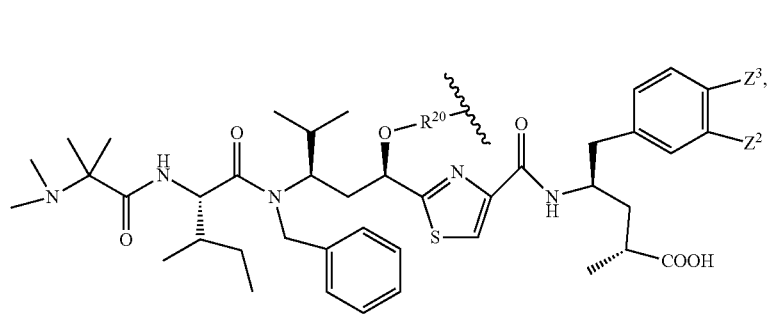
IV-11
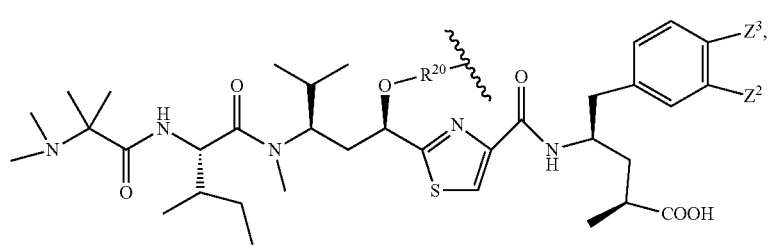

IV-12
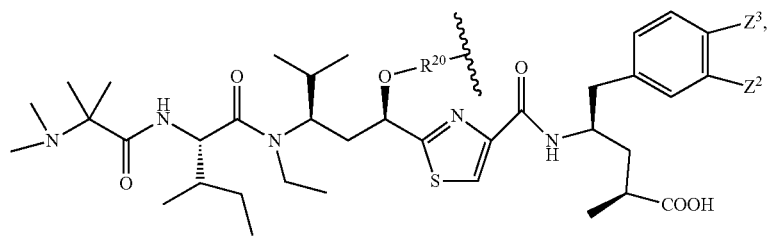
IV-13
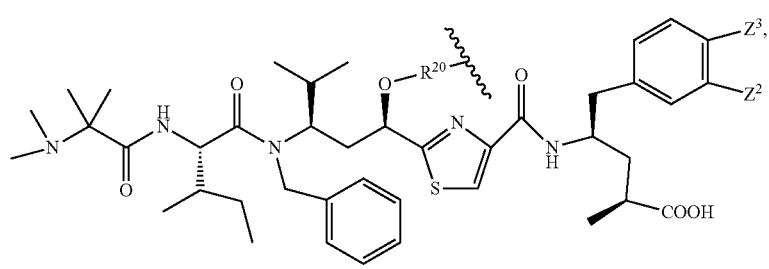
IV-14
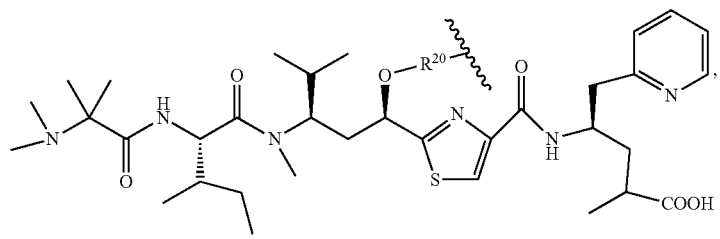
IV-15
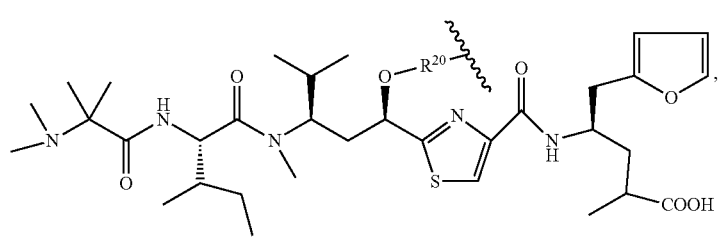
IV-16
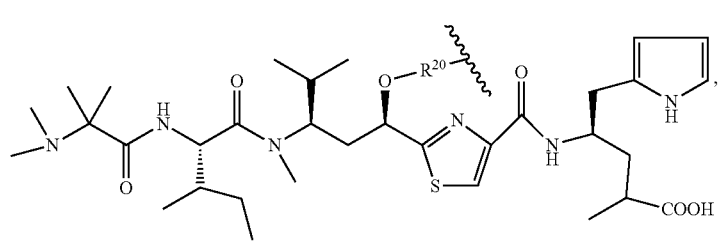
IV-17
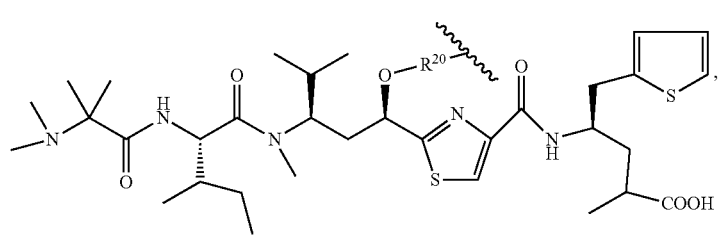

IV-18
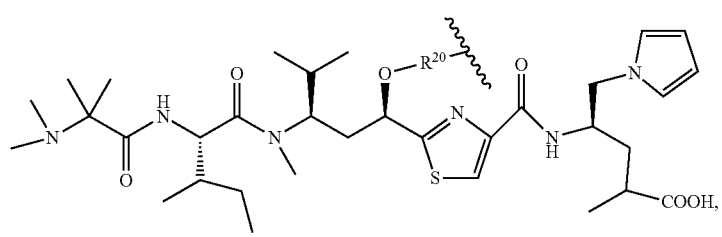
IV-19
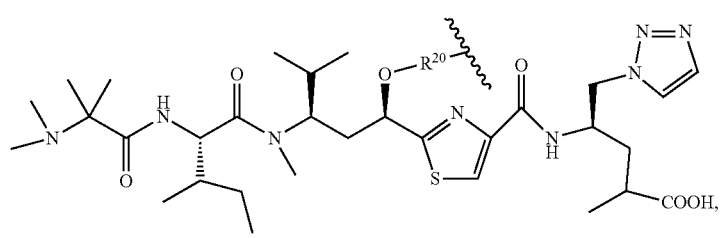
IV-20
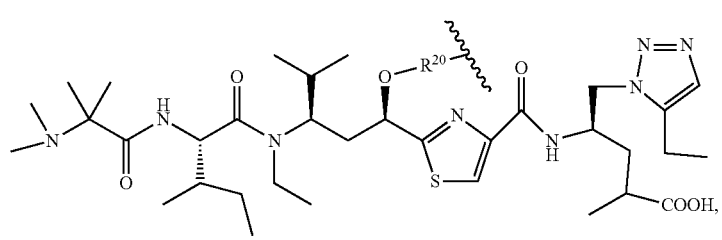
IV-21
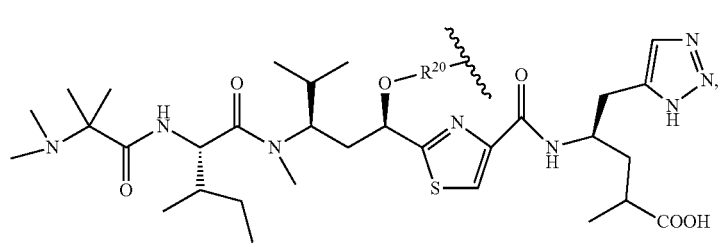
IV-22
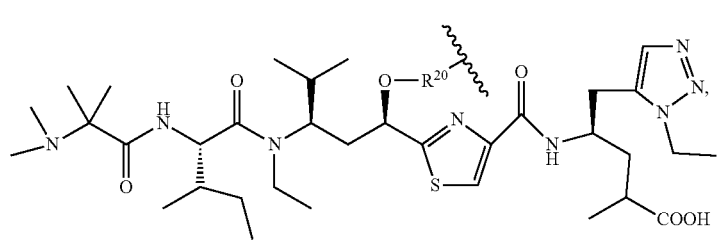
IV-23
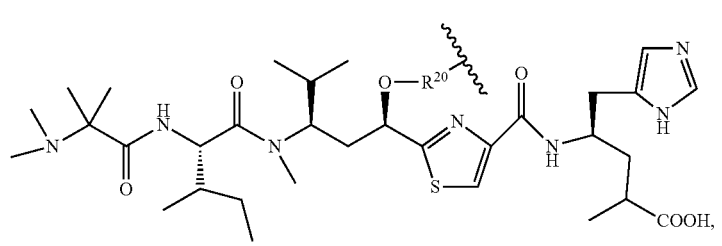
IV-24
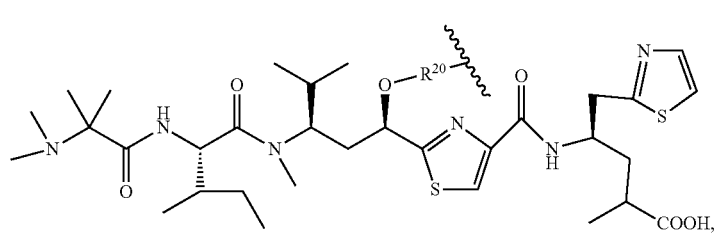

IV-25
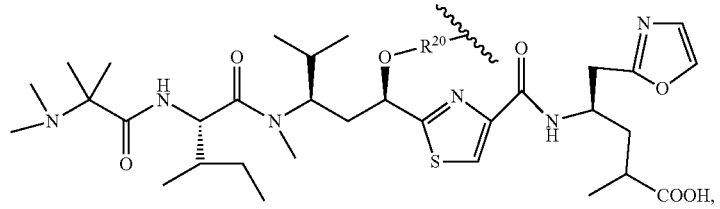
IV-26
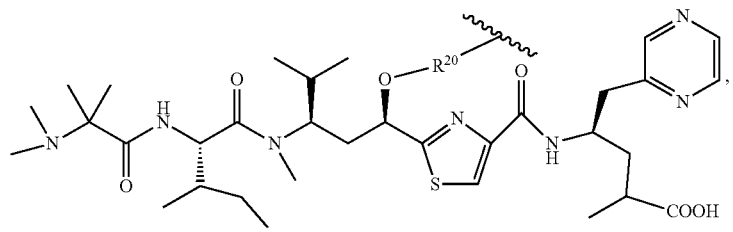
IV-27
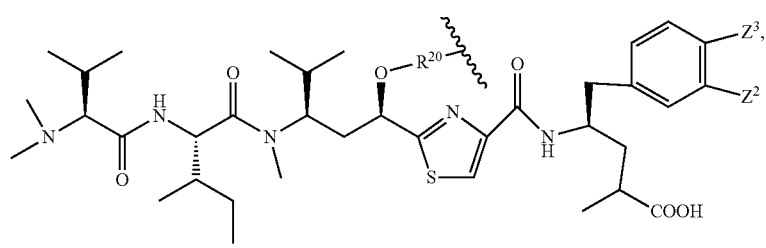
IV-28
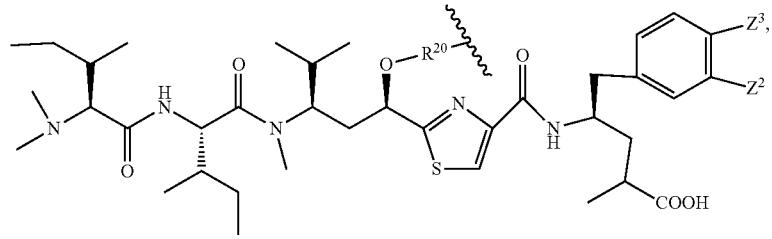
IV-29
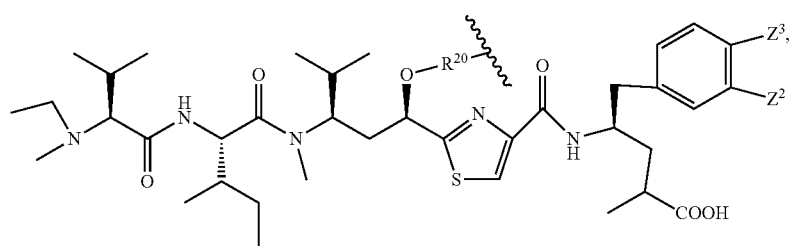
IV-30
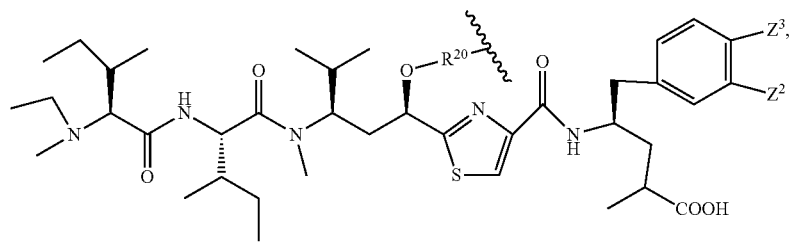
IV-31
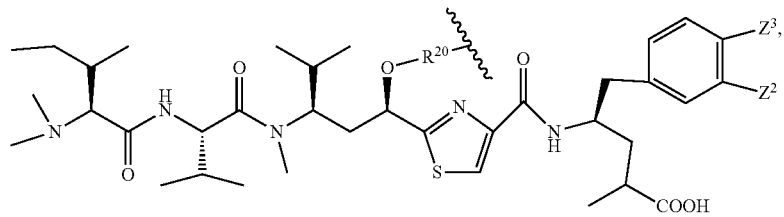

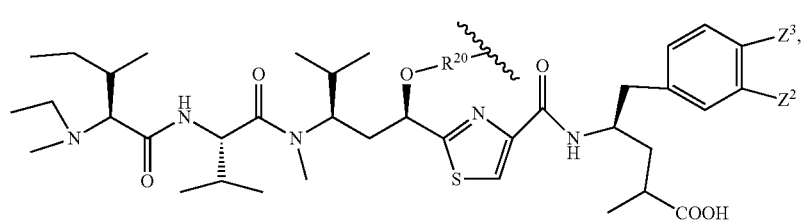
IV-32
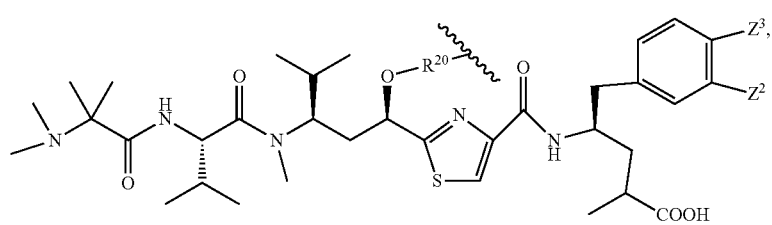
IV-33
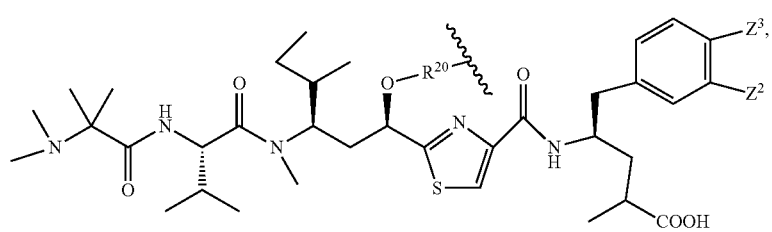
IV-34
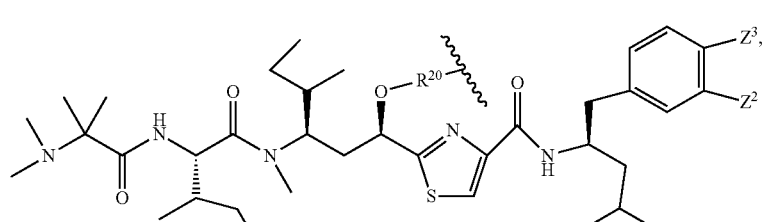
IV-35
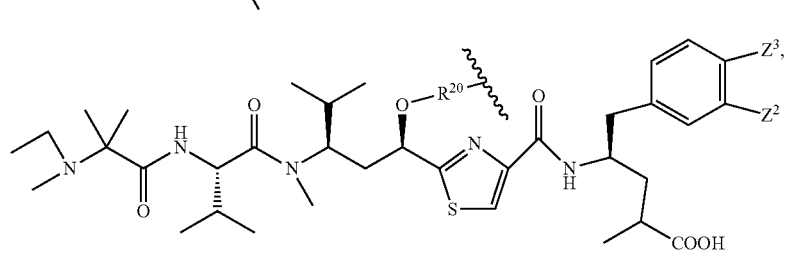
IV-36
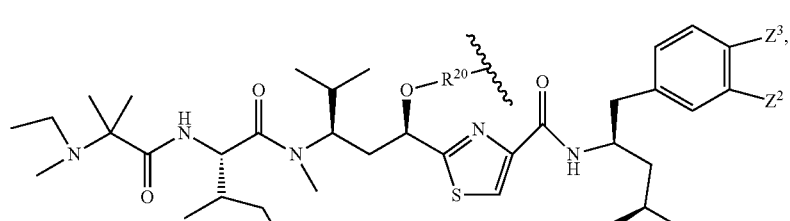
IV-37
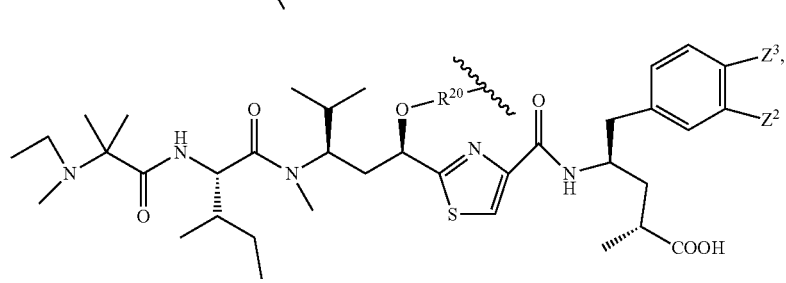
IV-38

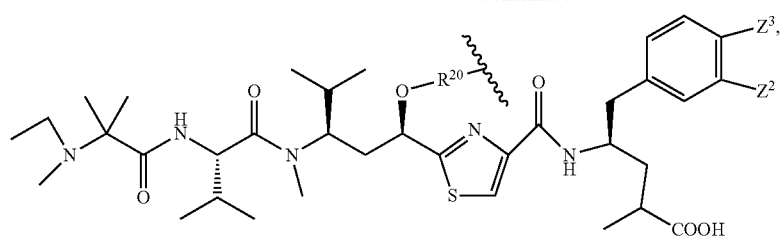
IV-39
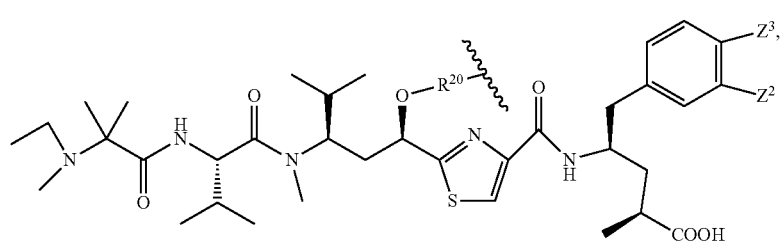
IV-40
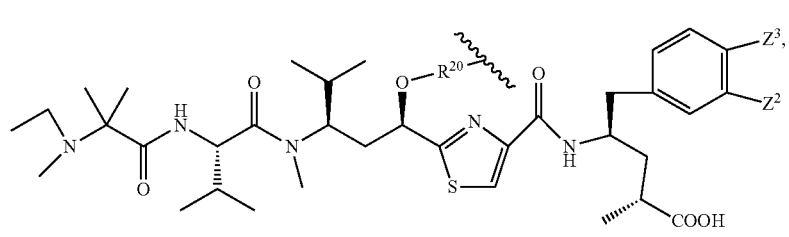
IV-41
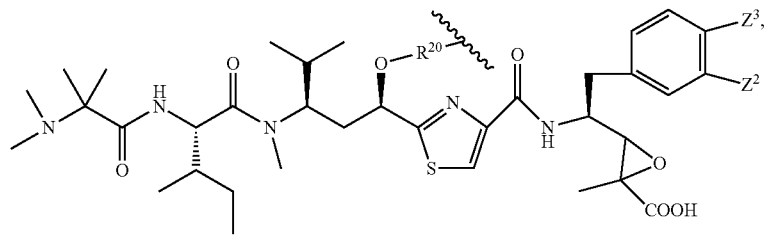
IV-42
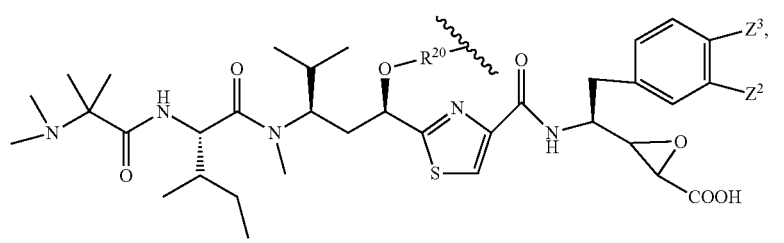
IV-43
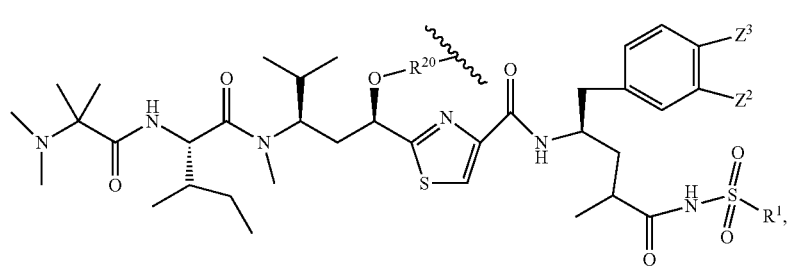
IV-44
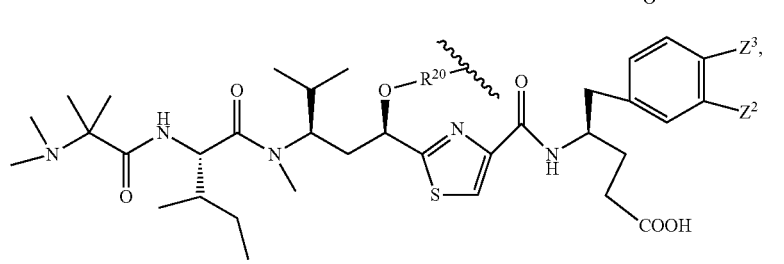
IV-45

-continued
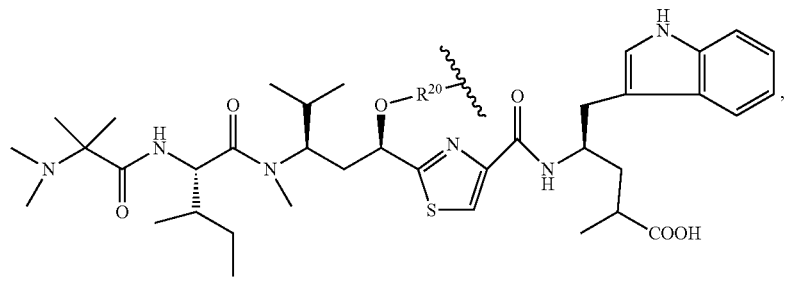
IV-46
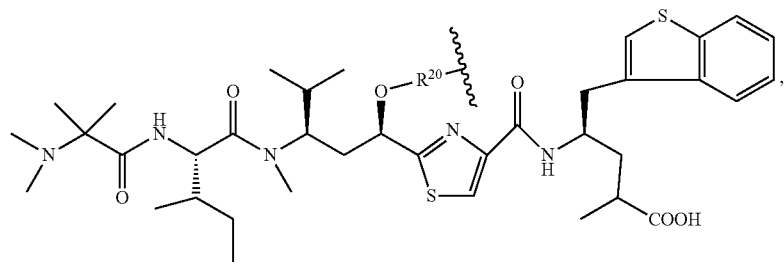
IV-47
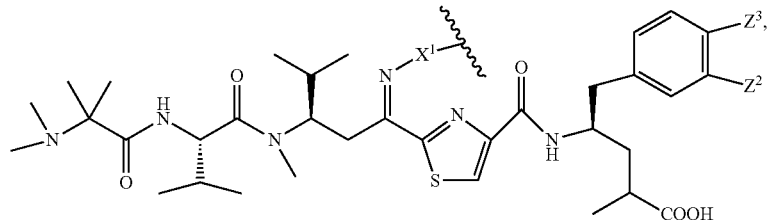
IV-48
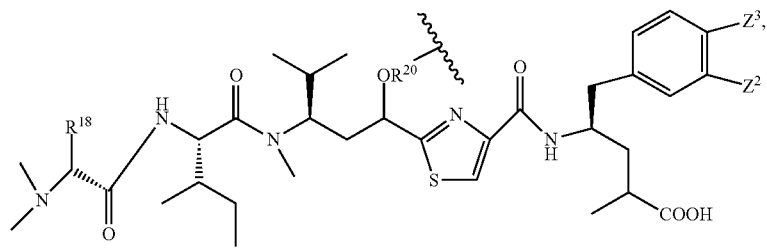
IV-49
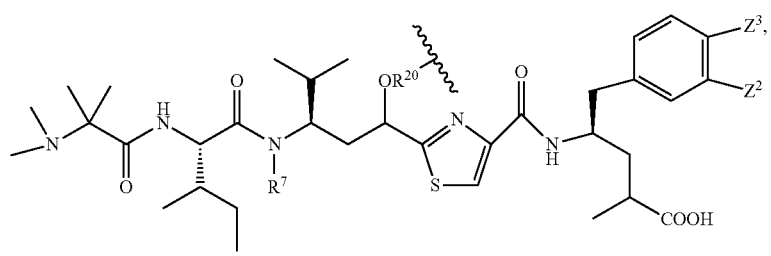
IV-50
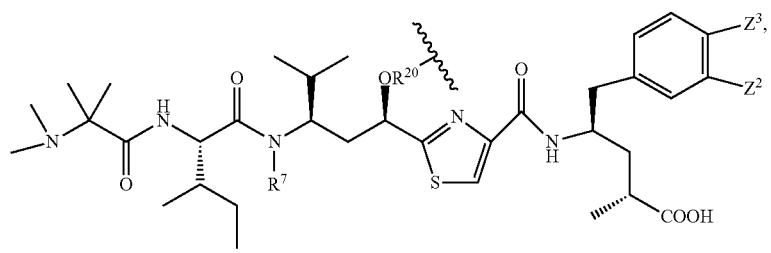
IV-51

-continued
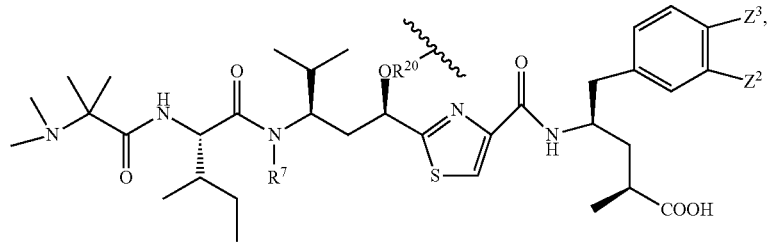
IV-52
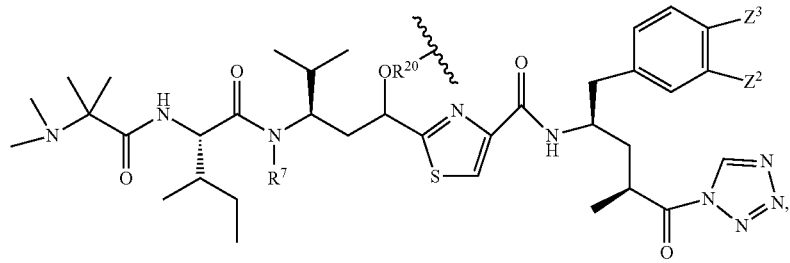
IV-53
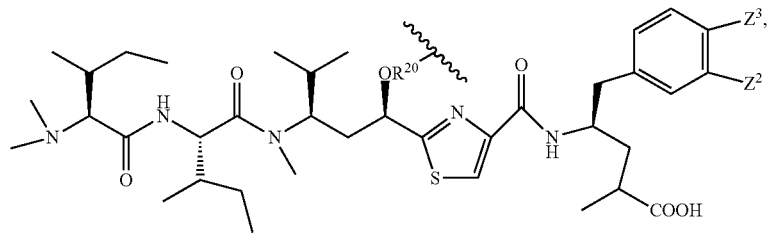
IV-54
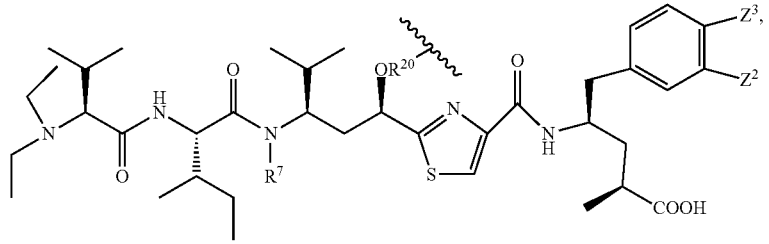
IV-55
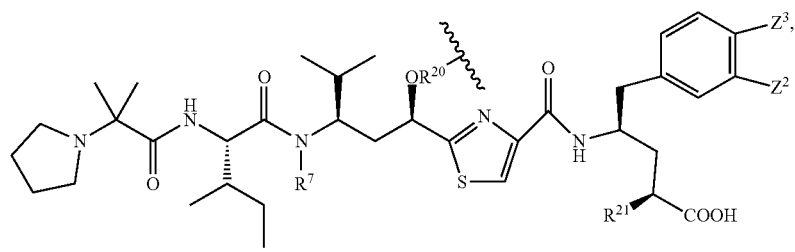
IV-56
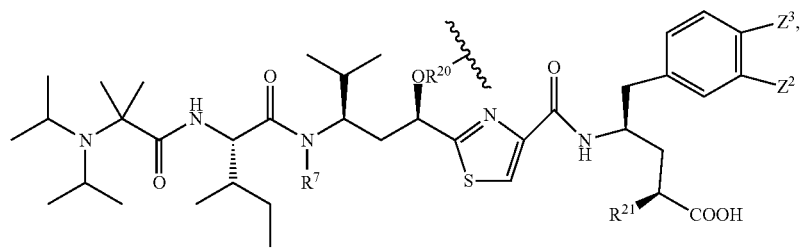
IV-57

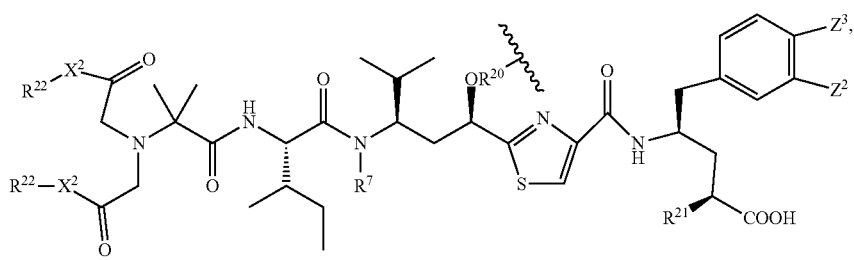
IV-58
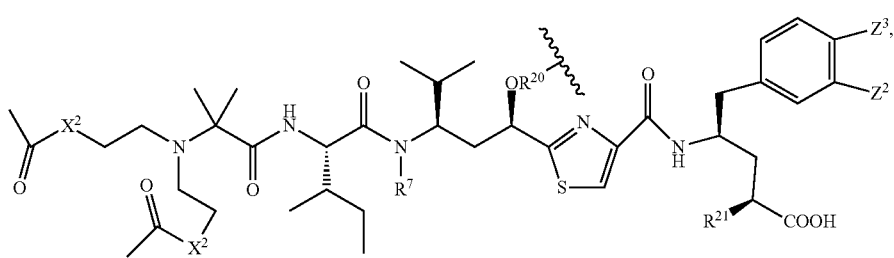
IV-59
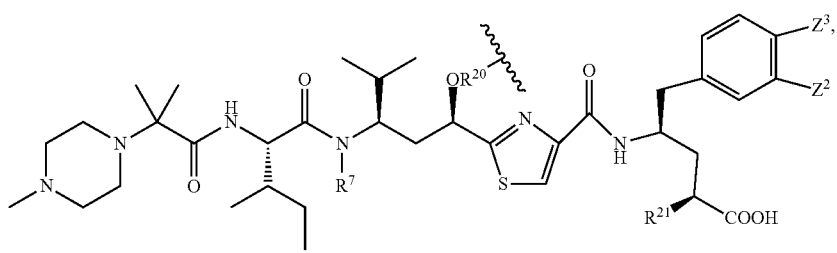
IV-60
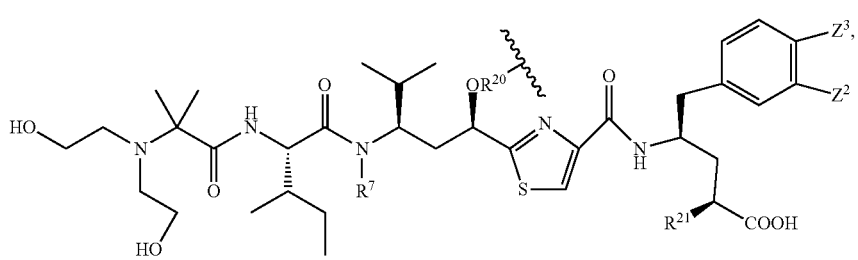
IV-61
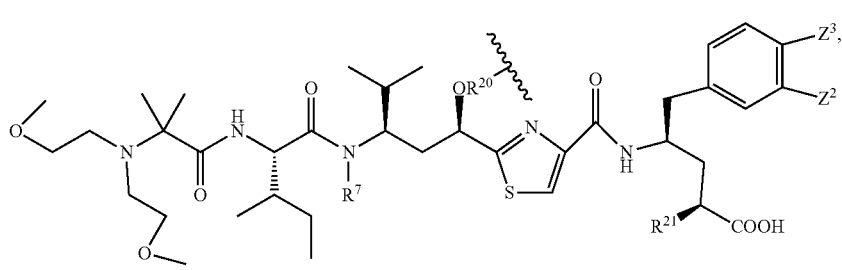
IV-62
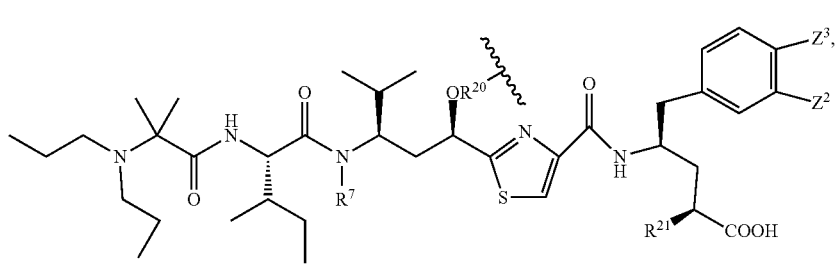
IV-63

-continued
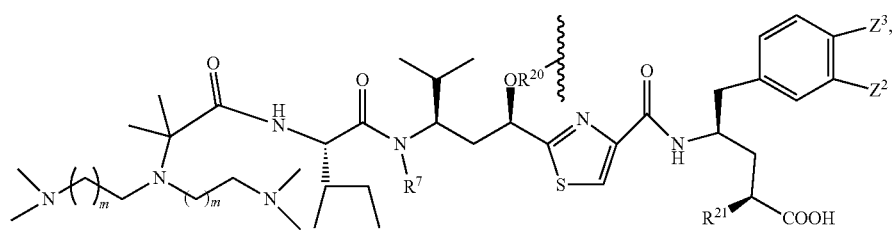
IV-64
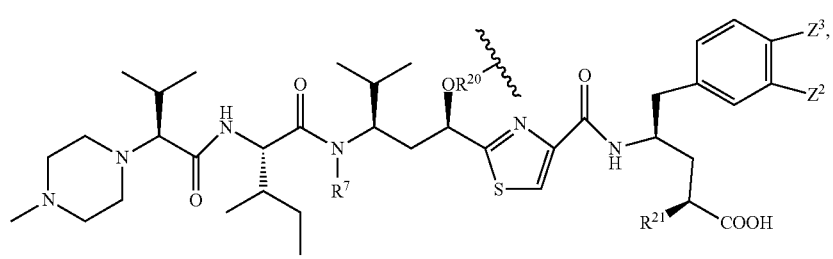
IV-65
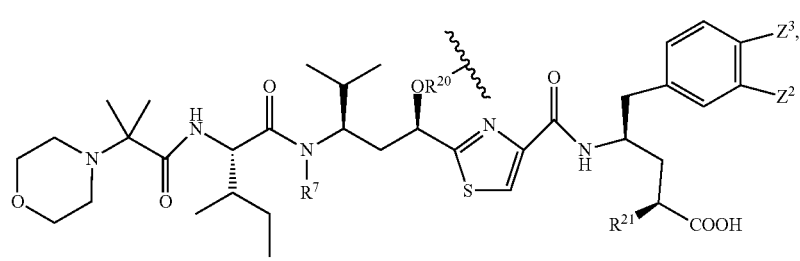
IV-66
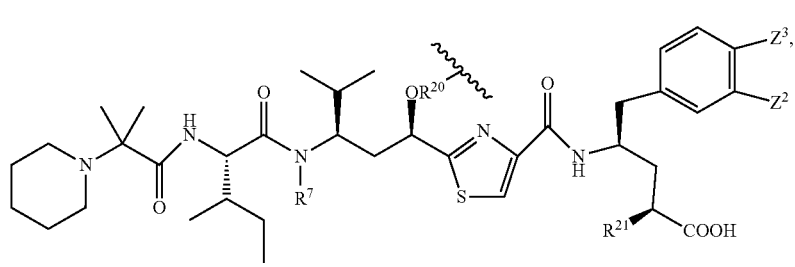
IV-67
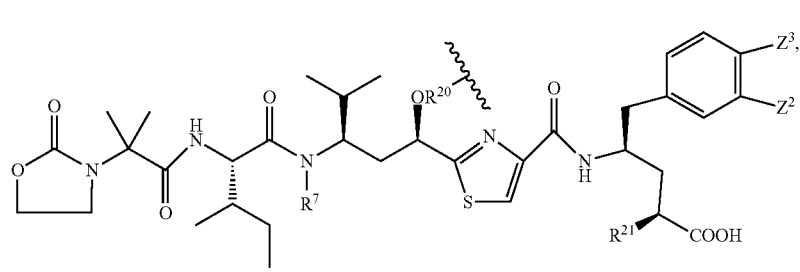
IV-68
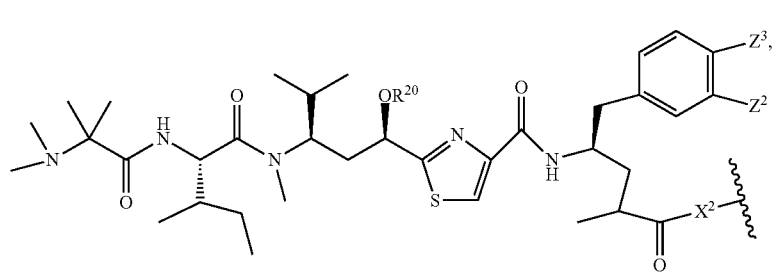
V-01

-continued
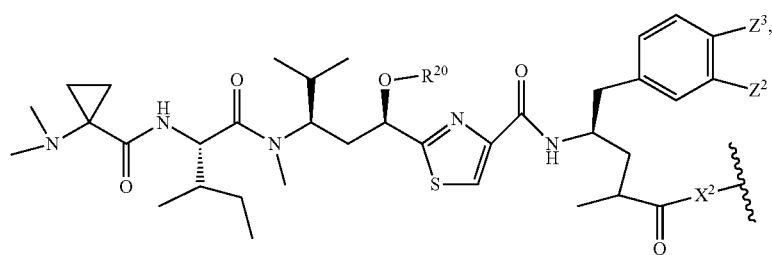
V-02
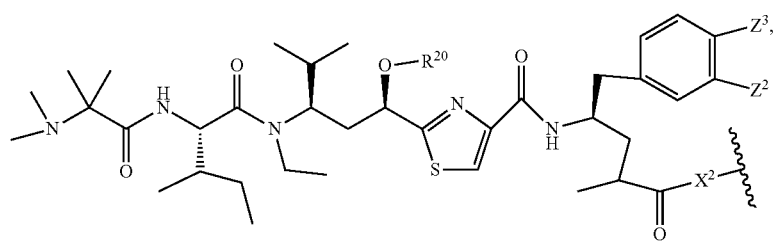
V-03
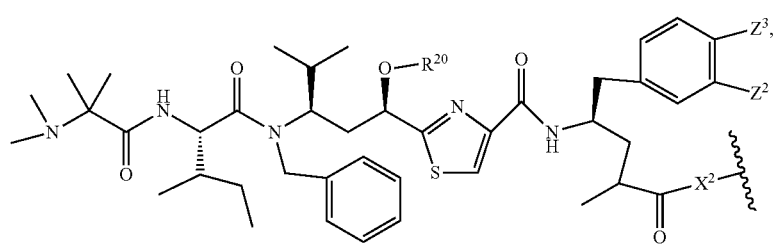
V-04
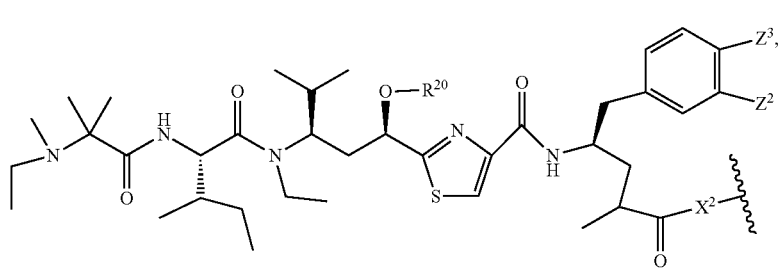
V-05
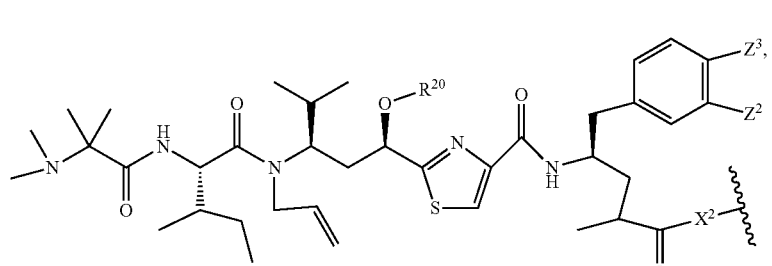
V-06
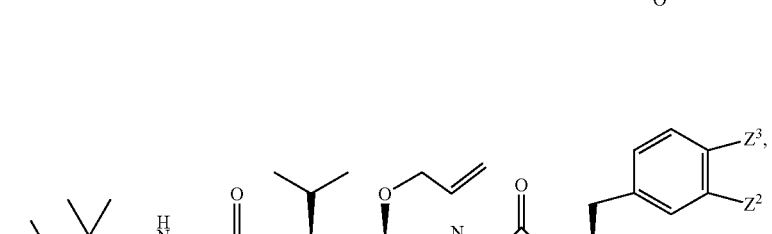
V-07
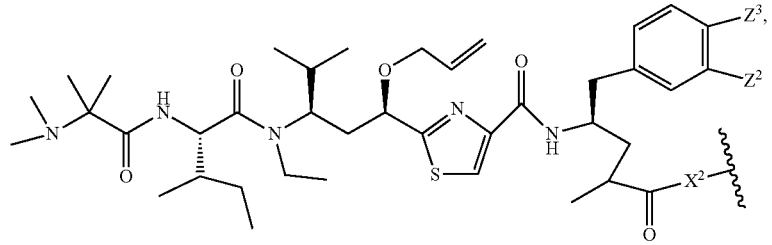

-continued
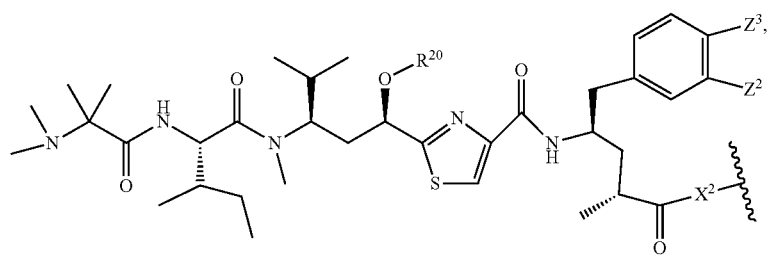
V-08
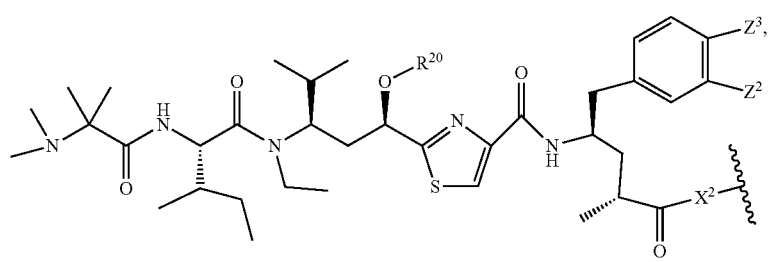
V-09
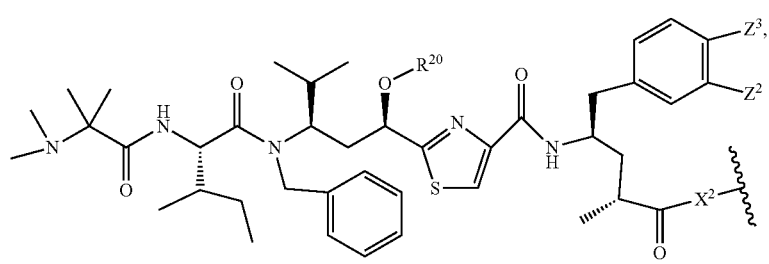
V-10
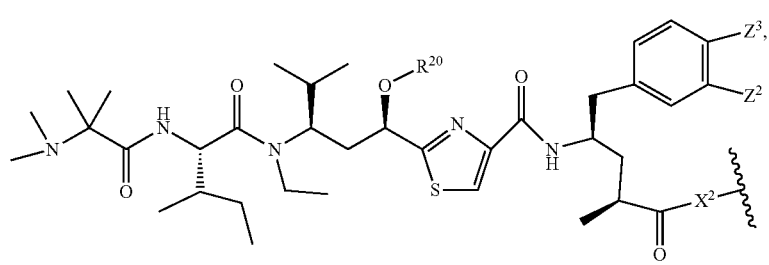
V-11
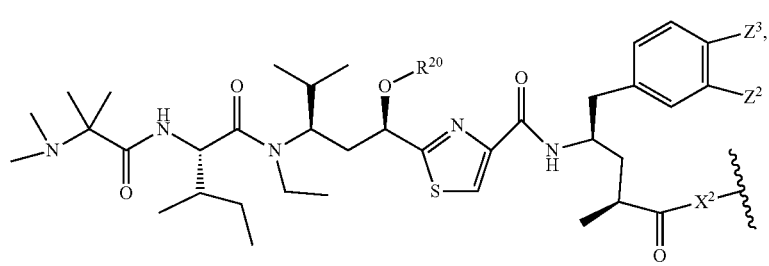
V-12
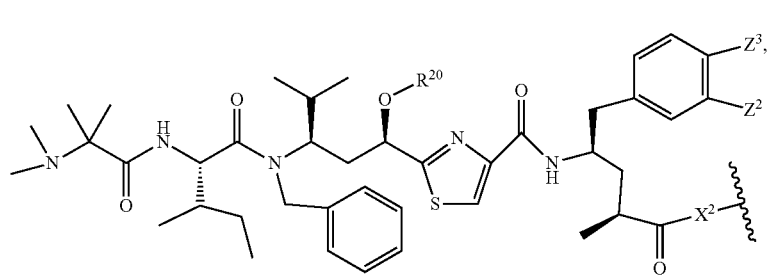
V-13

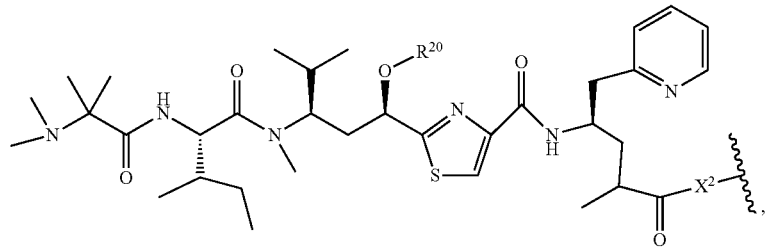
V-14
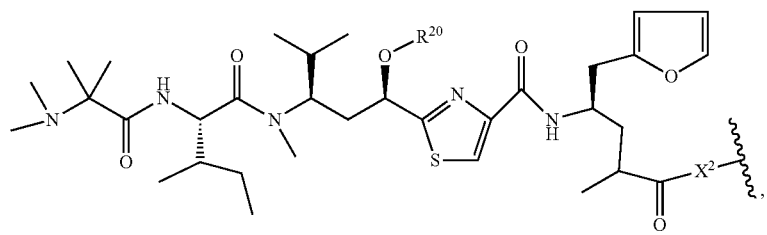
V-15
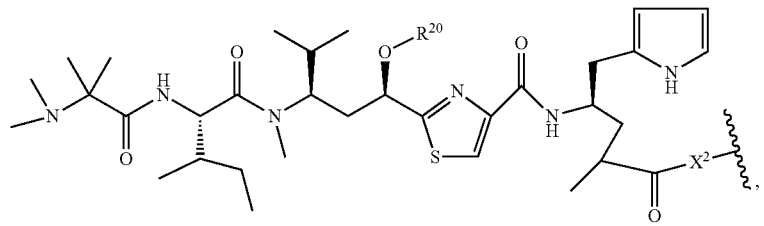
V-16
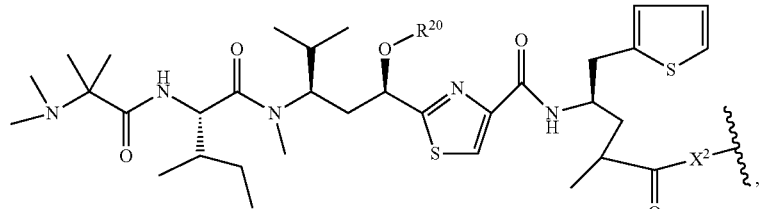
V-17
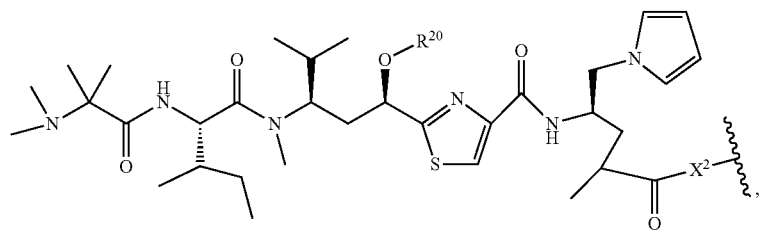
V-18
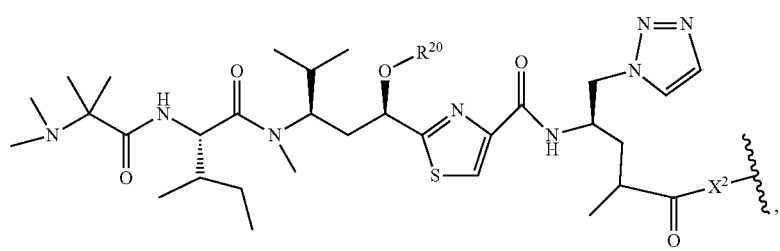
V-19
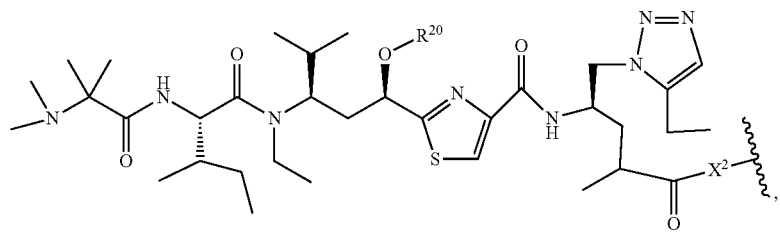
V-20

-continued
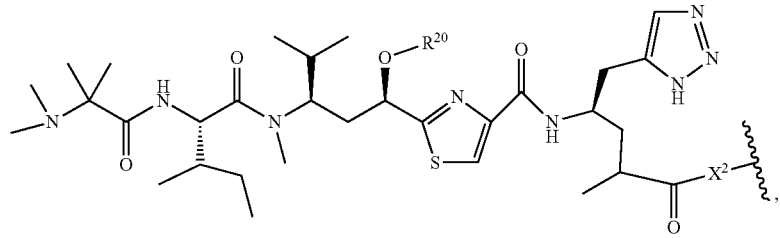
V-21
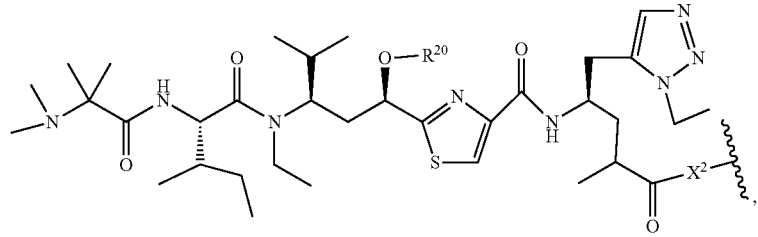
V-22
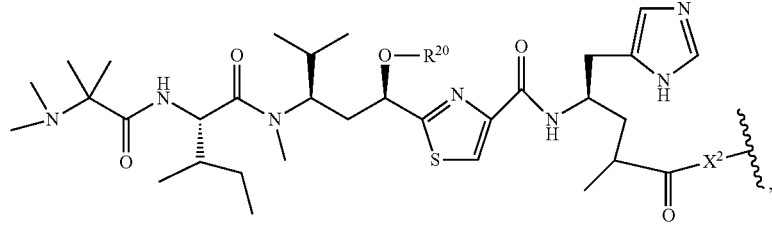
V-23
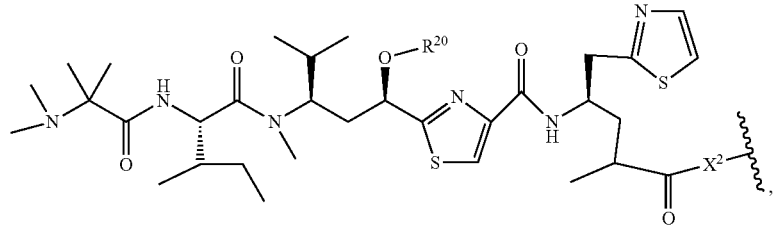
V-24
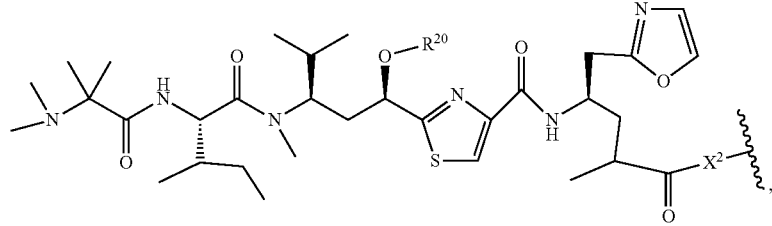
V-25
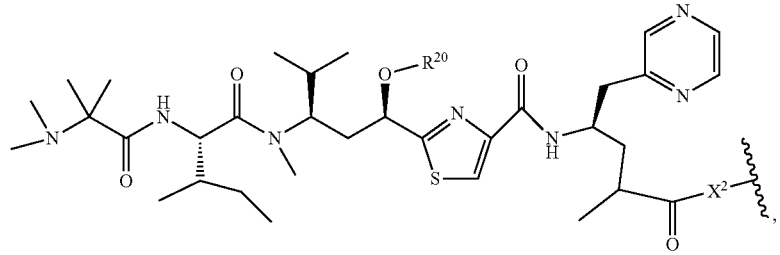
V-26

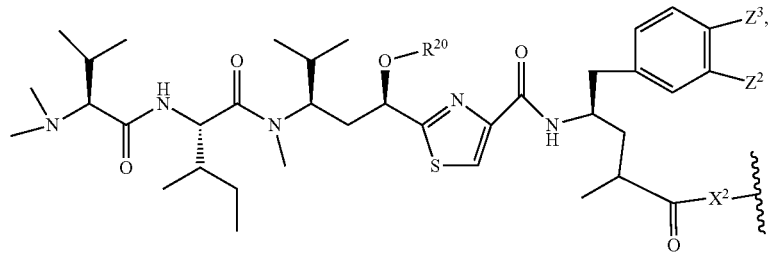
V-27
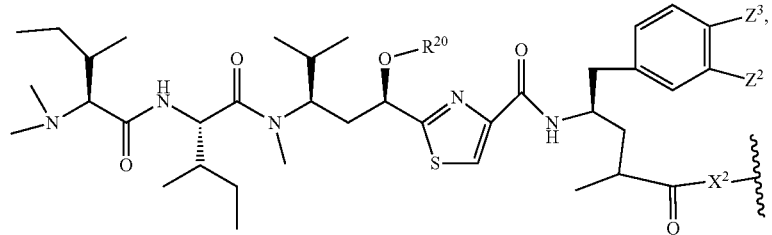
V-28
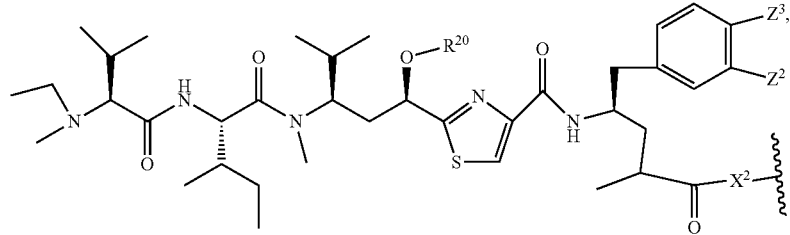
V-29
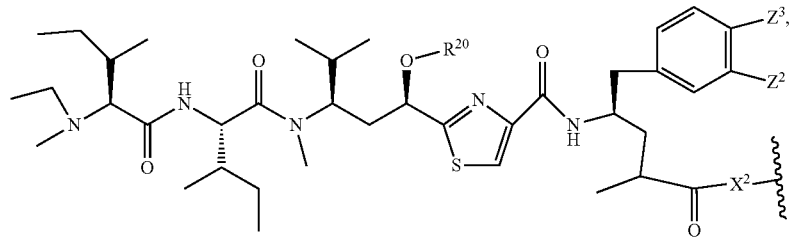
V-30
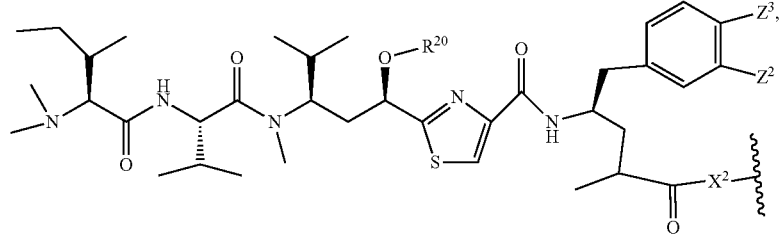
V-31
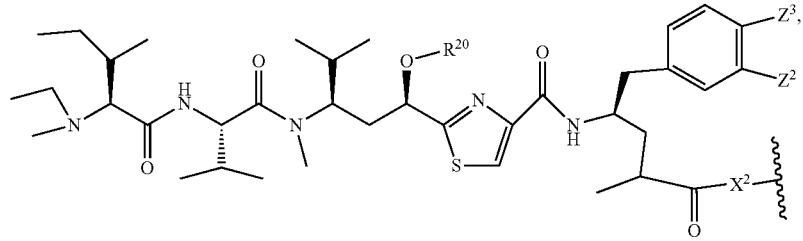
V-32

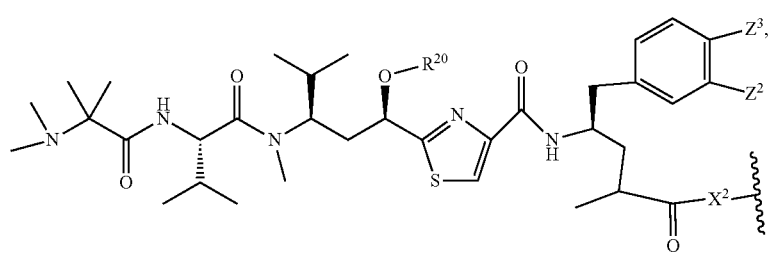
V-33
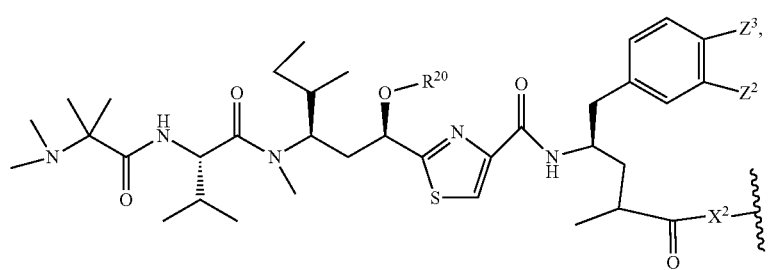
V-34
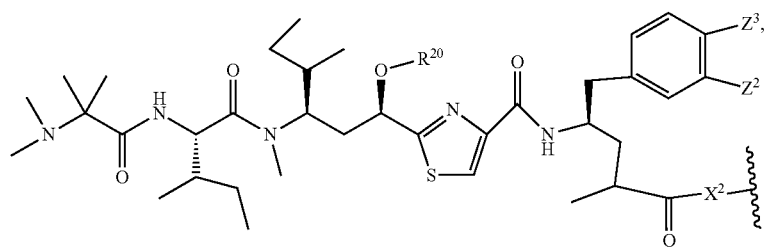
V-35
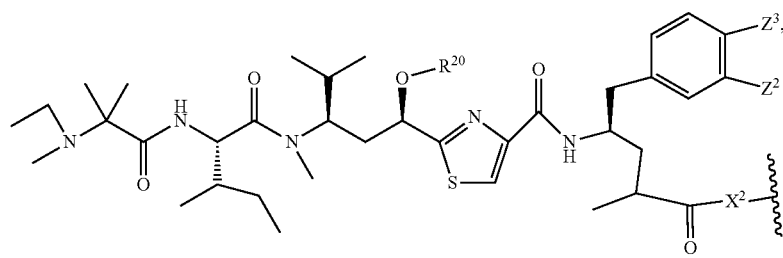
V-36
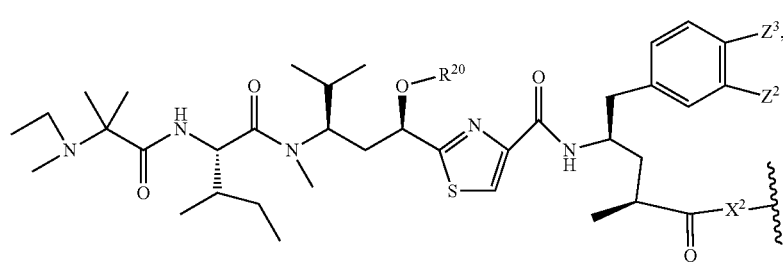
V-37
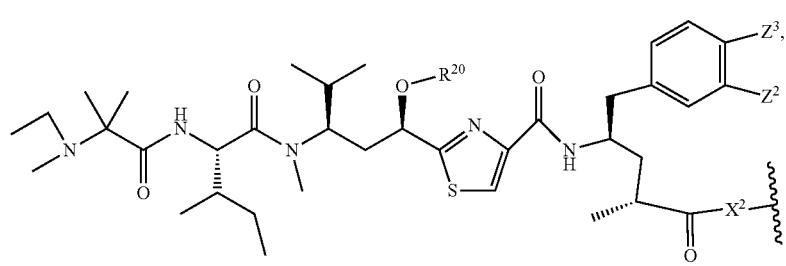
V-38

-continued
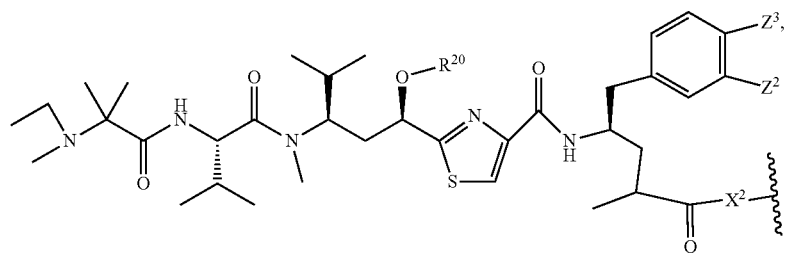
V-39
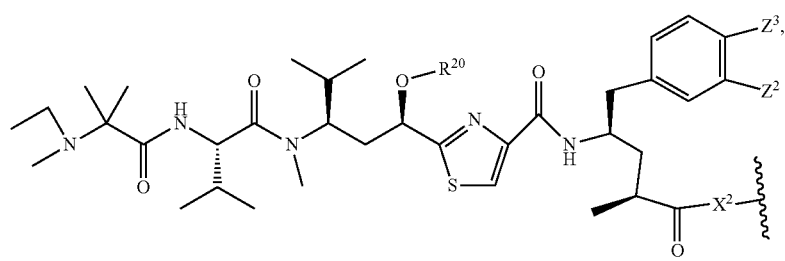
V-40
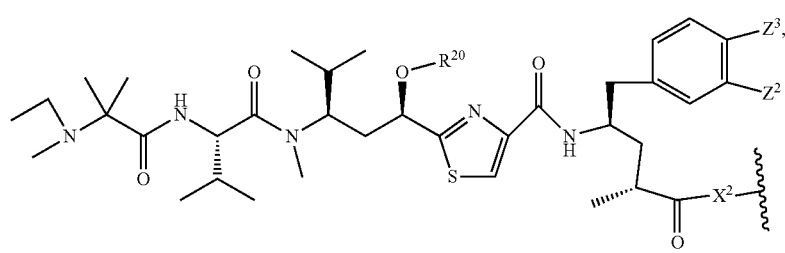
V-41
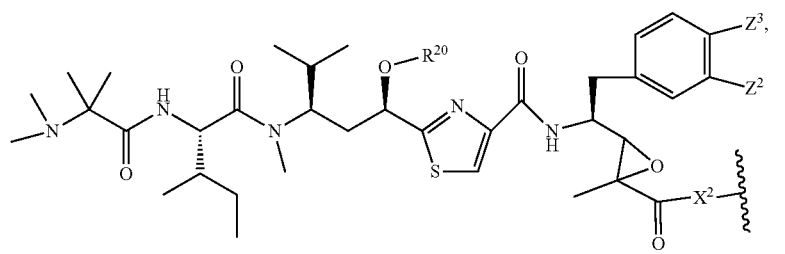
V-42
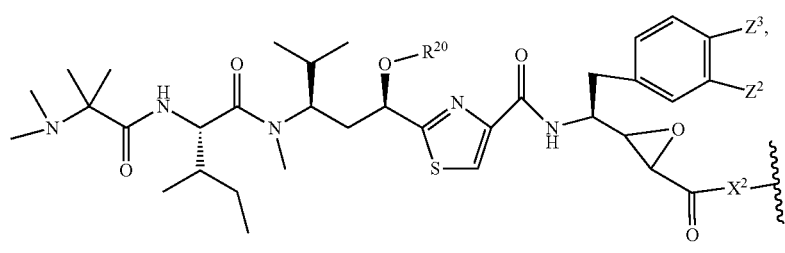
V-43
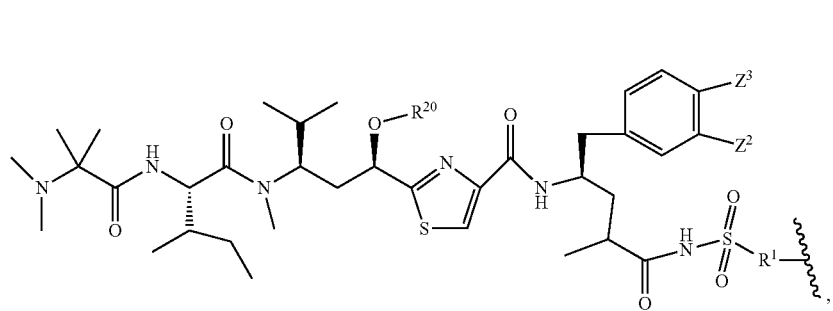
V-44

-continued
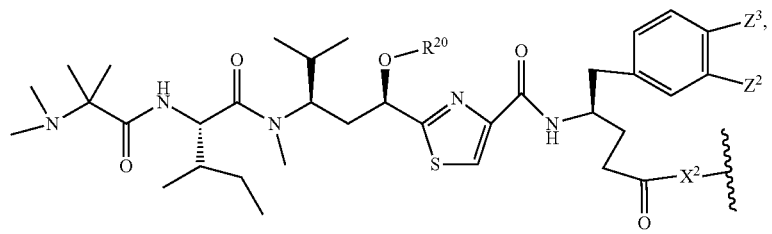
V-45
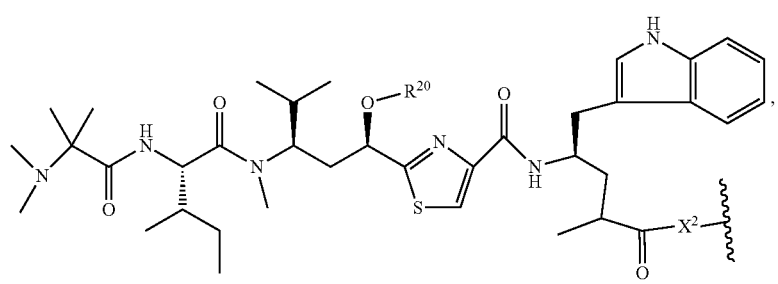
V-46
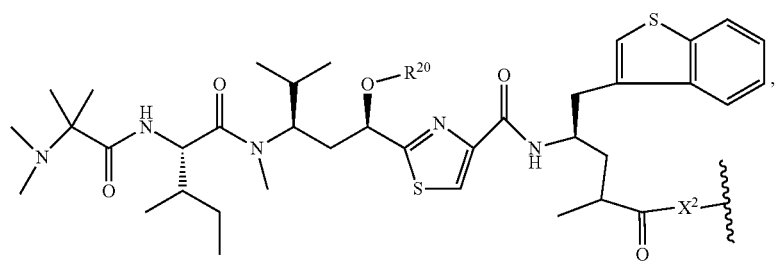
V-47
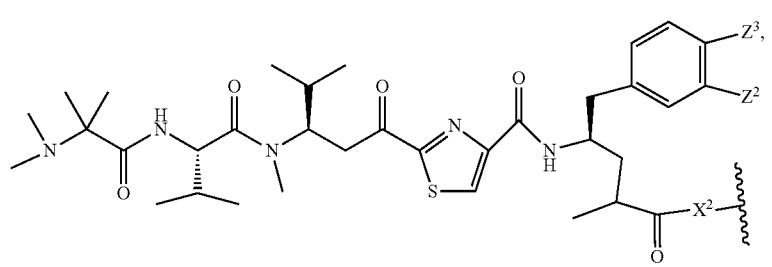
V-48
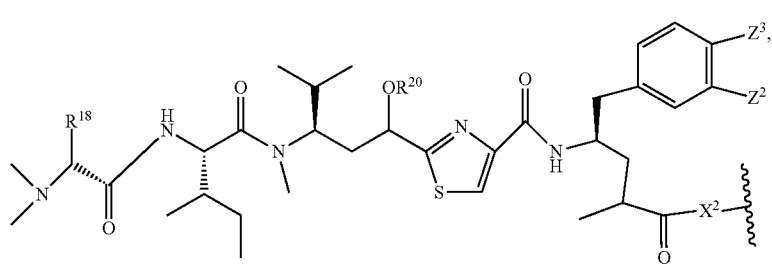
V-49
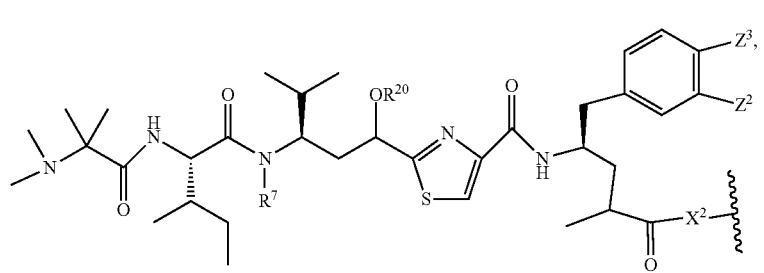
V-50

-continued
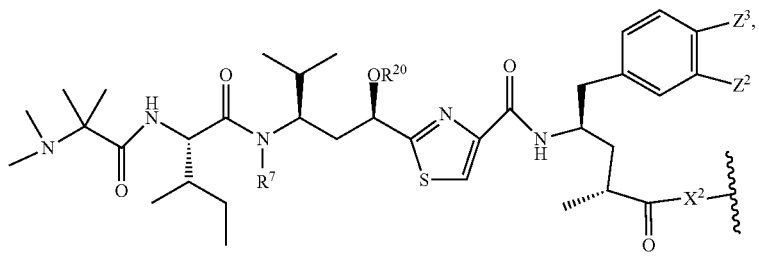
V-51
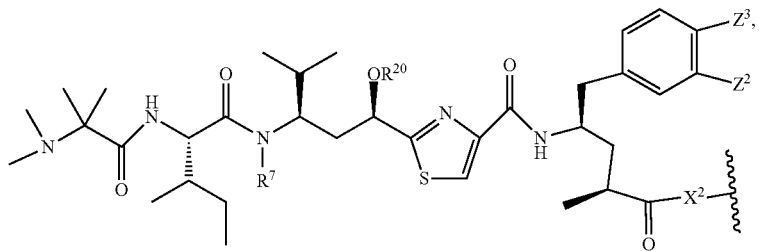
V-52
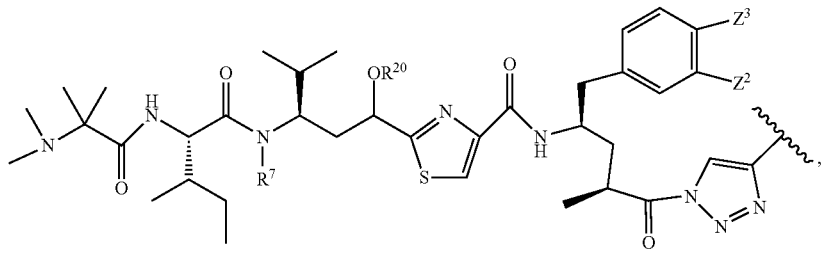
V-53
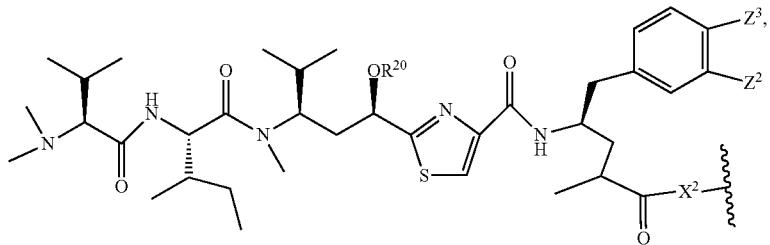
V-54
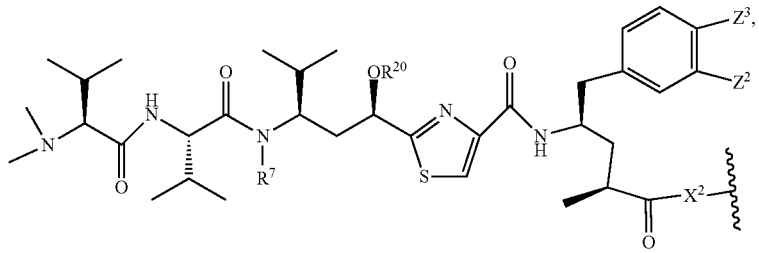
V-55
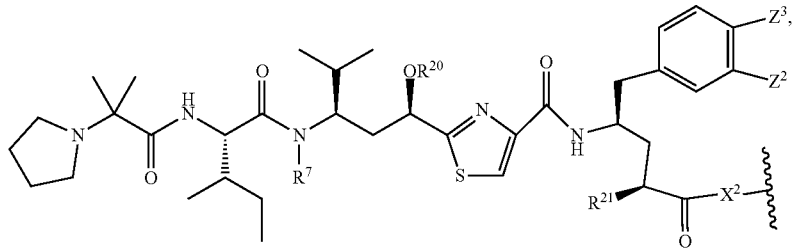
V-56

-continued
V-57
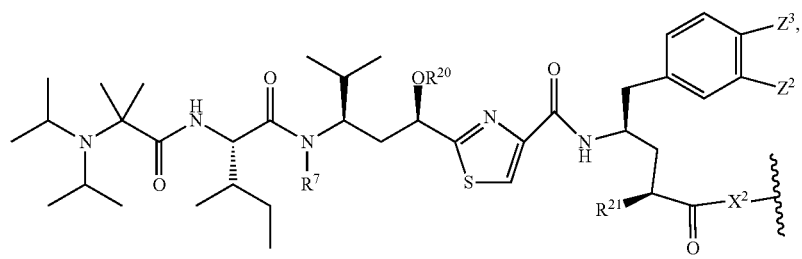
V-58
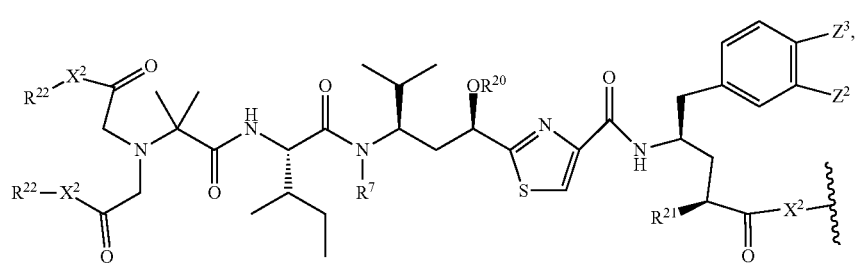
V-59
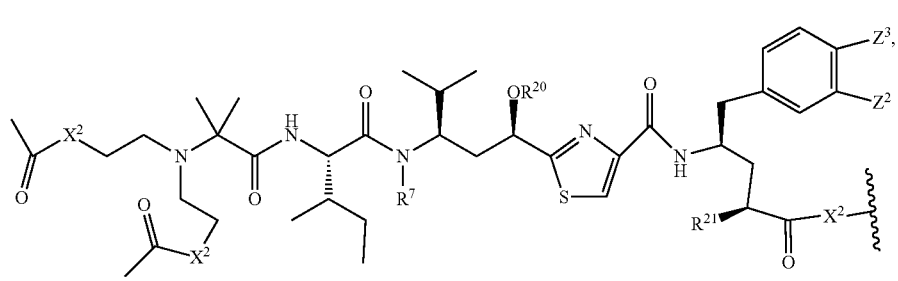
V-60
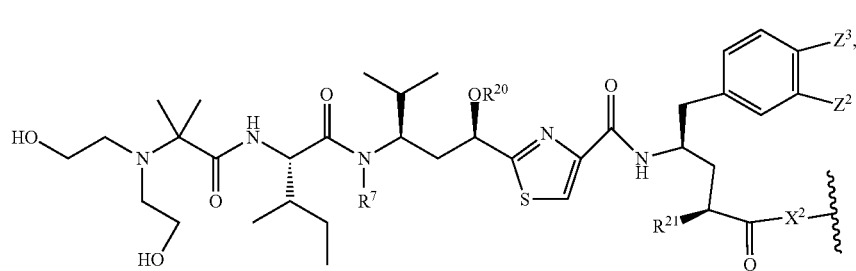
V-61
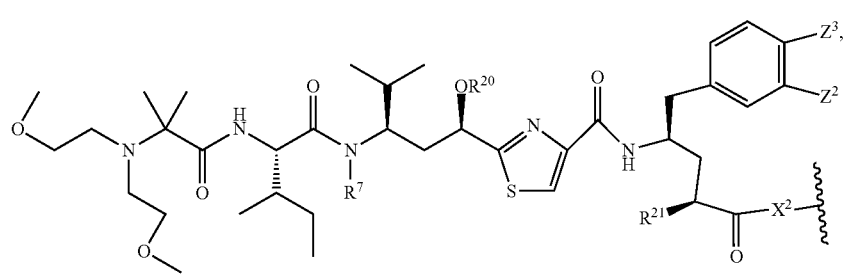
V-62
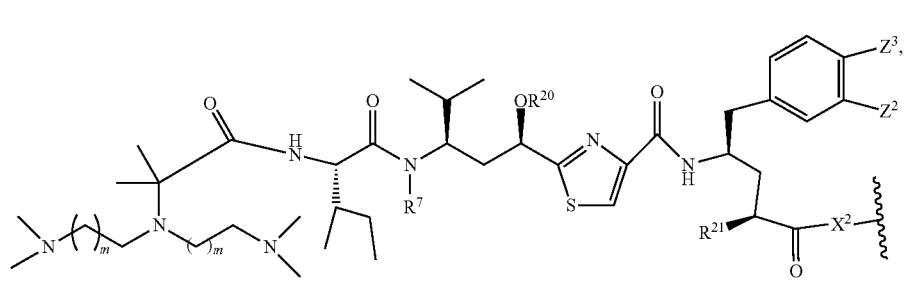

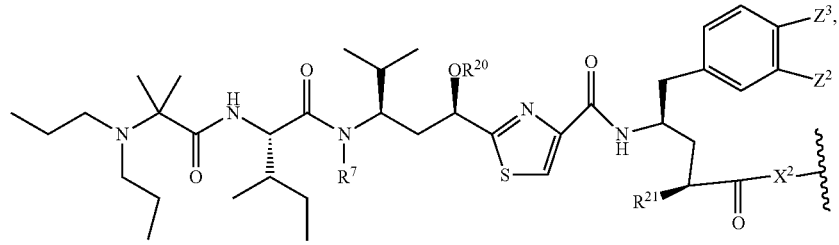
V-63
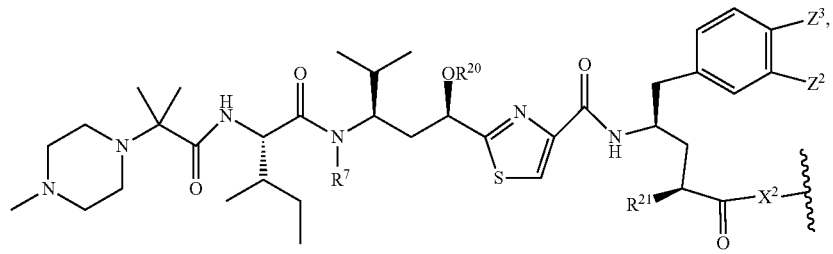
V-64
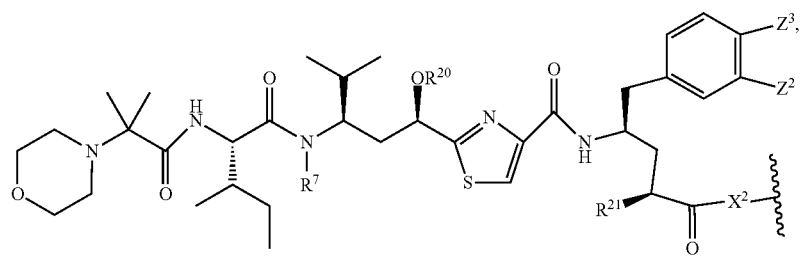
V-65
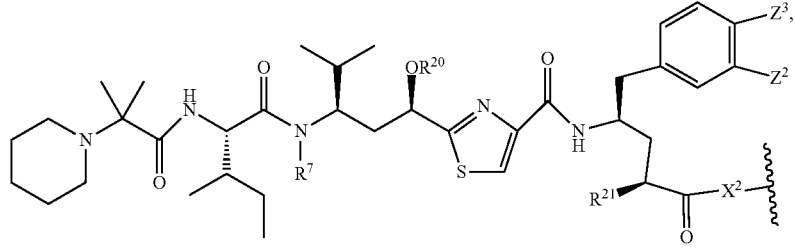
V-66
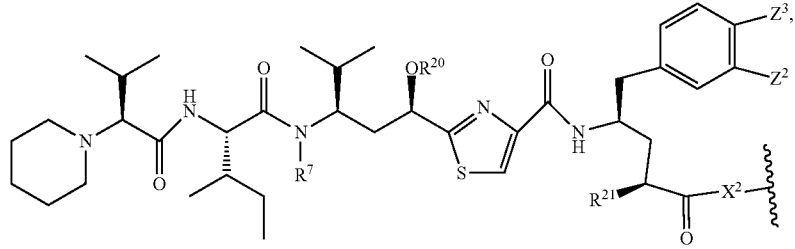
V-67
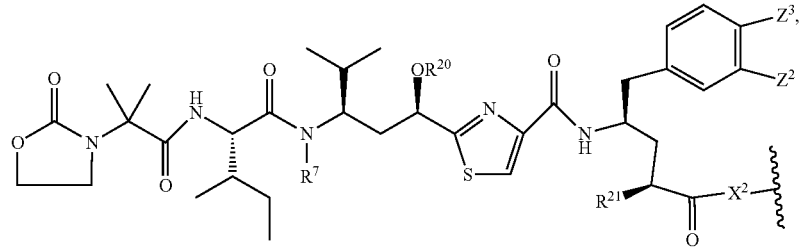
V-68

VI-01
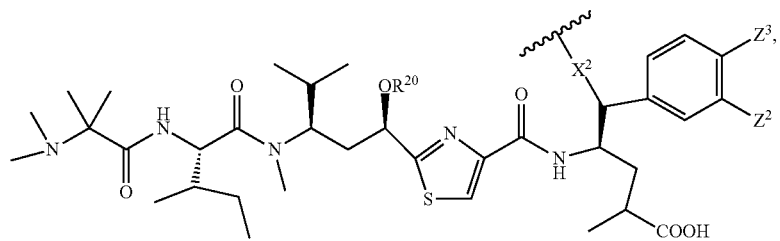
VI-02
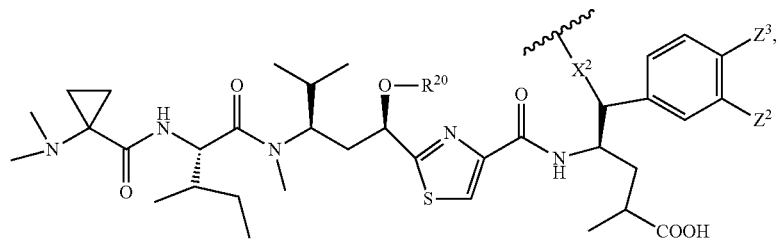
VI-03
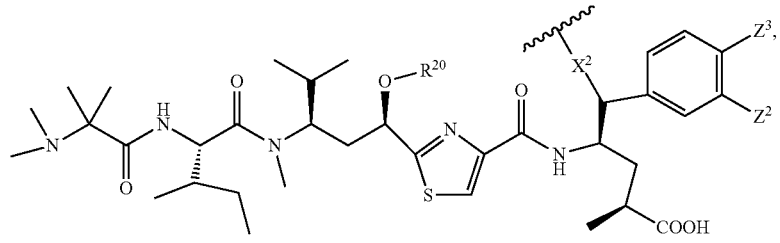
VI-04
VI-05
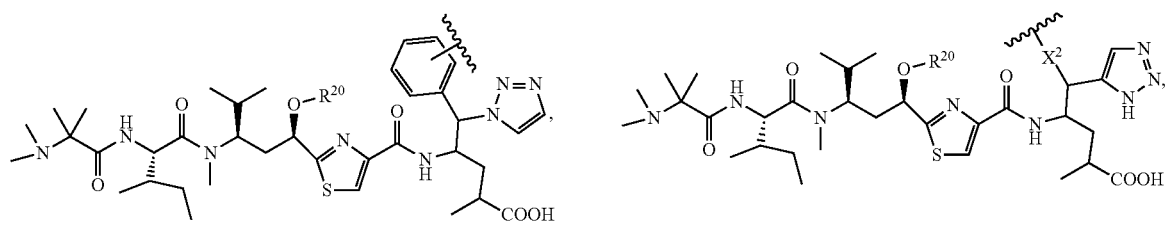
VI-06
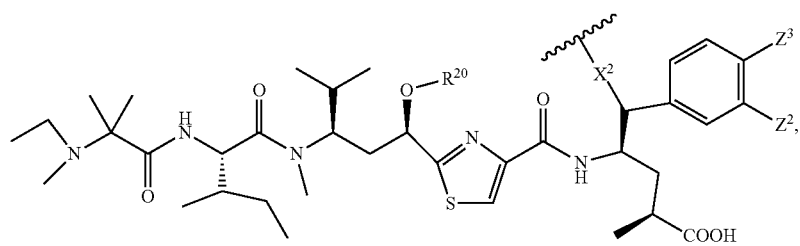
VI-07
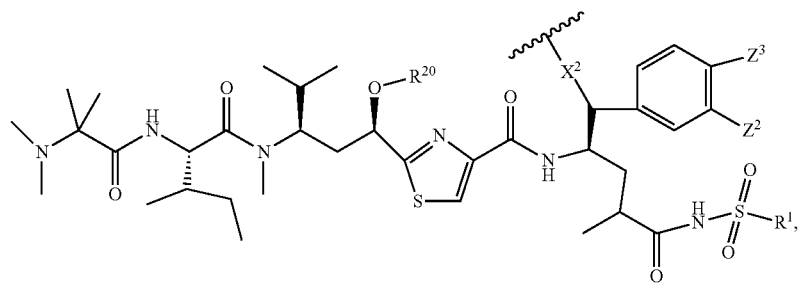

-continued
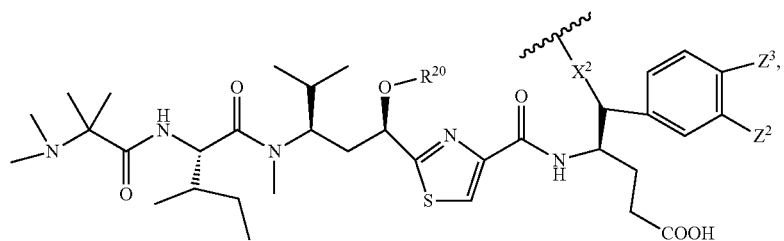
VI-08
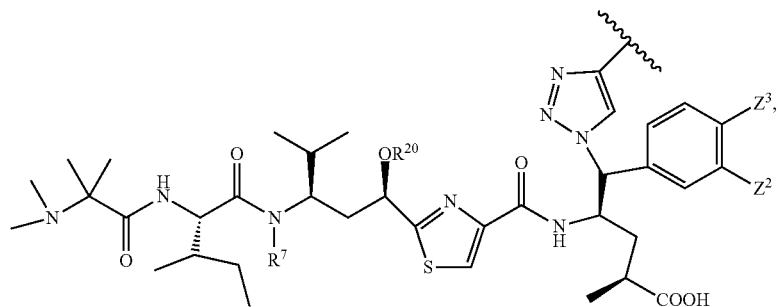
VI-09
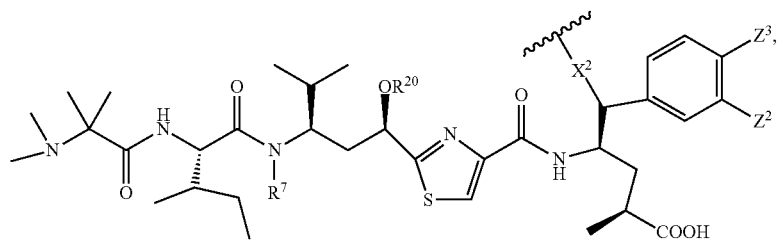
VI-10
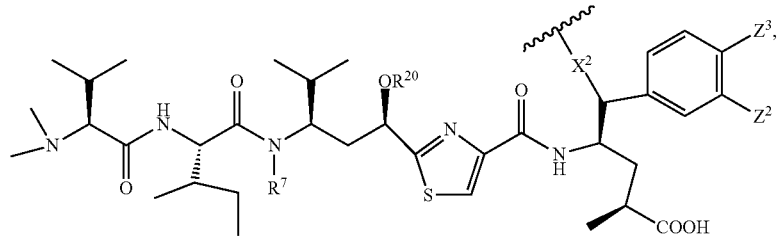
VI-11
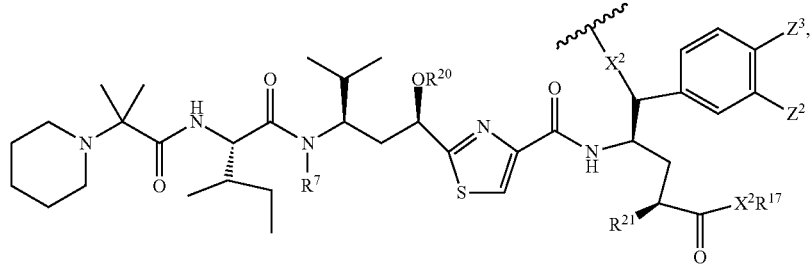
VI-12
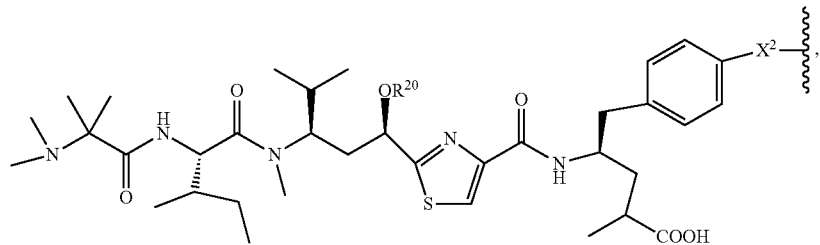
VII-01

-continued
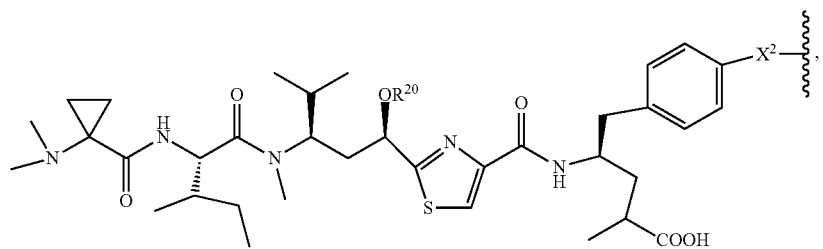
VII-02
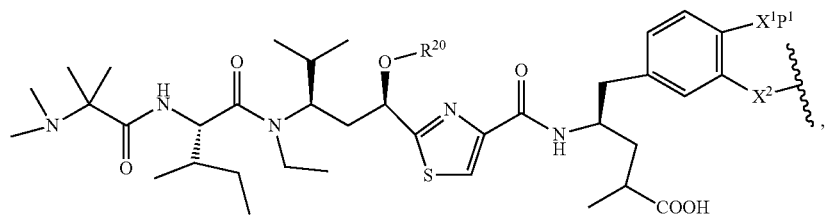
VII-03
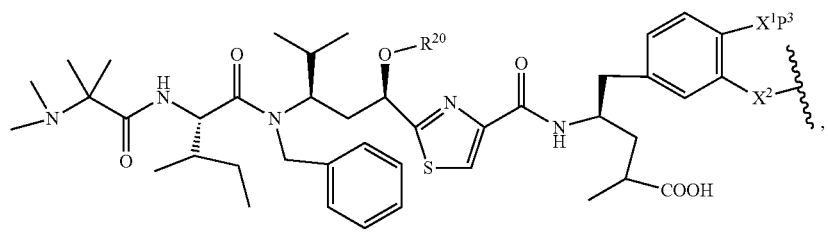
VII-04
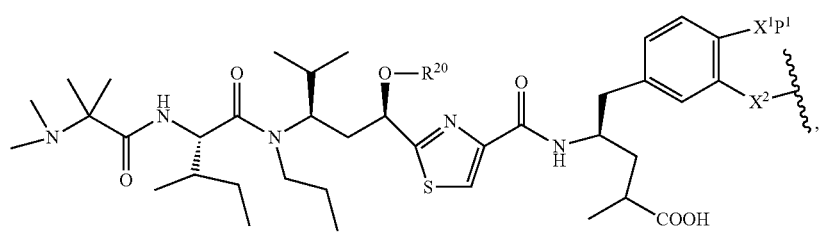
VII-05
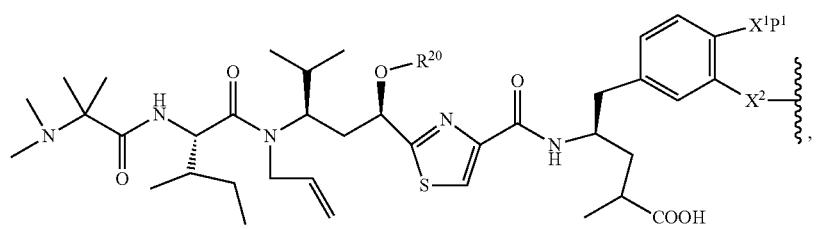
VII-06
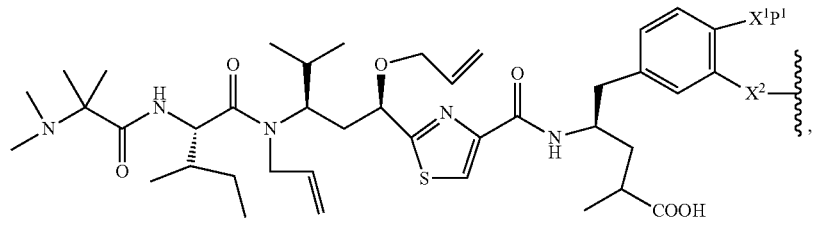
VII-07
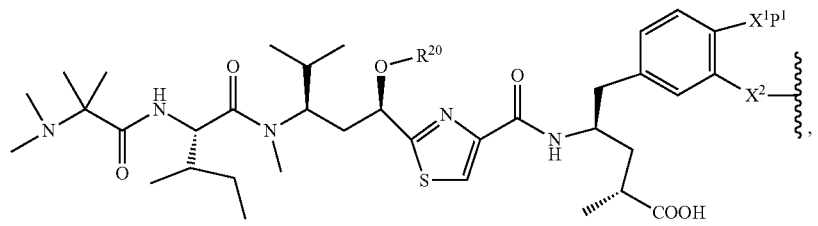
VII-08

-continued
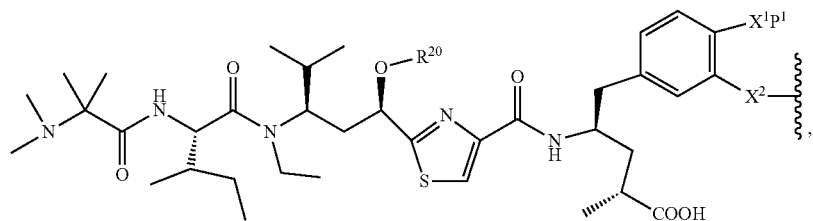
VII-09
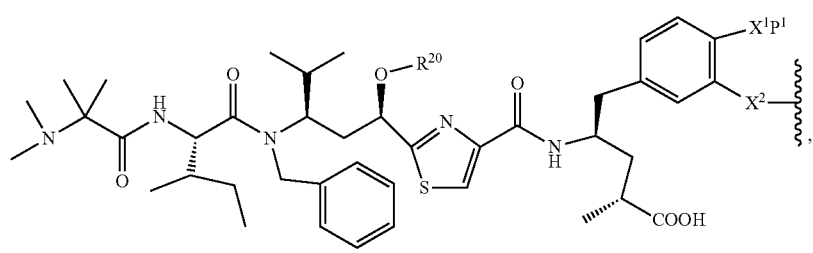
VII-10
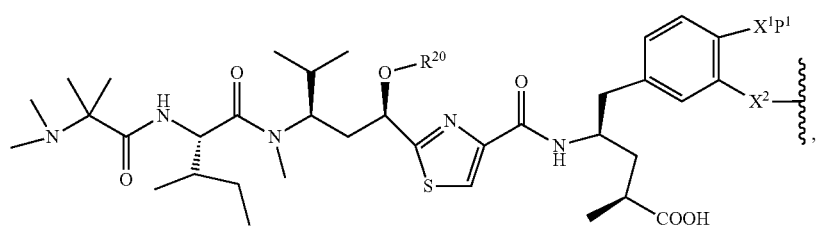
VII-11
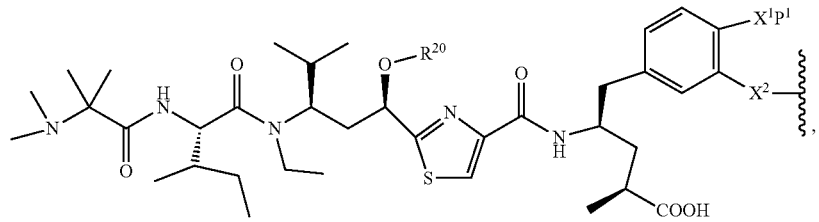
VII-12
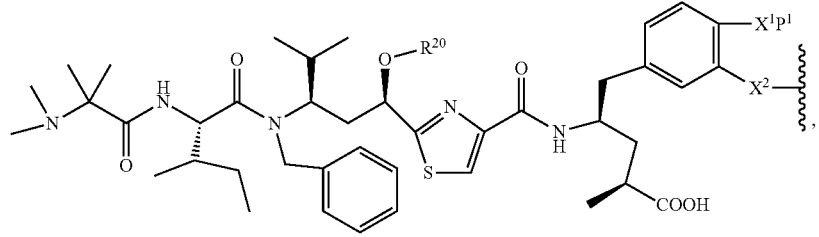
VII-13
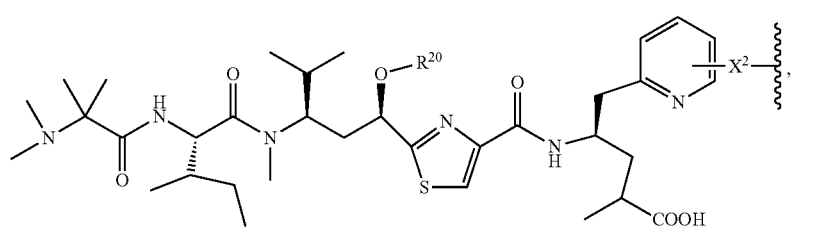
VII-14
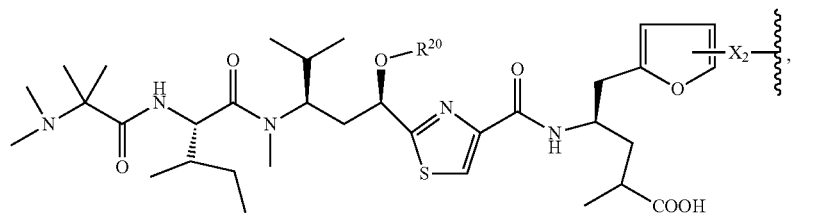
VII-15

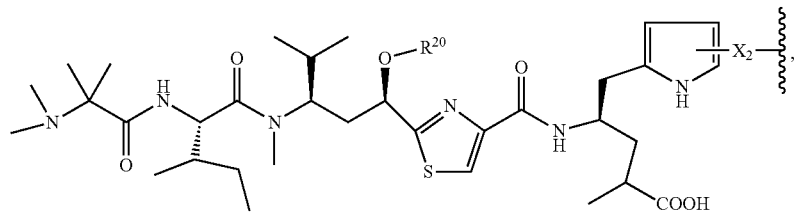
VII-16
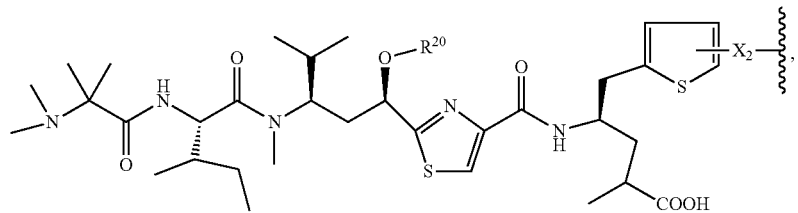
VII-17
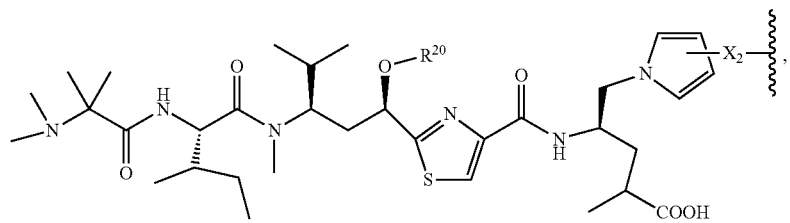
VII-18
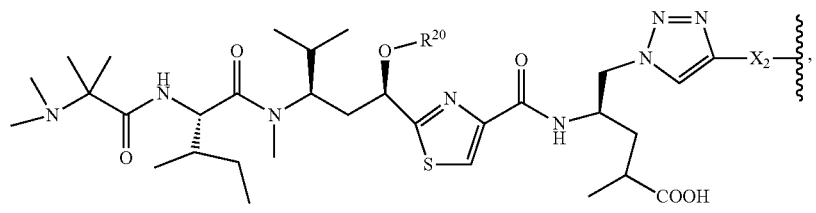
VII-19
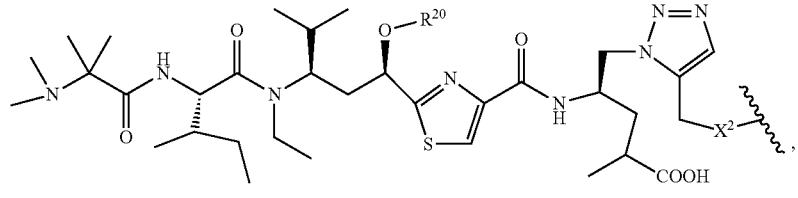
VII-20
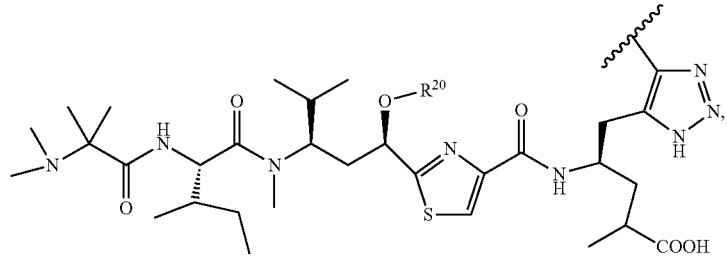
VII-21
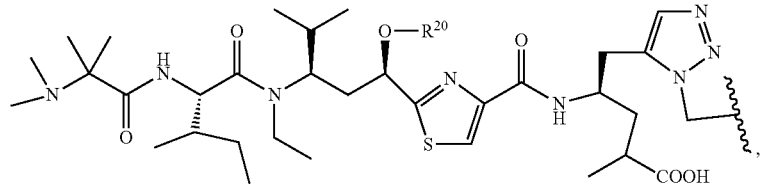
VII-22

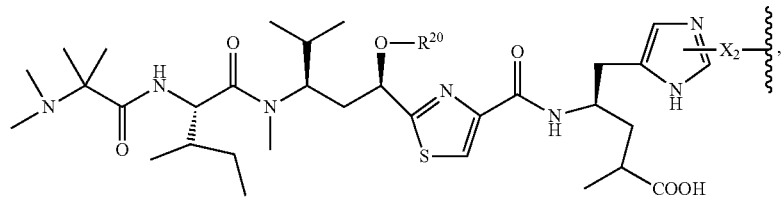
VII-23
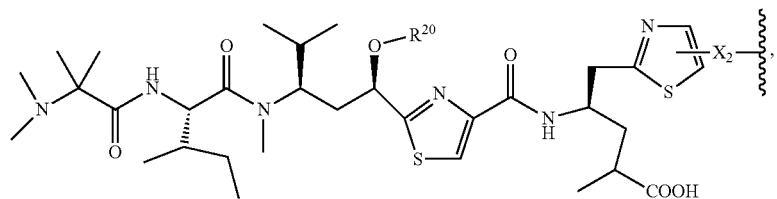
VII-24
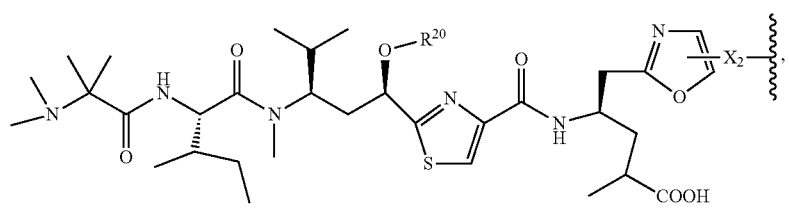
VII-25
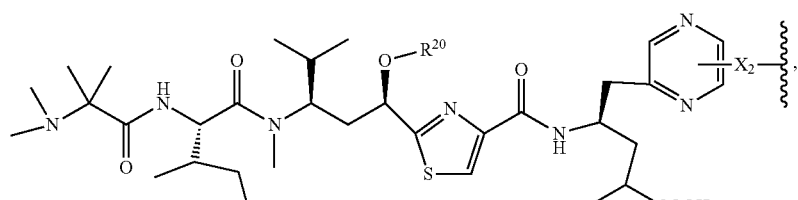
VII-26
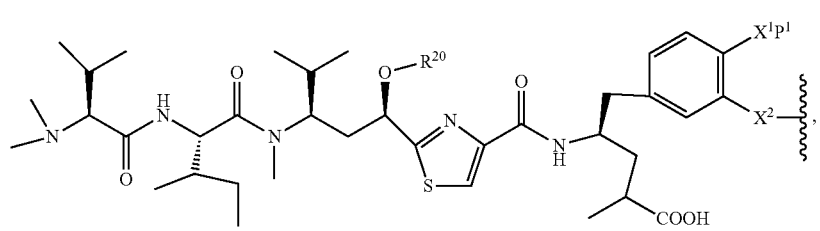
VII-27
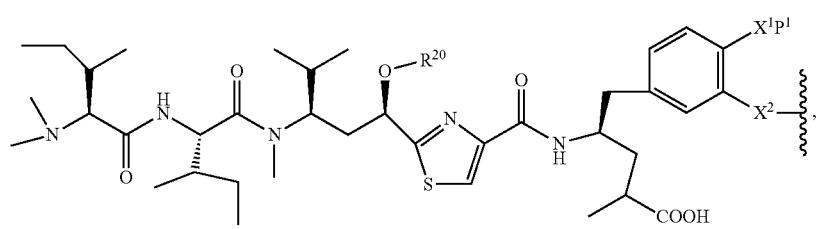
VII-28
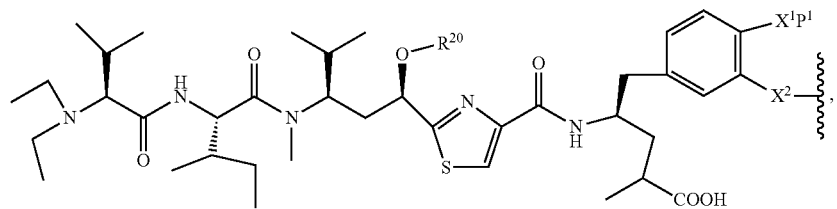
VII-29

-continued
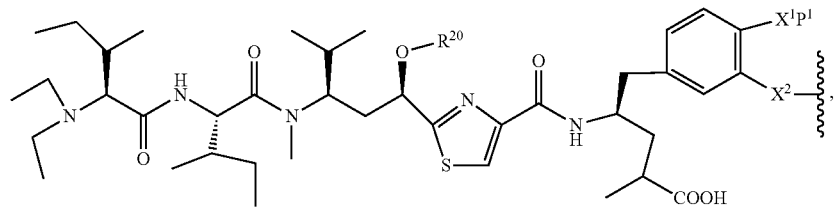
VII-30
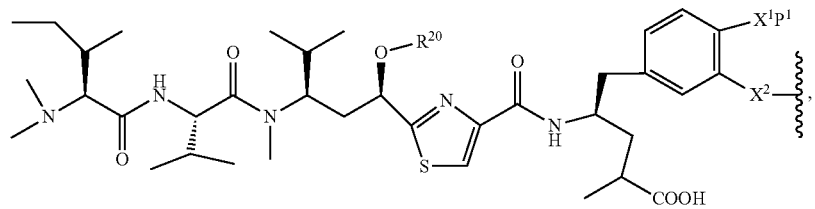
VII-31
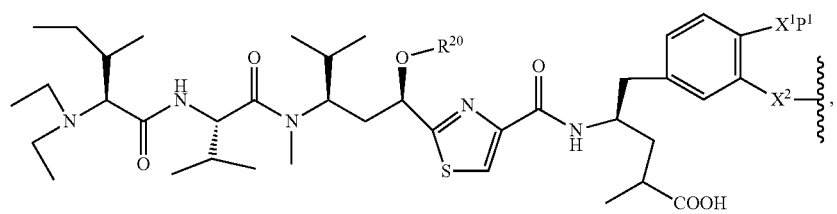
VII-32
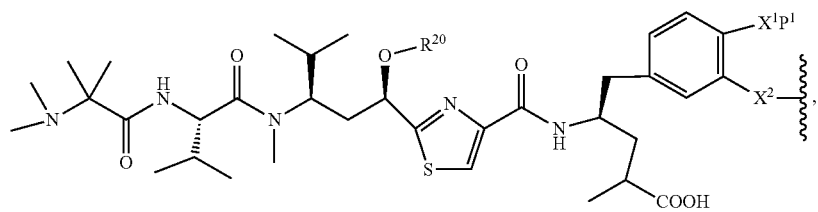
VII-33
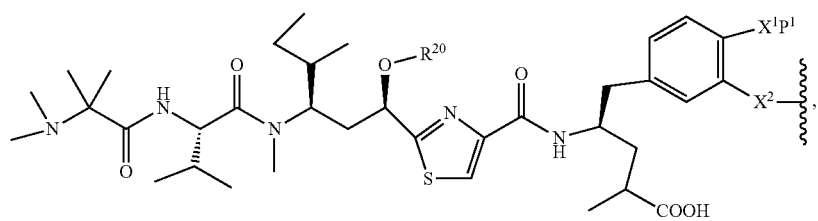
VII-34
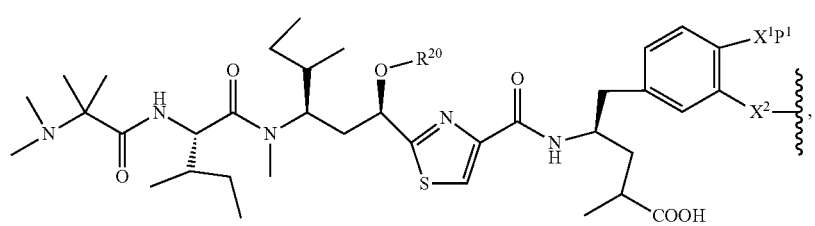
VII-35
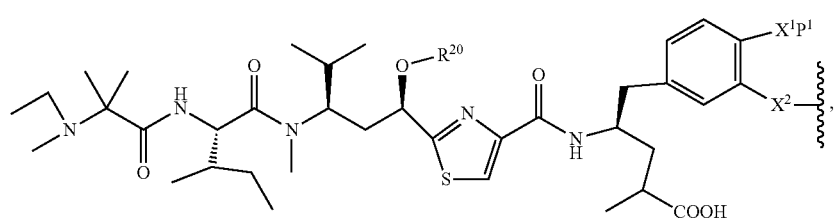
VII-36

411 412
-continued
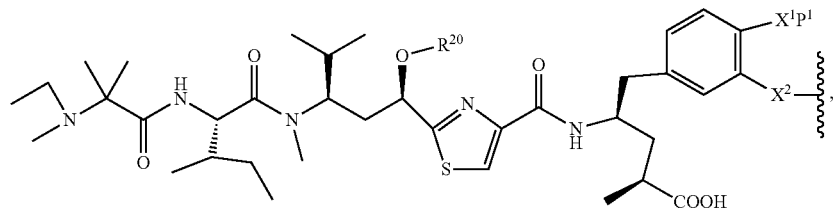
VII-37
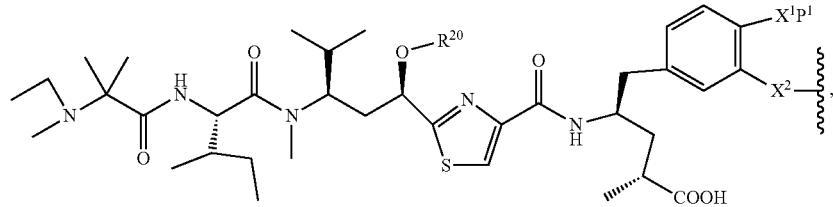
VII-38
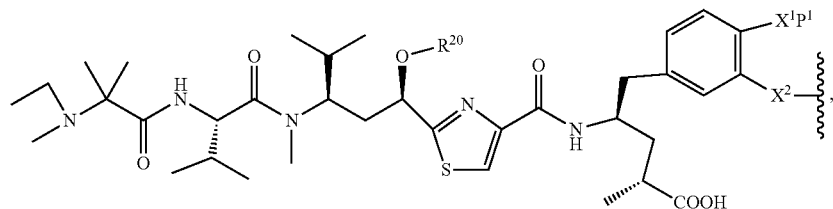
VII-39
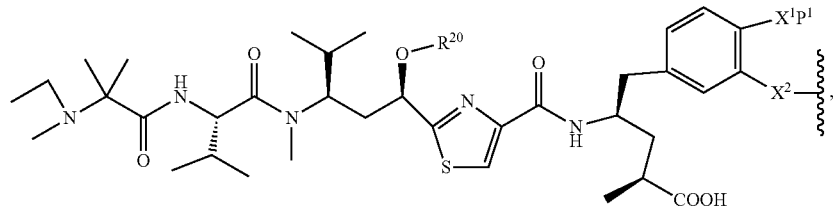
VII-40
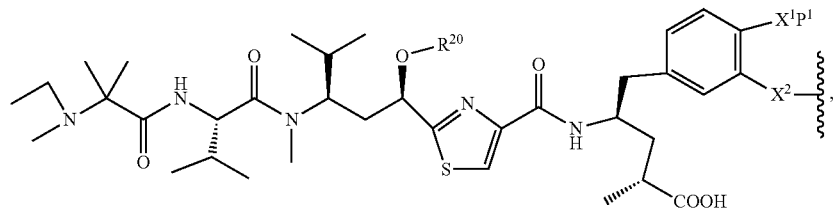
VII-41
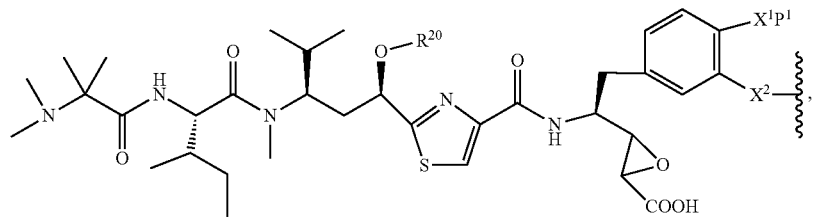
VII-42
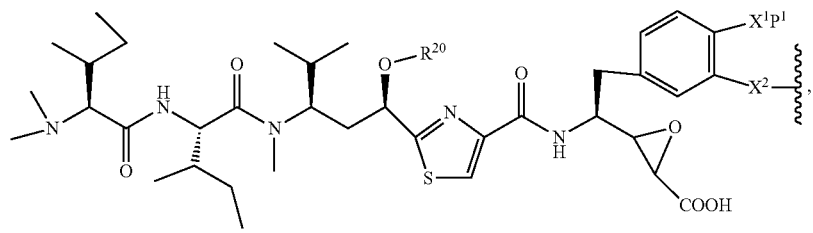
VII-43

-continued
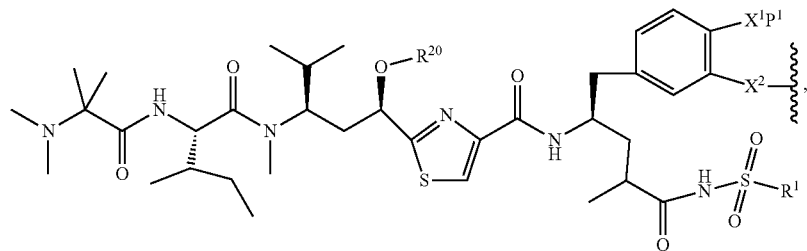
VII-44
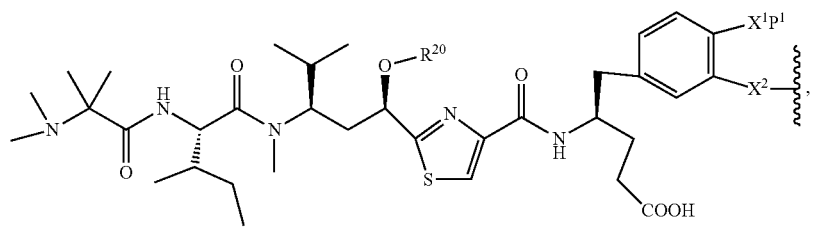
VII-45
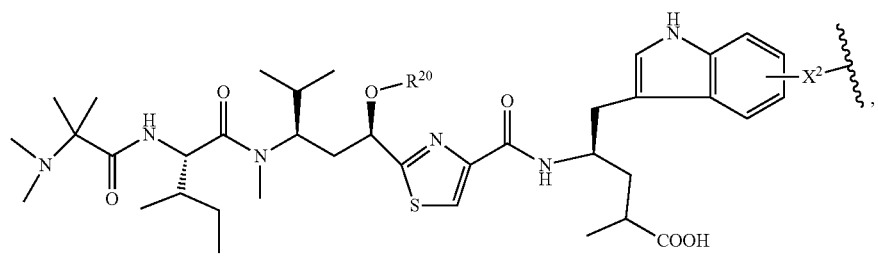
VII-46
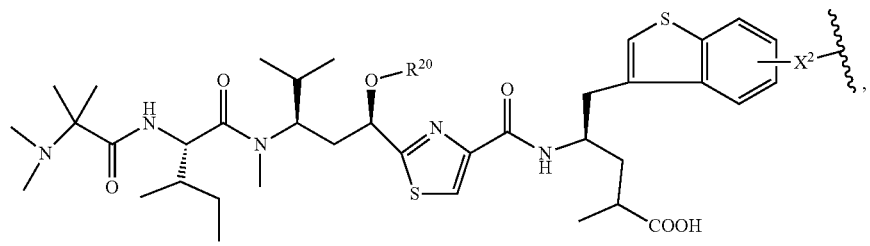
VII-47
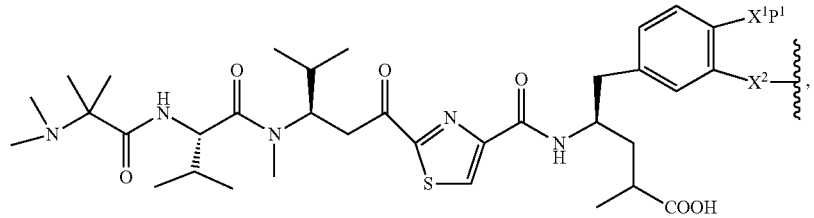
VII-48
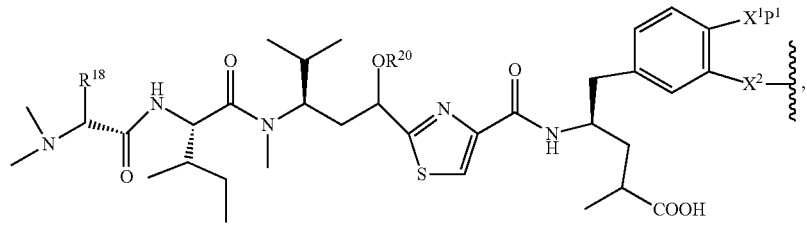
VII-49

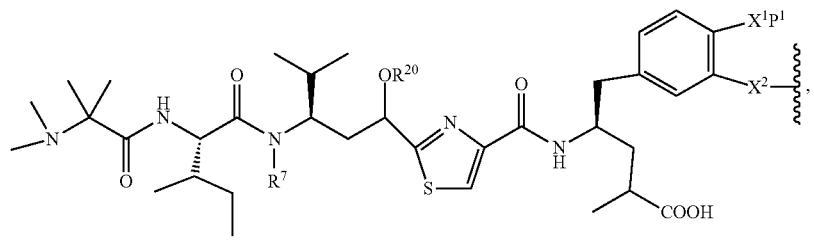
VII-50
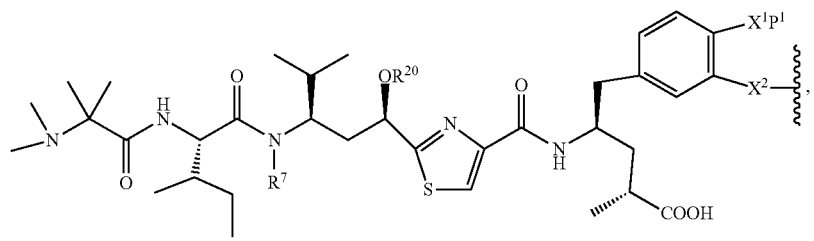
VII-51
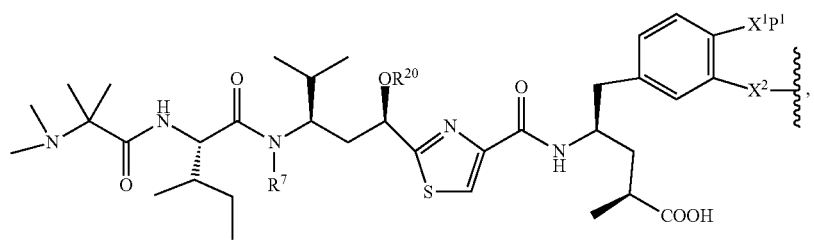
VII-52
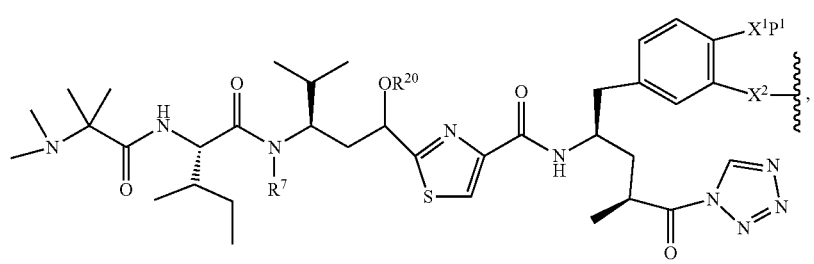
VII-53
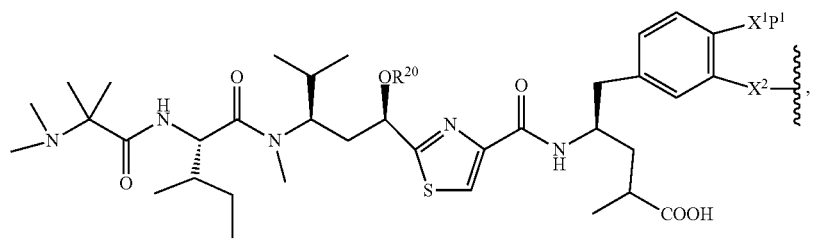
VII-54
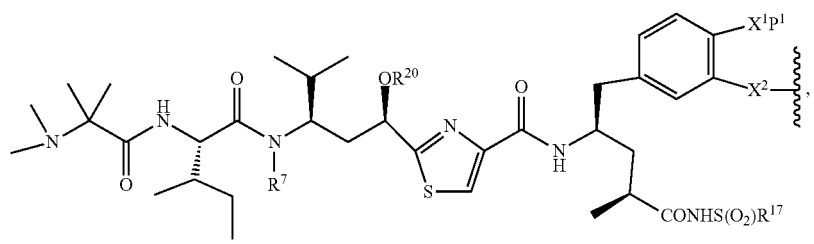
VII-55

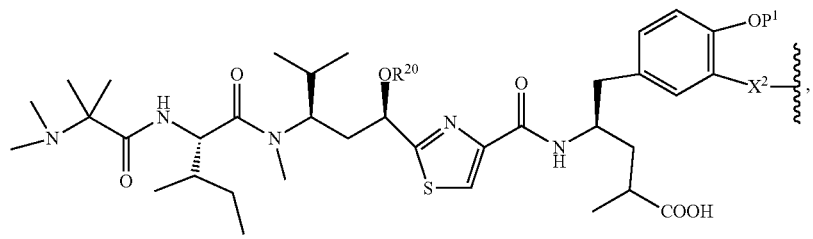
VII-56
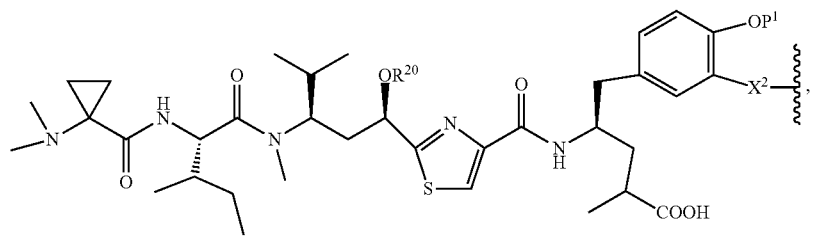
VII-57
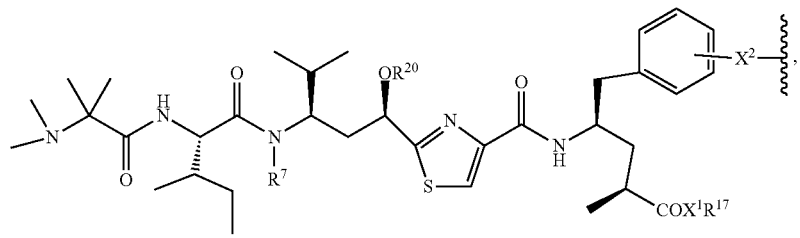
VII-58
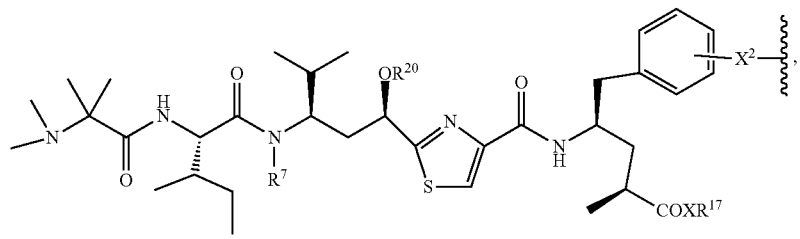
VII-59
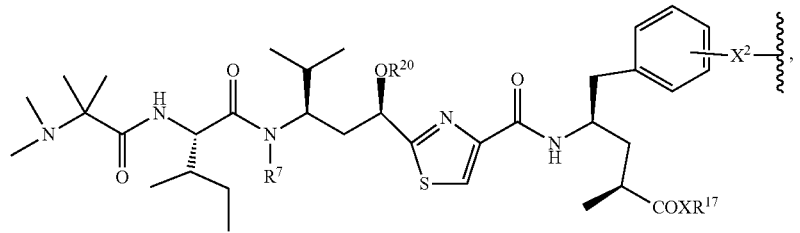
VII-60
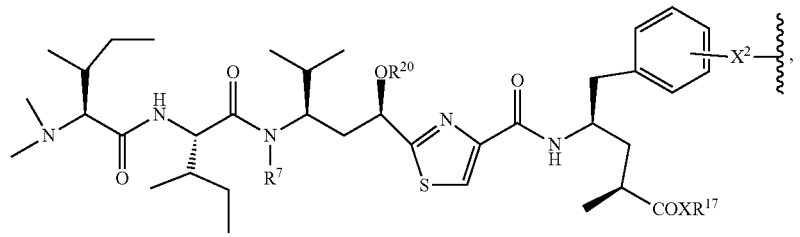
VII-61

-continued
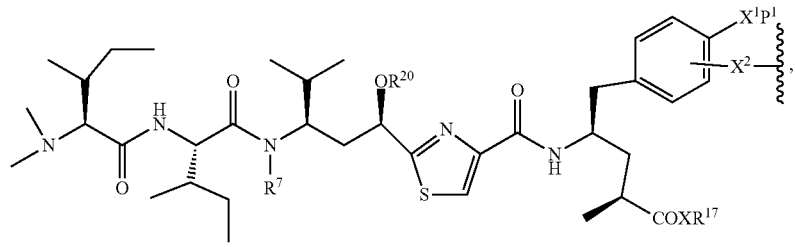
VII-62
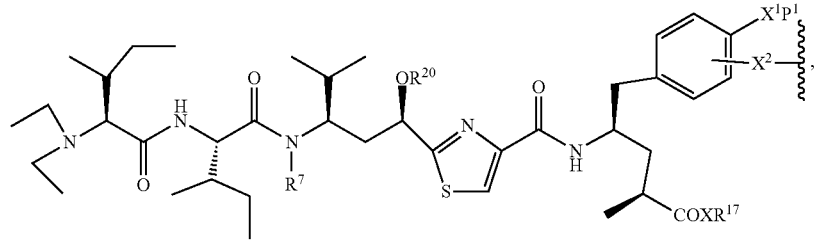
VII-63
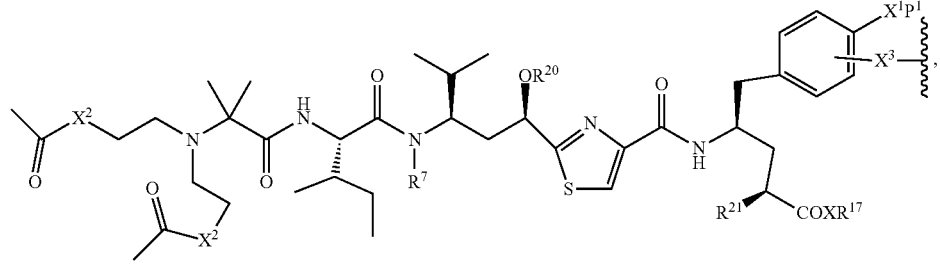
VII-64
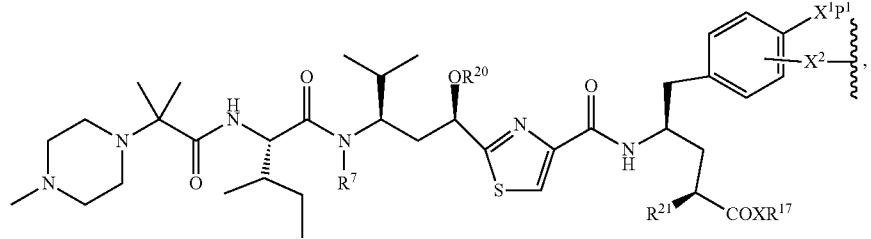
VII-65
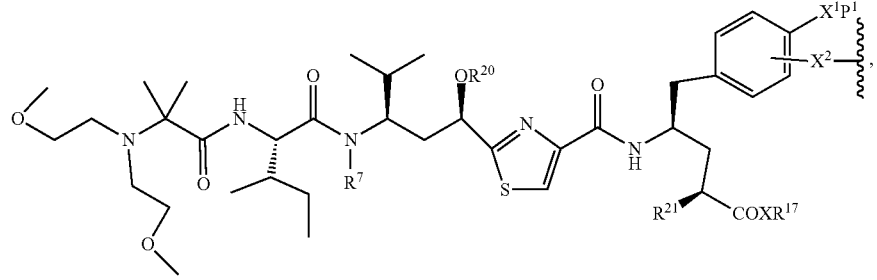
VII-66
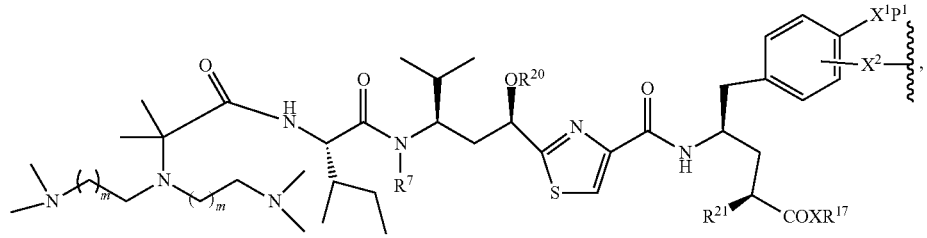
VII-67

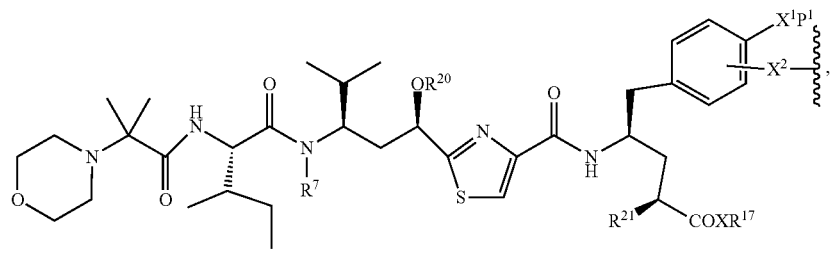
VII-68
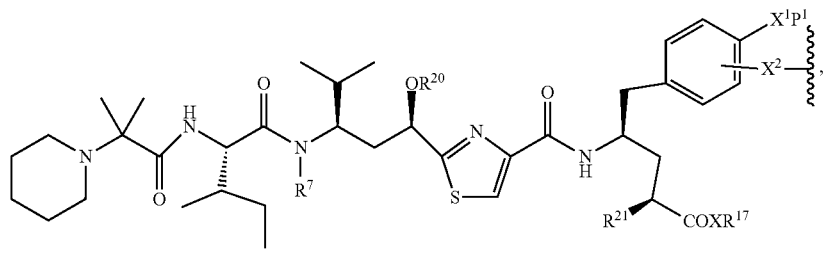
VII-69
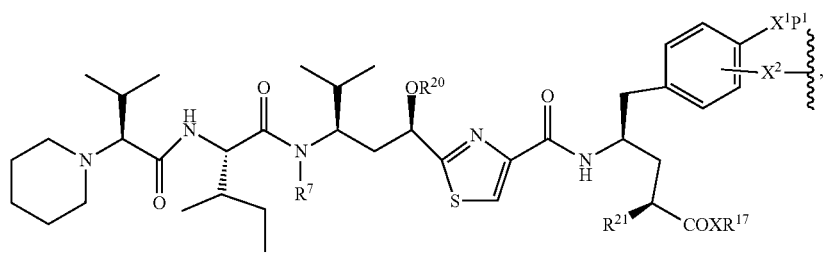
VII-70
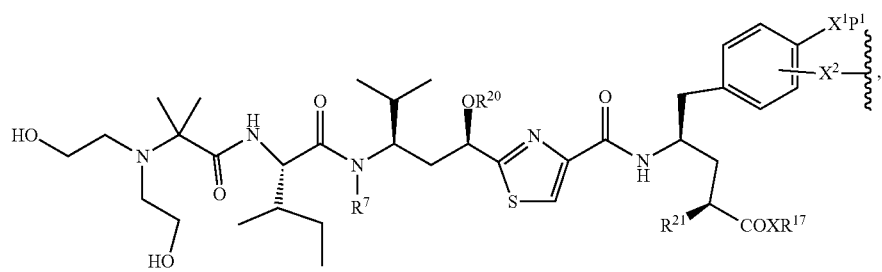
VII-71
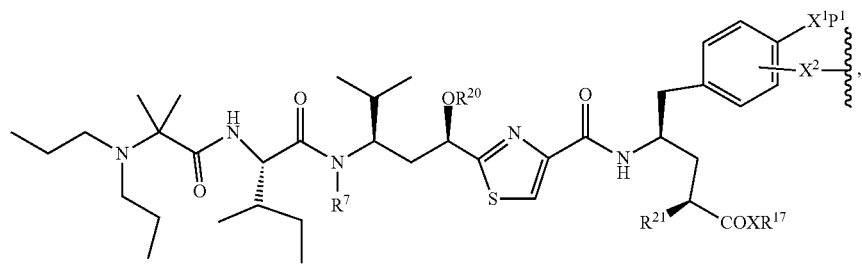
VII-72
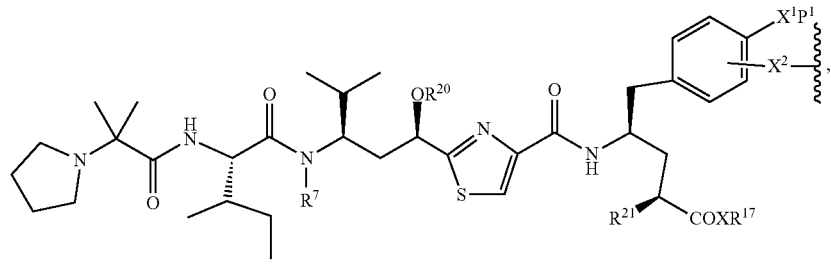
VII-73

VII-74
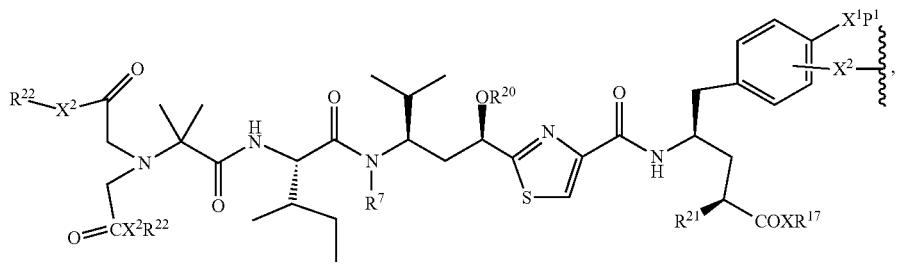

VII-75
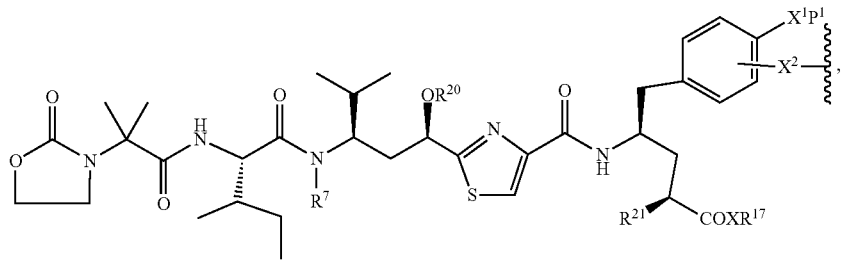

VII-76
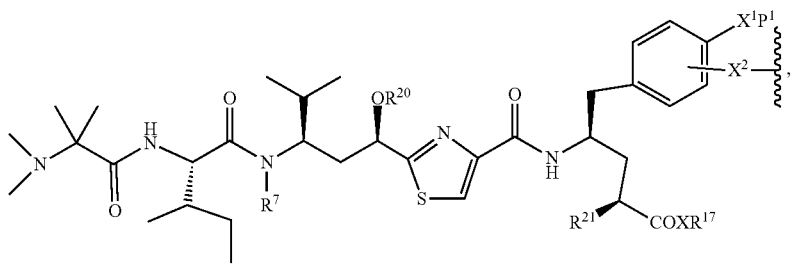

VII-77
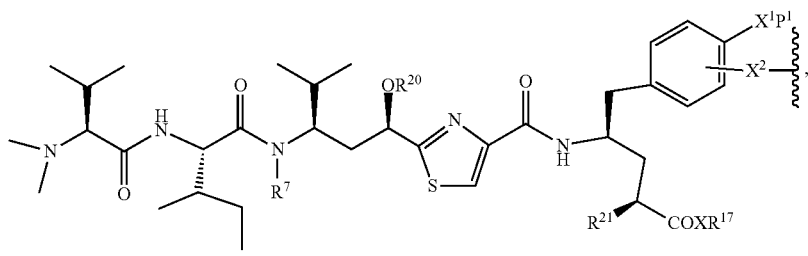

or a pharmaceutically acceptable salt, hydrate, or hydrated salt thereof; or a polymorphic crystalline structure thereof; or an optical isomer, racemate, diastereomer or enantiomer thereof;

wherein $R^{20}$ is H; $C_1$-$C_8$ linear or branched alkyl, heteroalkyl, or —C(O)$R^{17}$; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, or heteroaryl; —C(O)O$R^{17}$, —C(O)N$R^{17}R^{18}$; or $C_1$-$C_8$ carboxylate, ester, ether, or amide; or 1~8 amino acids; or polyethyleneoxy unit of formula (OCH$_2$CH$_2$)$_p$ or (OCH$_2$CH(CH$_3$))$_p$, wherein p is an integer from 0 to about 1000; or $R^{20}$ is absent and the oxygen forms a ketone, or a combination of two or more thereof, wherein $R^{21}$ is H, $C_1$-$C_8$ linear or branched alkyl; X, $X^1$, $X^2$, and $X^3$ are independently O, S, NH, NHNH, NH$R^{17}$, CH$_2$ or absent; $P^1$ is H, $R^{17}$, P(O)(OH)$_2$, P(O)($X^1R^{17}$)$_2$, CH$_2$P(O)(OH)$_2$, S(O$^2$) ($X^1R^{17}$), C$_6$H$_{12}$O$_5$, or (CH$_2$CH$_2$O)$_p R^{17}$, wherein p is selected from 0-100, and $R^{17}$ is defined above; in addition $X^1P^1$ can be together;

wherein $Z^2$ and $Z^3$ are independently H, OH, NH$_2$, O$R^{17}$, NH$R^{17}$, COOH, COO$R^{17}$, C(O)$R^{17}$, C(O)NH$R^{17}$, C(O)NHNH$R^{17}$, C(O)NH$_2$, $R^{18}$, OCH$_2$OP(O)(O$R^{18}$)$_2$, OC(O)OP(O)(O$R^{18}$)$_2$, OPO(O$R^{18}$)$_2$, NHPO(O$R^{18}$)$_2$, OP(O)(O$R^{18}$)OP(O)(O$R^{18}$)$_2$, OC(O)$R^{18}$, OC(O)NH$R^{18}$, OSO$_2$(O$R^{18}$), O—(C$_4$-C$_{12}$-glycoside), C$_1$-C$_8$ linear or branched alkyl or heteroalkyl; C$_2$-C$_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, or heteroaryl; —C(O)OR$^{17}$, or —C(O)NR$^{17}$R$^{18}$; R$^{17}$ and R$^{18}$ are independently H, $C_1$-$C_8$ linear or branched alkyl or heteroalkyl; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, or heteroaryl; —C(O)OR$^{17}$, or —C(O)NR$^{17}$R$^{18}$; R$^{19}$ is H, OH, NH$_2$, OSO$_2$(OR$^{18}$), XCH$_2$OP(O)(OR$^{18}$)$_2$, XPO(OR$^{18}$)$_2$, XC(O)OP(O)(OR$^{18}$)$_2$, XC(O)R$^{18}$, XC(O)NHR$^{18}$, $C_1$-$C_8$ alkyl or carboxylate; $C_2$-$C_8$ alkenyl, alkynyl, alkylcycloalkyl, or heterocycloalkyl; $C_3$-$C_8$ aryl or alkylcarbonyl; or a pharmaceutical salt; X is O, S, NH, NHNH, NHR$^7$, or CH$_2$; R$^7$ is defined the same above;

wherein "⌇" is the site that linked to a linker L.

9. The conjugate according to claim 1 having one of the following structures:

131

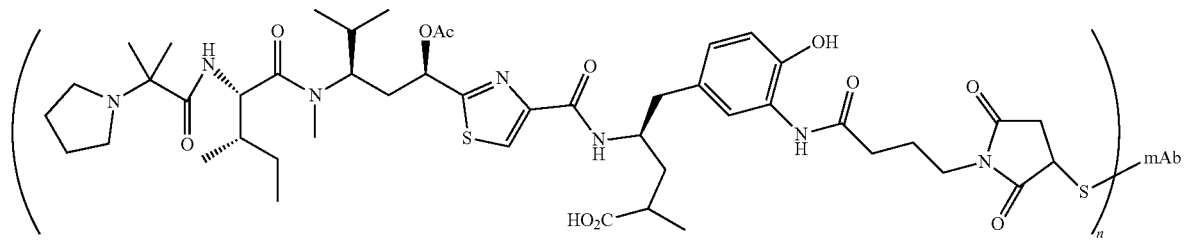

133

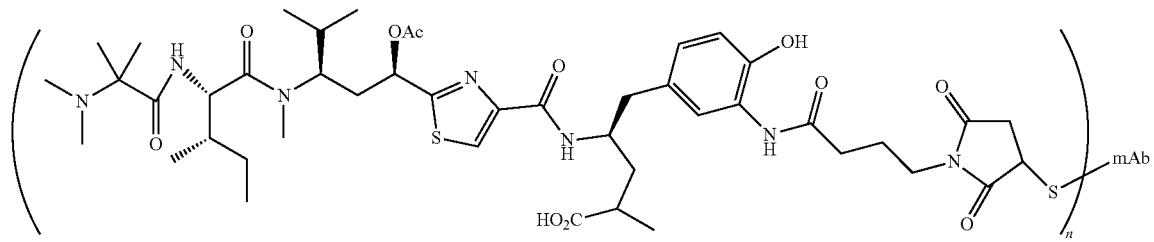

167

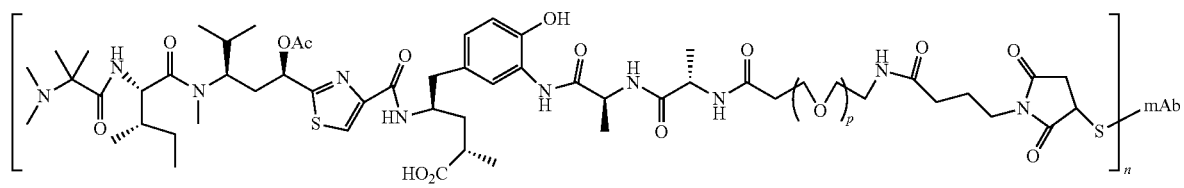

169

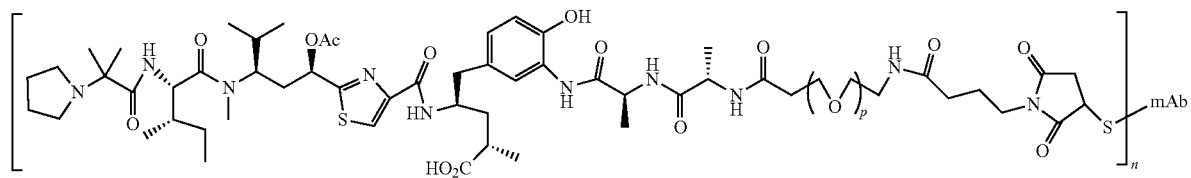

171

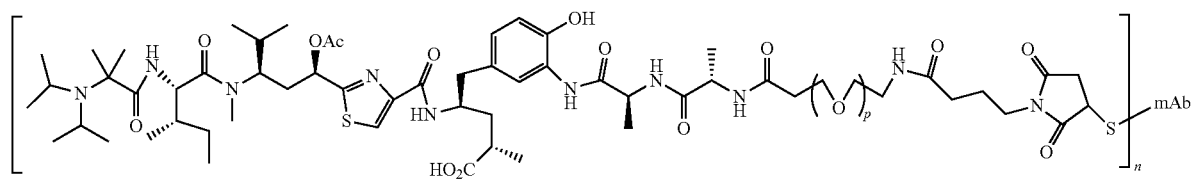

173

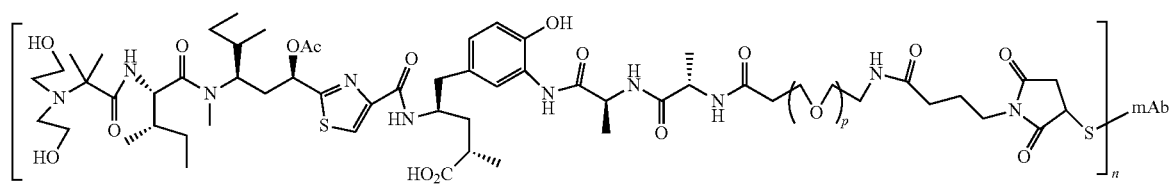

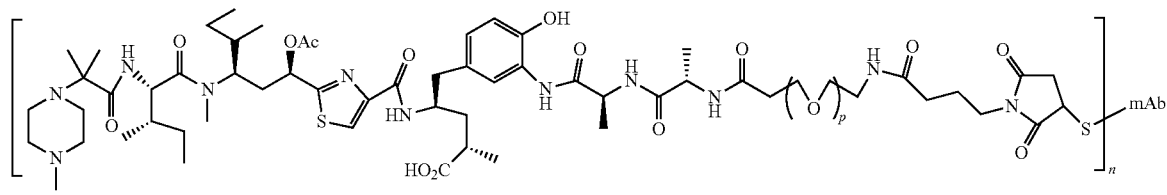
175
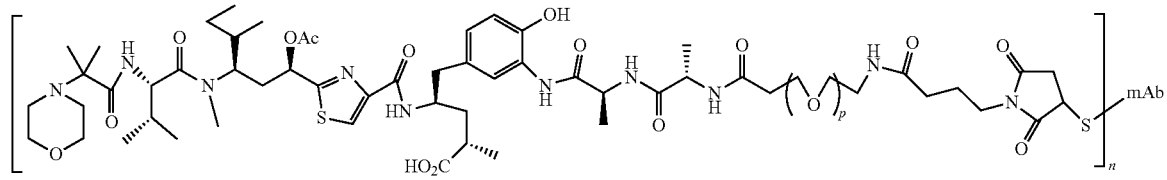
177
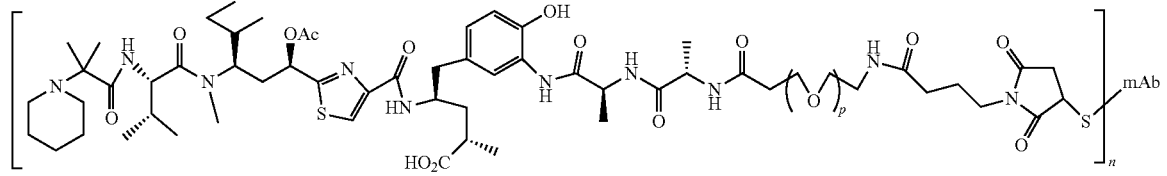
178
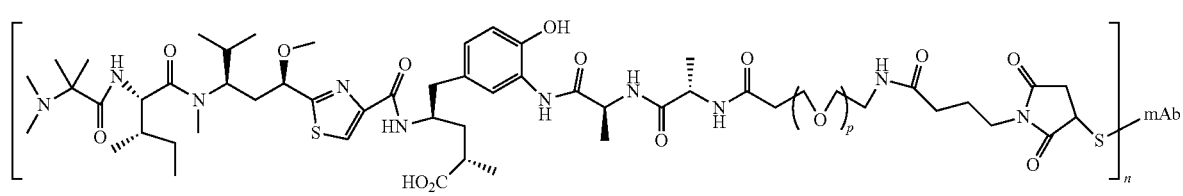
186
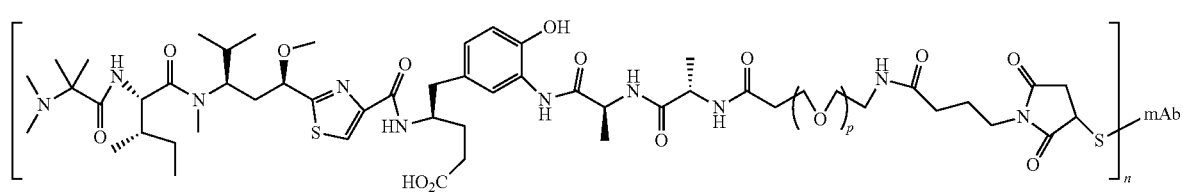
196
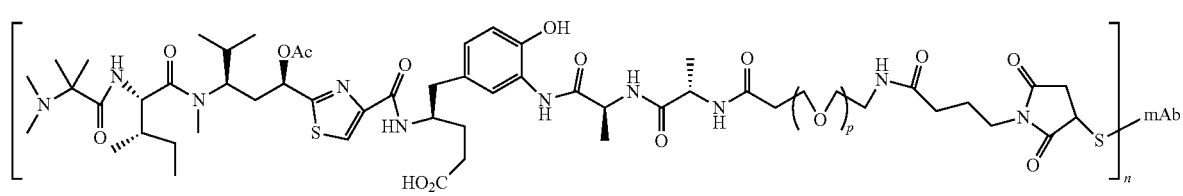
198
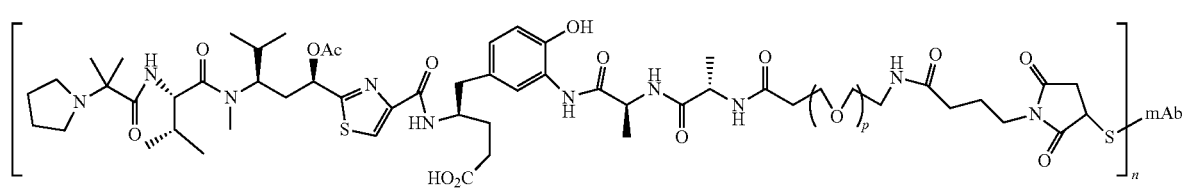
200

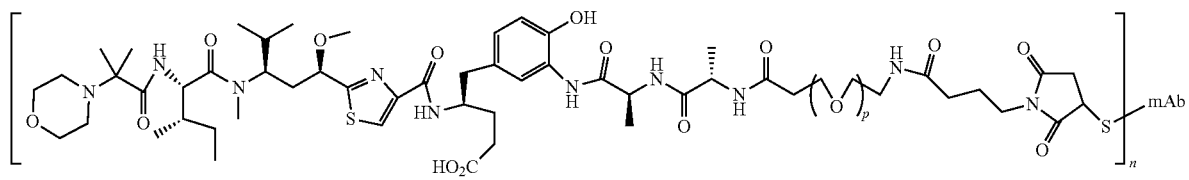
202
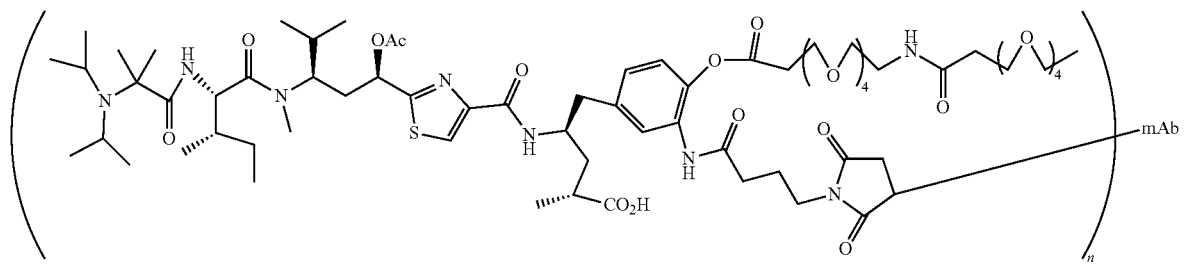
217
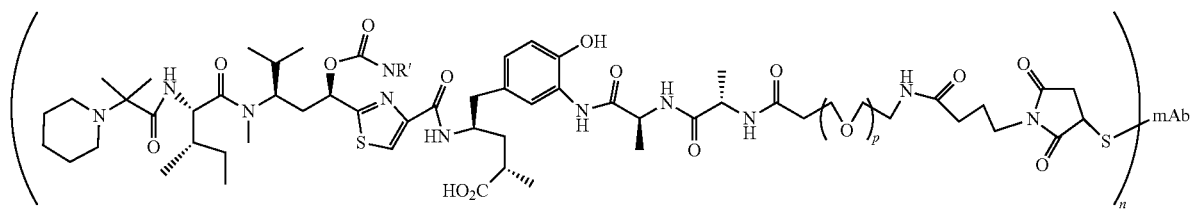
269, R' = HEt; 270, R' = Me₂; 271, R' = H'Pr
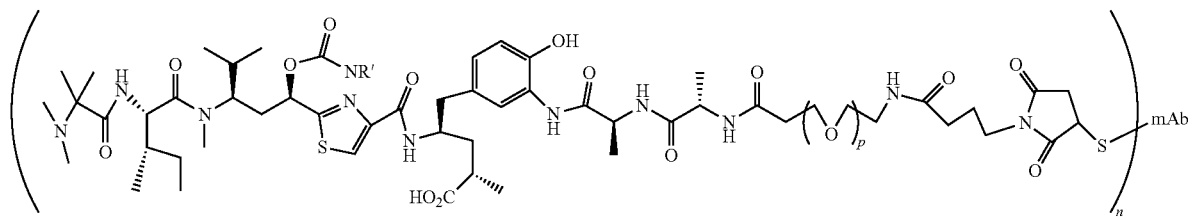
278, R' = HEt; 279, R' = Me₂; 280, R' = H'Pr
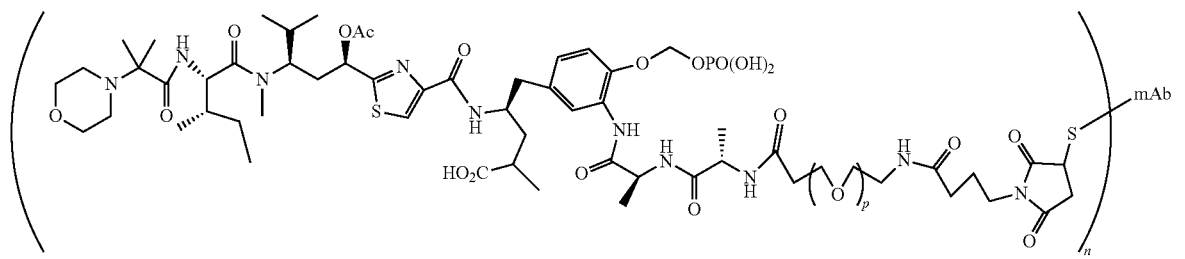
287
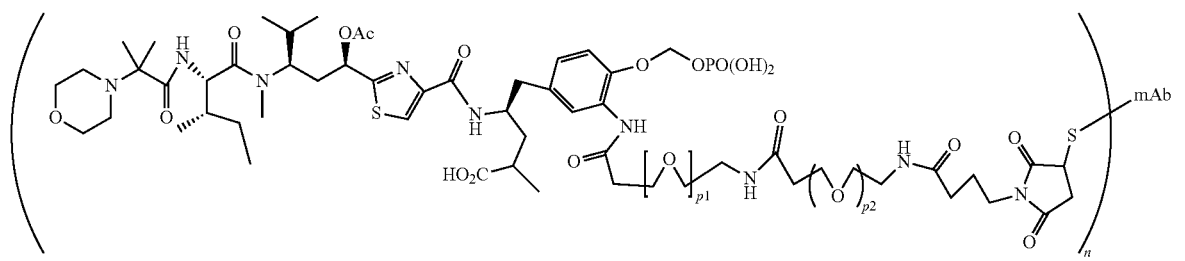
289

-continued
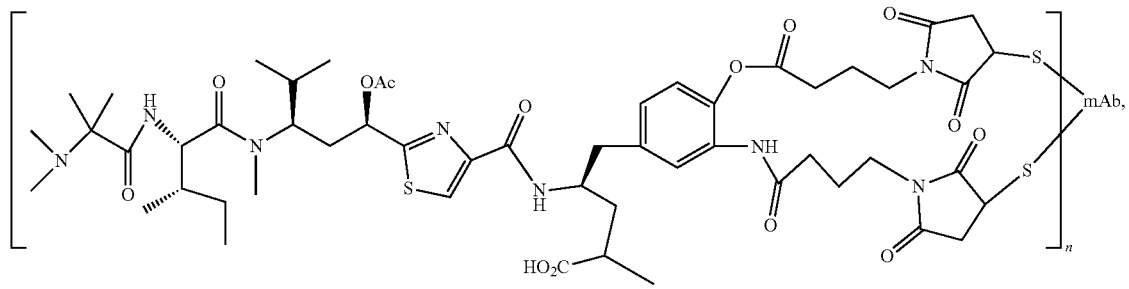
C-481
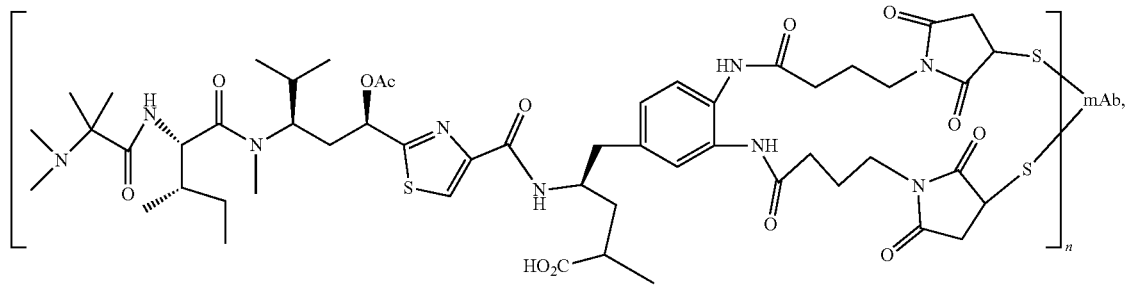
C-495
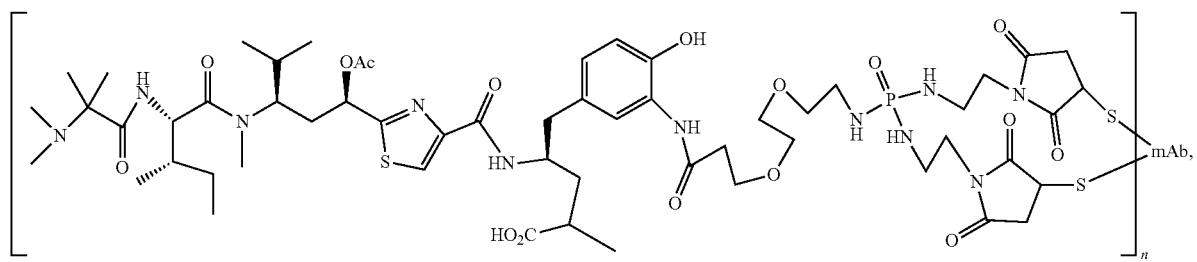
C-528
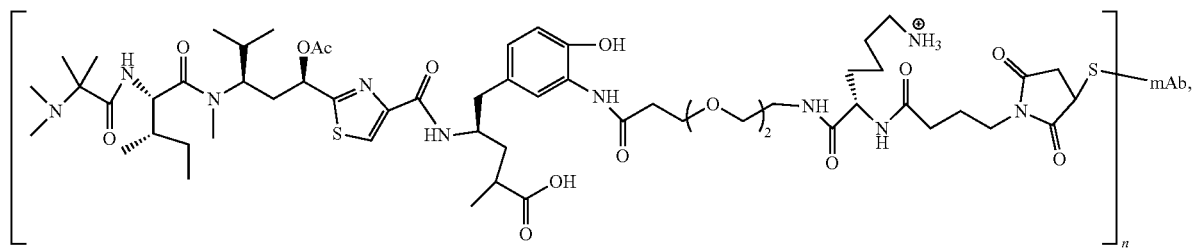
C-629
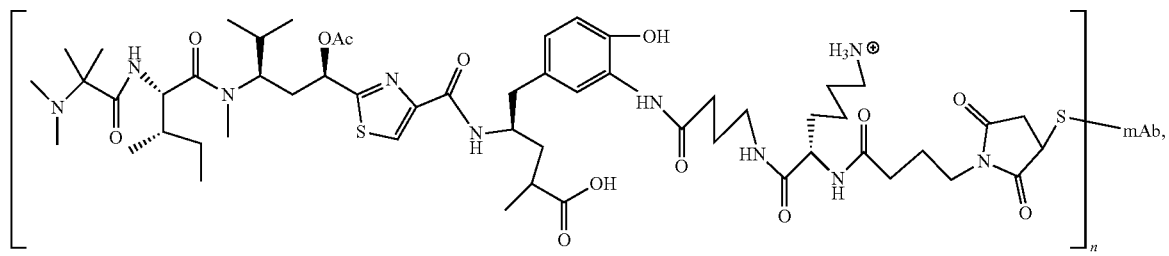
C-633

-continued
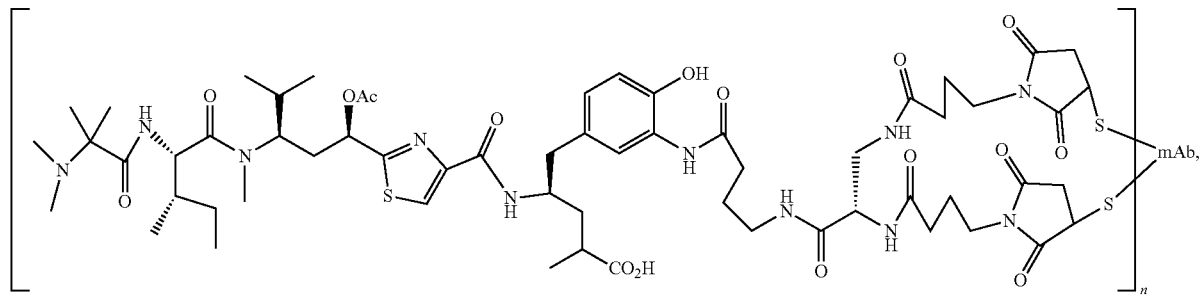
C-641
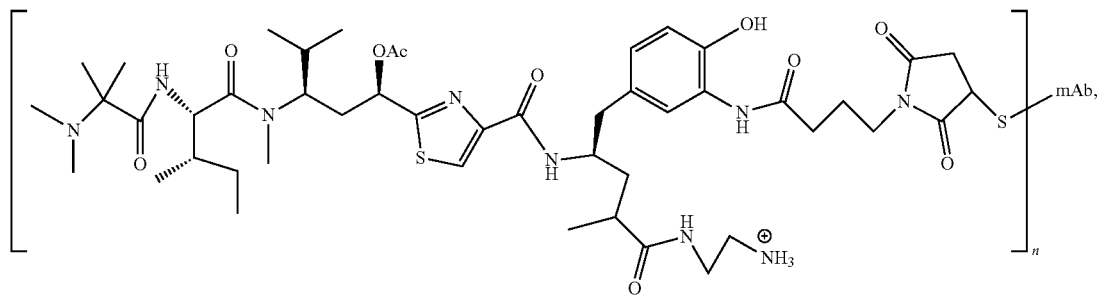
C-645
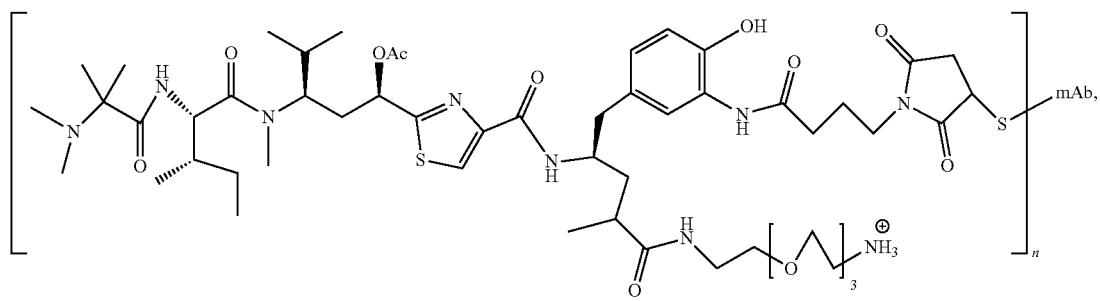
C-649
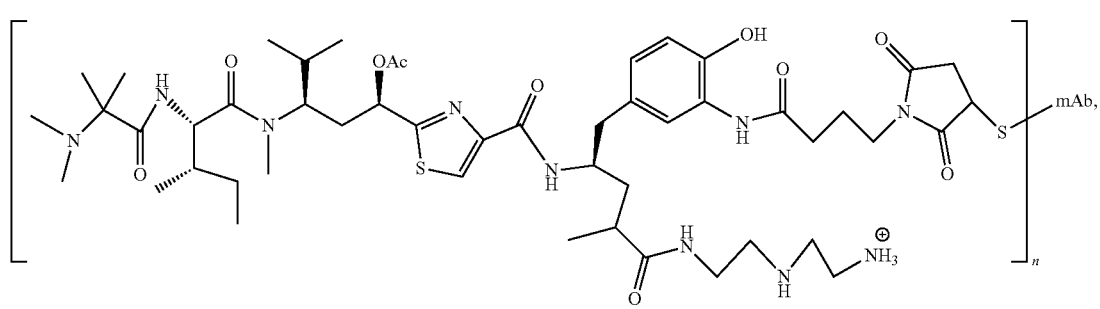
C-654
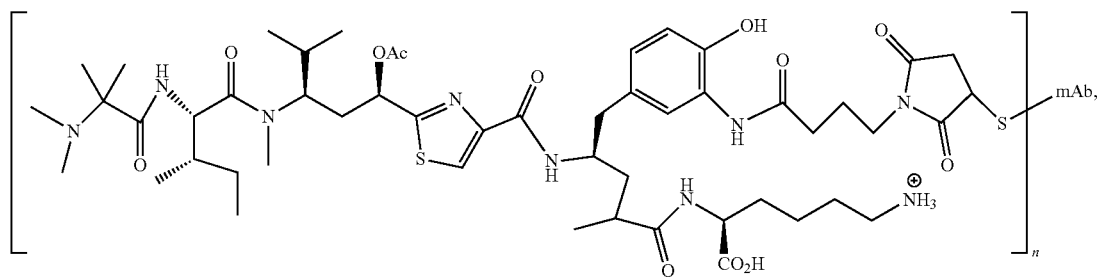
C-659

-continued
C-663
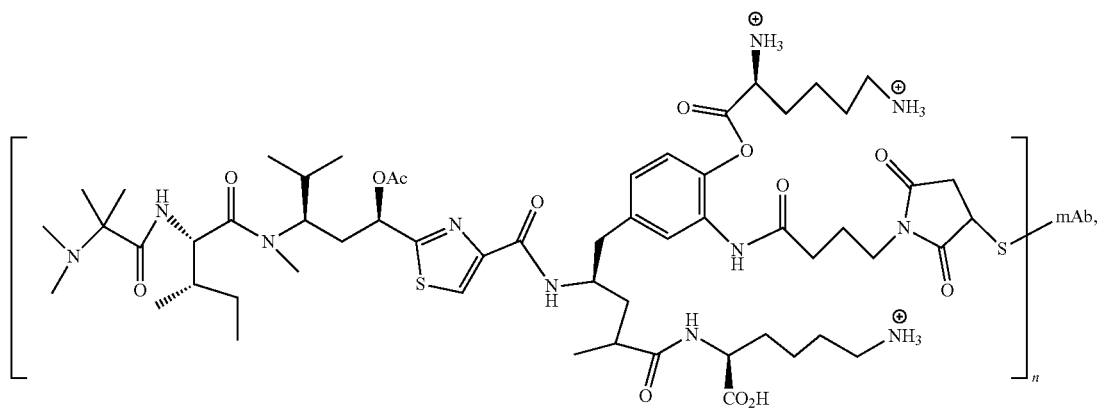
C-673
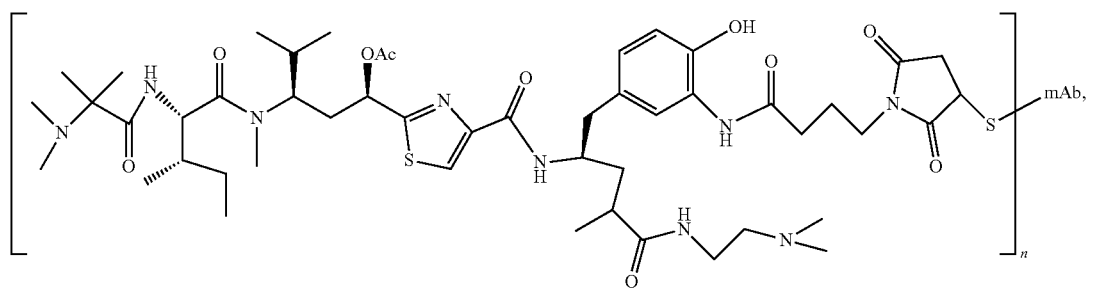
C-709
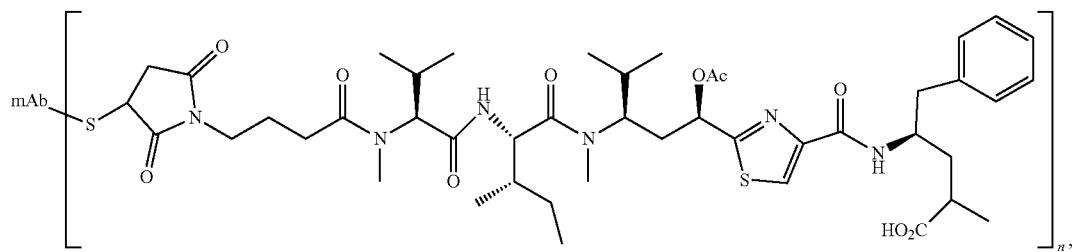
C-712
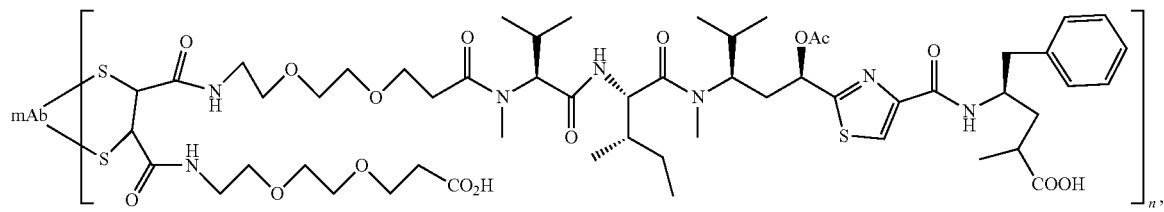
C-166a
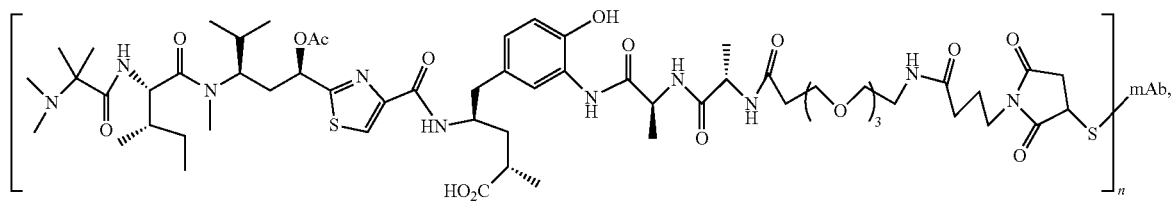

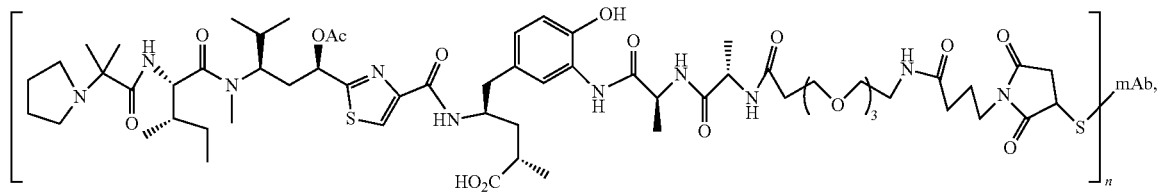
C-719
wherein mAb is an antibody; n is 1~20; and p is 0~100.
10. A method for preparing the conjugate according to claim 9, comprising reacting the antibody with a compound having one of the following structures:
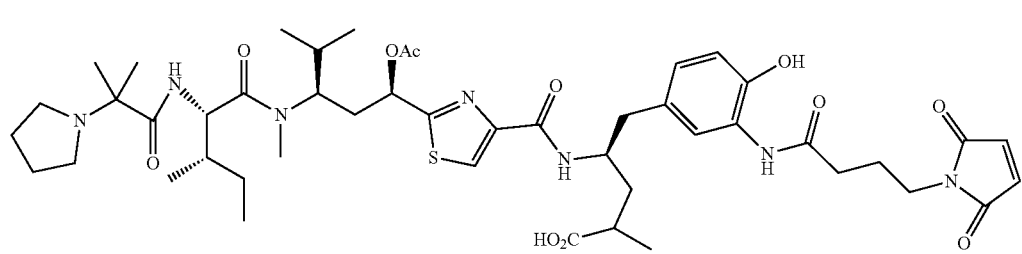
130
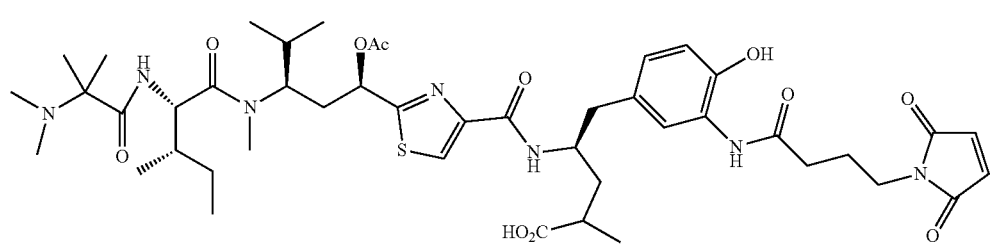
132
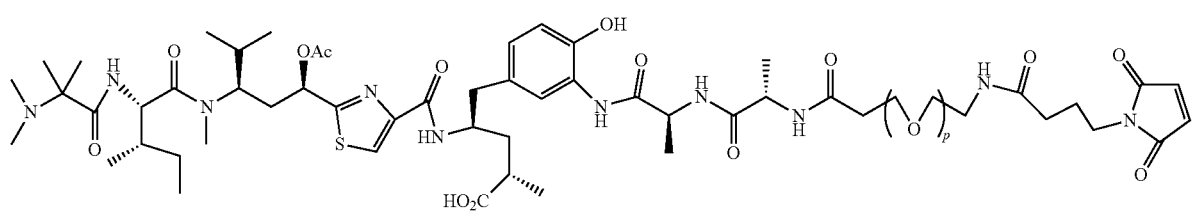
166
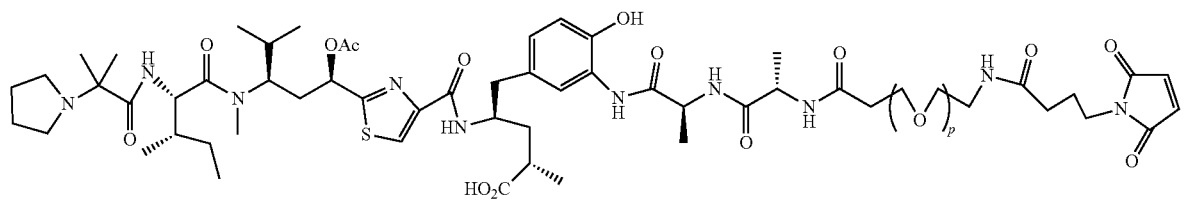
168
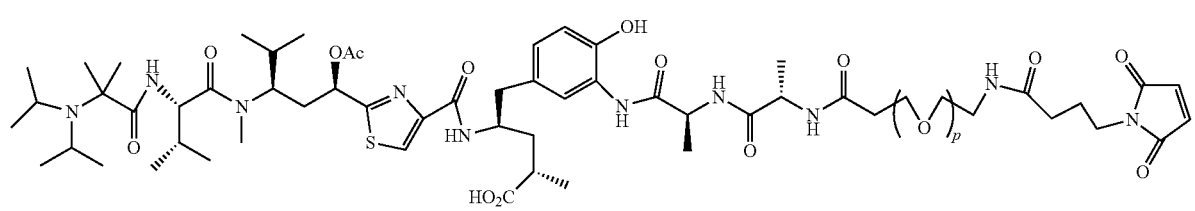
170

172
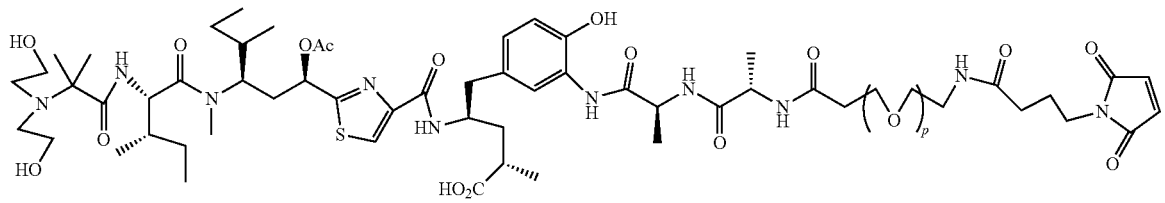
174
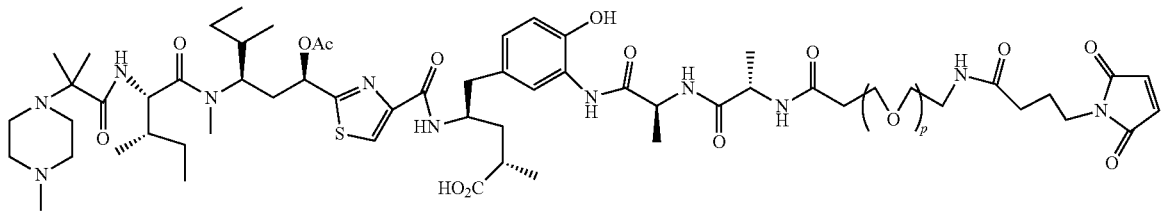
176
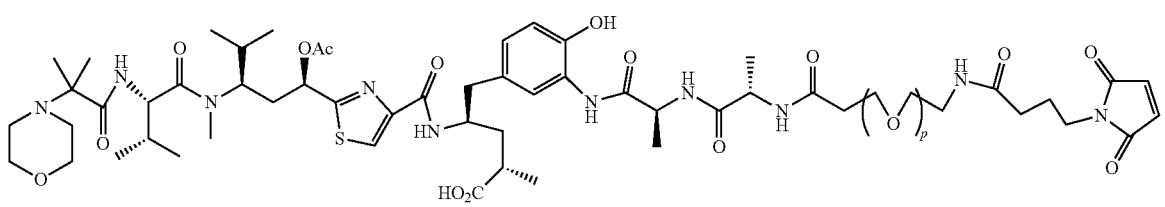
185
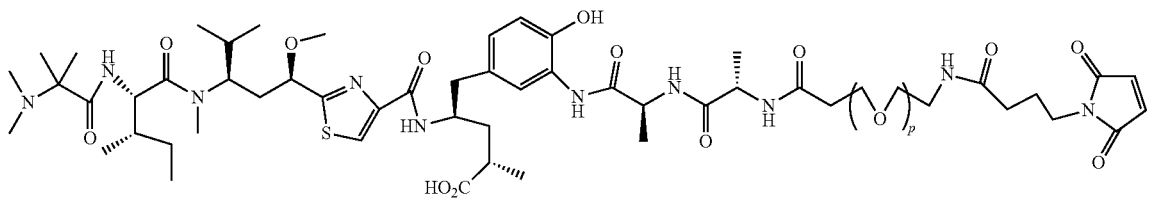
195
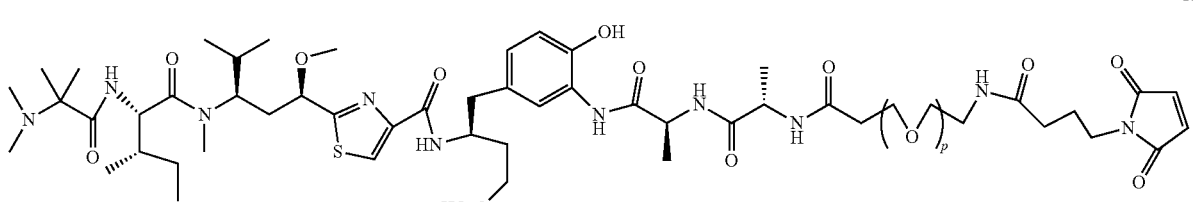
197
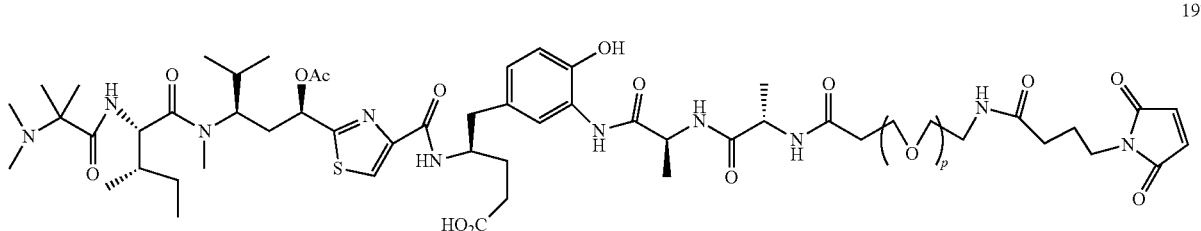
199
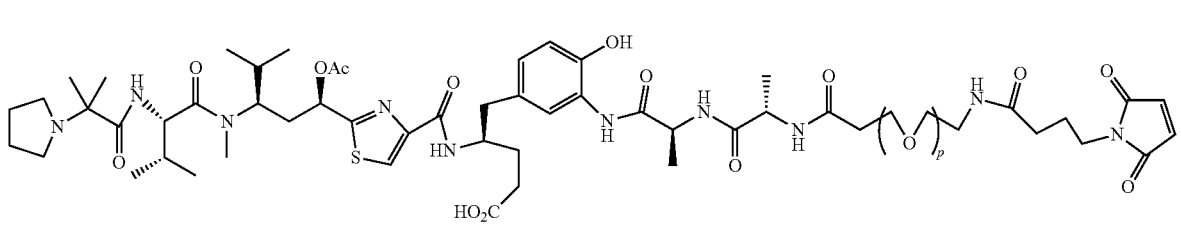

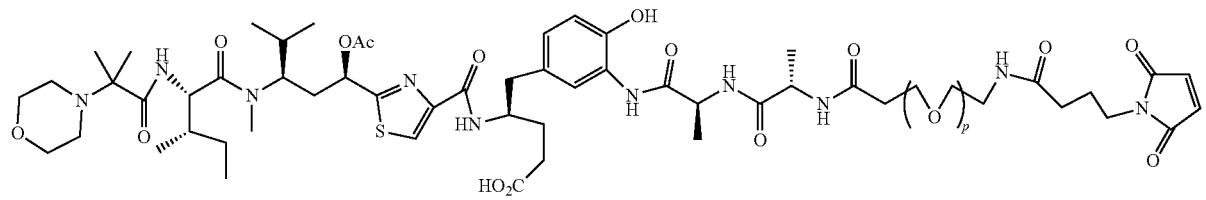
201
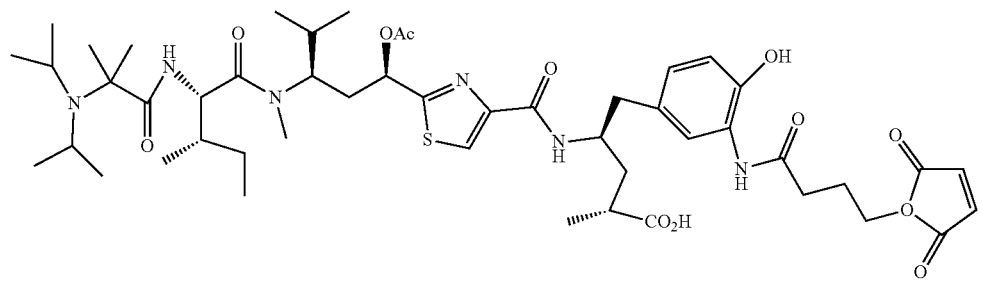
214
216
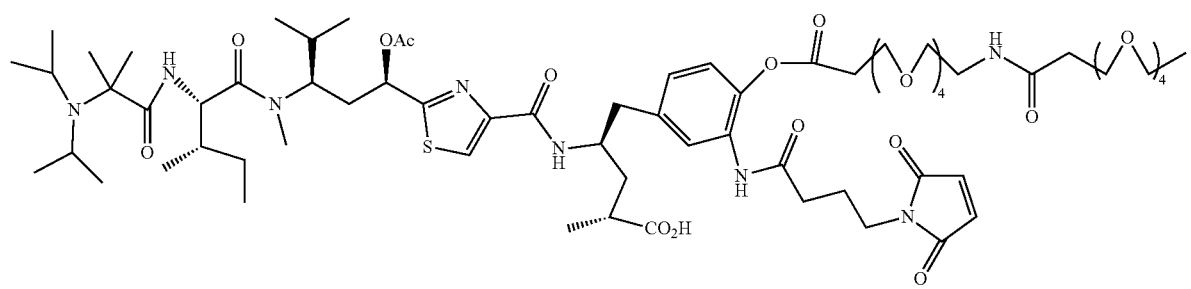
266, R' = HEt; 267, R' = Me₂; 268, R' = H$^i$Pr
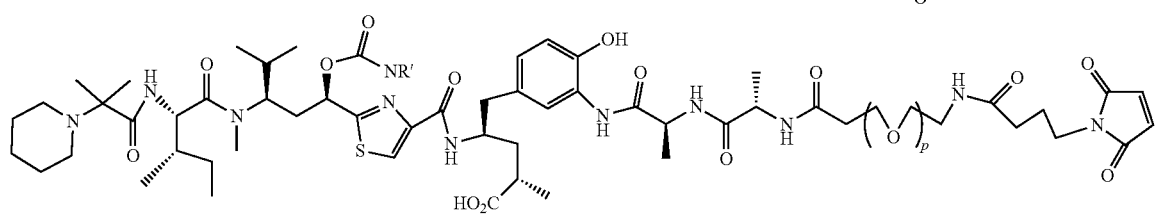
275, R'=HEt; 276, R'=Me₂; 277, R=H$^i$Pr
286
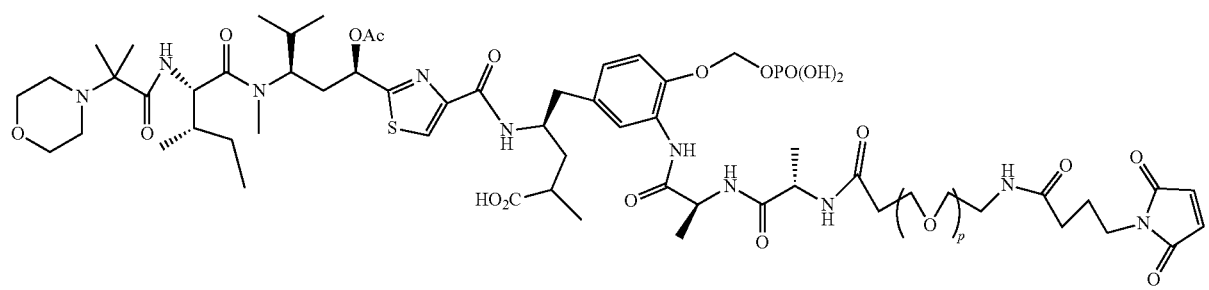

288
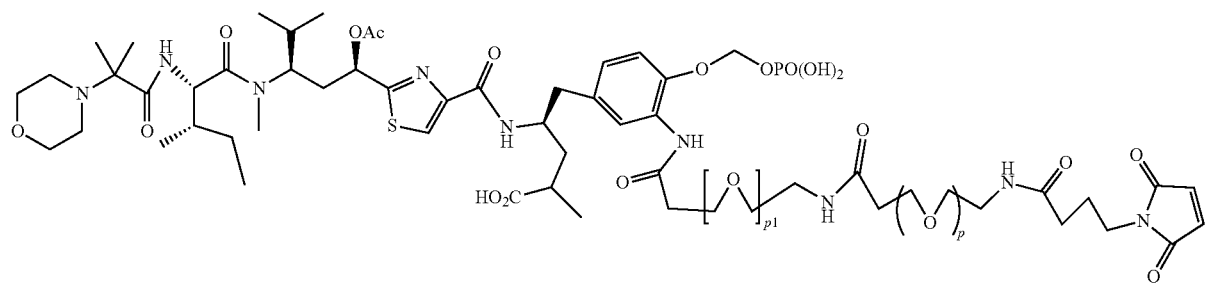
481
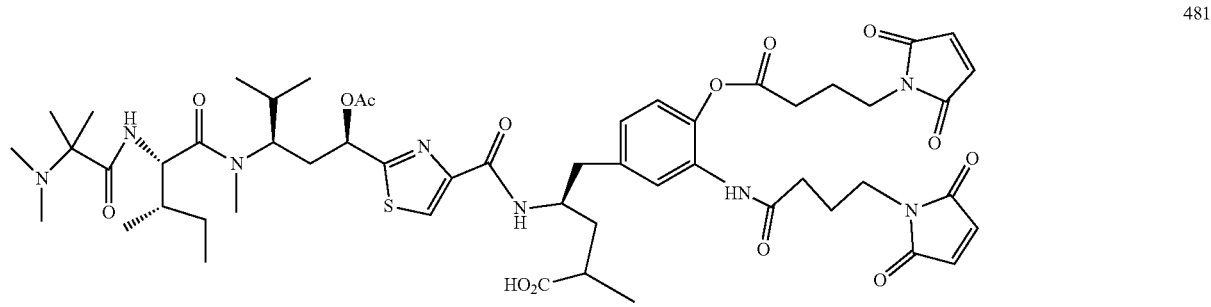
495
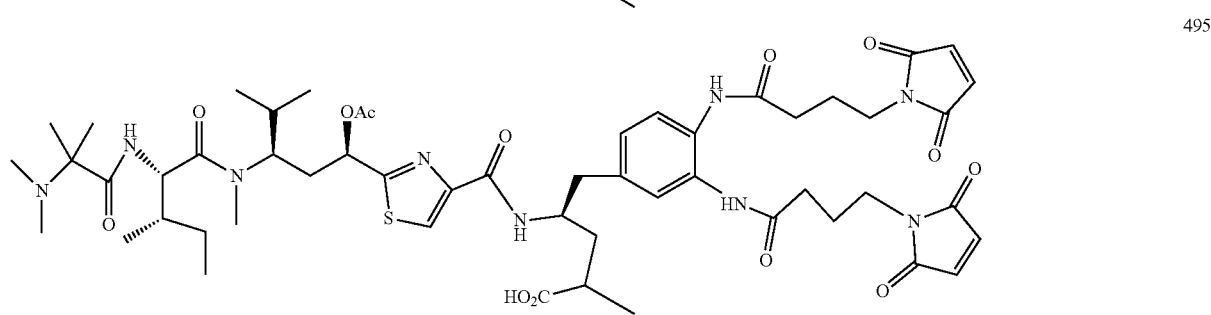
528
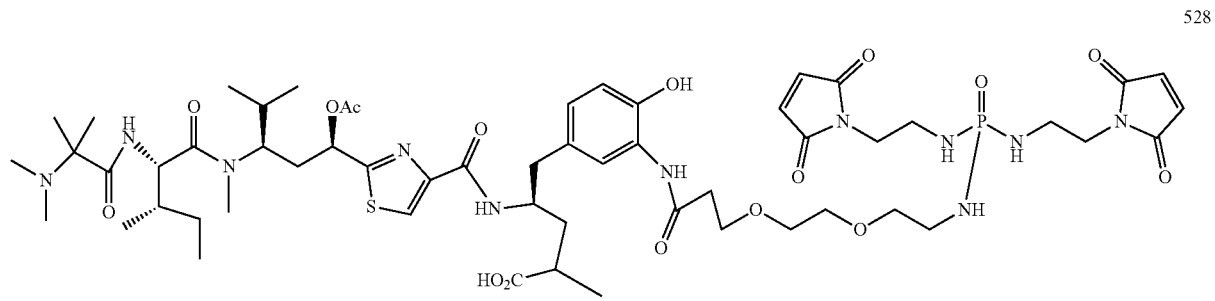
541
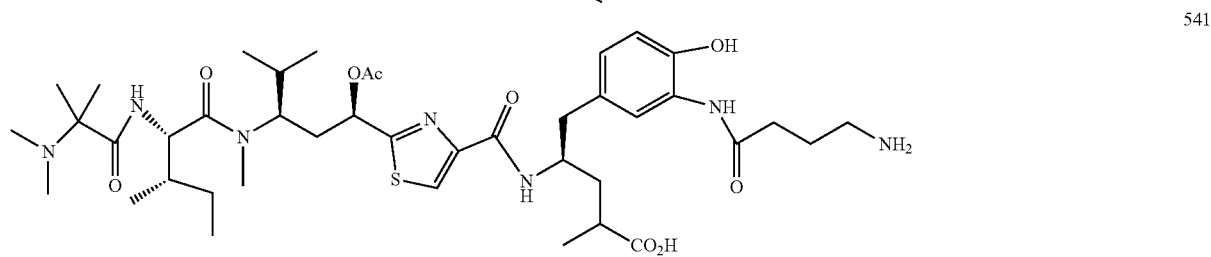
628
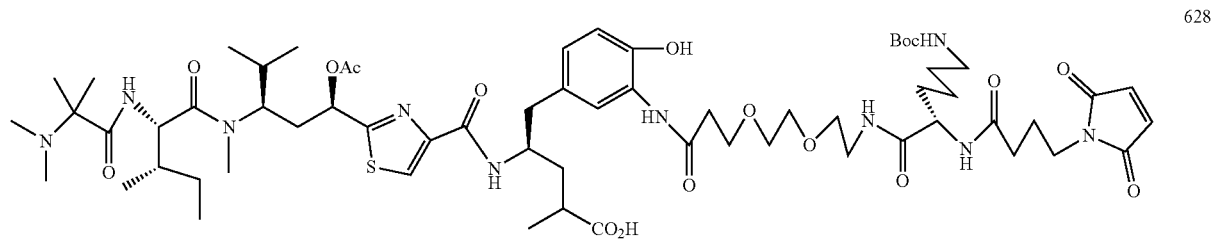

629
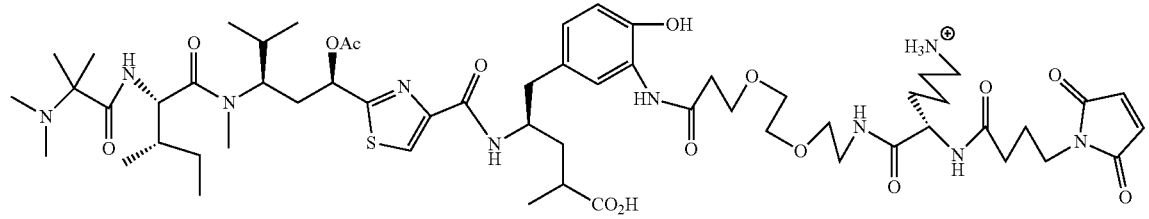
632
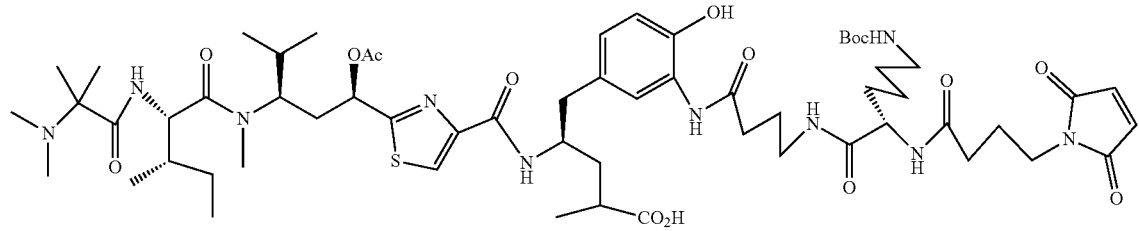
633
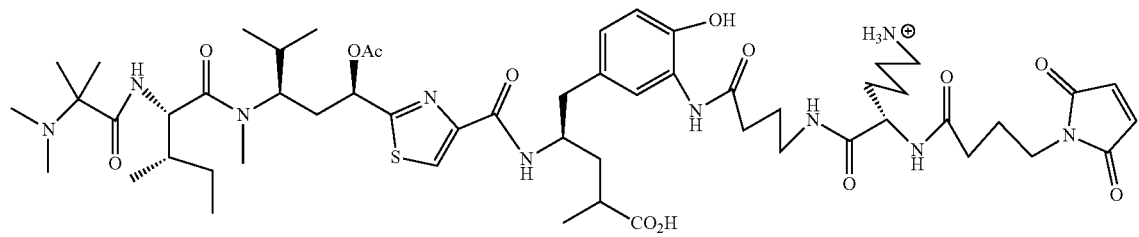
641
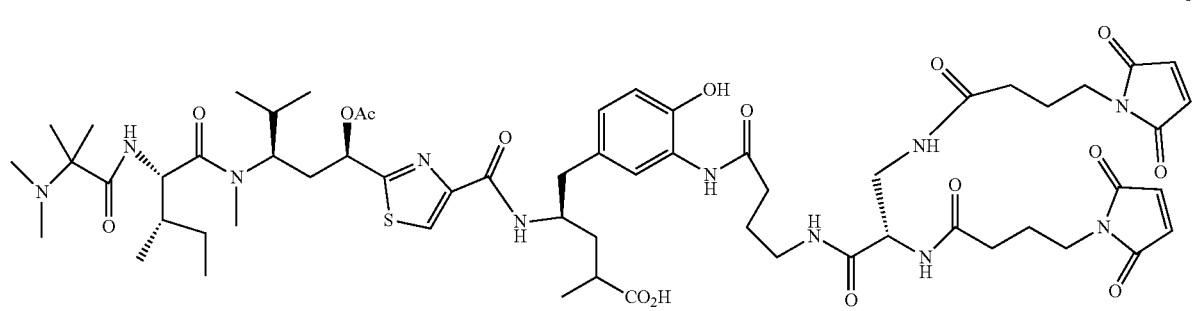
644
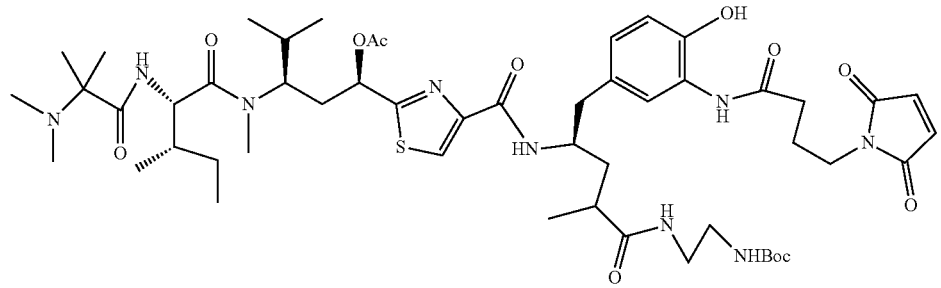
645
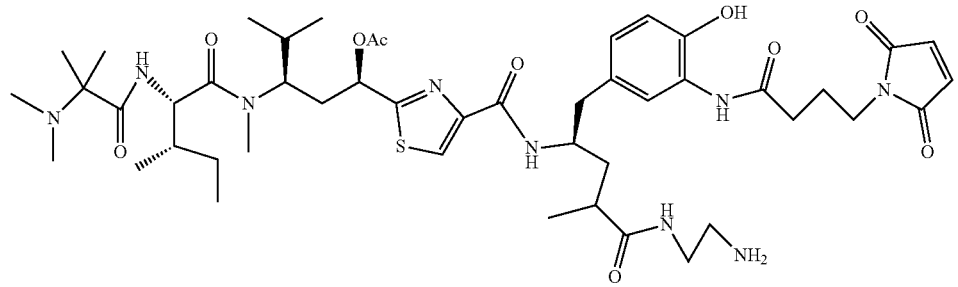

-continued
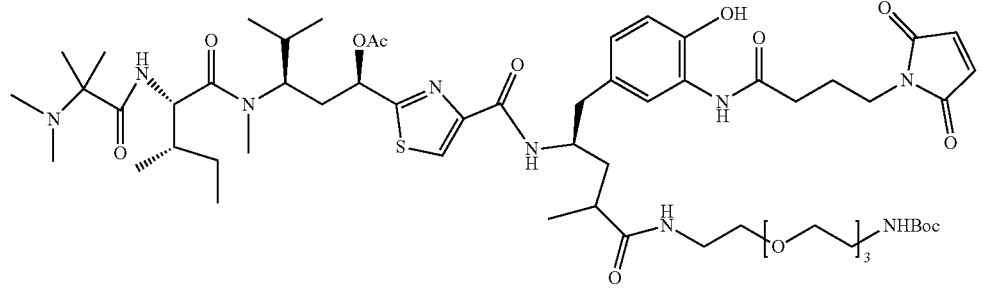
648
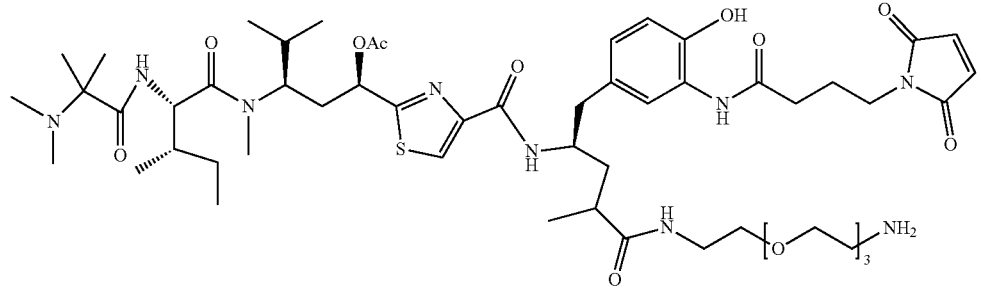
649
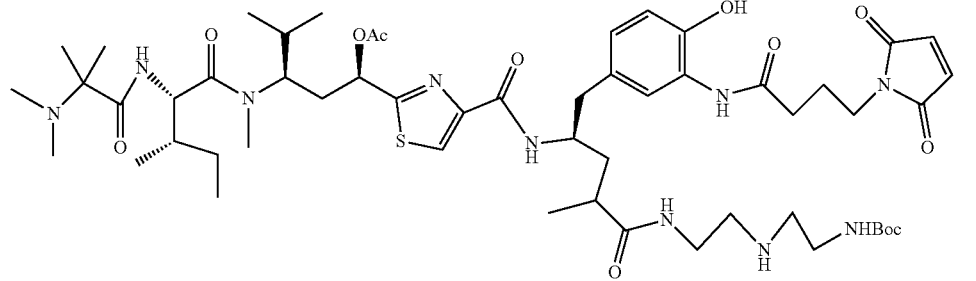
653
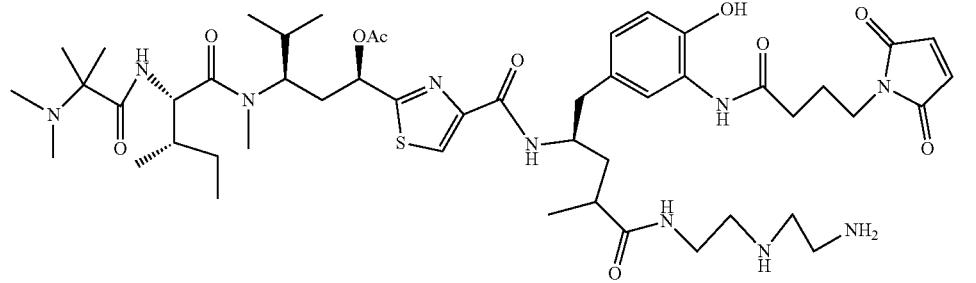
654
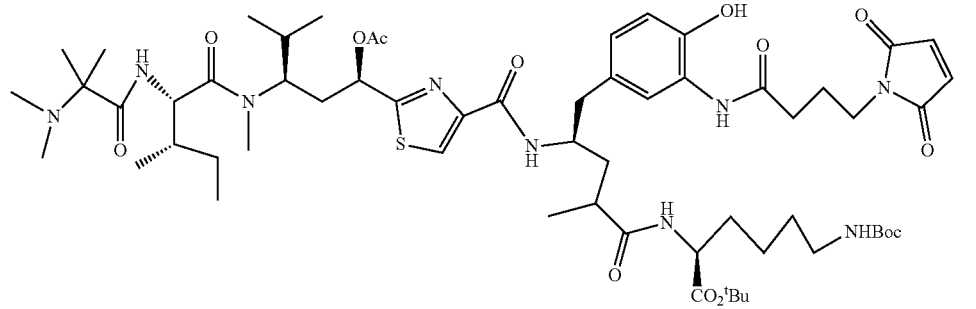
658

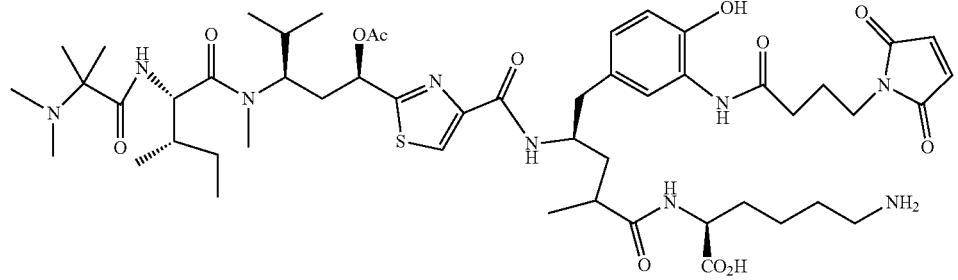
659
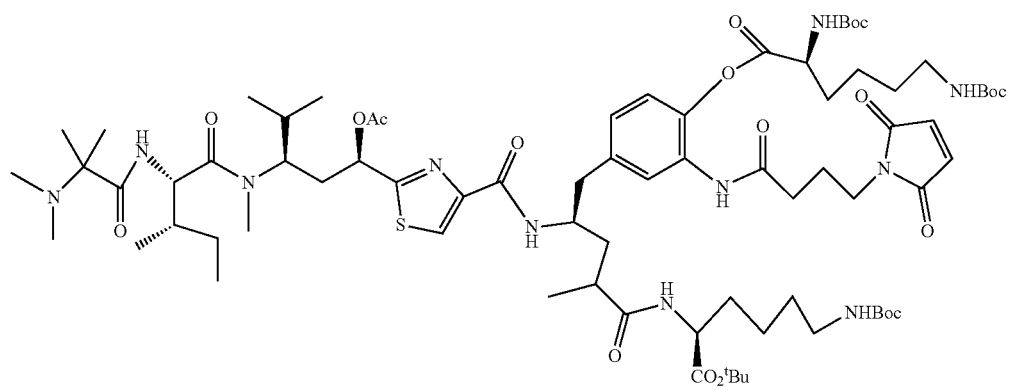
662
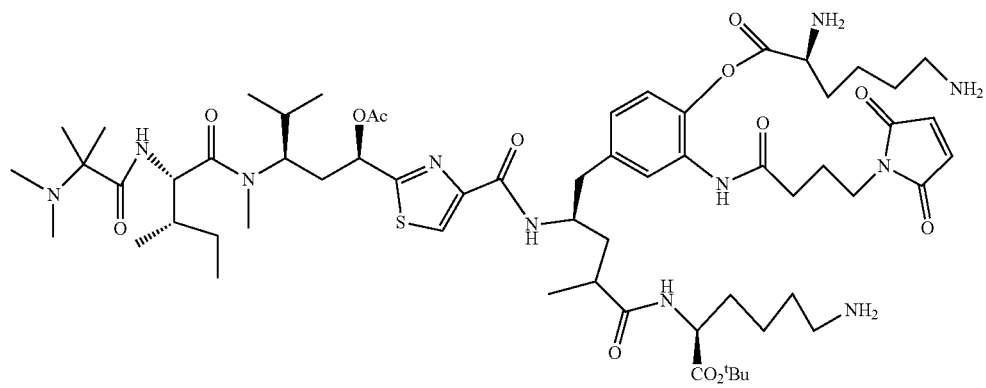
663
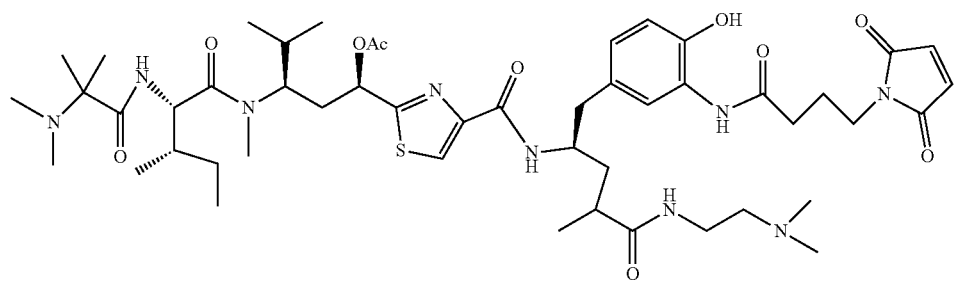
673
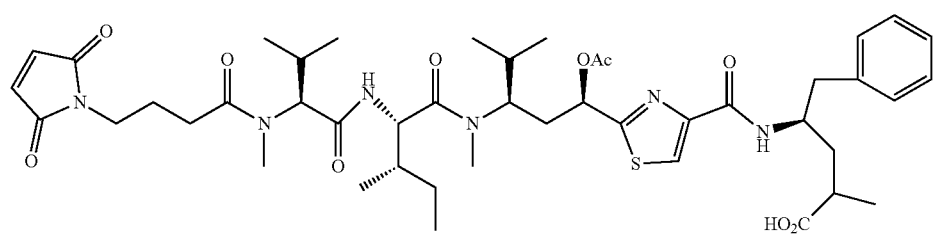
709

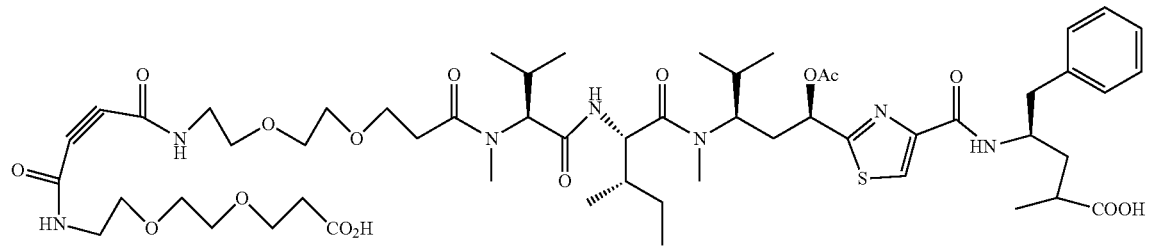

712

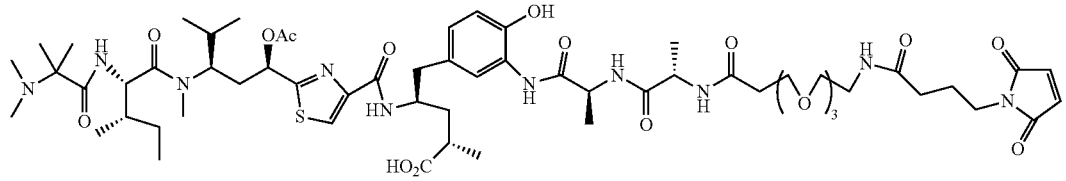

166a

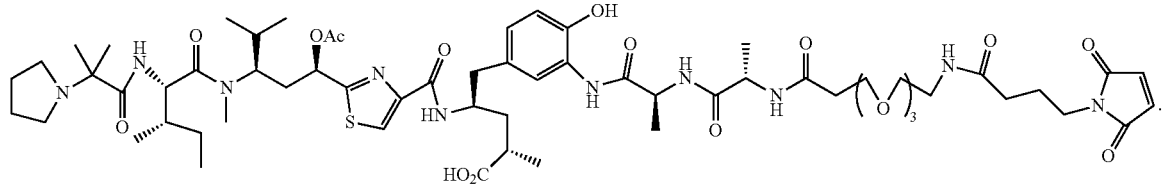

719

11. The conjugate according to claim 1, wherein the cell binding agent is capable of targeting against a tumor cell, a virus infected cell, a microorganism infected cell, a parasite infected cell, an autoimmune disease cell, an activated tumor cells, a myeloid cell, aw a T-cell, a B cell, or a melanocyte, or a cell expressing any one of the following antigens or receptors: CD2, CD2R, CD3, CD3gd, CD3e, CD4, CD5, CD6, CD7, CD8, CD8a, CD8b, CD9, CD10, CD11a, CD11b, CD11c, CD12, CD12w, CD13, CD14, CD15, CD15s, CD15u, CD16, CD16a, CD16b, CD17, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD42a, CD42b, CD42c, CD42d, CD43, CD44, CD44R, CD45, CD45RA, CD45RB, CD45RO, CD46, CD47, CD47R, CD48, CD49a, CD49b, CD49c, CD49e, CD49f, CD50, CD51, CD52, CD53, CD54, CD55, CD56, CD57, CD58, CD59, CD60, CD60a, CD60b, CD60c, CD61, CD62E, CD62L, CD62P, CD63, CD64, CD65, CD65s, CD66, CD66a, CD66b, CD66c, CD66d, CD66e, CD66f, CD67, CD68, CD69, CD70, CD71, CD72, CD73, CD74, CD74, CD75, CD75s, CD76, CD77, CD78, CD79, CD79a, CD79b, CD80, CD81, CD82, CD83, CD84, CDw84, CD85, CD86, CD87, CD88, CD89, CD90, CD91, CD92, CDw92, CD93, CD94, CD95, CD96, CD97, CD98, CD99, CD99R, CD100, CD101, CD102, CD103, CD104, CD105, CD106, CD107, CD107a, CD107b, CD108, CD109, CD110, CD111, CD112, CD113, CDw113, CD114, CD115, CD116, CD117, CD118, CD119, CDw119, CD120a, CD120b, CD121a, CD121b, CDw121b, CD122, CD123, CDw123, CD124, CD125, CDw125, CD126, CD127, CD128, CDw128, CD129, CD130, CD131, CDw131, CD132, CD133, CD134, CD135, CD136, CDw136, CD137, CDw137, CD138, CD139, CD140a, CD140b, CD141, CD142, CD143, CD144, CD145, CDw145, CD146, CD147, CD148, CD149, CD150, CD151, CD152, CD153, CD154, CD155, CD156a, CD156b, CDw156c, CD157, CD158a, CD158b, CD159a, CD159b, CD159c, CD160, CD161, CD162, CD162R, CD163, CD164, CD165, CD166, CD167, CD167a, CD168, CD169, CD170, CD171, CD172a, CD172b, CD172g, CD173, CD174, CD175, CD175s, CD176, CD177, CD178, CD179, CD180, CD181, CD182, CD183, CD184, CD185, CD186, CDw186, CD187, CD188, CD189, CD190, Cd191, CD192, CD193, CD194, CD195, CD196, CD197, CD198, CDw198, CD199, CDw199, CD200, CD200a, CD200b, CD201, CD202, CD202b, CD203, CD203c, CD204, CD205, CD206, CD207, CD208, CD209, CD210, CDw210, CD212, CD213a1, CD213a2, CDw217, CDw218a, CDw218b, CD220, CD221, CD222, CD223, CD224, CD225, CD226, CD227, CD228, CD229, CD230, CD231, CD232, CD233, CD234, CD235a, CD235ab, CD235b, CD236, CD236R, CD238, CD239, CD240, CD240CE, CD240D, CD241, CD242, CD243, CD244, CD245, CD246, CD247, CD248, CD249, CD252, CD253, CD254, CD256, CD257, CD258, CD261, CD262, CD263, CD265, CD266, CD267, CD268, CD269, CD271, CD273, CD274, CD275, CD276 (B7-H3), CD277, CD278, CD279, CD280, CD281, CD282, CD283, CD284, CD289, CD292, CDw293, CD294, CD295, CD296, CD297, CD298, CD299, CD300a, CD300c, CD300e, CD301, CD302, CD303, CD304, CD305, CD306, CD309, CD312, CD314, CD315, CD316, CD317, CD318, CD319, CD320, CD321, CD322, CD324, CDw325, CD326, CDw327, CDw328, CDw329, CD331, CD332, CD333, CD334, CD335, CD336, CD337, CDw338, CD339, CD340, CD341, CD342, CD343, CD344, CD345, CD346, CD347, CD348, CD349, CD350, CD351, CD352, CD353, CD354, CD355, CD356, CD357, CD358, CD359, CD360, CD361, CD362, CD363, CD364, CD365, CD366, CD367, CD368, CD369, CD370, CD371, CD372, CD373, CD374, CD375, CD376, CD377, CD378, CD379, CD381, CD382, CD383, CD384, CD385, CD386, CD387, CD388, CD389, CRIPTO, CRIPTO, CR, CR1, CRGF, CRIPTO, CXCR5, LY64, TDGF1, 4-1BB, APO2, ASLG659, BMPR1B, 4-1BB, 5AC, 5T4 (Trophoblastic glycoprotein, TPBG, 5T4, Wnt-Activated Inhibitory Factor 1 or WAIF1), Adenocarcinoma antigen, AGS-5, AGS-22M6, Activin receptor-like kinase 1, AFP, AKAP-4, Alpha integrin, Alpha v beta6, Amino-peptidase N, Amyloid beta, Angiopoietin 2, Angiopoietin 3, Annexin A1, AOC3 (VAP-1), B7-H3, *Bacillus anthracis* anthrax, BAFF, BCMA, B-lymphoma cell, Bombesin, C5, C242 antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL11 (C—C motif chemokine 11), CCR4 (C—C chemokine receptor type 4), CCR5, CD3E (epsilon), CEA (Carcinoembryonic antigen), CEACAM3, CEACAM5 (carcino-embryonic antigen), CFD (Factor D), Cholecystokinin 2 (CCK2R), CLDN18 (Claudin-18), CLDN18.1 (Claudin-18.1), CLDN18.2 (Claudin-18.2), Clumping factor A, cMet, CRIPTO, FCSF1R (Colony stimulating factor 1 receptor), CSF2 (colony stimulating factor 2, Granulocyte-macrophage colony-stimulating factor (GM-CSF)), CSP4, CTLA4 (cytotoxic T-lymphocyte-associated protein 4), CTAA16.88 tumor antigen, CXCR4, C-X-C chemokine receptor type 4, cyclic ADP ribose hydrolase, Cytomegalovirus, Cytomegalovirus glycoprotein B, Dabigatran, DLL3 (delta-like-ligand 3), DLL4 (delta-like-ligand 4), DPP4 (Dipeptidyl-peptidase 4), DR5 (Death receptor 5), ED-B, EGFL7 (EGF-like domain-containing protein 7), EGFR, EGFRII, EGFRvIII, Endoglin, Endothelin B receptor, Endotoxin, EpCAM (epithelial cell adhesion molecule), EphA2, Episialin, ERBB2 (Epidermal Growth Factor Receptor 2), ERBB3, ERG, *Escherichia coli*, ET-V6-AML-FAP (Fibroblast activation protein alpha), fibroblast surface antigen, FCGR1, alpha-Fetoprotein, Fibrin II, beta chain, Fibronectin extra domain-B, FOLR (folate receptor), Folate receptor alpha, Folate hydrolase, Fos-related antigen, 1F protein of respiratory syncytial virus, Frizzled receptor, Fucosyl GM1, GD2 ganglioside, G-28 GloboH, Glypican 3, N-glycolylneuraminic acid, GM3, GMCSF receptor α-chain, Growth differentiation factor, GP-14-GPNMB (Trans-membrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, HLA-HLA-DR10, HLA-DRB, HMWMAA, Human chorionic gonadotropin, HNGF, Human scatter factor receptor kinase, Hsp90, ICAM-1 (Intercellular Adhesion Molecule 1), Idiotype, IGF1R (insulin-like growth factor 1 receptor), IFN-γ, Influenza hemagglutinin, IgE, IgE Fc region, interleukins of IL-1, IL-2, IL-3, IL-4, IL-5, IL-6, IL-7, IL-8, IL-9, IL-10, IL-11, IL-12, IL-13, IL-15, IL-17, IL-17A, IL-18, IL-19, IL-20, IL-21, IL-22, IL-23, IL-27, or IL-28), IL31RA, ILGF2 (Insulin-like growth factor 2), Integrins (α4, $\alpha_{IIb}\beta_3$, αvβ3, $\alpha_4\beta_7$, α5β1, α60β, α7β7, αIIβ3, α5β5, αvβ5), Interferon gamma-induced protein, ITGA2, ITGB2, KIR2D, Kappa Ig, Legumain, Lewis-Y antigen, LFA-1 (Lymphocyte function-associated antigen 1, CD11a), LHRH, LINGO-1, Lipoteichoic acid, LIV1A, LTA, MAGE-1, MAGE-2, MAGE-3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (mesothelin), Mucin 1, cell surface associated (MUC1) or polymorphic epithelial mucin (PEM), MUC16 (CA125), MCP1 (monocyte chemotactic protein 1), MPG, MS4A1 (membrane-spanning 4-domains subfamily A), Myelin-associated glycoprotein, Myostatin, NARP-1, NCA-90, Nectin-4 (ASG-22ME), NGF, Neural apoptosis-regulated proteinase 1, NOGO-A, Notch receptor, Nucleolin, Neu oncogene product, NY-BR-1, OX-40, OxLDL (Oxidized low-density lipoprotein), P21, P97, PAP, PCSK9, PDCD1 (PD-1, Programmed cell death protein 1), PDGF-Rα (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI)), Rhesus factor, RANKL, ROBO4, Respiratory syncytial virus, RON, ROR1, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, STEAP1 (six-transmembrane epithelial antigen of the prostate 1), STEAP2, STn, TAG-72 (tumor associated glycoprotein 72), T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF-13B (tumor necrosis factor receptor superfamily member 13B), TPBG (trophoblast glycoprotein), TRAIL-R$_1$ (Tumor necrosis apoptosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-1 (Trop1), Trop2, VCAM-1, VEGF, VEGF-A, VEGF-2, VEGFR-1, VEGFR2, or vimentin, or a cell expressing an insulin growth factor receptor, or an epidermal growth factor receptor.

12. The conjugate according to claim 11, wherein the tumor cell is selected from the group consisting of lymphoma cells, myeloma cells, renal cells, breast cancer cells, prostate cancer cells, ovarian cancer cells, colorectal cancer cells, gastric cancer cells, squamous cancer cells, small-cell lung cancer cells, none small-cell lung cancer cells, testicular cancer cells, malignant cells, and cells that grow and divide at an unregulated, quickened pace to cause cancers.

13. A pharmaceutical composition comprising a therapeutically effective amount of one or more of the conjugate of claim 1, and a pharmaceutically acceptable salt, carrier, diluent, or excipient therefor.

14. The pharmaceutical composition of claim 13, having in vitro, in vivo or ex vivo cell killing activity.

15. A method for treating a cancer, an autoimmune disease, or an infectious disease, comprising administering concurrently the pharmaceutical composition a according to claim 13, with a agent selected from chemotherapeutic agent, a radiation therapy, an immunotherapy agent, an autoimmune disorder agent, or an anti-infectious agents-.

16. The method according to claim 15, wherein the agent is one or more selected from the following agents:
  (1) a chemotherapeutic agent consisting of:
  a) an alkylating agent: selected from the group consisting of nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 and adozelesin, carzelesin, bizelesin and their synthetic analogues; duocarmycin and its synthetic analogues, KW-2189, CBI-TMI, CBI dimers; benzodiazepine dimers and pyrrolobenzodiazepine (PBD) dimers, tomaymycin dimers, indolinobenzodiazepine dimers, imidazobenzothiadiazepine dimers, and oxazolidinobenzodiazepine dimers; Nitrosoureas: comprising carmustine, lomustine, chlorozotocin, fotemustine, nimustine, ranimustine; Alkylsulphonates: comprising busulfan, treosulfan, improsulfan and piposulfan); Triazenes and dacarbazine; Platinum containing compounds: comprising carboplatin, cisplatin, and oxaliplatin; aziridines, benzodopa, carboquone, meturedopa, or uredopa; ethylenimines and methylamelamines including altretamine, triethylenemelamine, trietylenephosphoramide, triethylenethiophosphoramide and trimethylolomelamine;

b) a plant alkaloid: selected from the group consisting of Vinca alkaloids: comprising vincristine, vinblastine, vindesine, vinorelbine, and navelbin; Taxoids of paclitaxel, docetaxol and their analogs, Maytansinoids of DM1, DM2, DM3, DM4, DM5, DM6, DM7, maytansine, ansamitocins and their analogs, cryptophycin 1, cryptophycin 8; epothilones, eleutherobin, discodermolide, bryostatins, dolostatins, auristatins, tubulysins, cephalostatins; pancratistatin; a sarcodictyin; and spongistatin;

c) a DNA topoisomerase inhibitor: selected from the group consisting of Epipodophyllins, 9-aminocamptothecin, camptothecin, crisnatol, daunomycin, etoposide, etoposide phosphate, irinotecan, mitoxantrone, novantrone, retinoic acids, retinols, teniposide, topotecan, 9-nitrocamptothecin, RFS 2000; and mitomycins and their analogs;

d) an antimetabolite: selected from the group consisting of methotrexate, trimetrexate, denopterin, pteropterin, aminopterin and folic acid analogues; mycophenolic acid, tiazofurin, ribavirin, EICAR; hydroxyurea, deferoxamine; Pyrimidine analogs of Uracil, analogs of ancitabine, azacytidine, 6-azauridine, capecitabine, carmofur, cytarabine, dideoxyuridine, doxifluridine, enocitabine, 5-Fluorouracil, floxuridine, ratitrexed; Cytosine analogs of cytarabine, cytosine arabinoside, and fludarabine; Purine analogs of azathioprine, fludarabine, mercaptopurine, thiamiprine, and thioguanine; folic acid replenisher, and folinic acid;

e) a hormonal therapy selected from the group consisting of Anti-estrogen of megestrol, raloxifene, and tamoxifen; goserelin, leuprolide acetate; bicalutamide, flutamide, calusterone, dromostanolone propionate, epitiostanol, goserelin, leuprolide, mepitiostane, nilutamide, testolactone, trilostane Vitamin D3 analogs of CB 1093, EB 1089, KH 1060, cholecalciferol, and ergocalciferol; verteporfin, phthalocyanine, photosensitizer Pc4, demethoxyhypocrellin A; Cytokines of Interferon-alpha, Interferon-gamma, tumor necrosis factor (TNFs), and human proteins containing a TNF domain;

f) a kinase inhibitor, selected from the group consisting of BIBW 2992, imatinib, gefitinib, pegaptanib, sorafenib, dasatinib, sunitinib, erlotinib, nilotinib, lapatinib, axitinib, pazopanib, vandetanib, E7080, mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, and ispinesib;

g) a poly (ADP-ribose) polymerase (PARP) inhibitors selected from the group consisting of olaparib, niraparib, iniparib, talazoparib, veliparib, CEP 9722, E7016, BGB-290, and 3-aminobenzamide;

h) an antibiotic, selected from the group consisting of an enediyne antibiotic (selected from tocalicheamicin, calicheamicin γ1, δ1, α1 and β1; dynemicin A, deoxydynemicin; esperamicin, kedarcidin, C-1027, maduropeptin, neocarzinostatin chromophore and related chromoprotein enediyne antibiotic chromomophores), aclacinomycins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, deoxydoxorubicin, epirubicin, eribulin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin;

i) a polyketide, bullatacin and bullatacinone; gemcitabine, epoxomicins and carfilzomib, bortezomib, thalidomide, lenalidomide, pomalidomide, tosedostat, zybrestat, PLX4032, STA-9090, a Stimuvax, allovectin-7, Xegeva, Sipuleucel-T, ipilimumab, Isoprenylation inhibitors and Lovastatin, Dopaminergic neurotoxins and 1-methyl-4-phenylpyridinium ion, staurosporine, Actinomycin D, dactinomycin, amanitins, bleomycin A2, bleomycin B2, peplomycin, daunorubicin, doxorubicin (adriamycin), idarubicin, epirubicin, pirarubicin, zorubicin, mitoxantrone, verapamil, thapsigargin, Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A; Anti-adrenals, selected from the group consisting of aminoglutethimide, mitotane, trilostane; aceglatone; aldophosphamide glycoside; aminolevulinic acid; amsacrine; arabinoside, bestrabucil; bisantrene; edatrexate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; razoxane; rhizoxin; sizofiran; spirogermanium; tenuazonic acid; triaziquone; 2,2',2"-trichlorotriethylamine; T-2 toxin, verrucarin A, roridin A, anguidine; urethane, siRNA, antisense drugs;

(2) an anti-autoimmune disease agent: cyclosporine, cyclosporine A, aminocaproic acid, azathioprine, bromocriptine, chlorambucil, chloroquine, cyclophosphamide, amcinonide, betamethasone, budesonide, hydrocortisone, flunisolide, fluticasone propionate, fluocortolone danazol, dexamethasone, Triamcinolone acetonide, beclometasone dipropionate, DHEA, enanercept, hydroxychloroquine, infliximab, meloxicam, methotrexate, mofetil, mycophenylate, prednisone, sirolimus, tacrolimus (3) an anti-infectious disease agents comprising:
a) aminoglycosides: amikacin, astromicin, netilmicin, sisomicin, isepamicin, hygromycin B, amikacin, arbekacin, bekanamycin, dibekacin, tobramycin, framycetin, paromomycin, ribostamycin, netilmicin, spectinomycin, streptomycin, tobramycin, verdamicin;
b) amphenicols: azidamfenicol, chloramphenicol, florfenicol, thiamphenicol;

c) ansamycins: geldanamycin, herbimycin;
d) carbapenems: biapenem, doripenem, ertapenem, imipenem/cilastatin, meropenem, panipenem;
e) cephems: carbacephem, cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cefoxitin, cefotetan, cefmetazole, flomoxef, latamoxef;
f) glycopeptides: bleomycin, oritavancin, telavancin, teicoplanin, ramoplanin;
g) tigecycline;
h) β-lactamase inhibitors: sulbactam, tazobactam, clavulanic acid;
i) Lincosamides: clindamycin, lincomycin;
j) lipopeptides: daptomycin, A54145, calcium-dependent antibiotics (CDA);
k) macrolides: azithromycin, cethromycin, clarithromycin, dirithromycin, erythromycin, flurithromycin, josamycin, telithromycin, cethromycin, midecamycin, miocamycin, oleandomycin, rifampicin, rifampin, rifabutin, rifapentine), rokitamycin, roxithromycin, spectinomycin, spiramycin, tacrolimus (FK506), troleandomycin, telithromycin;
l) monobactams: aztreonam, tigemonam;
m) oxazolidinones: linezolid;
n) penicillins: amoxicillin, ampicillin, pivampicillin, hetacillin, bacampicillin, metampicillin, talampicillin, azidocillin, azlocillin, benzylpenicillin, benzathine benzylpenicillin, benzathine phenoxymethylpenicillin, clometocillin, procaine benzylpenicillin, carbenicillin, cloxacillin, dicloxacillin, epicillin, flucloxacillin, mecillinam, mezlocillin, meticillin, nafcillin, oxacillin, penamecillin, penicillin, pheneticillin, phenoxymethylpenicillin, piperacillin, propicillin, sulbenicillin, temocillin, ticarcillin;
o) polypeptides: bacitracin, colistin, polymyxin B;
p) quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin;
q) streptogramins: pristinamycin, quinupristin/dalfopristin;
r) sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole);
s) steroid antibacterials: selected from fusidic acid;
t) tetracyclines: doxycycline, chlortetracycline, clomocycline, demeclocycline, lymecycline, meclocycline, metacycline, minocycline, oxytetracycline, penimepicycline, rolitetracycline, tetracycline, tigecycline;
u) antibiotics: selected from the group consisting of annonacin, arsphenamine, Bacitracin, cycloserine, dictyostatin, discodermolide, eleutherobin, epothilone, ethambutol, etoposide, faropenem, fusidic acid, furazolidone, isoniazid, laulimalide, metronidazole, mupirocin, fosfomycin, nitrofurantoin, paclitaxel, platensimycin, pyrazinamide, quinupristin/dalfopristin, rifampicin (rifampin), tazobactam tinidazole, uvaricin;

(4) Anti-viral drugs comprising:
a) entry/fusion inhibitors: aplaviroc, maraviroc, vicriviroc, gp41, PRO 140, CD4;
b) integrase inhibitors: raltegravir, elvitegravir, globoidnan A;
c) maturation inhibitors: bevirimat, vivecon;
d) neuraminidase inhibitors: oseltamivir, zanamivir, peramivir;
e) nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues of 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides of β-1-thymidine and β-1~2'-deoxycytidine, penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT);
f) non-nucleosides: amantadine, ateviridine, capravirine, diarylpyrimidines of etravirine and rilpivirine, delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine;
g) protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir;
h) Anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib;

(5) a radioisotope for radiotherapy selected from the group consisting of (radionuclides)$^{3}$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, and $^{213}$Bi;

(6) a cell-binding molecule-drug conjugate having a cytotoxic agent of a tubulysin analog, maytansinoid analog, taxanoid (taxane) analog, CC-1065 analog, daunorubicin and doxorubicin compound, amatoxin analog, dimer of pyrrolobenzodiazepine (PBD), tomaymycin, anthramycin, indolinobenzodiazepines, imidazobenzothiadiazepines, or oxazolidinobenzodiazepines, calicheamicins and the enediyne antibiotic compound, actinomycin, azaserine, bleomycins, epirubicin, tamoxifen, idarubicin, dolastatins, auristatins of monomethyl auristatin E, MMAE, MMAF, auristatin PYE, auristatin TP, Auristatins 2-AQ, 6-AQ, EB (AEB), and EFP (AEFP), duocarmycins, geldanamycins, methotrexates, thiotepa, vindesines, vincristines, hemiasterlins, nazumamides, microginins, radiosumins, topoisomerase I inhibitors, alterobactins, microsclerodermins, theonellamides, esperamicins, PNU-159682, and their analogues and derivatives above thereof;

(7) a pharmaceutically acceptable salt, acid or derivative of any of the above drugs (1) to (6).

17. The conjugate according to claim 1, wherein T is an antibody; a single chain antibody; an antibody fragment that binds to the target cell; a monoclonal antibody; a single chain monoclonal antibody; or a monoclonal antibody fragment that binds the target cell; a chimeric antibody; a chimeric antibody fragment that binds to the target cell; a domain antibody; or a domain antibody fragment that binds to the target cell.

* * * * *